(12) United States Patent
Flasinski et al.

(10) Patent No.: US 12,168,770 B2
(45) Date of Patent: Dec. 17, 2024

(54) PLANT REGULATORY ELEMENTS AND USES THEREOF

(71) Applicant: Monsanto Technology LLC, St. Louis, MO (US)

(72) Inventors: Stanislaw Flasinski, Ballwin, MO (US); Barrett C. Foat, St. Louis, MO (US); Mohammed Oufattole, Wildwood, MO (US); Randall W. Shultz, St. Louis, MO (US); Xiaoping Wei, St. Louis, MO (US); Wei Wu, Chesterfield, MO (US); Shiaw-Pyng Yang, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 405 days.

(21) Appl. No.: 17/488,189

(22) Filed: Sep. 28, 2021

(65) Prior Publication Data
US 2022/0090108 A1    Mar. 24, 2022

Related U.S. Application Data

(62) Division of application No. 16/722,287, filed on Dec. 20, 2019, now Pat. No. 11,180,768, which is a division of application No. 16/549,573, filed on Aug. 23, 2019, now Pat. No. 11,046,966, which is a division of application No. 15/802,843, filed on Nov. 3, 2017, now Pat. No. 10,550,401, which is a division of application No. 14/117,342, filed as application No. PCT/US2012/037561 on May 11, 2012, now Pat. No. 9,845,477.

(60) Provisional application No. 61/485,876, filed on May 13, 2011.

(51) Int. Cl.
C12N 15/82        (2006.01)

(52) U.S. Cl.
CPC .............................. *C12N 15/8216* (2013.01)

(58) Field of Classification Search
None
See application file for complete search history.

(56) References Cited

U.S. PATENT DOCUMENTS

| | | | | |
|---|---|---|---|---|
| 5,489,520 | A | * | 2/1996 | Adams et al. ....... C12N 5/0025 536/23.7 |
| 5,500,365 | A | * | 3/1996 | Fischhoff et al. ...... C12N 15/67 435/417 |
| 6,462,258 | B1 | | 10/2002 | Fincher et al. |
| 6,642,438 | B1 | | 11/2003 | Clendennen et al. |
| 6,660,911 | B2 | | 12/2003 | Fincher et al. |
| 9,845,477 | B2 | | 12/2017 | Flasinski et al. |
| 10,550,401 | B2 | | 2/2020 | Flasinski et al. |
| 11,046,966 | B2 | | 6/2021 | Flasinski et al. |
| 11,180,768 | B2 | | 11/2021 | Flasinski et al. |
| 12,060,564 | B2 | | 8/2024 | Flasinski et al. |
| 2003/0182690 | A1 | | 9/2003 | Clendennen et al. |
| 2004/0055039 | A1 | | 3/2004 | Hiroshi et al. |
| 2007/0006335 | A1 | | 1/2007 | Cook et al. |
| 2007/0204367 | A1 | * | 8/2007 | Flasinski et al. .. C12N 15/8216 536/23.6 |
| 2008/0000405 | A1 | | 1/2008 | Wu et al. |
| 2010/0058495 | A1 | | 3/2010 | Abbitt |
| 2012/0084885 | A1 | | 4/2012 | Alexandrov et al. |
| 2020/0056195 | A1 | | 2/2020 | Flasinski et al. |
| 2021/0310015 | A1 | | 10/2021 | Flasinski et al. |

FOREIGN PATENT DOCUMENTS

| | | |
|---|---|---|
| CN | 101880657 A | 11/2010 |
| CN | 101952435 A | 1/2011 |
| CN | 102016049 A | 4/2011 |
| JP | 2001-346580 A | 12/2001 |
| WO | 2000037662 | 6/2000 |
| WO | WO 01/44457 | 6/2001 |
| WO | WO 2005/098007 | 10/2005 |
| WO | WO 2006/039449 | 4/2006 |

OTHER PUBLICATIONS

Donald & Cashmore (1990) EMBO J 9:1717-26.*
Kim et al. (1994) Plant Mol Biol 24:105-17.*
Dolferus et al. (1994) Plant Physiol 105:1075-87.*
Potenza et al. (2004) In Vitro Cell Dev Biol Plant 40:1-22.*
Saha et al. (2007) In Silica Biol 7(1):7-19.*
Rose (2008) Curr Top Microbial Immunol 326:277-90.*
Cho & Cosgrove (2002) Plant Cell 14:3237-53.*
Odell et al. (1985) Nature 313:810-12.*
GenBank Accession No. LN713260, dated Mar. 5, 2015.
GenBank Accesion No. HN305077, dated Nov. 23, 2010.
GenBank Accession No. JG553522, dated Jun. 13, 2011.
GenBank Accession No. HN316421, dated Nov. 24, 2010.
Callis et al., "Introns increase gene expression in cultured maize cells," *Genes Dev.* 1:1183-1200, 1987.
Chee et al., "Expression of a bean storage protein 'phaseolin minigene' in foreign plant tissues," *Gene* 41:47-57, 1986.
Cho et al., *Plant Cell* 14:3237-53 (2002).
Christiansen et al., "Maize polyubiquitin genes: structure, thermal perturbation of expression and transcript splicing, and promoter activity following transfer to protoplasts by electroporation," *Plant Mol. Biol.* 18:675-689, 1992.

(Continued)

*Primary Examiner* — Russell T Boggs
(74) *Attorney, Agent, or Firm* — Dentons US LLP; Judith Koehler

(57) ABSTRACT

The invention provides DNA molecules and constructs, including their nucleotide sequences, useful for modulating gene expression in plants and plant cells. Transgenic plants, plant cells, plant parts, seeds, and commodity products comprising the DNA molecules operably linked to heterologous transcribable polynucleotides are also provided, as are methods of their use.

19 Claims, 6 Drawing Sheets

Specification includes a Sequence Listing.

(56) References Cited

OTHER PUBLICATIONS

Clancy et al., "Splicing of the maize Sh1 first intron is essential for enhancement of gene expression, and a T-rich motif increases expression without affecting splicing," *Plant Physiol.* 130(2):918-929, 2002.
Dean et al., "Sequences downstream of translation start regulate quantitative expression of two petunia rbcS genes," *Plant Cell* 1(2):201-208, 1989.
Dolferus et al., *Plant Physiol.* 105:1075-87 (1994).
Donald & Cashmore, EMBO J. 9:1717-26 (1990).
International Preliminary Report on Patentability regarding PCT Application No. PCT/US2012/037561, dated Nov. 19, 2013.
International Search Report regarding PCT Application No. PCT/US2012/037561, dated Sep. 12, 2012.
Jeon et al., "Tissue-preferential expression of a rice alpha-tubulin gene, OsTubA1, mediated by the first intron," *Plant Physiol.* 123(3):1005-1014, 2000.
Kim et al., Plant Mol. Biol. 24:105-17 (1994).
Kuhlemeier et al., "Upstream sequences determine the difference in transcript abundance of pea rbcS genes," *Mol. Gen. Genet.* 212:405-411, 1988.
Lasserre et al., "Differential activation of two ACC oxidase gene promoters from melon during plant development and in response to pathogen attack," *Mol. Gen. Genet.* 256(3):211-222, 1997.
Leon et al., "Transient gene expression in protoplasts of *Phaseolus vulgaris* isolated from a cell suspension culture," *Plant Physiol.* 95(3):968-972, 1991.
Li et al., Advanced genetic tools for plant biotechnology, *Nat Rev Genet* 14:781-93 (2013).
Loganantharaj, *Int. J. Bioinf. Res. Appl.* 2:36-51 (2006).
Mascarenhas et al., "Intron-mediated enhancement of heterologous gene expression in maize," *Plant Mol. Biol.* 15(6):913-920, 1990.
Mcelroy et al., "Isolation of an efficient actin promoter for use in rice transformation," *Plant Cell* 2(2):163-171, 1990.
Norris et al., "The intron of *Arabidopsis thaliana* polyubiquitin genes is conserved in location and is a quantitative determinant of chimeric gene expression," *Plant Mol. Biol.* 21(5):895-906, 1993.
Piechulla et al., Plant Mol. Biol. 38:655-62 (1998).
Potenza et al., *In Vitro Cell Dev. Biol. Plant* 40:1-22 (2004).
Rose et al., "Introns act post-transcriptionally to increase expression of the *Arabidopsis thaliana* tryptophan pathway gene PAT1," *Plant J.* 11(3):455-464, 1997.
Rose et al., "Intron-mediated enhancement of gene expression independent of unique intron sequences and splicing," *Plant Physiol.* 122(2):535-542, 2000.
Saha et al., *In Silico. Biol.* 7(1):7-19 (2007).
Sherf et al., "Dual-luciferase reporter assay: an advanced co-reporter technology integrating firefly and Renilla luciferase assays," *Promega Notes Magazine* No. 57, p. 2, 1996.
Sinibaldi et al., "Intron splicing and intron-mediated enhanced expression in monocots," *Prog. Nucleic Acid Res. Mol. Biol.* (42):229-257, 1992.
Vancanneyt et al., "Construction of an intron-containing marker gene: splicing of the intron in transgenic plants and its use in monitoring early events in Agrobacterium-mediated plant transformation," *Mol. Gen. Genet.* 220(2):245-250, 1990.
Vasil et al., "Increased gene expression by the first intron of maize shrunken-1 locus in grass species," *Plant Physiol.* 91(4):1575-1579, 1989.
Welsch et al., Planta 216:523-34 (2003).
Xu et al., "Rice triosephosphate isomerase gene 5' sequence directs β-glucuronidase activity in transgenic tobacco but requires an intron for expression in rice," *Plant Physiol.* 106(2):459-467, 1994.
Yamagata et al., "TGTCACA motif is a novel cis-regulatory enhancer element involved in fruit-specific expression of the cucumisin gene," *J. Biol. Chem.* 227(13):11582-11590, 2002.
GenBank Accession No. HN314561, dated Nov. 24, 2010.
GenBank Accession No. JG468661, dated Mar. 16, 2011.
GenBank Accession No. HN298588, dated Nov. 24, 2010.
GenBank Accession No. JG469358, dated Mar. 16, 2011.
GenBank Accession No. HN327993, dated Nov. 24, 2010.
GenBank Accession No. JG467489, dated Mar. 16, 2011.
GenBank Accession No. HN319913, dated Nov. 24, 2010.
GenBank Accession No. JG480182, dated Mar. 16, 2011.
Office Action regarding Chilean Application No. 201601540, dated Jun. 14, 2017.
GenBank Accession No. LN713263, dated Mar. 5, 2015.
Office Action regarding Eurasian Application No. 201690416, dated Jul. 28, 2017.
GenBank Accession No. HN320890, dated Nov. 23, 2010.
USPTO Written Description Guidelines. (2008).
Liu et al. Advanced genetic tools for plant biotechnology, Nature Review Genetics 14:781-793, 2013.
GenBank Accession No. LN713255, dated Mar. 5, 2015.
European Search Report and Written Opinion regarding European App. No. 22199610.1, dated Feb. 23, 2023.
China Office Action and Search Report regarding China Application No. 201710186179.8, mailed Nov. 7, 2019, 13 pages.
Australia Office Action regarding Australia Application No. 2019246918, mailed Jan. 15, 2020, 7 pages.
GenBank Accession No. AM740200, Sep. 27, 2007.
GenBank Accession No. HN296636, Nov. 23, 2010.
Gonzalez-Ibeas et al., "Melogen: an EST database for melon functional genomics", BMC Genomics (2007), 8:306.
Gonzalez et al., "Genome-wide BAC-end sequencing of Cucumis melousing two BAC libraries", BMC Genomics (2010), 11:618.
Clepet et al., "Analysis of expressed sequence tags generated from full-length enriched cDNA libraries of melon" BMC GEnomics (2011), 12:252.
Hondred et al., "Use of Ubiquitin Fusions to Augment Protein Expression in Transgenic Plants," Plant Physiology 119:713-723, 1999.
Yuebing et al., "UBI1 intron-mediated enhancement of the expression of Bt cry1ah gene in transgenic maize (*Zea mays* L.)," Chinese Science Bulletin 53(20):3185-3180, 2008.
Wang and Oard, Rice ubiquitin promoters: deletion analysis and potential usefulness in nplant transformation systems, Plant Cell Reports 22:129-134, 2003.
Joung and Kamo, Expression of polyubiquitin promoter isolated from Gladiolus, Plant Cell Reports 25:1081-1088, 2006.
NCBI (2014) XM_008459007.

* cited by examiner

| | | |
|---|---|---|
| p-CUCme.Ubq1-1:1:15 | (SEQ ID NO: 2) | TTCAAAGTGGATGTAGGCACTATTAGTCGAACCACCAATAAATTTGTTATGTTCTTTTGCT |
| p-CUCme.Ubq1-1:1:16 | (SEQ ID NO: 6) | TTCAAAGTGGATGTAGGCACTATTAGTCGAACCACCAATAAATTTGTTATGTTCTTTTGCT |
| p-CUCme.Ubq1-1:1:17 | (SEQ ID NO: 8) | ------------AGTCGAACCACCAATAAATTTGTTATGTTCTTTTGCT |
| p-CUCme.Ubq1-1:1:18 | (SEQ ID NO: 10) | ------------------------------------------------ |
| p-CUCme.Ubq1-1:1:19 | (SEQ ID NO: 12) | ------------------------------------------------ |
| | | |
| p-CUCme.Ubq1-1:1:15 | (SEQ ID NO: 2) | ATTCCTTGTAATCTCCATAAATATTTCTTACTAAGCTCTAGAAATCTGCTTGTCAAGAG |
| p-CUCme.Ubq1-1:1:16 | (SEQ ID NO: 6) | ATTCCTTGTAATCTCCATAAATATTTCTTACTAAGCTCTAGAAATCTGCTTGTCAAGAG |
| p-CUCme.Ubq1-1:1:17 | (SEQ ID NO: 8) | ATTCCTTGTAATCTCCATAAATATTTCTTACTAAGCTCTAGAAATCTGCTTGTCAAGAG |
| p-CUCme.Ubq1-1:1:18 | (SEQ ID NO: 10) | ------------------------------------------------ |
| p-CUCme.Ubq1-1:1:19 | (SEQ ID NO: 12) | ------------------------------------------------ |
| | | |
| p-CUCme.Ubq1-1:1:15 | (SEQ ID NO: 2) | ATTAGGTATCATTTATGCCTTTTATATTTCCTTCGGTTGCATATCTTGAGCTAGTTAAG |
| p-CUCme.Ubq1-1:1:16 | (SEQ ID NO: 6) | ATTAGGTATCATTTATGCCTTTTATATTTCCTTCGGTTGCATATCTTGAGCTAGTTAAG |
| p-CUCme.Ubq1-1:1:17 | (SEQ ID NO: 8) | ATTAGGTATCATTTATGCCTTTTATATTTCCTTCGGTTGCATATCTTGAGCTAGTTAAG |
| p-CUCme.Ubq1-1:1:18 | (SEQ ID NO: 10) | ------------------------------------------------ |
| p-CUCme.Ubq1-1:1:19 | (SEQ ID NO: 12) | ------------------------------------------------ |
| | | |
| p-CUCme.Ubq1-1:1:15 | (SEQ ID NO: 2) | ATCGAGAGGTTACTGTTGTTGAAACCGAGATTAGTATCTTTGGATTAACACGTGCCTACC |
| p-CUCme.Ubq1-1:1:16 | (SEQ ID NO: 6) | ATCGAGAGGTTACTGTTGTTGAAACCGAGATTAGTATCTTTGGATTAACACGTGCCTACC |
| p-CUCme.Ubq1-1:1:17 | (SEQ ID NO: 8) | ATCGAGAGGTTACTGTTGTTGAAACCGAGATTAGTATCTTTGGATTAACACGTGCCTACC |
| p-CUCme.Ubq1-1:1:18 | (SEQ ID NO: 10) | ------------------------------------------------ |
| p-CUCme.Ubq1-1:1:19 | (SEQ ID NO: 12) | ------------------------------------------------ |
| | | |
| p-CUCme.Ubq1-1:1:15 | (SEQ ID NO: 2) | AAAATTTGAAATTTGTATTTACCCCATTCATTGGATAATAAGCAATTCTTATAGTGTTA |
| p-CUCme.Ubq1-1:1:16 | (SEQ ID NO: 6) | AAAATTTGAAATTTGTATTTACCCCATTCATTGGATAATAAGCAATTCTTATAGTGTTA |
| p-CUCme.Ubq1-1:1:17 | (SEQ ID NO: 8) | AAAATTTGAAATTTGTATTTACCCCATTCATTGGATAATAAGCAATTCTTATAGTGTTA |
| p-CUCme.Ubq1-1:1:18 | (SEQ ID NO: 10) | ------------------------------------------------ |
| p-CUCme.Ubq1-1:1:19 | (SEQ ID NO: 12) | ------------------------------------------------ |
| | | |
| p-CUCme.Ubq1-1:1:15 | (SEQ ID NO: 2) | TCAATTAAACTCCTATAAAGTGTAATAATTGAATCCATGAACTATTTTCATATGTAATCT |
| p-CUCme.Ubq1-1:1:16 | (SEQ ID NO: 6) | TCAATTAAACTCCTATAAAGTGTAATAATTGAATCCATGAACTATTTTCATATGTAATCT |
| p-CUCme.Ubq1-1:1:17 | (SEQ ID NO: 8) | TCAATTAAACTCCTATAAAGTGTAATAATTGAATCCATGAACTATTTTCATATGTAATCT |
| p-CUCme.Ubq1-1:1:18 | (SEQ ID NO: 10) | ------------------------------------------------ |
| p-CUCme.Ubq1-1:1:19 | (SEQ ID NO: 12) | ------------------------------------------------ |

FIG. 1C

| | | |
|---|---|---|
| P-CUCme.Ubq1-1:1:15 (SEQ ID NO: 2) | TAATAAAATGAATTAGAAGTTTAATTAAAATAATATATTTTGTATGCTATTTTTCAAAG |
| P-CUCme.Ubq1-1:1:16 (SEQ ID NO: 6) | TAATAAAATGAATTAGAAGTTTAATTAAAATAATATATTTTGTATGCTATTTTTCAAAG |
| P-CUCme.Ubq1-1:1:17 (SEQ ID NO: 8) | TAATAAAATGAATTAGAAGTTTAATTAAAATAATATATTTTGTATGCTATTTTTCAAAG |
| P-CUCme.Ubq1-1:1:18 (SEQ ID NO: 10) | ------------------------------------------------------------ |
| P-CUCme.Ubq1-1:1:19 (SEQ ID NO: 12) | ------------------------------------------------------------ |
| | |
| P-CUCme.Ubq1-1:1:15 (SEQ ID NO: 2) | TTTGAAGAATGTGTTAATTGATACACATACAAAAAAATCTAGGTTTTACATGAAAAACTAT |
| P-CUCme.Ubq1-1:1:16 (SEQ ID NO: 6) | TTTGAAGAATGTGTTAATTGATACACATACAAAAAAATCTAGGTTTTACATGAAAAACTAT |
| P-CUCme.Ubq1-1:1:17 (SEQ ID NO: 8) | TTTGAAGAATGTGTTAATTGATACACATACAAAAAAATCTAGGTTTTACATGAAAAACTAT |
| P-CUCme.Ubq1-1:1:18 (SEQ ID NO: 10) | ------------------------------------------------------------ |
| P-CUCme.Ubq1-1:1:19 (SEQ ID NO: 12) | ------------------------------------------------------------ |
| | |
| P-CUCme.Ubq1-1:1:15 (SEQ ID NO: 2) | GGAAGTGAAAGATAGCATCTAATATTTTATGACACAAAATGCAAACTAATATATAAAGGA |
| P-CUCme.Ubq1-1:1:16 (SEQ ID NO: 6) | GGAAGTGAAAGATAGCATCTAATATTTTATGACACAAAATGCAAACTAATATATAAAGGA |
| P-CUCme.Ubq1-1:1:17 (SEQ ID NO: 8) | GGAAGTGAAAGATAGCATCTAATATTTTATGACACAAAATGCAAACTAATATATAAAGGA |
| P-CUCme.Ubq1-1:1:18 (SEQ ID NO: 10) | ---------TGACACAAAATGCAAACTAATATATAAAGGA |
| P-CUCme.Ubq1-1:1:19 (SEQ ID NO: 12) | ------------------------------------------------------------ |
| | |
| P-CUCme.Ubq1-1:1:15 (SEQ ID NO: 2) | TTTAATTAATTTTATAGGTTTCAAATTGTTAGACTTGTCAAATACAAAATTTATTGA |
| P-CUCme.Ubq1-1:1:16 (SEQ ID NO: 6) | TTTAATTAATTTTATAGGTTTCAAATTGTTAGACTTGTCAAATACAAAATTTATTGA |
| P-CUCme.Ubq1-1:1:17 (SEQ ID NO: 8) | TTTAATTAATTTTATAGGTTTCAAATTGTTAGACTTGTCAAATACAAAATTTATTGA |
| P-CUCme.Ubq1-1:1:18 (SEQ ID NO: 10) | TTTAATTAATTTTATAGGTTTCAAATTGTTAGACTTGTCAAATACAAAATTTATTGA |
| P-CUCme.Ubq1-1:1:19 (SEQ ID NO: 12) | ------------------------------------------------------------ |
| | |
| P-CUCme.Ubq1-1:1:15 (SEQ ID NO: 2) | ACCAAATACATACAAACATCAAAATTAAGAACAGAAAAATCTAAATTCAAATGAAATTTAT |
| P-CUCme.Ubq1-1:1:16 (SEQ ID NO: 6) | ACCAAATACATACAAACATCAAAATTAAGAACAGAAAAATCTAAATTCAAATGAAATTTAT |
| P-CUCme.Ubq1-1:1:17 (SEQ ID NO: 8) | ACCAAATACATACAAACATCAAAATTAAGAACAGAAAAATCTAAATTCAAATGAAATTTAT |
| P-CUCme.Ubq1-1:1:18 (SEQ ID NO: 10) | ACCAAATACATACAAACATCAAAATTAAGAACAGAAAAATCTAAATTCAAATGAAATTTAT |
| P-CUCme.Ubq1-1:1:19 (SEQ ID NO: 12) | ------------------------------------------------------------ |
| | |
| P-CUCme.Ubq1-1:1:15 (SEQ ID NO: 2) | TAATAGAAAAATTAGAAAAAAAAAGAAAATAAAAGGAATCGTATTGTTTTTCCTTC |
| P-CUCme.Ubq1-1:1:16 (SEQ ID NO: 6) | TAATAGAAAAATTAGAAAAAAAAAGAAAATAAAAGGAATCGTATTGTTTTTCCTTC |
| P-CUCme.Ubq1-1:1:17 (SEQ ID NO: 8) | TAATAGAAAAATTAGAAAAAAAAAGAAAATAAAAGGAATCGTATTGTTTTTCCTTC |
| P-CUCme.Ubq1-1:1:18 (SEQ ID NO: 10) | TAATAGAAAAATTAGAAAAAAAAAGAAAATAAAAGGAATCGTATTGTTTTTCCTTC |
| P-CUCme.Ubq1-1:1:19 (SEQ ID NO: 12) | ------------------------------------------------------------ |

FIG. 1e

| | |
|---|---|
| P-CUCme.Ubq1-1:1:1:15 (SEQ ID NO: 2) | CTTTTTCCCATTTGAGAGGTGAATAAAGCTAATTGAGCTGCTCTAACTTCCTAATCTTTA |
| P-CUCme.Ubq1-1:1:1:16 (SEQ ID NO: 6) | CTTTTTCCCATTTGAGAGGTGAATAAAGCTAATTGAGCTGCTCTAACTTCCTAATCTTTA |
| P-CUCme.Ubq1-1:1:1:17 (SEQ ID NO: 8) | CTTTTTCCCATTTGAGAGGTGAATAAAGCTAATTGAGCTGCTCTAACTTCCTAATCTTTA |
| P-CUCme.Ubq1-1:1:1:18 (SEQ ID NO: 10) | CTTTTTCCCATTTGAGAGGTGAATAAAGCTAATTGAGCTGCTCTAACTTCCTAATCTTTA |
| P-CUCme.Ubq1-1:1:1:19 (SEQ ID NO: 12) | ------------------------------------------------------------ |
| | |
| P-CUCme.Ubq1-1:1:1:15 (SEQ ID NO: 2) | TGCTTTCCCATAAAGCTTTCCCAACTGCGCGTAATCGTATAAATGGAAAATTGACCTTT |
| P-CUCme.Ubq1-1:1:1:16 (SEQ ID NO: 6) | TGCTTTCCCATAAAGCTTTCCCAACTGCGCGTAATCGTATAAATGGAAAATTGACCTTT |
| P-CUCme.Ubq1-1:1:1:17 (SEQ ID NO: 8) | TGCTTTCCCATAAAGCTTTCCCAACTGCGCGTAATCGTATAAATGGAAAATTGACCTTT |
| P-CUCme.Ubq1-1:1:1:18 (SEQ ID NO: 10) | TGCTTTCCCATAAAGCTTTCCCAACTGCGCGTAATCGTATAAATGGAAAATTGACCTTT |
| P-CUCme.Ubq1-1:1:1:19 (SEQ ID NO: 12) | ------------TCGTATAAATGGAAAATTGACCTTT |
| | |
| P-CUCme.Ubq1-1:1:1:15 (SEQ ID NO: 2) | CCAACTAGATTCTTCCAGAACTAAACAATACGTAACACGCAAGTAATCAAAGACACGTTT |
| P-CUCme.Ubq1-1:1:1:16 (SEQ ID NO: 6) | CCAACTAGATTCTTCCAGAACTAAACAATACGTAACACGCAAGTAATCAAAGACACGTTT |
| P-CUCme.Ubq1-1:1:1:17 (SEQ ID NO: 8) | CCAACTAGATTCTTCCAGAACTAAACAATACGTAACACGCAAGTAATCAAAGACACGTTT |
| P-CUCme.Ubq1-1:1:1:18 (SEQ ID NO: 10) | CCAACTAGATTCTTCCAGAACTAAACAATACGTAACACGCAAGTAATCAAAGACACGTTT |
| P-CUCme.Ubq1-1:1:1:19 (SEQ ID NO: 12) | CCAACTAGATTCTTCCAGAACTAAACAATACGTAACACGCAAGTAATCAAAGACACGTTT |
| | |
| P-CUCme.Ubq1-1:1:1:15 (SEQ ID NO: 2) | CATTTTCCTATAGAATATTATAGTTATTCGTGATTAACGGAAGTCGGCAATTTTAGGTAT |
| P-CUCme.Ubq1-1:1:1:16 (SEQ ID NO: 6) | CATTTTCCTATAGAATATTATAGTTATTCGTGATTAACGGAAGTCGGCAATTTTAGGTAT |
| P-CUCme.Ubq1-1:1:1:17 (SEQ ID NO: 8) | CATTTTCCTATAGAATATTATAGTTATTCGTGATTAACGGAAGTCGGCAATTTTAGGTAT |
| P-CUCme.Ubq1-1:1:1:18 (SEQ ID NO: 10) | CATTTTCCTATAGAATATTATAGTTATTCGTGATTAACGGAAGTCGGCAATTTTAGGTAT |
| P-CUCme.Ubq1-1:1:1:19 (SEQ ID NO: 12) | CATTTTCCTATAGAATATTATAGTTATTCGTGATTAACGGAAGTCGGCAATTTTAGGTAT |
| | |
| P-CUCme.Ubq1-1:1:1:15 (SEQ ID NO: 2) | AAATACGTGAATTCTCGAGCGCTAATTT |
| P-CUCme.Ubq1-1:1:1:16 (SEQ ID NO: 6) | AAATACGTGAATTCTCGAGCGCTAATTT |
| P-CUCme.Ubq1-1:1:1:17 (SEQ ID NO: 8) | AAATACGTGAATTCTCGAGCGCTAATTT |
| P-CUCme.Ubq1-1:1:1:18 (SEQ ID NO: 10) | AAATACGTGAATTCTCGAGCGCTAATTT |
| P-CUCme.Ubq1-1:1:1:19 (SEQ ID NO: 12) | AAATACGTGAATTCTCGAGCGCTAATTT |

FIG. 15

PLANT REGULATORY ELEMENTS AND USES THEREOF

REFERENCE TO RELATED APPLICATIONS

This application is a divisional of U.S. application Ser. No. 16/722,387, filed Dec. 20, 2019 (pending), which application is a divisional of U.S. application Ser. No. 16/549,573, filed Aug. 23, 2019 (now U.S. Pat. No. 11,046,966), which application is a divisional of U.S. application Ser. No. 15/802,843, filed Nov. 3, 2017 (now U.S. Pat. No. 10,550,401), which application is a divisional of U.S. application Ser. No. 14/117,342, filed Oct. 23, 2014, (now U.S. Pat. No. 9,845,477), which application is a 371 National Stage application of International Application No. PCT/US2012/037561 filed May 11, 2012 which application claims the benefit of priority to U.S. Provisional Application No. 61/485,876, filed May 13, 2011, which are herein incorporated by reference in its their entireties.

INCORPORATION OF SEQUENCE LISTING

The sequence listing that is contained in the file named "MONS_304USD3_Seq_Listing.txt", which is 463 kilobytes (as measured in Microsoft Windows®) and was created on Nov. 4, 2019, is filed herewith by electronic submission and is incorporated by reference herein.

FIELD OF THE INVENTION

The invention relates to the field of plant molecular biology and plant genetic engineering, and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel gene regulatory elements such as promoters, leaders and introns derived from *Cucumis melo*, a plant species commonly referred to as muskmelon, for use in plants. The present invention also provides DNA constructs, transgenic plant cells, plants, and seeds comprising the regulatory elements. The sequences may be provided operably linked to a transcribable polynucleotide molecule which may be heterologous with respect to a regulatory sequence provided herein. The present invention also provides methods of making and using the regulatory elements, the DNA constructs comprising the regulatory elements, and the transgenic plant cells, plants, and seeds comprising the regulatory elements operably linked to a transcribable polynucleotide molecule.

Thus, in one aspect, the present invention provides a DNA molecule, such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, a transcriptional regulatory expression element group, or promoter, or leader, or intron is at least 90 percent, at least 95 percent, at least 98 percent, or at least 99 percent identical to any of SEQ ID NOs: 1-199, 211 and 212. In particular embodiments, the heterologous transcribable polynucleotide molecule comprises a gene of agronomic interest, a gene capable of providing herbicide resistance in plants, or a gene capable of providing plant pest resistance in plants.

The invention also provides a transgenic plant cell containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. Further, the transcriptional regulatory expression element group, or promoter, or leader, or intron regulates the expression of a gene. The transgenic plant cell can be a monocotyledonous or dicotyledonous plant cell.

Further provided by the invention is a transgenic plant, or part of the transgenic plant containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, the transgenic plant may be a progeny plant of any generation that contains the transcriptional regulatory expression element group, or promoter, or leader, or intron.

Still further provided is a transgenic seed containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In yet another aspect, the invention provides a method of producing a commodity product from the transgenic plant, transgenic plant part or transgenic seed which contains a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In one embodiment, the commodity product is protein concentrate, protein isolate, grain, starch, seeds, meal, flour, biomass, or seed oil.

In another aspect, the invention provides a commodity product comprising a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In still yet another aspect, the invention provides a method of expressing a transcribable polynucleotide molecule in a transgenic plant using a DNA molecule such as a transcriptional regulatory expression element group, or promoter, or leader, or intron which has a DNA sequence which is at least 85 percent identical to that of any of SEQ ID NOs: 1-199, 211 and 212, or contains any of SEQ ID NOs: 1-199, 211 and 212, or consists of a fragment of any of SEQ ID NOs: 1-199, 211 and 212; and cultivating the transgenic plant.

BRIEF DESCRIPTION OF THE SEQUENCES

SEQ ID NOs: 1, 5, 7, 9, 11, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 are *Cucumis* transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element.

SEQ ID NOs: 2, 6, 8, 10, 12, 163 and 169 are promoter elements.

SEQ ID NOs: 3, 164, 166 and 170 are leader sequences.

SEQ ID NOs: 4, 165 and 171 are intron sequences.

SEQ ID NOs: 157, 160, 173, 179 and 186 are sequences wherein a promoter is operably linked to a leader element.

SEQ ID NOs: 158, 161, 174, 180 and 187 are sequences wherein an intron is operably linked to a leader element.

BRIEF DESCRIPTION OF THE DRAWINGS

FIGS. 1a-1f depict alignment of promoter variant segments corresponding to promoter elements isolated from the *Cucumis melo*. In particular, FIGS. 1a-1f show alignment of the 2068 bp promoter sequence P-CUCme.Ubq1-1:1:15 (SEQ ID NO: 2), found in the transcriptional regulatory expression element group EXP-CUCme.Ubq1:1:1 (SEQ ID NO: 1), vs. promoter sequences derived via 5' deletions of the promoter, P-CUCme.Ubq1-1:1:15. Deletion, for instance of the 5' end of P-CUCme.Ubq1-1:1:15, produced the promoters, P-CUCme.Ubq1-1:1:16 (SEQ ID NO: 6) a 1459 bp promoter which is found within EXP-CUCme.Ubq1:1:2 (SEQ ID NO: 5); P-CUCme.Ubq1-1:1:17 (SEQ ID NO: 8), a 964 bp sequence comprised within EXP-CUCme.Ubq1:1:3 (SEQ ID NO: 7); P-CUCme.Ubq1-1:1:18 (SEQ ID NO: 10), a 479 bp sequence comprised within EXP-CUCme.Ubq1:1:4 (SEQ ID NO: 9); and P-CUCme.Ubq1-1:1:19 (SEQ ID NO: 12), a 173 bp sequence comprised within EXP-CUCme.Ubq1:1:5 (SEQ ID NO: 11).

DETAILED DESCRIPTION OF THE INVENTION

The invention disclosed herein provides polynucleotide molecules obtained from *Cucumis melo* having beneficial gene regulatory activity. The design, construction, and use of these polynucleotide molecules are described. The nucleotide sequences of these polynucleotide molecules are provided among SEQ ID NOs: 1-199, 211 and 212. These polynucleotide molecules are, for instance, capable of affecting the expression of an operably linked transcribable polynucleotide molecule in plant tissues, and therefore selectively regulating gene expression, or activity of an encoded gene product, in transgenic plants. The present invention also provides methods of modifying, producing, and using the same. The invention also provides compositions, transformed host cells, transgenic plants, and seeds containing the promoters and/or other disclosed nucleotide sequences, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods are known in the to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term "sequence identity" refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NOs: 1-199, 211 and 212.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NOs: 1-199, 211 and 212, has at least about 85 percent identity at least about 90 percent identity at least about 95 percent identity, at least about 96 percent identity, at least about 97 percent identity, at least about 98 percent identity, or at least about 99 percent identity to the reference sequence. In particular embodiments such sequences may be defined as having gene-regulatory activity or encoding a peptide that functions to localize an operably linked polypeptide within a cell.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group (EXP) may be comprised of expression elements, such as enhancers, promoters, leaders and introns, operably linked. Thus a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects such as by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include any of SEQ ID NOs: 2, 6, 8, 10, 12, 163 and 169, or the promoter elements comprised within any of SEQ ID NOs: 13 through 199, 211 and 212, or fragments or variants thereof. In specific embodiments of the invention, such molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent sequence for recognition and binding of the RNA polymerase II complex for initiation of transcription.

In one embodiment, fragments of a promoter molecule are provided. Promoter fragments provide promoter activity, as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from any of the promoters presented as SEQ ID NOs: 2, 6, 8, 10, 12, 163 and 169, or the promoter elements comprised within SEQ ID NOs: 13 through 199, 211 and 212, such as internal or 5' deletions, for example, can be produced to improve or alter expression, including by removing elements that have either positive or negative effects on expression; duplicating elements that have positive or negative effects on expression; and/or duplicating or removing elements that have tissue or cell specific effects on expression. Compositions derived from any of the promoters presented as SEQ ID NOs: 2, 6, 8, 10, 12, 163 and 169, or the promoter elements comprised within SEQ ID NOs: 13 through 199, 211 and 212 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOs: 2, 6, 8, 10, 12, 163 and 169, or the promoter elements comprised within SEQ ID NOs: 13 through 199, 211 and 212, and fragments or enhancers derived there from can be used to make chimeric transcriptional regulatory element compositions comprised of any of the promoters presented as SEQ ID NOs: 2, 6, 8, 10, 12, 163 and 169, or the promoter elements comprised within SEQ ID NOs: 13 through 199, 211 and 212, and the fragments or enhancers derived therefrom operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NOs: 3, 164, 166 and 170, or the leader element comprised within SEQ ID NOs: 13 through 199, 211 and 212, or fragments or variants thereof. In specific embodiments, such sequences may be provided defined as being capable of acting as a leader in a host cell, including, for example, a transgenic plant cell. In one embodiment such sequences are decoded as comprising leader activity.

The leader sequences (5' UTR) presented as SEQ ID NOs: 3, 164, 166 and 170, or the leader element comprised within any of SEQ ID NOs: 13 through 199, 211 and 212 may be comprised of regulatory elements or may adopt secondary structures that can have an effect on transcription or translation of a transgene. The leader sequences presented as SEQ ID NOs: 3, 164, 166 and 170, or the leader element comprised within SEQ ID NOs: 13 through 199, 211 and 212 can be used in accordance with the invention to make chimeric regulatory elements that affect transcription or translation of a transgene. In addition, the leader sequences presented as SEQ ID NOs: 3, 164, 166 and 170, or the leader element comprised within any of SEQ ID NOs: 13 through 199, 211 and 212 can be used to make chimeric leader sequences that affect transcription or translation of a transgene.

The introduction of a foreign gene into a new plant host does not always result in a high expression of the incoming gene. Furthermore, if dealing with complex traits, it is sometimes necessary to modulate several genes with spatially or temporarily different expression pattern. Introns can principally provide such modulation. However, multiple use of the same intron in one transgenic plant has shown to exhibit disadvantages. In those cases it is necessary to have a collection of basic control elements for the construction of appropriate recombinant DNA elements. As the available collection of introns known in the art with expression enhancing properties is limited, alternatives are needed.

Compositions derived from any of the introns presented as SEQ ID NOs: 4, 165 and 171 or the intron element comprised within SEQ ID NOs: 13 through 199, 211 and 212 can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+leader and coding sequence. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In accordance with the invention a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter.cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron. This effect has been termed "intron mediated enhancement" (IME) of gene expression (Mascarenhas et al., (1990) *Plant Mol. Biol.* 15:913-920). Introns known to stimulate expression in plants have been identified in maize genes (e.g. tubA1, Adh1, Sh1, Ubi1 (Jeon et al. (2000) *Plant Physiol.* 123:1005-1014; Callis et al. (1987) *Genes Dev.* 1:1183-1200; Vasil et al. (1989) *Plant Physiol.* 91:1575-1579; Christiansen et al. (1992) *Plant Mol. Biol.* 18:675-689) and in rice genes (e.g. salt, tpi: McElroy et al., *Plant Cell* 2:163-171 (1990); Xu et al., *Plant Physiol.* 106:459-467 (1994)). Similarly, introns from dicotyledonous plant genes like those from petunia (e.g. rbcS), potato (e.g. st-ls1) and from *Arabidopsis thaliana* (e.g. ubq3 and pat1) have been found to elevate gene expression rates (Dean et al. (1989) *Plant Cell* 1:201-208; Leon et al. (1991) *Plant Physiol.* 95:968-972; Norris et al. (1993) *Plant Mol Biol* 21:895-906; Rose and Last (1997) *Plant J.* 11:455-464). It has been shown that deletions or mutations within the splice sites of an intron reduce gene expression, indicating that splicing might be needed for IME (Mascarenhas et al. (1990) *Plant Mol Biol.* 15:913-920; Clancy and Hannah (2002) *Plant Physiol.* 130:918-929). However, that splicing per se is not required for a certain IME in dicotyledonous plants has been shown by point mutations within the splice sites of the pat1 gene from *A. thaliana* (Rose and Beliakoff (2000) *Plant Physiol.* 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adh1 gene the ninth intron, hsp81 gene the first intron)) (Chee et al. (1986) *Gene* 41:47-57; Kuhlemeier et al. (1988) *Mol Gen Genet* 212:405-411; Mascarenhas et al. (1990) *Plant Mol. Biol.* 15:913-920; Sinibaldi and Mettler (1992) In W E Cohn, K Moldave, eds, *Progress in Nucleic Acid Research and Molecular Biology*, Vol 42. Academic Press, New York, pp 229-257; Vancanneyt et al. 1990 *Mol. Gen. Genet.* 220:245-250). Therefore, not each intron can be employed in order to manipulate the gene expression level of non-endogenous genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause IME.

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion and/or insertion of one or more nucleotides of a reference sequence, wherein the derivative regulatory element has more or less or equivalent transcriptional or translational activity than the corresponding parent regulatory molecule. The regulatory element "variants" may also encompass variants arising from mutations that naturally occur in bacterial and plant cell transformation. In the present invention, a polynucleotide sequence provided as SEQ ID NOs: 1-199, 211 and 212 may be used to create variants similar in composition, but not identical to, the polynucleotide sequence of the original regulatory element, while still maintaining the general functionality of, i.e. same or similar expression pattern, the original regulatory element. Production of such variants of the present invention is well within the ordinary skill of the art in light of the disclosure and is encompassed within the scope of the present invention. "Varients" of chimeric regulatory element comprise the same constituent elements as a reference chimeric regulatory element sequence but the constituent elements comprising the chimeric regulatory element may be operatively linked by various methods known in the art such as, restriction enzyme digestion and ligation, ligation independent cloning, modular assembly of PCR products during amplification, or direct chemical synthesis of the chimeric regulatory element as well as other methods known in the art. The resulting "variant" chimeric regulatory element is comprised of the same, or variants of the same, constituent elements as the reference sequence but differ in the sequence or sequences that are used to operably link the constituent elements. In the present invention, the polynucleotide sequences provided as SEQ ID NOs: 1-199, 211 and 212 each provide a reference sequence wherein the constituent elements of the reference sequence may be joined by methods known in the art and may consist of substitutions, deletions and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

The constructs of the present invention may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known in the art of plant transformation can function in the present invention.

Methods are available for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells can be found in, for example, *Molecular Cloning: A Laboratory Manual*, 3rd edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, FL (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology* 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA* 82: 5824-5828 (1985)).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' transcription termination molecule.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus 35S transcript promoter (see, U.S. Pat. No. 5,352,605). The expression properties imparted by such operable linkages of heterologous elements is not necessarily additive of the elucidated properties of each promoter and leader, but rather is determined through empirical analysis of expression driven by the operably linked heterologous promoter and leader.

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOs: 4, 165 and 171 or the intron element comprised within any of SEQ ID NOs: 13 through 199, 211 and 212.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules are the nopaline synthase 3' region (see, Fraley, et al., *Proc. Natl. Acad. Sci. USA,* 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbiol*

Mol Biol Rev 63:405-445 (1999); Proudfoot, *Nature* 322: 562-565 (1986); Kim et al., *Biotechnology Progress* 19:1620-1622 (2003); Yonaha and Proudfoot, *EMBO J.* 19:3770-3777 (2000); Cramer et al., *FEBS Letters* 498:179-182 (2001); Kuerstem and Goodwin, *Nature Reviews Genetics* 4:626-637 (2003)). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334 (2001). This may interfere with achieving adequate levels of expression, for instance in cases were strong gene expression from all cassettes is desired.

In plants, clearly defined polyadenylation signal sequences are not known. Hasegawa et al., *Plant J.* 33:1063-1072, (2003)) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *BioTechniques* 31:328-334 (2001)). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, so that it is difficult to detect transcriptional termination sites by conventional methods. However, prediction of functional and efficient 3' UTRs by bioinformatics methods is difficult in that there are no conserved sequences which would allow easy prediction of an effective 3' UTR.

From a practical standpoint, it is typically beneficial that a 3' UTR used in a transgene cassette possesses the following characteristics. The 3' UTR should be able to efficiently and effectively terminate transcription of the transgene and prevent read-through of the transcript into any neighboring DNA sequence which can be comprised of another transgene cassette as in the case of multiple cassettes residing in one T-DNA, or the neighboring chromosomal DNA into which the T-DNA has inserted. The 3' UTR should not cause a reduction in the transcriptional activity imparted by the promoter, leader and introns that are used to drive expression of the transgene. In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower and other tissues derived from Foxtail millet (*Setaria italica* (L.) Beauv). Libraries of cDNA are made from tissues isolated from selected plant species using flower tissue, seed, leaf and root. The resulting cDNAs are sequenced using various sequencing methods. The resulting ESTs are assembled into clusters using bioinformatics software such as clc_ref_assemble_complete version 2.01.37139 (CLC bio USA, Cambridge, Massachusetts 02142). Transcript abundance of each cluster is determined by counting the number of cDNA reads for each cluster. The identified 3' UTRs may be comprised of sequence derived from cDNA sequence as well as sequence derived from genomic DNA. The cDNA sequence is used to design primers, which are then used with GenomeWalker™ (Clontech Laboratories, Inc, Mountain View, CA) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library can be used to infer properties about patters of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5-bisphosphate carboxylase, ferredoxin, ferredoxin oxidoreductase, the light-harvesting complex protein I and protein thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442 (1987)) or the *Petunia hybrida* EPSPS CTP (CTP4) (See, della-Cioppa et al., *Proc. Natl. Acad. Sci. USA* 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NOs: 1-199, 211 and 212, operably linked to a transcribable polynucleotide molecule so as to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304, 730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380, 462), high oil production (U.S. Pat. Nos. 6,495,739; 5,608, 149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380, 466), fruit ripening (U.S. Pat. No. 5,512,466), enhanced animal and human nutrition (U.S. Pat. Nos. 6,723,837; 6,653,530; 6,541,259; 5,985,605; and 6,171,640), biopolymers (U.S. Pat. Nos. RE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476, 295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229, 114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998, 700).

Alternatively, a gene of agronomic interest can affect the above mentioned plant characteristic or phenotype by encoding a RNA molecule that causes the targeted modulation of gene expression of an endogenous gene, for example via antisense (see e.g. U.S. Pat. No. 5,107,065); inhibitory RNA ("RNAi", including modulation of gene expression via miRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The RNA could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers include those encoding proteins conferring resistance to kanamycin (nptII), hygromycin B (aph IV), streptomycin or spectinomycin (aad, spec/strep) and gentamycin (aac3 and aacC4). Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, delapon, dicamba, cyclohezanedione, protoporphyrinogen oxidase inhibitors, and isoxasflutole herbicides. Transcribable polynucleotide molecules encoding proteins involved in herbicide tolerance include, but are not limited to, a transcribable polynucleotide molecule encoding 5-enolpyruvylshikimate-3-phosphate synthase (EPSPS for glyphosate tolerance described in U.S. Pat. Nos. 5,627,061; 5,633,435; 6,040, 497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtI) described in Misawa, et al., *Plant Journal* 4:833-840 (1993) and Misawa, et al., *Plant Journal* 6:481-489 (1994) for norflurazon tolerance; a transcribable polynucleotide molecule encoding acetohydroxyacid synthase (AHAS, aka ALS) described in Sathasiivan, et al., *Nucl. Acids Res.* 18:2188-2193 (1990) for tolerance to sulfonylurea herbicides; and the bar gene described in DeBlock, et al., *EMBO Journal* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g. by ELISA), small active enzymes which are detectable in extracellular solution (e.g, alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant.

Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205 (1991)).

Any transformation methods may be utilized to transform a host cell with one or more promoters and/or constructs of the present invention. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, CA, 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses,* 2nd Edition, Monograph, 16:249 (1987); Fehr, *Principles of variety development, Theory and Technique*, (Vol. 1) and *Crop Species Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, CA) reagents and methods as described by the manufacturer and PCR cycle times determined using the TaqMan® Testing Matrix. Alternatively, the Invader® (Third Wave Technologies, Madison, WI) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1: Identification and Cloning of Regulatory Elements

Novel transcriptional regulatory elements, or transcriptional regulatory expression element group (EXP) sequences were identified and isolated from genomic DNA of the dicot species *Cucumis melo* WSH-39-1070AN.

Transcriptional regulatory elements were selected based upon proprietary and public microarray data derived from transcriptional profiling experiments conducted in soybean (*Glycine max*) and *Arabidopsis* as well as homology based searches using known dicot sequences as query against proprietary *Cucumis melo* sequences.

Using the identified sequences, a bioinformatic analysis was conducted to identify regulatory elements within the amplified DNA, followed by identification of the transcriptional start site (TSS) and any bi-directionality, introns, or upstream coding sequence present in the sequence. Using the results of this analysis, regulatory elements were defined within the DNA sequences and primers designed to amplify the regulatory elements. The corresponding DNA molecule for each regulatory element was amplified using standard polymerase chain reaction conditions with primers containing unique restriction enzyme sites and genomic DNA isolated from Cucumis melo. The resulting DNA fragments were ligated into base plant expression vectors using standard restriction enzyme digestion of compatible restriction sites and DNA ligation methods.

Analysis of the regulatory element TSS and intron/exon splice junctions can be performed using transformed plant protoplasts. Briefly, the protoplasts are transformed with the plant expression vectors comprising the cloned DNA fragments operably linked to a heterologous transcribable polynucleotide molecule and the 5' RACE System for Rapid Amplification of cDNA Ends, Version 2.0 (Invtrogen, Carlsbad, California 92008) is used to confirm the regulatory element TSS and intron/exon splice junctions by analyzing the sequence of the mRNA transcripts produced thereby.

Sequences encoding ubiquitin 1 transcriptional regulatory expression element groups (EXP) were analyzed as described above and each transcriptional regulatory expression element groups ("EXP's") was also broken down into the corresponding promoters, leaders and introns comprising each transcriptional regulatory expression element group. Sequences of the identified ubiquitin 1 transcriptional regulatory expression element groups ("EXP's") are provided herein as SEQ ID NOs: 1, 5, 7, 9 and 11 and is listed in Table 1 below. The corresponding ubiquitin 1 promoters are provided herein as SEQ ID NOs: 2, 6, 8, 10 and 12. The ubiquitin 1 leader and intron are herein provided as SEQ ID NOs: 3 and 4, respectively.

Sequences encoding other Cucumis transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element are provided as SEQ ID NOs: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 and are also listed in Table 1 below. Additional promoter elements are provided as SEQ ID NOs: 163 and 169. Additional leader elements are provided as SEQ ID NOs: 164, 166 and 170. Additional intron elements are provided as SEQ ID NOs: 165 and 171. Elements wherein a promoter is operably linked to a leader element are provided as SEQ ID NOs: 157, 160, 173, 179 and 186. Elements wherein an intron is operably linked to a leader element are provided as SEQ ID NOs: 158, 161, 174, 180 and 187. With respect to the subset of sequences provided as SEQ ID NOs: 13 through 199, 211 and 212, these sequences were selected and cloned based upon the results of experiments such as transcript profiling or expression driven by promoters from homologous genes of a different species suggesting desirable patterns of expression such as constitutive expression, root expression, above ground expression or seed expression. The actual activity imparted by the Cucumis sequences is determined empirically and is not necessarily the same as that of a regulatory element derived from a homologous gene from a species other than Cucumis melo when used in a transformed plant host cell and whole transgenic plant.

TABLE 1

Transcriptional regulatory expression element groups, promoters, leaders and introns isolated from Cucumis melo.

| Annotation | SEQ ID NO: | Description | Composition Type | Size (bp) | Composition | Coordinates of Elements within EXP |
|---|---|---|---|---|---|---|
| EXP-CUCme.Ubq1:1:1 | 1 | Ubiquitin 1 | EXP | 2611 | Promoter; Leader; Intron | 1-2068; 2069-2150; 2151-2608 |
| P-CUCme.Ubq1-1:1:15 | 2 | Ubiquitin 1 | P | 2068 | Promoter | |
| L-CUCme.Ubq1-1:1:1 | 3 | Ubiquitin 1 | L | 82 | Leader | |
| I-CUCme.Ubq1-1:1:1 | 4 | Ubiquitin 1 | I | 461 | Intron | |
| EXP-CUCme.Ubq1:1:2 | 5 | Ubiquitin 1 | EXP | 2002 | Promoter; Leader; Intron | 1-1459; 1460-1541; 1542-1999 |
| P-CUCme.Ubq1-1:1:16 | 6 | Ubiquitin 1 | P | 1459 | Promoter | |
| EXP-CUCme.Ubq1:1:3 | 7 | Ubiquitin 1 | EXP | 1507 | Promoter; Leader; Intron | 1-964; 965-1046; 1047-1504 |
| P-CUCme.Ubq1-1:1:17 | 8 | Ubiquitin 1 | P | 964 | Promoter | |
| EXP-CUCme.Ubq1:1:4 | 9 | Ubiquitin 1 | EXP | 1022 | Promoter; Leader; Intron | 1-479; 480-561; 562-1019 |
| P-CUCme.Ubq1-1:1:18 | 10 | Ubiquitin 1 | P | 479 | Promoter | |
| EXP-CUCme.Ubq1:1:5 | 11 | Ubiquitin 1 | EXP | 716 | Promoter; Leader; Intron | 1-173; 174-255; 256-713 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| P-CUCme.Ubq1-1:1:19 | 12 | Ubiquitin 1 | P | 173 | Promoter | |
| P-CUCme.1-1:1:1 | 13 | Phosphatase 2A | EXP | 2000 | Promoter; Leader; Intron; Leader | Reverse compliment; see SEQ ID NO: 155 |
| P-CUCme.2-1:1:1 | 14 | Actin 1 | EXP | 2000 | Promoter; Leader; Intron; Leader | 1-964; 965-1028; 1029-1991; 1992-2003 |
| P-CUCme.3-1:1:3 | 15 | Actin 2 | EXP | 1990 | Promoter; Leader; Intron; Leader | 1-1243; 1244-1319; 1320-1982; 1983-1990 |
| P-CUCme.4-1:1:2 | 16 | Ubiquitin 2 | EXP | 2005 | Promoter; Leader; Intron; Leader | 1-1646; 1647-1704; 1705-2005; 2006-2008 |
| P-CUCme.5-1:1:2 | 17 | Ubiquitin 3 | EXP | 2004 | Promoter; Leader; Intron; Leader | 1-748; 749-819; 820-2004 |
| P-CUCme.6-1:1:1 | 18 | Tubulin beta chain | EXP | 1935 | Promoter; Leader; Intron; Leader | 1-1436; 1437-1482; 1483-1919; 1920-1935 |
| P-CUCme.8-1:1:2 | 19 | Tubulin beta chain | EXP | 1606 | Promoter; Leader | 1-1527; 1528-1606 |
| P-CUCme.9-1:1:2 | 20 | Tubulin beta chain | EXP | 1487 | Promoter; Leader | 1-1384; 1385-1487 |
| P-CUCme.10-1:1:1 | 21 | Tubulin beta chain | EXP | 1448 | Promoter; Leader | 1-1363; 1364-1448 |
| P-CUCme.11-1:1:2 | 22 | Elongation Factor 1 alpha | EXP | 1235 | Promoter; Leader; Intron | 1-617; 618-677; 678-1213; 1214-1235 |
| P-CUCme.15-1:1:2 | 23 | Elongation Factor 1 alpha | EXP | 2003 | Promoter; Leader; Intron; Leader | 1-1330; 1331-1435; 1430-1975; 1976-2002 |
| P-CUCme.16a-1:1:2 | 24 | Ubiquitin 7 | EXP | 2015 | Promoter; Leader | |
| P-CUCme.16b-1:1:1 | 25 | Ubiquitin 6 | EXP | 2006 | Promoter; Leader | |
| P-CUCme.17-1:1:2 | 26 | ubiquitin-40S ribosomal protein S27a | EXP | 2017 | Promoter; Leader | 1-1969; 1970-2017 |
| P-CUCme.18-1:1:2 | 27 | ubiquitin-40S ribosomal protein S27a | EXP | 1353 | Promoter; Leader | 1-1308; 1309-1353 |
| P-CUCme.19-1:1:2 | 28 | Chloropyll a/b binding protein | EXP | 2005 | Promoter; Leader | 1-1960; 1961-2005 |
| P-CUCme.20-1:1:2 | 29 | Chloropyll a/b binding protein | EXP | 1445 | Promoter; Leader | 1-1390; 1391-1445 |
| P-CUCme.21-1:1:1 | 30 | Chloropyll a/b binding protein | EXP | 1282 | Promoter; Leader | 1-1233; 1234-1282 |
| P-CUCme.22-1:1:3 | 31 | Elongation Factor 4 alpha | EXP | 2002 | | |
| P-CUCme.24-1:1:2 | 32 | S-Adenosylmethionine Synthetase | EXP | 2003 | Promoter; Leader; Intron; Leader | 1-1067; 1068-1165; 1166-2001; 2002-2003 |
| P-CUCme.26-1:1:2 | 33 | Stress responsive protein | EXP | 1372 | Promoter; Leader; Intron; Leader | 1-577; 578-654; 655-1366; 1367-1372 |
| P-CUCme.28-1:1:2 | 34 | Ribosomal protein S5a | EXP | 1122 | | |
| P-CUCme.29-1:1:2 | 35 | Ribosomal protein S5a | EXP | 2017 | Promoter; Leader; Intron; Leader | 1-490; 491-571; 572-2012; 2013-2017 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF143981.G5150 | 36 | LHCB6 (LIGHT HARVESTING COMPLEX PSII SUBUNIT 6) | EXP | 2000 | | |
| CumMe_WSM_SF144839.G5080 | 37 | EIF2 GAMMA translation initiation factor | EXP | 1760 | | |
| CumMe_WSM_SF146040.G5050 | 38 | EIF2 translation initiation factor | | | | |
| CumMe_WSM_SF16408.G5350 | 39 | elongation factor Tu | EXP | 2000 | | |
| CumMe_WSM_SF16429.G5670 | 40 | unknown protein | EXP | 2000 | | |
| CumMe_WSM_SF16444.G5140 | 41 | histone H4 | EXP | 2000 | Promoter; Leader | 1-1947; 1948-2000 |
| CumMe_WSM_SF16530.G6000 | 42 | HMGB2 (HIGH MOBILITY GROUP B 2) transcription factor | EXP | 2000 | | |
| CumMe_WSM_SF16553.G5090 | 43 | PBG1: threonine-type endopeptidase | EXP | 1115 | | |
| CumMe_WSM_SF16563.G5560 | 44 | ATARFB1A (ADP-ribosylation factor B1A) | EXP | 2000 | Promoter; Leader; Intron; Leader | 1-1329; 1330-1427; 1428-1988; 1989-2000 |
| CumMe_WSM_SF16675.G5720 | 45 | chromatin protein family | EXP | 2000 | | |
| CumMe_WSM_SF16920.G5650 | 46 | CSD1 (COPPER/ZINC SUPEROXIDE DISMUTASE 1) | EXP | 2000 | | |
| CumMe_WSM_SF16953.G5180 | 47 | SCE1 (SUMO CONJUGATION ENZYME 1); SUMO ligase | EXP | 2000 | | |
| CumMe_WSM_SF17051.G5470 | 48 | 60S ribosomal protein L9 (RPL90D) | EXP | 2000 | | |
| CumMe_WSM_SF17111.G5790 | 49 | ubiquinol-cytochrome C reductase complex ubiquinone-binding protein | EXP | 2000 | Promoter; Leader | 1-1895; 1896-2000 |
| CumMe_WSM_SF17142.G5920 | 50 | peptidyl-prolyl cis-trans isomerase, chloroplast | EXP | 2000 | | |
| CumMe_WSM_SF17190.G6200 | 51 | PRK (PHOSPHORIBULOKINASE) | EXP | 2000 | | |
| CumMe_WSM_SF17250.G5910 | 52 | LHCB5 (LIGHT HARVESTING COMPLEX OF PHOTOSYSTEM II 5) | EXP | 2000 | | |
| CumMe_WSM_SF17252.G7330 | 53 | nascent polypeptide-associated complex (NAC) domain-containing protein | EXP | 2000 | Promoter; Leader; Intron | 1-1195; 1196-1297; 1298-2000 |
| CumMe_WSM_SF17253.G5150 | 54 | RPS9 (RIBOSOMAL PROTEIN S9) | EXP | 1547 | | |
| CumMe_WSM_SF17322.G5110 | 55 | 60S ribosomal protein L22 (RPL22A) | EXP | 2000 | | |
| CumMe_WSM_SF17349.G5770 | 56 | PGRL1B (PGR5-Like B) | EXP | 2000 | | |
| CumMe_WSM_SF17357.G5630 | 57 | 40S ribosomal protein S10 (RPS10B) | EXP | 2000 | | |
| CumMe_WSM_SF17494.G5140 | 58 | MEE34 (maternal effect embryo arrest 34) | EXP | 1591 | | |
| CumMe_WSM_SF17524.G6410 | 59 | SUS2 (ABNORMAL SUSPENSOR 2) | EXP | 2000 | | |
| CumMe_WSM_SF17672.G5610 | 60 | PSAK (photosystem I subunit K) | EXP | 2000 | | |
| CumMe_WSM_SF17773.G6620 | 61 | aconitase C-terminal domain-containing protein | EXP | 2000 | | |
| CumMe_WSM_SF17866.G6050 | 62 | ATPDIL5-1 (PDI-like 5-1) | EXP | 2000 | | |
| CumMe_WSM_SF18004.G6600 | 63 | hydroxyproline-rich glycoprotein family protein | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF18045.G6670 | 64 | | EXP | 2000 | | |
| CumMe_WSM_SF18053.G5410 | 65 | endomembrane protein 70 | EXP | 2000 | | |
| CumMe_WSM_SF18287.G5380 | 66 | CP12-1 | EXP | 2000 | | |
| CumMe_WSM_SF18488.G5340 | 67 | caffeoyl-CoA 3-O-methyltransferase | EXP | 2000 | Promoter; Leader | 1-1923; 1924-2000 |
| CumMe_WSM_SF18504.G5090 | 68 | vacuolar ATP synthase subunit H family protein | EXP | 2000 | | |
| CumMe_WSM_SF18530.G5750 | 69 | GUN5 (GENOMES UNCOUPLED 5); magnesium chelatase | EXP | 2000 | | |
| CumMe_WSM_SF18536.G6480 | 70 | MBF1A (MULTIPROTEIN BRIDGING FACTOR 1A) transcription coactivator | EXP | 2000 | | |
| CumMe_WSM_SF18575.G6410 | 71 | unknown protein | EXP | 2000 | | |
| CumMe_WSM_SF18634.G5190 | 72 | 60S ribosomal protein L23 (RPL23A) | EXP | 2000 | Promoter; Leader | 1-1971; 1972-2000 |
| CumMe_WSM_SF18645.G5380 | 73 | GS2 (GLUTAMINE SYNTHETASE 2) | EXP | 2000 | | |
| CumMe_WSM_SF18716.G5860 | 74 | 40S ribosomal protein S12 (RPS12A); reverse compliment: Auxin-induced protein x10A-like | EXP | 2000 | Promoter; Leader | Reverse compliment; see SEQ ID NO: 184 |
| CumMe_WSM_SF18801.G5040 | 75 | | EXP | 2000 | | |
| CumMe_WSM_SF18806.G6220 | 76 | unknown protein | EXP | 2000 | | |
| CumMe_WSM_SF18850.G5630 | 77 | PAC1; threonine-type endopeptidase | EXP | 2000 | | |
| CumMe_WSM_SF18863.G7550 | 78 | ATP synthase gamma chain, mitochondrial (ATPC) | EXP | 2000 | | |
| CumMe_WSM_SF18986.G6110 | 79 | GER1 (GERMIN-LIKE PROTEIN 1); oxalate oxidase | EXP | 2000 | | |
| CumMe_WSM_SF19064.G5690 | 80 | histone H3.2 | EXP | 2000 | Promoter; Leader; Intron | 1-1581; 1582-1670; 1671-2000 |
| CumMe_WSM_SF19323.G5120 | 81 | chloroplast outer envelope GTP-binding protein. putative | EXP | 2000 | | |
| CumMe_WSM_SF19452.G5090 | 82 | glucan phosphorylase, putative | EXP | 1072 | | |
| CumMe_WSM_SF19631.G5170 | 83 | RuBisCO activase, putative | EXP | 1730 | | |
| CumMe_WSM_SF19647.G5760 | 84 | 6-phosphogluconate dehydrogenase family protein | EXP | 2000 | Promoter; Leader; Intron; Leader | 1-936; 937-1021; 1022-1992; 1993-2000 |
| CumMe_WSM_SF19839.G5090 | 85 | ATPDX1.1 (pyridoxine biosynthesis 1.1) | EXP | 1020 | Promoter; Leader | 1-928; 929-1020 |
| CumMe_WSM_SF19850.G5130 | 86 | HMGB2 (HIGH MOBILITY GROUP B 2) transcription factor | EXP | 2000 | | |
| CumMe_WSM_SF19902.G5260 | 87 | universal stress protein (USP) family protein/ early nodulin ENOD18 family protein | EXP | 2000 | | |
| CumMe_WSM_SF19992.G6100 | 88 | unknown protein | EXP | 2000 | | |
| CumMe_WSM_SF20132.G5560 | 89 | peroxidase 21 | EXP | 2000 | Promoter; Leader | 1-1962; 1963-2000 |
| CumMe_WSM_SF20147.G7910 | 90 | CSD1 (COPPER/ZINC SUPEROXIDE DISMUTASE 1) | EXP | 2000 | | |
| CumMe_WSM_SF20355.G5130 | 91 | ATP synthase family | EXP | 2000 | | |
| CumMe_WSM_SF20359.G5870 | 92 | NADH-ubiquinone oxidoreductase 20 kDa subunit, mitochondrial | EXP | 2000 | | |
| CumMe_WSM_SF20368.G5700 | 93 | PGR5 (proton gradient regulation 5) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF20409.G5240 | 94 | elongation factor 1B alpha-subunit 1 (eEF1Balpha1) | EXP | 2000 | | |
| CumMe_WSM_SF20431.G6340 | 95 | DHS2 (3-deoxy-d-arabino-heptulosonate 7-phosphate synthase) | EXP | 2000 | | |
| CumMe_WSM_SF20505.G5440 | 96 | THIC (ThiaminC); ADP-ribose pyrophosphohydrolase | EXP | 1373 | | |
| CumMe_WSM_SF20509.G5920 | 97 | Y14; RNA binding/ protein binding | EXP | 2000 | | |
| CumMe_WSM_SF206458.G5970 | 98 | FAD2 (FATTY ACID DESATURASE 2) | EXP | 2000 | Promoter | 1-2000 |
| CumMe_WSM_SF206534.G5200 | 99 | unknown protein | EXP | 2000 | | |
| CumMe_WSM_SF20997.G6990 | 100 | ALD1 (AGD2-LIKE DEFENSE RESPONSE PROTEIN 1) | EXP | 2000 | | |
| CumMe_WSM_SF21035.G5090 | 101 | sodium/calcium exchanger family protein | EXP | 1078 | | |
| CumMe_WSM_SF21117.G5370 | 102 | 30S ribosomal protein, putative | EXP | 2000 | | |
| CumMe_WSM_SF21141.G5630 | 103 | 40S ribosomal protein S24 (RPS24A) | EXP | 2000 | | |
| CumMe_WSM_SF21198.G5180 | 104 | | EXP | 1974 | | |
| CumMe_WSM_SF21366.G5980 | 105 | GRF12 (GENERAL REGULATORY FACTOR 12) | EXP | 2000 | | |
| CumMe_WSM_SF21828.G5150 | 106 | cpHsc70-1 (chloroplast heat shock protein 70-1) | EXP | 1643 | | |
| CumMe_WSM_SF21886.G5080 | 107 | NPQ4 (NONPHOTOCHEMICAL QUENCHING) | EXP | 2000 | | |
| CumMe_WSM_SF22008.G5670 | 108 | NAP1;2 (NUCLEOSOME ASSEMBLY PROTEIN 1;2) | EXP | 2000 | | |
| CumMe_WSM_SF22070.G5280 | 109 | fructose-bisphosphate aldolase, putative | EXP | 2000 | | |
| CumMe_WSM_SF22097.G5540 | 110 | APX3 (ASCORBATE PEROXIDASE 3) | EXP | 2000 | | |
| CumMe_WSM_SF22254.G5760 | 111 | 40S ribosomal protein S7 (RPS7B) | EXP | 2000 | | |
| CumMe_WSM_SF22275.G5780 | 112 | ribosomal protein L17 family protein | EXP | 1027 | | |
| CumMe_WSM_SF22355.G5310 | 113 | | EXP | 2000 | | |
| CumMe_WSM_SF22531.G5120 | 114 | eukaryotic translation initiation factor 1A, putative | EXP | 2000 | Promoter; Leader; Intron; Leader | 1-759; 760-858; 859-1979; 1980-2000 |
| CumMe_WSM_SF22870.G5370 | 115 | ATSARA1A (ARABIDOPSIS THALIANA SECRETION-ASSOCIATED RAS SUPER FAMILY 1) | EXP | 2000 | | |
| CumMe_WSM_SF22934.G5290 | 116 | T-complex protein 1 epsilon subunit, putative | EXP | 2000 | | |
| CumMe_WSM_SF23181.G5100 | 117 | CEV1 (CONSTITUTIVE EXPRESSION OF VSP1) | EXP | 1025 | | |
| CumMe_WSM_SF23186.G6160 | 118 | ubiquinol-cytochrome C reductase complex 14 kDa protein, putative | EXP | 2000 | | |
| CumMe_WSM_SF23397.G5210 | 119 | RPL27 (RIBOSOMAL PROTEIN LARGE SUBUNIT 27) | EXP | 2000 | | |
| CumMe_WSM_SF23760.G5200 | 120 | NDPK1; ATP binding/nucleoside diphosphate kinase | EXP | 2000 | Promoter; Leader | 1-1901; 1902-2000 |
| CumMe_WSM_SF23906.G6180 | 121 | PSBX (photosystem II subunit X) | EXP | 2000 | | |
| CumMe_WSM_SF24040.G5450 | 122 | RPS17 (RIBOSOMAL PROTEIN S17) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF24045.G5400 | 123 | EXL3 (EXORDIUM LIKE 3) | EXP | 2000 | | |
| CumMe_WSM_SF24117.G5600 | 124 | 60S ribosomal protein L26 (RPL26A) | EXP | 2000 | | |
| CumMe_WSM_SF25084.G5580 | 125 | | EXP | 2000 | | |
| CumMe_WSM_SF25141.G5160 | 126 | isocitrate dehydrogenase, putative | EXP | 1397 | Promoter; Leader | 1-1322; 1323-1397 |
| CumMe_WSM_SF25355.G5000 | 127 | LOS1; copper ion binding translation elongation factor | EXP | 2000 | Promoter; Leader; Intron; Leader; CDS | 1-734; 735-811; 812-1340; 1341-1360; 1361-2000 |
| CumMe_WSM_SF25370.G5000 | 128 | PSBP-1 (PHOTOSYSTEM II SUBUNIT P-1) | EXP | 1657 | | |
| CumMe_WSM_SF25455.G5370 | 129 | GLY3 (GLYOXALASE II 3) | EXP | 2000 | | |
| CumMe_WSM_SF25936.G5450 | 130 | mitochondrial substrate carrier family protein | EXP | 2000 | Promoter; Leader | 1-1878; 1879-2000 |
| CumMe_WSM_SF27080.G5510 | 131 | LIP1 (LIPOIC ACID SYNTHASE 1) | EXP | 2000 | | |
| CumMe_WSM_SF27222.G5150 | 132 | DRT112; copper ion binding/electron carrier | EXP | 2000 | | |
| CumMe_WSM_SF27957.G5450 | 133 | SMAP1 (SMALL ACIDIC PROTEIN 1) | EXP | 2000 | | |
| CumMe_WSM_SF28729.G5340 | 134 | RNA-binding protein cp29, putative | EXP | 1696 | | |
| CumMe_WSM_SF28805.G6200 | 135 | unknown protein | EXP | 2000 | | |
| CumMe_WSM_SF31264.G5380 | 136 | ATPH1 (ARABIDOPSIS THALIANA PLECKSTRIN HOMOLOGUE 1) | EXP | 2000 | | |
| CumMe_WSM_SF35856.G5150 | 137 | TIP4; 1 (tonoplast intrinsic protein 4; 1) | EXP | 1575 | | |
| CumMe_WSM_SF40859.G5250 | 138 | SMT2 (STEROL METHYLTRANSFERASE 2) | EXP | 2000 | | |
| CumMe_WSM_SF41124.G5080 | 139 | 40S ribosomal protein S2 (RPS2C) | EXP | 1006 | Promoter; Leader | 1-883; 884-1006 |
| CumMe_WSM_SF41128.G5410 | 140 | CRY2 (CRYPTOCHROME 2) | EXP | 2000 | | |
| CumMe_WSM_SF41254.G5160 | 141 | GDP-D-glucose phosphorylase | EXP | 1556 | | |
| CumMe_WSM_SF41588.G5470 | 142 | PRPL11 (PLASTID RIBOSOMAL PROTEIN L11) | EXP | 2000 | | |
| CumMe_WSM_SF41644.G6400 | 143 | SHD (SHEPHERD) | EXP | 2000 | | |
| CumMe_WSM_SF41983.G5000 | 144 | catalytic/ coenzyme binding | EXP | 1337 | | |
| CumMe_WSM_SF42075.G5100 | 145 | CPN60B (CHAPERONIN 60 BETA) | EXP | 2000 | | |
| CumMe_WSM_SF42141.G5110 | 146 | cathepsin B-like cysteine protease, putative | EXP | 1212 | | |
| CumMe_WSM_SF44933.G5290 | 147 | EBF1 (EIN3-BINDING F BOX PROTEIN 1) ubiquitin-protein ligase | EXP | 2000 | | |
| CumMe_WSM_SF44977.G5000 | 148 | PAP26 (PURPLE ACID PHOSPHATASE 26) | EXP | 1254 | | |
| CumMe_WSM_SF45441.G5510 | 149 | GAPA-2 (GLYCERALDEHYDE 3-PHOSPHATE DEHYDROGENASE A SUBUNIT 2) | EXP | 2000 | | |
| CumMe_WSM_SF45882.G5120 | 150 | fructose-1,6-bisphosphatase, putative | EXP | 1680 | | |
| CumMe_WSM_SF47806.G5070 | 151 | ATP synthase epsilon chain, mitochondrial | EXP | 1524 | | |
| CumMe_WSM_SF53106.G5190 | 152 | CPN60A (CHAPERONIN-60ALPHA) | EXP | 1851 | | |
| CumMe_WSM_SF65588.G5230 | 153 | vacuolar calcium-binding protein-related | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF9060.G5120 | 154 | APE2 (ACCLIMATION OF PHOTOSYNTHESIS TO ENVIRONMENT 2) | EXP | 1288 | | |
| P-CUCme.1-1:1:1rc | 155 | Phosphatase 2A | EXP | 2000 | Promoter; Leader; Intron; Leader | 1-1135; 1136-1249; 1250-1990; 1991-2000 |
| EXP-CUCme.4:1:1 | 156 | Ubiquitin 2 | EXP | 2011 | Promoter; Leader; Intron; Leader | 1-1646; 1647-1704; 1705-2005; 2006-2008 |
| P-CUCme.4-1:1:4 | 157 | Ubiquitin 2 | P;L | 1698 | Promoter; Leader; | |
| I-CUCme.4-1:1:1 | 158 | Ubiquitin 2 | I;L | 313 | Intron; Leader | |
| EXP-CUCme.5:1:1 | 159 | Ubiquitin 3 | EXP | 2010 | Promoter; Leader; Intron; Leader | 1-748; 749-819; 820-2004; 2005-2007 |
| P-CUCme.5-1:1:3 | 160 | Ubiquitin 3 | P;L | 1107 | Promoter; Leader; | |
| I-CUCme.5-1:1:1 | 161 | Ubiquitin 3 | I;L | 903 | Intron; Leader | |
| EXP-CUCme.eEF1a:1:1 | 162 | Elongation Factor 1 alpha | EXP | 1235 | Promoter; Leader; Intron; Leader | 1-617; 618-677; 678-1213; 1214-1235 |
| P-CUCme.eEF1a-1:1:1 | 163 | Elongation Factor 1 alpha | P | 617 | Promoter | |
| L-CUCme.eEF1a-1:1:1 | 164 | Elongation Factor 1 alpha | L | 54 | Leader | |
| I-CUCme.eEF1a-1:1:1 | 165 | Elongation Factor 1 alpha | I | 545 | Intron | |
| L-CUCme.eEF1a-1:1:2 | 166 | Elongation Factor 1 alpha | L | 19 | Leader | |
| P-CUCme.19-1:1:3 | 167 | Chloropyll a/b binding protein | EXP | 2003 | Promoter; Leader | 1-1958; 1959-2003 |
| EXP-CUCme.SAMS2:1:1 | 168 | S-Adenosylmethionine Synthetase | EXP | 2004 | Promoter; Leader; Intron | 1-1067; 1068-1165; 1166-2003 |
| P-CUCme.SAMS2-1:1:1 | 169 | S-Adenosylmethionine Synthetase | P | 1067 | Promoter | |
| L-CUCme.SAMS2-1:1:1 | 170 | S-Adenosylmethionine Synthetase | L | 92 | Leader | |
| I-CUCme.SAMS2-1:1:1 | 171 | S-Adenosylmethionine Synthetase | I | 845 | Intron | |
| EXP-CUCme.29:1:1 | 172 | Ribosomal protein S5a | EXP | 2018 | Promoter; Leader; Intron; Leader | 1-490; 491-571; 572-2012; 2013-2018 |
| P-CUCme.29-1:1:4 | 173 | Ribosomal protein S5a | P;L | 565 | Promoter; Leader; | |
| I-CUCme.29-1:1:1 | 174 | Ribosomal protein S5a | I;L | 1453 | Intron; Leader | |
| P-CUCme.CumMe_WSM_SF16444.G5140-1:1:1 | 175 | histone H4 | EXP | 1999 | Promoter; Leader; Intron | 1-1946; 947-1999 |
| P-CUCme.CumMe_WSM_SF16563.G5560-1:1:1 | 176 | ATARFB1A (ADP-ribosylation factor B1A) | EXP | 2004 | Promoter; Leader; Intron; Leader | 1-1331; 1332-1429; 1430-1992; 1993-2004 |
| P-CUCme.CumMe_WSM_SF17111.G5790-1:1:1 | 177 | ubiquinol-cytochrome C reductase complex ubiquinone-binding protein | EXP | 2005 | Promoter; Leader | 1-1901; 1902-2005 |
| EXP-CumMe.WSM_SF17252.G7330:1:1 | 178 | nascent polypeptide-associated complex (NAC) domain-containing protein | EXP | 1978 | Promoter; Leader; Intron; Leader | 1-1167; 1168-1269; 1270-1972; 1973-1975 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| P-CUCme.WSM_SF17252.G7330-1:1:1 | 179 | nascent polypeptide-associated complex (NAC) domain-containing protein | P;L | 1263 | Promoter; Leader | |
| I-CUCme.WSM_SF17252.G7330-1:1:1 | 180 | nascent polypeptide-associated complex (NAC) domain-containing protein | I;L | 715 | Intron; Leader | |
| P-CUCme.CumMe_WSM_SF18488.G5340-1:1:1 | 181 | caffeoyl-CoA 3-O-methyltransferase | EXP | 2000 | Promoter; Leader | 1-923; 1924-2000 |
| P-CUCme.CumMe_WSM_SF18536.G6480-1:1:1 | 182 | MBF1A (MULTIPROTEIN BRIDGING FACTOR 1A) transcription coactivator | EXP | 2000 | Promoter; Leader; Intron | |
| P-CUCme.CumMe_WSM_SF18634.G5190-1:1:1 | 183 | 60S ribosomal protein L23 (RPL23A) | EXP | 1989 | Promoter; Leader | 1-1960; 1961-1989 |
| P-CUCme.CumMe_WSM_SF18716.G5860-1:1:1 | 184 | Auxin-induced prtoein X10A-like | EXP | 1463 | Promoter; Leader | 1-1392; 1393-1463 |
| EXP-CUCme.WSM_SF19064.G5690:1:1 | 185 | histone H3.2 | EXP | 2006 | Promoter; Leader; Intron; Leader | 1-1581; 1582-1670; 1671-2000; 2001-2003 |
| P-CUCme.WSM_SF19064.G5690-1:1:1 | 186 | histone H3.2 | P;L | 1664 | Promoter; Leader | |
| I-CUCme.WSM_SF19064.G5690-1:1:1 | 187 | histone H3.2 | I;L | 342 | Intron; Leader | |
| P-CUCme.CumMe_WSM_SF19647.G5760-1:1:1 | 188 | 6-phosphogluconate dehydrogenase family protein | EXP | 2003 | Promoter; Leader; Intron; Leader | 1-939; 940-1024; 1025-1995; 1996-2003 |
| P-CUCme.CumMe_WSM_SF19839.G5090-1:1:1 | 189 | ATPDX1.1 (pyridoxine biosynthesis 1.1) | EXP | 1024 | Promoter; Leader | 1-904; 905-1024 |
| P-CUCme.CumMe_WSM_SF20132.G5560-1:1:1 | 190 | peroxidase 21 | EXP | 2001 | Promoter; Leader | 1-1962; 1963-2001 |
| P-CUCme.CumMe_WSM_SF206458.G5970-1:1:1 | 191 | FAD2 (FATTY ACID DESATURASE 2) | EXP | 4175 | Promoter; Leader; Intron; Leader | 1-2171; 2172-2325; 2326-4155; 4156-4175 |
| P-CUCme.CumMe_WSM_SF22531.G5120-1:1:1 | 192 | eukaryotic translation initiation factor 1A, putative | EXP | 1999 | Promoter; Leader; Intron; Leader | 1-759; 760-858; 859-1978; 1979-1999 |
| P-CUCme.CumMe_WSM_SF23760.G5200-1:1:1 | 193 | NDPK1; ATP binding/ nucleoside diphosphate kinase | EXP | 2000 | Promoter; Leader | 1-1901; 1902-2000 |
| P-CUCme.CumMe_WSM_SF23906.G6180-1:1:1 | 194 | PSBX (photosystem II subunit X) | EXP | 2000 | Promoter; Leader | |
| P-CUCme.CumMe_WSM_SF25141.G5160-1:1:2 | 195 | isocitrate dehydrogenase, putative | EXP | 1400 | Promoter; Leader | 1-1325; 1326-1400 |
| P-CUCme.CumMe_WSM_SF25355.G5000-1:1:1 | 196 | LOS1; copper ion binding translation elongation factor | EXP | 2019 | Promoter; Leader; Intron; Leader; CDS | 1-734; 735-811; 812-1340; 1341-1360; 1361-2019 |
| P-CUCme.CumMe_WSM_SF25936.G5450-1:1:1 | 197 | mitochondrial substrate carrier family protein | EXP | 1999 | Promoter; Leader | 1-1877; 1878-1999 |
| P-CUCme.CumMe_WSM_SF35856.G5150-1:1:1 | 198 | TIP4;1 (tonoplast intrinsic protein 4;1) | EXP | 1578 | | |
| P-CUCme.CumMe_WSM_SF41124.G5080-1:1:1 | 199 | 40S ribosomal protein S2 (RPS2C) | EXP | 1023 | Promoter; Leader | 1-945; 946-1023 |
| P-CUCme.20-1:3 | 211 | Chloropyll a/b binding protein | EXP | 1416 | Promoter; Leader | 1-1390; 1391-1446 |
| EXP-CUCme.29:1:2 | 212 | Ribosomal protein S5a | EXP | 2018 | Promoter; Leader; Intron; Leader | 1-490; 491-571; 572-2011; 2013-2018 |

As shown in Table 1, for example, the transcriptional regulatory expression element group (EXP) designated EXP-CUCme.Ubq1:1:1 (SEQ ID NO: 1), with components isolated from C. melo, comprises a 2068 base pair sized (bp) promoter element, P-CUCme.Ubq1-1:1:15 (SEQ ID NO: 2), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:2 (SEQ ID NO: 5), with components isolated from C. melo, comprises a 1459 bp promoter element, P-CUCme.Ubq1-1:1:16 (SEQ ID NO: 6), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:3 (SEQ ID NO: 7), with components isolated from C. melo, comprises a 964 bp promoter element, P-CUCme.Ubq1-1:1:17 (SEQ ID NO: 8), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:4 (SEQ ID NO: 9), with components isolated from C. melo, comprises a 479 bp promoter element, P-CUCme.Ubq1-1:1:18 (SEQ ID NO: 10), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:5 (SEQ ID NO: 11), with components isolated from C. melo, comprises a 173 bp promoter element, P-CUCme.Ubq1-1:1:19 (SEQ ID NO: 12), operably linked 5' to a leader element, L-CUCme.Ubq1-1:1:1 (SEQ ID NO: 3), operably linked 5' to an intron element, I-CUCme.Ubq1-1:1:1 (SEQ TD NO: 4).

Figure 1A:
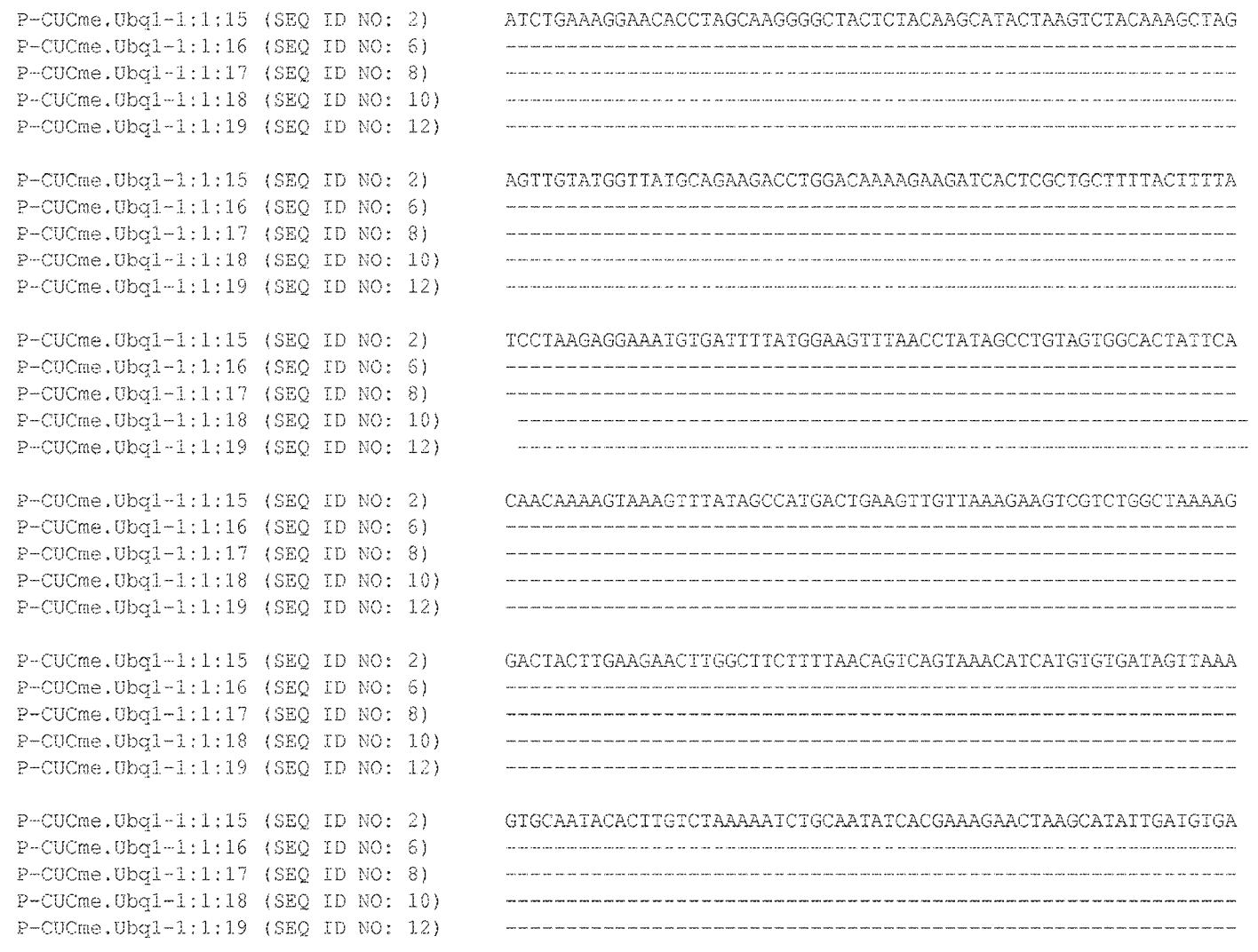
Figure 1B:
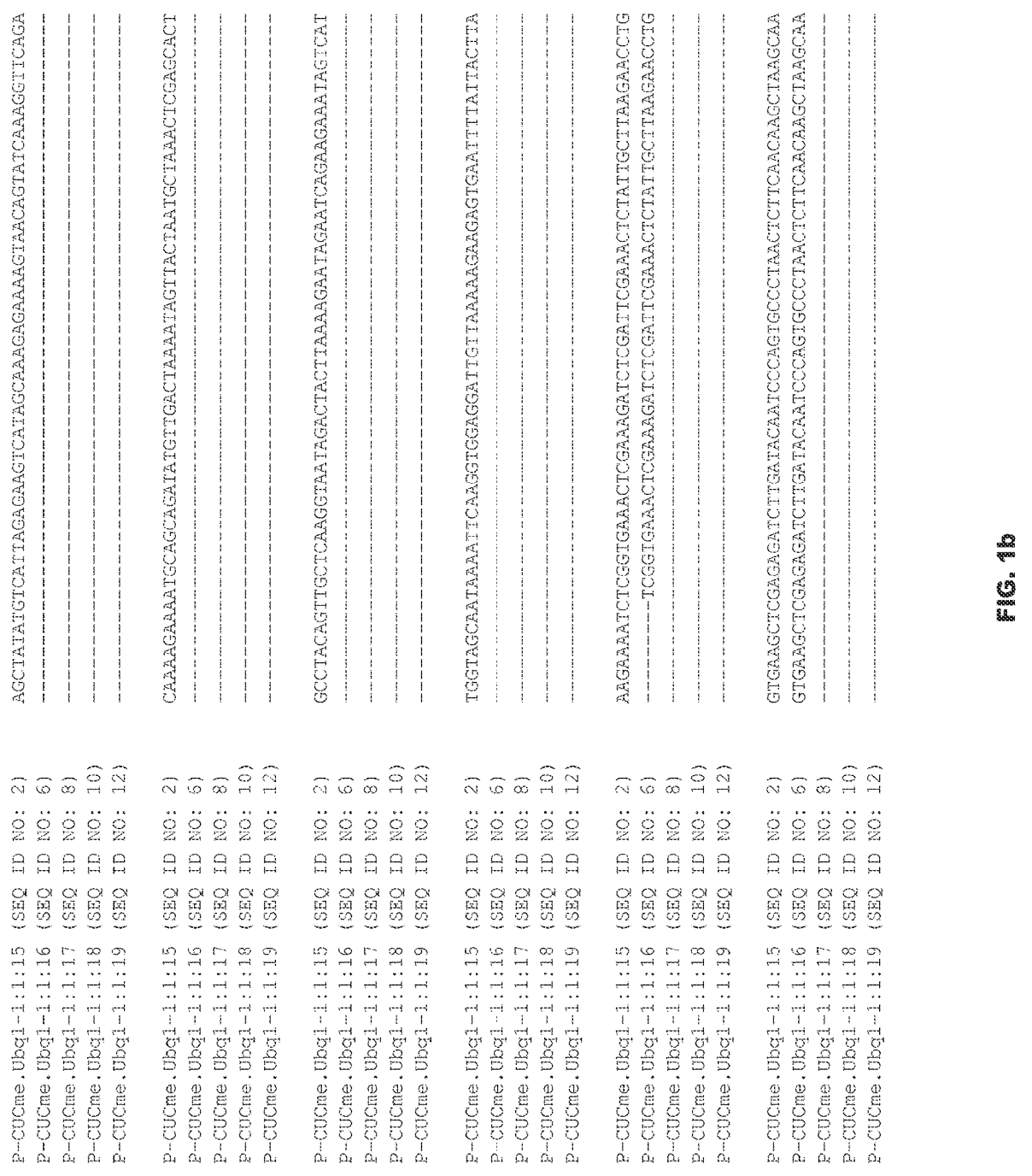
Figure 1C:
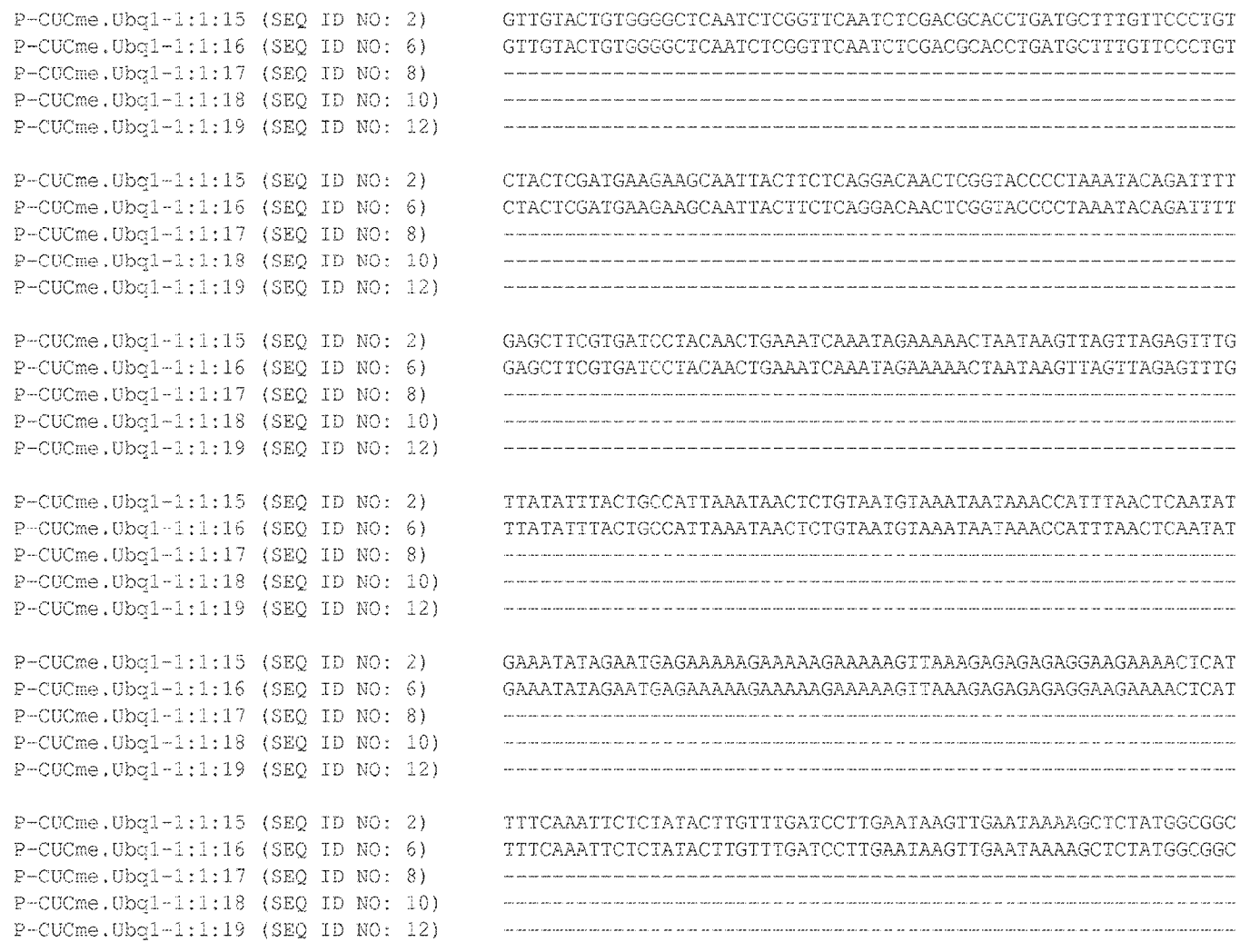

An alignment of the ubiquitin 1 promoter sequences is provided in FIGS. 1a-1f. The promoter elements, P-CUCme.Ubq1-1:1:16 (SEQ ID NO: 6), P-CUCme.Ubq1-1:1:17 (SEQ ID NO: 8), P-CUCme.Ubq1-1:1:18 (SEQ ID NO: 10) and P-CUCme.Ubq1-1:1:19 (SEQ ID NO: 12) were built by introducing varying lengths of deletions from the 5' end of the promoter, P-CUCme.Ubq1-1:1:15 (SEQ ID NO: 2).

Example 2: Analysis of Regulatory Elements Driving GUS in Soy Cotyledon Protoplasts Soybean cotyledon protoplasts were transformed with plant expression vectors containing a test transcriptional regulatory expression element group driving expression of the β-glucuronidase (GUS) transgene and compared to GUS expression in leaf protoplasts in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters. Each plant expression vector was comprised of a right border region from Agrobacterium tumefaciens, a first transgene cassette comprised of an EXP sequence or known constitutive promoter operably linked 5' to a coding sequence for β-glucuronidase (GUS, SEQ ID NO: 206) containing a processable intron derived from the potato light-inducible tissue-specific ST-LS1 gene (Genbank Accession: X04753), operably linked 5' to a 3' termination region from the Gossypium barbadense E6 gene (T-Gb.E6-3b:1:1, SEQ ID NO: 204), the Pisum sativum RbcS2-E9 gene (T-Ps.RbcS2-E9-1:1:6, SEQ ID NO: 203), or the Gossypium barbadense FbLate-2 gene (T-Gb.FbL2-1:1:1, SEQ ID NO: 205); a second transgene selection cassette used for selection of transformed plant cells that either confers resistance to the herbicide glyphosate (driven by the Arabidopsis Actin 7 promoter) or the antibiotic, kanamycin and a left border region from A. tumefaciens. A promoterless control plant expression vector (pMON124912) served as a negative control for expression. The foregoing test and constitutive expression element groups were cloned into plant expression vectors as shown in Table 2 below.

TABLE 2

Plant expression vectors and corresponding expression element group and 3' UTR.

| Expression Vector | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | No promoter | | T-Gb.FbL2-1:1:1 |
| pMON138776 | EXP-CUCme.Ubq1:1:1 | 1 | T-Gb.FbL2-1:1:1 |
| pMON138777 | EXP-CUCme.Ubq1:1:2 | 5 | T-Gb.FbL2-1:1:1 |
| pMON138778 | EXP-CUCme.Ubq1:1:3 | 7 | T-Gb.FbL2-1:1:1 |
| pMON138779 | EXP-CUCme.Ubq1:1:4 | 9 | T-Gb.FbL2-1:1:1 |
| pMON138780 | EXP-CUCme.Ubq1:1:5 | 11 | T-Gb.FbL2-1:1:1 |

Two plasmids, for use in co-transformation and normalization of data, were also constructed. One transformation control plasmid was comprised of a constitutive promoter, driving the expression of the firefly (Photinus pyralis) luciferase coding sequence (FLuc, SEQ ID NO: 207), operably linked 5' to a 3' termination region from the Agrobacterium tumefaciens nopaline synthase gene (T-AGRtu.nos-1:1:13, SEQ ID NO: 209). The other transformation control plasmid was comprised of a constitutive promoter, driving the expression of the sea pansy (Renilla rentfortnis) luciferase coding sequence (RLuc, SEQ ID NO: 208), operably linked 5' to a 3' termination region from the Agrobacterium tumefaciens nopaline synthase gene.

The plant expression vectors, pMON80585, pMON109584, pMON118756, pMON124912, pMON138776, pMON138777, pMON138778, pMON138779 and pMON138780 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, WI; see for example, Promega Notes Magazine, No: 57, 1996, p. 02). Sample measurements were made using 3 or 4 replicates per transformation. The average GUS and luciferase values are presented in Table 3 below.

TABLE 3

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON80585 | EXP-At.Atntt1:1:2 | 200 | 55173 | 6498 | 30503 | 8.49 | 1.81 |
| pMON109584 | EXP-CaMV.35S-enh + Ph.DnaK:1:3 | 200 | 24940 | 5050.75 | 35495 | 4.94 | 0.70 |
| pMON118756 | EXP-At.Act7:1:11 | 201 | 9871 | 6880 | 40850 | 1.43 | 0.24 |
| pMON124912 | No promoter | | 2000 | 11670 | 73187 | 0.17 | 0.03 |
| pMON138776 | EXP-CUCme.Ubq1:1:1 | 1 | 26972 | 6467.25 | 37200 | 4.17 | 0.73 |
| pMON138777 | EXP-CUCme.Ubq1:1:2 | 5 | 41307 | 5902.5 | 24396 | 7.00 | 1.69 |
| pMON138778 | EXP-CUCme.Ubq1:1:3 | 7 | 90140 | 10710.5 | 60983 | 8.42 | 1.48 |
| pMON138779 | EXP-CUCme.Ubq1:1:4 | 9 | 35526 | 5590 | 28001 | 6.36 | 1.27 |
| pMON138780 | EXP-CUCme.Ubq1:1:5 | 11 | 23298 | 4483.25 | 19075 | 5.20 | 1.22 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3.

Table 4 below shows the GUS to firefly luciferase (FLuc) ratios normalized with respect to EXP-At.Act7:1:11 and EXP-CaMV.35S-enh+Ph.DnaK:1:3. Table 5 below shows the GUS to *renilla* luciferase (RLuc) ratios normalized with respect to EXP-At.Act7:1:11 and EXP-CaMV.35S-enh+Ph.DnaK:1:3.

TABLE 4

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON80585 | EXP-At.Atntt1:1:2 | 200 | 5.92 | 1.72 |
| pMON109584 | EXP-CaMV.35S-enh + Ph.DnaK:1:3 | 201 | 3.44 | 1.00 |
| pMON118756 | EXP-At.Act7:1:11 | 202 | 1.00 | 0.29 |
| pMON124912 | No promoter | | 0.12 | 0.03 |
| pMON138776 | EXP-CUCme.Ubq1:1:1 | 1 | 2.91 | 0.84 |
| pMON138777 | EXP-CUCme.Ubq1:1:2 | 5 | 4.88 | 1.42 |
| pMON138778 | EXP-CUCme.Ubq1:1:3 | 7 | 5.87 | 1.70 |
| pMON138779 | EXP-CUCme.Ubq1:1:4 | 9 | 4.43 | 1.29 |
| pMON138780 | EXP-CUCme.Ubq1:1:5 | 11 | 3.62 | 1.05 |

TABLE 5

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON80585 | EXP-At.Atntt1:1:2 | 200 | 7.49 | 2.57 |
| pMON109584 | EXP-CaMV.35S-enh + Ph.DnaK:1:3 | 201 | 2.91 | 1.00 |
| pMON118756 | EXP-At.Act7:1:11 | 202 | 1.00 | 0.34 |
| pMON124912 | No promoter | | 0.11 | 0.04 |
| pMON138776 | EXP-CUCme.Ubq1:1:1 | 1 | 3.00 | 1.03 |
| pMON138777 | EXP-CUCme.Ubq1:1:2 | 5 | 7.01 | 2.41 |
| pMON138778 | EXP-CUCme.Ubq1:1:3 | 7 | 6.12 | 2.10 |
| pMON138779 | EXP-CUCme.Ubq1:1:4 | 9 | 5.25 | 1.81 |
| pMON138780 | EXP-CUCme.Ubq1:1:5 | 11 | 5.05 | 1.74 |

As can be seen in Tables 4 and 5 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in soybean cotyledon protoplasts. Expression levels were greater than that of EXP-At.Act7:1:11 and was 2.9 to 5.8 (FLuc) or 3 to 7 (RLuc) fold higher than EXP-At.Act7:1:11 in this assay. Expression was equivalent or higher than expression observed for EXP-CaMV.35S-enh+Ph.DnaK:1:3. Expression levels were 0.8 to 1.7 (FLuc) or 1 to 2.4 (RLuc) fold higher than expression observed for EXP-CaMV.35S-enh+Ph.DnaK:1:3.

Example 3: Analysis of Regulatory Elements Driving GUS in Bombarded Soybean Leaves and Roots Soybean leaves and roots were transformed with plant expression vectors containing a test transcriptional regulatory expression element group driving expression of the β-glucuronidase (GUS) transgene and compared to GUS expression in roots and leaves in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters in particle bombarded soybean leaves and roots. The plant expression vectors used for transformation of leaves and roots was the same as those presented in Table 2 of Example 2 above.

The plant expression vectors, pMON80585, pMON109584, pMON118756, pMON124912, pMON138776, pMON138777, pMON138778, pMON138779 and pMON138780 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, CA) for bombardment. Macro-carriers were loaded with the DNA-coated gold particles (Catalog #165-2335 Bio-Rad, Hercules CA). A PDS 1000/He biolistic gun was used for transformation (Catalog #165-2257 Bio-Rad, Hercules CA). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of "0", "+" to "++++++" reflecting the level of GUS expression is assigned to each construct (0—no expression, + to ++++++—low to high, respectively).

Expression of the GUS' transgene demonstrated in each tissue is used to infer the relative potential level and specificity of each element's capacity to drive transgene expression in stably transformed corn plants. Average GUS expression ratings are provided in Table 6 below.

TABLE 6

GUS expression ratings for particle bombarded leaf and root.

| Construct | Regulatory Element | SEQ ID NO: | Leaf Expression Rating | Root Expression Rating |
|---|---|---|---|---|
| pMON80585 | EXP-At.Atntt1:1:2 | 200 | ++++ | ++ |
| pMON109584 | EXP-CaMV.35S-enh + Ph.DnaK:1:3 | 201 | +++++ | +++ |
| pMON118756 | EXP-At.Act7:1:11 | 202 | ++++ | ++ |
| pMON124912 | No promoter | | 0 | 0 |
| pMON138776 | EXP-CUCme.Ubq1:1:1 | 1 | ++++ | +++ |
| pMON138777 | EXP-CUCme.Ubq1:1:2 | 5 | +++ | ++ |
| pMON138778 | EXP-CUCme.Ubq1:1:3 | 7 | +++ | ++ |
| pMON138779 | EXP-CUCme.Ubq1:1:4 | 9 | +++ | ++ |
| pMON138780 | EXP-CUCme.Ubq1:1:5 | 11 | ++ | + |

As can be seen in Table 6 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in particle bombarded transformed leaf and root tissues.

Example 4: Analysis of Regulatory Elements Driving GUS in Soy Cotyledon Protoplasts Soybean cotyledon protoplasts were transformed with plant expression vectors containing a test transcriptional regulatory expression element group driving expression of the β-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCine.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens*, a first transgene cassette comprised of a test promoter or known constitutive promoter operably linked 5' to a coding sequence for β-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 7 below.

TABLE 7

Plant expression vectors and corresponding expression element group and 3' UTR.

| Construct | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140822 | EXP-CUCme.5:1:1 | 159 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 207), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 208), operably linked 5' to a 3' termination region from the *Agrobacterium tumefaciens* nopaline synthase gene.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON 140829, pMON140830, pMON140831, pMON140832, pMON140833, pMON140834, pMON140835, pMON140836, pMON140837, pMON140838 and pMON140839 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, WI; see for example, Promega Notes Magazine, No: 57, 1996, p. 02). Sample measurements were made using 3 or 4 replicates per transformation. The average GUS and luciferase values are presented in Table 8 below.

TABLE 8

Average GUS and luciferase expression values and GUS/luciferase ratios.

| Construct | Regulatory Element | SEQ ID NO: | Average GUS | Average FLuc | Average RLuc | GUS/FLuc | GUS/RLuc |
|---|---|---|---|---|---|---|---|
| pMON80585 | EXP-At.Atntt1:1:2 | 200 | 586 | 5220.7 | 8323 | 0.1100 | 0.0700 |
| pMON109584 | EXP-CaMV.35S-enh + Ph.DnaK:1:3 | 201 | 5768 | 4275 | 15098 | 1.3500 | 0.3800 |
| pMON118756 | EXP-At.Act7:1:11 | 202 | 773 | 7722 | 10545 | 0.1000 | 0.0700 |
| pMON124912 | Promoterless | | 48 | 9746.5 | 13905 | 0.0000 | 0.0000 |
| pMON140818 | P-CUCme.1-1:1:1rc | 155 | 194 | 4772 | 6363 | 0.0400 | 0.0300 |
| pMON140819 | P-CUCme.2-1:1:1 | 14 | 171 | 6855 | 10123 | 0.0200 | 0.0200 |
| pMON140820 | P-CUCme.3-1:1:3 | 15 | 37 | 7089.3 | 9593 | 0.0100 | 0.0000 |
| pMON140821 | EXP-CUCme.4:1:1 | 156 | 4211 | 7626.8 | 13935 | 0.5500 | 0.3000 |
| pMON140822 | EXP-CUCme.5:1:1 | 159 | 626 | 15609.3 | 21140 | 0.0400 | 0.0300 |
| pMON140823 | P-CUCme.6-1:1:1 | 18 | 331 | 15178.5 | 22818 | 0.0200 | 0.0100 |
| pMON140824 | P-CUCme.8-1:1:2 | 19 | 238 | 17514.5 | 28429 | 0.0100 | 0.0100 |
| pMON140825 | P-CUCme.9-1:1:2 | 20 | 510 | 13208 | 19567 | 0.0400 | 0.0300 |
| pMON140826 | P-CUCme.10-1:1:1 | 21 | 352 | 14805.3 | 22200 | 0.0200 | 0.0200 |
| pMON140827 | EXP-CUCme.eEF1a:1:1 | 162 | 724 | 9326.8 | 14476 | 0.0800 | 0.0500 |

TABLE 8-continued

Average GUS and luciferase expression values and GUS/luciferase ratios.

| Construct | Regulatory Element | SEQ ID NO: | Average GUS | Average FLuc | Average RLuc | GUS/FLuc | GUS/RLuc |
|---|---|---|---|---|---|---|---|
| pMON140828 | P-CUCme.15-1:1:2 | 23 | 304 | 11798 | 17486 | 0.0300 | 0.0200 |
| pMON140829 | P-CUCme.16a-1:1:2 | 24 | 88 | 5429 | 9596 | 0.0200 | 0.0100 |
| pMON140830 | P-CUCme.17-1:1:2 | 26 | 180 | 10477.8 | 15291 | 0.0200 | 0.0100 |
| pMON140831 | P-CUCme.18-1:1:2 | 27 | 111 | 5059.3 | 6778 | 0.0200 | 0.0200 |
| pMON140832 | P-CUCme.19-1:1:3 | 167 | 121 | 3765 | 6032 | 0.0300 | 0.0200 |
| pMON140833 | P-CUCme.20-1:3 | 211 | 155 | 10458.8 | 14748 | 0.0100 | 0.0100 |
| pMON140834 | P-CUCme.21-1:1:1 | 30 | 582 | 7760 | 11440 | 0.0800 | 0.0500 |
| pMON140835 | P-CUCme.22-1:1:3 | 31 | 400 | 11393.8 | 18654 | 0.0400 | 0.0200 |
| pMON140836 | EXP-CUCme.SAMS2:1:1 | 168 | 568 | 9466.3 | 13962 | 0.0600 | 0.0400 |
| pMON140837 | P-CUCme.26-1:1:2 | 33 | 87 | 6683 | 8494 | 0.0100 | 0.0100 |
| pMON140838 | P-CUCme.28-1:1:2 | 34 | 171 | 19104.8 | 29619 | 0.0100 | 0.0100 |
| pMON140839 | EXP-CUCme.29:1:2 | 212 | 90 | 11247.3 | 15919 | 0.0100 | 0.0057 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 9 below shows the GUS to firefly luciferase (FLuc) ratios normalized with respect to EXP-At.Act7:1:11 and EXP-CaMV.35S-enh+Ph.DnaK:1:3. Table 10 below shows the GUS to renilla luciferase (RLuc) ratios normalized with respect to EXP-At.Act7:1:11 and EXP-CaMV.35S-enh+Ph.DnaK:1:3.

TABLE 9

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON80585 | EXP-At.Atntt1:1:2 | 200 | 1.12 | 0.08 |
| pMON109584 | EXP-CaMV.35S-enh + Ph.DnaK:1:3 | 201 | 13.48 | 1.00 |
| pMON118756 | EXP-At.Act7:1:11 | 202 | 1.00 | 0.07 |
| pMON124912 | Promoterless | | 0.05 | 0.00 |
| pMON140818 | P-CUCme.1-1:1:1rc | 155 | 0.41 | 0.03 |
| pMON140819 | P-CUCme.2-1:1:1 | 14 | 0.25 | 0.02 |
| pMON140820 | P-CUCme.3-1:1:3 | 15 | 0.05 | 0.00 |
| pMON140821 | EXP-CUCme.4:1:1 | 156 | 5.52 | 0.41 |
| pMON140822 | EXP-CUCme.5:1:1 | 159 | 0.40 | 0.03 |
| pMON140823 | P-CUCme.6-1:1:1 | 18 | 0.22 | 0.02 |
| pMON140824 | P-CUCme.8-1:1:2 | 19 | 0.14 | 0.01 |
| pMON140825 | P-CUCme.9-1:1:2 | 20 | 0.39 | 0.03 |
| pMON140826 | P-CUCme.10-1:1:1 | 21 | 0.24 | 0.02 |
| pMON140827 | EXP-CUCme.eEF1a:1:1 | 162 | 0.78 | 0.06 |
| pMON140828 | P-CUCme.15-1:1:2 | 23 | 0.26 | 0.02 |
| pMON140829 | P-CUCme.16a-1:1:2 | 24 | 0.16 | 0.01 |
| pMON140830 | P-CUCme.17-1:1:2 | 26 | 0.17 | 0.01 |
| pMON140831 | P-CUCme.18-1:1:2 | 27 | 0.22 | 0.02 |
| pMON140832 | P-CUCme.19-1:1:3 | 167 | 0.32 | 0.02 |
| pMON140833 | P-CUCme.20-1:3 | 211 | 0.15 | 0.01 |
| pMON140834 | P-CUCme.21-1:1:1 | 30 | 0.75 | 0.06 |
| pMON140835 | P-CUCme.22-1:1:3 | 31 | 0.35 | 0.03 |
| pMON140836 | EXP-CUCme.SAMS2:1:1 | 168 | 0.60 | 0.04 |
| pMON140837 | P-CUCme.26-1:1:2 | 33 | 0.13 | 0.01 |
| pMON140838 | P-CUCme.28-1:1:2 | 34 | 0.09 | 0.01 |
| pMON140839 | EXP-CUCme.29:1:2 | 212 | 0.08 | 0.01 |

TABLE 10

GUS to *renilla* luciferase (RLuc) ratios normalized with respect
to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON80585 | EXP-At.Atntt1:1:2 | 200 | 0.96 | 0.18 |
| pMON109584 | EXP-CaMV.35S-enh + Ph.DnaK:1:3 | 201 | 5.21 | 1.00 |
| pMON118756 | EXP-At.Act7:1:11 | 202 | 1.00 | 0.19 |
| pMON124912 | Promoterless |  | 0.05 | 0.01 |
| pMON140818 | P-CUCme.1-1:1:1rc | 155 | 0.42 | 0.08 |
| pMON140819 | P-CUCme.2-1:1:1 | 14 | 0.23 | 0.04 |
| pMON140820 | P-CUCme.3-1:1:3 | 15 | 0.05 | 0.01 |
| pMON140821 | EXP-CUCme.4:1:1 | 156 | 4.12 | 0.79 |
| pMON140822 | EXP-CUCme.5:1:1 | 159 | 0.40 | 0.08 |
| pMON140823 | P-CUCme.6-1:1:1 | 18 | 0.20 | 0.04 |
| pMON140824 | P-CUCme.8-1:1:2 | 19 | 0.11 | 0.02 |
| pMON140825 | P-CUCme.9-1:1:2 | 20 | 0.36 | 0.07 |
| pMON140826 | P-CUCme.10-1:1:1 | 21 | 0.22 | 0.04 |
| pMON140827 | EXP-CUCme.eEF1a:1:1 | 162 | 0.68 | 0.13 |
| pMON140828 | P-CUCme.15-1:1:2 | 23 | 0.24 | 0.05 |
| pMON140829 | P-CUCme.16a-1:1:2 | 24 | 0.13 | 0.02 |
| pMON140830 | P-CUCme.17-1:1:2 | 26 | 0.16 | 0.03 |
| pMON140831 | P-CUCme.18-1:1:2 | 27 | 0.22 | 0.04 |
| pMON140832 | P-CUCme.19-1:1:3 | 167 | 0.27 | 0.05 |
| pMON140833 | P-CUCme.20-1:3 | 211 | 0.14 | 0.03 |
| pMON140834 | P-CUCme.21-1:1:1 | 30 | 0.69 | 0.13 |
| pMON140835 | P-CUCme.22-1:1:3 | 31 | 0.29 | 0.06 |
| pMON140836 | EXP-CUCme.SAMS2:1:1 | 168 | 0.55 | 0.11 |
| pMON140837 | P-CUCme.26-1:1:2 | 33 | 0.14 | 0.03 |
| pMON140838 | P-CUCme.28-1:1:2 | 34 | 0.08 | 0.02 |
| pMON140839 | EXP-CUCme.29:1:2 | 212 | 0.08 | 0.01 |

As can be seen in Tables 9 and 10, most of the expression element groups tested, demonstrated the ability to drive transgene expression in soybean cotyledon protoplast cells. One expression element group, EXP-CUCme.4:1:1 (SEQ ID NO: 156) demonstrated levels of transgene expression higher than that of EXP-At.Act7:1:11 in this assay.

Example 5: Analysis of Regulatory Elements Driving GUS in Bombarded Soybean Leaves and Roots Soybean leaves and roots were transformed with plant expression vectors containing a test transcriptional regulatory expression element group driving expression of the β-glucuronidase (GUS) transgene and compared to GUS expression in roots and leaves in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups in particle bombarded soybean leaves and roots. The plant expression vectors used for transformation of leaves and roots was the same as those presented in Table 7 of Example 4 above.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, CA) for bombardment. Macro-carriers were loaded with the DNA-coated gold particles (Catalog #165-2335 Bio-Rad, Hercules CA). A PDS 1000/He biolistic gun was used for transformation (Catalog #165-2257 Bio-Rad, Hercules CA). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of "0", "+" to "++++++" reflecting the level of GUS expression is assigned to each construct (0—no expression, + to ++++++—low to high, respectively).

Expression of the GUS transgene demonstrated in each tissue is used to infer the relative potential level and specificity of each element's capacity to drive transgene expression in stably transformed corn plants. Average GUS expression ratings are provided in Table 11 below.

TABLE 11

GUS expression ratings for particle bombarded leaf and root.

| Construct | Regulatory Element | SEQ ID NO: | Leaf Expression | Root Expression |
|---|---|---|---|---|
| pMON80585 | EXP-At.Atntt1:1:2 | 200 | +++ | +++ |
| pMON109584 | EXP-CaMV.35S-enh + Ph.DnaK:1:3 | 201 | +++++ | ++ |
| pMON118756 | EXP-At.Act7:1:11 | 202 | ++++ | +++ |
| pMON124912 | Promoterless | | 0 | 0 |
| pMON140818 | P-CUCme.1-1:1:1rc | 155 | +++ | + |
| pMON140819 | P-CUCme.2-1:1:1 | 14 | ++ | + |
| pMON140820 | P-CUCme.3-1:1:3 | 15 | 0 | 0 |
| pMON140821 | EXP-CUCme.4:1:1 | 156 | ++++++ | +++ |
| pMON140822 | EXP-CUCme.5:1:1 | 159 | ++ | + |
| pMON140823 | P-CUCme.6-1:1:1 | 18 | ++ | + |
| pMON140824 | P-CUCme.8-1:1:2 | 19 | + | + |
| pMON140825 | P-CUCme.9-1:1:2 | 20 | ++ | + |
| pMON140826 | P-CUCme.10-1:1:1 | 21 | +++ | +++ |
| pMON140827 | EXP-CUCme.eEF1a:1:1 | 162 | ++++ | +++ |
| pMON140828 | P-CUCme.15-1:1:2 | 23 | + | + |
| pMON140829 | P-CUCme.16a-1:1:2 | 24 | + | − |
| pMON140830 | P-CUCme.17-1:1:2 | 26 | ++++ | + |
| pMON140831 | P-CUCme.18-1:1:2 | 27 | +++ | + |
| pMON140832 | P-CUCme.19-1:1:3 | 167 | + | + |
| pMON140833 | P-CUCme.20-1:3 | 211 | + | + |
| pMON140834 | P-CUCme.21-1:1:1 | 30 | + | + |
| pMON140835 | P-CUCme.22-1:1:3 | 31 | ++++ | + |
| pMON140836 | EXP-CUCme.SAMS2:1:1 | 168 | +++++ | +++ |
| pMON140837 | P-CUCme.26-1:1:2 | 33 | + | + |
| pMON140838 | P-CUCme.28-1:1:2 | 34 | + | + |
| pMON140839 | EXP-CUCme.29:1:2 | 212 | + | + |

As can be seen in Table 11 above, all but one of the expression element groups demonstrated the ability to drive transgene expression in particle bombarded soybean leaf and root tissue. Two expression element groups, P-CUCme.28-1:1:2 (SEQ ID NO: 34) and EXP-CUCme.4:1:1 (SEQ ID NO: 156) demonstrated similar or higher levels of expression relative to expression driven by EXP-CaMV.35S-enh+Ph.DnaK:1:3 in this assay.

Example 6: Analysis of Regulatory Elements Driving GUS in Soy Cotyledon Protoplast Using Transgene Cassette Amplicons Soybean cotyledon protoplasts were transformed with transgene cassette amplicons containing a transcriptional regulatory expression element group driving expression of the β-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 12 below shows the mean GUS expression values conferred by each transgene amplicon. Table 13 below shows the GUS to firefly luciferase (FLuc) ratios normalized with respect to EXP-At.Atntt1:1:2 and P-CaMV.35S-enh-1:1:102/L-CaMV.35S-1:1:2

TABLE 12

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| No DNA | | | 0.00 | 0.00 | 0.00 |
| pMON124912 | No promoter | | 54.67 | 34905.00 | 0.00 |
| pMON33449 | P-CaMV.35S-enh-1:1:102/L-CaMV.35S-1:1:2 | 210 | 107064.67 | 21757.67 | 4.92 |
| pMON80585 | EXP-At.Atntt1:1:2 | 200 | 4962.33 | 40778.67 | 0.12 |
| 56969 | CumMe_WSM_SF16429.G5670 | 40 | 283.67 | 53452.00 | 0.01 |
| 56877 | P-CUCme.CumMe_WSM_SF16444.G5140-1:1:1 | 175 | 5297.67 | 46576.67 | 0.11 |
| 56749 | P-CUCme.CumMe_WSM_SF16563.G5560-1:1:1 | 176 | 280.67 | 41958.33 | 0.01 |
| 56918 | CumMe_WSM_SF17051.G5470 | 48 | 1088.00 | 36321.00 | 0.03 |
| 56849 | P-CUCme.CumMe_WSM_SF17111.G5790-1:1:1 | 177 | 196.00 | 48128.00 | 0.00 |
| 56754 | P-CUCme.WSM_SF17252.G7330-1:1:1 | 179 | 175.67 | 45427.00 | 0.00 |
| 56892 | CumMe_WSM_SF17349.G5770 | 56 | 34.00 | 38016.00 | 0.00 |
| 56477 | CumMe_WSM_SF17866.G6050 | 62 | 862.00 | 52203.33 | 0.02 |
| 56842 | P-CUCme.CumMe_WSM_SF18488.G5340-1:1:1 | 181 | 2892.67 | 49144.33 | 0.06 |
| 56852 | P-CUCme.CumMe_WSM_SF18536.G6480-1:1:1 | 182 | 3462.67 | 46549.33 | 0.07 |
| 56497 | CumMe_WSM_SF18575.G6410 | 71 | 92.67 | 47628.33 | 0.00 |
| 56847 | P-CUCme.CumMe_WSM_SF18634.G5190-1:1:1 | 183 | 122.33 | 36815.33 | 0.00 |
| 56746 | P-CUCme.CumMe_WSM_SF18716.G5860-1:1:1 | 184 | 14.33 | 62483.33 | 0.00 |
| 56883 | CumMe_WSM_SF18986.G6110 | 79 | 863.33 | 54379.33 | 0.02 |
| 56734 | EXP-CUCme.WSM_SF19064.G5690:1:1 | 185 | 142.00 | 46962.67 | 0.00 |

TABLE 12-continued

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| 56912 | P-CUCme.CumMe_WSM_SF19647.G5760-1:1:1 | 188 | 7659.00 | 46935.67 | 0.16 |
| 56482 | P-CUCme.CumMe_WSM_SF19839.G5090-1:1:1 | 189 | 3279.00 | 37070.67 | 0.09 |
| 56963 | CumMe_WSM_SF19902.G5260 | 87 | 1629.00 | 55649.00 | 0.03 |
| 56747 | P-CUCme.CumMe_WSM_SF20132.G5560-1:1:1 | 190 | 340.33 | 40577.00 | 0.01 |
| 56479 | CumMe_WSM_SF20359.G5870 | 92 | 192.00 | 61341.67 | 0.00 |
| 56744 | CumMe_WSM_SF206458.G5970 | 98 | 154.67 | 33139.33 | 0.00 |
| 56948 | CumMe_WSM_SF206534.G5200 | 99 | 62.00 | 52118.00 | 0.00 |
| 56896 | CumMe_WSM_SF22008.G5670 | 108 | 1585.00 | 53540.00 | 0.03 |
| 56919 | CumMe_WSM_SF22275.G5780 | 112 | 8.33 | 48546.33 | 0.00 |
| 56967 | CumMe_WSM_SF22355.G5310 | 113 | 74.33 | 36202.67 | 0.00 |
| 56837 | P-CUCme.CumMe_WSM_SF22531.G5120-1:1:1 | 192 | 1526.67 | 52799.33 | 0.03 |
| 56940 | CumMe_WSM_SF22870.G5370 | 115 | 14.67 | 53663.33 | 0.00 |
| 56495 | P-CUCme.CumMe_WSM_SF23760.G5200-1:1:1 | 193 | 196.33 | 49870.67 | 0.00 |
| 56868 | P-CUCme.CumMe_WSM_SF23906.G6180-1:1:1 | 194 | 1584.33 | 42532.33 | 0.04 |
| 56998 | CumMe_WSM_SF24045.G5400 | 123 | 80.67 | 47553.00 | 0.00 |
| 56976 | P-CUCme.CumMe_WSM_SF25141.G5160-1:1:2 | 195 | 4506.00 | 57213.00 | 0.08 |
| 56742 | P-CUCme.CumMe_WSM_SF25355.G5000-1:1:1 | 196 | 4.00 | 41114.33 | 0.00 |
| 56915 | P-CUCme.CumMe_WSM_SF25936.G5450-1:1:1 | 197 | 965.33 | 34494.67 | 0.03 |
| 56854 | CumMe_WSM_SF28729.G5340 | 134 | 208.33 | 53956.00 | 0.00 |
| 56936 | CumMe_WSM_SF31264.G5380 | 136 | 292.67 | 42320.67 | 0.01 |
| 56863 | P-CUCme.CumMe_WSM_SF35856.G5150-1:1:1 | 198 | 125.00 | 48705.33 | 0.00 |
| 56751 | P-CUCme.CumMe_WSM_SF41124.G5080-1:1:1 | 199 | 31.33 | 53595.00 | 0.00 |
| 56921 | CumMe_WSM_SF41254.G5160 | 141 | 11.67 | 52643.67 | 0.00 |
| 56884 | CumMe_WSM_SF42141.G5110 | 146 | 48.33 | 40556.67 | 0.00 |

TABLE 13

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| No DNA | | | 0.00 | 0.00 |
| pMON124912 | No promoter | | 0.01 | 0.00 |
| pMON33449 | P-CaMV.35S-enh-1:1:102/L-CaMV.35S-1:1:2 | 210 | 40.44 | 1.00 |
| pMON80585 | EXP-At.Atntt1:1:2 | 200 | 1.00 | 0.02 |
| 56969 | CumMe_WSM_SF16429.G5670 | 40 | 0.04 | 0.00 |
| 56877 | P-CUCme.CumMe_WSM_SF16444.G51140-1:1:1 | 175 | 0.93 | 0.02 |
| 56749 | P-CUCme.CumMe_WSM_SF16563.G5560-1:1:1 | 176 | 0.05 | 0.00 |
| 56918 | CumMe_WSM_SF17051.G5470 | 48 | 0.25 | 0.01 |
| 56849 | P-CUCme.CumMe_WSM_SF17111.G5790-1:1:1 | 177 | 0.03 | 0.00 |
| 56754 | P-CUCme.WSM_SF17252.G7330-1:1:1 | 179 | 0.03 | 0.00 |
| 56892 | CumMe_WSM_SF17349.G5770 | 56 | 0.01 | 0.00 |
| 56477 | CumMe_WSM_SF17866.G6050 | 62 | 0.14 | 0.00 |
| 56842 | P-CUCme.CumMe_WSM_SF18488.G5340-1:1:1 | 181 | 0.48 | 0.01 |
| 56852 | P-CUCme.CumMe_WSM_SF18536.G6480-1:1:1 | 182 | 0.61 | 0.02 |
| 56497 | CumMe_WSM_SF18575.G6410 | 71 | 0.02 | 0.00 |
| 56847 | P-CUCme.CumMe_WSM_SF18634.G5190-1:1:1 | 183 | 0.03 | 0.00 |
| 56746 | P-CUCme.CumMe_WSM_SF18716.G5860-1:1:1 | 184 | 0.00 | 0.00 |
| 56883 | CumMe_WSM_SF18986.G6110 | 79 | 0.13 | 0.00 |
| 56734 | EXP-CUCme.WSM_SF19064.G5690:1:1 | 185 | 0.02 | 0.00 |
| 56912 | P-CUCme.CumMe_WSM_SF19647.G5760-1:1:1 | 188 | 1.34 | 0.03 |
| 56482 | P-CUCme.CumMe_WSM_SF19839.G5090-1:1:1 | 189 | 0.73 | 0.02 |
| 56963 | CumMe_WSM_SF19902.G5260 | 87 | 0.24 | 0.01 |
| 56747 | P-CUCme.CumMe_WSM_SF20132.G5560-1:1:1 | 190 | 0.07 | 0.00 |
| 56479 | CumMe_WSM_SF20359.G5870 | 92 | 0.03 | 0.00 |
| 56744 | CumMe_WSM_SF206458.G5970 | 98 | 0.04 | 0.00 |
| 56948 | CumMe_WSM_SF206534.G5200 | 99 | 0.01 | 0.00 |
| 56896 | CumMe_WSM_SF22008.G5670 | 108 | 0.24 | 0.01 |
| 56919 | CumMe_WSM_SF22275.G5780 | 112 | 0.00 | 0.00 |
| 56967 | CumMe_WSM_SF22355.G5310 | 113 | 0.02 | 0.00 |
| 56837 | P-CUCme.CumMe_WSM_SF22531.G5120-1:1:1 | 192 | 0.24 | 0.01 |
| 56940 | CumMe_WSM_SF22870.G5370 | 115 | 0.00 | 0.00 |
| 56495 | P-CUCme.CumMe_WSM_SF23760.G5200-1:1:1 | 193 | 0.03 | 0.00 |
| 56868 | P-CUCme.CumMe_WSM_SF23906.G6180-1:1:1 | 194 | 0.31 | 0.01 |
| 56998 | CumMe_WSM_SF24045.G5400 | 123 | 0.01 | 0.00 |
| 56976 | P-CUCme.CumMe_WSM_SF25141.G5160-1:1:2 | 195 | 0.65 | 0.02 |

TABLE 13-continued

GUS to firefly luciferase (FLuc) ratios normalized with respect
to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| 56742 | P-CUCme.CumMe_WSM_SF25355.G5000-1:1:1 | 196 | 0.00 | 0.00 |
| 56915 | P-CUCme.CumMe_WSM_SF25936.G5450-1:1:1 | 197 | 0.23 | 0.01 |
| 56854 | CumMe_WSM_SF28729.G5340 | 134 | 0.03 | 0.00 |
| 56936 | CumMe_WSM_SF31264.G5380 | 136 | 0.06 | 0.00 |
| 56863 | P-CUCme.CumMe_WSM_SF35856.G5150-1:1:1 | 198 | 0.02 | 0.00 |
| 56751 | P-CUCme.CumMe_WSM_SF41124.G5080-1:1:1 | 199 | 0.00 | 0.00 |
| 56921 | CumMe_WSM_SF41254.G5160 | 141 | 0.00 | 0.00 |
| 56884 | CumMe_WSM_SF42141.G5110 | 146 | 0.01 | 0.00 |

As can be seen in Table 12 above, not all EXP sequences demonstrated the ability to drive transgene expression when compared to the promoterless control. However, the EXP sequences, CumMe_WSM_SF16429.G5670 (SEQ ID NO: 40), P-CUCme.CumMe_WSM_SF16444.G5140-1:1:1 (SEQ ID NO: 175), P-CUCme.CumMe_WSM_SF16563.G5560-1:1:1 (SEQ ID NO: 176), CumMe_WSM_SF17051.G5470 (SEQ ID NO: 48), P-CUCme.CumMe_WSM_SF17111.65790-1:1:1 (SEQ ID NO: 177), P-CUCme.WSM_SF17252.G7330-1:1:1 (SEQ ID NO: 179), CumMe_WSM_SF17866.G6050 (SEQ ID NO: 62), P-CUCme.CumMe_WSM_SF18488.G5340-1:1:1 (SEQ ID NO: 181), P-CUCme.CumMe_WSM_SF18536.G6480-1:1:1 (SEQ ID NO: 182), CumMe_WSM_SF18575.G6410 (SEQ ID NO: 71), P-CUCme.CumMe_WSM_SF18634.G5190-1:1:1 (SEQ ID NO: 183), CumMe_WSM_SF18986.G6110 (SEQ ID NO: 79), EXP-CUCme.WSM_SF19064.G5690:1:1 (SEQ ID NO: 185), P-CUCme.CumMe_WSM_SF19647.G5760-1:1:1 (SEQ ID NO: 188), P-CUCme.CumMe_WSM_SF19839.G5090-1:1:1 (SEQ ID NO: 189), CumMe_WSM_SF19902.G5260 (SEQ ID NO: 87), P-CUCme.CumMe_WSM_SF20132.G5560-1:1:1 (SEQ ID NO: 190), CumMe_WSM_SF20359.G5870 (SEQ ID NO: 92), CumMe_WSM_SF206458.G5970 (SEQ ID NO: 98), CumMe_WSM_SF206534.G5200 (SEQ ID NO: 99), CumMe_WSM_SF22008.G5670 (SEQ ID NO: 108), CumMe_WSM_SF22355.G5310 (SEQ ID NO: 113), P-CUCme.CumMe_WSM_SF22531.G5120-1:1:1 (SEQ ID NO: 192), EXP-CUCme.WSM_SF19064.G5690:1:1 (SEQ ID NO: 193), P-CUCme.CumMe_WSM_SF23906.G6180-1:1:1 (SEQ ID NO: 194), CumMe_WSM_SF24045.G5400 (SEQ ID NO: 123), P-CUCme.CumMe_WSM_SF25141.G5160-1:1:2 (SEQ ID NO: 195), P-CUCme.CumMe_WSM_SF25936.G5450-1:1:1 (SEQ ID NO: 197), CumMe_WSM_SF28729.G5340 (SEQ ID NO: 134), CumMe_WSM_SF31264.G5380 (SEQ ID NO: 136) and P-CUCme.CumMe_WSM_SF35856.G5150-1:1:1 (SEQ ID NO: 198) demonstrated the ability to drive trangene expression in soybean cotyledon protoplasts at a level similar or greater than EXP-At.Atntt1:1:2. As shown in Table 13 above, the EXP sequence P-CUCme.CumMe_WSM_SF19647.G5760-1:1:1 (SEQ ID NO: 188) demonstrated the ability to drive transgene expression in this assay at a level greater than EXP-At.Atntt1:1:2.

Example 7: Analysis of Regulatory Elements Driving GUS in Cotton Leaf Protoplasts Cotton leaf protoplasts were transformed with plant expression vectors containing a test transcriptional regulatory expression element group driving expression of the β-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens*, a first transgene cassette comprised of a test promoter or known constitutive promoter operably linked 5' to a coding sequence for β-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 14 below.

TABLE 14

Plant expression vectors and corresponding expression element group and 3' UTR.

| Construct | Regulatory Element | SEQ ID NO: | 3' UTR |
|---|---|---|---|
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless |  | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 206), operably linked 5' to a 3' termination region from the *Agrobacterium lumefaciens* nopaline synthase gene.

The plant expression vectors, pMON80585, pMON109584, pMON118756, pMON124912, pMON140818, pMON140819, pMON140820, pMON140821, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform cotton leaf protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, WI; see for example, Promega Notes Magazine, No: 57, 1996, p. 02). Sample measurements were made using 4 replicates per transformation. The average GUS and luciferase values are presented in Table 15 below.

TABLE 15

Average GUS and luciferase expression values and GUS/luciferase ratios.

| Construct | Regulatory Element | SEQ ID NO: | Average GUS | Average FLuc | Average RLuc | GUS/FLuc | GUS/RLuc |
|---|---|---|---|---|---|---|---|
| pMON109584 | EXP-CaMV.35S-enh + Ph.DnaK:1:3 | 201 | 5322.8 | 14842.8 | 27990.5 | 0.3586 | 0.1902 |
| pMON118756 | EXP-At.Act7:1:11 | 202 | 1006.3 | 19746.8 | 25582.3 | 0.0510 | 0.0393 |
| pMON124912 | Promoterless |  | 21 | 19248.5 | 25012 | 0.0011 | 0.0008 |
| pMON140818 | P-CUCme.1-1:1:1rc | 155 | 170.3 | 17796.8 | 22026.3 | 0.0096 | 0.0077 |
| pMON140819 | P-CUCme.2-1:1:1 | 14 | 34.8 | 16326.3 | 21407.5 | 0.0021 | 0.0016 |
| pMON140820 | P-CUCme.3-1:1:3 | 15 | 51.5 | 17356.8 | 21523.8 | 0.0030 | 0.0024 |
| pMON140821 | EXP-CUCme.4:1:1 | 156 | 3497.8 | 18745.3 | 26065.3 | 0.1866 | 0.1342 |
| pMON140823 | P-CUCme.6-1:1:1 | 18 | 40.8 | 19533.8 | 26361.5 | 0.0021 | 0.0015 |
| pMON140824 | P-CUCme.8-1:1:2 | 19 | 22 | 19701 | 26278 | 0.0011 | 0.0008 |
| pMON140825 | P-CUCme.9-1:1:2 | 20 | 372.5 | 21972.3 | 28755 | 0.0170 | 0.0130 |
| pMON140826 | P-CUCme.10-1:1:1 | 21 | 198 | 21362.8 | 28902 | 0.0093 | 0.0069 |
| pMON140827 | EXP-CUCme.eEF1a:1:1 | 162 | 725 | 21589 | 27635.3 | 0.0336 | 0.0262 |
| pMON140828 | P-CUCme.15-1:1:2 | 23 | 55.3 | 17706 | 28846 | 0.0031 | 0.0019 |
| pMON140829 | P-CUCme.16a-1:1:2 | 24 | 14 | 23289.5 | 30190 | 0.0006 | 0.0005 |
| pMON140830 | P-CUCme.17-1:1:2 | 26 | 155.5 | 23178.3 | 31602.8 | 0.0067 | 0.0049 |
| pMON140831 | P-CUCme.18-1:1:2 | 27 | 86.8 | 19085.8 | 22396.5 | 0.0045 | 0.0039 |
| pMON140832 | P-CUCme.19-1:1:3 | 167 | 130 | 21520.3 | 27270.5 | 0.0060 | 0.0048 |
| pMON140833 | P-CUCme.20-1:3 | 211 | 88.5 | 22223.8 | 30786 | 0.0040 | 0.0029 |
| pMON140834 | P-CUCme.21-1:1:1 | 30 | 98.5 | 18579 | 20506.3 | 0.0053 | 0.0048 |
| pMON140835 | P-CUCme.22-1:1:3 | 31 | 363 | 21780.3 | 28816.3 | 0.0167 | 0.0126 |
| pMON140836 | EXP-CUCme.SAMS2:1:1 | 168 | 515 | 17906 | 23031 | 0.0288 | 0.0224 |
| pMON140837 | P-CUCme.26-1:1:2 | 33 | 125 | 15529.3 | 15169.3 | 0.0080 | 0.0082 |
| pMON140838 | P-CUCme.28-1:1:2 | 34 | 115.8 | 17013.5 | 22236.5 | 0.0068 | 0.0052 |
| pMON140839 | EXP-CUCme.29:1:2 | 212 | 15.5 | 16370.3 | 20409 | 0.0009 | 0.0008 |

To compare the relative activity of each promoter in cotton leaf protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 16 below shows the GUS to firefly luciferase (FLuc) ratios normalized with respect to EXP-At.Act7:1:11 and EXP-CaMV.35S-enh+Ph.DnaK:1:3. Table 17 below shows the GUS to *renilla* luciferase (RLuc) ratios normalized with respect to EXP-At.Act7:1:11 and EXP-CaMV.35S-enh+Ph.DnaK:1:3.

TABLE 16

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
| --- | --- | --- | --- | --- |
| pMON109584 | EXP-CaMV.35S-enh + Ph.DnaK:1:3 | 201 | 7.037 | 1.000 |
| pMON118756 | EXP-At.Act7:1:11 | 202 | 1.000 | 0.142 |
| pMON124912 | Promoterless |  | 0.021 | 0.003 |
| pMON140818 | P-CUCme.1-1:1:1rc | 155 | 0.188 | 0.027 |
| pMON140819 | P-CUCme.2-1:1:1 | 14 | 0.042 | 0.006 |
| pMON140820 | P-CUCme.3-1:1:3 | 15 | 0.058 | 0.008 |
| pMON140821 | EXP-CUCme.4:1:1 | 156 | 3.662 | 0.520 |
| pMON140823 | P-CUCme.6-1:1:1 | 18 | 0.041 | 0.006 |
| pMON140824 | P-CUCme.8-1:1:2 | 19 | 0.022 | 0.003 |
| pMON140825 | P-CUCme.9-1:1:2 | 20 | 0.333 | 0.047 |
| pMON140826 | P-CUCme.10-1:1:1 | 21 | 0.182 | 0.026 |
| pMON140827 | EXP-CUCme.eEF1a:1:1 | 162 | 0.659 | 0.094 |
| pMON140828 | P-CUCme.15-1:1:2 | 23 | 0.061 | 0.009 |
| pMON140829 | P-CUCme.16a-1:1:2 | 24 | 0.012 | 0.002 |
| pMON140830 | P-CUCme.17-1:1:2 | 26 | 0.132 | 0.019 |
| pMON140831 | P-CUCme.18-1:1:2 | 27 | 0.089 | 0.013 |
| pMON140832 | P-CUCme.19-1:1:3 | 167 | 0.119 | 0.017 |
| pMON140833 | P-CUCme.20-1:3 | 211 | 0.078 | 0.011 |
| pMON140834 | P-CUCme.21-1:1:1 | 30 | 0.104 | 0.015 |
| pMON140835 | P-CUCme.22-1:1:3 | 31 | 0.327 | 0.046 |
| pMON140836 | EXP-CUCme.SAMS2:1:1 | 168 | 0.564 | 0.080 |
| pMON140837 | P-CUCme.26-1:1:2 | 33 | 0.158 | 0.022 |
| pMON140838 | P-CUCme.28-1:1:2 | 34 | 0.134 | 0.019 |
| pMON140839 | EXP-CUCme.29:1:2 | 212 | 0.019 | 0.003 |

TABLE 17

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
| --- | --- | --- | --- | --- |
| pMON109584 | EXP-CaMV.35S-enh + Ph.DnaK:1:3 | 201 | 4.83 | 1.00 |
| pMON118756 | EXP-At.Act7:1:11 | 202 | 1.00 | 0.21 |
| pMON124912 | Promoterless |  | 0.02 | 0.00 |
| pMON140818 | P-CUCme.1-1:1:1rc | 155 | 0.20 | 0.04 |
| pMON140819 | P-CUCme.2-1:1:1 | 14 | 0.04 | 0.01 |
| pMON140820 | P-CUCme.3-1:1:3 | 15 | 0.06 | 0.01 |
| pMON140821 | EXP-CUCme.4:1:1 | 156 | 3.41 | 0.71 |
| pMON140823 | P-CUCme.6-1:1:1 | 18 | 0.04 | 0.01 |
| pMON140824 | P-CUCme.8-1:1:2 | 19 | 0.02 | 0.00 |
| pMON140825 | P-CUCme.9-1:1:2 | 20 | 0.33 | 0.07 |
| pMON140826 | P-CUCme.10-1:1:1 | 21 | 0.17 | 0.04 |
| pMON140827 | EXP-CUCme.eEF1a:1:1 | 162 | 0.67 | 0.14 |
| pMON140828 | P-CUCme.15-1:1:2 | 23 | 0.05 | 0.01 |
| pMON140829 | P-CUCme.16a-1:1:2 | 24 | 0.01 | 0.00 |
| pMON140830 | P-CUCme.17-1:1:2 | 26 | 0.13 | 0.03 |
| pMON140831 | P-CUCme.18-1:1:2 | 27 | 0.10 | 0.02 |
| pMON140832 | P-CUCme.19-1:1:3 | 167 | 0.12 | 0.03 |
| pMON140833 | P-CUCme.20-1:3 | 211 | 0.07 | 0.02 |
| pMON140834 | P-CUCme.21-1:1:1 | 30 | 0.12 | 0.03 |

TABLE 17-continued

GUS to *renilla* luciferase (RLuc) ratios normalized with respect
to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON140835 | P-CUCme.22-1:1:3 | 31 | 0.32 | 0.07 |
| pMON140836 | EXP-CUCme.SAMS2:1:1 | 168 | 0.57 | 0.12 |
| pMON140837 | P-CUCme.26-1:1:2 | 33 | 0.21 | 0.04 |
| pMON140838 | P-CUCme.28-1:1:2 | 34 | 0.13 | 0.03 |
| pMON140839 | EXP-CUCme.29:1:2 | 212 | 0.02 | 0.00 |

As can be seen in Tables 16 and 17, most of the expression element groups tested, demonstrated the ability to drive transgene expression in cotton leaf protoplast cells. One expression element group, EXP-CUCme.4:1:1 (SEQ ID NO: 156) demonstrated levels of transgene expression higher than that of EXP-At.Act7:1:11 in this assay.

Example 8: Analysis of Regulatory Elements Driving GUS in Cotton Leaf Protoplasts Using Transgene Cassette Amplicons Cotton leaf protoplasts were transformed with transgene cassette amplicons containing a transcriptional regulatory expression element group driving expression of the β-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 18 below shows the mean GUS expression values conferred by each transgene amplicon. Table 19 below shows the GUS to firefly luciferase (FLuc) ratios normalized with respect to EXP-At.Atntt1:1:2 and P-CaMV.35S-enh-1:1:102/L-CaMV.35S-1:1:2.

TABLE 18

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| Empty Vector | No DNA | | 32.8 | 14087.5 | 0.002 |
| pMON124912 | No promoter | | 12 | 20486.3 | 0.001 |
| pMON80585 | EXP-At.Atntt1:1:2 | 200 | 55.5 | 18811 | 0.003 |
| pMON33449 | P-CaMV.35S-enh-1:1:102/L-CaMV.35S-1:1:2 | 210 | 12472.5 | 19126.3 | 0.652 |
| 56741 | CumMe_WSM_SF143981.G5150 | 36 | 5.8 | 17449.5 | 0.000 |
| 56492 | CumMe_WSM_SF144839.G5080 | 37 | 27.5 | 16674 | 0.002 |
| 56877 | P-CUCme.CumMe_WSM_SF16444.G5140-1:1:1 | 175 | 96.3 | 17237.8 | 0.006 |
| 56485 | CumMe_WSM_SF16530.G6000 | 42 | 27.3 | 17858.5 | 0.002 |
| 56844 | CumMe_WSM_SF16953.G5180 | 47 | 22.3 | 19398.5 | 0.001 |
| 56500 | CumMe_WSM_SF17250.G5910 | 52 | 12.3 | 23980.3 | 0.001 |
| 56754 | P-CUCme.WSM_SF17252.G7330-1:1:1 | 179 | 16 | 13848.8 | 0.001 |
| 56740 | CumMe_WSM_SF17672.G5610 | 60 | 12 | 16646.8 | 0.001 |
| 56870 | CumMe_WSM_SF18287.G5380 | 66 | 39.3 | 13930.5 | 0.003 |
| 56478 | CumMe_WSM_SF18504.G5090 | 68 | 11.8 | 15830.5 | 0.001 |
| 56481 | CumMe_WSM_SF18530.G5750 | 69 | 6.5 | 15211.3 | 0.000 |
| 56498 | CumMe_WSM_SF18645.G5380 | 73 | 36 | 14569.8 | 0.002 |
| 56746 | P-CUCme.CumMe_WSM_SF18716.G5860-1:1:1 | 184 | 11 | 18054.5 | 0.001 |
| 56490 | CumMe_WSM_SF18801.G5040 | 75 | 21.5 | 14147.3 | 0.002 |
| 56488 | CumMe_WSM_SF19323.G5120 | 81 | 15.3 | 11985.3 | 0.001 |
| 56499 | CumMe_WSM_SF19631.G5170 | 83 | 12.5 | 20140.5 | 0.001 |
| 56482 | P-CUCme.CumMe_WSM_SF19839.G5090-1:1:1 | 189 | 75 | 18690.5 | 0.004 |
| 56489 | CumMe_WSM_SF19850.G5130 | 86 | 38.3 | 19756.5 | 0.002 |
| 56476 | CumMe_WSM_SF20355.G5130 | 91 | 10.5 | 27901.8 | 0.000 |
| 56895 | CumMe_WSM_SF20431.G6340 | 95 | 34.8 | 16283.8 | 0.002 |

TABLE 18-continued

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| 56744 | CumMe_WSM_SF206458.G5970 | 98 | 11 | 19659 | 0.001 |
| 56480 | CumMe_WSM_SF21366.G5980 | 105 | 10.8 | 17367 | 0.001 |
| 56930 | CumMe_WSM_SF22070.G5280 | 109 | 25.3 | 14210.5 | 0.002 |
| 56484 | CumMe_WSM_SF23181.G5100 | 117 | 20.3 | 13506 | 0.002 |
| 56495 | P-CUCme.CumMe_WSM_SF23760.G5200-1:1:1 | 193 | 7.8 | 15138.5 | 0.001 |
| 56971 | CumMe_WSM_SF25084.G5580 | 125 | 16 | 16135.3 | 0.001 |
| 56742 | P-CUCme.CumMe_WSM_SF25355.G5000-1:1:1 | 196 | 18 | 13782.8 | 0.001 |
| 56494 | CumMe_WSM_SF25455.G5370 | 129 | 10.5 | 16089.8 | 0.001 |
| 56751 | P-CUCme.CumMe_WSM_SF41124.G5080-1:1:1 | 199 | 24.3 | 17884.3 | 0.001 |
| 56483 | CumMe_WSM_SF41644.G6400 | 143 | 14.5 | 13130.5 | 0.001 |
| 56904 | CumMe_WSM_SF44933.G5290 | 147 | 33 | 13369 | 0.002 |
| 56743 | CumMe_WSM_SF9060.G5120 | 154 | 11.3 | 15230.8 | 0.001 |

TABLE 19

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| Empty Vector | No DNA | | | |
| pMON124912 | No promoter | | | |
| pMON80585 | EXP-At.Atntt1:1:2 | 200 | 1.000 | 0.005 |
| pMON33449 | P-CaMV.35S-enh-1:1:102/L-CaMV.35S-1:1:2 | 210 | 221.025 | 1.000 |
| 56741 | CumMe_WSM_SF143981.G5150 | 36 | 0.113 | 0.001 |
| 56492 | CumMe_WSM_SF144839.G5080 | 37 | 0.559 | 0.003 |
| 56877 | P-CUCme.CumMe_WSM_SF16444.G5140-1:1:1 | 175 | 1.893 | 0.009 |
| 56485 | CumMe_WSM_SF16530.G6000 | 42 | 0.518 | 0.002 |
| 56844 | CumMe_WSM_SF16953.G5180 | 47 | 0.390 | 0.002 |
| 56500 | CumMe_WSM_SF17250.G5910 | 52 | 0.174 | 0.001 |
| 56754 | P-CUCme.WSM_SF17252.G7330-1:1:1 | 179 | 0.392 | 0.002 |
| 56740 | CumMe_WSM_SF17672.G5610 | 60 | 0.244 | 0.001 |
| 56870 | CumMe_WSM_SF18287.G5380 | 66 | 0.956 | 0.004 |
| 56478 | CumMe_WSM_SF18504.G5090 | 68 | 0.253 | 0.001 |
| 56481 | CumMe_WSM_SF18530.G5750 | 69 | 0.145 | 0.001 |
| 56498 | CumMe_WSM_SF18645.G5380 | 73 | 0.837 | 0.004 |
| 56746 | P-CUCme.CumMe_WSM_SF18716.G5860-1:1:1 | 184 | 0.207 | 0.001 |
| 56490 | CumMe_WSM_SF18801.G5040 | 75 | 0.515 | 0.002 |
| 56488 | CumMe_WSM_SF19323.G5120 | 81 | 0.433 | 0.002 |
| 56499 | CumMe_WSM_SF19631.G5170 | 83 | 0.210 | 0.001 |
| 56482 | P-CUCme.CumMe_WSM_SF19839.G5090-1:1:1 | 189 | 1.360 | 0.006 |
| 56489 | CumMe_WSM_SF19850.G5130 | 86 | 0.657 | 0.003 |
| 56476 | CumMe_WSM_SF20355.G5130 | 91 | 0.128 | 0.001 |
| 56895 | CumMe_WSM_SF20431.G6340 | 95 | 0.724 | 0.003 |
| 56744 | CumMe_WSM_SF206458.G5970 | 98 | 0.190 | 0.001 |
| 56480 | CumMe_WSM_SF21366.G5980 | 105 | 0.211 | 0.001 |
| 56930 | CumMe_WSM_SF22070.G5280 | 109 | 0.603 | 0.003 |
| 56484 | CumMe_WSM_SF23181.G5100 | 117 | 0.509 | 0.002 |
| 56495 | P-CUCme.CumMe_WSM_SF23760.G5200-1:1:1 | 193 | 0.175 | 0.001 |
| 56971 | CumMe_WSM_SF25084.G5580 | 125 | 0.336 | 0.002 |
| 56742 | P-CUCme.CumMe_WSM_SF25355.G5000-1:1:1 | 196 | 0.443 | 0.002 |

TABLE 19-continued

GUS to firefly luciferase (FLuc) ratios normalized with respect
to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| 56494 | CumMe_WSM_SF25455.G5370 | 129 | 0.221 | 0.001 |
| 56751 | P-CUCme.CumMe_WSM_SF41124.G5080-1:1:1 | 199 | 0.461 | 0.002 |
| 56483 | CumMe_WSM_SF41644.G6400 | 143 | 0.374 | 0.002 |
| 56904 | CumMe_WSM_SF44933.G5290 | 147 | 0.837 | 0.004 |
| 56743 | CumMe_WSM_SF9060.G5120 | 154 | 0.251 | 0.001 |

As can be seen in Table 18 above, not all EXP sequences demonstrated the ability to drive transgene expression when compared to the promoterless control. However, the EXP sequences, P-CUCme.CumMe_WSM_SF16444.G5140-1:1:1 (SEQ ID NO: 175) and P-CUCme.CumMe_WSM_SF19839.G5090-1:1:1 (SEQ ID NO: 189) demonstrated the ability to drive trangene expression in soybean cotyledon protoplasts at a level similar or greater than EXP-At.Atntt1:1:2. As shown in Table 19 above, the EXP sequence, P-CUCme.CumMe_WSM_SF19839.G5090-1:1:1 (SEQ ID NO: 189) demonstrated the ability to drive transgene expression in this assay at a level greater than EXP-At.Atntt1:1:2.

Example 9: Analysis of Regulatory Elements Driving GUS in Stably Transformed Soybean Soybean plants were transformed with plant expression vectors containing an EXP sequence driving expression of the β-glucuronidase (GUS) transgene.

Expression of the GUS transgene driven by EXP-CUCme.Ubq1:1:1 (SEQ ID NO: 1), EXP-CUCme.Ubq1:1:3 (SEQ ID NO: 7), P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) assayed both qualitatively through inspection of stained tissue sections and quantitatively. Each plant expression vector was comprised of a right border region from *Agrobacterium tumefaciens*, a first transgene cassette comprised of an EXP sequence operably linked 5' to a coding sequence for β-glucuronidase (GUS, SEQ ID NO: 206) containing a processable intron derived from the potato light-inducible tissue-specific ST-LS1 gene (Genbank Accession: X04753), operably linked 5' to a 3' termination region from the the *Gossypium barbadense* FbLate-2 gene (T-Gb.FbL2-1:1:1, SEQ ID NO: 205); a second transgene selection cassette used for selection of transformed plant cells that confered resistance to the herbicide glyphosate (driven by the *Arabidopsis Actin* 7 promoter) and a left border region from *A. tumefaciens*.

The foregoing EXP sequences were cloned into plant expression constructs as shown in Tables 20 through 23 below and used to transform soybean plants using an *Agrobacterium* mediated transformation method. Expression of GUS was assayed qualitatively using histological sections of selected tissues and quantitatively.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ generation plants were inspected for expression in Vn5 Root, R1 Root, Vn5 Sink Leaf, Vn5 Source Leaf, R1 Source Leaf, R1 Petiole, Yellow Pod Embryo, Yellow Pod Cotyledon, R3 Immature Seed, R3 Pod, R5 Cotyledon and R1 Flower.

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 microliters. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

Tables 20 and 21 below show the mean quantitative expression levels measured in the $R_0$ generation plant tissues. Those tissued not assayed are shown as blank cells in both tables.

TABLE 20

Mean GUS expression in Vn5 Root, R1 Root, Vn5 Sink Leaf, Vn5 Source Leaf, R1 Source Leaf and R1 Petiole of $R_0$ generation transformed soybean plants

| Construct | Regulatory Element | SEQ ID NO: | Vn5_Root | R1_Root | Vn5_Sink_Leaf | Vn5_Source_Leaf | R1_Source_Leaf | R1_Petiole |
|---|---|---|---|---|---|---|---|---|
| pMON138776 | EXP-CUCme.Ubq1:1:1 | 1 | 4 | | | | 4 | 4 |
| pMON138778 | EXP-CUCme.Ubq1:1:3 | 7 | 16 | | 1 | 2 | 13 | 23 |
| pMON140818 | P-CUCme.1-1:1:1rc | 155 | 48.21 | | 22.35 | 20.24 | 33.01 | 78.17 |
| pMON140819 | P-CUCme.2-1:1:1 | 14 | | | | | | |
| pMON140820 | P-CUCme.3-1:1:3 | 15 | | | | | | |
| pMON140821 | EXP-CUCme.4:1:1 | 156 | 96.82 | | 28.32 | 39.17 | 322.98 | 280.03 |
| pMON140822 | EXP-CUCme.5:1:1 | 159 | 28.88 | | | | 41.11 | |
| pMON140823 | P-CUCme.6-1:1:1 | 18 | 23.94 | | | | 32.14 | 30.22 |
| pMON140824 | P-CUCme.8-1:1:2 | 19 | | | | | | |
| pMON140825 | P-CUCme.9-1:1:2 | 20 | 22.06 | | | | 21.22 | 23.08 |
| pMON140826 | P-CUCme.10-1:1:1 | 21 | | | | | | |
| pMON140827 | EXP-CUCme.eEF1a:1:1 | 162 | 189.24 | 153.52 | 59.6 | 37.44 | 103.01 | 130.6 |
| pMON140828 | P-CUCme.15-1:1:2 | 23 | 30.53 | | | | | |
| pMON140830 | P-CUCme.17-1:1:2 | 26 | 51.62 | | 30.07 | 31.08 | 30.49 | 60.14 |
| pMON140831 | P-CUCme.18-1:1:2 | 27 | 57.38 | | | | | 30.03 |
| pMON140832 | P-CUCme.19-1:1:3 | 167 | 23.07 | | 50.21 | 59.73 | 65.58 | 137.42 |
| pMON140833 | P-CUCme.20-1:3 | 211 | 23.15 | | 61.6 | 118.76 | 502.55 | 119.46 |
| pMON140834 | P-CUCme.21-1:1:1 | 30 | | | | | 25.49 | |
| pMON140836 | EXP-CUCme.SAMS2:1:1 | 168 | 230.89 | 184.88 | 65.44 | 53.36 | 118.82 | 351.49 |
| pMON140837 | P-CUCme.26-1:1:2 | 33 | 56.21 | | 26.81 | 45.07 | 51.61 | 47.42 |
| pMON140839 | EXP-CUCme.29:1:2 | 212 | 82.17 | | 45.2 | 28.27 | 64.96 | 109.9 |
| pMON144926 | P-CUCme.CumMe_WSM_SF25355.G5000-1:1:1 | 196 | 28.53 | | | | | |
| pMON144927 | P-CUCme.CumMe_WSM_SF17111.G5790-1:1:1 | 177 | 23.62 | | | | | |
| pMON144928 | P-CUCme.CumMe_WSM_SF22531.G5120-1:1:1 | 192 | 75.62 | | 23 | 20.46 | 21.78 | 39.77 |
| pMON144931 | P-CUCme.CumMe_WSM_SF18488.G5340-1:1:1 | 181 | 43.2 | | | | | 52.55 |
| pMON144933 | P-CUCme.CumMe_WSM_SF23760.G5200-1:1:1 | 193 | 25.61 | | 20.45 | 0 | 0 | 28.69 |
| pMON146941 | EXP-CUCme.WSM_SF19064.G5690:1:1 | 185 | 33.5 | | 0 | 0 | 24.27 | 47.82 |
| pMON144932 | P-CUCme.WSM_SF17252.G7330-1:1:1 | 179 | 32.54 | | 23.76 | 21.5 | 0 | 22.21 |
| pMON146940 | P-CUCme.CumMe_WSM_SF18634.G5190-1:1:1 | 183 | 0 | | 0 | 0 | 0 | 0 |
| pMON147340 | P-CUCme.CumMe_WSM_SF19647.G5760-1:1:1 | 188 | 28.9 | | 0 | 0 | 29.77 | 25.82 |
| pMON147342 | P-CUCme.CumMe_WSM_SF25936.G5450-1:1:1 | 197 | 50.15 | | 24.26 | 0 | 29.38 | 29.91 |
| pMON147343 | P-CUCme.CumMe_WSM_SF19839.G5090-1:1:1 | 189 | 36.05 | | 25.7 | 27.54 | 22.85 | 37.15 |
| pMON144929 | CumMe_WSM_SF206458.G5970 | 98 | | | | | | |
| pMON147304 | P-CUCme.CumMe_WSM_SF18716.G5860-1:1:1 | 184 | 35.01 | | 21.17 | 21.23 | 22 | 44.57 |

TABLE 21

Mean GUS expression in Yellow Pod Embryo, Yellow Pod Cotyledon,
R3 Immature Seed, R3 Pod, R5 Cotyledon and R1 Flower of $R_0$ generation transformed soybean plants

| Construct | Regulatory Element | SEQ ID NO: | Yellow_Pod_Embryo | Yellow_Pod_Cotyledon | R3_Immature_Seed | R3_Pod | R5_Cotyledon | R1_Flower |
|---|---|---|---|---|---|---|---|---|
| pMON138776 | EXP-CUCme.Ubq1:1:1 | 1 | 12 | 9 | 13 | 11 | 10 | 7 |
| pMON138778 | EXP-CUCme.Ubq1:1:3 | 7 | 3 | 1 | 13 | 9 | 13 | 27 |
| pMON140818 | P-CUCme.1-1:1:1rc | 155 | 100.79 | 117.5 | 38.31 | 84.72 | 132.27 | 66.8 |
| pMON140819 | P-CUCme.2-1:1:1 | 14 | | | | | 20.35 | 36.18 |
| pMON140820 | P-CUCme.3-1:1:3 | 15 | | | | | | |
| pMON140821 | EXP-CUCme.4:1:1 | 156 | 86.68 | 225.53 | 105.62 | 342.07 | 119.08 | 184.92 |
| pMON140822 | EXP-CUCme.5:1:1 | 159 | 21.48 | 32.27 | 21.47 | 21.66 | | 36.88 |
| pMON140823 | P-CUCme.6-1:1:1 | 18 | 38.75 | | 23.03 | | 25.32 | 58.7 |
| pMON140824 | P-CUCme.8-1:1:2 | 19 | | | | | 90.33 | 25.77 |
| pMON140825 | P-CUCme.9-1:1:2 | 20 | 132.04 | | | 20.56 | 34.78 | |
| pMON140826 | P-CUCme.10-1:1:1 | 21 | | | 22.34 | | | |
| pMON140827 | EXP-CUCme.eEF1a:1:1 | 162 | 200.28 | 291.26 | 58.21 | 131.17 | 114.29 | 130.38 |
| pMON140828 | P-CUCme.15-1:1:2 | 23 | | | 142.24 | 26.2 | | |
| pMON140830 | P-CUCme.17-1:1:2 | 26 | 343.34 | 302.94 | 65.55 | 80.94 | 137.02 | 62.7 |
| pMON140831 | P-CUCme.18-1:1:2 | 27 | 103.17 | 135.97 | 30 | 34.62 | 88.14 | 23.73 |
| pMON140832 | P-CUCme.19-1:1:3 | 167 | 30.96 | 64.46 | | 316.66 | | 53.46 |
| pMON140833 | P-CUCme.20-1:3 | 211 | 174.62 | 524.88 | | 222.04 | 59.43 | 124.68 |
| pMON140834 | P-CUCme.21-1:1:1 | 30 | | | 28.15 | 20.52 | 23.89 | |
| pMON140836 | EXP-CUCme.SAMS2:1:1 | 168 | 110.23 | 159.43 | 61.99 | 248.96 | 49.17 | 224.24 |
| pMON140837 | P-CUCme.26-1:1:2 | 33 | 56.73 | 50.06 | 70 | 143.05 | 25.06 | 49.92 |
| pMON140839 | EXP-CUCme.29:1:2 | 212 | 251.76 | 237.2 | 49.16 | 89.28 | 114.92 | 57.84 |
| pMON144926 | P-CUCme.CumMe_WSM_SF25355.G5000-1:1:1 | 196 | | | 21.41 | | 22.23 | |
| pMON144927 | P-CUCme.CumMe_WSM_SF17111.G5790-1:1:1 | 177 | 58.84 | 28.94 | | | 20.97 | |
| pMON144928 | P-CUCme.CumMe_WSM_SF22531.G5120-1:1:1 | 192 | 135.62 | 152.48 | 30.45 | 51.71 | 129.72 | 42.2 |
| pMON144931 | P-CUCme.CumMe_WSM_SF18488.G5340-1:1:1 | 181 | 866.94 | | 23.26 | 21.49 | | |
| pMON144933 | P-CUCme.CumMe_WSM_SF23760.G5200-1:1:1 | 193 | | | 29.03 | 34.9 | 69.63 | 24.42 |
| pMON146941 | EXP-CUCme.WSM_SF19064.G5690:1:1 | 185 | | | 36.69 | 83.08 | 89.81 | 33.99 |
| pMON144932 | P-CUCme.WSM_SF17252.G7330-1:1:1 | 179 | | | 34.29 | 39.89 | 113.83 | 0 |
| pMON146940 | P-CUCme.CumMe_WSM_SF18634.G5190-1:1:1 | 183 | | | 30.25 | 0 | 0 | 0 |
| pMON147340 | P-CUCme.CumMe_WSM_SF19647.G5760-1:1:1 | 188 | | | 25.73 | 28.28 | 24.04 | 23.35 |
| pMON147342 | P-CUCme.CumMe_WSM_SF25936.G5450-1:1:1 | 197 | | | 104.02 | 80.27 | 31.06 | 26.8 |
| pMON147343 | P-CUCme.CumMe_WSM_SF19839.G5090-1:1:1 | 189 | | | | | | 29.09 |
| pMON144929 | CumMe_WSM_SF206458.G5970 | 98 | | | 24.42 | 25.33 | | |
| pMON147304 | P-CUCme.CumMe_WSM_SF18716.G5860-1:1:1 | 184 | | | | 283.49 | | 61.43 |

As can be seen in Tables 20 and 21, the EXP sequences, EXP-CUCme.Ubq1:1:1 (SEQ ID NO: 1), EXP-CUCme.Ubq1:1:3 (SEQ ID NO: 7), P-CUCme.1-1:1:1rc (SEQ ID NO: 155), P-CUCme.2-1:1:1 (SEQ ID NO: 14), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) demonstrated quantitatively the capacity to drive transgene expression in some or all tissues assayed, depending upon the EXP sequence used to drive expression.

Histological analysis of selected tissue sections provided further evidence of expression for many of the EXP sequences. EXP-CUCme.Ubq1:1:1 (SEQ ID NO: 1) and EXP-CUCme.Ubq1:1:3 (SEQ ID NO: 7) demonstrated a constitutive expression pattern with staining observed in all tissues, even though quantitative analysis showed fairly low levels of expression. This type of expression pattern can be most adventitious to driving expression of transgenes that require a low level of constitutive expression. Expression driven by P-CUCme.1-1:1:1re (SEQ ID NO: 155) demonstrated expression in sink and source leaf vascular bundles and xylem and in the root cortex, phloem, xylem, endodermis, stele and tip. Expression driven by EXP-CUCme.4:1:1 (SEQ ID NO: 156) was observed in all tissues with the highest expression observed in the reproductive phase of the plant. Expression driven by P-CUCme.10-1:1:1 (SEQ ID NO: 21) was observed only in in V5 Sink Leaf and R1 Flower anthers. Expression driven by EXP-CUCme.eEF1a:1:1 (SEQ ID NO: 162) demonstrated a consititutive expression pattern with highest expression being observed in yellow pod embryo and cotyledon. The yellow pod embryo activity was 5fold higher in the R1 generation than in the R0 generation (see Table 23 below). Expression driven by P-CUCme.15-1:1:2 (SEQ ID NO: 23), P-CUCme.17-1:1:2 (SEQ ID NO: 26) and P-CUCme.18-1:1:2 (SEQ ID NO: 27) demonstrated a constitutive level of expression histologically. Expression driven by P-CUCme.19-1:1:3 (SEQ ID NO: 167) demonstrated a constitutive pattern of expression histologically with the exception of the V5 root and R1 petiole. R3 pod showed the highest expression.

Expression driven by P-CUCme.20-1:3 (SEQ ID NO: 211) demonstrated a constitutive expression pattern histologically with the exception of expression in V5 root. Expression was highest in the R8 stage cotyledon. Expression driven by EXP-CUCme.SAMS2:1:1 (SEQ ID NO: 168) demonstrated a constitutive pattern of expression with expression observed histologically in all tissues. GUS expression was observed to increase in the R1 generation (see Tables 22 and 23 below). The R1 stage flowers and petioles demonstrated the highest levels of expression in soybean. Expression driven by P-CUCme.CumMe_WSM_SF22531.G5120-1:1:1 (SEQ ID NO: 192) demonstrated a constitutive pattern of expression histologically with highest expression in the R8 stage cotyledon and embryo. Expression driven by P-CUCme.CumMe_WSM_SF18488.G5340-1:1:1 (SEQ ID NO: 181) demonstrated a constitutive level of expression while quantitatively high expression was observed in the yellow pod embryo.

$R_0$ generation plants transformed with the plasmid constructs comprising EXP-CUCme.eEF1a:1:1 (SEQ ID NO: 162) and EXP-CUCme.SAMS2:1:1 (SEQ ID NO: 168) were allowed to set seed and the $R_1$ generation plants analyzed for GUS expression. The $R_1$ generation plants were analyzed for expression in Vn5 Root, Vn5 Sink Leaf, Vn5 Source Leaf, R1 Source Leaf, R1 Petiole Yellow Pod Embryo, Yellow Pod Cotyledon, R3 Immature Seed, R3 Pod, R5 Cotyledon and R1 Flower. Tables 22 and 23 show the mean GUS expression measured in each tissue of the $R_1$ generation transformed plants.

TABLE 22

Mean GUS expression in Vn5 Root, Vn5 Sink Leaf, Vn5 Source Leaf, R1 Source Leaf, R1 Petiole of $R_1$ generation transformed soybean plants

| Construct | Regulatory Element | SEQ ID NO: | Vn5_Root | Vn5_Sink_Leaf | Vn5_Source Leaf | R1_Source_Leaf | R1_Petiole |
|---|---|---|---|---|---|---|---|
| pMON140827 | EXP-CUCme.eEF1a:1:1 | 162 | 145.84 | 50.24 | 43.73 | 107.98 | 357.67 |
| pMON140836 | EXP-CUCme.SAMS2:1:1 | 168 | 260.41 | 65.52 | 51.12 | 129.86 | 623.42 |

TABLE 23

Mean GUS expression in Yellow Pod Embryo, Yellow Pod Cotyledon, R3 Immature Seed, R3 Pod, R5 Cotyledon, R1 Flower of $R_1$ generation transformed soybean plants

| Construct | Regulatory Element | SEQ ID NO: | Yellow_Pod_Embryo | Yellow_Pod_Cotyledon | R3_Immature_Seed |
|---|---|---|---|---|---|
| pMON140827 | EXP-CUCme.eEF1a:1:1 | 162 | 1098.51 | 764.83 | 288.77 |
| pMON140836 | EXP-CUCme.SAMS2:1:1 | 168 | 219.04 | 291.58 | 241.48 |

| Construct | R3_Pod | R5_Cotyledon | R1_Flower |
|---|---|---|---|
| pMON140827 | 214.6 | 459.62 | 394.77 |
| pMON140836 | 382.73 | 397.91 | 653.23 |

As can be seen in Tables 22 and 23 above expression driven in $R_1$ generation by EXP-CUCme.eEF1a:1:1 (SEQ ID NO: 162) and EXP-CUCme.SAMS2:1:1 (SEQ ID NO: 168) shows a constitutive level of expression with increase in expression observed in many tissues at $R_1$ generation relative to $R_0$ generation.

Having illustrated and described the principles of the present invention, it should be apparent to persons skilled in the art that the invention can be modified in arrangement and detail without departing from such principles. All modifications that are within the spirit and scope of the claims are intended to be included within the scope of the present invention. All publications and published patent documents cited herein are hereby incorporated by reference to the same extent as if each individual publication or patent application is specifically and individually indicated to be incorporated by reference.

What is claimed is:

1. A DNA molecule exhibiting a gene regulatory functional activity comprising a polynucleotide sequence selected from the group consisting of:
   a) a sequence with at least 95 percent sequence identity to any of SEQ ID NOs: 212, 173, 172, or 35 and having promoter activity;
   b) a sequence comprising any of SEQ ID NOs: 212, 173, 172, or 35; and
   c) a fragment comprising at least 150 contiguous nucleotides of any of SEQ ID NOs: 212, 173, 172, or 35 exhibiting promoter activity;
   wherein said DNA molecule is operably linked to a heterologous transcribable polynucleotide molecule.

2. The DNA molecule of claim 1, wherein said polynucleotide sequence has at least 97 percent sequence identity to the polynucleotide sequence as set forth in any of SEQ ID NOs: 212, 173, 172, or 35.

3. The DNA molecule of claim 1, wherein said polynucleotide sequence has at least 99 percent sequence identity to the polynucleotide sequence as set forth in any of SEQ ID NOs: 212, 173, 172, or 35.

4. The DNA molecule of claim 1, wherein the heterologous transcribable polynucleotide molecule comprises a gene of agronomic interest.

5. The DNA molecule of claim 4, wherein the gene of agronomic interest confers herbicide tolerance in plants.

6. The DNA molecule of claim 4, wherein the gene of agronomic interest confers pest resistance in plants.

7. A transgenic plant cell comprising the DNA molecule of claim 1.

8. The transgenic plant cell of claim 7, wherein said transgenic plant cell is a monocotyledonous plant cell.

9. The transgenic plant cell of claim 7, wherein said transgenic plant cell is a dicotyledonous plant cell.

10. A transgenic plant, or part thereof, comprising the DNA molecule of claim 1.

11. A progeny plant of the transgenic plant of claim 10, or part thereof, wherein the progeny plant or part thereof comprises said DNA molecule exhibiting a gene regulatory functional activity.

12. A transgenic seed comprising the DNA molecule of claim 1.

13. A method of producing a commodity product comprising:
   a) obtaining a transgenic plant or part thereof comprising the DNA molecule of claim 1; and
   b) producing the commodity product therefrom.

14. The method of claim 13, wherein the commodity product is protein concentrate, protein isolate, grain, starch, seeds, meal, flour, biomass, or seed oil.

15. A commodity product comprising the DNA molecule of claim 1.

16. A method of expressing a transcribable polynucleotide molecule comprising:
   a) obtaining a transgenic plant comprising the DNA molecule of claim 1; and
   b) cultivating said transgenic plant, wherein the transcribable polynucleotide is expressed.

17. The DNA molecule of claim 1, wherein said polynucleotide sequence comprises a sequence with at least 95 percent sequence identity to SEQ ID NOs: 212, 173, 172, or 35 and having promoter activity.

18. The DNA molecule of claim 1, wherein said polynucleotide sequence comprises SEQ ID NOs: 212, 173, 172, or 35.

19. The DNA molecule of claim 1, wherein said polynucleotide sequence comprises a fragment comprising at least 150 contiguous nucleotides of SEQ ID NO: 212, 173, 172, or 35 exhibiting promoter activity.

* * * * *

SEQUENCE LISTING

<160> NUMBER OF SEQ ID NOS: 212

<210> SEQ ID NO 1
<211> LENGTH: 2611
<212> TYPE: DNA
<213> ORGANISM: Cucumis melo

<400> SEQUENCE: 1

```
atctgaaagg aacacctagc aaggggctac tctacaagca tactaagtct acaaagctag     60
agttgtatgg ttatgcagaa gacctggaca aaagaagatc actcgctgct tttacttta    120
tcctaagagg aaatgtgatt ttatggaagt ttaacctata gcctgtagtg gcactattca    180
caacaaaagt aaagtttata gccatgactg aagttgttaa agaagtcgtc tggctaaaag    240
gactacttga agaacttggc ttcttttaac agtcagtaaa catcatgtgt gatagttaaa    300
gtgcaataca cttgtctaaa aatctgcaat atcacgaaag aactaagcat attgatgtga    360
agctatatgt cattagagaa gtcatagcaa agagaaaagt aacagtatca aaggttcaga    420
caaaagaaaa tgcagcagat atgttgacta aaatagttac taatgctaaa ctcgagcact    480
gcctacagtt gctcaaggta atagactact aaaagaata gaatcagaag aaatagtcat    540
tggtagcaat aaaattcaag gtggaggatt gttaaaaaga gagtgaatt ttattactta    600
aagaaaatct cggtgaaact cgaaagatct cgattcgaaa ctctattgct taagaacctg    660
gtgaagctcg agagatcttg atacaatccc agtgccctaa ctcttcaaca agctaagcaa    720
gttgtactgt ggggctcaat ctcggttcaa tctcgacgca cctgatgctt tgttccctgt    780
ctactcgatg aagaagcaat tacttctcag gacaactcgg taccctaaa tacagattt     840
gagcttcgtg atcctacaac tgaaatcaaa tagaaaaact aataagttag ttagagttg    900
ttatatttac tgccattaaa taactctgta atgtaaataa taaccatttt aactcaatat    960
gaaatataga atgagaaaaa gaaaagaaa aagttaaaga gagagagaa gaaaactcat   1020
tttcaaattc tctatacttg tttgatcctt gaataagttg aataaaagct ctatggcggc   1080
ttcaaagtgg atgtaggcac tattagtcga accacaataa atttgttatg ttcttttgct   1140
attccttgta atctccataa atattttctt actaagctct agaaatctgc ttgtcaagag   1200
attaggtatc atttatgcct tttatatttc ctttcggttg catatcttga gctagttaag   1260
atcgagaggt tactgttgtt gaaaccgaga ttagtatctt tggattaaca cgtgcctacc   1320
aaaatttgaa attttgtatt tacccccattc attggataat aagcaattct tatagtgtta   1380
tcaattaaac tcctataaag tgtaataatt gaatccatga actattttca tatgtaatct   1440
taataaaatg aatttagaag tttaattaaa ataatatatt ttgtatgcta tttttcaaag   1500
tttgaagaat gtgttaattg atacacatac aaaaaatcta ggttttacat gaaaaactat   1560
ggaagtgaaa gatagcatct aatatttat gacacaaaat gcaaactaat atataaagga    1620
tttaattaat ttttataggt ttcaaatttg ttagacttgt caaatacaaa attttattga   1680
accaaataca tacaaacatc aaattaaga acagaaaatc taaattcaaa tgaaatttat    1740
taatagaaaa attagaaaaa agaaaagaa ataaaagga atcgtattgt ttttccttc     1800
ctttttccca tttgagaggt gaataaagct aattgagctg ctctaacttc ctaatcttta   1860
tgctttcccc ataagctttt cccaactgcg cgtaatcgta taaatggaaa attgaccttt   1920
ccaactagat tcttccagaa ctaaacaata cgtaacacgc aagtaatcaa agacacgttt   1980
cattttccta tagaatatta tagttattcg tgattaacgg aagtcggcaa ttttaggtat   2040
aaatacgtga attctcgagc gctaatttc catacagact cgaaatactc taaactttct   2100
```

-continued

```
catcgcgctt tattcctatt tcgtaattcg ctcttcttca acctctcaag gttttcatct    2160
tttctctatc ttctgttttc agattgcatc ttttccccct cctgttcgat taattgatgt    2220
ttgaattttc gagaaacgat ttgaagtctt tgttgtattt ttcatttctg ttcgttaggt    2280
aggtcgattt ttaatcgtga tgtccgacgt tgttcggatg attcacattt ggttttgtc     2340 atcttctttc tatgttgtga ttatcatgat ttttatcttt ttttcttctc aagatttgta    2400
atttatcgat tccccatggt tcttggtttt ttatacatgt attgaatctg gttactagaa    2460
ttatgttctt cgacggacgt ctttcagatt taaattgcat tgtaggaaat atgatttgct    2520
atctgagtaa cgttttttcca gagtattctt gattgcgcga tctatcttca attgttaaat   2580 tgttttttgtt taattggggt catgacaggt g                                   2611
```

<210> SEQ ID NO 2
<211> LENGTH: 2068
<212> TYPE: DNA
<213> ORGANISM: Cucumis melo

<400> SEQUENCE: 2

```
atctgaaagg aacacctagc aaggggctac tctacaagca tactaagtct acaaagctag      60
agttgtatgg ttatgcagaa gacctggaca aaagaagatc actcgctgct tttactttta    120
tcctaagagg aaatgtgatt ttatggaagt ttaacctata gcctgtagtg gcactattca    180
caacaaaagt aaagtttata gccatgactg aagttgttaa agaagtcgtc tggctaaaag    240
gactacttga agaacttggc ttcttttaac agtcagtaaa catcatgtgt gatagttaaa    300
gtgcaataca cttgtctaaa aatctgcaat atcacgaaag aactaagcat attgatgtga    360
agctatatgt cattagagaa gtcatagcaa agagaaaagt aacagtatca aaggttcaga    420
caaaagaaaa tgcagcagat atgttgacta aaatagttac taatgctaaa ctcgagcact    480
gcctacagtt gctcaaggta atagactact taaaagaata gaatcagaag aaatagtcat    540
tggtagcaat aaaattcaag gtggaggatt gttaaaaaga agagtgaatt ttattactta    600
aagaaaatct cggtgaaact cgaaagatct cgattcgaaa ctctattgct taagaacctg    660
gtgaagctcg agagatcttg atacaatccc agtgccctaa ctcttcaaca agctaagcaa    720
gttgtactgt ggggctcaat ctcggttcaa tctcgacgca cctgatgctt tgttccctgt    780
ctactcgatg aagaagcaat tacttctcag gacaactcgg tacccctaaa tacagatttt    840
gagcttcgtg atcctacaac tgaaatcaaa tagaaaaact aataagttag ttagagtttg    900
ttatatttac tgccattaaa taactctgta atgtaaataa taaccatttt aactcaatat    960
gaaatataga atgagaaaaa gaaaagaaa aagttaaaga gagagaggaa gaaaactcat    1020
tttcaaattc tctatacttg tttgatcctt gaataagttg aataaaagct ctatggcggc    1080
ttcaaagtgg atgtaggcac tattagtcga accacaataa atttgttatg ttcttttgct    1140
attccttgta atctccataa atattttctt actaagctct agaaatctgc ttgtcaagag    1200
attaggtatc atttatgcct tttatatttc ctttcggttg catatcttga gctagttaag    1260
atcgagaggt tactgttgtt gaaaccgaga ttagtatctt tggattaaca cgtgcctacc    1320
aaaatttgaa attttgtatt taccccattc attggataat aagcaattct tatagtgtta    1380
tcaattaaac tcctataaag tgtaataatt gaatccatga actattttca tatgtaatct    1440
taataaaatg aatttagaag tttaattaaa ataatatatt ttgtatgcta ttttttcaaag   1500 tttgaagaat gtgttaattg atacacatac aaaaaatcta ggttttacat gaaaaactat    1560
```

-continued

| | |
|---|---|
| ggaagtgaaa gatagcatct aatattttat gacacaaaat gcaaactaat atataaagga | 1620 |
| tttaattaat ttttataggt ttcaaatttg ttagacttgt caaatacaaa attttattga | 1680 |
| accaaataca tacaaacatc aaaattaaga acagaaaatc taaattcaaa tgaaatttat | 1740 |
| taatagaaaa attagaaaaa agaaaaagaa aataaaagga atcgtattgt ttttccttc | 1800 |
| cttttttccca tttgagaggt gaataaagct aattgagctg ctctaacttc ctaatcttta | 1860 |
| tgctttcccc ataaagcttt cccaactgcg cgtaatcgta taaatggaaa attgaccttt | 1920 |
| ccaactagat tcttccagaa ctaaacaata cgtaacacgc aagtaatcaa agacacgttt | 1980 |
| cattttccta tagaatatta tagttattcg tgattaacgg aagtcggcaa ttttaggtat | 2040 |
| aaatacgtga attctcgagc gctaattt | 2068 |

<210> SEQ ID NO 3
<211> LENGTH: 82
<212> TYPE: DNA
<213> ORGANISM: Cucumis melo

<400> SEQUENCE: 3

| | |
|---|---|
| tccatacaga ctcgaaatac tctaaacttt ctcatcgcgc tttattccta tttcgtaatt | 60 |
| cgctcttctt caacctctca ag | 82 |

<210> SEQ ID NO 4
<211> LENGTH: 461
<212> TYPE: DNA
<213> ORGANISM: Cucumis melo

<400> SEQUENCE: 4

| | |
|---|---|
| gttttcatct tttctctatc ttctgttttc agattgcatc ttttcccccct cctgttcgat | 60 |
| taattgatgt ttgaattttc gagaaacgat ttgaagtctt tgttgtattt ttcatttctg | 120 |
| ttcgttaggt aggtcgattt ttaatcgtga tgtccgacgt tgttcggatg attcacattt | 180 |
| ggttttttgtc atcttctttc tatgttgtga ttatcatgat ttttatcttt ttttcttctc | 240 |
| aagatttgta atttatcgat tccccatggt tcttggtttt ttatacatgt attgaatctg | 300 |
| gttactagaa ttatgttctt cgacggacgt ctttcagatt taaattgcat tgtaggaaat | 360 |
| atgatttgct atctgagtaa cgttttttcca gagtattctt gattgcgcga tctatcttca | 420 |
| attgttaaat tgttttttgtt taattgggggt catgacaggt g | 461 |

<210> SEQ ID NO 5
<211> LENGTH: 2002
<212> TYPE: DNA
<213> ORGANISM: Cucumis melo

<400> SEQUENCE: 5

| | |
|---|---|
| tcggtgaaac tcgaaagatc tcgattcgaa actctattgc ttaagaaccct ggtgaagctc | 60 |
| gagagatctt gatacaatcc cagtgcccta actcttcaac aagctaagca agttgtactg | 120 |
| tggggctcaa tctcggttca atctcgacgc acctgatgct tgttccctg tctactcgat | 180 |
| gaagaagcaa ttacttctca ggacaactcg gtaccctaa atacagattt tgagcttcgt | 240 |
| gatcctacaa ctgaaatcaa atagaaaaac taataagtta gttagagttt gttatattta | 300 |
| ctgccattaa ataactctgt aatgtaaata ataaccatt taactcaata tgaaatatag | 360 |
| aatgagaaaa agaaaagaa aaagttaaag agagagagga agaaaactca ttttcaaatt | 420 |
| ctctatactt gtttgatcct tgaataagtt gaataaaagc tctatggcgg ttcaaagtg | 480 |
| gatgtaggca ctattagtcg aaccacaata aatttgttat gttcttttgc tattccttgt | 540 |

```
aatctccata aatattttct tactaagctc tagaaatctg cttgtcaaga gattaggtat      600
catttatgcc ttttatattt cctttcggtt gcatatcttg agctagttaa gatcgagagg      660
ttactgttgt tgaaaccgag attagtatct ttggattaac acgtgcctac caaaatttga      720
aattttgtat ttaccccatt cattggataa taagcaattc ttatagtgtt atcaattaaa      780
ctcctataaa gtgtaataat tgaatccatg aactattttc atatgtaatc ttaataaaat      840
gaatttagaa gttaattaa aataatatat tttgtatgct atttttcaaa gtttgaagaa       900
tgtgttaatt gatacacata caaaaaatct aggttttaca tgaaaaacta tggaagtgaa      960
agatagcatc taatatttta tgacacaaaa tgcaaactaa tatataaagg atttaattaa     1020
tttttatagg tttcaaattt gttagacttg tcaaatacaa aattttattg aaccaaatac     1080
atacaaacat caaaattaag aacagaaaat ctaaattcaa atgaaattta ttaatagaaa     1140
aattagaaaa aagaaaaaga aaataaaagg aatcgtattg tttttttcctt ccttttttccc    1200 atttgagagt tgaataaagc taattgagct gctctaactt cctaatcttt atgctttccc     1260
cataaagctt tcccaactgc gcgtaatcgt ataaatggaa aattgacctt tccaactaga     1320
ttcttccaga actaaacaat acgtaacacg caagtaatca aagacacgtt tcatttttcct    1380 atagaatatt atagttattc gtgattaacg gaagtcggca attttaggta taaatacgtg     1440
aattctcgag cgctaatttt ccatacagac tcgaaatact ctaaactttc tcatcgcgct     1500
ttattcctat ttcgtaattc gctcttcttc aacctctcaa ggttttcatc ttttctctat     1560
cttctgtttt cagattgcat cttttccccc tcctgttcga ttaattgatg tttgaatttt     1620
cgagaaacga tttgaagtct ttgttgtatt tttcatttct gttcgttagg taggtcgatt     1680
tttaatcgtg atgtccgacg ttgttcggat gattcacatt tggttttttgt catcttctttt   1740 ctatgttgtg attatcatga tttttatctt ttttttcttct caagatttgt aatttatcga    1800
ttccccatgg ttcttggttt tttatacatg tattgaatct ggttactaga attatgttct     1860
tcgacggacg tctttcagat ttaaattgca ttgtaggaaa tatgatttgc tatctgagta     1920 acgttttttcc agagtattct tgattgcgcg atctatcttc aattgttaaa ttgttttgt     1980 ttaattgggg tcatgacagg tg                                               2002

<210> SEQ ID NO 6
<211> LENGTH: 1459
<212> TYPE: DNA
<213> ORGANISM: Cucumis melo

<400> SEQUENCE: 6
tcggtgaaac tcgaaagatc tcgattcgaa actctattgc ttaagaacct ggtgaagctc       60
gagagatctt gatacaatcc cagtgcccta actcttcaac aagctaagca agttgtactg      120
tggggctcaa tctcggttca atctcgacgc acctgatgct tgttccctg tctactcgat       180 gaagaagcaa ttacttctca ggacaactcg gtaccccta atacagattt tgagcttcgt      240
gatcctacaa ctgaaatcaa atagaaaaac taataagtta gttagagttt gttatattta    300
ctgccattaa ataactctgt aatgtaaata ataaaccatt taactcaata tgaaatatag      360
aatgagaaaa agaaaagaa aaagttaaag agagagagga agaaaactca ttttcaaatt      420
ctctatactt gtttgatcct tgaataagtt gaataaaagc tctatggcgg cttcaaagtg     480
gatgtaggca ctattagtcg aaccacaata aatttgttat gttcttttgc tattccttgt     540
aatctccata aatattttct tactaagctc tagaaatctg cttgtcaaga gattaggtat     600
```

| | |
|---|---:|
| catttatgcc ttttatatttt cctttcggtt gcatatcttg agctagttaa gatcgagagg | 660 |
| ttactgttgt tgaaaccgag attagtatct ttggattaac acgtgcctac caaaatttga | 720 |
| aattttgtat ttaccccatt cattggataa taagcaattc ttatagtgtt atcaattaaa | 780 |
| ctcctataaa gtgtaataat tgaatccatg aactattttc atatgtaatc ttaataaaat | 840 |
| gaatttagaa gtttaattaa aataatatat tttgtatgct atttttcaaa gtttgaagaa | 900 |
| tgtgttaatt gatacacata caaaaaatct aggttttaca tgaaaaacta tggaagtgaa | 960 |
| agatagcatc taatatttta tgacacaaaa tgcaaactaa tatataaagg atttaattaa | 1020 |
| tttttatagg tttcaaattt gttagacttg tcaaatacaa aattttattg aaccaaatac | 1080 |
| atacaaacat caaaattaag aacagaaaat ctaaattcaa atgaaattta ttaatagaaa | 1140 |
| aattagaaaa aagaaaaaga aaataaaagg aatcgtattg ttttttcctt cctttttccc | 1200 |
| atttgagagg tgaataaagc taattgagct gctctaactt cctaatcttt atgctttccc | 1260 |
| cataaagctt tcccaactgc gcgtaatcgt ataaatggaa aattgacctt tccaactaga | 1320 |
| ttcttccaga actaaacaat acgtaacacg caagtaatca aagacacgtt tcattttcct | 1380 |
| atagaatatt atagttattc gtgattaacg gaagtcggca attttaggta taaatacgtg | 1440 |
| aattctcgag cgctaatttt | 1459 |

<210> SEQ ID NO 7
<211> LENGTH: 1507
<212> TYPE: DNA
<213> ORGANISM: Cucumis melo

<400> SEQUENCE: 7

| | |
|---|---:|
| agtcgaacca caataaattt gttatgttct tttgctattc cttgtaatct ccataaatat | 60 |
| tttcttacta agctctagaa atctgcttgt caagagatta ggtatcattt atgccttta | 120 |
| tatttccttt cggttgcata tcttgagcta gttaagatcg agaggttact gttgttgaaa | 180 |
| ccgagattag tatctttgga ttaacacgtg cctaccaaaa tttgaaattt tgtatttacc | 240 |
| ccattcattg gataataagc aattcttata gtgttatcaa ttaaactcct ataaagtgta | 300 |
| ataattgaat ccatgaacta ttttcatatg taatcttaat aaaatgaatt tagaagttta | 360 |
| attaaaataa tatattttgt atgctatttt tcaaagtttg aagaatgtgt taattgatac | 420 |
| acatacaaaa atctaggtt ttacatgaaa actatggaa gtgaaagata gcatctaata | 480 |
| ttttatgaca caaaatgcaa actaatatat aaaggattta attaattttt ataggtttca | 540 |
| aatttgttag acttgtcaaa tacaaaattt tattgaacca atacataca aacatcaaaa | 600 |
| ttaagaacag aaaatctaaa ttcaaatgaa atttattaat agaaaaatta gaaaaagaa | 660 |
| aaagaaaata aaaggaatcg tattgttttt tccttccttt tcccatttg agaggtgaat | 720 |
| aaagctaatt gagctgctct aacttcctaa tctttatgct ttccccataa agctttccca | 780 |
| actgcgcgta atcgtataaa tggaaaattg acctttccaa ctagattctt ccagaactaa | 840 |
| acaatacgta acacgcaagt aatcaaagac acgtttcatt ttcctataga atattatagt | 900 |
| tattcgtgat taacggaagt cggcaatttt aggtataaat acgtgaattc tcgagcgcta | 960 |
| attttccata cagactcgaa atactctaaa ctttctcatc gcgctttatt cctatttcgt | 1020 |
| aattcgctct tcttcaacct ctcaaggttt tcatctttc tctatcttct gttttcagat | 1080 |
| tgcatctttt cccctcctg ttcgattaat tgatgtttga attttcgaga aacgatttga | 1140 |
| agtctttgtt gtatttttca tttctgttcg ttaggtaggt cgattttaa tcgtgatgtc | 1200 |
| cgacgttgtt cggatgattc acatttggtt tttgtcatct tctttctatg ttgtgattat | 1260 |

| | |
|---|---|
| catgatttttt atcttttttt cttctcaaga tttgtaattt atcgattccc catggttctt | 1320 |
| ggttttttat acatgtattg aatctggtta ctagaattat gttcttcgac ggacgtcttt | 1380 |
| cagatttaaa ttgcattgta ggaaatatga tttgctatct gagtaacgtt tttccagagt | 1440 |
| attcttgatt gcgcgatcta tcttcaattg ttaaattgtt tttgtttaat tggggtcatg | 1500 |
| acaggtg | 1507 |

<210> SEQ ID NO 8
<211> LENGTH: 964
<212> TYPE: DNA
<213> ORGANISM: Cucumis melo

<400> SEQUENCE: 8

| | |
|---|---|
| agtcgaacca caataaattt gttatgttct tttgctattc cttgtaatct ccataaatat | 60 |
| tttcttacta agctctagaa atctgcttgt caagagatta ggtatcattt atgcctttta | 120 |
| tatttccttt cggttgcata tcttgagcta gttaagatcg agaggttact gttgttgaaa | 180 |
| ccgagattag tatctttgga ttaacacgtg cctaccaaaa tttgaaattt tgtatttacc | 240 |
| ccattcattg gataataagc aattcttata gtgttatcaa ttaaactcct ataaagtgta | 300 |
| ataattgaat ccatgaacta ttttcatatg taatcttaat aaaatgaatt tagaagttta | 360 |
| attaaaataa tatattttgt atgctatttt tcaaagtttg aagaatgtgt taattgatac | 420 |
| acatacaaaa aatctaggtt ttacatgaaa aactatggaa gtgaaagata gcatctaata | 480 |
| ttttatgaca caaaatgcaa actaatatat aaaggattta attaatttt ataggtttca | 540 |
| aatttgttag acttgtcaaa tacaaaattt tattgaacca aatacataca aacatcaaaa | 600 |
| ttaagaacag aaaatctaaa ttcaaatgaa atttattaat agaaaaatta gaaaaagaa | 660 |
| aaagaaaata aaaggaatcg tattgttttt tccttccttt ttcccatttg agaggtgaat | 720 |
| aaagctaatt gagctgctct aacttcctaa tctttatgct ttccccataa agctttccca | 780 |
| actgcgcgta atcgtataaa tggaaaattg accttttccaa ctagattctt ccagaactaa | 840 |
| acaatacgta acacgcaagt aatcaaagac acgtttcatt ttcctataga atattatagt | 900 |
| tattcgtgat taacggaagt cggcaatttt aggtataaat acgtgaattc tcgagcgcta | 960 |
| attt | 964 |

<210> SEQ ID NO 9
<211> LENGTH: 1022
<212> TYPE: DNA
<213> ORGANISM: Cucumis melo

<400> SEQUENCE: 9

| | |
|---|---|
| tgacacaaaa tgcaaactaa tatataaagg atttaattaa ttttatagg tttcaaattt | 60 |
| gttagacttg tcaaatacaa aattttattg aaccaaatac atacaaacat caaaattaag | 120 |
| aacagaaaat ctaaattcaa atgaaattta ttaatagaaa aattagaaaa agaaaaaga | 180 |
| aaataaaagg aatcgtattg ttttttcctt ccttttccc atttgagagg tgaataaagc | 240 |
| taattgagct gctctaactt cctaatcttt atgctttccc cataaagctt tcccaactgc | 300 |
| gcgtaatcgt ataatggaa aattgacctt tccaactaga ttcttccaga actaaacaat | 360 |
| acgtaacacg caagtaatca aagacacgtt tcattttcct atagaatatt atagttattc | 420 |
| gtgattaacg gaagtcggca attttaggta aaatacgtg aattctcgag cgctaatttt | 480 |
| ccatacagac tcgaaatact ctaaactttc tcatcgcgct ttattcctat ttcgtaattc | 540 |

```
gctcttcttc aacctctcaa ggttttcatc ttttctctat cttctgtttt cagattgcat    600
cttttccccc tcctgttcga ttaattgatg tttgaatttt cgagaaacga tttgaagtct    660
ttgttgtatt tttcatttct gttcgttagg taggtcgatt tttaatcgtg atgtccgacg    720
ttgttcggat gattcacatt tggttttgt catcttcttt ctatgttgtg attatcatga     780
tttttatctt tttttcttct caagatttgt aatttatcga ttccccatgg ttcttggttt    840
tttatacatg tattgaatct ggttactaga attatgttct tcgacggacg tctttcagat    900
ttaaattgca ttgtaggaaa tatgatttgc tatctgagta acgttttcc agagtattct     960 tgattgcgcg atctatcttc aattgttaaa ttgttttgt taattggggg tcatgacagg     1020
tg                                                                   1022

<210> SEQ ID NO 10
<211> LENGTH: 479
<212> TYPE: DNA
<213> ORGANISM: Cucumis melo

<400> SEQUENCE: 10
tgacacaaaa tgcaaactaa tatataaagg atttaattaa ttttatagg tttcaaattt     60 gttagacttg tcaaatacaa aattttattg aaccaaatac atacaaacat caaaattaag    120
aacagaaaat ctaaattcaa atgaaattta ttaatagaaa aattagaaaa aagaaaaaga    180
aaataaaagg aatcgtattg ttttttcctt cctttttccc atttgagagg tgaataaagc    240
taattgagct gctctaactt cctaatcttt atgctttccc cataaagctt tcccaactgc    300
gcgtaatcgt ataatggaa aattgacctt tccaactaga ttcttccaga actaaacaat    360
acgtaacacg caagtaatca aagacacgtt tcattttcct atagaatatt atagttattc    420
gtgattaacg gaagtcggca attttaggta taaatacgtg aattctcgag cgctaatttt    479

<210> SEQ ID NO 11
<211> LENGTH: 716
<212> TYPE: DNA
<213> ORGANISM: Cucumis melo

<400> SEQUENCE: 11
tcgtataaat ggaaaattga cctttccaac tagattcttc cagaactaaa caatacgtaa    60
cacgcaagta atcaaagaca cgtttcattt tcctatagaa tattatagtt attcgtgatt    120
aacggaagtc ggcaatttta ggtataaata cgtgaattct cgagcgctaa ttttccatac    180
agactcgaaa tactctaaac tttctcatcg cgctttattc ctatttcgta attcgctctt    240
cttcaacctc tcaaggtttt catcttttct ctatcttctg ttttcagatt gcatcttttc    300
cccctcctgt tcgattaatt gatgtttgaa ttttcgagaa cgatttgaa gtctttgttg     360 tattttcat ttctgttcgt taggtaggtc gattttaat cgtgatgtcc gacgttgttc      420
ggatgattca catttggttt ttgtcatctt ctttctatgt tgtgattatc atgatttta    480 tctttttttc ttctcaagat tgtaattta tcgattcccc atggttcttg gttttttata    540
catgtattga atctggttac tagaattatg ttcttcgacg gacgtctttc agatttaaat   600
tgcattgtag gaaatatgat ttgctatctg agtaacgttt ttccagagta ttcttgattg   660
cgcgatctat cttcaattgt taaattgttt ttgtttaatt ggggtcatga caggtg        716

<210> SEQ ID NO 12
<211> LENGTH: 173
<212> TYPE: DNA
<213> ORGANISM: Cucumis melo
```

<400> SEQUENCE: 12

```
tcgtataaat ggaaaattga cctttccaac tagattcttc cagaactaaa caatacgtaa      60
cacgcaagta atcaaagaca cgtttcattt tcctatagaa tattatagtt attcgtgatt     120
aacggaagtc ggcaatttta ggtataaata cgtgaattct cgagcgctaa ttt            173
```

```
<210> SEQ ID NO 13
<211> LENGTH: 2000
<212> TYPE: DNA
<213> ORGANISM: Cucumis melo
```

<400> SEQUENCE: 13

```
cttattcagc gctttcctgt aaaattaaag acttgatgag ggagaaaaag aaaaccggtt      60
cgcagcttca agaagacggc ttccgaataa gaatcagata ctcgatgatg gggaaacaat    120
aacaaagata tcaaaagaaa tcatgaaaca tagcataaga acgaaaaccc agaggtgaag    180
aacagtgccc aaacgcaact ttacccaaag aacatgtata aacgtcttc cagacgttca     240 aaataagaaa gtggacaaaa tcaaagctac aaacgatctc caataactag atggaaaaca    300
ctaattgcac tagagatttt gaatgctttg ttgttgattt ataatcctcg acttccaaga    360
aaaagtaaca agtagaaatg aacgaatcag atccgcaatc gaagatctga aggcaagata    420
aggtaaggct aaagaaccat aggaaaacgg taaaaacgtc caaaacagtg tgagaaatat    480
cgcagattca aaggtccgaa ccctaagaac ggtgttatgc agctataaag gtgagaatca    540
aaaccctcta tccataacgt ggacggcgcg gttaatcat tgtcttgttc cttgaaactg    600
aaggtatgcg agacatagaa ttcgatctca ctattatctt ctaatcaacg acgaagtaaa    660
gaagtgaaat ccagaacaaa gaatggagaa ttggaaatga caagaaaaac ggcagaggaa    720
agtggaaaag tgaaagcgga ctcacctaga tcaatgccct tggctggtcg agcttcagga    780
acctgtcgtc ggagagaaag agaaagagaa aagagcaaga gagagagaga gagagcacaa    840
ggagaagaga acgaggacaa tggaggcttt tgtttcgata ctccctgatc tggaattcta    900
taataacata actataaact tctctgggtt ggcccatcat cacgtatatt gggcttttag    960
cccaattatt tgttcactgc tcatgggccg gtgattttgg gctttcttct gggccttggt   1020
acataacaac ccagtatatg acgtattttc ggtgatagct attttcaaga acaccaactt   1080
ttttgttcaa caatgtggag atcaaataac agtatgtata tatacacaaa catatgctca   1140
tttatgaaaa atagaagaa aagaatgtt ggtaatttgt tacaaaatta taatttctct   1200
ctctttgttt gatttcatga acggtgtgtt ctatataaaa caatgaaata acataattat   1260
taaaatgatt cttaaaacat gatgatttca atattcatgg tttacatttg gtgggatgat   1320
tcgtttaatt attattgata atgtatagtt attgtgtgtc ccgttttctt tttctttggt   1380
ggaagaaaag aaaaaagtag gaaggcatgt aatattgcga tccttcacgg gacagatcca   1440
ttttccaatg tgatcgagta ctagttaggg ggagagtgga agaatcttcg tgcatgcata   1500
aatcaagtca caacttgcca atttggaaag aatcatgtta tattctacct ttactttcaa   1560
gtagggttaa gtgaattaga ccacaacgaa gcaatcaagt ccaaccaaac tcacttaggt   1620
caagcagttt agtgatatag acaggtcagt ggtcgttttt ttaatactaa gaaatgtcaa   1680
ttctatctag ttgactatta ttcatataga aggagaaaaa tgataactat gattgtccca   1740
caaacaacaa ctaccgatcg atctaaacca acaagtcgat gattggtgcc actttaaatt   1800
taaatctgac gccactcaat tgatgatcac ccctattcaa gcacacaaga acgcatgctc   1860
```

```
ttaaaacatt tggtaatatg attggaatta gtacaaaatg tttattcgat ctatacaaac    1920 aactccttt  taacacaaat gttttattgt actttcccgt gaaatggggt tagtaaaact    1980
atggagttaa taaaacataa                                                2000
```

<210> SEQ ID NO 14
<211> LENGTH: 2000
<212> TYPE: DNA
<213> ORGANISM: Cucumis melo

<400> SEQUENCE: 14

```
tataacaaaa tatgtgaaat tagccattat gtttgtcctt tcgttcttct tattcacttc      60
gttgcgattt ctttctatcg tctatcgtct ttcttctttt ttctgttgaa atttattttc     120 atcgttttc  ttcttttcc  atcgtgaaaa aaatagtcaa atctaaatga tcgtgtataa     180
agaataaacg atcgtgtaga caaatctaaa tggtcgaata ttaagaaaat tgataggaaa     240
atttattcat tagaaaaatt ttagtaagaa aaattagaaa tgaaagggtt gaaccagaaa     300
gaaataaaag taatagacaa atgaaaattt taaataaaaa gaaatttggg atgggtgcat     360
ttactattta gtcttgagtt ttaattcttt tattacttta cataagatgt attaaattaa     420
agaggtaaga tagaattttt ttttaaaaaa aactatcatt agtaaattta acaaaagtga     480
catagcacca ttttcgttaa aagaataatt gttttatgta gtaaaattgg tagaaatatt     540
ttttaagtat agcaaaatat ctttgtcttt ttatatcttt cactgacaga taataataat     600
ttattaatat atcatttata tagtcccatt ttcggtaaat tttaatattt gaacataaaa     660
cactatttaa aataatgaaa aaaaacttta caaactttt  tatttttatt atatttgtaa     720
atatttctaa aaaatttac  atttaaaata atattttcaa ggttaataca gaagaaaaaa     780
aacaaaaaaa gaggaaaagg caatttaaga agaatgacaa gaaaatcggg aggtggtgtg     840
gctaagagga agaagggacc ggttcttcaa gatccaacgc tccacattca atctcacttc     900
cttcttcaat tccgtcttct ccgtttcctc ctttatatgc ttctctcttt ccctcccttt     960
ctttctctcc ttcaatcaat caatcaatca atcaatcaat cctcccattc ccattacatt    1020
gccaaaaggt tctattctca ttctctacat ccatttccct ttctttcctt cttcttcctc    1080
tgtttcttct tcgtttcctt gattcatttc tctttgtacg ttccttcctt ccttctgcat    1140
tttgattatt ttcttttgtt ttacgtccgg aattgcaatg tggtttatct ttatttctgt    1200
ttttggacgt caagatgcct gttgttttta acattttgat ttgattcatc gttcatggcg    1260
taatcatgtc ttttggaatt gtttgaaatc caaggatcac attgatttca ctattgtttc    1320
atttgttctt ttttgttaat tttgtataat gaatcgtata ggggatcatt tttccattgg    1380
ttctcttgaa aatctttaag agttgcatta tgtatactaa gtctctctta tggcgtctgt    1440
ttgagtgaga attgataaaa gatccatggg aggaagaagt tttctttcat gaggcttggt    1500
tttattcagc tgtttcttct cgttgcaatt tgttgaagaa gggacatggg tatcttttac    1560
atcaaagtat aactaactat ataattcaat ttggttgata agtagatac  atgtaggagt    1620 caaccgattt gagtgtataa taatgttgtt atgtcccttg caacttaatg tagtgcatat    1680
ttgggagtga ttataaaatt gtataaatca tttatgtttt agaatcatct tgaaacacgt    1740
tttttagtat ttaaaaacta atttaatatt tagttttgca cttttaaatg aaattttgt     1800 ttcactaata ttagttttga ttcattaaat gcatgctcca tcgtaatatt aaagtaact    1860 agtgatttta accattttat aatcacatgt ctgtgatata gtgaagtgta cggctgcctt    1920
gttgagaatt gttacccttt agaagaaaca caggatgtat ttgatgttta acttgcattt    1980
```

```
tcttctggca ggcttagaaa                                                 2000

<210> SEQ ID NO 15
<211> LENGTH: 1990
<212> TYPE: DNA
<213> ORGANISM: Cucumis melo

<400> SEQUENCE: 15
tatttgtaca atgaaaatat ttatttcttt tctcgattct ttaacaaaag ttcaaaatct       60
tttatcataa atacaaatat ttagtaattt aagtttagac taggtgtatc agatgtgcac      120
caagtgtata ttacgtgcat caagtatata tcaaatgtgt accaaacgta tatcacgtgt      180
atcaagtgtg tatcaagtgt ctatttgaag tcaagtgcat taagaatata tcacatgtgt      240
accaaatata tcaaaataaa tactgattga gcatcaagta tgtctattag tagtgtatca      300
agtgtattaa ttaagtttgt agcaaaggtg tatcatgatg tataacgtgt attatgtggg      360
ttggtttttt tttttttttg tcattttttgc aaaagtaatt aagtttgtgt tatgaaccta      420
attttttaaa tttcttttg tcacgtataa gagacttgaa aataggttta aaaggtctta      480
agggtatttt agtttgactt ttttaaaaag tatttatatg atatttaaaa attagaattt      540
tttagaaaga ataggagttt tataaattat tcttttaaga aaaattgcat cagatgacaa      600
aaaaaattta gaaataagca gcccataata actcttaaaa tttgctatca gacgactatc      660
cgagggttat catcttttaa atttgctact tttacaattt agaaaatgta gtgacatgga      720
ccctattatc ataagatttt tttttgctat ttttgcaaac acatgttctt ttaaaatgac      780
ataattattt aaaataaaaa tataaagtta tttgatggat cttttgaacc tattttttaaa      840 agctaaagta ctaaaaagat acatattgaa aacttgaggt caaatgggct attattataa      900
atatgtggac taaaaatgta catttctaaa acttagagac taaatgcaca tatttaaaaa      960
agcatgtgaa ctaaaaaagt cgttttttcct aatattttt tacaacaatg actaaattga     1020
acctcaaatt tgaagggtgg aaaaccatac taattattca ctaatgaact aaactcattt     1080
gatgatttca agacatatga ggttcattga gtagttgggt ttgagggggat gaaatgagtg     1140 gtggaagaaa gtttatgtaa cgacccaacg aaataggaag gtcatcccaa ggaagtcgca     1200
catccaatga gtaattacca caaaacaacc tctccttttt tctcaaattc ccttttaata     1260
aataatttga ttccccattc cttcctttct cccttggcag ccttctcctt ttttcaaagg     1320 ttttgttt ttcttttctt tttaaattt cattcctttg tttctctctt tctttcttca     1380
ttaacattct tcttatttcc tcattactga tcatctcctt tcttggtat tattcttctt     1440 tcttttctca aagttttgtt tttcattgat gtagatgttt ttgtatcaat caatggaaat     1500
ttgagttttt cttatctcat tgtatcatca ttgagtgtgt gtttatgtta gggatccatt     1560
attaggatgg atgagaatca taattcatt gctaatctat gaaccatgaa taaagaaatc     1620
taaatccaac atagaagata gaacatttgc attgtgttat gagtaaccag ctctgtcact     1680
tcaattggtt cttctacaca tttgatggca atggcttgt ttgatattcg tgatggcatc     1740
taagcattgg ttcttcctat gtttttcgtt ggctcttggt ttgatttgca attagtgaag     1800
agcatgtttg gaatgaatga gttgaaatca cctttaacat ttttaaaatc actttaaata     1860
ttaaattaat tttgagtgat aaaagtaatt ttaacaatga taaaattact ttcaaatgtg     1920
ggccgaatca aattgtctag aatgtttagg gttctccaac taatagcaat ttatccaaac     1980
agggtaaaaa                                                           1990
```

<210> SEQ ID NO 16
<211> LENGTH: 2005
<212> TYPE: DNA
<213> ORGANISM: Cucumis melo

<400> SEQUENCE: 16

```
ttgttagagg agttagcttt tcagggagtc ggttacaact tacaagacag acaaccatac      60
tgtacaatca atcactactg cctcaaagtc gaaaccattt aataccagtt gagcctcatt     120
gtgactgcat aattttgacc cctaccacga ggtaatttca gttcaaatca attgtatctc     180
tcttctggat atcagtcaag aatctcatgt tctcaagtta tagtacattg ataattactg     240
tgcattttta ttaatttatg agttaaaatc ctgctgatta attcaactaa aggaataaaa     300
tagttattgg catttggatg agaatagaat gtgaatccca tcattcatcg ctagattgga     360
ccgtaattat aagtgagagg gagaaacttc tgttgctatt cccttttttat ttcttaattc    420
atttataaat tgttttttagg cctttttatat atatatattt ctaccatttt tacatttaaa    480
attcttttaa ctttattatg tatggactca aactaacaag ctttatttga taaaattgtt     540
caaactatta tattagtttt atatttgtaa accataaaac aaatccataa aattccacct     600
gcatcactca ctcatgttgt tgaatggtac gaaataaaca atacatgtga aagatgaaaa     660
taagaattgt tctcttatta aatctaaaat ctagattttc ttttagtac atttaacact     720
tcaatgaaag gtctaaaaca ttattgaatg acgtcacgaa ctattacaaa agattattcc     780
gatttatctc aaaaggggtc tatttcacta atttttggtgt cccacatctg taaagagaat    840
tttcgtgata tgtgtagata tttaaatata attgaattcg atgaaagcaa agcaagaatc    900
gatatccgta gttattttga tatagatcgg tgataaataa aagacaatat gcataaagtt    960
tgtgggtaca gagtcggcta gttgcaatga ggggtatggc cccaagactt tccccaacc   1020
ccaacggtca attaatcacc ccaatggggc atcgaatctt ccccaccatt ttcctttttct  1080
tcgccgactc ttctacccat ctctttttgcc gactctttct cacaggtttg attaaatccc   1140
attcatattc agatacacta tttcaaaata actcgcaaat taatttgttt tttaaatatt   1200
ggtataataa taaaattaat tataaattgt gacctaaaaa gtactttgtg aagaggggga   1260
tatagtctgt ctaatatatt attgattaaa tatataatag aaccataaat gcaaaccact   1320
agaattgtta ataaaaatca acgctctttt aagtctttcc atagaaagaa aggcaaagac   1380
gcgcaacgtc tagaattttc tttataacgg aagctaactc tgttataacg gccgtccaca   1440
taatatggta gatttaaaat gacgtcagca tgtcgcttct aaatttgggt ccaaagggggg 1500
gattcattta tagggaaggg aaacggcaaa tgcaagcata gtgagtaaat acgtggcggc   1560
aaagtaatgg ataattctgc ctctgccgtg acgacattgc ccttccattt cactataaat   1620
acacctcctc tatccctcga tttcttcgca attgaatttc tcttctcatc tctgtcgtag   1680
caaaccaaat cgattcttc aaaggtattt cttcctttcc tttttttttt tttttttttt    1740
ttttttaaatc atgttgttca aactttgaga gatgaaatga ttaggggctt tcaaagtggt   1800
tttcgtttga tatgtttctt agatcgatag ggtttagaat cgagcatcct tgtaggtatc   1860
ctgaggtttg gtggttggat ctgcttaatt tttatgtggt tgcatggaaa attgggatt    1920
ttttttttcta attacgtgat tctggaaata ttgatctgtg gttcagatgg aattgaatct   1980
gatctttctg ttttgttctg tatag                                          2005
```

<210> SEQ ID NO 17
<211> LENGTH: 2004

```
<212> TYPE: DNA
<213> ORGANISM: Cucumis melo

<400> SEQUENCE: 17
tagaaaaaaa ttgaagatct tcttaatgct aataataaaa gcatatataa aaaggcttca      60
tattacacaa gcatcttaaa accaaaccga acttgatttg aaattatccc actaattctg     120
tagatttcac caaagtcctt aacctttata ctaacatctg catttgactc tttcatttga     180
cctccaacat attcttttctc attttccttc cattcaccac aaaaaccaac aaatacaaaa     240
aaccacaaat acatagaaaa ttaataaaaa aatcaaaatt tcgagatgaa atcattataa     300
actcatccga taactttgag atttgaaacc ttacactata taaagaaact catccgataa     360
ctttgaattc gcatcgaaat tacgtaagtg aagacgaaaa tgtaaatgat tagatgcgaa     420
taacaaaaaa aacataattt ctaaacgtaa aacactatat tcaccttatt atacttgatt     480
attttggaaa agtatgaaat ttgagtgtgg gagaggagcc aaagaattgg aaacttgtta     540
ttaggagtcg ttatgaaaca ttttcaacaa gccaatattc tttcacatac tataatgata     600
tacatagaaa taatacaata atatttttga aattgaggca tttttgtcgt aatttatcta     660
aaaatgtcag ggtagattca tcatgtatac aaatctctcg ctatcaaaac tatataaaaa     720
tcttgtgaat gatttcaatc gaaatggacc gagaaaaaac atcgtaacca cctctaaaat     780
cgataaattt gtttcaattt caaatcccta aaactaaagg tgctactttg tacaatttcc     840
cctgattagg gtgctaaagt taaaccctaa ataaaggtgt gtacgtttcc ggaagtttct     900
agaatcccca gcgaagttct ccaaatcgtg gcttgcagac caaggacccc cattaaaatt     960
cgtttcttcc tctaaacctc ctcccttaat tttggcattt tggtattttg gctcctataa    1020
attcaccccc tccttatccc taatcctttg tcttccaaat tttccttcaa agcctgcttt    1080
tcccatttcg tcgtgctttt tcttcatcta aaggtatatt tcagttctag ttttctttct    1140
ctgttgatct cttggatttg agggacgttt gaagttggct ttgtttaatt ctttgttatt    1200
caatctcttt ttttgttaga gttgttgttt aatcgtttcc cttgttgttt ttctcccttc    1260
tagttcgatt ttagaacgct ttttgtgggt tgattttaat ttctccgttt tcttacatct    1320
ttcacaaaga aacgattgaa atcgtgtttg ttttttttcc cacggcatac gttattagat    1380
cttgtagata atgatctcaa tctattgttt agttttttgca aataagaagt tggttttta    1440
tctccaactt ttatatattc gattcgatga gatgttctac accgttagga tggaaccaag    1500
aagtgaggta agggtgtttg attgaaaaat tgaactgaga agttaaagtt ccttcctaac    1560
ttttttaatgg attgtataat tcgttcaatt ccttgtcgtt ccatttttat ttctgtttcg    1620
tttttcgtgt tgctgcgtat cgcttcccctt gttgttttcc tcccctattg attttgcgtt    1680
tcttggagtt tctctgtttt ctctcttcat ttttctacaa aaatcaattc tatttttatt    1740
cgttttcaat tcccgagctc cttggaatgt tatccttttc tcctgtgtaa ataagaaccc    1800
gtattcaatc ccagttcata gtttggcttt cccaaataag agcaaaaaga ttgtactgag    1860
aagttgaaga tttcaaaatt ttgtacatga tttcttctaa tttatcaatt tgattggact    1920
ttttgtatat agatttggtt cttgagctat ttatgttatg acgttttcat attgaggcca    1980
tgcgttgaat tggtttctta acag                                           2004

<210> SEQ ID NO 18
<211> LENGTH: 1935
<212> TYPE: DNA
<213> ORGANISM: Cucumis melo
```

<400> SEQUENCE: 18

```
tatacaaatg acaaaatatc gttgaagtcc aaaaaagatt tattgttggt aaatatcgtt      60
aaagttagta aatagatttt agagaaagga gatatagccc ttgtagtaga acacacaca     120
caaattgaat tagatgtgtt taatgtttaa ttaaattaga tatgagtcaa cttatatcta     180
atataggaca ttattaaaca aataagaaat aagaaacatg aaacaagaaa aacaagaaat     240
agaaacaata tcaaacacat tcctatttct tgttctaaaa aaagaaaaaa catggtacaa     300
gaaataggaa acggaaaaga ggaaacaagg aacaaatgct accaaacggg cctaagtttc     360
taacaaaatg agctaggtgt agtttattgg tatagatagt gactttcaat tattttaaat     420
tttttatcc atacctccac gtctttagaa tctttcttat ttatatgtga tcttaattca     480
ttcatgtctc aatcttaaaa ttagaacatt acatgttcat cattttttcc ttttgttact     540
gtgtttaatc tttcctaaca agacaaatag tttaaccttc atccacacat tattataacc     600
aaattaaaat aatctacctt caaagaaaac attattataa tcttatatta accacaaatt     660
ataataccaa actctaacgc tccaacccaa cctaggaaga atgacaaggc tgtcataatt     720
tagttggttt ggcacgttgt tggaagttct caaaattatg gaaatatttta tttccttctt     780
ctttatccat catcctcctt gggagggtga atttgtgtta aaaagaata gaaactaaag     840
tctaagtggc aggacttaca ttatgtgtgt atgtggaagt aaaattgcag taacagttta     900
caaaacaac tcatccatga ttcataacca acttaaatga atataatttt ttgcctaaag     960
attttaaatt aatatataag cggaagaatt aacctataac ttcaagttta acaacacaaa    1020
tattatatca tactgattaa ttattggaat gatgtttagg ctttaaacat aaagtattga    1080
gaggctaatt tgagtttaac tcactaaact atcattaccc tttcaaaata gatccaatca    1140
tccatttatt ataatactca atgaaataaa gcaaagatg agtaaaataa ttcaccatga    1200
acattgataa ttaattttcc cactaagata aactactact cctcaaatct tcatatgtgt    1260
ttttccttt tgagttgcac tcaaattttc atagttgaaa tttacccatc aaaacaacca    1320
acaatctttc aaattcaaca aacatttgac cttacaccct tgatgccaa atccttaccc    1380
tctccctctt ccataaaaat tcttatataa accaccatca ctctcacttc tcaattcact    1440
ctcttctcta ctcccaatca cctgacttgc ctcttactcc accgccaggt tccgccccaa    1500
cttccccggt aagttccagt tcttcagatc tggttaccac atttgatttc ttgcttgtat    1560
ttgacgtggg aattttcata tcggcgtttt ttcgaactgg gttttgcttt atgatcatat    1620
tcttgtagta aaatgccatg aatctgttat ttgattccgt tttttttgga gatcggtcta    1680
gctttatggc catattctgg catttaaatg ccatgaatcc gtgatttggt tgaatttcac    1740
ttccgatcca atgtttatgc tgatattgac atctttgcat tcaatgcaga ggagttttgt    1800
ttcgatttat tactgatctc atcacactga tcttgaattt tttatacttt tatgtgtgtg    1860
tgtgtatttt ctttaatatc tatgccaatt gaactatgtg gttaacttca gagtgttctt    1920
gtgggcagtg agaag                                                     1935
```

<210> SEQ ID NO 19
<211> LENGTH: 1606
<212> TYPE: DNA
<213> ORGANISM: Cucumis melo

<400> SEQUENCE: 19

```
atatattgta tcgattcttt agttgctcta tgttttttgtt tgcttcattt gtcgattaaa      60
ctgtaaaatt aatttctttg acaaggaaaa agatataatt taattctata atttattaca    120
```

| | |
|---|---|
| atctaatcca tatggtttaa taaaacactg aaaattgttt atgaaaattt tatcgaacta | 180 |
| caagaactat taataaagtt ttttaaacc gtaaattgaa tgaattttct ccacggtgta | 240 |
| aatttgaaaa cattaattaa ttaattaatt aattttaatt tcaaggtttt ttctgaccca | 300 |
| tgaacctatt ttatgatata agttgttcag gggttgcaat agtaaccaaa taagttgat | 360 |
| cagaaaaggt taacaactca tgaaaacttc caaatgcatt tgtgtttcaa ttattttctt | 420 |
| aaccctcttt ttttggtaat tttagtttaa aagtgagtc ggttgatcat tattgttctt | 480 |
| taatttcttg ggagaaaaat attaatgttg attatggtga tgagttaagt ccaattcttc | 540 |
| atcaaatcat accaaattag gaacaaaaaa aacatcaatt ttaaggtgca aatccatttc | 600 |
| taatggctaa aatgtcaagc atcccaccaa accaacaatc tctaaaccca ttttactcc | 660 |
| actaatctaa tgtttaataa taatcaacaa ggttttgctc attccttttt tagttaataa | 720 |
| tcatttaaca ccaaagctca aaagtaccca cccaatggat caaaatcgag aatatatagc | 780 |
| atttaaggat ataagactaa gagataataa taacctagct tagagcttaa agggatacac | 840 |
| tagccatcaa gtcaatttgg tagacaatct aaaaacaaat aattcgatga aataaagtt | 900 |
| gtattttgt gttttcaaac atgtttaag acgaaggttc ttgataaatt tgatctcaat | 960 |
| aggtaaacaa tggtaattac tcgattataa ttactcacta aataccaaat cgaatataaa | 1020 |
| ttattactaa ttaattatga acatgtttta cattttaaaa aatgaataat ttttttttta | 1080 |
| gaatttgtgt tattgaaaat aattttcaaa acaatattga atgaatctta agtgaaatca | 1140 |
| atgtattaaa agaacataaa acataatcta gatggtctat cgaacaagct agaaaatatc | 1200 |
| ttccataaat ccaatgatta agacaggcag gcaggcatga agataagagg attggattaa | 1260 |
| ttggtgattt taagttatga ataaagacac aagaactagc agctctcctc ttcttgtcac | 1320 |
| cttcctttgt catccagctc acacaactcc aacttggaat ttgacaggtc tctcttcact | 1380 |
| catacattcc cacatgaaat tattaattga atcttcaaca ttgtctttga ttcttcagct | 1440 |
| gcactgtcct tttccaccat ttttttcttc aagataaaga ctaataaact ccttatatat | 1500 |
| tcctctcttc ccattcacct gtgcatactc acaaagcaac tgccatttcc ttcttgttta | 1560 |
| tctctgtttt tttcttacac atttgttgaa ctttccctct gaaaaa | 1606 |

<210> SEQ ID NO 20
<211> LENGTH: 1487
<212> TYPE: DNA
<213> ORGANISM: Cucumis melo

<400> SEQUENCE: 20

| | |
|---|---|
| taatgaattt gtatttgtta gtggattgag tttatatgat attaattttg acccaaacag | 60 |
| ttgagtacgt aattaatgtg gcttgcattg aaagtgatat gggcatatag tatgtgtaga | 120 |
| atgtagctga cacaacacat taacaaaacc caattttaac tttttctttt ctttttcttt | 180 |
| ttaattttat atggatcaga tcacatgtca ttttccatta caactcactc tctaccaatc | 240 |
| atcccatccc ataggccata ccccataaca tccctttcta aatatctaaa tcatctccct | 300 |
| aaattattac atttttttc tctcaaatat aactattcaa ttcataaata ttattctttt | 360 |
| tttagctctt attatttcaa ttatgatttt aaatattcct tttcaattta cgaccttta | 420 |
| ttaccatat caacatttta attctactca attaaagatc attataatga aatttcaggt | 480 |
| ataacaaaat aaataggtgt gatataatga tggactacta atttcactaa tttcgtcatc | 540 |
| tgaaataagg acaagttcca actatcacta ttgtgaaaac ctcataactc ctaaaagtgt | 600 |

```
taaaattgga ccctcaagtt tataataatt ttgcaaattg aatcccaaaa ttaaataatc        660
agtataattt atacgttttg agagtcaaat ttaatatttg aataagcttg aatacttaac        720
ttctaatttt gaaaatttaa aaatgcaact gcgagagtaa cttttgcaat tagccgtcga        780
aacaattaat tatattggtt aatttatgtc tcattctctt ttgatgacca taaagataaa        840
cccatttata atataaatat caagcaaagc taaaacaaaa tctttttttt ttcaaattag        900
atctaaatat gaataaaagc agaactttct agaagtacaa atttgattat ttttcttgag        960
ataaaatttt cgctatgaac cttttttataa taggaaaaag agaaaaagga tggttttata       1020
taaatgtatg ataaaaaggt aataatatcc attgtaatag taaaaagaa aaaagaaaa         1080 aaagaaaaag caattttctt tttcatgatt aggaaatata aaaacaaaaa ttggctccca       1140
attgacatct ttaatcttct tttttctttt cttagaaaat aaaattagtg agagaaggaa       1200
aaaaacgaag ggttgagaga tagagagaga aaaaattgat ttttaattta gtttattttc       1260
cttttttgga gcacaaaata aatagataaa taaatatta gtttgcaaaa aagcccctcg        1320
agtttatctt atttgctcaa aaaagcaagg ataaatacct cccgacatcc ctgtttatcc       1380
ctctcagttt cataattcca ttggttcgat aagaaaacaa ttctcccaat attcccgctg       1440
tagatctcgt cgatttttccg tttgtttccc gggaagatca atcaaag                    1487
```

<210> SEQ ID NO 21
<211> LENGTH: 1448
<212> TYPE: DNA
<213> ORGANISM: Cucumis melo

<400> SEQUENCE: 21

```
ggtgtcttgt tgtaaggaaa tggaaagaaa agagaaaggc tcttgttgtt gtccttgttc         60
tgtgtatcga tgaaaatgga tcgacgcgaa gaagatgaag gacgagagtg gggattataa       120
gacagagaaa ctccgaaatt tgagggctaa tatggtaata acaaatggcg ggatactttc       180 aatgacgtg gacccattgc ttctttaact caccgtctga tctttatttt acggtcatga       240
tttccctctt tccccaatat ttttgggagg gaaaaccaac tttgttttg taattttaat       300 cattttttcct caaatcgtaa aaaaaaaatt atagatttt tcaaaaatag aaaaaattca       360
tataagaaaa ccaagataaa atattttgaa aaatatccta ttttttactt cttaaaaata       420
attcataaaa gaattattat aaatattaaa aaatatcagt accactatag caactatttt       480
atatagcaca tatagatata tttgttggtt tttctattta gtatttgaaa acaactccaa       540
aaacaataca tttcaatata cctacgaagc atacaaatat aattattaat tttaataagt       600
tcaaaaatat ctaatggcat ccttatttaa tcaatttttt catcgacgtt atacacggta       660
aggatgtcct aatccttgac cattgaaaga cgtttgtttt gataattata tcttttgata       720
tatacaaaca tttatctcat gattagaata gtcacctttt tatttgattt aacgattata       780
cataatattt gaaattttt aaatccatca acacaatcaa accaaaaatt tcctaactac       840
ataatctaca agagatttac catcttcttt aaacaattgg tcattacgtt tgttaatgtt       900
taaaattaaa tgcaaccata ttgggtgtaa aagccaaaca ttgatttgat tattaaagtt       960
ttttctatat agactgatg tgtaaaccta ataccaact tgagctaaat aacttttaatt      1020 tctaaaattc attaaactgt cctcatccaa attataatat caaagatttt tgaaatattt      1080
aaaaattccg aacatgggaa ctactggaac ttggcaataa attcaagcaa gaaagaggaa      1140
aacgatataa tcaaacaatt aaaaaacaac agaaatttat ttaatcaaag gaataatctc      1200
atcttttatt tattgggttt tacttttaat actgtgagtg atgattggaa cattaattaa      1260
```

-continued

| | |
|---|---|
| catttaagac attaatttgc aacaatcaat caaaattgta taaatccact tgttttgatt | 1320 |
| tatttgaacc atcactttt tttttatata tatatataat atgggagtga aagatcaaac | 1380 |
| gtataatcat gaaatgaaag atgggatatc attgaactta attaaatatc attgaactgc | 1440 |
| aattttt | 1448 |

<210> SEQ ID NO 22
<211> LENGTH: 1235
<212> TYPE: DNA
<213> ORGANISM: Cucumis melo

<400> SEQUENCE: 22

| | |
|---|---|
| aaatttaat aattaaaatg aacaattttt caagagtaat agagtttgag agatgtcaga | 60 |
| gaagtttgag gaagaagata acaagtggga gaagagaata agtttgttgt gtgaaagaga | 120 |
| aggggaaatt tcattcaagg gtatattgaa cttttactc aaattttgta agtctatttt | 180 |
| ttccgatcaa tcctaaaatc acacacaccc ttaaaaaatg gattatattt ggcaattttc | 240 |
| catgataaac tcatttttaa tttagagtta ttttttcaac gagatattaa cagttttagt | 300 |
| tcatatacta attgtaagaa tagtttcttt taagttgaat agaatttttg aaactttaa | 360 |
| tagttcaaaa ggtatttttg aaacaaaata agaatgtttt tgaactttt ataaaaagaa | 420 |
| ttgagatttt tttgaaattt ttgataaaga gaaagaaaa gaagaaagaa aaagaaaaa | 480 |
| caagtttgta gaactccgtg ggaaaatcgt cgagggccct gtgaaggaat tttgaaatta | 540 |
| taatgagggt atttctgtca acaagggaat ttagacatcg tatataagca tcctcaaacc | 600 |
| ctataattaa gcccttcaat ccaattgcca ttctccatct ctcgccgcaa gggtttaaga | 660 |
| gcagcttctc tcctcaggtt ggggtttccc cctatcttct tcattcttcc tcttctcgat | 720 |
| ttcttcttc tatttgctcg atagtctctt atttcttgag cttttgctgt ttttctcctg | 780 |
| tacatcctaa catgaattat aacttggttt tgattttgtc ttttacttct gtattaaaca | 840 |
| actttctta ccctttatt cttctcttct tcttcgtgtc cctgcccttt tgttttatg | 900 |
| ctaattttat gtttctgttt atcaatctat cgaggcgtga cctgtcgttc ttccaatagc | 960 |
| gtagatctgc acttaatcta ttctagctga ttggattggt cgttttcgt tttttaatt | 1020 |
| tattttctct gttctagttc cgataaattt ttttatatat aattaacaag ttctccagcc | 1080 |
| aaaagggtta atattgcgtt ggatatttta attttacgt tatttagatg tgtgaatcta | 1140 |
| ataaaattag ggttattcat aaatttcagt aatgatattt tggttatctg ttcttgctgt | 1200 |
| tcctgtttcg cagttctttt acctaatatt caagc | 1235 |

<210> SEQ ID NO 23
<211> LENGTH: 2003
<212> TYPE: DNA
<213> ORGANISM: Cucumis melo

<400> SEQUENCE: 23

| | |
|---|---|
| ctagacattt ttgtctaacc tttcaaatgt tttgttttaa tcttccctct cccaaatagt | 60 |
| gaaggacatc cagtgtcaac cgtgaacgca tactgtgtca ttcatgaaac aaatcttttt | 120 |
| tgtagtgggc attgtcagca tacatagcat gtagaagcta tagacagatg ttgctttgag | 180 |
| ttgtatttag ttctctttaa aggaactttg tacaaagtac tgaatgtact ctgttatttg | 240 |
| aaatatcaat gaagtcctct taattctttt gagttcccat tccacgttta agttgttagt | 300 |
| tgtattcatt ttcgcttact aggtgttctg catgtatctc acagagagac tcacgtgaaa | 360 |

```
tgtttaggcg gtcacatccc taatgacttt tgaaggggtg tgacacgatc atttgaatat      420
atcacttatc taatagtgac agtggtctat atctttgtct atctgtatag atcattggtt      480
gtttagatat tggtacacta ttgtgtagtg aaaaagaag aagaagaaga aaaatataat       540
acttgataat gagaaaagaa taagaaaaaa tattgtcttt atgaaagatg aaaaaatgat      600
gctgaagacg agaaatgacg gaaaggaat aaattctaga tgaagagatg aagaaattct      660
agaagaacaa atctagaatt tataaatggg ataacaataa agataaatgg gataacaaag     720
aaaaaaaatc aagaaattac ctaaatgttt caatcttgct acgccttaat tagaaaaaga    780
aaagaaacaa aaaagaaaat gcacaaaaat atctatatat atatacacac acaagcacaa     840
gaaaaaaatg aatattggaa aaagacgaaa atgcattatt ttttatttgc gttagcgagt     900
tgttgtgatt ttgtgagcaa gaaaaggata tgcaggagaa ttaagataaa taaggaagat     960
tgaatagaga ttaaaagaga aatatgggaa tagagtgggg atgaaaggtt taaagatagg    1020
gagggaggga gcgagagaga ggagaaacaa acataccttg agaaagggag aatgagagag    1080
ataataaata aatacggtga tttggaactc ataaaaagat taaaaaaaaa aaccttagag    1140
taaagacttt tccatgcatt tcgagaaaat ggaaagaat attctattct atttgcttgg     1200
acaccaagtt ccttttgtc gcatgcatac gtctatttat ttctgcttgc ttgcataggc    1260 agttttgtc caaggaaatt cagcaaaggc ggtatcaatt tcgtcaactt agaatccact    1320
cagtactatt tgaagttcct cactaccaat ttgcaccatc caatctcttc tctctccaac    1380
ttcctgccag ggcttaacct ctcttaattc cttatcctta cttgttaccct tacctggttc   1440 cactcttcac gtctctctat tctatattgt ttttttttca ttcataattt tgttactctc    1500
ttctctgtcc cctttgtctt ggatttatc tctccatata ttcattggaa taatttaagt   1560
tctttgtaga tttatgaaa ttaccaattt aattttttcaa acagttttg gatttgttta    1620 atttctcctt ctctaaatcg cgttgacttt atgttatttc gcccttgctc tgttttctct   1680
gatcataaag tatgtacttg attttatggt gaatgctttc ttgatttaac aaccctggtg   1740
ctgaaatctt ttttaaatcc tacttttgtt gttttacata tgttcttact ctaaaatgag   1800
cgacttattt cctttattc ttccttcttg attaaggatt taatcgttga agtatgctta    1860
tattgtggaa atttggtttt aattgatcat acgagctagt attactagct tctcggtttc   1920
tttggatgag ttatatgcat atgatgattt caattccaat ttttatttg caacagattg    1980 tttttttgtgg ctgaaattca agt                                           2003

<210> SEQ ID NO 24
<211> LENGTH: 2015
<212> TYPE: DNA
<213> ORGANISM: Cucumis melo

<400> SEQUENCE: 24
gatcagagta gcagttgagc aaacccaaac caaacccttt atctatacaa tcctctcaaa     60
ataaaattat tgtttaatta ttcccatatc tattatcatt tttccataat tgcattgaga    120
gaaaaaaaaa aaattctagg agacctaaat acaacaacaa ctatttaata atagccccat    180
gtcacattaa ataaaactaa caaaaagttt aatcgtcaa gaaacgatac ttgtggatat     240
tgaggcatgg gtccctcctt ctttgtatat tcaaatctgt ggtctgccat cagataaggc     300
ctttaccata taatagtttt tcaaaaaagt aagcaccact tgctgctttt ttaatttaat    360
tatatttaat ctaattattg aaacttatag ttgttttcta tccttattct tttcttctct    420
tcaaacaccc tcctattaat ttaaaataac caaacaacct ttttctttac atagacaaac    480
```

```
ttaattagat taaatataac ttgtaattag attaataata tagtttaaaa agaattttat      540
tttaagtaga attattagta aaaatgaatt ttgtggatag atacttggaa tttaagagaa      600
agttaaaaga gagaaaaata tgaaaaggaa ttaaatgatt aaagttgaat gtaagaaatc      660
aataaacata aattccatgt attaaatttt tgtcggtgtg tgaataaaat aatatctatt      720
actattagat tacccagctt tgtttataaa agaaaaaga aaaagttttt aaaatattgg      780
aaaattttgt ataattattg aagaaattgc gtggtctttg caatttgggc atcgttctta      840
tcgcttccaa tgaaggggcc gtttacctcc accactattt ccaacttgtt tttgtaccat      900
tctctatatt tctttgacac ctatattaca cgtgtcttta atccattgga ccttcgtcct      960
actatatttt tacccgaaat gacgaatctg tccttctcat ccacctataa attcacctct     1020
ccggctcctt ccctttcatt cagttttcct ctattcttct ctctatacgt catattcatt     1080
tcttccaagg ttcgtcctcc ttttatcttt cttctttctt tcactttttt tcgcttttt      1140 cttttctttc ggttttgtt cttttaattt cattcgtttc ttttgttat atggtatgtg       1200 gtatttgttg aattgagatg ttttagggtt tcgatttagg ttttatttct tatcctactt     1260
aagggctatt gtgattttgg agaaaggagt tcttatttgt ttttttttt ttccttttc       1320 ttatctggca gatgcaaatc ttcgttaaaa ccctaaccgg taagacaatc acccttgagg     1380
ttgagtcgtc tgatacgatc gacaacgtca aggccaagat ccaggacaag gaagggattc     1440
ccccggatca gcaacgtctc atcttcgccg gtaaacaact cgaggatggc cgtaccttgg     1500
ccgactacaa catccagaag gagtccaccc tccaccttgt cctccgtctt cgtggtggca     1560
tgcagatttt cgtgaagacc ctgaccggaa agaccatcac ccttgaggtt gagtcgtctg     1620
acaccattga caacgtgaag gccaagatcc aggacaaaga aggcattccc ccagaccaac     1680
agcgtcttat cttcgctgga aagcaactcg aggatggccg cactttggcc gactacaaca     1740
tccagaagga gtctaccctc cacttggtcc tccgtcttcg tggtggtatg caaattttcg     1800
ttaagaccct gacgggtaaa accatcaccc tcgaggtcga atcctctgat accatcgata     1860
acgtcaaggc aaagatccag gacaaggagg gaattccccc agaccaacaa agactcatct     1920
ttgctggtaa gcaattagag gacggccgta cccttgccga ttacaacatc cagaaggagt     1980 ccacccctcca ccttgtgttg cgtcttcgtg gtggt                              2015
```

<210> SEQ ID NO 25
<211> LENGTH: 2006
<212> TYPE: DNA
<213> ORGANISM: Cucumis melo

<400> SEQUENCE: 25

```
accaccacga agacgcaaca caaggtggag ggtggactcc ttctggatgt tgtaatcggc       60
aagggtacgg ccgtcctcta attgcttacc agcaaagatg agtctttgtt ggtctggggg      120
aattccctcc ttgtcctgga tctttgcctt gacgttatcg atggtatcag aggattcgac      180
ctcgagggtg atggttttac ccgtcagggt cttaacgaaa atttgcatac caccacgaag      240
acggaggacc aagtggaggg tagactcctt ctggatgttg tagtcggcca aagtgcggcc      300
atcctcgagt tgctttccag cgaagataag acgctgttgg tctgggggaa tgccttcttt      360
gtcctggatc ttggccttca cgttgtcaat ggtgtcagac gactcaacct caagggtgat      420
ggtctttccg gtcagggtct tcacgaaaat ctgcatgcca ccacgaagac gcaacacaag      480
gtggagggtg gactccttct ggatgttgta atcggcaagg gtacggccgt cctctaattg      540
```

```
cttaccagca aagatgagtc tttgttggtc tgggggaatt ccctccttgt cctggatctt    600
tgccttgacg ttatcgatgg tatcagagga ttcgacctcg agggtgatgg ttttacccgt    660
cagggtctta acgaaatttg cataccacca cgaagacgga ggaccaagtg gagggtagac    720
tccttctgga tgttgtagtc ggccaaagtg cggccatcct cgagttgctt ttccagcgaa    780
gataagacgc tgtttggtct gggggaatgc ctttctttgt cctgggatct tggccttaaa    840
agaacaaaaa ccgaaagaaa agaaaaaagc gaaaaaagt gaaagaaaga agaaagataa     900
aaggaggacg aaccttggaa gaaatgaata tgacgtatag agagaagaat agaggaaaac    960
tgaatgaaag ggaaggagcc ggagaggtga atttataggt ggatgagaag gacagattcg    1020
tcatttcggg taaaaatata gtaggacgaa ggtccaatgg attaaagaca cgtgtaatat    1080
aggtgtcaaa gaaatataga gaatggtaca aaaacaagtt ggaaatagtg gtggaggtaa    1140
acggccccct caattggaaa gcgataagaa cgatgcccaa aattgcaaaa gacccacgca    1200
atttcttcaa taattataca aaattttccc aatattaaaa acttttcttt ttctttttat    1260
aaacaaagct gggtaatcta atagtaatag atatttattt attcacacac cgacaaaaat    1320
ttaatacatg gaatttatgt ttattgattt cttacattca actttaatca tttaattcct    1380
tttcatattt ttctctcttt taactttctc ttaaattcca agtatctatc cacaaaattc    1440 attttttacta ataattctac ttaaaataaa attctttta aactatatta ttaatctaat    1500
tacaagttat atttaatcta attaagtttg tctatgtaaa gaaaaggtt gtttggttat     1560 tttaaattaa taggagggtg tttgaagaga agaaaagaat aaggatagaa acaactata    1620 agtttcaata attagattaa atataattaa attaaaaaag cagcaagtgg tgcttacttt    1680
tttgaaaact tattatatgg taaaggcctt atctgatggc agaccacaga tttgaatata    1740
caaagaagga gggacccatg cctcaatatc cacaagtatc ggtttcttga cgtattaaac    1800
tttttgttag ttttatttaa tgtgacatgg ggctattatt aaatagttgt tgttgtattt    1860
aggtctccta gaatttttt ttttctctc aatgcaatta tggaaaaatg ataatagata     1920
tgggaataat taaacaataa ttttatttg agaggattgt atagataaag ggtttggttt    1980
gggtttgctc aactgctact ctgatc                                         2006
```

<210> SEQ ID NO 26
<211> LENGTH: 2017
<212> TYPE: DNA
<213> ORGANISM: Cucumis melo

<400> SEQUENCE: 26

```
atggataagg cagagcttac cactaacctt ctaagatatt ttcgtcgctc ggcatttatt     60
cttggaggga accacaccaa ctccaaaata cccatgaaac ataggaaaaa atggttcata    120
gtctaagttt ccatttcgat tcggtttggt tcggtctttt attttaaaaa caataaatat    180
aaacctacta atttgatgat gacaagttta ctaatgttaa gtaagaattc atcaatacct    240
aagaatttgc aagttttctt taagtttgat ggtaaggatt tcgtaatcct tgaaatacaa    300
caattgtata gaaatgaagc gttgcatttt taacgtctat ataggaacac tattttactc    360
caatcaagtt gtaatttgat agataatagt ttgtataact taatgatgaa gagcttttt    420 ttttatatat aatttttatt aatacgtata gttcaaaatt ggaattagct atcactaaca    480
cgtgcttgcg atagaaacaa caataaattc aattagtgtc gcatgtattt catatggtat    540
tgatgacata agagtagttt gatacgatgg gttacatgga gtgacatgat aattgtatta    600
aatttcaata gttatgatct caagtttggg ttgtgtctca ctttgagctt tttgagaaat    660
```

```
tggcctcaag actcgcctaa tttaatgttg cttcaagcta tagatgctta catcgtgtgt    720
atgaaacata ttgcactttg atgcttaaag ttaatatagt gagtaactaa ccagatatta    780
cacgctactc ttttaaaatg gtcaaataag aacatttatt agtatgtgat ataacacgta    840
ccctccaatt acatacaata attgatcaac ccaaatcttg aggtatttaa taataacaaa    900
tacaaaatag atggattata tatctgaata gctaaagaat aaagaatatg tgttatgttg    960
tagttacata gtacaataag tcctctcaaa attagaatgg tataataaaa aataagaggt   1020
acattcttaa agaaaatgtt atcaaaactg ttgcatcata ggcattttgg caggaagaat   1080
agtggaagaa aattcttaaa cctaaattct atcgatatta aatagatttt ataagggata   1140
attgcaaatg tagcaattat atttaaaata attaagtata tagcaacatt ttaaaaaaat   1200
ggcaaatata gcaaaatttg tcaaaatcta tcgatgaccg atagatcatg taagtctatc   1260
actgataaac cataggagtt tatcaacgat agaagtctat caccgataaa ttttgttata   1320
tttataattt ttttaaaata ttgctacata gttaataatt attctaaaaa ttgctattac   1380
caccggtttt taaataggac ctaaatttaa ggtatttgac ataaattttg atgaaccaaa   1440
ctagcccaaa tcaagaagt ttgggcccaa agcccaacga atccacaaca aacaaagccc   1500
acacaacact tcatgaaaat gatttttttca aattttagaa aaaggttata aatataaaa    1560
aaaataatca aactatccct ggtagctaag tagttattat tattttatg gatacgaatt    1620
gagtagtatt tattttaaaa taggataatt gatcttagtt tcacttgtga tgaactattt   1680
cactttatta tttgtttgta attcaataaa attagggttt gattgtcaat gataattatt   1740
acaacctcaa tattatactc agtaaagaaa aataaaaatt taaaattgag aaattaatac   1800
caattttttt tgtgaaataa aaggaaaagt aagtaaatat tataaaattt tggacttgga   1860
aattaaaatg cattaataat aatatttagt attattgaat taaaatggac accggaaacc   1920
ctaaaagagg gagtggccac ctataaaagg gaagcactca tctcacccaa acccttgtta   1980
ttcccaattg gccgtgcggc aaagaagcct ctcaacc                            2017

<210> SEQ ID NO 27
<211> LENGTH: 1353
<212> TYPE: DNA
<213> ORGANISM: Cucumis melo

<400> SEQUENCE: 27
tgagggtcaa aggaggagga agaacaagaa gtaaatgaag tggagtcatg ggaaaaggaa     60
aacaaatgtg agaaaagaaa gaaagccaga gagggaacat aaaattatta gtcagaatta    120
caacagaaaa tttctgaaga attgagtttg tatgcagcaa taatatattg aacaaataag    180
gagagaagga ggagggaaa ttcaataaac agcagaggaa gaagaatggc gaaaacccaa     240
tatctaaaac tagttaattc aacaagaagc aacacaatca tttcattaaa aaaagaaaag    300
gtaaagagaa attcccagat tcgttactct agattggtcc aatggagtgg aaagggatgc    360
aatgaaatca gtaatagaaa agaaaagagt taaagtagta ttggtaggta ccgattaaaa    420
atggaaggcg tcggaaggaa acggagagtt caataaaagg aagattcttt gcttcctccg    480
gccatttgat gagaaacaaa aactccgcac ctccaagttc cttccgggg aaggagaaga    540
ctcttctatt ctggggtaca caccctccct tcctgctaca gaatcaaatc taaattattt    600
tggattggaa tggcatggga ttggtctaac ttccaatttc tcgacacaca accccaatct    660
acccgccacc tgtacccagt tttcccaaaa cgcaactcac attgcaattg caattcttgt    720
```

| | | | | |
|---|---|---|---|---|
| ctttaataaa | tacaaattga | ttttctttt | tcttttttt | tttttttaat aacgattaac | 780 |
| cctaaaaaa | ataagaaaa | gaaagccgat | cctaaaagta | gaattacttt ttttttgttt | 840 |
| ttcaaggttc | acgtctgtgt | ttgcatagac | gtgttgtagt | cggtgggtgt gtaaattaga | 900 |
| gtttgttttt | ctcatctctt | gttctttta | acgaaattc | aaagatacaa aagcataatg | 960 |
| aagaaagta | tacaaagcaa | cgtaaactta | gcattttgca | catgatacaa atttagtcaa | 1020 |
| actcaaaccc | tggacaacct | agcactctct | tgggcacgtg | gtagatttat gtgaatttcc | 1080 |
| ctatttttct | tttgaactca | caaatgggca | aataataata | ataaattta ttgttgattt | 1140 |
| ttcttatatt | tcaatttatt | acctctagtt | ttaacctaaa | gtttagatgt atataattat | 1200 |
| aaatgagcgg | tgaaacgggc | actgattgat | gaatatattg | ggccttgggt tggcccaaca | 1260 |
| aacctaatgc | ccaaatataa | aactttggca | accatagtta | accctaatct gtcaatctac | 1320 |
| tctcctcgac | tcggtaaacc | tgcgactccc | aca | | 1353 |

<210> SEQ ID NO 28
<211> LENGTH: 2005
<212> TYPE: DNA
<213> ORGANISM: Cucumis melo

<400> SEQUENCE: 28

| | | | | |
|---|---|---|---|---|
| cagtgtgctg | gaattcgccc | ttatccaagg | agattaatgt | cgagagatta ttatcgaggt | 60 |
| ttgaatttat | tttgtccaat | catatgattc | caagagctga | ccatcaattc aacagaacat | 120 |
| gaaccggaac | ctcataccta | ttgtaatggt | tcacagcatc | ctaatacaga acatgaaccg | 180 |
| aaacctctta | cccattgtaa | tggttcacag | catctttata | cgtattatag gtagtaccat | 240 |
| tgaagatgca | tttaaatgct | gtccatgctc | tgttctctaa | aaagttggac ttggacttgg | 300 |
| acgtcagctg | aaagtatgaa | atgcactgta | gccaacgaag | ctatgttttc aggcttcaac | 360 |
| atggttttag | gaaagtggag | gctctttggt | tgaaggggttg | aatgaatgct tttctaattc | 420 |
| cagcatgatc | ttcaaatttc | gacacaaaaa | gcttaagtat | tttgttccgt tattctttta | 480 |
| atccttgtat | tgttatatat | tctttctct | gaactgaatg | tacgatgatt gcaggggtcg | 540 |
| agagcaagtc | cgatataatg | aaacacgtaa | ggacgtgatt | gaatgaaaaa ctatgagcag | 600 |
| agatacaaag | tctaacttac | gggatgaacg | atgagaggtt | tgaccaagag ctgtgacgcc | 660 |
| tgtatatttc | aacaaaagtt | gatgactaac | atcacatgtc | agagtaatca agaaatgca | 720 |
| gccgcacata | tatatatcta | tatatatatc | gtttagtttt | ttttttttt ttttatttt | 780 |
| ttttttatc | taattatatt | ttaattctat | tttcctctgc | cctcctcccc ctcctcttcc | 840 |
| cccacccttc | ttctgcacat | agtagccaag | gattgatcgg | tttctttga ttcgggggga | 900 |
| aaatgttgta | caatttttgc | ttccatagaa | gcttgaaagt | tttgcagatt atgttgtaaa | 960 |
| attacccttg | tgtactcaca | ctagttcttc | tcgtggaaac | ttatattaca atggttgagt | 1020 |
| tttaagggc | atattcacac | tggtaactac | catttctaa | tttatgaatg ccagtttct | 1080 |
| ctccatgaaa | gaccttcaa | atgccctttc | ctccgcggtg | cgtttgttgt tgtaaatgtg | 1140 |
| cagtgtcgtt | ggatacacga | ttgtgtgaaa | gggaaaaggg | aatacgatta actcttaaat | 1200 |
| tcaacccta | tctccatcag | tatcaatcac | atttcagcaa | ctagctcttg aataacattg | 1260 |
| agattcttgt | ttaatccacg | tactactact | actattacta | ctatttgaca gccgatatct | 1320 |
| caaataacat | ccatatttat | caaattggta | ttttaaggac | tttaatttc ttcgtacata | 1380 |
| tttcattata | atttaactac | tctgaccatc | attgaaaatt | tcacaaagaa gacattttaa | 1440 |
| attgaattga | gttgaattaa | gttgatataa | tggttgaacg | ttggatttaa tttataattt | 1500 |

```
agtggtgtat gggtccattg taataattct taaaaaaaat atcatattct gaattctaaa    1560
gaaccatcta agaccaaaac taaggggtca ccaatgagta tggtaaagtc aacaaagttt    1620
gtctactttt cttatcctta tcatcaagag tgcaatatga tatcaaagat aaattgtacg    1680
tgggcgtcat ccattgggta agaccaagaa gcaaatatc atagagaagt tgttttagta    1740
gccataggaa ggaaggaagc aaaataataa tatagatttg aaattgtgga tgataaactg    1800
ccaaatggga attcaaaata aactaaataa ataaataaa aagagaaatc ttgggagttt    1860
ccattttagc caatgaggaa acagatagag atctcatcaa gataaggacc ctattctctt    1920
cttcatctat aaaacaaaaa caaatcaaac cctcatttca ctcattcaaa acaaaaagta    1980
ctccaaagtc aaactaacaa atacg                                          2005

<210> SEQ ID NO 29
<211> LENGTH: 1445
<212> TYPE: DNA
<213> ORGANISM: Cucumis melo

<400> SEQUENCE: 29
tcccttcagc cacttaacac ttaaaaatct taggaaactc cattggctcc tctttctcca      60
atgaaatttt gacatctgtg ttgttgatag ctcctatatc ctttgagaat ttgatataca     120
cctgtcattt gctgatttgt ggataactgt tagccttttg atattgatac gttccttttt     180
tatgaatttt tgtaaatcca ttcaatttta atgctgtcgt aaatgaaaag cccttttcatt    240 aatgttgttt atatacatat tttaaaatta attcaataac aagtttagtt ctgttagctt     300
ctaggtttgt atctatttta tctattaaag gtatgtttgg gcttcaggtt ggaatggagt     360
agaattgaat gggttgggga gtaaattttc cattcaacaa gttcaatttc aaaatggcta     420
ataagttttg aactcaattt tattttcaat aaattcctta attttttgtt ccttgtttgt     480
aaactattga cttattcgat atattttaaa attgaggtat tttaaaaaaa taatacaata    540
ttaaaattat ttataaaata taacaaaatt tatgtatagt ttatttgaaa attttactat    600
agtttcattt ttatattatt cctaaccatt tccatttaaa attatttcaa ttatttcttt    660
tattaatata attgaaattt catggattta ttagacacat gatttgaaat tttatgggtt    720
tattaagtat tttctaacac aaaatcgctt ccgcatcgtt ttcaattcat tcagtaatag    780
aagtaatttt ttaaaagaac caaatttgcc aaatttgag ttccataagg actctgaaaa    840
ctcattatgt ctattactct tcactaattg tagagactta aattcaagat aagagacact    900
aattgatgat aattgcccaa aaaataaaaa taaaatgtt tcttccccat cctcaacctc     960
catgaattca cagagcccaa agattaatta ttgggccca attcctactc atatatacct    1020
tacagtccct caaagaaatc ttaggaagta atcaatttct gtttattcaa gatgtagcct    1080
cccaaaagaa aaatacatca catcaaattc aaacaaaaat atctacagct agcaaaacct    1140
caaaccgtta aaatttcaag ccacataaat gaaattttca tctgaaaaaa ggacaatcta    1200
tctagacgtt agatttcagc cctaatatga atctgaagca tttggtggac gagaaagagc    1260
catgtaggaa tgcatcaaac aaaggaaaaa tctttgaact ccaatgggat tgaagataca    1320
gataccaatg gataagaatc tgttctcttt gcccactatt taaactcacc aaacccacca    1380
gtatcttcct caccacaaaa tacattccac cgttgatcac aagccttatt ccaccacctc    1440
caaca                                                                1445

<210> SEQ ID NO 30
```

<211> LENGTH: 1282
<212> TYPE: DNA
<213> ORGANISM: Cucumis melo

<400> SEQUENCE: 30

```
tgcaattaag aataagctaa tcttaatgaa gaaaagaaaa tgttctttgt atttgataaa      60
tggtggcgtt ttgggggact ttatatgctt ttttttttccc atgagattgg ttatcttcat    120
ttccgtcatg atgtcgccaa gtggcgcttc attgatgata tcttaaaatc tataatgatc    180
atcctctttg ccaatggtgt ggtgacacgt ggaaggactc tccatcttct aaaagattct    240
tcaaataaaa ataaataaat aaagaaaaaa cttgtaagaa gatacatatg tacatttttta   300
tatgaaatta atatgagaaa taatcgactt tacagtgact tgatcaaact ttcttatttg    360
tttcatatgt taggttaaat tactaatcaa ttcacgtact ttactagatg agatttcacg    420
tactttactc attgagtcca acggttgatt aacttatttc aagaaaattg attcattcaa    480
ggatgttttcc aactctcata taatttccat gttgttccac ttctatcaag tacaatccta   540
tcgaacacaa gtttgtttaa ctgaagttca ataatcgaga tcaagatagg ccttattatt    600
tcttctagag gttcaagtga tcaatcaaaa aaggtttatc acatgattca ttccaattca    660
actaagctaa taagtggtgt tgcatgatag agtatcggac tagctcgaac ccctatcaat    720
atgataaatg tctatgtata taaataggta cttaacccaa cgaacaatgt gtcttacgtg    780
agaaagcttt tttctaatat acataaaaag cttgcatgac tttttgatga attgtgtttt    840
gataaaacat atttgtgagt atattatctt tataaattta agttataaca acaatgtata    900
ggtgtgagta tgcttttaaa cttaataaaa aaattagaaa aaattacctt tttagtatga    960
aagttttaat gatatatcaa tttgtgtctt tatgatcaaa atgtatactt ttagtctcaa   1020
atgtttataa gaattaactc cttaataatt atcctaaaca atcatgttca aacttggatt   1080
cttattgaca catatttcat tttaatctaa gtttagaaat gaagataatt aggataagga   1140
tctttagctt atgatatctt atccaatatc ttaaataaat cttcaacacc aagaaatttc   1200
cctattgcgg atatttcaat atcgaatgcc ttggagtatc aaaggcattg gataacaagt   1260
gggacataat tgcgataaaa aa                                            1282
```

<210> SEQ ID NO 31
<211> LENGTH: 2002
<212> TYPE: DNA
<213> ORGANISM: Cucumis melo

<400> SEQUENCE: 31

```
ccgtagattg aacttatggc ttcggtcagt tattgagatt ttaattctct ttaacattag      60
gctaatccat gagtttacgt gtgctaacat gttaatatga aagtatagt agaaaagtaa      120
aataatataa ataaataaat tggattgttt tgaaaagttg aaagattaga atatacataa    180
gattctgaaa tatctcaaat ttttgaccca gcaaactgaa attagccaaa gtaggttgtg    240
ttgtaaataa ttatacttta tattgttctt tttgtataag cttttatgtg tcaatgacaa    300
ttttaacagc taaataattt aaacagaata ttgccaagat gggtggctac aaaaataatt    360
gtaaatagaa cccaataata attagtttaa tcaattatgt ttttattaac ttgtaaatta    420
aatttacact gaaaagttga aagagtttgg aaaatatttt atttgaataa atcaaacaat    480
tgaatactaa tttgcgtaaa atacgtagtt taaaatatat atatatgtat atatatatat    540
atagtgtaat tttcaagtaa taaataaaat gaaaattaaa ggtttaaaaa taagctaatg    600
ggtgcttaaa gtatctacgg aaacgagatt gcattcgact cacgtacgac atgaaaaaga    660
```

```
tataaatgaa ttttacatta aaactattaa attgcacata tgattgtcca acaagtaaga    720
agaatcacaa tcaaagtaaa aagaatcaca atcaaaagag aatgtatcta atggatgatg    780
acaatttact taagatttaa gaattaatct aaaaatttag agagagggt aaagatatca     840 acttttattt accagaacta aaaattatcc ttaggcctca attgctttag taatggatat    900
atatatatat atatacacat ctacctaaca aagctttaat aatagtaata ataaaaattt    960
aaataataaa taaagaaat cgaccaatat aaaaacatat aaaaaatgta tagttaaaaa     1020
gaaagagaga aagagagaaa gagagaagag tacatgcaag agatttgatt tggaaggagc   1080
acataatagg acaagagaag ggtaattttg gaatttgggt caattattct tagtccaagg   1140
gttacactac aaaaacctaa cagccttcac aaattttcc ctctttcgct cgcttcgctt    1200
tgcccaaaca ctcgcctcca actcacggaa tcagatccga agagtttggc aaaccctagc  1260
ttcctctctt caatctccat ctttttcttc tctaacaatc cacaggttt tttttcattc    1320 cttttctctt cgattttgcc ttcctcttct acttattcga ctgcacgaat atggttgtat  1380 gtatgttttcc gccctctttt catatccctt tttgttcctt tagccttgaa ctactctggg 1440 ttttctttc tttttttact tttttctatt attgtatatc tcaagatttg acgctaatct   1500
ggtctgtggt tgtgggttga gttcgttttt attcgtttgt ttgtttgttt gtttatggcc  1560
atggcttgta attgcttctg taatctacgt gaatctgttt ttgctttgga acgttttgt   1620 tgttcaactc atacgagaat cgtcgtctat agttgggttg ggtttttttt ttcagtagca  1680
tcttgctttg ggaaaaggtt aatgcggtgt cttttttttt ttttggaga aaaaagtta    1740 ttagacatcc ctcaactcct tttcctacat tgagacagaa gtttaatgct tgttttcctc  1800
tttatctgga ttgcaagttt ggcttttctg ttacagattt cctttctcag gatagctttg  1860
aacagatttg taatgttgtt ctgttattc cttggtgggg ttgataaaat ggttatgatt    1920
ttttgtttgt tggcggcata attctggata tttttatctg tttggtctgt gttcatattt   1980
gcattgtttt ccacttacag ct                                             2002

<210> SEQ ID NO 32
<211> LENGTH: 2003
<212> TYPE: DNA
<213> ORGANISM: Cucumis melo

<400> SEQUENCE: 32
tggatcgacc atgacattca aaacccttta agatatggat cttataaaat aaatgtaaag    60
ggtaaacaat tcttccttgc ttaacccaag ctatatattt tatgcactaa tttaggtatt   120
agagtatatt cagctgaaca ccacctacca atgctagtac tttaatcagt caattctaac   180
ttcgataata tatctcaacc aaattagtga aaaagagtcg taaatgaaaa actatgtacc   240
aagatattct atttgttttt tttatgttta aatatctcaa agataatacc taaaacgttt   300
tctcctcgta caaagattcc tcatttactt tttattgtcg taaactctaa tacaataaac   360
taaaacaagt acaaatacac tagctttaga aatctacttt ttattgaaac caaaaccaat   420
aattcaacat ttcattttca ccgacaaacc tttgtaaaca attgaagtaa tttttgttgg   480
tactatgaat agtaacatca agtcttcaag tgcatcatat caaccaagac atgttcttaa   540
aagcgacact aaaagattta aaaccaaaag catttatgaa atccgaactt aatcaaatcc   600
taaatatttt tcacttaaaa aaaaaaaaat aggaagaaaa attgacataa atgggatatt   660
ttcgttttca aactggcaag ccagcatgca ccacgttgtt gacgtgtcct tccacgtcgg   720
```

| | |
|---|---|
| aaaaaaaaat attaccacag taaaaagaga ataaaatgaa agtcgttgac tctcccttag | 780 |
| tcggaggaag cgcgtgaagc tgaagccgga ttagaaatcg gcaataaccc cgacacgtca | 840 |
| tcgaaatgct agtatcaaat attgtccgtt ggatcttcct tcaccaactc tatttgaacg | 900 |
| gccacgatct tccaggtcca acggttcgga agaatctttt cgaaattcca tggctagtcc | 960 |
| ctacactcct ccctattggc tccctagggc atcccgaccg gttattccgg ttgccgggaa | 1020 |
| ggtggctgga cgctataaat acccgctttg ttcatctcgt agtccttgta ccgttgagct | 1080 |
| tcgccttcta atagagctct ggttcggttg gcgtattagc tcgaattctt tctctcttcc | 1140 |
| agatctacgc tgccgatttc atcaggtttg cgagctctgt tccaccattt ttcttttcct | 1200 |
| gaagctttga gcatgcttgt gattcttcat ttcctcattt ctttgatggt ttatgaaaga | 1260 |
| atttaggggga atttttctctt tttgtattct agtggtactg gtagatttgt ttgaagtttg | 1320 |
| tttctcttct tctgagaagt gaattcttcc agatctgaca gttgcttttg atttttttctt | 1380 |
| tgggaattag tgaatgatac ttcgatactg ttttttgctc tctgagattc tggatctcgg | 1440 |
| gccttggggt tttctattgt cttttggtag ctatgtttcg tttgtcagct tgtatttgtc | 1500 |
| attgttgaat ggttcgatcc ggtttgtaaa taaaataaat tttgtaggcg cacttgtttt | 1560 |
| ccacggtttt cgtgttacgg tttcatgatt ccctagatct ctggttagaa ctaagttttt | 1620 |
| tgtcggtaat tggatttggt aagggactgt tactgtggtt gaattgtaga tccagtcatc | 1680 |
| ttctacatga gtgtagggtt ccttagggca gatcttgtgt tttataattt taattttgtt | 1740 |
| gtttccctga ttttgaacct gtttggttgt tcagattcgt cgagtcattt ccattcatta | 1800 |
| aaagtttcta taatttttatt tgaatcttct gaatctgtgc ttgtattacc cagatttcta | 1860 |
| taaacctatc ttgatttcaa gtgtgctatg tggtaactgt tgatatttc aagcttaagc | 1920 |
| aatactgatg tgactaaaac ttaactaatg aactgaatgt ttttttgtaca cgaactaata | 1980 |
| tggtgttttg ttatgtttca gag | 2003 |

<210> SEQ ID NO 33
<211> LENGTH: 1372
<212> TYPE: DNA
<213> ORGANISM: Cucumis melo

<400> SEQUENCE: 33

| | |
|---|---|
| aaataaaacg cggagacaaa cttggacttc cattcccttc ttcttccttt ttcttgtagg | 60 |
| aattcttctt tcttccttat aaaattctcg gaccctttttt ttttcctttt taatttatt | 120 |
| tttccttctg tagttcgttt cttgatttag attttcgaca aaggtaccct ttacaggttt | 180 |
| gttccttctc ttcatcgttt actccgattg atgcatttcc tctatttttca cttttggatt | 240 |
| ggaattatta cgatctatgt tcaatatcgt ttgatccatt ccctagatgg aaattatgtc | 300 |
| tctgtaatta tacatagtgt ttgatttgtt tgggaaattt tgtttctttg tgataatgtc | 360 |
| ttcatcgatt tgatgatgta tttgtttttt tttttttggt ggaatcgata tgattttatga | 420 |
| tttgggtgtt ttttgctttt tgagaattat gatttgatca gagttttttct tattatttct | 480 |
| gttgtttttgt ttcatttcct gccgtttta aagatgtgtt tagattctgg ttgttttttgt | 540 |
| cctttttgatt atgttttttat ttttcatgta gttggaaatc aataggattt cagataattc | 600 |
| atttggttgc atagggattt gaggattgga agttcggcac tctataactt tgcagtgaat | 660 |
| gatttgggtg aagttttttcc tcttgttttgt gctttcatgc ttcagttgcc tcaaccaata | 720 |
| tcgcttttttg gaagtcttga aaatctgtag ctttgagctt tgtttagtt cgcaactgaa | 780 |
| gcttcaagga aaaagtaatt tctttcgatt ttcgtaaaag gggggaaaaa ggaagtaatt | 840 |

| ctactaaaat tttctcctat gaactcgtag gtcacatagt tgttatttgg tcagttgaca | 900 |
| ctctagacta tcttgttacc attccacata actcaaaggt tttaagaata aactcaatat | 960 |
| gggaatggtt tcattaggat tgcagagtca ggaacaagag aggttgcttt gcacaagtta | 1020 |
| catactttct attcttaggg agaaaagcca gttgtcattg ttcagggaga agattaattt | 1080 |
| ggttggaaag atttattgtc cttctgtctt taggttgtca ttggtttgtt ataattaaag | 1140 |
| tttcttgttt cctagaaaat agaagttttt ccctatgagt aatgttatac ttcattgtct | 1200 |
| tttattttgt gacaagcaaa cagtgattta ttggatgaac tacagttaaa ttctgaatcc | 1260 |
| attaattttt ctgaaatcca ttgtgattag aatcatgcaa tgccaactga agaaattttc | 1320 |
| accaattatt aaatgaatat gtttatttgc agggtgtttt aaatagatca ag | 1372 |

<210> SEQ ID NO 34
<211> LENGTH: 1122
<212> TYPE: DNA
<213> ORGANISM: Cucumis melo

<400> SEQUENCE: 34

| atatatttat tgctagggtt ttccggttcc tgtttgctcc actatttcag ccgcctaggg | 60 |
| ttgaaacaac tcattcctcc gatttcagga ttactatctt cctcctcgac cttctccggt | 120 |
| aatactttct cttcacaccc cttttgttgt ttgtgatttt taacttcctt tggattgaaa | 180 |
| tgcgagatct gtgtgtttct accactcttc tttcttaact tttcgatagt attgcatgtt | 240 |
| ccttacttat ggagaggata atgtgtactt agggatatca atttcgttc acagtattca | 300 |
| atattcatga cttactgagg tgtgaggagt tttcatttca tagaccgact gatgctatga | 360 |
| tctcaagccg agtttgaccc ctgttttct ttttatattc ttttctttat ttttgtgtca | 420 |
| atatattagg tgatcaatga catcctaatc tattattagt gaattgagta ataagaagta | 480 |
| aagtcttgtt tatccaattt tttggtttgg atttattact attttgttgg aatgcttgaa | 540 |
| tgaattctaa tggagtccgt agaaatttgt ttcaggcgtg cgccttttct tctcactaaa | 600 |
| tttttcatta ggaatgggtg tatttatttt caggagaatt tgtcgattgg cgatagttgt | 660 |
| cttgttcttt tcatttcct ttataaattc tttatggaaa aaatgtatt gctgcaacct | 720 |
| ctgtcttatt acccctattt gaatcaatag agttcctgat ccttcctacg atgtggtttc | 780 |
| tggggatttc tctctgggtt cgtgtgatag atgggtgacc gagggaacac cctttattgg | 840 |
| aaatgctcct attcttcaga gtcggttct cattttctca cctttacgct tgctgctgc | 900 |
| tctcattgac agtcgaaccg ttttggaatt cgtgatattg tgtgtatttt ggggatgaaa | 960 |
| gttttctttta ataagactag tgacagttca ttattgattg tggagaaatt tatgaccatc | 1020 |
| taattttaat ttgaacaagg gaggatgaaa atgattgggc gcattgcatg ttttatccaa | 1080 |
| ctagtactca ttttttcttt gttctgatat tcttcaggaa ca | 1122 |

<210> SEQ ID NO 35
<211> LENGTH: 2017
<212> TYPE: DNA
<213> ORGANISM: Cucumis melo

<400> SEQUENCE: 35

| actattggag acgacgaagg aaaactctaa tgtgagctta gaattgaaga tggtgaacaa | 60 |
| ttgggagtct tttttaaaaa tctttcgtcg gtatattgaa atttccttt acactcaaat | 120 |
| aacccccctt ttcacgcgtt caacgtcttc aaaccttcct ttttcaatta ttttttcgtt | 180 |

| | |
|---|---|
| tacattaatg acatttaggt aataagataa attagtggat tcttttgtga aaaatgttag | 240 |
| cccatttaag acttttatga aatatattag aaaaaaatca tatagcaatt tatattattc | 300 |
| tagttaaaag cccataatag aaactaaccc aacctaaagt aacgtaaaca ttcaataaga | 360 |
| gagacaaatt ttaaaataat ttctaattaa aaaaaaaatt gtcaagaccg tccgggtcgg | 420 |
| atccaaaata taacccgaac cggccggttt agcatctata taaatacacc tttagggttt | 480 |
| ttattctctc aagacttcac cgcatttcca cttctctgag gccacggtca gccattggag | 540 |
| cagctcaata atcctttgac tccctactac ggtaagtcga ccttactgct ttcggcttct | 600 |
| agttttttca atcctgtcat tagtcctttg gagttcttct gtacatttat gacgttttcg | 660 |
| gctcgtgttt tgtttcgcct gtatgtagtg ggttttttcga gttttgtttt tacttttttt | 720 |
| tatacttgca ggaattagtt gaaatctatg tacttcatgc cttggataat actcttgatc | 780 |
| tgttgtgtta ttcaaaaatg aattgtttta agatggtatt tgagaatggt catgtgagtt | 840 |
| ttgcctactt ggttattaaa atgaattgtt ttaggatggt atttgagaat ggtcttctgg | 900 |
| gtatttggtt ggaacctttg tgctctgcta tgaattaggg tgttctcccc gttttttttt | 960 |
| tttttttct tttggttatt aatatatctt ttatgactac ttattcatat atgatatctt | 1020 |
| ttactcgtaa attttgactc atttgaaagt tttatcctta gtcctttctc attcagggtg | 1080 |
| taaaggtatg ttgttagggt taaaatagcc tatgcaggaa agttctgtat ttgttctaat | 1140 |
| tattgcattt gtgtgcattt gtatctagtt tatttcttgc tgagagtatg cttcattttt | 1200 |
| tagtacacat cacttgtgcc actttattat agttgcacat ttttgtttat ggagaggatg | 1260 |
| aatagcattt agggatgtca attttttatt gagaaacccc tctctcctac ttaagcttgg | 1320 |
| ggaattttttg ttctaaatgt ggtaaacata atacttcttc ttatttttaat ttgaatggaa | 1380 |
| ggggaagacg aatactaata ttttcaacga accttcacaa cttttttttc ttatttagga | 1440 |
| agccatgttt ttcaaaattg tactgtgtga tccacatatt tatcgattat tagtgaatcg | 1500 |
| aataataatt agagttttat tggtataatt ttgaagttca gacttattac atttgtggaa | 1560 |
| agtttggtta caattttcaa tttttattgga atcctaagaa ctttgtgtta acatatattg | 1620 |
| agttttcttc tctttttttt tactcattaa gttctctatt aggaatgttt ggttcaatgt | 1680 |
| cacatagtcg atagctaaga ccagtgaccc acaaagctat gattgaacga aaaacaagcc | 1740 |
| tttcacatct tggtaggaat ttgttatttc tcaatagatt tacagagctg tttcatgtga | 1800 |
| tcacaatttt tttctatttt tctgaagttc tctattagga atgggctatc tggttagttg | 1860 |
| cttttgagag aacatgtgga ttggtgttgc tcggtttcct tgcctttgta attttgtcct | 1920 |
| tggaaaaagc aaaatgatta ggtatcctga tatgcataac atgtttaagc caactagttc | 1980 |
| tcactttttt agtgcaaata attgatcttc aggaatc | 2017 |

<210> SEQ ID NO 36
<211> LENGTH: 2000
<212> TYPE: DNA
<213> ORGANISM: Cucumis melo

<400> SEQUENCE: 36

| | |
|---|---|
| aagttgttga ggctttcaat ccaaccaaat aattgtttcg ttttccacta caatttccta | 60 |
| gtactaaggt agcaatggat cgatccatag agaaccattt gattttttcac taaaatcaat | 120 |
| ggttgctaag taaccaaggg aggattggtt gaattgattc ctaatttcac ttcaataatt | 180 |
| aaagcaatgg caataaaaca aaaattggaa gattgttgaa ttaaatttag caatgagata | 240 |
| aatacctagg ccaagactta cgtaggttac tttagattca caactcaatt attgattcat | 300 |

| | |
|---|---|
| aatgatatta gattccttgc aacatatgaa caaaatctta gttgaccacg tctagagaag | 360 |
| ctaatgtgat gttctataaa tcaaatcaat ccttatgtct agattaaaag catcctagag | 420 |
| atgaaaatca attggcatta aggtttgagg ctaaagctaa gtcgatcaaa caatttggag | 480 |
| ttgtctaatt gattgttcga tgtgatacaa ttctaaacta gttagataaa cgtaattaga | 540 |
| atggaattgt caattcaata aatgattcta acttagctta tgttatcttg cagtctaaaa | 600 |
| ataacaatta catattagat ctagatctat aacaattaat taaacatgct tggaaaatcg | 660 |
| ccaatatttc cgaacacact caatcaaaga aataagtcca aggaaagaat tcattaaatc | 720 |
| ttaagattca caggatgaaa atgttcataa catcacacaa gtgtgtgaat caaaagataa | 780 |
| gactagaatc tcgagataat agtaccttag ctatgataca tcctcgaaaa catccaacaa | 840 |
| aatcaatgaa agtcttgagt caattcgtct agtaaaatac gaagagttca agagaaaatg | 900 |
| cctaaaattt agtgccaaaa attgtgtaaa aagtgttggc ggctagggta ataatgcaaa | 960 |
| attaagtcac agcaccgcaa caacgtgcaa aacacatgtg ctatactctc gaaaaactct | 1020 |
| atagcatcgc agtcaacacg ataccgctac acaacacgtt gtagggctga ggtgtttgca | 1080 |
| tgaaattaga ccattctacc ttacagcatc gtgccttctt cgttccattt caattttctt | 1140 |
| gccccagttg acacactaaa cctccaatta atctcgttta atataaaaga taattatgat | 1200 |
| tttctttatc tacgaacaac attattgtga aaagatataa ggatgatata tcacaatttt | 1260 |
| tagggaaaaa aggaaaatat attggcattt attatctcta tcaaatagat gattttacaa | 1320 |
| ttatatgtta agatgtttta atccttgcta atgtgaatat ttatttttatt tttgttcaca | 1380 |
| tgaaacaatg gtattttgta cactccaagt acaatagttt ctttaaaaaa atttaaaatg | 1440 |
| atacgtaaat tatctaaatt gacatcttaa ctaagcaaac aaaaatagtt gtttgaaaac | 1500 |
| tagacttatt tagtttacaa aaacatgcac cagatatcct cacttaatca ctagctctac | 1560 |
| acccaaaata tagactaaat aacttccacat ataatataca aatttaccaa actcaattcg | 1620 |
| gcatctcaat tggcgaaaga tcttttttaac ccaaaagaag acgttggggc attaactttt | 1680 |
| caaaatgaac tttggcttca tagtaggaaa ttgggagtga acatgaggc tgaaaaaggg | 1740 |
| ctaacaaaga gagcgatcgt ccacgtggtt ggcagtcaag aggtctttat agaagaggat | 1800 |
| gaagaacttg tttcccattg gtccgaaatc tatccaacac cctcctatta gatttccctt | 1860 |
| ccagattctc atcttcatga ttcctacttg gctccatttta aacccacaat tcaattcaca | 1920 |
| atatctccca cacatcctct tcttcatcat atcataaaac acagtccgtt acatacctga | 1980 |
| aatcttccat ctcaaaaacc | 2000 |

<210> SEQ ID NO 37
<211> LENGTH: 1760
<212> TYPE: DNA
<213> ORGANISM: Cucumis melo
<220> FEATURE:
<221> NAME/KEY: misc_feature
<222> LOCATION: (1)..(1760)
<223> OTHER INFORMATION: n=g, a, t or c.
<220> FEATURE:
<221> NAME/KEY: unsure
<222> LOCATION: (1)..(1760)
<223> OTHER INFORMATION: unsure at all n locations

<400> SEQUENCE: 37

| | |
|---|---|
| ataatgaata gcaaactacg taagttaagt tttggttact caaatttaaa cgacgtaaaa | 60 |
| aaagaagaa gaaaagaaaa aatacgatgg aaagaaatca cagagaaaaa aagaaaggaa | 120 |

| | | |
|---|---|---|
| aaaaagaaag acgatggaaa gattaaacga cgtatagaaa gaagaagaaa agaagaaann | 180 | |
| nnnnnnnnnn nnnnngcagc gaaaaaaaaa gaggaaaaca ataaagatga caaaagaaat | 240 | |
| cggagcgaag agaagaaaaa gatggaagaa taaacttgaa ttggacaaat tttatggact | 300 | |
| ttttacatag acactaattt ggttttttg ttagcttcct acaaattttc ctcttttatt | 360 | |
| ttattttgt aaagtaaat aaatatgtgt cattagtcta attttttgaa cttattttgg | 420 | |
| gagagataga ggaagacttt aaaaaattat tattactctc cattttaatt ttgagaagag | 480 | |
| attgtgttgt accattcctc ttattgcttc caatttcttt gagggcagcc ctagcctttg | 540 | |
| tacaacgcaa gcttcctgta gtatctctat ctctctctct ccctcttccg acggtgatct | 600 | |
| cttttctctc tctcacattc atcacccgcc gccgccggta gcttctcttt ctctgacgcc | 660 | |
| accgccgccg gtaatctctc actcgtcgct ctcaacacag agaaatttct gattgagcat | 720 | |
| caccaggtcc ggcaactaac attccttgct tctgcatctc ttttttcttca atttctggta | 780 | |
| tagtttgat ggatggattg tgtgtattca atcatttatt gtgttttgat ggatgaaccc | 840 | |
| gtttattatt ctttttatg acttcaagta attgcaactg ggtacttcta tctgcaactt | 900 | |
| cttggctgaa gtaattttta gttaagtgca aacggacggg ctgggaccga gccaatctaa | 960 | |
| cgcttatttt atcgaatttt gaggagttgg ttttgtttgg gttatagct taggaagggt | 1020 | |
| ttttggtttc gaagaaccta ccatttgaag ggttgggtct aaaatgtcgc ttaattcgac | 1080 | |
| ccaatatgac tctgaatgtt aaatattgaa tagaaaagaa atgaaatact atccctaacc | 1140 | |
| tgtctgccaa tttcgtgcaa aaaagcctaa tagccagttt tttctcgccg gcagtacatt | 1200 | |
| cgccttcccc ttccaagcgc tacgactgt tgctcaatct ccagaatctc tcaattcgca | 1260 | |
| gggggcaagt tctttccatc aatcatttta tgtatttttg cttctgccct agatcgttca | 1320 | |
| tctaaagttc tttaccttt tcttctgtt tgttttttgg tgtataactt atttgatggt | 1380 | |
| gatggattat gattcagtat cattttctta ttttatatca gcaacaaatt tggatttgaa | 1440 | |
| atcatttttt aaataccttt tgatgttaag ggttaggct tattattatg attcagagtc | 1500 | |
| attttctacg tgttaaatta gtttactttc caagtatgca gttatgttca agcagttatg | 1560 | |
| cagtcatttt ctgatgtggg agatagtgct gttttcctta aatgttttct atttaaacca | 1620 | |
| ttgtgcgctt ggttggtggc cgtgcagata attgcatttc ttttttttgga ttggggcagg | 1680 | |
| ttggttactc tctggtttaa cttttcacaaa gaaccaagac agacatccgt aacttgtttg | 1740 | |
| cataaagaca ttcaaccaag | 1760 | |

<210> SEQ ID NO 38
<211> LENGTH: 1767
<212> TYPE: DNA
<213> ORGANISM: Cucumis melo
<220> FEATURE:
<221> NAME/KEY: misc_feature
<222> LOCATION: (1)..(1767)
<223> OTHER INFORMATION: n=g, a, t or c.
<220> FEATURE:
<221> NAME/KEY: unsure
<222> LOCATION: (1)..(1767)
<223> OTHER INFORMATION: unsure at all n locations

<400> SEQUENCE: 38

| | | |
|---|---|---|
| aatataaata aatctcatta ctctttatga gctagaaagg atgcctaatg gacctacaga | 60 | |
| ctagaagcta caacgatatg agattaattg gctaaactca ttaaccacat tatgatatat | 120 | |
| ttgttaactg tgtgtacact ccactaaaga ctcgcagcta aactcttctc actgtagata | 180 | |
| tatttatgtg tccacggata tagaccaata ccaataagtt agtccttcac aagtgttcat | 240 | |

```
aacactagct gggtcaaatt actgttttcc ccttgggtta cttctagtcc ttaaatacca      300
atgctcctct aatgaacaac ctgtttaatg tccaaccact aaacagaatc ctttctcatg      360
ccatagagag ggtaagacct tcaagtcctg gatacaccat ttaaaggagc gcttatctat      420
ttaccataaa gtcaagaagg agtgaattcc atcttnnnng attatgttcc cagctcccca      480
cccggttttg tcctcaaaat gataaatata ttgagttgac aatctgacca ctctcacccg      540
tacaaatcaa aagacaatcc ctcgcgaata ggagttcata atatactcat aattaagact      600
aagttatcca tgtcattcta atgaaataga aacccaacta gttaatggag ttacatcttg      660
tggttactat ttcgtggtcg ggtcttatgc aaactcatta catacgatac cctcactcgc      720
atgtcgctta cttgaacatg ttgaataaat gcatttatat tagatacaaa gtaagtcgta      780
tccatagtgt taccaggata agttacctag ccttaacccct atactataga cnnnttaagc      840
tgatcttgaa cattgtttcc tgtatgtctc tacatactgt tcaagactca tcaaacaact      900
caagatgtta atttattgga tttaggttat aagataaaaa cgaataatat aattaataac      960
acttcttgaa attataataa tataacactt tattaataac taccaatgaa ttatatttac      1020
tatatacgag ttttaagaca taaaatccaa tataagggtg tatgaactgt taaagatgat      1080
gtgctattct tgttggatat tataggaggt atttagtgga ttatttgtga agaataagg      1140 aggtacttat gggaagactg ctggaggtta gggaggatct ttgaaaatta ggaagtaggg      1200
atcaacaaaa aaaacgaaag ggaaagctta aagcttaaaa aagaaacgaa ataaagaaaa      1260
atgatttaga ccagcatact aaaatggcaa tgtaatctga ggctaatgta tcaattgaga      1320
actttgtagt cataatgatt aatcccaaac aaattagttt tcaagaaatc aaccccaaat      1380
aaaatgactt aaatattgaa gagtttaaat ggtctaaaat tattgttact gttttttatt      1440
tttggaaaag agacgaaaaa ggaaaaataa gaaacgccca ccgtggggct cgaacccacg      1500
accacaaggt taagagcctt gcgctctacc gactgagcta gacgggcttg gtgtccaaaa      1560
atccaataat attgaaaata ccatatagtt taatgaactg ggcaattgga ataggcccaa      1620
tatattagat atagcgaccc aattgttagg cgtgtcttct tccaaaaatt ggaggcaaaa      1680
cacaaaccct agcatccgct tctgctcctt tatcgtttct ctcggcgatc aattttcacg      1740
gagctaggtt taatcaagct tcaagca                                         1767
```

<210> SEQ ID NO 39
<211> LENGTH: 2000
<212> TYPE: DNA
<213> ORGANISM: Cucumis melo

<400> SEQUENCE: 39

```
tttaaataaa aataaaaacc atctctttat tttaagtagt taaatgattg tcgtttacta       60
aattaactct agcctatttt aagacggtct ggtcaaaaaa tcgattacga ccgaccaata      120
ttcatctaac ggtcttatta ttttaaaag atatagaaat gtatctcgtt aataaagcca      180
cgacggtctt tttctaataa aaattcaact aaaccatata acaaaattat tgtaccatga      240
aaaacacttt catacataat gcaaacaac aatagcaaaa aaccaaagag gaaggggaca      300
atttggggaa aagtaatctc aaatttccct ttttgacttt gttctaaatt agtttattga      360
aataaaatct actaatttcc catttccaaa ttaaaatgct taatctttgt ctcattagca      420
ttgctagaac aaaattgtct tctcaaaataa aaataaaaat acaatatcaa ctatttatac      480
ttaattatct aacatttctc caacataaaa agagttatat atatatccta ttttgttctc      540
```

```
taatttttcc tctttttttg gtaattaatt ataatattgt cctaacatat tatattagat      600
agcttcgaca aaccgttgct taaaaaaaga aaagagaaat ccaacctaac tcaatccgaa      660
aatatacaaa gtacaaaata attataataa ggtagatggt atatgcatca atgaaataat      720
attgtcaact ttcctcgatg atgatggtaa taataataat aattttatat ttattaggcg      780
taatattttc ctcaatttta gtgtttgtat atactttcat atgtttaatt taagttttaa      840
aatttagtcc ctcaattaac ttgaaattaa ttaaagaatg tgaaaatgtt aatgggtgaa      900
ataaataatt tagagaaaaa ccaaaataaa ttagaggtag ggagtaattt tagaagttca      960
aaaaaaaaaa aaaaataaat tagatgtttg aaagtacaga tttgtttaaa tatgaaccaa     1020
cttcgaatag tctttccatt ttttcttata aaaagtcttt ctgatgtgga tactagttag     1080
agtatcctat caactcatcg atccaaagaa catactttca atcgtaagtc gtccattcta     1140
cttcgatcta aaatgatgct aggtttgctt caccttcacc cttcacaaag acaagtgcag     1200
gtgtgcttcg ctctatcaca tgattttgat tatgtcttca agaacttcac agcggtttta     1260
aaaaaacaag aaagaaaaga gtgagagtgt ttttatgtca gaaacatatg cccaagctta     1320
tgaaacttgt tgatcttgta gcgattgaat aacaaatgga aagtatctca tacaatttct     1380
ctatttttca cttttatcga agaactttgt ctcactaact cgtaatctaa aatacaaact     1440
cttcgactct aatatattaa ctccaaactt cattttcac atctatggaa cagataaagg      1500
tctaattttt taaaaatatg atgggaatta agtatagta aagagattag cttcatcaat      1560
gggcttggat tggagtccaa agggttagcc caaacccaaa acatagtaaa tccaagccct     1620
ggaacaatga atagcacgga aagtttgtgc tgccggagga gcgtattgga aatgaagggt     1680
ttaggatagt tatggagcag aaaacgacac cgcatcatta aggacggatt tgggatttta     1740
agaatatatt agggacagaa taggaatttg aaaagtagcc ctagccactc aatttggtaa     1800
cagtagcaca aaaattggag gatacctaag gtaagcgaca tggggtaata cacagaattg     1860
tggctatggc agaattggat agaactccca tttgaggctc tcttttctct taccatttct     1920
acaagataac actactcttc ttcactctcc aaaaccccat cttcttcttc ttctcttagg     1980
ttcctctctc ccttcctcca                                                 2000

<210> SEQ ID NO 40
<211> LENGTH: 2000
<212> TYPE: DNA
<213> ORGANISM: Cucumis melo

<400> SEQUENCE: 40
aattggaacc tgctgatatg aaatgcataa gagaactgaa cctatcagta tcatgcgaaa       60
cctgcagcat agacatacta ccgtgatgtt tcaattttc aagcaaacaa aatatccaaa      120
aacacacaaa atagaggaaa ataaggcgaa attacaaacc tctctaggat tttcaagatc      180
ttccatattc ctctcagatc cgggtgtaaa gacaaccagt tcgaagttcc aaagctgttg      240
caatactact tgtctaaacg tcatagcaag tatattttg gacgaggtac ttgaatggaa      300
atcttgagcg agagactttc tgagcttcgt ggccttttcc ttgacttctc tggcaggtaa      360
aaactgttaa cacagtcaac ttaggaatga caaatacaat cggatagcta aattttatct      420
aacgacaata ttccagagag gggagagaga cacattgttt tataacaaga ctcccaattt      480
catgagatga caacatcgca cgacagtcaa acaaaattct aagagaacat caaataatac      540
tagaaacgga catattagtg aaggagctct taaaggtagc cttgaccag agatgggaac       600
gccatcaaat caatctcatt catcaatcat ggagttaatt gttccgatgg tggaattcaa      660
```

| | |
|---|---|
| aatcggtcat agatttttat tttaagaata aaaattaaaa tggaggctcc tgaagctaac | 720 |
| atgccaggtg caaaagtttg ggagaacgcg ttcacgtcaa cattcgaatt cagtctcata | 780 |
| aatggaaatt gtagcaatga cgaaaaatat tcatagttgt tagtcacgga aatcggttcc | 840 |
| ataatacacc accgtcgaat gcgagctaaa acgagcacca aattacgcag tcaggttaaa | 900 |
| aaataactaa ccagccgggt cgagacagtg ctgtgttcat cagaaattcc cggaaataca | 960 |
| gtctccacaa ccattgcagg catcccagaa tcaaggtgct cagtggcggt ttcaccgcca | 1020 |
| tcagccgcag ccgcagtaac agactgccgg aaatcgacgc ctccgaccag agaaagccga | 1080 |
| gacaagtcat tctcgtacgt ccggacacag ggaagaatct tctcatcgga ctccagcaca | 1140 |
| gcttgaagaa cctcttcctc ggtcgtcgga attggcctcc cagcagagca agagaaggta | 1200 |
| gaaaagcaat gccttgagtt tttcagaaca attttgggag tataaattaa gggtatagca | 1260 |
| aacagttggc gagctggtat agcctgtata ggagaataat ggataaaaga caaactcaac | 1320 |
| gccattggag aaatggccat aaacctctga gcgagtgcta gggttttcgt tttatagtgc | 1380 |
| tactagctgt gcgtcgccgg agaagcgatg tctcgtgccc acatcttttt ccctccattt | 1440 |
| cttttcgggg ttatttctct ataccctc ccaaaatatt acaattaaaa cagttccatt | 1500 |
| ttgttttaaa aaaataataa aaatttattt ctcaataatt ttttttgaaa attgaccgtc | 1560 |
| aatttcgtac aatctacttt taaagaaatg attacttcat ggatggtttc taaagggaat | 1620 |
| ccaaaattta aaagtttaat taatttagat tatgttttat ataacattga ttaaatgaaa | 1680 |
| tatgaaataa ggtgtaagtt gatattagcc ctaaatatcaa agatgagggt aaaagtaaaa | 1740 |
| taatagtgaa aagatatcca actgattctt gggtaccggt tcgggtaggg tttgggggaa | 1800 |
| tccggttggc gttttttgag cacagagaga tgtaaacggg acgggaagaa ataaaggcca | 1860 |
| acacaactat aaattctcct ctcggcggaa aggcggagca gcgtccaact tcgcctttca | 1920 |
| caaaatttac taagagggggg cttccattct acgtcgattc tgctcctctt ctactttttc | 1980 |
| ccttctgctt tttgtcgacg | 2000 |

<210> SEQ ID NO 41
<211> LENGTH: 2000
<212> TYPE: DNA
<213> ORGANISM: Cucumis melo

<400> SEQUENCE: 41

| | |
|---|---|
| ggtctcagac ccataggaat agatcattta ttgccttatg aattagttta tgagtacata | 60 |
| ataattgtca accgtataca aatcaacatg aaagaatata atgttgtaca tagtcattcc | 120 |
| aagtttacta atattatatt ttaggagtgt tctacaccga acctgtcaca tgtacactgg | 180 |
| gtatgctacc cctgaattca atatcataaa gcaactttaa ttgtcaagca ttctcttgac | 240 |
| catttgtgac ccatttgctc ctactttttc aatcaataac tatcacaaaa agctagatac | 300 |
| cacatgtgat aaactcactg aaatcaggta tatggttacc tgtgcttggt cagcactcaa | 360 |
| tcagattcga aggcctagtc tttgtatttc cccccctctg cacactacaa atagtcctcc | 420 |
| acgtaaagac cctaacaaa acgcaaacca agtacagaaa atctagccga aatccagacc | 480 |
| actcaaacat aacaaatctt ctggtaagtt tgaataaaat ataaaactaa cctaatttaa | 540 |
| tcaaataata caataaaatg gaagcaacta acataacata tctaaatatg atcacgtagt | 600 |
| aggaaaaaaa aaaacattcc aaaactatta acaatcattc ttaatggtat gggtcaatcc | 660 |
| ccattatttta ggactataac aagaattcct cataccctaat gccacatcct atgtccaacc | 720 |

```
ctcgagatta cctcgtgagt aatcaatctt attcatcctt atttcaaatt atgtgaaatt      780
tctcatcagg ttgatcatat tgactttcaa tacaacttat gattaatctt tcccttgata      840
taatttcgta tgaaaaggaa gttgacatta tgtgattttc cataaggta aaccaagtaa       900
acttgacatg acgtcttaac aagtcttggt ttctaagtgt aatttactgc agaaaaaatc      960
ctaaattcta tgactttcc tatgagattg accaaatcaa ctttacgaga atcttggga       1020
agccatacct acaagtcttt cccccaagaa attacaattt ctagtaaaga ttgttgaaat     1080
ttaccctcca atttttccgt gaaatttgac aaacttgtaa gaatatcaaa tttgggttgg     1140
atattgacat tccaaaataa gtagttttaa aaaggattta tccaacaata atagaagaaa    1200
aaagatagga aataacatac ccacgtaaat ggaatgtaaa tatttatata ttaggtgtct   1260
tgaacgaccg tcaaacgaaa ataaattgtt catccgaagt tgaaactctt taagtgtaca   1320
tttatctttt cgtaagaata aatgtaaaa ttaacgtgtg aaaggttggg ttaaataagt    1380
tatgtagaga taatattgaa gatgatagaa taatcacgat cgatgaatta gtatagtccc   1440
agagcggatt taaacctctc tcactttcat gctttctata tatatcaaaa taatttcaag   1500
tagttggttt agtcgtaaaa aagtcaacca atctctttta gataaaccctt gagttattaa   1560
aaaattagat caaagataat cgttgaaatt gaaattttaa gagtataatt ataacaaatt   1620
ggaaagttct aaagtagttt ttgcaatatt ctccatcaaa atagagtaga aaaatattt    1680
agtaattttc ttatcttaat tttagtttg taatagttat taggatggtc ctaagttctc    1740
aatccgcttt tagtccataa aaagaaagaa gagagagaaa aaaagtcccc gatccgcgac   1800
acataccaat ccaaccaatt atgcacaatc catgtgatat cgaacggtca caagaataaa   1860
tgctttctac acacggatca ccatccaacg gcttttcctt ccatctcatc ctctatataa   1920
tctaccaact ctgtcatctt cgacacactt caattatctc agcttttatt tcatcggatt   1980
ttccatcaaa caaggcaaca                                              2000

<210> SEQ ID NO 42
<211> LENGTH: 2000
<212> TYPE: DNA
<213> ORGANISM: Cucumis melo

<400> SEQUENCE: 42
actccattat ttggtttgat taaagcttcc atctgattaa taaataataa taattataaa       60
ataaaaaaaa gcgagagttc cattaagtaa tattatctac cgaaagagag caactatcac     120
ctcaaacttc aaaagataa aatagagacg aaacttgacc aagtcaaaca caaaccacaa     180
acaaccgatc tgacagaaag tttgccagaa tcttcaatgt acacgcgaag ataaacaaat    240
aattaaatct cgttcgtctg gataacataa cacagcaaat gaattttttt aatacatatt    300
ttaaaaaaga aatttaaaat tggtagattt tataaatcat ttccaaaggg ttttttcttgt   360
tttaaaatgt ttttttgttt aaaataggca gttcatcacc acttgagaag atccaaactg    420
ggcggcaccg gttctgcgac gcttgagggc cgtctccgac tcttcgccgt aggaggccga   480
tttacgcaaa gaataaccgg acaatgttgg acagttttga cgagaagtta aaccgagtaa   540
gggcttatgc ttcttctcaa tgcgctcgtc gtcgtcgtcg gcgacggcgg cagcggtgat   600
ggggacttgc tctgttgcgg ggtgaacatt gggattccga caagaaggtg ggttcttagg   660
gttggaggga aagtggaaag cgttatgggg ttcttgatgc tgttcctgca acttttgctg   720
tttgaggaag cgcttttgga gatctaaaag agaagggcga ccctttttct tcttcttctt    780
catggtggat ttagaaacct cgccattgt tcttcttccc tttctcgcag gaacgaagcg    840
```

-continued

```
cagggaggtt aattgatttc agttttcacg gcggagggtg caggatttct aggcacgtgc    900
gaatcgcatg accctatcac gtgcgaatca gtgacggtat aacgtgcatg caaaggaata    960
gaaacacaaa ccgctcttac aattataaaa ctctaaacta aactacgaac gcatctcata   1020
atgggcccac tccatcatcc tatgggcctt ttgaatttta tgtatactat ttttttttt    1080 tttttttttt tctttaatca caatcaattt ttctggtatt tttttaaata ttcaacaaac   1140
tttttgtttt aatgttgtgt atatctaatt aatttagttt tattggatgt cattttttct   1200 attttttgaaa aaactcttaa aaaaaatata aacaaaaaaa gaatggaaaa agaatatcaa   1260
acaaagagag gagagagcaa ccatacctaa aaagtttgaa agtaaaattg aaaaaaagaa   1320
tatacattga gggcagtgtt gaaatgaaa ttaatgaaaa aggaaagggt acgtaacaat    1380
aaattacatt ttcttgcagg cttaaacgaa ggcccatata tgaaaaggga agcttcgatt   1440
tgggttcagt tatgcgggcc tggggttggt attgggctta attttataaa gaaggcccaa   1500
atgttggaaa gacgggcttt gagagagggt gttcggcttt tgcccgaggg gggtggggga   1560
gtggcaccgc caagcgaaga caacgaatat taggagagaa aacacaaaga ggcggagaga   1620
tggaagagaa tgaggtggac caatgagata agagtgcgca gattattgag gtggcaataa   1680
atttagaatc ccgcctaaat cccagctttc atttcatgcg caattgaatt tcaatttgcc   1740
attcccctcc atagggactt aattatcccc ttttttttac tctcataact ccctctcttc   1800
ccaccacgtt cgcttcttcc tcccccttcc tcttcaaacc ctaaacctaa cctaacctaa   1860
cctccttccc caacttcttc cgtcggtacg tttcatccat ctcctcccac ttttcatctt   1920
tttttccttc taatttcatc tcttttcttt gttttccctt ccaattgttg ctgatcccat   1980
actatactgc aggattcgaa                                                2000
```

<210> SEQ ID NO 43
<211> LENGTH: 1115
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(1115)
<223> OTHER INFORMATION: unsure at all n locations

<400> SEQUENCE: 43

```
aaagaaatca aagcgaaaaa acgagaggaa aaagaagaaa aacgannnnn nnnnnnnnn     60 acataaataa agaatagaaa aataaggaag atgaggaaag aaatcgcaga aaagaaaaag    120
agaaaagaat aaagacaaaa ttgcagggaa agatggagaa gatgaaataa taggaagaag    180
acgaatcgcg agaagaaaat aaagatgaga gggcaaacct gaaatattta aaaaattgct    240
aactttatgg gttttgttac acgggccgta aatagttttg ttacatttat gtaaatttac    300
aatcaattaa ttatacaatt aatcaaattt ccacaaatac aataattgga tattttccca    360
aaatatctaa taagtttcaa tttctaccca tcaaatattt caaccattat aacaccaaa     420 aaattcaaag attaaactta agataattac aaanaaatta ccttaaattt ggggcattac    480
acatttacat tgaactatac aattgtttac cataatcaaa acgatcgttt tttatgatc     540 gacatgataa tttcctatga tcaacacgat ttttatcat atcaacaccct tcatttaaat    600 ttgaagtttt tttcccatcg ttaaaaagaa gtacacgatc ttttagaaga agattacttg    660
```

```
cgcgggctga ttaatcgtct gttgactgtg acattttta tatttttcat catgagcctg    720
tatgtctttt ttgtttttat aattgtttta catcgtgtaa atagtttgcc gattagttat    780
atttgttaga aaacactttt tcaaatgtcg aaaatttgat tttgatttat aaaacttta    840 gtaaaggata gtgtttatta cgtatagaat cccaaatttt cacaataatt tttcaaaagt    900
aatccaaaag aaaaaagcaa caataataaa aggctcaaag cgacgtcgtt tagggcaaca    960
gctggggaga agaggacgat ctgaaaaatc atttcttgag cgaagggaaa aggagctcta   1020
ctaaagcagt cgaaaaaga aaactcaaac ctcgctgcga ctctcgacat tgattctgtt   1080
ttcaattcat tttgccaaag ttaatcgatc cgaac                              1115
```

<210> SEQ ID NO 44
<211> LENGTH: 2000
<212> TYPE: DNA
<213> ORGANISM: Cucumis melo

<400> SEQUENCE: 44

```
tatagtttgt aacaatctac tctatgttct ttcaattttg atacatttga atcttaaact     60
ttattgagtt acacaatata gtccttgtat tttaaaattt ataatgactc tatttatatt    120
aatattatag aaattttgt taaggtttaa taaaaatttt tctgtataaa taaatcgaac    180
acgaagtcta tatttagact gcaatatagt aaaacctgac atctaagttt ggtgaatttt    240
gttttgcttt aaaaactaaa ctattacaat tttaaaata ttttaattta gttaatgcac    300 attaactta cggagtaaat ttttacaaga ttgaatatac atagattaaa tagttataaa    360
accaaagatt agagtaaaaa catttaaata gaaagaacta agatttttt aaaacgaaaa    420 tgatactaga tacatatata tgtatctata ttataattac tcattttaac atatagtttt    480
gaaagaacaa agattagttg catgtgttga ttgtttttaa gaaggaaata atttttgaat    540
ggaaaatttt caaagttttt aaatttgaca ataaactcat atttaaagtg tactacaaat    600 tttaacttt ggttaaactc cttgtttagt tcaatcatgt aataaattct cattccaaga    660
atcgttttag aaaattttat tgtgcattta ataaaatata gaacatatat ggcatataaa    720
aattgattac ttttttctt ttttgggacg aaaaacacat tagatataat cttttttgaa    780
agtttatgaa cttttaaaaat gggttatttt atacggtggt caactttatt ttattgaaat    840
tattgagttt ataagattg ttatatcatt ttcttcttct ctttcactag aatacaatca    900
aacctatcaa actctctatg acttatttag aattcttttt gttatatttt tgaaattaat    960
aaatgaaaag cttagagtct aaattataac aattaaaatt gaaatttg caataattt   1020 attttttagca aaatgacgtt tggtttttgg ggattgggaa tggatcgata ctatcccgat   1080
tccggacaaa gaaaccgacc cgagattcga attttttcca ttcccaaaca gagcacttaa   1140
aatttaagca acgttataac ggcgtcaccg aactaaacgg aaaaatatga agaaaattag   1200
aaaaagaaaa acgaacagt caaacgttac ttcacgtcaa tggcaatatt cattttttt   1260 tttgttaaa taattgaatt taattaattt ggtttataaa aatagagtcc tcatatatcg   1320
cgaatgcgca tttgatcgtg aaggacagct tctcccttgt gttcaagaga gagagatcta   1380
tcattcttat ttggggccga tctctctatt ctcctctctt ctattccgta agtttttctc   1440
attcattctc ctctctcatt tctctccgag atctgtttac aatcctttg attttcattt   1500 ttcctgcttc gatctgtgct cctggtgatt ccctttttcct gttttatctt ttgttgatct   1560
tggaattgat tgttctttg tgggttttca ttgatttgta ttttctgatc tgggtttctg   1620
ttttctcgcc ttgatgtttt gtatttggat ctgatctgac gtacccttt tttttttttt   1680
```

-continued

```
tatttgaatt gcttttccaa tgtttatacc tggatttttta ttgatgcatg ggtttaaccg    1740
attggttgga tgcgttttct ttgtgctgga tctaggtgtc cttgttttta atttgaattg    1800
tgggtaaaaa tggcattatt gtaatgtgtt tggagtttga ttttgaatct tggctagttg    1860 attttttgaat tacaaagatc ggatcctctt ctttttttggg ttgtcttaag attttttggct    1920 ggtttaagta tttgatgtcg ttgtattta aggggtaact gatgccggct tgttgtgttt    1980
gtattcagtt tacttgaaaa                                                2000
```

<210> SEQ ID NO 45
<211> LENGTH: 2000
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 45

```
attatctaaa cattaactgc aactaataca gattacagta aatttgaatt atgatgttat      60
ctagagtcat ttgtcttcaa tgatattgac tcagattcaa actttatgaa aatgttaccc     120
tggaaaatat tctaccgcaa aatttcaatc caaagttaaa ggttgaataa tttagaagtt     180
ttctgcgact tccacccact tattatttag aagacctgaa atcaaaatga tagaagatga     240
atataaatat attttttttgc tttaaaattt ataaatcaaa catttgaccct agtaattgat    300 aatacataat attatgtgac tcgtaagtaa aaaagaaatt gaataatat atatatacgg     360 agatcgcaaa aaataaaaat gaaagtaata taaagtaaac gcaaagtaag aaagcaagca     420
ttttcaagta agattgaaac ccccgtccct gggggctcca agataacacg ggtgcccaat     480
tacccggtac acgactttg ttgaacaaca ttgaataatt agcccaaatg aaaatatttg     540
tcgacatatc tttcttataa tatgtaaatt agataccaac acaaacactt gtaacaatat     600
cctaactaac ttggttttaa atatatatat atatattatt ttttttctta tttatttatt    660
tnnnnnnnnn nnnnnnnnnn nnnnnnnnta gataccaata tttagtggcg ggtccataaa    720
ttttatatag ggttattata taataaacac taaaaattta gatattatta ttttcaaagt    780
taggccacaa gtaaaagtgg ggatataatt attatactat aaccatattt tggtaaaatt    840
aagtattaaa tatactttaa aattaatatt aaatataaa aatcgataat gtgtgggata     900
aatttatgga tgtaaatatc aatgtttaa tgttcaaata aataaatagt aaatagaaac     960
aaaacaagaa gtcagtcttt actactaatc gggactaaaa tttgaatttg atttaaaatt    1020
taaaacttaa ataggactaa aaatgttagg acaaaatagt aacaaacacg aaatttaggc    1080
aaagaaatat aatttttattt atttattatc atttttttta tatatataat tgaaaattga    1140
ttactaaaaa aaacaaagaa cggtaaaacc ctagattaaa atcaaaatag aaannnnnaa    1200
cccgaaagga gaattttgat ttccagagct aaacataaca cgatccaaac ccataaatcc    1260
cgcatcgagt ggaaccgata tcttctcccc ttcgaagttc caactctccg tttccgtctt    1320
tcttttcgat tctccttcaa accctctttt cttcgtcttc ttcaaatctc tacatttcaa    1380
aatcttcgct aatctcttct tccccttctc ttccgatctg accgtgaccc cattcgaagc    1440
ttcttctttc accaagcttt ctctccgcta tcaactttaa ctttcgtcct gtattcctta    1500
```

```
gccttcccctt gcttttgcag tctccgccac cgaacaattc ctatcccgag ataatcccac    1560
ttttgggtcg tgtttctcac ttattcaaat cgctggttct ttgattttgg gcttatttca    1620
ctctgcatct gctgcgactt ggaggttata acatctctct ctcggtcttg ttaggtatga    1680
aggatttgag atattttcta atctatctga actgggtttt ctttcgcttc cgtttatgag    1740
atgtaatttg ttgttctggg aagttttcag atcctttcta atgggcttct ttaatttaat    1800
ttaaagcttc tttgtttgta cgagatgtca agtcttaatt tctagcaata tcagtatctg    1860
ggttggtggt atttaggatg atcaagtctt ttgttattta atggatgaga acaattattg    1920
tcattgttat tattatttt tggaaaaaaa atcaatgggt tttcactggt tttgttgatc    1980
tttttagata attgaagttc                                                2000

<210> SEQ ID NO 46
<211> LENGTH: 2000
<212> TYPE: DNA
<213> ORGANISM: Cucumis melo

<400> SEQUENCE: 46
cttctcgatc gcagcaattc aacttcataa acaagtccaa gaacgaagag tttgattccc      60
ctaatttaac ttaattttct ggtgaaaatg gaccatactt ttaattacat attattttgg     120
ttattgcctt ttaaatggtc tattttaatc tctaattttt tttattaaac aatgatggtg     180
aatcttttct aaaagaaaga aaaaacttct ttacaaacta ccaactcta ataacaacac      240 taattataaa ctagtctact acctttatta taacagcaat taaaagaaaa atcgtattc      300 actgacaaaa attcgttctt ttgaatgctt atcgaatgtt ttaatttttt taaaaaaata    360
tataaatatt tgtaagggaa ggatcagaat taaaactctc tccctcaat gaaattgaat     420 tatttgttt tcttgttttt ctttttttaa aataaaccta tggatttagt tggtcggtcg      480
aattaaaatc gtgaggtcgc acacgcggtg tcttgtggat tcaaaattat gattatttcc    540
atcacccctt ggcttttcg ctccattcgg ccatgcctta caaatttcgc tccactccca     600
ttcttctctt cctctcctct ttcaactgca ttgaggccga tcctttaggt aaatggttct    660
ctcccatttc atctctaatt cctctgtttc tttttatttt acttgttctt tttccagccg    720
gatcctccat ttctgtggtg aaactgaatt gttcttatcg atttcttgtt tgaattctgt    780
ttttctctgt ttgtgtctgt gtgtgttttt aatttgtttt ggcatgttga agtttaaaga    840
taccaaaagt tgcgcttcac tactttccag tttcgatggt agctgctagt tgtaacgctt    900
acgttcttgg tttttagtt aaaatttttt tgcttcttgt tgtttactgt ttagcaaaaa     960
gcatggggaa tactaccaaa gtcccgaact taatagatag atgatcatgt gctaagaagt   1020
gcgatacttt ccgtagctga tacgtgacac agtgtctgac atttgtttga cacatattag   1080
aaacttgtta gtataacata tgtgttaaac aggcatagaa cacctgttgt actaaaaaaa   1140
atatttgtat gataataata ataactttga agtgtaaaat atatccagct aagttttttc   1200
aagtatacaa gtgcattaac tcatttcctc ttgattttct tttggtataa aaattatata   1260
tattttgaaa accgtatact ttaataaatg tatccttgtg cattatgtcc tagatttta    1320 gaatatggtg tgttgttgtg tctatatcgt gtcgtatcaa tatctcgtat tcgtatctgt   1380
gtttgttaga tcatatgtat aagcgaggac agctatttct gatgttacaa gaccttcttc   1440
aaattttaca ggaaatcatt caatttgaaa attcaagatt acaaatgcaa tctaaaccaa   1500
acttcaagaa caaaaagtgt tatttgttaa tatccttgcg acctcaccca agtatctat    1560 tacaaacttc agaaaaaact tcataataag ggttgggttg aaaaaaaaca tgaagaagtc   1620
```

```
ccacccccaac ctaactctaa aaagcataaa aaattcaacc caacccaaac cttacaattt    1680 ggggttgggta gtccgtgttg ttcgggttgt cggggttattt gaactcctag ttttagctaa    1740
gtgtaaactt atttaaggat gttgaaggtt agcattgatc tttctctctc aaatttggtc    1800
aagaggaatt attttttgag tcattcatat agttccattt tgcttttgag catttgaatt    1860
gtttgttaac tacttctttg attaatatat tcgaaagtga aatttccttg gtttacttta    1920
ttgatcagtg tcccatttta ccagttattt cagttctcct aataaccttc attggacttg    1980
agttcggtta acacaaaaca                                                 2000
```

<210> SEQ ID NO 47
<211> LENGTH: 2000
<212> TYPE: DNA
<213> ORGANISM: Cucumis melo

<400> SEQUENCE: 47

```
aatgtatcgt gggcatttat tatgacaata gtgtaaaaat gttgttaaca tatctgtgta      60
ttgtcgatga tgtagatcta ctacgccaat agttatagtt tccatcggta tatctatgaa     120
atgtcaacgc cttaaaatag ttgcatgggc atagacttgt ttttttagaa aaatatgttt     180
tatatttgta ttttttttcac taacatcctt ttggttttgt atctaaacac aactcaaaat     240
atatcaaata ctgaaattca tttcctaaaa aagttacaat tgtttcaaat ataagtcacc     300
tgaatgaagt tcttaaaaca caagaattg ttccttacaa aattaacata agcaaaatag     360
taagatcgtc caaataaca aacattacat aaactttaga ccaacttcta atttgtttgc     420
caggaagtga tctccattga aagtttgtct taaaaaacaa ataaaaagaa aataatagaa     480
acatattcaa taaactagta cattttgcac cttacatata tatacaaaaa ctttacctac     540
tttaatttct tgaaaatcta aattttgaat taagaacttt tcttacaacg ccaaaacaat     600
aataacttat aaatcttagt gatggaataa taagttataa ttcattggtt gattgtatca     660
ttaaccattt ctttcttttg gtgtgagaaa cttatccaac taaaaatatt cacaatagta     720 gggcggggttt gtcgtggctt tgtctgaatt tctacaacat gtgtaaatat tttcaactgt     780
tttatcctct aagacaattt tcctaaaaac aatcatgttg ttcacacgag atttccaagg     840
aaatttaatt caaggagttg aacttgtatt tatgttgatt tgatgcctat gcttaatttt     900
aagatttgag aaagcacgtt atatttgtaa agttggagta ttggaagaaa agtttgtatt     960
ttcaaaagaa cctcaatatt cgagatcgac ggttggcttc aaaagttagg aagtctttga    1020
ctcataggag aatcctatct agactttatg caatataaag agagttctgt tttatggact    1080
tagttggata ataattaat ttgattcaac ggtcataatg aaaacatgtg acatcattat    1140
aattaaccaa tttatatctt taatacacat atcaactttt aaatagttct aaattcaatt    1200
atttgtattt atcatcatta attaaataaa taatgtgaca atttgtgatt gatccaaaaa    1260
tttcatattc aatctatact atattagtta agcttaaaat tttactaaat gcttaaagtt    1320
ttggattatc gagcttccta ccaaacaaaa gcctctattg cacatttaaa atatagaata    1380
gtaggtttat ataatatgaa agattgactc ttaagaccat actctatgac ctaatgaaat    1440
cgacatttat gtaattgata attaataatt aataaaaaaa gtgtgacaaa aaagtggaca    1500
taataaaaga aaggaaattg tgaagcatta gcatccgaat ttcgaagaaa acaaagggcg    1560
ccctcagatc aaagaggaca tactataaag tctccacgct atttcaagaa ttggcgtgat    1620
tctcaagcga catttccgta attcaccaca aaaattaaaa acaaaaaaga actcacagat    1680
```

-continued

| | |
|---|---|
| tctgatttga cttttgaaac cccaaccccc atcatctccc aatttaattt tccctcgata | 1740 |
| tttatccaaa ttcagaaaca taatcttgac aattttatgc tccattcttc caatctcagc | 1800 |
| cgtacgtttc attcaaactc caattctccc ccactgcgcc ttccactacc tttttccttt | 1860 |
| ctattaaagt gtcctcacaa actcacctcc tctctctgtt tctgtctgcg gtaggatcgc | 1920 |
| cgactccgga tttacatttc aggggtcgaa gatttgttct ggggtttctt taatttcttt | 1980 |
| atatatatac acacacaatc | 2000 |

<210> SEQ ID NO 48
<211> LENGTH: 2000
<212> TYPE: DNA
<213> ORGANISM: Cucumis melo

<400> SEQUENCE: 48

| | |
|---|---|
| gccaaggaaa atgaattgtc taagaagaag aaagaaaaga aagaacatttt tttgcaaggc | 60 |
| tacaaatcaa aacttaaatt atccacgtga cacaacaagt tcagagagga aagaaccctc | 120 |
| taaaactccc atataccttg gcaataacca tgacaatagc aataaataaa caagtccatg | 180 |
| acataaaata aatattgttt tcattaaatc tcaataattc atatgtagtc cgctccgatt | 240 |
| atgccacagt catatatcaa gttcagtatt ttaacaattc aagtagacat acataaagct | 300 |
| actatggaaa acataaacaa gaatggaaga aggagggtta aggaaacctt tatccctgat | 360 |
| ggagtttcag taaaactgag cttgtaggta ttagtacgaa agctgtgaaa tgaacaacct | 420 |
| tggccaggta attgaggcac cccaagattt cctttatcaa cactatcaaa gaaagtaaag | 480 |
| aaagttatca cttcaaaacc caactcccaa aagcagctca tcattttcca gtaagttaat | 540 |
| actttgaaag atcaaaatca aatctacaat caaattagac ttcttaatag ttattgccac | 600 |
| gaaccatgca tttgtcacgt tattaagact atggtttgca ataatctcct atctggttgg | 660 |
| atcactactt atactaggca cagcataaac taaagtagtt tcccagagaa ggaagaaaca | 720 |
| tgaacctggt tgggtccatc ttggcagtaa aggatttaag ggagaagagc aaaccaaaca | 780 |
| taagtttatg gtcttgctgg ggattcaatg tccggagagg ccgattccac tccctgtaga | 840 |
| acaagcaaac tccattccta ttgaaaatat acatcatatg cacattgttt ccagtcgctg | 900 |
| tcggtaccgg aggcgaggga ctaatttctg acccaccaaa gaactgcatg gtttctggaa | 960 |
| taaactaaac taaatcaaat caattgtcat ataaaatgat ctacgaatct aagattctaa | 1020 |
| caaacccaac atttcactca actctacaat cagtaaccta gcaaagcaac taataattca | 1080 |
| atcattccta taattcatt gaggttaaaa ataaaatagc gaattgtcaa caggtaaaat | 1140 |
| ctaacccgac ccaaatcagg aatcactaaa gcaagaagct gtatgactcg atcaaaaata | 1200 |
| acccagatgc atttccctttt ggcctctcta cagaaccact caatatagtt agaaacaaat | 1260 |
| ctagtgtaaa attgggagtc ctattcatac ataattccaa ggaaaatgga ttttacttat | 1320 |
| gcatcgtata agagactgtg agcagggaa aatggagaga taatcaccaa tgagctggat | 1380 |
| ggtgacagat tcaagaagaa gcatcaaaat caaacaacgg agagcagaaa gataccctcaa | 1440 |
| agagcagaga ctgcaaagta aaggaagcga tcaattcaac gacgaagctc ttgattcgtc | 1500 |
| aggcaatgat tgccggcgac aacaacgtca gcagatcgga gccttacggc accggagacc | 1560 |
| cctccgacaa ggacagagtg aacgaacgtc gtttgtgaac ggtgtaagca atcgatctc | 1620 |
| tcggagtcca actccaaagt actgtttcga tatgcattaa tacatttgat ttttgttata | 1680 |
| tcaaaaataa atattatatt aaatttata aacattaaca aaaaaaaatt aatttcacat | 1740 |
| aatttaaagg accatttggt aatatataca aaattgcaaa aatcaaattg ggcctatttt | 1800 |

```
gttgttattg gaggcccaag atgggtggtg ataaatatgg gcctccaaaa gaataagcaa    1860
aaaaccctaa tttcctctct tcctctcttt cccaatacta taaatcttca ccattttcct    1920
gattagggtt tttgttcgtt cttggccgtc cccttcatcg ttcccagaga gagggagaga    1980
gtaagttgca atagtaaaac                                                2000
```

<210> SEQ ID NO 49
<211> LENGTH: 2000
<212> TYPE: DNA
<213> ORGANISM: Cucumis melo

<400> SEQUENCE: 49

```
aattagcaaa ttgtatgtaa caacgtcatg aagaggcatt tcatcgaaca atttaatagc      60
agagtcaaga tggcccagtt ttataagttt attgatttct cgattcttaa ggtaaatgag     120
atcgcgagca tggaaatgca gacccaaacg agaatatggg tgtggtaaat ggaccggtga     180
tgttgtggct acaaattcgg attttacagc agtaatagtt ctgacgaagg aagcgaattt     240
agtgaccttt cgcatcacag tttaagctta tcagagacct gaacaagggc tctagctcta     300
caacttagaa aggtttgata tggtccgtga tcggggaggga ccgaataaca ggcgcttaaa    360
ttgttgttca taaagaagag gattgtcgtt gatgtatttt aaccaagaga tgattagtta     420
tccacatcca cagagagaac agaagacggc tttctaaatc tacaccgata aaaataaccc     480
taccactttg tttctttaga aagggtcac attctttaaa aacattagcg tcgaggatta     540
atagggtata ttgactaatg ctctgtttgg atttcgagaa ataccaattt acaattgatt     600
tcaaattaat tatgttttgt tgttgcacga agataaaaa gaatttaaaa ttcaaaagga     660
tctcaaatct tatttttaac ttaaaaactt ttatgaccca acggtttat gtatgattta      720 aaagtagaat acctctgtga attcttaatt ttttttctt tccaattacc acataaatat     780 gaaatttaa atacatttat tttaaatttt atatccgaaa caaaataata atttaaaact     840
atttctcata tatgaagtgt gattcgatct aaattataaa ataataaaaa tttacatcta     900
gttttgatta ttttttttcg ttagatacta aattgttaag aaaataacat ttttaatcca     960
aagttttgaa gaatatatga cttttaaaat ggtatttatc tttttagtgt ctgattttta    1020
aaaaatggat ttcaaaagtt catcaaatag cattgtatttt ttattttaaa taattttgac    1080
atttaaaatt agagtaatgg tttataaaag cacttgatc tctaaaacta tttttcttaga    1140 tataaatacg tatgattatt tttaaaaatc aatcaaaata ggtaaattgt aaaaaaaaaa    1200
aaaaatcaca tgaatagtag ttgtaattat gctctcaaac tttcggttat gaaaaataaa    1260
cattttaact tttagacgtg tcaaagttga gtcaagttgg accttcaaag ttatgtagtt    1320
atataaattg taatatatgt ataagcttgt ggattcaatt ttatcattta tgggtccaat    1380
ctctacaatt atcgtaagtc tatgggtcaa ttgtaacaca tgtggagttt aagagctcaa    1440
ttttggacgt ggatgtgttt tgcaaccaac tccacacctt aaaaggtgt ttttttttaa     1500 tttatcaaaa aacaagaatt tagaatcttt aagtttatct ttaaaaatca acggacattt    1560
tgaaaaccaa ttgaaactac tgttataaac ctaacaacta aaagtatatt ttttaagacc    1620
gaaagcataa atccataaaa aaaaaatcca gaactgaaaa tgtaactttt atagttgaaa    1680
atttagctaa attatacata ttaaaattca aggaccatat aaaattaaag tacctgatta    1740
aataataacg aattaatgtt tggtatttttt aacctacatt agaaaaaaaa aacaaaagaa    1800
aaacggcata ctatttgtca agcgtccgat gggaagaaaa tccaacggtg agtgttagta    1860
```

```
ttgaaatacg cagttctcgt gaatgagcct ggcttagatt tgggaacaag agccaacccc   1920
tttcgaccga aagccgtcg tcttcaccat attcgcctca accattcgat agccacgttt   1980
gaagaagaat taggattgcc                                                2000

<210> SEQ ID NO 50
<211> LENGTH: 2000
<212> TYPE: DNA
<213> ORGANISM: Cucumis melo

<400> SEQUENCE: 50
agccaatggt tcaattaaca gctctagttc tagcatggct accgctggta acctttctat     60
gactagagac gtcttggagg tggagggtag ggcacgagga ttgaaaggtg agggtttggt    120
gaaaactcaa gcctttcaaa ttcaagaaag catgcttgac ctagtagcat ctggtgatct    180
tggggaattt gcaatggata ctcatacctt agtcggcat tcgtctcttg gttctgctgg     240
tatatatttt tttctcttgt tttctagtga tattttcttt tatcaatttc cattatgaag    300
atggaatctt atgttctatt ttttcatttg gaatgtaggc tttcacaatg aaaaaattgc    360
taatacgttt ccagaagagg ttgctaaaga cccgtaagtt cttatttctt aacaatttcc    420
tcagtttaac aagttttatt tactaacata tccttagttg tataaatatg aatctattat    480
attaactatt tcatttatct atcttttaac agggtgacca ttcacaacaa agataatact    540
tcattgaaac gccctcctgt ctcacgcact tcggcatccc aggatggatt gtctgtcctg    600
attcctgatc cggttgttag aggaaagaac tcagatggta ataataagt gatccattct     660 gttatcttct ttattcattt tcaattttgt attttgtata tatttatata atattttaga    720
aagataaaag atccatcctg aaactttgtt tcaggtggaa gaccggaccc aactagtatc    780
ttggtgaacc aagaaaacat ggcagccatg aagaaagaga tgcgtttccg gcgctcttct    840
tcttgtagtg acagcgacgt gtcagagact tcttttattg atatgctgaa gaagacagct    900
ccacaagaat cccatttgac aacggcggga gttccagagc catctgatgg aatgcaggga    960
gggaaaggtg ggaaaaagaa agggaagaag gggagacaga tagatcccgc actactcgga   1020
ttcaaagtca ccagcaaccg aattatgatg ggtgaaatcc aacgcttaga cgattgatcc   1080
attaggcaag atatagaaca gaattgatt tttttttttt tttttccaat cattttgta     1140 gattgtgcag ttatttgttt tcgtgtttgt ttaaccctct tgtaagttgt tgtatatagg   1200
tttcttagag ttgtcagctg cgttgaaaca tgtggccggt atatgtattc caattctttt   1260
cttttttccc gcagttgtaa atgatcaaat ttgagttggt caaattacca aacctttgta   1320
caggaacttc gaagagagtt gaaattttat tcttttctt ttttgttctt ttatagagtt    1380
cgagattatt tgtatgaata taatcaaaag caaagcatgt aaaaataaaa tgatttgaaa   1440
gggaggtttt ctatcccatt caatgtgacg aatccaacac ttaaagtaaa tttgaaaact   1500
gtctaattta tatgtatgga atgtaatgct cttcaagaaa ttatcttatc ttctaatatt   1560
taatgggatt cacataaata tgaaatttca acgttttct tttccttttt gttgtgagat    1620
taaggatact agataataac cgacctcaac cttttaggcc aagaggtctg gagtctttat   1680
acttgaaaaa agtttacaca tattctaaaa gattaaaagg ttaattgttt ggtaaaacat   1740
taatgatgac gatacttaag gtttcattaa aaaatatttt ggaacaattt gtttataatt   1800
taataaaatt gtaactttga acatttgaa ttacattttg ttttccatt tttacggtcc     1860 tcgaactcat cgatactcac aatggagaaa aatatcacaa tgccgaaaat acccttcttg   1920
ttcccttctt atacaaaagc aacactattg gccttatcaa cggagcagca gctactctcc   1980
```
tttagcacaa atctccatcc                                         2000

<210> SEQ ID NO 51
<211> LENGTH: 2000
<212> TYPE: DNA
<213> ORGANISM: Cucumis melo

<400> SEQUENCE: 51

```
tggtgtaccc acttggtttt ttctcttttt ttcttttagc tttttgctcc taaatttctt      60
gccttagttt tcaaaagctt gtttttattt ttgaaattta accaagtgaa tagaaaaaaa     120
aaagagaaaa caaagcttt taaaagcttg tttttatttt tgaaatttaa ctaagtgaat      180
aggaaaaaaa gaaaaagct tataaaattt gacgaaattt gctgtatttt gtacattta      240
ctattttct attttaaaaa atgtgtctga acgaaaaact tatattatga gatttaattt     300
tcaaaataaa attataccaa acagacttta gaattgtcaa tcaaatttga caatgattag    360
gtgcattttt taaagttatc ctaaagtttt ttttttttc gtagtcttgc ccttgctttt    420
atcgttaaca ataaaattt tccttatata tatatacaca tttaactact caaggtctgt    480
attttttcca cctgatttat ttaatatttt ttttttttgc agaaaatcta tttgtatttt    540
aggggaaaca aatgagtgaa gagatcatca agcaacggtt gcgatgttgc agcggaaaaa    600
tctttggttt gtcatttctt gtgatgggg tttatagggt agtatggtta ttgtatttta    660
ggatgttgat ttttatttta atgagccaag agagagatgt ggattctaaa attgatgatt    720
gatattattg atgtgatata aatatataat tttgtgcgaa aattgctatt ttattttctg    780
tatgctcatt cagatcacac aataatattt gatgtagctt tacttattga caaaatatag    840
gttttaatct tgtgctcata caaacaacag ctatgggtga aattattttc tgattttatt    900
tggcaaagat gatgtcagca ttgtgtaaat ttaatgtgaa ttacacttct gatttcttcc    960
caatgtgccc tctcaaatat tggcaccaag ccatttaatt gtaaatacgg aaaggtcata   1020
aatttccatg caagatttat ttcatgttta aaatgattgt gtgaaacaaa atgaaaaaca   1080
agaaattctt acctccaacc tcaaagtagt cgatatgtca aggttcaata tcaattttaa   1140
atatccatga atagctttga tatctttat aaatgcttgt aatatatata tactaatagc    1200
aatgtctata agttagtttt gagagtaata cttgttatag ataacaatgt tactctattt   1260
accactctac tattgaaagc ttcttttct tccatttatg aattaataac ggtcaagatc    1320
caattgcatg agttacttt aattaattac aatctaaaat gttaatataa gtctaaaatt    1380
gtccaatata tgtgattttt tttttctctc tcaaaccttc ccttcttttc attgaacttg   1440
tggttcaaat ttgatggagg acactgggaa acagcacaat tcaaagagcc aaagattgag   1500
taatttttg atttcagagt tttcatctct tcttcattct cacctttca cttctcatcc    1560
acaactatcc aatcaaccat tgccacgtgg catcaaaaat atccaaaact gaatgagatc   1620
caccacaaag ttcctctcat cactgtttgt catcaactca tcaagaactt catcatcaat   1680
cagaaatcca acatttcaac ttctcttagg aaatgacatt tttaccagtc tccaatgtca   1740
aaaactcaca caaatcccct cttccaatc taaatttac aaagataaca ggggtaattg    1800
aagaaactta gcagtaagtt aacatattat agctttcatc aacccaagtt ttttggttc    1860
ctttctaaac tgtagtttgt tttcttgatc cattctaaat attcctctg catgaaaga    1920
agaaaggaaa agtgaaggcg aaacctgttt tatgcttcag aaaaccaatt cagagtaacc   1980
aaagatctga acttcagacc                                                2000
```

<210> SEQ ID NO 52
<211> LENGTH: 2000
<212> TYPE: DNA
<213> ORGANISM: Cucumis melo

<400> SEQUENCE: 52

```
cgctcaaatt actaacatcc ttctctttct tgttcccatt cgactagaga gacactatct      60
tatccacctc agttggctgg gtgaaatcat tgaaactaac ggttgattgt ccagattgtt     120
aaactaccct atgttttatc atcttggtta catttatagg attgtcagaa taataattcc     180
ttttgaaatc atattctaat tggcacagga ctaaaataat gcctttctta agctgtaata     240
attagaatct aaacagtgaa gttagtaact gattgatgac atttccacga ttttcattta     300
tatcctgtgc agctattctg acatcacaaa acatttcttg attttcattt ttacttgtca     360
tccatcagtc aggacgatat cggcgcgctt gttgacgacc ttgtcctaaa tacaaagagg     420
cttatccgag ctacttcaag ggagattgac aagtggaaaa gatgaaatta ctcatttgtt     480
attacattgt acaagtgatc tattaggaag aaccacaatc aaaactgaag aaaaaagaaa     540
cgtgctggct gtctacgtgg cttttagagg tagaatttat gtacaattgt ttagaaagat     600
gtatttaatt gctctaaatc tcatatgcat tggattttga gcaatcttaa aatgccgaat     660
acttaatgta ttatcgtagg ggtccctaga tggcagattt atcatgtcca ttctccagaa     720
agaaagaaaa aaacccttttt tattatactt gttcatttta agcttttttct ggttgattat     780
aatgtcagta atttaaaaaa aaaaaaaaat tactgtgtat tggcatcggt tatatgttat     840
atacaaccct agttaaaagg taagttttg ttcattcggt cattagtcat tcctatacga     900
acgtcacatt gtgctttata atttcaatag gttaaaagta ttcaatatag tttttttaagt     960
tacctagtag aggtgatcat tggttgatcg gaatcggttc tttgacaaaa ccgccactga    1020
accgatcata gtcggtttag taaatgttca aatcgacctt gacatcgatg agtaaagatc    1080
ggtcggtcgg tttttgtcgg atgggccggt ttaacacttg gaaatactat tttgaaattt    1140
ttcgaaatta atccctcttg ttttcctacc gaccgatttt gggtttggtc ggtcagttcg    1200
attttttcgg cctatcttac tcactcttat tacctaggga ttgaatttca ttttatcctt    1260
agttttaggg ttctttttttt atacttttga aatatttatg tcgatgtcta gagtttaaaa    1320
ataacacttg aaattataat ataatttttt ataattgtta gctataattt tacgtccaaa    1380
tatcaactca ctcgcaactt gtttaatcaa ccaataatat gtgtctggaa tagtaagtat    1440
ataacttgtg gaaaatgact ttaaaagact tttttaaagt atttatttaa tgccaaaata    1500
tctatatttta tgtttataca ttaacataca tatccaaagt tacatattag atttgttaaa    1560
taattcaaaa tgagctaaag aaaaaaagaa gttccatata ccaaaataaa atataaaaag    1620
ttgaagacta aaatagagat tttgaaacaa ggtaagttag atttacaaat tgcaatatgg    1680
gagaccaaac caccacataa caaaaatccc aatgtccaaa tggcgcaatt ttgtttagga    1740
tagctcacgt tatccaaatc actcaatcgg agagaccaac ttaaaggcca catctgccac    1800
gtcaccatac tccaccaatc acaacacagc attggatttc tcagcttatg agaccaatca    1860
caaacctgaa tccgacgtgg catgtccaca tccaccagta ccaaccatat agcttctacg    1920
ttctccacat ctaatcttca ccatttacac aatattcttc attcttcttt cctcccttca    1980
atccttcatc ctctccgccc                                                2000
```

<210> SEQ ID NO 53
<211> LENGTH: 2000

```
<212> TYPE: DNA
<213> ORGANISM: Cucumis melo

<400> SEQUENCE: 53
aattctaaca actccggaac caaataattt agcatggatt gaaatataaa tcttcttgac      60
ttgcaaaaaa atcattgtaa tggtcttatg ttggttatag ttagggtatc gaaacgccat     120
acaggaatat gggattaaag ttaacttttg ttcatcaatt tcagcttatg aacttctaaa     180
atatcaattt tacctttgaa cttatatgtt attacccctt tcgattgtgg tatgttaatt     240
aatatctgaa tctcagtcct tatgaaactt ttttatactg tcacaaacat atgaagtttt     300
attgtaagtt cttagaaatc atctaaaaag agtagtttgt tggactattt attttatttt     360
ttcttattaa gttgttttca cgccatttca gtaaaataac tatagtgaat agagaatcaa     420
acttctaatc ttaagttaag gtagtagggt atatgctaat tcaataagat aatccgtgat     480
gcttgacatc tgacttaatt gttataagtt ttaaatttt tattgtaata tttaaaatac     540
tagttttgg tttctaataa agaaataatt gaacaattac aaatatttat acaaaattaa     600
actagaatat atgatcattt tccttcgtgt tagaaaaagg gaaatatatg tgtgtattta     660
tacatattag atattgtttt actatattcc attttcctca cgggaaatgg aggattgagt     720
gggagataaa cattgtcccc aagagaattg ggaatggaaa tgcaaatgac atggccctcc     780
acaaaattgt tcgcctaaaa atgggctttc tcacttctca ctccgcaaga aaaatatcgt     840
ttcccttcga attattcggg cggcaagatc tcaaaaccac atgttttct ttcttatt     900
ttcaagccta cattatttat aaaaatataa cttaagcaga gaattatgta aattcaagtc     960
cattttcgc ttcacttagc taaatcatta acaaatctgt aattttgttc ataaattagc    1020
tcaccaatta tgttttagcc cactaaggcc cattagacat tttattaga aaacatgaa    1080
ccgttggatc aagatgtgtg ttttctttc tttttctttt tatttttttt gggttttggt    1140
ggggttttgg tggatcatgg tggatcaatt cgtagcttta gcaacctatt attatatgga    1200
gggaaagggc gtattaatct gttagcgccg tccgggagtt tagctttctt ccccgagcct    1260
cggtcttatc ccctaactcc aaaacccag cccaaaggta atccactcct tcccctccg    1320
ctcttcatct ttttctattc atcatcttta atctgttctc ccttttggtt cttagattct    1380
tcttttgttg gattctttta atctttactc atggttggcc ttgtaagttt agacgacgtt    1440
tttatacatt ggttaatcct gcttctctat ctattcgcac gctagggttt tcctattgtt    1500
ttctattctg ctctacttct gcaaggttgt gttcttcttc gttcaggtcc ctttttttaa    1560
ccgaaattaa attaatgcaa attcgttgt gcttctaatt aggaagcctt ttggaacatc    1620
tcgacatttt gattgctgca tttcatttcg ggtatatttc tatgattgaa ggatgtgggt    1680
ctgttcactg catggtcatt acttatgcag ctatgcttat cgagtccatt atgtttgtgc    1740
aatctgtttc cggattcata attttttagt aattgatcag tagatgaaaa aagatattgt    1800
aatattcctt gagtgttgca ccagtcttgg tgggtatctg ctcctgctct ttgcttgtgg    1860
attttacttt tattatatct gtattattcg aaatgttctg ttcttgttat aacttatacc    1920
cgaagatgtg ttcctccccg cgtctagcgt tgtgggttac ttatgatgga catggttttg    1980
attctgtttg gtttgtgcag                                                2000

<210> SEQ ID NO 54
<211> LENGTH: 1547
<212> TYPE: DNA
<213> ORGANISM: Cucumis melo
<220> FEATURE:
```

```
<221> NAME/KEY: misc_feature
<222> LOCATION: (1)..(1547)
<223> OTHER INFORMATION: n=g, a, t or c.
<220> FEATURE:
<221> NAME/KEY: unsure
<222> LOCATION: (1)..(1547)
<223> OTHER INFORMATION: unsure at all n locations

<400> SEQUENCE: 54
ataatgtgtt gatgttgatg atcatgcatg gtatattaat ctcatgatta aagacgttaa      60
gattaatatt cattccatgt ttatgatggg tgttcttagg gttgtaccca tatgggtgtc     120
cctcgggatc accaccttt ttatgactgt atggttctac gagaccacca gtctgtcatg     180
atatgtttat gaatggtacg acggggtcac ttacagccca attgcttaag tgttccttcg     240
ggttcactga agacctattt ttcctaggtt ttcctttgac ttcagcaaaa atcagttttg     300
tcctaggtgt tcctcgagtt cactgaagac tagttttgtc ctaagtgttc ctttaggttt     360
atcgaagatc agatgtgttc ctacagaatc attagattgc aagtgttcgg gaacacatcg     420
gtttaggggt acttctttac atgaacccta atggaaaatt aacagacatc tagcggaatt     480
agtagttggt cccttactga gtatatattt atactcactc tttttatgtt taatatttca     540
ggcaaaggtt aaggtagagg aaagttgacg agtgatagaa aaggatctgt gacatgtcat     600
atggggactc agtttcgttt ctgcttctat gtatcagtgt ttcagtattt tgtttnntaa     660
tgaaaattta gtcttcctct attcaagaaa gtgtctcttg ttattgttta tttttagtaa     720
tgatttcaac ttagtataaa tagttggatc attacaaata atatattggt gatatacttt     780
gtaatgatac attgagttat attattcata tgtttaatat acaaaactgc aatattaaaa     840
aatgaaaatc acgtaataag tatatcaaca aaataataca tatattacaa gcacgtcaca     900
acactaatat acaaaactaa tataaagtaa gatcaaagca aaaccaacgt aaaaaataaa     960
acaaaatcat ttgaaattaa atttaactca aaatacacat cgaagaaagt ggagaaaaat    1020
cacaatagag ttaaattact ttgattaata accattatat ttcatattga aaataatatg    1080
tcattagtat tttaaaatca agattaagat aggaagaatg aattgctctt ttcgtataaa    1140
aagggatgat tggggcctta cgaaaggaga aaaatacata tgttatcgaa aaacaaatt    1200
atttttcttg taagagagaa tgattatatc cttaaaaaaa tgaaagaaag aaacaatcat    1260
ggcattaaaa aggaaaataa ataaattatt aaagggcagt tcgataataa taacaaattc    1320
aacgagagta ttaaaagaaa atgagaattt gcaaaattta aacaaatgtg tatattaagt    1380
acagccaatg caatttttcaa attttaattt atttggttta cccaaaattc aatttctaaa    1440
ttgagaggag gatatagtaa attcacacgc attatcccct tcgagtttca tcatctcacc    1500
cattcttgca tacagtgcag ttacaattcc ttcattctgg atagaca                  1547

<210> SEQ ID NO 55
<211> LENGTH: 2000
<212> TYPE: DNA
<213> ORGANISM: Cucumis melo

<400> SEQUENCE: 55
aaacacttat catgttatgt atcccacatc gaaaagataa aagagacttc atgatcttta      60
catgatatat gagttactcc ttcgactacc attggttttg gagatggatt caacccaata     120
atatgaatct gacccaacaa tggtcaactc aaagagacac catcttgaga tacatgttgt     180
gtacccatat tagatgaatg actataccto gcaatattta taacatacat gaattacttc     240
tcttactgta atttggtttt gacgtggagc ccatgattat ctaattaacc ataactggta     300
```

| | | | |
|---|---|---|---|
| tatgatatat | tagtaggtaa | cccgaagagg | ttctaagata aacacagaat tcaatagaat | 360 |
| cagagccttt | ccaatgatat | ggctttagat | gggaatgatt tgaagtataa tcattctacc | 420 |
| acacccttta | tatttgtctg | tcaccagaaa | tctcatcttt tcttgaggta ttattcactc | 480 |
| gaaaagaggg | aggcattttt | gggttaccca | tctaatgcac gatgaactaa gggaggtcaa | 540 |
| gttctgggaa | tacagctagg | caaccttcac | agtggataca ttcgaacaaa tgataaatgt | 600 |
| gaaaatgaat | catttcatga | gtgtgactaa | cccaatcatt cctccttcta tatctttgaa | 660 |
| tcccacagtg | agtcagagta | aaagttccag | caacaagtcc tacaacccaa attctttagc | 720 |
| tatttcttcc | accagaacaa | aaccaagcaa | aaaatcagcc acaaacacag ctcaacaatc | 780 |
| tataaaggcc | aaaatactaa | gacagtcacc | attaccacat gaaagccgt attttccaac | 840 |
| agactttgcc | tgcaaaatag | atcacaaaga | cacgatttca cattggacag acgccacagc | 900 |
| tccacaatct | caatttcaat | caaataaaag | taaatcaaag ctaaatagca agtgtatggt | 960 |
| accacgaaag | cagcatggct | gacgccactg | aggcctgtaa gagagaaaac aaaataagtg | 1020 |
| tagaagataa | agtgaaatag | aaaaatcaat | cgataagata gattttcaga ttaccatttt | 1080 |
| tacgggaatt | gtacggaccc | aaacacaaac | cccatagagc gccggcctga agatgaacag | 1140 |
| gggcaggaaa | ttcagaggaa | gaaattaaag | aaaatgaatc atagtttgag aaattattcg | 1200 |
| taaagtttac | cgttccgacg | cgaatgctgg | attcgacggc gagggaagaa caaggaacga | 1260 |
| cgccgttgag | ttcgtcttcc | atcttccaat | tctcaatttc cttcggaggt ccgtatgctg | 1320 |
| agagctctgt | gtctaccaag | ttccaaccat | actacgtcgt tttggatttt tattttatt | 1380 |
| ttctttcctc | tcttttgcca | aaaagaaaa | aaatagtatt ccaacctaaa acctcaaaat | 1440 |
| aacatatttg | ttgtacaaat | tataattagt | aaacatttgt cattgtgagc ttggtatgta | 1500 |
| atattaacac | gaactttatc | gctaataatt | tagacgttaa tgaataattt gagcattgcc | 1560 |
| ttcttatatt | gttattgtgt | ttataatagg | attgcttaca atgtaaccta gtatgttgtt | 1620 |
| gagctcgtta | acttttttgt | ttttcttgaa | tattcaaagt taaaaaattg tacaagtttt | 1680 |
| tggtgacgtt | ttcttactac | attatcggga | tgaagatcaa atatagctta gattagagaa | 1740 |
| gataatcatg | ttgatttatc | gttaaacttt | gactacaaaa tccgtttaat ttttttttgg | 1800 |
| atgaattagt | tatacaattt | aaacttaaaa | ggggtgaatg aagaaagagg atagttttac | 1860 |
| aaattcgaag | tgaaatgagt | tatttctgct | taaagaaaac aaatctcctt cgtgctttaa | 1920 |
| aacacaaact | caaaacccta | aattcagcgc | cgattcttca atacatctct gcaggaagtt | 1980 |
| agggcaaagc | agaagcaaaa | | | 2000 |

<210> SEQ ID NO 56
<211> LENGTH: 2000
<212> TYPE: DNA
<213> ORGANISM: Cucumis melo

<400> SEQUENCE: 56

| | | | |
|---|---|---|---|
| acttccaaaa | atcagcctca | tgggatattt | aaagaaaacg taaattaaaa ttagcatcat | 60 |
| ttcatattga | acaaactaca | aaaattaact | ctaaagatg atggtaacta caactaaacc | 120 |
| ttcattttt | cattgtaaaa | atcgaactct | taaacttgtt caaatattaa aatttgaccc | 180 |
| tcaaacttaa | aagagctaaa | aaaagacctt | caaatagtaa aagtagaact ctcaagctta | 240 |
| tagaattatt | acggttatga | ttatagccat | agatgattca atcgattttc ctccaagatg | 300 |
| atggagtata | attcttcaaa | tctagctgct | tagatgttat cacgataatg aaatcatatg | 360 |

-continued

```
ggaactcaac aaaaagaaag cacttaatgt tgaaagacat tattctttgg gtgttgagtt      420
gggcgaactt gattttatt attaatccgc aaaggacctt ttgagtaagt tgtggcaatc       480
tttattggag tgctaagatt tgttattcga aatttcttgt tttgatattt ttccaactaa      540
aactaatttt tttaagaaat gcaccttcaa ctgatttcat gcgtgtcctt ttgcaagact      600
cgcatgggac ataacacatc atcttatatg gcaaggccta tgtgtcagtg gagatttgac     660
gtcaatttct ttccactgag agtcgtcctc tttgtgatgg cagaactttg gagagtcatc     720
aaaattggtt ctttgaaaat gtttcttatt ttgattttt tttttgaaag aaatgagagg      780
aataagatat ttttacgagg actctactag tgggtcaatt tgcccgcata tggatatgca    840
taagagtcct tttggagaga aagggtatga tggaaagaca ttgcaaaggc ccgtccacta     900
actttctatt atacaattag gtggaagcca cccatagcaa tgtcttggtt gaacactgat     960
attacttgaa accatgcatt taagatgtga aatctcgact agatgcttta ggaatttgga   1020
ttgtgtctgt tttgttgaat tcaagttcat tcctaaatac catgaagtta agatccttga   1080
agcaatgaag accattatt tagatcctta attcaaatct ctttactaaa gatgattgtt    1140
tataaatgat caattgttg aatgatgttc tacttgatat ctctaaagca tctcttttcg    1200
gtgagaagcc cacaacttga atagtattcc ataaatcatc tattttagt ttctatcatg   1260
ttctttaaca tcaaaacatt ttagcgcact ctcttataac taagacttag aaaaacacga    1320
atcttccttt cttacgatat atatcctaaa tggttttcta tatttgtgcc ttacaatata   1380
atcaattctt tttctatttg atattgtcat aaaataatac tgataacata gttttatgt    1440
tttattaaca cctaacaaga aatatggaag acgttaatat atcttcaatg tcgatattga   1500
atcattttat ttatgaatat atccacgcgt caaaaatat tttaatcatt aacttctagg    1560
actaaattca acattcttg gaaccataga caaaagaaca aaatttgcaa cctcaacaaa    1620
caaaattta tctttacatt tgcggctaca attcacaaat tcccaaacca tgatagaaag   1680
gccccaatct cccacgtgat aaacacacat atggcacgtg accaaatcaa aatcatccac   1740
atgatgaaaa cttaatggac agctcggatc ccaacaccca ataaaaagca gccatgaagc    1800
tgacgtggca gatttccccg aaaacctttt aaataataaa caataaaaaa atatatacat   1860
aaccgttggc aacgttttc cctccacaca ttttcccatt gccttatctt tctttccctc   1920
caaacagcga gggaagaaga atccaatcat cttcttccaa taatttctaa aacgaaattc   1980
tgctcgattt tccctctcca                                               2000
```

<210> SEQ ID NO 57
<211> LENGTH: 2000
<212> TYPE: DNA
<213> ORGANISM: Cucumis melo

<400> SEQUENCE: 57

```
tgggtaacat tatgagtttt attataattt aaatgaagat caaactttaa gttgtagggt       60
caccatagga ataaaatata atcaataagt tagggcccct tagtcccacc tcgtaaagga     120
gttctgtcat acatatacat tatgatatta attctatctc catgagtcat acatgtgatt     180
ttagtacttg taattttcat tcttttttcct attataattc attcaagtac tgtcaatatg    240
gttaggtatt gaaattaatt atagactcag atatcatctt cattaatgga aatggaatgt    300
tatattctac ctctcatttt tacacgttga tgataaatta gaagaaaaaa aattattatt    360
tatattgttt taattgtgag atattagttc aaaatgtaat taataaaatg atacgtgtct    420
tataataaaa ttaaacaagt ataattaaat ataaaacaac atacacactc tttaactaaa    480
```

```
agacacaact cacctaatgc tcgacttaaa atcactttgt gtcgtaactt aaccatcaaa    540
gcatgttagg gtaaacacaa taaagatgat ttttgagtta tgcatgtcat ataatgtcac    600
ttccaatttg acttatcttg cttgcttgat tcatgtatat aaacaaaaac atgaaaagta    660
gtgtaaggat accaattacc tactgatttt ttttaaaagt agtttgtcta agacgtgtta    720
aattactaac ttagtcacat ttgagtttta gttctaactt attaaacata agtaggtat     780 ctcccttact catgtgtgtt tcgataatgt caaattccaa tgtttgatta accaaattgg    840
gtaatttaac ataaatattc ataatataat attttttatg gaataccgac atctaaaaag    900
aaatcaaaat gaatattatt aggaggtgag ttttaagag agaggaaaat aataaaatat     960
ggcatcaaca agaacaataa taataagaat agaaatccga caaggaaga agtggatgcg    1020 tgttagtact attgacattg gcatatgaac ggttgggttg ggcctcaaat aatttgcatt    1080
tctaacttcc aaacacctaa ttcctttttt tttatccata cttgcaaata tatatttata    1140
tatattcaac aagtagttta atttatttga tataccactt taagttttaa attgatggta    1200
gtgtataaat aaataattta ggattaagca tgtctatgaa ccttttgaaa tttgatggag    1260
tatatataaa acagaatact catgggttca ttataaaaat ctaatagtaa atgtatttt     1320 tatttcattt aaacattttc aaactttaa aattaaaat tatcttaaaa aacacgtgtg      1380
gtttcgaacc atatggttaa aaatattgag gttctctatt ttgcaaaaaa tttggaaacc    1440
ttcatggaag ttgatataaa ttgttgtaat tagttagtat ttttctta tttgtggctt      1500 aatcatgcta tgattgatca ttttatcatc atttctataa tgtaaaacaa tatatttgat    1560
gtgtattgta aattttatg caagagtaga aaattaataa aaaaaaaga gagaaaata       1620 attataaagt aatataaagc tattaacatt ttaagaaaaa taatagtgaa aatgaaagtt    1680
tcggacaata attcaataaa gaaatttgta gatttcgatt aaaatttcca aaattaagat    1740
tttcattaac acgtgtgcct cgcaaccgtc tcctacgtta tcccgtaagt agcccaatct    1800
atcccattct tacacaagcc gtcggcccaa attgattgta ggccatcggc ccactcaaca    1860
cccacaaacc ctagccccctt gctcctcctc ctctcttttt cacggctgct cactccctct    1920 cttttttacac cttctccttc tccttctccg tccctcttcc cttttctgct actatcttca   1980
gcacttgctg agcttcaacc                                               2000
```

<210> SEQ ID NO 58
<211> LENGTH: 1591
<212> TYPE: DNA
<213> ORGANISM: Cucumis melo
<220> FEATURE:
<221> NAME/KEY: misc_feature
<222> LOCATION: (1)..(1591)
<223> OTHER INFORMATION: n=g, a, t or c.
<220> FEATURE:
<221> NAME/KEY: unsure
<222> LOCATION: (1)..(1591)
<223> OTHER INFORMATION: unsure at all n locations

<400> SEQUENCE: 58

```
aatgttgatt taccttgct ttgtttgaat ttcgtcctcg tggacttgac ctttggtctg      60
cttcgtatag gactatttac ggctgccctc atagtccaag tccttgtccg ccttacccta    120
tactctctat ctctagacaa tgtgaagcgg gcccttctat aatattgggc cttgaagttt    180
tgggctttgg atctgccgaa ttgtgttggg tttctctccc aatttattc atttctttat    240 tcaaataatt ataaatatgg aattttattt tatttaaaat ataaaagtta aaattgaacg    300
```

| | |
|---|---|
| aatccaaaaa taatggaatc aaatcgacgt tttaacatat ttttcaatta tgtttttaca | 360 |
| ttcattttcg tcctacaaaa atattcccac ctttatttcc tcgatatcgg aggtcacttt | 420 |
| gtatgtttca ttcgggtgat gtgatataga tcgagtttct atgcttgatt gactatggaa | 480 |
| atatatttta agaagatgtt ataaaagtaa aataaatgtt ttgattgtgg atataattat | 540 |
| attttaaaca agatgaggaa taattagatc cgaaccaata atcttgagtc aagagtgtac | 600 |
| attgaaagtc gtatattaaa taatggttga gtttataata atattgatag attgcagtta | 660 |
| accatatttt ctcaagttgt tgaccaaagt acttatttta taaacagttt agggaatgtt | 720 |
| tatgaagttt tgccaagtgt tttgaaccta tgagtatt gacttaattg gtatataagt | 780 |
| gcattaacaa tcaagaggta tttaatttga atcgtcctac ccctatcatg ccaacaaaac | 840 |
| aattatatgt ttgtcatatt ttattgaaag tgttttcagc gcaatttagt ttgatttgcg | 900 |
| tacaaaacat gtctacacgt atcgagttag tagtaatggt tgctagttaa gactgtgaac | 960 |
| taaaacttta aatttacatt aaaaanaaaa acattatggt cgtttggtcc tcatatgtga | 1020 |
| ttgatagata ttgattaatg agtatttgtg gttgttgcca acaataaaga tgtagacaag | 1080 |
| tgaactatgt tggttgtcaa atcttgtttg tatttgttat gtgtggtttt caccaccaat | 1140 |
| gttgtagagt gtcagatcca gaatagcttg atcattttc atatatatct acagactcaa | 1200 |
| ttagtagata aaaactataa gactttgact tatttctctt aaaatgtctc ctcgttctgt | 1260 |
| acaatcctca caacgtttg gtgactttaa aacatcacaa gaatctaaga agaatgatga | 1320 |
| attagatgca atgcaaagat ttggacctta atttgttac tttaaactttt atatccgaac | 1380 |
| attggaagag gcaagcaaaa agcgcgcttt agaatcgcgg tttctttggg ccgagtgggt | 1440 |
| tgctcataac agcggaggtt tgcttttctg ccaagaaaac ccctcaaaga aaagggctt | 1500 |
| aataagcagc tgctccattt ctaagtgggt ttagccttta gcacggaagc gccaattcga | 1560 |
| ttcaactctg atacactgca aaaattccgc c | 1591 |

<210> SEQ ID NO 59
<211> LENGTH: 2000
<212> TYPE: DNA
<213> ORGANISM: Cucumis melo

<400> SEQUENCE: 59

| | |
|---|---|
| aaagaatgga gcaagctgat attgctaagc aaaagcttct gcatgattgt gaagttcttc | 60 |
| accaccgcct tcaagattct actgtcgact ttttcattga gcaggaaaat aaactaattt | 120 |
| tggaaactgc ttcgacagct gacgacgcaa tagatctgtt ggcaacatct gataatcaca | 180 |
| ttaaccttct tttagcagag gtacttgcgt ttgtttccat tgaaatgcat ttgcatattg | 240 |
| aacttcttca tcctgaatgg cacaagtttt tgtccataca aacaggcaaa gcttctggct | 300 |
| catgatgcta acaacagcga tgacactgct ggatcagccc gtccaaatgg aactgataaa | 360 |
| ggggcagctg accaagtatt aagtaacata ctagcaaata tgcttgtcga aaatgcccga | 420 |
| ttaaggatgc agatgaacgc cgtcatccgc tgtgttctaa atgcaaatgg acaagtgag | 480 |
| aaagatgaag atgaatctct caaggaagaa ctgttctaag caagttttta gaggaagaga | 540 |
| ttcctgaatg cacatataca atgaccttat actgtcgtgg caagaaatgg gagagctgta | 600 |
| gattttgaat aaatgcaaca gatgttgccc attaatttgc aagtcctgac aaatttggtt | 660 |
| gtcggaggtg tagaaatgat gtatcaatta aatatttaac aaagtgcctt ttggcttggc | 720 |
| taatcatggg catttgaaga ctttgcactt ggtaagagct caaacaaaat ctgggtggct | 780 |
| aaatttagtg ttgattaaat ggaatttcac tgatattcat gatctgtctc ttcttccttc | 840 |

```
attgatatat tatcttctca gtaaactcct gggcctgatg cagaattgct tttaaccatc      900
tgcatacaga gaagaagtaa aaactagctc acgtggataa agggaaattt ctactgacat      960
gttggcatta gaagaaaatt ttgaaagagt tctattacca taacatcatc tacttccgtg     1020
tattattgaa actattattt ctcttacccg gagatattaa attaataaat ttctatttac     1080
attttgaaga tgctcgtgat tattgataaa aatgatgaat cattattttg attacgttac     1140
aaaaaagtca aagagagtaa caaagctatc aacaaaatat tagtaatata tacaaaaaaa     1200
gtgtaaattt aatattaaca ctgagaaata tacacttaag ctaatgggtt aaaatattta     1260
tccattgaat taaatatggt ttttctgtat ttgtgatatt ccaataaata tgaagctgtt     1320
atactgtcaa attcatattc tgcctataca atcaatttca agtcactcaa ttttgcaaaa     1380
ccatatcata ttgagttcaa ataaaatttc atatctatat acataacgaa atgttatgt      1440
ttttgctttt aatgttttgg gtatctttct aagctacaag aaaatgtaaa aatgataata     1500
agaaatagat tatattaaaa ttattttaca aatcaaattg cggggatagc tcagttggga     1560
gagcgtcaga ctgaagatct gaaggtcgcg tgttcgatcc acgctcaccg caaatttttt     1620
tcttcttttt ttccccttgt gtatcatttt aaatgggctg ttcttacttt gaactgcgga     1680
agcccatgaa agctaggccc aatttagaaa ccgaccatct caagggtcgg ttcgtcattt     1740
atcaagatcc gataacccga ttcgctccat tttagtctct gctctttcat ctccctcacc     1800
cattctcgct tccactgagc gggcaaggga gcttaacccc tcaaagccct agaaaccgcc     1860
attggagaag ctccactagc ttcttcttct atcagcgaac gtattttcgt cttgtataga     1920
cctttcatct ctggaaccga tcggaagttt ggagtttctt ggtctcagtt tgtagattag     1980
ttttatcttg gcgtctcaat                                                 2000

<210> SEQ ID NO 60
<211> LENGTH: 2000
<212> TYPE: DNA
<213> ORGANISM: Cucumis melo

<400> SEQUENCE: 60
gtgcatttaa aataatctag ttgcatgttc taggttcgat ttattatttg gggatttagt       60
tgtgtctgta tgattgaaaa aattaatgtt gatcttgtaa cacaattgtt tttccctcga      120
tgatttgaga ttatttcaac aatttagatc caatgtttaa aaagccacct tggcatcttg      180
ccttcctcat tcgcaacctg cctccagttg aagcctcgag gctcaaagcc cagtgcccta      240
ggacttcttt attaatttta cttaaaaata agtttgtat ccctaaatgc ataaaatacc       300
cttgtgttta aggctttctg tttcttcgcg tttcacgtca ggtcagacca tgctcagcta      360
tttttccacc attcttcttc ttctctccca agtctatca agtattttat ttccacacat       420
atattcacct acgccaattt cttttttaaaa ttttatagat atatacagtg cacctcacga     480
aaacaaagtt tgcacttctt cagttttttg tttcgcctca cacttaagct acaaaaggtt     540
attacgtttt agtaacccac tactcagctt taaaaacact atttgtatca tatgacgtcg     600
cccttatgga ataatttcac ttgattatcg ggttgtttca taaacaatct tactctgttg     660
tacctttgac aggcctggag agcatgcaac tcctctcttg cttgagtttg agtaacaata    720
aaatcggaaa ttttactgca ttggagcctc tgagactgat aaaattctta aaagttttgg    780
atatatcgta caacgagata ggttcgcatt cgatcgacac aaccagatat ctcttctcat    840
ctccactgtc gcattccgaa gaaattgatt tgagcagtga tgaaatggca acaaatttta   900
```

```
ctgatatggc aagttactgg gaagcatatt ttctattcaa agatataagc ttgatgcaat    960
tggatataga aggaaacaca atatctagtg aaagtttcaa agcatttctg gtaaagattc   1020
ttcccaaact ccactggctt gatgggaaac gggtacaata gatatggctt aatttatcta   1080
catccaatcc tctgtccatt gtggttgttc atcccctgaa tgtaaaaagg tacgctacga   1140
actagcattg atcctaaatt gaagacattg gttttgattt cttcccaatg caaggttaag   1200
aactaaggat tgatattgc atccaataag cataggttat ttaagatttt ggtgatagtg    1260
aaaattaggt gacatgtctc gaaagcttaa agggatacat gaggtatgga gatggagatg   1320
gatgtggtta caacatggaa atgaatacgg tgcccagttt tttggactgc tctaaatcaa   1380
attttatcat atacattatg atactgtgtg ccaattgtat ttaaaaaggt actgaacttt   1440
acatttttgt tgtcccaaat tttgaaggat tgtagtttta ataattctta taataactat   1500
caatgttaat taaaaacttc agtatattta caattttttct aaaaatgttt gctatacgtt   1560
tagttattat cttgatcaat tgccccaaga gaaaaattac cctggactat ttcccaaaaa   1620
catcttctag tcgtccatca gctatagttt caaatctgtg tgggcccagt cggcccagtt   1680
cattgggcct gagaatagag atcatgaacc ggacggccca aaccttttc aggccccagc    1740
caagcctggc ctacaaactt ctaacctaaa accttatccg ttgaagcaat ccaataaaac   1800
aaagccacgt aagcacccag gatctaaaaa tgtatccaaa tccaccaatc tgaggccaca   1860
aatttagcct ctgtggctga atggatgtcg aattacaaga atctctcgat ttcttcctct   1920
taaatccatt taccccttcaa acaaataaac acaaaataaa gaaaggaga agaaacaatt   1980
gtcgtaatta gcagcaagaa                                              2000

<210> SEQ ID NO 61
<211> LENGTH: 2000
<212> TYPE: DNA
<213> ORGANISM: Cucumis melo

<400> SEQUENCE: 61
acctagaact tctaaacgat aatctcggaa aaaaaattgg aacaaatcat aataatgaca    60
attaagaagc aagaaccgtt gacaaaagca agatttagag ggagtaaatt tgcatggttt   120
ggtgatgatt atttagttga atttagccta ctcttaggaa gtatccaata atcatacgca   180
aatttcacgt agcatatgaa gcaagtgcat cataataccg cataacctgc ggggttttgt   240
catctcgatt aaacacaatg tgaacatgat gatgtctatg tgtttccagc ttttgttcta   300
atgatgatag acgatagtgt ggtatagttc atatccttga tttaattgtt tccatgtata   360
ctatcgaatt tttaatatat aattaatgta tgaaatcaaa tatcaaataa tgattgtgat   420
ttaatggaat aagatcatgt ctaaaattgg taatagtaat aacgaagaag gaagagaata   480
ataaactacg atttcttgtg aatctcctag ataaattagg ataaaaacta cgagtaagaa   540
tagaataatt atactatata aaataggagt tacaaatttt gtttcttaaa ataccaagct   600
ctgttacaag aaaaaacttt aggtattata tcttcaacat tttgttaatt tgttagagat   660
tttaggatag tttgtcaact atgggtcttc taagaaactt ggtcatcaag caaatctaat   720
gactcgaatt gtccttgatc gatgtgaaag atccaatgac ttcgaattat ctttatgcaa   780
tgtgtaagat ctaattgtca taaattgatc tcatgtgcaa agtgtaagat ccaatgatcc   840
aaaattgtct ccaacaactt cttgaacaat aagataactc tttgaagaat cttgaatatt   900
aattttgaca tagatagatt gatcttgaat attaggaaat aaggaaattt tcttatgtac   960
atgcctgaac tccttcaaca tagcattttg aatcatatct cttctctagt aacttgtata  1020
```

```
gttgcaatat attttgcttc tgttgttgat atatcaacac tgattgaagt tttgaaaccc      1080
aacatatagc tctagtggca agagttaaga catatatgtg gtgaatttac ttctatcaag      1140
atcacaatct aagcagatat actttgaaaa taaagttaga ttatccatta tacaatgtaa      1200
tatttacgga ccatttaact cgcttagaaa ttagagttat tttgcaaact ttattgacaa      1260
atatcttcaa aaatttcata caccgtatag acactatcat aagatgttaa agaaaaaaaa      1320
aaggtgaatt ttccatacaa ttaaaaaaaa tcttaaacta taaaggtggt ttcgatacct      1380
ttaaactttg aaaagtttca ttttaattct cgcacttatt gttttaaaac aaacttagta      1440
aaattttcgt ataaatttag aaagaaattt tatatttaca ggtggggaaa attctaaaca      1500
catagatgaa gataaataaa aacacgatca actataaact atacctatta ttaccttcat      1560
ccttaacacc atgcactcaa atattcatta attctctata tttttttcta tcttagcctc      1620
aaaatttact ttcatcctaa acttcgagcc ctcaaatttg cgttatttca ttcacgatat      1680
tcctttttta cgttctttca tttatggtat tcttctttac gttcttctat ttacgatatt      1740
cttcttgctt ttatagtgtt ttagatttgt tcataaacaa cgtataaatt gaaaacttta      1800
taaatttagg gcattaaggt ataattgaaa ttaaaaccat atttatagtc attaaccaca      1860
gtattattta tcctttattt attaaaaaaa aaatctactt ttagttttaa atttaggcat      1920
tttacgcaaa gctaattacg acataaaaca ccaaaaggag accccgttcg atcttcacat      1980
cttctcggcc agaaacgacc                                                 2000

<210> SEQ ID NO 62
<211> LENGTH: 2000
<212> TYPE: DNA
<213> ORGANISM: Cucumis melo

<400> SEQUENCE: 62
gcaatggcgg aaataacgta gcagagggca caaacaacga agaggagctt cgttcttcgg       60
tgcgccatct gggaaagtga gaaatggtgg acgaaacaca aacgggggaa tcggattgga      120
tctctcagaa aagaaatggt tggattcgat cacagatcaa tgaagcacat tactcggttt      180
ttcaagaaga ttacaagaac ttgcttcttg aaacctctct tcttctgttt gaaattttgg      240
ggcgtagaat tgaggaccgg agcagtcgcc tgaatttggt cgtcgaatcg attccacgga      300
aacaaaaata tgaagaaacc aaatgaatga cttagcccac tcactacgct tggcgacgtg      360
ttcttcttac gaacggacca atcaaatgcg agcctgatga atatgggcca atcatattat      420
gccacgtaag actttacttt tgcccctgac ctatgggaag aaaattgtgg tctttttctta      480 tgtcaataga agaaaaataa aattatatga agtcttaaa aggaaaaaaa caaaccatgt      540
taatattact gtttaaaacc ataacacaaa atcaattatt gtttatgttt tgagactccc      600
ttatggtgtt tgctagatag tgtggatttt gttttttgaaa attgttttttg aattttgtta      660 ttcttaagtt tttttatccg aaaatttcat tctagaaaac aaaattatat aaaaccatttt      720 taaaacataa tatatcgtgt tatagttttt taatgtaacg ggattacacg gcctattatc      780
aattatataa taagatagat taaataaaca aaaatgattt tatatggcttt tttaaaaata      840 aaatttaatc tctaccgctt ataactataa ttaagtcatt ttggtttaat aaaatcatat      900
tatatagtct cactcgtatg tattatttac aaaagatgtc gacttttat caaattatag      960 actaaactat aattttcttc gaggctaaaa ttataattta accaaattta taaatgtaaa     1020
atgtatttat aaataaacga ataatagctt gtcgtcaact atatttagt ggataagtaa     1080
```

|   |   |
|---|---|
| gattagtttt atgatttata aatatatagt ataaaacaca tttaaacatg ttttgttcat | 1140 |
| tgcgtttggt tgatatttaa acctagtaac gaaaaagtat taggtattac attaaattag | 1200 |
| catccaccta caatgttaaa tttttaagtc agttaataat ttaagagact ctcttcaaca | 1260 |
| ttgacttcat gcaacataaa atggtagaaa ttttcacacc attgtttatc gacattacta | 1320 |
| cgtaggagaa tggcaaaact ttcttatatg tatgtgtgct tttagatgtg tctttacatc | 1380 |
| ccttatcaaa acgaaaacct aattctaacc aaatcaaacc aacccgggtt gttgggttat | 1440 |
| tcttacaagc catttgttgg attaaaaaac caaaatagag gatgttcggt tcaagcattt | 1500 |
| taaagttttg ggctatttag ttcgaccact ggtttgttca aagtcgggtc ggaccaaacc | 1560 |
| gtgagcgatg taaacaacaa aggtctaaat tgggccggga tcagatgggc tgaagatcca | 1620 |
| cgattctggt ttccaaccca aggcccatg aattacaaca aaaaagcgta ctcaggaaat | 1680 |
| ccgaatctgg atctcaacgt actctaacct ctcacagttc gccacgtcaa gaaaacacgt | 1740 |
| caatacttta ggcgaaaatc aagtgaagaa ttccccacaa taaggaatcg tatatccacg | 1800 |
| aaactatcca atcagcttac gccatcggaa gattcggaac aaagcaacag ttcaatggta | 1860 |
| tatcataggg tgagaataag tcggttccgc agactagtat ttcttagtca aactttacct | 1920 |
| gcttcaatcg gccgccgatt tcccgatatt tacaacattt agttccgatt tttccctcga | 1980 |
| agctctgaag tatcgtaaaa | 2000 |

<210> SEQ ID NO 63
<211> LENGTH: 2000
<212> TYPE: DNA
<213> ORGANISM: Cucumis melo

<400> SEQUENCE: 63

|   |   |
|---|---|
| gatcaacctt gaatttttcc cacatactgt gttgtaaagt tgtccccaat ttcattcaca | 60 |
| aattacctac ttgaggaatc ggcagtaaga agagatcata atgtattttt gctactacac | 120 |
| tcgcaagtct aatcagagga tttgattaca atatcttgct gctgtaatag attcgttcat | 180 |
| aaattaatcc agattgaaaa gtcaagcttt acttcatttt catcgacaat gtagaaattt | 240 |
| tgttatataac tttgtactat tgaatctatt gctcctcgat ttgcccccct ggtacgatat | 300 |
| caagccatta ttttccaac tcttactcgc aacttcaacg catgaacttg accagcttca | 360 |
| acctataatc ttatgcatgt ttttaatgat taaagctgaa atagattgtg aaacgtacct | 420 |
| tattctcact accgctgcca aagccaacca agcttccacg ggtacccata aggtccacaa | 480 |
| tcatggcact cttggatgac atgtattggt tcctactgtc tcttccgggt tctcttatta | 540 |
| atggccccga aagcaacctc tcccggcatt ctcgaaattc ggctcactaa tattctttag | 600 |
| ctactaaaac acatgtcctc aaatttctca tttaaatgtg atctgagaaa gtcattcgac | 660 |
| ccatttttagt ttaaataagc atcaagtcaa aaaccattta acgtgggctt aaaaatttac | 720 |
| agcagcgcag cgtacactaa agtttatgaa cgatgaaagt gggtggcaga agaaagcaag | 780 |
| aagtccgaga gacatgccaa aaagagtaaa agtcatttgt tggggccttg acagcaaggt | 840 |
| tccatatgca tcggtccatt gcagcatggc ggctcaaaat taaattttca cccttgcttt | 900 |
| tgcttctcta acctacccctt ctacgcatcg tgtctatctt ccttcacact cattttgtgg | 960 |
| taagctttaa cgcaacattt tcttaatgta atttaagctt ggcccaccaa tcccttttgaa | 1020 |
| aagtttcctc tagatggtgc gtgtcaattt caaattaaca atttgaactt atagttctaa | 1080 |
| cccccatatt gtctgcccctt tttctcttct tcttcttctt cttctagttt tgttctggtt | 1140 |
| taatcttttt cggttttctc tgtgcagggt agtagctttt aagcttagtg attttctctt | 1200 |

```
gttaacaact ctaagcagtg aattgttaga gacctattat ttcatataaa tactagatga    1260
cttcgactca ttgattaggc tggaagctgt caaaattaaa gagtttgaca aatacccact    1320
aatttggtaa ccaagagcca gcaggaacat ttgtatttat tgagacaagt gaaagtttgt    1380
tattttcttt actcaaaatc tctctttaat tttatagata tagacattac ttggataaga    1440
aagggagttc accggccgga ggttttcctt caaatttaac agtgactgag gtctctttca    1500
gctttgtttt tttggtgtta ttactgtttg ctcaatcctt tgaacgagtg gtgtaacttg    1560
ttaaatgccc acaaattcat gggacgcaat cctttaggag aaaggttggc cactagttat    1620
tggtggttac cgtggctctt agcaacttag catcagaatt tgtcttgaac ttctagtcgt    1680
tgaaaattct cttcatacaa agctaagtct gcttatttgt aggatccata aacatgagat    1740
gataagggtg atgggcctaa gaatgcttga tggaaacatg gtcattggac ttgcttatta    1800
attgaaaaaa ccagccccgt ctctggttag aaccctcatt aggattgtat tgtttcaatt    1860
ctttcagctt gttctggatt ttaaaggctc caatggtttg agatgatagt catggaggtg    1920
ggaaggaatg gacaatacag ttttgaagaa ctgggttatc tcaaatggga aggtgaaatg    1980
tttatgtcag tatttgcttg                                                2000

<210> SEQ ID NO 64
<211> LENGTH: 2000
<212> TYPE: DNA
<213> ORGANISM: Cucumis melo

<400> SEQUENCE: 64
atcttcaccg ttaaatcgcc gtggttgtta gcggcggcga ggagagagag tgctcttcct      60
ctgagaactc ctgccatagt agacctaaag gaagaaagtg gtagtgaaac aaggaatggt     120
gaggagggtg agaattgagg aagtggttag ggctttgaag gaacggggaa ttttatttcc     180
gggaagggaa acaacagggg agaacacagc cggagcggtg tggttgtgag aaaatttaag     240
caagcagatg agacgacggc ctggcgccga ggacaggcat atgaatatca cgtggctatg     300
gctatgggaa attgaacgta ggccctttct cattcttata ccaatcttca ttttctatt     360 ttctagggtt tcttttcttt ctttttttctt tttccttttt cacatttta tatgtcattg     420 aatttcgaag tttggagtta atatgttgga gtcgtgtatc tatttagctt catgggttat     480
aacattattt tggatgatgt atgatattta atctcaattt aagaaggaaa cgagtaacca     540
aaaaatctta taatgaggtt tgtccatctt ttatgtatta ttctccactt atcacatttg     600
tttgaaataa ataaataaat aaatgttgtg tcacctcaaa cacaaccata tggttcaaat     660
tgaaatttaa cacttgatgg tccctatgtt ccatacgacc taacaaggtc atcttttgat     720
tgtgaggttc atccaacata aagttgttat aaactaagaa tatttcactt atgagtgttt     780
atgtgcacgt tgttggtata ggccataatt ttcaatcatt taaaactttt attaaccatg     840
atttcacatt atcttgatct ctcccattcg aatatgattt tggttcatct atattcccct     900
tataaactca acgttacgtg cctaccagtt ttcgcttggc tcatccccaa cccatatctt     960
actgtggaat gttttttctc tgataccatt tgtattgttt cacaccttcg aatcatattt    1020
tagaatgtta atacagtacc taatgcatgt gatattcccc tccatttgtt gtgacatggc    1080
agcatttgtt cttacttgtg tttgaattgt tttctaagag aaaaaaatga tatctccaca    1140
aaccaacgca catcattttta gcatatcatg tgtctcattc acgtggttct taaaaaaaaa    1200
tcaggacatt atccaataag acgtggtcaa gggatgaacc aaatgaaaat taaagggca     1260
```

| | |
|---|---|
| tgtaatggcc gagttcatga atgcgtcata aatgaatcaa tcacacta aaataagacc | 1320 |
| gatcacaagg gtgtgaaagc atagttaaca ataatataaa aaaaactaaa agctcatatc | 1380 |
| tatgccaaca acatacacat tattttcgat tgcttaatcg tatgaacttt aaagttaaac | 1440 |
| gtgtttattt taaagttaaa cgtgcttatc ttaaaacaat cttatgttgg acgacctcca | 1500 |
| caatttttc cattacgcat gtgagaaaca cattgaaagg actcgaatta gcatgtagag | 1560 |
| aatggtgtag cccccattct ataaaagcaa ctcaagatct gaacatgcat tgaaatttca | 1620 |
| ctcttcattc ctgacacata cataaagaga agcaagtacg agaatcatcc tctacttttt | 1680 |
| attcacaagt tttaagtcaa atttcaactt gatttgtatg tttcaaaacg acacacctac | 1740 |
| tcatttaatc ttgagcgtta cttcaattgt ttttatgttt caaaatgtta aaaagaaaa | 1800 |
| aaaaaaaag ttcaatagtt ttgtaaattg caaaaaaaga gaattacgag tatgcccctg | 1860 |
| tacatttaga agaagcgtaa ggtccatatg ggaatcagaa caatcaatcg acggccacat | 1920 |
| ctcacgagac ataaacaggg ggagttggag gaatcgacgg agatcggaat ctggtttagg | 1980 |
| gtttagcaa aagaagaaca | 2000 |

<210> SEQ ID NO 65
<211> LENGTH: 2000
<212> TYPE: DNA
<213> ORGANISM: Cucumis melo

<400> SEQUENCE: 65

| | |
|---|---|
| aactcagtga atacgataag aaatttaatt gaagttaaca aactcaaact taaatatttt | 60 |
| ttaacacgga caatttaaaa ccaaattcat agtctccttg tatagtgttt agagtgtgtc | 120 |
| gcttcattaa accttctat cgtggaacaa atctcttcta atattttgtc aaaaacctat | 180 |
| catcacccaa aatatcatga taattattg atgaggatca aggcttagag aggaacaagg | 240 |
| gaactttca caagggtgga gagatttagc tattaggttt aactcgttgc ttctaatggt | 300 |
| ggatgaataa cgacaaattt taaacaatga acgttatcac gttgaaacta tctacttctc | 360 |
| tcaacctact actttatcat aaggtttgaa aagttctatc gaaaatttta aatacataaa | 420 |
| acataaaaag gaaaattttc attggagaat tttccatata tgtttaccca caaaactaag | 480 |
| gctaattaaa aagctaacct taagactaag gctaaaatgg tatcttatgc tacatttttc | 540 |
| agttgctatg ttttgaagca aaagctaatt atttgctaat aatgagatag gcatgtgggt | 600 |
| gagtgatgag cttagcctgg cctgcctttg tgtttcttct tattctctta aatatcattg | 660 |
| ttcaatcaaa atagttttgt taaatttagc ccatcctcac ttcaacctct tatatttgga | 720 |
| ttggccttct ttgttttttg ggcttttgat atttgatgta atggacttca atcatttata | 780 |
| gaagccttac cctacagaaa caaacaaaca aaaagaggaa aaaaaaatg gtgagttggt | 840 |
| taataacaac tttctaactc aaccaatata tggtgtgtgt atatatatat atatatcgaa | 900 |
| tacaaaatat gaatatgata tgaccacata aaattgttga aagggttgaa aattagtgaa | 960 |
| ttggactttt aaattttgta gtgtagtggt ttacctatga tgctcgtaat gttatttaat | 1020 |
| tttaaatgtg ttttttttt ttacaaaaaa agtctcgcg gtgcaagttc aataagttga | 1080 |
| tttaaaaaca aatccatcaa aataatgttc gcttgatatg atcgagtata gagccgaatg | 1140 |
| tgtatcaaac ataaattcaa actttaatag agtgaaaaat aaatgctacg caaacaaagt | 1200 |
| ttttgtatta gcttcttaaa tgtacatata tactttccg attcaaacac ctccaaaata | 1260 |
| aaactcaaaa gttaaaattt agactcagaa aatgagagaa aagaaaact aaaaacgaat | 1320 |
| tctaaagata agcatttca aatataggaa aatgaacaat aaatatttac aaaatagaag | 1380 |

```
aattgtaaaa aacgacaaat tgacataata cttacaaaac ataacaaaat ttcagattct    1440
atcaatgaca tacactgata tatcttatt  agtcatagaa agtctatcat ttataaaatc    1500 caaattttg  ttatatattg taaatattta aatttgtttt accatattta aaaattttag    1560
atttatcacc aacaaataac catagatttc aaattttgct ataaatattt ttaaccgttt    1620
atttaccata attttctat  tataaaaaca aaaaaaacaa aaaacagata aaagcgaaga    1680
aaaagtaaga gagcagaaat attttttgat ttaggtttca tttggtaaaa aattgttatt    1740
aaaaaataca aactaatggg aaacaataat aataatttaa ttttttttaaa atctaaaaag   1800 aaaatagttg acaacaataa tttaataatt taatacacaa gccagtgtta ttaatctctt    1860 ttttctaac  aacgcctttc acgagacatc ctctcaatcc tcgacatcca gtggaaaaac    1920
agtatccctc aaccctcagc tttccccaac cgccctccgt cgttcttctg atcgtcgcca    1980
ccctactccg tcatcggaaa                                                2000

<210> SEQ ID NO 66
<211> LENGTH: 2000
<212> TYPE: DNA
<213> ORGANISM: Cucumis melo

<400> SEQUENCE: 66
catatattta ttatgttcca cttgataacc attttgtttt tgaaaattaa gtttaaagac      60
gacactaatt ccatcttcaa ctttcttctt ttgttatcaa cattcgacca atagtccaga     120
aaaccaatta agttgttgaa actaaaaaaa aaaaaaaatt cttataaagt tgttttttt     180 ttaaatttgg ttaaaaattt taatcattat acttaaaaaa tatatacacg aatcatagta     240
gaaaattgaa aacaaataaa cttaattcca aatctacttt aaaggctcac tatctgtcaa     300
gaggctttgg tatagttgtc tgtactgatt aagtgtgaga gttcttttaa tatttgtagc     360
tgaccaataa attctttcct ttcttttctaa ttttgcttta actccctatc ctattcatac    420
acaataaata tacaccatat tctaattgac aatattgttt ggatttgttt gttttctta     480 cggtaggcaa gaagttgcct agttgttgtc tgacctcaaa acccttgtt gataagagca     540 aacaaagtct agttttccaa aaaaaaaatc accaactcaa ccaaatcttg agccttttac    600
taatttccat cccaaactaa tatctaatca gtgcttacat gtttgagcct tcaactcaat    660
ttaacatcaa aacatcttgc aaccacacct tgacatgagt atgaaaacaa tataggagag    720
aactttagta ttacattgag ttccattatc attgtacatt ctcaaccaac gaaaccaacc    780
caaaacaaaa tagttttttg taacatatga gattaggtat cgtcctagtt aatgatttta    840
caaagttata tgagtattca tttgttgata tagtttgacc ggatcggaca gttggctaca    900
atggtatatt tctataaact aaggtataca attttttcatg tatgttgttt gatattgttt   960
tattattggc acatgtcttt tgtgtccaat agtaataaca aggttgtttc ttatctaaat   1020
aaaataaact cttgccagat aattgaagtt agacttttaa tcaaaacgta atattaaatg   1080
gggatgagaa ataattgatt attaggtaaa cctaacaata aaatctttaa attgtgttag   1140
aatcatttag ttagtcgagt tctacactaa aaaaaattaa aaacactaaa atcatttata   1200
aataaaatat tcaatatctt caaaatgtac taaaacattg aagctcataa aactaatcat   1260 ttttctttg  attaaatttc tctctcatat taccaagaaa cctaagataa cattaccaac   1320
gattcatacc aaaaaaattt attatcattg aacatatctc aaactagtgt attcaataat   1380
ggttagagta gtagttatat taaggtgcca tgagtttgat atttttcttt tttgcctaaa   1440
```

| | |
|---|---|
| ttaggttaag ccgtagctag cttgaacaat gctaaagatc ttcttaagag tttcgtagtt | 1500 |
| taacgtttat atgataaatt ttattacatc cgaacttgat atttaatttt tgtggctctt | 1560 |
| atctgtgttt agttttttctt attctctttt aacttgtagt aatcaaatga aagccatttg | 1620 |
| caaatgagga caaatgcatc tgcaagatat atattagcca atctcttgat atttttatgc | 1680 |
| tctatgagac aatatattct gccatttgcc catcaaatgg ccataatttc tcaagatttt | 1740 |
| tccatttcga gtttgtttca atcttctact ccttttgttt ttcctttgtt caatttttg | 1800 |
| gacctttgat gaaatatctt cataactcct atgacgtggg caccatccat tggttgtcat | 1860 |
| ttgataagaa atatgtgtca atggcacaat tcccattcca tttatatatt atatagttcc | 1920 |
| taaagccata tccccatgat ttatatcctt cttcaagctc acaattgaac tttaacatta | 1980 |
| cttcttccct acacaaagat | 2000 |

<210> SEQ ID NO 67
<211> LENGTH: 2000
<212> TYPE: DNA
<213> ORGANISM: Cucumis melo

<400> SEQUENCE: 67

| | |
|---|---|
| aaataatttg tggattttat catattatgt accttagact ttgtaaggtt tataacacaa | 60 |
| gatgtggaga aatcccatga tgaacatgga cgttattata tcctttgaaa ctaaaaacaa | 120 |
| aggaaaaaaa gacaaatggc tgagtataag aaaaagagaa gaaacaacca aaaagctaaa | 180 |
| atgtcatgct ctcatatgta acatatttga attgggattg atttcaagat gtattttaaa | 240 |
| ataatttaac acacgataaa ataattctaa caaactcaaa attactctta aacatttact | 300 |
| tgatatcttc gacataatga cttttgtttt aatacaactc aaaacataat taaggttggt | 360 |
| tttaaatgac aacaaacgaa aaactcgatt ctaatttcaa tactagtctt tgaaagccct | 420 |
| aaggagcgtg gttttgaatt gtatagcaag gtttcgaaaa ttttaatcat caaacaatag | 480 |
| gtatatttac ctgttcctca agtacagtta attcatagct acttgtcgtg cttcctacga | 540 |
| caacattgta agacttgcca cacactaatt gaagccgttg ttgaaggtag ttttccatgt | 600 |
| atagcttgaa tcgacggatg accaaagagg ttgaagaagg tttgaaaaat aggggaaggg | 660 |
| atatacaaag tttgagagtg agagagggag agaaatagaa atagaagaga ctgaaaaatg | 720 |
| taaaagaaag gatgaaaaaa tgtggggtaa acgcaaattg gatttttata gtagtatttt | 780 |
| gaaaatgcta tagaaaggct atgtatagta gtgcttccaa agttctatat gaatgagaca | 840 |
| aatcaaaata tattttttt gattaattaa ccccaaaaag actcataaaa aaatcttata | 900 |
| aatcccacta agatattgca tgttatatgt agtaaaattt atcgttcaaa taaaccttaa | 960 |
| acataattca aacgaagaaa gtaaaaattt gaatttctta tcttacatca ttcaaccaaa | 1020 |
| caatttccat ataagagatt aaacttctaa ctttaagaga gagatatcca gcatatgcaa | 1080 |
| cctaaaccaa cagtgacttt gctatatatt tgcacaaaat gtgggggaca agttgtaat | 1140 |
| ttcggaatat caatgattaa agaaaaggta aatttaaaa ttcggaagct tgacgtggca | 1200 |
| acacggaatg gtgatgatat ttccaactcc tcgcgacttt tagaagttgg cctcaccaac | 1260 |
| cgcatatccg cccctttgcc acgtgtcaga ctacaacaac ttccaacaat ttcctttaag | 1320 |
| aacaccaaat tatatcaata aatatttaac ttaaattaag aatatatttg ttacaatttt | 1380 |
| cctactgagt tagatagata gacagacttg tcaattaact aataagtcca aagtcaattt | 1440 |
| actcaacata gatacaattc taatttgagt gtgaaataca tattcaaatc aaaattatta | 1500 |
| ttaagaggaa aaactgattt gctttctcaa tttaaaatat aatattttga aaagaaaca | 1560 |

```
cacatgtatt atggttttca atatatttac tttcttagtc acctaatctc aaactaattt      1620
ttgaagaaat taaatatata tattatcatt tttatttttct tggttatgat attggtatag     1680
aatcaacaaa actacaagtg tcctctcctc tgctatcgat ggggattaga ctctaaactt      1740
gtttagcgat tagtaattat atattagaaa aagtttatgt taatgtggac ccgacaatct     1800
caccaatagg ctcttcactt caccaacccc cgacccattc cctctaataa ttcgacacgg      1860
ctcatccccg gttcgaaccg ggccgacgtc ttcctatttta acacacctcc atttcctctt    1920
ccctccgcaa cacaaacaga gacctcaccg gaaaatcaag ttaaagcaaa accaaagaga      1980
agcttcatca ctctccggaa                                                  2000
```

<210> SEQ ID NO 68
<211> LENGTH: 2000
<212> TYPE: DNA
<213> ORGANISM: Cucumis melo

<400> SEQUENCE: 68

```
taatagttgc aggtcttgtt taaaatacta atctaggtgt gtaaaacata gaaagtttaa      60
tgtggaattt cttatgagaa cgattaaggc tggtgaatct cgcttggtta aatttgaagt      120
agtttcactt cgatggagac tagacgttta ggcattcgta atttcagaga caacataacg     180
aggctacgtt gggaaaatag ttatgtcatt ttatcataac tgcatacttt gtggtaagga     240
tcatactgat tagtaagtac ggtttccact ctatagtgtt tgagtcaact tctgtgcccc    300
tttactaatc tcacgagaga atccgcctgg tcctgtaaca tttgggtgtc aaagaaactt    360
gtaggaaaga ttccgaccac catggattga atcataagtc aagggccatt agtaaaaacc     420
tctaacttgc tcttgcttta aattttcctc tattctcctt attcgttaag cattgggtgt     480
gggtgctata ctaacttttg tgggttgtta atggcctttg tttctgtaga tagtaaggac    540
ttctactgta aacttgcttt ttgttttgcac tttctcactc tttcatttttg ttaaaaaata  600 taagacaaca taacagagcg acagagagaa agagagacta accatagcaa ctggagctcc    660
ttgtgaaatt tatccaattc ctcagaagta gacaatatag gcttctttac agcaactttt   720
ctaccatcca accttccttc atacacagta ctctcggccc ctgcatcacc attcgataaa    780
aatccaatat gtcaacagaa cctctcaggc aattgaaccg gaataaatta gtgcagcgtt    840
gagtgcttac ctcgggcaat tggagagagc agcgtgaatg cggaaggttg aagatgaaga    900
ggaatcgaat tgctggagca gcagccctga tgcaggtgtt cggatccata attcccaaat    960
ccatatccgt tttcgtgaag aaatgttgag gaaaaattca ttatgcgttc agtttatacc    1020
attggagagt gggaaagttc gtattgtttt gctaatttcg tcgattctca ggtcttggag    1080
taaaaacgtt gtaccgcca cttcccattg ggccattgtc caatattgtt tgggttgggc     1140
gggtggatga cccaaatttt ggggaagata tgagatttgt ccaactctgt tatcaaatat    1200
gaccaaatga acaaaatatt gactttttt tttctatatt ttttttgaatg aagtataagt    1260 agttgtttta ttttgtttat tttaactcaa aattaccaaa tttggatttc acaaacataa    1320
aatagatttt atacttttta taattcaatc gaaagttgat cgtatatgaa aagaacaatg    1380
aataaagaaa gaaatgtaaa atttatatca acttaattaa aacctcgcaa tacaaaaatc    1440
gagtgaaata gagggtggag gatgagagga agagggagaa gacatccata ccctccatgg   1500
acatgggtag atgtatgggt tgggttgggt tgggttgaat tgggtcaacc catccactcg    1560
gttcatatag acagcattcg ttttataatt tatccaaaat aaaatataat taaaagaaga    1620
```

```
aaataaaaga aaaacgaaat ctccaattcg cgtaggaaat taaaaaggaa gagttaattc    1680
aattcgattc tctcccatct tcatcataat tttgcgaaag gatcgtaagt tgtatacttc    1740
tctccttgct gcttttcgaa tcgggataag aatattttct ttttgtcttc cccattccta    1800
ctcttcaaaa ttctctgcat tttctaccca tcacttttac ttcaaccatt tttgttgttg    1860
ggagttccat attttgattt cctctacaac gcctaaactc ttcttcttct tcttcttctt    1920
cttcttcttg gagtgatttt tcagttcaat tttggggatt tcatctattt ctttgatctg    1980
cagcgttgct ggaagttgcg                                                 2000
```

<210> SEQ ID NO 69
<211> LENGTH: 2000
<212> TYPE: DNA
<213> ORGANISM: Cucumis melo

<400> SEQUENCE: 69

```
agtttattct gttgtagcaa ttcaaagcag tgtgatccag atgagtacat atttggtagt      60
agactcaatt atcattttat ggttgaaaac cacatcctct tctgtcattg ttcatattat     120
tacgaggaaa aaagccacgt cctctttcaa aatttcttcc acaaactctt tcttaaaagg     180
aggaattaga gtttgaaaga ctaattagat cgagaattat tcatattcag attggtacct     240
aattgagtag caaccatcgc agtaggttga agagaaaggt cctcttgttt acgatgtttt     300
gcaagagcaa attcttcaaa tttcaagaga gtatgaagtt cttcaaagat tactgattgt     360
gaacgagtgc gcatagagat gtgaaaatat tgtattcatc tagaaatcaa atgagagtat     420
agatcaacaa atcttcatcg tttactattg aaacacacat ttgcaagttt atctttgatt     480
tttttgcccc tcctcatgta tgaattaata gattcatcaa cttctttgaa atcgattgaa     540
gattagtttt gagattaaca atatttgatc gtaaatttga gtagtgattt tcaagtgcga     600
cccagacttc ctttgatgaa gtacaaccaa caattagggt ttttacagac atagtagcac     660
tgatcaaggt cataaaagct tgatctttag caatttaatc tttatatata aaagattcaa     720
cattgtcgtc gattgatttt gtattgtaga tgaactagtg gtcgaagaaa tcaaaatcga     780
ttttgaaatc aaaatcgatt ttgctagagc tgtacttatg tcatcaacaa atccatataa     840
atccatatag cttgtgtgct ctcaaaatag tggagaattg gaatttctaa gaaacataat     900
ttgttgattc gagtctgata aatatgaggt acatatattt gtgaggaaga tcaaaaaatt     960
gatttctttt gttcaagaag actcagcgga agccattgat ggagagaaca aaaatcggag    1020
gggatggtta atcatgggtc tttgatctgc tctaatacca tgtgatcttt accaagttgt    1080
gaaaaaataa tctctcattt tctcattaat ttacaataat agaatatggg tatctattac    1140
aacccaatttt acagaggaaa tactagctga ttacaacaga atcagtgcca aatcaattat    1200
taaaactaat actcaacact aattaccaaa gaattagtgg tttttttacc acgaatttat    1260
ggggtaaaaa aagtgaactt ttaccaaatt agtaaaataa aaaagaaag aaaaaaaaac    1320
gtaatattca aatggatggt gaggcatgaa gaagagtagc ctaaagtaca tgaagagcta    1380
aaagacttat tatcttccat tggtcccatt gaagaccaca agaaaatat cagtccttt     1440
tctctttaga gacacaaacc caaagtagaa agaatctttc acaagaatta ggaatttaat    1500
gcaattttc ttttaaaaa aaatctccaa ttttctatct cattatccac cctttccact    1560
ctaaacttca ctacaatttg atgaaatctg tttccaccaa tcagattgca ccaaattcca    1620
tcaaaaacgc cccatcagat aattatggat gtcttcttct tcctctcttc tttcgtggct    1680
gaaattgaag ctcaactcaa aaatacattt cattttcaaa attccctgat gacccaattc    1740
```

```
gccacgtgtc ccttccactc accactaccc acacaaaaca actgcttctc ttcctcttcc    1800
tcttcttctc cattaaattc ccagacccat ccctctgcaa cttcgaatgc aacagaaaga    1860
aaacggacca aaaatcccctt gaggaatttc tcattttttga agcataattc aaagattaaa    1920
cccgtattaa ccctcttcat cttaccagag gtttgattta ttgatcgaat tgttttattg    1980
gttttttttc aaggtcacca                                                2000

<210> SEQ ID NO 70
<211> LENGTH: 2000
<212> TYPE: DNA
<213> ORGANISM: Cucumis melo

<400> SEQUENCE: 70
gcatcttatg gatgtagtca caacatatttt atatggatttt tctgataatg atatttatat    60
gaaagtccca aaaggattta agatacctaa acatataaa tcaaattccc ataaactatg    120
ttcaataaag ttacagagat cattgtatgg attgaaaaaa tcatgacgaa tgtgatacaa    180
tcgcctgagt gaatatttag ttaaaaaaat aatatcaata taattcaata tgtccatgcg    240
tttttataaa gaaatcaccg tcaggatttg ctattataac tgtatatgtt gatgatttaa    300
atataattga aattttgaag agttttcaaa ggcaatagaa tattaagaaa gaatttgaga    360
tgaaagatct cagaaaaata aaattttgtc ttgattttca aatcgagcat ctagtaaaag    420
ggatatttgt tcatcaatta acttatacag agaaaatttt aaaaagattt tatatagata    480
aaacacattc attgaacatt ctaatgcaag ttcattcatt aaatgtgaag aaagatattt    540
ttcgacgtcg agatgataat gaagaactcc ttagtccaga agtaccatac cttaatacaa    600
ttggtgcact tattttgtca ataatcaaga ccagatattg catttctat aaatttatta    660 gctagattca gttctccaac aaaacaacat tggaatgaag ttaaacatat acttcgttat    720
tttcgaggaa caattaatat aagattattt tattcaaata aatcaaattt taacctagtt    780
agttttgcat attcttgatt tttatctgat ccacataaat ctagatctca aacaggttat    840
ctattcacat gtggaggaac tgctatatct taacgatcag tgaaacaaat taccataaca    900
gtcaactctt caaaccgtgc tgaaattctt acaattcttg aggcattcat gaggctagcg    960
gagaatgaat atggttaagg tcgatgactc aacacattcg aaaattatgt ggtttgtctt   1020
ctagtaaact ccttccaaca acattatacg aagcaacac aacttgtata gctcaaataa   1080
aatgaggtta tattaaaagt gatagaacaa aacacatctc accgaagttt tctatactc   1140 atgatcttga agaaaatggt gacatcacag tacaaaaaat ttgttcaaaa gataaattgg   1200
tagatttatt tacaaaatta ttacctactg caacctttga aaaattggtg cacaacattg   1260
gaacgcgacg acttagatat ctcaagtaat gttacatctt acttgccaag ttaactatac   1320
atagtgacat ttggtggagt tgtaagaaac actaatattg gagaaaaatc gaaagaaatt   1380
ggaaaatatg gagaattgaa tttttttttag atttttctta ttttctaatt ttaggtttcc   1440
gtattctgat tatgcctcat tttcacaaca ttaataactt taataagatg atttcttggg   1500
ttaagggaaa aaatcatttt tttagagttg cacgtacaaa aatattatca taacatatcg   1560
attataataa accaattcac cgtcaaccta acctaggtag agtttgagtt aaatgttaaa   1620
agaatatcca cccctcaaca ttgtaatccc aactaataaa tcagcaacct aaagtttttt   1680
ttaaaaaact aaaagaaga gcaatatatt ttttttacta ttattttttt aaagagtgga   1740
tttatttatt aaattaaaaa atgaaaagaa gaaaatttgt tagtttgggt aatccgaaaa   1800
```

| | | |
|---|---|---|
| cccgattatt tgggcccgag aaaccgacgt tttgtttatt gttcctcacg gcaataagta | 1860 | |
| atggcgtgaa tcgaccgcgt gcgcttcaag ctatctagac attttatat cctccgatta | 1920 | |
| gaaaccctaa ttcagattct ccgtattacc caccctggaa catctttgaa acgcgaaaag | 1980 | |
| gtgacccgaa gaaacttgaa | 2000 | |

<210> SEQ ID NO 71
<211> LENGTH: 2000
<212> TYPE: DNA
<213> ORGANISM: Cucumis melo

<400> SEQUENCE: 71

| | | |
|---|---|---|
| taataaagtc gatgatatga attaattaga cggatgggtt atactatagt tattttattg | 60 | |
| tcttttatag agaatttaac attggtagcg gggaaaatcc gatagatatt ggtgaagagg | 120 | |
| aattcgttgg tggatgtaaa ggaaagttag tttcgccttg gcacaacgaa gggtttgaat | 180 | |
| ggaaaatcat gataagttcg actgcctgtt caactaaacg aaagatacca agtcaaacct | 240 | |
| tagttttctt taaggattta tgatcttagt agtgtatcta tttaaagatt caaaggtatc | 300 | |
| aatagactat ttatttcaat cgttgtgttg aaatctagga gtatatttaa cgattaactt | 360 | |
| aaaagatttt gctatcttgt tttgtgtttt tcattttttt gggaaaacct agtgtctttt | 420 | |
| tatttatt gatacaataa gtattataaa aatgactaga atgactatat acttgatcat | 480 | |
| tatttgaca tatttgcaat atattaaaaa tgactactta ttttaattac cttcatggtc | 540 | |
| tttttttaat ttatgaaggg gtgggctcgt gtggcagatg aggcctgtca taattagcct | 600 | |
| taccttaaat aattgggccg gttctttggg aaatatcggc ccaacctaac ttttcatggg | 660 | |
| ctcaaatgat gctttatcta atacccatac tttccattac ctttgtatat tgaattagaa | 720 | |
| tgatagaaaa acatactaca cagttgagtt aggatataaa taaatgcatt gaactatgta | 780 | |
| ttacatagtt gagaaaaatg agaatgaagt tttgtctttt gaatatatat tctgtgaaag | 840 | |
| ttagatgtat atagaaatga tgatacttcg gcgtttgttg aagattgagt gggggtgtcaa | 900 | |
| cctaatcata gttggtttaa gaaaagttttt aattataaga taaccgttttt aagtgactta | 960 | |
| tgccatattt tgattgcagg ttcacaatga aatgttttaa tttggtgatt agactttgac | 1020 | |
| aatgtggtaa tttatgttaa gtgagttgtt gtctcgttta ccttgatcat ttgtctctac | 1080 | |
| tcatttctca ttttgtttca tcccttgtta tatggcatcc attgttgttg tatttgtcat | 1140 | |
| tgttcacatt cgatgcttaa ctaggtaaga acaacatttt catttagaa ttggaacgat | 1200 | |
| agaaattcat aagttttatt tttgaggcac ttggttcatt ttaatcatag aacattagtc | 1260 | |
| cacaatcgtt tggaataaat ttacactcta tctagatatg gaactcttga caacctctac | 1320 | |
| caaggaagga tgaaaagcaa aaaaagagta gaaaaacgaa agtagacact ataacaagcc | 1380 | |
| aattagccca ttgacaaata ttaccacgtt attaaagttc attttaatca tcgtgtcaat | 1440 | |
| tatcaacctt ataggtcaaa taccatttat aattattttc aaattcaatt aatgaaacaa | 1500 | |
| gactcaaaaa accaaacaaa tatccaaacc caatatttga gtttagaata taataatttc | 1560 | |
| atagttagac ttggagacag atttgtacgt atatgttaaa ttaaaaattt aatcaaagta | 1620 | |
| taaataaatg atttggagtg gcaagaaaat attggccaaa atttcataag aaaaaggaag | 1680 | |
| aaaataaaaa ggtgtattgg ctaacaaaaa cccaattcca tggggaggag aaaatttgag | 1740 | |
| tcctcaaaaa aggatttcag atagggaacc aaccaatcaa aacgaaggac gtctccacgt | 1800 | |
| gtcgctacaa gaggccatct ttccaaaatg agatcgcgga taaacaagcc ttttctgagc | 1860 | |
| atagaaaaat ggcgaatttt aacaaaaaga aaaatctcag taaagtcatc agctacagct | 1920 | |

```
gctctttgac ggccacttga ttcactattt ccctctcttt ccggcgctga ttctagtgtg    1980
gttgaacttt ctgcaaagaa                                                2000
```

<210> SEQ ID NO 72
<211> LENGTH: 2000
<212> TYPE: DNA
<213> ORGANISM: Cucumis melo

<400> SEQUENCE: 72

```
attacttgaa cttaatccac atttatgtct ttatataaag ttcgaatact cataatatag      60
ccaagaaacc ttgtttattg gattttgagt tttatcataa gcaaatctct tatccaataa     120
caaattatta aacaacactt caacaataac tttattcaac aatatattag tttaacattc     180
acaaatcacg agtattagaa cataaaacgc aacaaagaat ggactaaggt actatattct     240
aacttaggtt gtttaggatt tccatatgtc aatgcttttg tgattttttga actagatttt     300 cttgttagat taattcaatt ctattttaa atggcttaat atcttatttt cggatgcttg      360
gggattgcta gactaccgct ttgttgaagc aataagttaa atttgtttgt tacaggtatt     420
gatcaatcta acatagaatt gaatttgtat gaatatttag ttagacgctt gaaaactaat     480
tattctacca atgagccgta gatcttaatg caattgttat taatttgaac tttgtatgct     540
tctcatcgat taaatttata tcaagtagtt aattaggaca aatctattgg cttttttcatt     600 taattttgtt aagtaaaagc aacttagaat tttgaaaatg atgaacccat gatccaatac     660
attgaaagag aattttgttt aactcaaact aggattcttc tcacattgat ttcgtataat     720 ttaactttt caatttatat caatcccccc agggtgaaaa aaatttgttt gaagaattca     780
tgtgctttct aaatctgatc tagacttgcc actaaaatta acttttgata tgtaatttgg     840
ttaaatattt gattcggatt tcgacgacaa acaattgatc aatgtggtat taaattctga     900
tctccatgta agaaatttac acattttcat aagttcaatg ttgacacaaa gagagtaaga     960
gcattttaaa aaaaaagata ctttttaatct tttctaaaaa aacaccaaaa tgccattatg    1020
taaatgtaac ctaaataata aacatttaaa cttagaattc atgcaattag ctttgtatg     1080 ggacattgaa ttgattatta aaatcagtag ttatagaccg tgagttataa tggtttgtat    1140
tagaagcata aattatttta atttttgatcg taatagcatg tatttgagat ataaattaat    1200
ttagtttggg tggcaaatag taaacagtaa agcaaaatat aaaaaaatga atttaaaata    1260
gtaagatttg taacaaatga ttaatactat aacaaacgtg gttttaaaat aacgttgatc    1320
gtagctaatt gaacattatt tattgtaaaa ttgagtgttt taatatttg gagcctcaaa    1380 cttcgggtgg atcaccacaa tataatcata ttcaaattta aatttttatt tttttttatta    1440 attataaata ttgattgtta atagatgctc attatgggcc atctgtcact ccctccgtgc    1500
atatcctacc tgaaacatca tatatcttaa acaatgtcca ttgccatgtg tcactatttt    1560
tacatcccat ccacttgaca aatatgttga agatgcctac ttttttaggg atcatgtaat    1620
ctatctcatg cttgtcaaat tgttcgataa tagtgttaca aaaaatttag taattattat    1680
tattatattt cttcgatatt tatgcttcat atgccattgt gctctccatt tttaccatac    1740
ttaaaaaaat ttcttattat aaattttttc aaaaaaaaat ttactatata gtcatcatct    1800
ttattaaaat taaaattgag aacctgatat ttttgatatt aataatttaa aatttgaatt    1860
aatccacttt aaaattatta ataatttatt cgaatttggg ccttaaggaa gagatacgga    1920
aacaaaccct agatcccatc tatatataaa tcgccacaaa accctacctt tctctcagtt    1980
```

| | |
|---|---:|
| tctcgttta gccggcaaaa | 2000 |

<210> SEQ ID NO 73
<211> LENGTH: 2000
<212> TYPE: DNA
<213> ORGANISM: Cucumis melo

<400> SEQUENCE: 73

| | |
|---|---:|
| tgaaaaacta aattaaattg tccttacatg tgtataaaag aaaccttcgg acatttgatc | 60 |
| tgagaactat gttaaataat aagatccaaa aaactgaacc ccaacatctt cgaaatcgat | 120 |
| ttgatttcaa ttcttaagat aagctacatt caagttacct agatgatcta agaaactaat | 180 |
| gattggacaa agttagaaac tcccaataaa ccaatgatct tcaaagcact ctacgatcaa | 240 |
| gacagattaa ttttagtttt gaatgctttg aacactcgtg cattctatca caagaacaaa | 300 |
| aattatacgt tttagaattt tcaaatatca ttcatcccaa ttttttatttt aaacgtgaaa | 360 |
| attacaactc tatttatact aattaaaata ttaattaaca tgttacaata tttaatttta | 420 |
| tgtcatttca actaatgtaa taaataaaaa caaataagac aacgtaaaata cacaatttca | 480 |
| taaacattta atttcacgac ttttaagttt tctaaataaa ttttcaactt tttcatttga | 540 |
| tttaattatg atttctcgga tcatatctat atatatatat atatatgaag ctgagtttta | 600 |
| gaaattgtaa attcaaattt cttaaaatgg tacaaattca attagtaaga ggaaaaacag | 660 |
| ctaattaaat aatgtgtgat gccccactcc ctaaaacagt gggtttggat cgattaatca | 720 |
| actaaaactg accacaaaac aatattcttc tacaaccccca ttgattttt taatcattaa | 780 |
| gtgccgattc aaagaaacaa taaacaaaag aagttgaaaa gattgagact tttaaattaa | 840 |
| atctgcaaga ttctctccaa actcatgttg tattcaagtg tttaaagctt aaaatatcag | 900 |
| taattatgtg ttatttaacg gtgaaaccaa tcaaatcaag caagattctt caatattcaa | 960 |
| ttccaaatcc tcaagtttcc atgaaaactt cataacgcct ttatccctcg aaagccaaaa | 1020 |
| ttcaatttcc tccattcatc ttgcagcccct atctactttc caaaagccaa caaataccct | 1080 |
| tttaagcagt agccttttgt ttggttgtag taggatcttt gtttctcttc catttttaaca | 1140 |
| caagccacag gagaatctct atctctatcc tgcaaccttc atccccacat tgttcttcct | 1200 |
| ccattatcgg aaaaacccag tacagggttt gctttccggc cactatccgg ttgttctttg | 1260 |
| taagttttttt gggttttcat tatctgggtt tgtggctgct tgtggattca gggtaatgtg | 1320 |
| gccatgttttt atagtccaca gcctttttttt cttctttga catgggatta tttctgattc | 1380 |
| tatttgtcta ttgttacttt gtgctttttc tggtttgttc ttgtggtcat catttcttat | 1440 |
| gcttggaagt tcgaacatga atcaattcaa caactaagtt gagagtgttc gactctctca | 1500 |
| tctcattgac cctgatggta tatcttggct tggaagttag aacatgaatc aattgaacag | 1560 |
| cttacttgag actcgagagt gttcaactct ttcatctcat tgaccctgat gatatatctt | 1620 |
| ggctttggag ttatgaacta tgagagcttg gaggatgaac taaaaagaag ggactattt | 1680 |
| ttgagatgga tatttagttt tagtaatttta gcttttttttt tttagtacat agtacattaa | 1740 |
| ctttgttcgc gaggaaatag tggtcttgtt gacgagcatt tcttaaacaa tgtagttttt | 1800 |
| gtctcatctc tttaaaagtt tatggagggg caaacaagtg agatcaatag ttatagtatt | 1860 |
| tcaatctata actttggaac agctgatttt taacttttcc tttgtctttt ttttattata | 1920 |
| gaacacatta gagtgcgtta gattcttcag ttctgagatt ttgatctttg agtgctctct | 1980 |
| tttagcagta gaggcaaaca | 2000 |

<210> SEQ ID NO 74
<211> LENGTH: 2000
<212> TYPE: DNA
<213> ORGANISM: Cucumis melo

<400> SEQUENCE: 74

| | | | | | |
|---|---|---|---|---|---|
| actttcagta | gattttatct | cataaaagag | tcataaagat | aattagtaat | gaataaagct | 60 |
| ttgtttgaag | aaatgtttca | ttgcaactga | tatttgtcat | tgatgtacaa | atggctttgt | 120 |
| aactctccac | ttttttctaat | ctaaccattt | acatacaaaa | tatctacgat | acactaaaat | 180 |
| gaataaagaa | attttttttg | tcaaaaactg | tggggagaat | tgctccttgt | tctcaaatca | 240 |
| ttcatgaact | ttgcaattta | gaagtaacat | caatgaaggc | ttcttccttg | cagggaattc | 300 |
| tcaaacctcc | agttgggtgg | ctgaatccaa | actcttcttc | agccttgttg | agcaagtcta | 360 |
| tgaatgaagc | ctgactcaag | tacgatattg | gaacgaaaaa | ccgctttctg | tcggtttctc | 420 |
| ccacgtacac | tggaatgtgg | cctttgggaa | caatggactg | acatcttgct | gagacagact | 480 |
| gcatcttgag | aacttgcttg | gcagcggaaa | gaagaaccga | aggcaaacga | attcccatgg | 540 |
| ctaaattgga | ttgaatcttt | ttggaagtgg | taaacttcaa | tgcttgaatg | agaatatgtg | 600 |
| aaagatttga | agttggagat | tagttgtttg | tttagagtct | atatatagaa | tgagaaaaga | 660 |
| gaaggtattg | tgacatatga | atagaagatg | ggaaaccaag | aaagttgggt | tcatcaatgg | 720 |
| ctcacatggg | ttgctccatt | ggttaaggta | cattcatttt | ctcattggca | ccaatttctg | 780 |
| gtaagatggc | cccatatgtc | ataatacgtg | aagtcatatt | gatctaaaca | aaatgggaca | 840 |
| caaaaattgt | aactatttca | attagcatta | aaatcatgtc | aagaaaacta | cattaaaatat | 900 |
| agatatatta | gttaatgatg | taataatagt | ttcatgtgag | atcaaactac | gatttttttt | 960 |
| tataaataat | gttacttttta | aaaaaatgtc | aaaaatatgg | tagaagaaaa | gctattacaa | 1020 |
| aaagttaagt | catctactcg | gttcataatg | cgttatcgtg | gatcgggtac | acgacaaggc | 1080 |
| aatgaagaca | tagacccagt | ctatgacttc | gatgtaaaat | gtgggttttt | cctaattact | 1140 |
| cgtaaaaaaa | tattttttgaa | aacttttctt | tttaacaaac | ttaaattttg | gttaattata | 1200 |
| tatataaata | ccatctttac | tttcttatta | tccaaaacaa | tttaccatat | ataattatat | 1260 |
| ttattcaata | aataataata | taaaatattt | agataaacaa | aatcaattat | ttcaatctta | 1320 |
| tatattttaa | atatacacta | agctaattta | aatttacatt | ctgaaaattt | taattatatt | 1380 |
| tctatctaat | ttaagatttt | aattatattt | ctatttaatt | taaaattttta | atggaaaatt | 1440 |
| aaattgtaaa | taagaataag | agtacaaact | tactattttt | atttcattttt | taatttataa | 1500 |
| acttcatctc | ttttttcata | tatttttaag | aaatccaacc | ttatatttcg | aaatttattt | 1560 |
| aaaaaaatta | taaaattttt | taaactatat | ataaataaaa | attgtaattt | ttgaaataat | 1620 |
| ttattaattc | ttcaacaaa | cttataataa | taacaataat | aataataata | atgagggtac | 1680 |
| tcgattctca | aaaaaaccga | accgatcaaa | caacgttaga | tcaccaacac | agaagtaggg | 1740 |
| tttttcatcg | gcacataaaa | accctcactt | cttcttcata | aaaaccctca | cttcttcttg | 1800 |
| acctaattcg | cgccgttgat | ctccggttcg | atcggtttct | acgctgtaat | ctcaagctat | 1860 |
| ctcctacctt | atccttccct | ctctttttct | tcttcttctt | cgtatatgca | tatcttcaaa | 1920 |
| tttgctgctt | ttttttgtctg | attattcatc | tgggtttgtt | tgcaacagga | aggaggaaga | 1980 |
| atttcaaatc | aagaagaaaa | | | | | 2000 |

<210> SEQ ID NO 75
<211> LENGTH: 2000
<212> TYPE: DNA

<213> ORGANISM: Cucumis melo

<400> SEQUENCE: 75

| | | | | | |
|---|---|---|---|---|---|
| tttattaatc | tgaatcattc | tgtttcttct | gagagtttta | ttccttttaa | gattctaatt | 60 |
| ttattttgga | tagttgaatt | ttggtgtgct | ctctttgccc | cttctttatt | atacattcct | 120 |
| ttatcttaaa | aaagccaaaa | agttaaaaaa | caaaaactaa | tcaaaattgt | aacatttaca | 180 |
| attttatgag | catgacattt | aaaatatcga | ttttgaagtt | aagacgttgt | attctcacca | 240 |
| tcggttttta | tctcttccca | ttccattaga | gtgataggct | ttatctttca | tcactgtcaa | 300 |
| aattcatcca | acgtccaaga | tctcttctgc | aaagagttac | ccacaattct | ctcagactca | 360 |
| ttggcccacc | ggataccgag | tggatggata | gaacctccaa | gattgcgaga | gcaaaagctc | 420 |
| agccaaaact | tgcacaaact | cacccatggc | ttccctctct | tgtactacct | ccattaatct | 480 |
| caccccaaga | tccttcaatt | ctcgccccca | ttcaaattag | cttcccattt | tcttggtctt | 540 |
| cagtccaacc | ttcgatggct | ctcacccctc | tccattggac | cctccaatgg | gtctagagca | 600 |
| acttgctggt | tcaatttaag | gcaaaatgcc | gagggtgcag | gcatttatgg | cagccagtcc | 660 |
| cgagatgatt | tcaacagaga | tgatgttgag | caggttcttt | tactaatttc | tctcttcttt | 720 |
| ctttgtattt | tgttttgtga | ctttgattgt | tgaagagtgg | tgtcttttgt | ttaattgctg | 780 |
| gtttgggctg | attcttatgg | gtttggagtt | gaaattgttc | ttaccctctg | gctgttctgt | 840 |
| tttcttttaa | gtattgtgaa | ttttcaatgg | ctccttagt | gaagatagat | gaagaaattt | 900 |
| aaattagtaa | tttttcgtac | cgatgactct | cttccagtgg | tgttaatgtc | aaactaacct | 960 |
| tttctttacg | tcataaagca | cttaatcggt | tggaactcag | tagacgtctc | actcatgttt | 1020 |
| gtagccctaa | cctaatgcca | tggcaatcga | aatttatatc | gtatccctat | tgcgattatt | 1080 |
| aaacatcacc | ataggtgaga | cattcctaac | gtgatatact | gagttctaga | tggttaagtg | 1140 |
| ctctgacatt | tcacattaac | gcctcatccg | cactggttag | tcgaaagaag | aaggtgtttc | 1200 |
| tgttatgaga | ttgtgagaaa | ggacctcctt | aaacattata | accaacctca | taacttgtgc | 1260 |
| atttgtgtat | caaactctgc | tttcacataa | agaaactaaa | acaaggtatc | acattgccgt | 1320 |
| tatgaaaagt | gcatagaact | tcctgcttcc | ctcaaacaaa | acttgcaaat | attactgatt | 1380 |
| ggccttagcc | tttaggtaag | ggaagaatca | aaagtattcc | ttcatccttc | tgctttaaaa | 1440 |
| atgtgctaaa | tgacgttgtc | catagtttaa | aaactcgacc | aaatcgcatt | tgtcttacag | 1500 |
| tctctcaacc | ctttttaagc | actctcagag | tcaatccaaa | tagattccta | gttcctaata | 1560 |
| tgtaacaaga | agagtgatac | tatgaaaacc | cacaaaaaac | ccacaaacat | gtgacttgag | 1620 |
| ttaagatgac | tcccaatccc | actgtatcaa | gcttttcaaa | tagaggaatc | acgatgagat | 1680 |
| gaacaataat | atcccaacgt | gctgctatcc | caaattagat | acagaagtct | acttgtggtg | 1740 |
| ttcttaatcc | aataattcat | tatgaaattc | ttatataatt | tcttaatgag | tatcttagaa | 1800 |
| ttaatgttac | aacttatctc | ttattctata | gatagaatc | ttaacataag | tattcatatt | 1860 |
| aagagcaaga | ttatgttgat | acttctcgaa | tcataccaaa | aacttggaac | catgacatta | 1920 |
| acttcattcg | tggaaacaag | ttttgaagga | aaagaagga | ttgacaaatg | aacgttatgg | 1980 |
| ttgtgcagta | ttttaactac | | | | | 2000 |

<210> SEQ ID NO 76
<211> LENGTH: 2000
<212> TYPE: DNA
<213> ORGANISM: Cucumis melo

<400> SEQUENCE: 76

-continued

```
atctaaaact gcattttta ctacatacag attcaccttt aggtgctggg gcttcccta      60
tttcatttta tcaatgaaat gtttcttatc tagaaataaa agaaactaca tacagattca    120
caccactgca gaaaggtcaa ataaaacatt catcataatt caaggtaagt aagcataatt    180
ttgtgaaact tatgtgatgc acttaatata tgaacgattg ccccttgttc tctcaaagtc    240
agatcttctt tttcctaaca attgaagaaa gtggaaataa gttaattacc acggccacgc    300
aataatctcc tgatggcctc caatgaaccc cccaaacata atgctgtagg gaatgtcttc    360
ttgcaatcct tcaagacgca caatgtgaga catgcaaaat attaaaaagt gacatcttca    420
aatatagcaa aagaaatcaa aatatttaca aaaaatatag caaagtttca tattttatca    480
attatacaca ctgatcgaca tattttgtaa atattttcaa tagttttgac atctacaata    540
attagttgag attttgtagt caacaggatc cagatttgtg tgttgaaagt tgaaacccat    600
gataagataa aatcccggtt aaatatttca ttttcattct taagttttg aaaaaggaat     660
agcttggtaa gctacattcc gcatggtaaa caagcataca acttttgttt caagaaacca    720
acaagtacta caaacaaaag agtaattgat ttaatccaag ttaacaatga caaattggta    780
atatttatag gatattagtg agataataca atcaagttcc aaaagatgtt atatttacaa    840
ctatgagcat tcatcttgtt actaccacca agaaaaagta gcggttttcc aatctctgtc    900
aagtatccat ttgagttatg atttcatatt caagactgtc acaaaattt cattaaaagg     960
tgcaagtgca acatttcctt aagaaaagga taactgagag atcaatgact ggaattcaca   1020
agttaaaatg aacacaactt cagaacatca caagctaata cctccaaacg gtccaataag   1080
ttttctgcaa cactgtcaac aagcgaatcc tttgggcgca tcaaccaagc agctcggtcc   1140
cgctgttacc aagaaacagc aatttcagca agaacaaaat atagaaatcc tccaagaaaa   1200
ataaacaaac aaataagttc gaaggcacca catatcagaa agcttatgga ggagtacatg   1260
tagtacaaac gctcttgcca tttagtttta cttgttaaaa gtgatttgct cagaataaac   1320
ataaccaaag cagaatccga acatatgaac caatgaatta ataaccccca tcacagaaag   1380
acaagtaata ctcccagaat tgtactctat acagacgacc actacaattt agccacacaa   1440
tatcaccatg ttctctccaa atatatttaa aaaaaaaaaa aaaacccctc ctattgttgc   1500
ggttaacaca aatagatcaa aaagaagaaa gaaaaaacta aaaggagaca aaggtgttaa   1560
atttggttta cctgtttacg cttaagatca cgatcaaaaa ccttaacctt tgagctgtgc   1620
attccatcac cgattcttcc gtcataatta tcatcaccag tagagaaaga acaacaagga   1680
attgaatttg gaaaatctcg ccatcttgca cttctcaaca ctgagaacga tcttatgatc   1740
gtagacggcg acagccctct catttcacag tcaccgattg aacctcgccg gagagacgga   1800
gggaaatttt gtaaatttt aatgggcctg ggccgtaaag tcgtgtccaa acactcctta    1860
aacggaccaa aaccggcgta gaaatgaaac tatccagata agggacgtgc tatacattta   1920
tccaaacgag gtctcttatc gtatcttgta caagttcgtt gcttttcacg gctgtctcta   1980
gaattttggg ttgggcgaaa                                                2000
```

<210> SEQ ID NO 77
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:

<221> NAME/KEY: unsure
<222> LOCATION: (1)..(2000)
<223> OTHER INFORMATION: unsure at all n locations

<400> SEQUENCE: 77

```
aaacctactc tgtaaatgaa ggtttacatc tcttaaggca gtaccatttc tgccattact      60
tctaccattc ccacgaaacc acctcttttc tctttcattc tccccgtcag gtatgcattt     120
ctcatctcta agtccgccca ctgttttccg actgattttt cgattttaa ttagtgagtc     180
ggttttattg tttcttattc taagctttct tttactcttt atattttag atatttaatt     240
tcggatccat tcttcccatc atgcccaatc caaagactgt cgaaagtttt gattgttggt     300
aatgggacat taggtctggg gtttctgttt ttcttatcct ataaattggt tatccttcgt     360
ttcctctatt ttgactttat tccgtagtta ggttagaaga agaaactact gaataatgtt     420
tactatacaa acacctcaaa atagccaagc ctgtcgaaac acatttagct gataagctag     480
ggatgaagag atcaagagat ggttagctca gctgtattgc atctcatggg ggacgggtga     540
aacgaaccag agaagtaata tacacgtttt tttttaaaa aaaaaccga ataatttacc     600
tgttcttgct acaattacac cgataagttt tcaacttgag caattacacc gtctaatttg     660
cattgctgaa gaaattggtc tgttccatta ccactgttga ttaaaaagtt ctacttgtca     720
gcacagcatg tccatgtgcc cagatagttc ttgatctttg gaaaagtgc tatgtttgca     780
tgcttcggta agatgtgagg ttaaaatgag gaggacataa tgttggcata gggaggtcaa     840
aatgtgttaa ttgagagaaa aaatgtggtg gatattggag aggagacatg gaagtagaga     900
gaaagagatg aggagggagg ggtgaaggta aagggaaata gacatacaga aataaagaac     960
tgtgcgagta atgtgttgcg ataagtgaaa gagagaaagc aagagaaaca gtggtagaaa    1020
attgaagtat agagagagat gtagagaggg aaaatatgga gaactacaag ataaaatatc    1080
tttattcttt ctctatctaa gtatttatct ctttagaagt tatctctctt tgtttctgag    1140
tttaccccta gtattttctt ttttctttct caagcccttc ctctctaaca caatttctct    1200
ctctctcttc tccctctctc tctgtatctg gctgtggcac ttttttttgac ctcttcctttt    1260
ctgtctttat ctccttttgaa gacattttga ttttcctaca cccctcaatt ggtcttctac    1320
tcaaactcat ctacttgtta ttatattaaa tgcatgaaat cctaatattt taggaagctg    1380
gagactcatt gtgcgtgcat ctgcttgctt gtagaaaagtt ttaaattgaa aggcaagccg    1440
aaggggccta attattcagg ccaggacaat gatgttggtt ttagtttttt gttttttgaaa    1500
nnnnnnnnnn nnnnnnnnnn nnnnnnnnnn nnnnnnnnnn nnnntttga aactaatttt    1560
tttcttagtt ttcaagactt ggcttggcat ttaaaaacat tggtagaaaa tggataacaa    1620
aaccaagaaa cttacatgtg gaagtagtat ttataaagct tacttatgtg tggaagtagt    1680
gtttagaagc ttaatttta aaagtctata accatatggt catcagtaga gtctcatgca    1740
acttatgttg tgacagtggt gtaattgttc taattaaaaa ttttcgggta caaatgtaaa    1800
aaacattatc gaacagtggt ggtttgtgaa atatgcatta acttttttgaa aatttgatgt    1860
gtcatcatat tcattccatg ccgtgccttg tttccctccc agctccttat ccatgctaat    1920
tagattcaga ccattatccc tttggaacag ctatgcttaa ctctgttctt ttctccctct    1980
gtacaacagt atatcaaaaa                                                2000
```

<210> SEQ ID NO 78
<211> LENGTH: 2000
<212> TYPE: DNA
<213> ORGANISM: Cucumis melo

<400> SEQUENCE: 78

```
tagcttgtta attcttgtgt tgaagacgtg tttcaacaaa tctgatgggg tattcatctt    60
aagtgtccac tgaagaatgg gggttctgtg gcagatctgt atgttatgta gtgaaaacaa   120
atctgtaaag ttttttttta cttcgaattt aacgttgctt aagcttctgt gtacagtttt   180
atcactgcct cgaggttatg attattattg gattaaatta caatttagtt tacgtttacc   240
ttggaactgt gtatttcttt tgattgctca acttttctcg gggattttc aagaattgta    300
tttttaaaat tttaatttat ttggaacatt aagaagttgg ttatttacag atgagatata   360
acactgtgat tggggtggaa aataaacaca gcttcaaaca cggagtgaga tatagttaat   420
tacattacat agtactagag attatataaa tcactccact cacatgagtt ttcatcttaa   480
aagattggaa tttacatctt aacagatgca atctttaat gtagagttct taacgtgttc    540
tcttacggtt gtatcttttc gttttcatta ttctttggtc aaatcaaaat tagactttat   600
agttttaat gaaatattgg acacactacg attcatcaaa gtaacccatg atcttataaa    660
gttgtgaaat gtatgtatat tgtctttgat caaactttac gtttaattat atcttgaatt   720
tataatttg tatttaagag atgaatgaat tttagaaaat tctaaagttc ctaggccaaa    780
gttgttatag aagggtaaag aatgctttaa atcatttatt ccataatcat tagttttata   840
attttattc ttcgtaacta ttttttaaca aaaaaaaaaa aagttatgca tctcttaaat    900
actatcttt aaaagggaaa ttttcataaa taaataaaaa aagacgatag tatacacata    960
aaaaaaactc aaatgattta tagagagttt gatgaatttt gctggattta taaatagttt  1020
agaaaaataa gtattaacct aaaattttgc ctatatctca atggccttct atgtctatgt  1080
tatttcttaa ctaaaatcga aaggatatag gcttatggat tggcttaagc taaaaaatgt  1140
cggtccaaat agttgagatg tcaaacctta aaagtactac gattatgtga ttttcacatg  1200
acatagtgtt ctatggtcaa attttatagc gtacttattc caatccatca ctttttatag  1260
aactaaaatt catagttcct atttaatat atatatatat attaaaaaca cacattaaat   1320
gatgatttta tctcttctag gttgattgaa aattactaac taaaaaacac ggtgcctcaa  1380
acctccaacg taaatacgat ttctaagaac tgtgttttt gtaaacgcca agtgactgat    1440
taaatctctc cattctctgt ttacttctat ttggggttat ttatgctaaa ggatattatt  1500
cattcaatag aataaatgtg agatagtcga gttatattca tagatgttac aatgaggtga  1560
ttcattcctt tgtcaaacaa tgctttctcg actcgtattt tactgtattg gatcgaaatc  1620
cttcttactc gcatggtttg ccttcgttga ttagttttgg tatgaattga tgctttgttt  1680
aaggggggaaa atgaaaatgg ttcaattgga ggacaattgt ccaaatttcg ggacattatg  1740
ggttaaacac aaagaagaag tccaacagtg taattttgtt aaagattgcg ttacatttcc  1800
gaaatataaa tgagggtatt ttggggaaag gaaatcaata taggccttgg ccgggtgaga  1860
tgcgaaaaag tctcaaaact gagtgagaag cgtttgagct gggctcgcag ctattgaaaa  1920
agagagaaca aacccttcg tcgctcttat tttcttcctt tgatctgaaa tttcctgttc    1980
cgatctcgct ttaggacgca                                              2000
```

<210> SEQ ID NO 79
<211> LENGTH: 2000
<212> TYPE: DNA
<213> ORGANISM: Cucumis melo

<400> SEQUENCE: 79

-continued

```
aattcattcg ggattgttat gaggtaataa aaaatatctg agtgcgaaca tgataattgg     60
taaagtgaaa aaatgttcag ctattctgtt ctagatacag ggatggaagt gggaacaatg    120
ccaccttgct tattgacaat aaaatgagga gtggcaatat tttgtttctg aataaatatt    180
cactagcata acatattagt gatgattcaa actaaagtgc actaggtcac tagtttcttg    240
attcatcgtg tttggtagta atggtaggta ttgtatctta tagtattgga caaagcttta    300
ccgaccataa attgtggata atgtgcagag aagaattggc agttgaacgt tcctggatat    360
tcaagtgatg agtggaagaa tcacaacaaa aatgtaagaa aattatatta ccctctctaa    420
aacatcattc tattctcctc cctaaaaaat cattctgttt caatttaact ttcaaaattt    480
tgttttagtt taaccatatt gagttttttt tctttttttaa ttatcgtagt tatcatcaag   540
tgatgtccac aagaaacgtt tggacatggt aagttggact tatctcttca agtgtttgct    600
ccatttcttc ttttatcatt tgtctcaaat tttctcttct ggggtttcat cagatacgcc    660
tattgaagga agcctcctgt gtcgaaacaa atgtaaacag ccctaaagag atggtacgac    720
aaggggttgg aatgtcaatt ggtcccaaca ctctaacaag gccttcaccg agttcagaac    780
aactattatc acaaacgtct ggttcacagt tgctgcagca aatgatgagg ttttagtgta    840
ttaactacgt ttgaaactaa tgcttggtag agatcccaac tacttggtga ataaccaacc    900
ccagtgtcag ttcagggata caacaaataa aatgagattt agaggatgcc atatcagagg    960
gaacctggac tggacatctg tgtggagtgg agtgtgatga tttttagtga tacgtctttc   1020
ggaatcaatt tttttaggct gtataatatg aagttgcatt atctggaaca cgggcgtaat   1080
gttaattgta caaaatattt ggcaggtcat attagtatag gccttaagta ttgttgttgt   1140
ctaccatgaa ggacattttc caatttatga ttgataatct ttacttacaa tctcgagtca   1200
tatgaagttt gttgatcagg atcatagcac aattattaca aaaatgaaat agaagatatg   1260
atttttcacc cccccccac ccccccccc cccccccctc ccattcccat cccccctttt     1320
aaactgttac attacaactt gttaactgtt gattttccag atgagagaaa gggcctactt   1380
gtcttgtaca gaaaattcat ccatgacgat aaatgcagat gacctgaacc aaacgtgaca   1440
gtaggggttt cttctatgcc acaaagctcc aagccattca tggtgcgcat gtggtacaga   1500
gaggcttgat ggagcctctt caccttggtc cttagctatc taaaaattgg cttcttatgc   1560
tgatatatct cttcccatgt gcatttggtc cactccactt tcttcgtcga atatccttgg   1620
gttaatcctg aatggtaagc acaacattct tgctaattaa tccctctttt tatcctactt   1680
gccaactgta caagatgagc agaagaagaa ttgcccaatc atgaggtcat taactgcaaa   1740
aaagagaatt tatttctttc tttgagaatc tgatcttctt gagagttcat tgacagccac   1800
atgcatcaca aaatgaaatg ctgtgtggcc ctcattcatt cattcatcaa tcttcctatc   1860
ctgccatttg agtgaatgtt actccaactt gcaggaagct aaattagtac tttttttatat  1920
aaaccctatg aaactcatca agaaaccaca ccatcccaaa aaggaaacga gtgaacaact   1980
agacaactca ccccgaaaaa                                               2000
```

<210> SEQ ID NO 80
<211> LENGTH: 2000
<212> TYPE: DNA
<213> ORGANISM: Cucumis melo

<400> SEQUENCE: 80

```
cagcgatctt cgtagaaact aattcaatgc tagctcatta tttgactttt ctcaggcaag     60
gctccgcgag gaagagaaaa ggtccaattt caggaaccaa gggcatggac aggttccggt    120
```

```
cagaagaagc tttttacgta aaccctttgc cagattgttt atgtcaagga gaattaccaa    180
atggaagtac gacttccatt ttcagatagt tcagtagaac atcaaagata aaatgctctt    240
agagagctca atgtatatgc aggcgaccac tcaacgtgtc accagctttg tacatccaat    300
aagccagcta cgatggaacg acggagtgtt tataacctga gttttggtag ttggcggagg    360
cggtgatggt ggtatagaag gaaggtcgag ggatggcaaa ccctttacgc caagtagtgg    420
aagggagtag ttggagatga acacattttg agaagtttcc aagatcactc catttggggg    480 agagggatg ttggttattt agcacaattg ttttcatgtt ttagtaattt tatccaataa    540
tgagcgaggc attgaagcaa ttaaatttat ttttaatgat ttttcaccc ttccataggc    600 ttttctttt ttcttttcct tttagtttgc aaactttagc tccttttatc ggctgtcgaa    660 ctcattttg aagttattga atgaaacaca gtttgggctg tgtcagatgg gtggtgaaat    720
tttatacatt ataattacta cataaaatga aatcatattg taattttcta tctatgccac    780
aatttttttt tattgcatca tgaggattaa attgtacgag tccaaatttg tacagtcatg    840
tttttaaagc tttcgagcat tgttactaat gcatggaaag gatcgattat caagtatcct    900
cccaacttca tgaaagttat tatttgtctt ctaaatttgt tttagaaaat gtttaattaa    960
ttatttgaga agaaagttta actaaatcct attggtttcc tctaaggttg tcatacttat   1020
ccaataacaa ttacgtttaa aatcaaaatt attctaatgg tataagacta atgttttaaa   1080
agcataaaat tgatgaggaa ggattggaag taatactatt tattttgaag gtaaacattc   1140
ttgaatgtct gtcctaaaat cactaatgtt ttcttagttt gagactttga gtcgttgaac   1200
ctctccatct ttataaaata taatacgagt ccttcacaat aacttaaaat atatactaaa   1260
tcctaattaa tgaaaaataa ataaataaaa ggtacaaaat cattaaagcc taaaaatcta   1320
ttactccttt aaaactttc aagggtccct acaaccaatg agaaactacc acgtcattt    1380 cacaatccgt tcagtgttta gaaaagtcaa atcgcaccgt ccatttatcc actcgtacca   1440
agtacggtag gaatctatct accgtccgat taagcacaaa gaagcacagt aaatgtcaat   1500
cgtgtccatc cgccgccata ccgcacatcc ttcgtccgac cggaaggccc tatataaagt   1560
cctttggttt tccgaatttc tacttcattc gcttttgaaa gatttcccaa tctcttcgtc   1620
ggccaaaatt ctctctcgct tctcaaccct tcttcggctt tttcatccag gtttgtttct   1680
cttctctttt ttcttcctt gttgttcttg gaatatgttt aatttcattt gttttccat    1740 tcaatttcat gctagatttt acgattaggt tgattttctg ttcgtagatt gtaattgatg   1800
gttagggtta gcttttttctc ccattccttc tggaatctgt ttcttgacct tcgaacttcg   1860
ttgataaatc tttagaaaca tttacataac caaacaataa ttgaacaact cgtgttgtta   1920
tgcctatata atagcggtta ggaaactgga aacgcccta taattgaaat cgccttagaa   1980
atttgttttg attcatacag                                                2000
```

<210> SEQ ID NO 81
<211> LENGTH: 2000
<212> TYPE: DNA
<213> ORGANISM: Cucumis melo

<400> SEQUENCE: 81

```
tgtaatgact aaacatacta tagcctattt ggaccgggtc gaaaatccaa attaaccaat     60
ctcccctcag cctcacacca aggataaatc atgtcaacct tctccatttg acatgctagc    120
tggacaaaga gaaatactaa ctcaaattcc atataaatat atctttacga ctccttatca    180
```

| | |
|---|---:|
| ggtaatttag actcaacaat tagtaataaa tttagtataa tgaatgatag tttccataga | 240 |
| tcaattatat catttattga tttgctagat ctagagtgaa cttattgact aatataccaa | 300 |
| atataaaata tatcaatgaa cttacccacc aaacataaaa atgtaatatt tatatctaca | 360 |
| tgaattttac aataaaaagt gtatcatata aaatacttat atacataaac cctattatat | 420 |
| atatatatat ataaaaggaa ggtaagatgg aaaaaattgg aagagaataa tttgacctaa | 480 |
| aaaaatcgaa agagaaaaga gtatttaata tataaataaa aagaaaaaga gagaaagaaa | 540 |
| aaaatcttgt tcgtcgactc ctcaaaaacc ccagcgtgta gcggttgtga gagaaggaga | 600 |
| gctcgtttcc atcacgataa aaccttatct ttctccattc ttctatcttc tcttccggag | 660 |
| ctctctccat ttctcagccg ctccccacaa tttcctctaa acacacacat acacgactat | 720 |
| ttttccattc aaattccttc acttcgtttt ccattttcct tttctttacc ccacccactc | 780 |
| acccacctct cgtcgatgga ctccatggac ttggcccaac aaccgtcgca acagaattca | 840 |
| gtctcctcag gttcttcttc cacttcctcc tcctctttta cgtcttctac cgttgattcc | 900 |
| catgtcgata ctccctctct cgatgaacct gagatggggg ttgctgaaat taaaactagt | 960 |
| gtagttgccg atgggggtgg tagtgatggt gctggttccg aaactgaagg gttttttgagt | 1020 |
| ggggaggagg aatttgagtc tgcttcagat agaccaattg tgggttatcc agaggaagag | 1080 |
| tccatcggga agtccgccca aggggctgat actggtactt cttttgtggg ttattctcaa | 1140 |
| ctttctgctc cggttagtgt taggccaatt gcgaaggttt ctgttgatag tgacgttgag | 1200 |
| gaggaggatg aggaggagga ggaggaggag gatgaccttc aggtggatga gaacttgagg | 1260 |
| ggaaggagg aaattgagga taaagtgggt ggagaagatg ttttttgttga gagtaagaag | 1320 |
| gggaaggaag ttgaggttcc agtggaaaag gaggagacta ttgttgtatc tgatggaaac | 1380 |
| aagaatttgg atgatgtggt gaatgatgat gatgatgcca gtcaagtgca ggaaagaaca | 1440 |
| attgagttgt cggggaactc aaaagagggc aatgtgcctg aaagcttagt agctgaagat | 1500 |
| gttggctctg tgcccgagga atctgttgat ggtgggaagc aggtgtcaga aggggatgaa | 1560 |
| ttgaatgatg tgacagttaa acagtcacaa aatgaggctt cagatggaaa aaagaagcag | 1620 |
| agttggataa agaaactctg gcgtctggga agcaggctgg taaagggatt gacttgagtg | 1680 |
| agaaggtggt tgctgaggat gtagagcaat tgaaagaaca ggaaacacct ggttcttctt | 1740 |
| ctgacgagaa agctgttttg ggagaccaag caagctctaa gcttgtgaaa ctagcagatg | 1800 |
| aaaaacaaga agaggagacc tctgcggctg agaagcaggt agatgtggag gtcaaattga | 1860 |
| atgacacggt ggctgctgct gaagatggag agcagttaaa aaatttagaa actgattctc | 1920 |
| ctgttgacga caaaattgtt ctagctgatg acgaaaactc taaggtttta gaaccagcag | 1980 |
| atggaggaca agaagcagaa | 2000 |

<210> SEQ ID NO 82
<211> LENGTH: 1072
<212> TYPE: DNA
<213> ORGANISM: Cucumis melo

<400> SEQUENCE: 82

| | |
|---|---:|
| tttaatatgg tatcagagca aatggtccag agaggtcttg tgttcaagcc cctgcattta | 60 |
| cgtttccttc ccaattaaaa ttgtttccac ttgttgggct tttcaaatat ttcaagccca | 120 |
| caagtgaggg ggagtgttag tgtatataat taaatttgcc ttcttcaacc actagctgaa | 180 |
| gtttgtgggt gaattggtgg tttaatagta actatatcat gcaattagct tttttgagtt | 240 |
| caacaatatc tgtggtggag atttgaaatc gagattatga tgccttaacc atgtgaacta | 300 |

```
tgcttaggtt gacaactata tcatgcaact atcgaaaaca tcatctctaa tttataggtc    360
ttttttaaca tagttgaagt ttcaatattc tatatgaaca cagctggcta tttaaattac    420
catattgaaa agcagcactt gaaatgcttc taaaaattaa tgccaattag aagtgtttat    480
gattctaatt ggttaacatt actgaacaca gattagttat agttattgaa agaataaaaa    540
ttgtaaaatg ccgaactaat accaaatgga tgggtagtct gcaaatttta ccaaatggta    600
ctacagctgg tgatgaactt agaaggggta aaggtatagt gtaactgtct aagttaatgc    660
cataaaggta tagtgtaact gtctaagtta atgccattag cagatcaagt ccgttgtatt    720
atgtactgaa cacatttttt aatcgtatag ttctaaatcc tataatctgt cgaccaagtt    780
ttaggtttgt taggctgaaa gttcatgcaa atctaggtgc ttttttgtac taattgtttg    840
agattcagaa attgtatctc aatgttctcc atgattatgt gcgtgtattt gcaaacagct    900
ctttggtttt ttcttcttct tctgacaagg atagtcaaat caattacagg acataatttc    960
aagatttaag gagagaaagc aagggaaaga ttcacgggag tggactgagt ttccaagcag   1020
agttgcagtg caattaaatg atactcatcc aacccttgca attcctgaac tg           1072
```

<210> SEQ ID NO 83
<211> LENGTH: 1730
<212> TYPE: DNA
<213> ORGANISM: Cucumis melo

<400> SEQUENCE: 83

```
gttcaactcc acaagtcaaa ttttttttgga aatctcgtgt gaacacttgt gaaacactt     60 attttatat taaagaaac aagaagattt aagatgagaa tcccgtattt gtttggttga     120
aggacaatga aattggtaaa tatatcccat cgaaaaataa tcaaatctag acacaaaaat    180
ttaaagttaa aacttactta ataatcagct ggagcatagt ttaatttgaa tgaaaataaa    240
aatcctaaac tagagaagtt tcttatggta ttgaaaggcc agtttagaaa gcccaatagc    300
gtgggttttt cttggaccca tgtgtatgtc tcactcatga aattaaatta attggcctcc    360
acattcacct ctctcctccc aattcccata actcaatttt agacctctta aatgaaacat    420
atcatatttt cataaacttc tttttttacgt tacttatgag attaaaagac tttaaataaa    480
gtgtcaattt atattatagt agatgagatg gagtgtgtgt ctttgtgccc tccttggggc    540
ccaaggacta agtaaggatg aaagggcaaa gaaatacaaa atagaagaga gtagaaagaa    600
aatgaaatgg aatatatagt aagggttatc gtttatggtt attatgaggg aagggctgaa    660
attgataatg aacctatcct tatcttccct tcttcacctc tcattttgct tgaaattaca    720
aatgactttt ttttcaatta ttttgtgtgt acatccaaat gtggtatgca catatgggcc    780
tcccattaac ttgtgatcca aattaattct tttgcaacct aagttgaaat taaacacttt    840
tacctctctt ttttttcccta acaatttttac tttcattgtt agatggttga ttatcttgac    900
atgtaacaaa aagttctctc atgtcaagat agaaaaatcg aatatttgat tttgagattg    960
ataatattat aatatcagtt gagctatact cattttaact atcagtaaag cttcattaac   1020 atattttta tttagtaaac taagattaat ataaatagaa tcttactttc attatatact   1080
ttgacgagac ttaaaaccta tttagcgcat gattttttaaa agttggtagg attttaaccc   1140
ttgaaaaatt ggtcattcgg gaatcaaaac attagttttcc ctttgagcat ttattttttaa   1200 agcacttcaa aagctaaatt agtagcatta aaaaaaaag tcaaatagta tatatatata   1260
ccaaaacttt gttttttcaaa actatatttt aaaccaacat tcttttttttt ttattattta   1320
```

```
ttactaattaagtgcagattatagtggttctcttttgtagttggatcaaatatttcattc    1380 ttttttgacaataacaaaagttaaaatactcattaaatgctaaaaacttccatactaaca    1440 ttattgaaccattaaatatatgagcaacgaagtataggtaagaatttatattgttgttg    1500 tttagtttggaaatagaaaatggaccaatgggtgagcttggtttaagttagggttcttgt    1560 ggttggatgataatgaaataaaatggccaaaattttaatgagaagaagatccctttaag    1620 ttcaaccactaatggagtctttttaggatcaattcacaaccctttctcctctgccacgt    1680 gtcatctcagctaatctcaactgtgtggttgttgagaaattttgaaactc            1730
```

<210> SEQ ID NO 84
<211> LENGTH: 2000
<212> TYPE: DNA
<213> ORGANISM: Cucumis melo

<400> SEQUENCE: 84

```
aactagactagcgagtgcacaaccaaattacaaaatccttaacagagacaaccatctatc    60 tcctttaaagcaacaataacatcaaccgaattagaatccacaatcagtaaagacgatgcc    120 gacaccaatgaccaaaaccgatcaaatatagcttattacgaccattactcaacagtta    180 catcaacaaaaaaaaaaattaaacattgctaataaaatctgaaaatgaggaaaaagaga    240 ttaaaagtttttgaagatagaaagaataaatctgaaatgttctaatttgatatataagaaa    300 tatgaggtaatatgacgaaagcattttgatagttttcaccaactccctttgtgaaaggat    360 acatccaaccaattttacaatttctgttcaaattttgtccacctaccctctcttctgcc    420 ccccaaggctgctttctttcttttattattgctaaattaccaaaaactattttttcgaatt    480 aaaccatctatttcaattatatacgtcattcgaattttaacttaattaacattagtatat    540 gtttcggatcaaggatagtggtataaatcatcctaatttcaatttgtatttagaaaagtt    600 caattatactaaaacttctaaaaattttatattttaaattggatataaattaaattta    660 agatttatggaaggtaaataattagagcaaaacaaacttcaaactatatgaaaaatagaa    720 aaggaatatttttagccaaacaaaaacacttattatattttattttttgttttttttgttttttttt    780 aatttaacaatttttttttttttattggttgaatgtgtttctccactggtgagtctccaact    840 ttgacctgcaaagggtctatatagcgagttcacgagcactaaccaatatctgtgtaat    900 aattcccatttttctttcatacccacttcatttgatcatcttttttcacaaccccggatct    960 ctaattcttgggaattgcctctttctcgatccatttccacccgtaattgaaaaatattca    1020 ggtttgattttcttctgggttttcattcaactgtctaacttcattatgccctttatgtgtt    1080 tgttgaaagcccccccaccccaatcgttcaatgcggttttcttttacctttttgttcggttc    1140 aacgatgatttagaagttatagatggatgctaattgtttcgttgttggttgatccactg    1200 atctgcctttgattggcataaaaggagattctagatcttgttttgatgttgtgatttatg    1260 gatattattgttatagtcgtggaagttttcttgtcgttctgcggtatatggttgtttta    1320 tttttgagtggtaaattgagcagattgtgaacttttgggttttatggtgaaagcatgaa    1380 ttagtaaatgtagagctgctgaaacaaaatggaggtttgctagacctcttttgtgaattct    1440 taatggtcagcctccatcttaagaggctaagtccaaaaattttaaggcagtcttttgttat    1500 tgttacaaaggacaagaaataacagaggagttatttttaatgaatcaagttggaaagaag    1560 tactacttcatgcttctttcaaaagcaggtcaaagtgcttttaaagtcttcttattttattt    1620 atttttttcctgaatcaattttaaactaatgatagaaagaagttgttttttttaatgggttatta    1680 taagtaacatcaattttttaaccattccaaagttacatcaaattcatcatagtgtgagtt    1740
```

```
tacgaatttt ggaagttgta attttaagtt aatacttctt ttaaggaaat gtacactttg    1800
catgttgtgt tcataagggg tatttctttg acaaacgcag caaccacccc ttaatgaaaa    1860
ctacaccacg gtggttggtt ttttcttgtt atttttttac ttggaattta caataagttg    1920
ttatattcgg atatatggca aagcagatat ctgttttat ccgaaacctc ataaatcttg    1980
aatgtgcagc aggtaaaaac                                                2000
```

<210> SEQ ID NO 85
<211> LENGTH: 1020
<212> TYPE: DNA
<213> ORGANISM: Cucumis melo

<400> SEQUENCE: 85

```
tcattgatga agaaggaaac tttaagccaa ttcgacaact tatccattca acaactttcc      60
accttcagac attcagattc aactataata taacataaat tgatagtcaa gtctttttg     120 agacaaccat aaatcatctt agcttcgaga actgtcactt ccttaaattg gtgaatatat     180
cacattccat ccattcaaaa ctttgttttc gaactttac tgtagttatg aatcaataaa     240
ttgggagaga tattgtttaa aaagagagag catatttgtt tctattattt actctctcct     300
aagagagggt taattagtct ataaatgatc tattcttctc gtccattgaa attttgttat     360
cctaaattta tgaatacttc tacccaaaat aaagactttt tttttgaaa agtgtcaaaa     420 aaacataaag aaattgacaa acattcatt tttagtggat tttacggac gtaaatagtt     480 tgttttgttt cttttaataa tacaattttt ttactttaaa aaatattttt gttataaaac     540
caccgtattt ttattcaatt ttaataaata aataaatgaa agaatataaa aagaggaag     600 gaaaaagaag ccaacgaacc aacggttgcc acgtatcaaa ggtctaaagt gcgcaaaacg     660
aggccttcgg aaaccaaaat gcgtggcttc aattggagca agtaaacatg gaaaccacgt     720
ccattgtaac gcttcctgat ctcttcttta caaccgttgg attcgagtac ttttctcaa     780 cgattaacga ctgagtggac ctccacttgc ttctgttcca cgcgcgtggg attgacgtgt     840
ggtccacgca actcttctcg ataggatcat tcgagaacat cctttactta aaccgcctct     900
ctctgcctca atttctcgtc acttccttct ccttctttac ccttttccact gcggctgatt     960 cttcttcgcc ttttattctc tcgtacgccg ccatattctt cacttctttt ccggcgaca    1020
```

<210> SEQ ID NO 86
<211> LENGTH: 2000
<212> TYPE: DNA
<213> ORGANISM: Cucumis melo

<400> SEQUENCE: 86

```
aaatcatctt ctcccatttg catgtgttaa cgcctaatgt agtacattta ccatgattcc      60
tagaataaga ccgattttac caacgagaag ttgctttcaa cttgctacaa tatacataac     120
atttctttgg tacgttattg atgagaagag gtataaagca tttcacagta ttctctcagc     180
aactcattag tttaaaaaaa aattaaagga atatttgaat atcggggat gaattaagta     240 tagcctcaca atttgccagc tccttctcct tagcggctgc caacctccga agctttgcag     300
cctgtgcaaa tgtagacggt ctacaagaac ataaagcaa tgaatacga tcccatgac     360 agccataaca gttgcaaaca atcatataga atgaatgatt tgagcctttt ttttttgtaa     420
gatgatttga gccgaattaa cagtgtctaa tgctgaatcg agctggaaaa tactacttac     480
tgagataagg tgctagcctc cctcagaagt tgctttattg atttgcgcaa ctccaattcc     540
```

| | |
|---|---|
| acctggctgt tggaacctcc ctgaaaagta cacgcatgat ggaaacatga ttgtttcaaa | 600 |
| acaaacaagt tgacaagatt gaacggataa caattataac atagcaaatt cccagacatt | 660 |
| aaaactgaaa atgtcaatag atctccacat taaatgcatc acgtccctaa actaatcaaa | 720 |
| tcaaatgtct tcaatccaat atcgtaaact taacgaagca cagttaggca tattgcattc | 780 |
| tcaagtctgt caacgaaata ctgaaacgcg ctacagccca aacctcaaaa ttttcaacta | 840 |
| taaataacaa gctttgaatt gaaaacaaa cggaatgata gaaatacaa acacgaaaaa | 900 |
| attccgacgg gaaaagaaa atcaaacgaa aaggcgaacc ttcttcaggt gctccagcca | 960 |
| tctagcgaga aactgaaaac cgataacgat aaagaaaata aatggagcgg caatggagct | 1020 |
| tccatgctct acgattcctt ccgcttccat ttccatttcc agaggacttt tctgccacaa | 1080 |
| cggtgaatta atcaaacaaa gaaactccgt tcatcgtcgc aattcgacgg aggttattct | 1140 |
| ggaagaagtt gagatcgtaa ttgggctacg aatatcatca aaggggcttc aataaaaggt | 1200 |
| ctctcaaaac ccaaggccca aaaaacgaa agcccagcc caattagtgg agaatcaaaa | 1260 |
| cgctgcgttg tagatacaaa tatcttagga aagggaacca agttacgaaa ataccctga | 1320 |
| gtagtgagat caatgattac ctcaacgacg cgttaatcgt tttatcacgt ttattgtgat | 1380 |
| aagttccgca ctaaggaagg gacgagttgt aggaagggag gggtaaactg gtgatttcgc | 1440 |
| attcaaacaa cgggctttaa ctcacgtgtc cggatctgtt gagagggaac aattcacagc | 1500 |
| gaggaaattg caaataacac acaaaggaaa cacaaaagag cggaaagcaa atgtgaagag | 1560 |
| acgaagagta gccaatgaga aaaaggacg aggatcgatg acatggcaaa agattttga | 1620 |
| aatcccgcct aaacccggag tttcaattga tatcgcgatt tatctctccc tctctttaac | 1680 |
| gaaaccgact ccccttcatat ccctctctct cgctccctct tcacttcaaa gggcttttcc | 1740 |
| ttctttccac ataaacacac gcactcgaag ccaatctcaa aaccgcatca cacgaaccaa | 1800 |
| actaagccta acccaatttt ttctcctcat atttcactct cacactcttt ccttatcttc | 1860 |
| ttcttccccc aaaccctaga gttttacagg taaactccca atctctccgc cgctccctcg | 1920 |
| ctcgattctc cttcgtttct ccgccttttt tcttataatc attacctgtt ttctccttcc | 1980 |
| ctctatctgc aggattcatc | 2000 |

<210> SEQ ID NO 87
<211> LENGTH: 2000
<212> TYPE: DNA
<213> ORGANISM: Cucumis melo

<400> SEQUENCE: 87

| | |
|---|---|
| gtgtagagtg agtgacggtg ccgacagtt cgtaacattt agttgttagt gagagacggt | 60 |
| gagacgtttg gtaacaaact ttgtttttag ttcaatcatt gctttgtttt ctctttcttt | 120 |
| tccttaatgt ctaatgtttt catcttcctt tctttatttc ttacccaatt tccgaatcaa | 180 |
| attttaattt ctaaaaagt atttaaaaaa aaaaaaaa ttagtcgctt tattcgagaa | 240 |
| tttcataatc aacctaattt tcaaaattaa tcatcaatct ggaaactttt ttattttttt | 300 |
| tctcctttgg attatcctgt atgaaagtca acatactttg cactccttga gaatattttt | 360 |
| agtggtgttt ttttttctc ttaataaata aaaaagttta catctataat aatcaagatt | 420 |
| ccttggcagg tgtcactgtc aaaataattc ctatttgttg aagttgaaaa taatttaact | 480 |
| ataaacttta tttgaacgtc aaaaaaagaa aaaaaaaga tatatgaatt cacccattcc | 540 |
| ataatttaac tatataactt tatttgaatg ttgaaaaaga aaaaaatgaa gacaaagcaa | 600 |
| attcacctgt tgccattacg acaaaatttc aaatgcgttt tattttgttt ttatgtccac | 660 |

```
aagattctct atttgtattc tgcgaaatta aagtcacggg cttcgcacgt gtgtgattaa    720
tagtatttgt aaaagggcat gtagtcgaac aggatgggaa ttaaaggaga ttatgaatgg    780
gttgggtcgg aaggcccat ttctataatg aattgatggg ccgtcaagga catttgtcta    840
cataaagggc atggaccatg aagttaagcc cacttcctaa acgagttcct tagtgtgtct    900
acattcatat ttaaatcatc tttaattcag aattttcacc atcatcaaat aatgtcttat    960
aaacctccca ttttatagtt taattatgga ttctaataaa aaatctctaa cttcaaagtg   1020
gataattttt ttttttttt aagttgaacc atgttcattc atttaattac atggaataaa   1080
aataacgtaa tttaggttaa aagttgagag ataagatga agttgaaaaa ttacaacaag   1140
ttaagaaggg aatatgaaga agaagaattc aaaattgaga acataataaa ggaattaggt   1200
ccaaagctgt aaagactagg agaaacgagt agagaaggga aggactcgtt tttcaaagaa   1260
aagaaaagtg tggaaaagga aaaaggttca ttaggggtgg tgaggaaatg gatggatatg   1320
gaatgatgat gatgagaaag aacagcacgg gaagtttccg agtagttgcc ttttgcatat   1380
accaacaagt tatctaataa aatgttttga ttaattacat taatttattc aattgattta   1440
tcggaaattt ccatactctt cacgtgatat gcacgtggtc ttcccatgtt ctaatatttt   1500
ttgtttttga aaatttgaat tcctactctg ttttgttatt ctgctcattt aactactcaa   1560
atattttagt ttgtagatat aacttttgtaa attttttatta taacattttg taaatatttt   1620
aaattgtgcc catagattat gagtagataa attttacgaat taaaaaaagt ttaattctca   1680
cttcaattta attttttttt attattatcc aaatctattt gtcgcagtgg ggaaaacggg   1740
gacgtacggc cgattggagt ccaattagtg gatgtgaaac gtggacggta gagatgcaat   1800
atgaagctgg acatcaactt tgcgaaggaa ttgttccttc tttccctctg acgcttgtcc   1860
cgttattgct cgttttaaag caattcgagc tccgcgttgt ctcttccctc acgttttcct   1920
ttcaatccca ctgctcctcc tttcaccaat aaaacaaaaa cgcctcaaag aagaagaagc   1980
aacgaccaga aacctcaaaa                                              2000
```

<210> SEQ ID NO 88
<211> LENGTH: 2000
<212> TYPE: DNA
<213> ORGANISM: Cucumis melo

<400> SEQUENCE: 88

```
gttcgagcat gtgaatgtct tctgttgttt gatgttagaa ggaaagagat gggttaggga     60
gttcctgttg atgtctagta ggttcttttt tttttctctt gtgcaatgta acatagtaac    120
ttcgctgcaa agcagctctt atccttagaa tacgaaaatc ttctgttttt tgttatgttt    180
ctaactttat cccttcttga ttttaacttt tgagttaaat tccatctctc tgactttgct    240
ttgtggtatt ctgtttctgt tgtatgataa ttcttatgga actcctatgc tctctctcat    300
tgccttcttt ttcggctgtt acttaattac tttcttcact tgaaatttat agcttctctc    360
acaaatttga gctcattcaa gtatcaaaat tacacccatc tcataccata tttctatctc    420
tgaaggagga ttttttcccct tttaaggagg gtagattgac aaagctgata gggtgagaca    480
atttaataac tcaggtcaga tgaattatac attgaagaac tctcatccag gccagtgct    540 ttgtttataa caagatgatt aatgtgttgc tatcaaaact tgctggttc actaaaaaaa    600 actcttggtc cttgaaagta ggcttttact agttttagct ttaatgcaca tctgtatgtc    660
aaccacgaac tccattttc ttacttgatg catgtgcaac tttagcagct ttctaagttc    720
```

| | |
|---|---|
| atatcaaagc aaatgtacct ttattcctat tgtaattcct tttctgctttt cctcttttat | 780 |
| gaattgtcaa aaatatggac aggaaagtaa gctgagcacc aacaggttgt accccttttt | 840 |
| catgtcttga aaatgaacta ccaggacaca aatcagatga tgattgttgg gagaaggaat | 900 |
| gtaagattat tcgttctgtt tgatataaga gatgtaagtt cacatgtctt acaactttt | 960 |
| gaaatttgtg tgtcgcttat gtgcagattc ctgtatgtca ttagtggcat ttgtaagcta | 1020 |
| caattgttga atttttgtat tattatctta aaaggaaatg acaaaaggta taatcaaatc | 1080 |
| aagctgaacc taaaagaagg tacaggtttt tagtattatg catgaagaag ttttttcatg | 1140 |
| tctcttctgc catttggatt ttgtctgtga caagggacta agacactaca catgatgctg | 1200 |
| gaaactgcaa gagtgttttt accctaataa gattaaaacg tgaaaagcaa ttagattttc | 1260 |
| gtgcatatct atcttttttgt gcattccacc aaactgttcg atcataactt gtcaagatct | 1320 |
| tgcttttttcc tttttttat aaatatttta atatccttct aatgtgaatg gtgaaaagag | 1380 |
| atgcacaaag ataagtgata ctatagatgt atctaagtat tacccttata cctttgccac | 1440 |
| gtaagattag atacgagaag agaaaaaaat ctatgagtta gtaataggc aacaataaac | 1500 |
| cacagaaaaa ccaattaata cctttcctca ttgtctaata atatctaaaa gaaacttctt | 1560 |
| ttcatgttaa tgaaccaaac tatgttgtgc tatagcatga gcacattatt tctacccttt | 1620 |
| agacaagtga tgagaatgga caatatttcg actgagttca ccagaatgta accaacggtt | 1680 |
| ttgcatttgt aatatgaatt tgaaagtttg agattcctta tacgaggacc ttttttcatg | 1740 |
| tatctaacaa cacgagaacc accaaaatga aagggagtt ggtccaagcc aaaagaattt | 1800 |
| tgacctccat gaaaatccag atagtgggc atccttatct aaacaatcag aacctgaagt | 1860 |
| ccgacgtagc cttatccaca tttcaacttc aaaaacactc cctctaagat cctttcgaac | 1920 |
| caccaaaatc taagaaaatt tctcttcctc atcctcctcc gacacaaaat ctagcttcaa | 1980 |
| tttcattcct ctgtaaaaac | 2000 |

<210> SEQ ID NO 89
<211> LENGTH: 2000
<212> TYPE: DNA
<213> ORGANISM: Cucumis melo

<400> SEQUENCE: 89

| | |
|---|---|
| attcgtcttc gcattatcag taaatttatc attttaagag tttgttctttt tttaaaaaaa | 60 |
| attaatcatt tcgataaagt tggagaattc aaaaatttct ccaataatt tataaaaact | 120 |
| ttcggttata tatcgaaaaa attaacatgg tattaaaacg atcataactc aattaacata | 180 |
| aacactccct ctcaacttta ataccaaatt tctttattaa cgcaaaattt aaaatttgtt | 240 |
| tttaaaattt tcacataaca taatagaaat acttttctttt atggcaaaaa tacaataatc | 300 |
| aaaattgatt gatggtgaca ggacaccaca caatattttt aaattttgaa tatacgaact | 360 |
| atataataag atatttatga gattcccatc ctaaagattc ctagagattt ccttgtgtac | 420 |
| aatattacac aagtatcttg gaagtccaaa gtcctgagaa aaaagctatg tataaagtaa | 480 |
| tgtgtttgtc gtaggaaatt tacttcattc gtgtcattag ctttttattg aaaaaaaaaa | 540 |
| ttaggtatat cttagtgaat ctcacttaat cgttgtcgat agttattctt ttaatatcat | 600 |
| tatatactaa aatataacaa tattgaaaag ctaaactgt ataaaaaaa aatgttacct | 660 |
| ctaaactttt atcgtttatt taaagataa atatattctt tcaaaactta caatcaacat | 720 |
| cctacgacta tcattatagg tacaaatctt ttcatgtttta cacaaaaatt agatttttaa | 780 |
| atggtgtaat gatgatatat aacgaaattt tgaatgatta ctatttgagg ttaccattgt | 840 |

| | |
|---|---|
| aattggtcgt gttgtttgaa atttaattt attagaaaat ttgtcaaaag tagcaaaaat | 900 |
| gaataaacta tttaaacttt aggataaaat caagtgttat gagttttgt ctagttata | 960 |
| tattttatt tttattgaaa acccttttcc tatcttttca ttacttcaaa atagttttaa | 1020 |
| aatgtctatt aaggctaaag ttagtataaa taaaatttcg gaattttt ttcgaaaaaa | 1080 |
| attgataaat tatttatt ttatattaaa gtcaaaattt attacgcgta gatgtttatc | 1140 |
| aaattttctt tcttttgtt gataatttc caaaatttgg ataatttt aaaatagtaa | 1200 |
| aattattaaa aaatgaaaac aaactattta taccttaagc aagaaatact aaaaaggcaa | 1260 |
| aaattcattt acttcatgaa gcgtaaaaat taaatattt accacttttt gttatttt | 1320 |
| accatctcta tcaattattt gtaaaagaa aactacaaaa ttagatgttt tttcttttt | 1380 |
| aaggtttaat caatattaaa atttcttaaa ttggcagaca agttggtgtt ggtaattacg | 1440 |
| aataaatccc gaattgacta aaaataaatt cttctccaag taaaatagac acgtggatga | 1500 |
| agaaataagt gaatcaaagg catccacagt tcaataaatg gaaaaaacta ctttctgctg | 1560 |
| actcattcat aagttttcat aaaatttcat aagaaaggcc aaagggctta tgaaagtgaa | 1620 |
| tgtcatagca gtaaatgaag cacagcgcca ttgaaagaca actcaaattg catgcaaacc | 1680 |
| cacataatta ttcaacaaac ccacatcaaa tttcccataa agatcaattc tttaggggt | 1740 |
| tcaattaccc aaaagtgagg tagttgaaaa ccattaaaca acaagaaatc aacaattttg | 1800 |
| taatttgttt gtacagaagt aagagataaa atcatcgtta accattcctt tatttcgtaa | 1860 |
| tacaacccat caaccatctc tctctctctc tctctctctc tctcggcctt tatcttctc | 1920 |
| ttcctcaatt aatttaagta ctacccaagt gagctaaaag caagttcagt ggacagtgtt | 1980 |
| gtaagaacca ctacagaaaa | 2000 |

<210> SEQ ID NO 90
<211> LENGTH: 2000
<212> TYPE: DNA
<213> ORGANISM: Cucumis melo

<400> SEQUENCE: 90

| | |
|---|---|
| aatcatcagg tctccttcca atgaaaccga cgacaacgac agtgtcggaa aagcgaggaa | 60 |
| gggatggcga aggcgaggaa ggagaaaacg aagtagaggg ttccggtaaa gcagaatgag | 120 |
| gagggagagg agttggggaa ggtgaagagg aagaggaagt gggagttgat aatggtggcg | 180 |
| gccggataag tactcggaca gaggaggaat tgggtacgtc catggatgag agaaaatttt | 240 |
| gagctttcag atgcaactga aaactgcttc actgctttca cttccgatga ccgccgaggg | 300 |
| gaaacttatt ttttccttgc ccttttgcc tcctcaatat tttccttta ccatttcctt | 360 |
| tccaaattta ttttctatg ttttgatttt atgtttgtt atattttga tttacttta | 420 |
| cgttattttt aaatatttt gatttaattt tgttatattt gaaacaaga tattcattat | 480 |
| atactgtaaa tcttacttta ttattgttta aatgtcgttt tggtaattca aaattaagtt | 540 |
| gaataaacac aatatttaa atattatttt agtaaaataa ttttaggtt ggagaatggc | 600 |
| aaaagaaaca aaggattgaa agactgaacc catatttgag gatagaagtc aaagccaatg | 660 |
| tcaataagtg aaactcactt ggaccaaaat accaatttta gttttatatt ttaattgtt | 720 |
| caatcttagt ttccatactt tcaatgcata ttaaacttat agttcattat tctttttcaa | 780 |
| taaatcttaa cattttacta caaatttta aaatgtttca catactttat tttttacat | 840 |
| gaaaatgatt gttattgttt aatccattc aataaaatta aaatttgaaa agctaaaaat | 900 |

```
tcaagaatta tcgatagaca attacaattt tgtcccatta aaattatcaa attgaagtgg      960
ctacacaatg gaatggtaaa tcctttattc ttgtattggt gtgatttgga ttgagatatg     1020
aaacattata atctaaagga acatgtttaa accgaacatc acgtattttg tctttcaaaa     1080
tttcgtaagt ttgtaggttg tttttttttt gtcatttat atagttacaa ttatttaagt     1140
cagatcggat aaattttgtt atacaccaat aggaaactaa aaattccaca aggagtatga     1200
atgacctcct acgggagcat taatgaaaat gaccaagggt taaaaaatgg taagaaaaat     1260
gttcttcact aatgacaatt cctcgtgaaa gtactaacat gttcttaaaa tgcttgcaag     1320
catatatgtc accaagaatt ctcattcatt cctctggctt ctttctctca tttctcatca     1380
acattaatat gacacacttt ttccttcttc tttttgtatg tgtttataat cttactcatt     1440
ccttattctc attgtcactc aacgattcca acaagcaata tgggaacaaa cgaaggaaga     1500
agagaaaaat acactaagaa gaagagatga acaaagttgc attagaacaa ggcgtagaat     1560
atcaaagaat tcaaaataaa aaggaaaaaa agattactag acgagagaga acgagacttg     1620
aaaagaatta gaataatttc ggtaatttta cattggacga cgaaagcaaa tgacaaaaac     1680 aattttttt tcaaaaacat agctcaaatt tcatttagat cttcatccc aaatggcata     1740 atttctctaa tttcacatac accacaaata taatgatgac tgattaaacg aagtaaatta     1800
caataggact aaatatataa ttaaacttct taaattgagt ttgagataaa acctttgaag     1860
ccacgagggg tcgggtcggg ggcgaaagag acatgccata taagcagttg gttgctgtaa     1920
agtggcacac gcatatctac tggaagcctc catttccaat ctcccattat cccattatca     1980
tcggcagttc cccatagcta                                                  2000

<210> SEQ ID NO 91
<211> LENGTH: 2000
<212> TYPE: DNA
<213> ORGANISM: Cucumis melo

<400> SEQUENCE: 91
ctttcctgac ccaataagag atcaaatcac tgtctcctgt agcctttccc ttgccgctct       60
attattgaca tttgggccta ccttcccccc ccccccttct cccgattcat cacccttggg      120
ccttggccca ttaaaacatt acccagctcc ttactacttt ttaataacta tcacgtctat      180
tccttcgcaa gtgggtggaa gcgaatattt ataccaatta tcttttggtt gatcatgtag      240
ccaaaatttg gctcaccaaa ctcgtacaaa gacatttact tgttttccac tgtagatttt      300 aatttttggaa gaagagatca gttgccaata gattgaatta atgcatttat gtacactttc      360
atacttaact tttggcaaag agttgaaagc aaggttttaa agaataaaat gaacttactt      420
tttttacaaa tctcatgatt tacgctagct caaacttagg attcttttcg tttgaaaaat      480
tggaccaaat atatatacaa tagattgaat aggagtcttt taaaatactg gcctcaaaga      540
aatagacaag ttagctaggt cgggataatt gcctcactca ttcttcacct cagagatgcc      600
tctcctccta ggcatgtttt ctaccctcat aatttaattc actcatttt gcttccttat      660 tgattagtaa aagtaccgat ttgccttctt ttctatgttg acaagttccc actagaaaac      720
aaattagatt atgagtttat aggaaagaat taaacacaaa tacataagtc aaattgtgaa      780
gtatcaagat aggctgttag gacagaaagt tcaaatttgg aaaacaaata tatatgttat      840
tgagttgtca tcttcttaga taatgataaa atgtgaactt ttgacacata taataaatag      900
catgttcttg ataaatagtt ttccattaaa acaataagct attattggat gatagaaact      960 ccctgggac tacaagaaaa agctaaaata gaatcagcat taaaacttcc tttaatagga     1020
```

-continued

```
tcgttatccc aaataacaac tccatctcaa aacacttcta aagaagtagt taaagaataa    1080
caatgtatat tagttatgga tgttgatgat agagaacttg gattttagct aaatttagaa    1140
tcttaaaaag ggaaggaaga aaaaaggaac aaaataaaaa gataacagta tgattactcc    1200
aacttgtgat gaacagtacc actcatggta tgtcaaacat atacatagaa tgagaacaat    1260
ttagatcaat taatttactc atttatcctt cttgctacag attgttgaga aatagaaaa     1320
acaaattaaa gtaggaaaaa aaagaataaa tggggaatta tggaaccaaa atatcaagaa    1380
aaaggagggg caataaatta aagaggaata gtgtaggcct tctcacagtg gaagtattag    1440
cgtttaagtc agtaccttac ctttatttgt tttcatacta agttctttct ctttcatgtt    1500
aataaatttt caatcgatcc atctattcaa aatggtgtgt tttattagga agaaaggtaa    1560
tttcatacaa gaaggctaaa aaatagttga cagctgtggg atttgaaccc acgccctttc    1620
ggaccagagc ctaaatctgg cgccttagac cactcggcca aactgtcgga attgtgagtt    1680
gaataactaa gatgatcgga aatgtgacga aataaattgg gctaaagaaa agaaaagccc    1740
aaacaatgaa gaacaattcg gcccacttaa tttcacgcgc atggcacgtg taaagaaatc    1800
ccaatctgtt ctactaggtg gtggtggtgg cgaggcgaag caaagcaaag caagatcagc    1860
cttatcaaat tgtgtggtga agaatgaaga ttgtataatg tagatagaaa aagatccccc    1920
cattcccatt cccattccct tttctgaatc cgccattgtt atctctctca gacctccata    1980
acctccattt ctacccagcc                                               2000
```

<210> SEQ ID NO 92
<211> LENGTH: 2000
<212> TYPE: DNA
<213> ORGANISM: Cucumis melo

<400> SEQUENCE: 92

```
cttctaaaca tcctcaatgt tcgattttga tcaaggtcgt ttgcttctaa acatcctcaa      60
tgttcgattt tgatcaagag gtcgtttctc tatagtaaac atctgttaca ccttccattt    120
ctgttattca atttttccaa ttttattgag cagtttattt atttccgtaa ctactttgca    180
tcggaggcga tcatcagttt ttaaggtaca aaactgagat atatataatt atgaagcaca    240
gcaaagtata aaattttgaa gatgaaattg attggaacctt gtgaacagaa ctctaaagag    300
aaaatgcatc agatagtctg gatcgttaga atttgaaatt taaatttcta tcttccacta    360
aagatatctc tgttttgcaa actaatgttc ctcattctaa acagagaatg ccagtggtat    420
tttgttcgtt ttttgcgaat atgattaaat tacccatttt atttgcatat tttatttatt    480
ctcatatcag ctccaaaaga atatgatccc tttttcctcg ataagaaaaa atatttaata    540
ctttcaactt catgcattgt gagactgccc atttgttttg tttaaagtag caccaacttc    600
tcaattgtat aagtttgtga tttttttttct atctaaattg acttgaatta tttttagata    660
taattaaatt aattgctttt aagagcaagt taaattaagg tttcgtaagg atatggatta    720
aatttaatta agaattggct tcttgctcta aatacaaatt agagtgagat tgaaatagg     780
aggaaaaaga gagtatggtt acaaaggata tgaaagatca aatttcaaac ctttgccaac    840
tgaggctttt cagaactctt aaaccatcac agttttttct ttgcccaaat gaaatcaaac    900
attaagaaac agtgataacg aaaacgaatt atccctatgc caaccgtgac agatgatagg    960
caagaaaccc acgattagtc tctcatccgg attgttccaa caaatgaaaa agcgttttct   1020
gagactacac aaacaacaaa cacagagtta gatagttcaa gcaaatgatt ctagcagatt   1080
```

```
agaggataag gtttcttatt aaatgtttga atacattcta accaaaaacc aaaaacccta    1140
tttgcaaatc agcttatgta aaccaaaaac atatttacta agaattcaga atttcgctgc    1200
ttgaaatttg aaggatacca tataaaacaa taatagattc ccccaatcgt gttcagtagc    1260
tcaatatagg caccgtgcaa aaggttgttt gttgtaagat taatgaacaa acacccgtgt    1320
ctgattttaa tgccaattca aactctaatt caaaaaccct acaaagacct aattgcagat    1380
aatgggatta gaaattttaa aaaatgtcga ccgggcattg tatcttaaaa ctattaagtt    1440
tcaaggatct tcctccggta acaaaatatc ggctccatgc ggcagacgga tcgccattaa    1500
aacggcgcct gctgctgact cgatgataga gccaattcag aataaccaac ccatttcatc    1560
gaaattttta aagagagaga aaataaacga ttcaagatat caaacgcatt tcgcttctat    1620
tgaaggagaa gacaatgaaa atcaaaacaa atcggaaatt aaagttaaag aagaaggaga    1680
taatctcagg acggacggaa gataattcta aaggtgcgat tcggttgaaa tttatagagg    1740
atttgtgaag gaaccctaaa ttctgattgt gaatttatc ggaaagaccg gagaggaagc    1800
ccattgtgtg aggcccaaag taactgatct gggcctttt tagtttcagc ccaaacggaa    1860
gcgacacgtc gtttctatgt agagccaaga gcgtgccacg tcaacagacg acgtcggtta    1920
gtaggaataa taccgatttg tggatttaag aattgttcat ttcggtttgt atcggaagtt    1980
ctgaatcttg atccgtggca                                               2000
```

<210> SEQ ID NO 93
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c
<220> FEATURE:
<221> NAME/KEY: unsure
<222> LOCATION: (1)..(2000)
<223> OTHER INFORMATION: unsure at all n locations

<400> SEQUENCE: 93

```
aagtagaaat tcagcgaaaa atgcagatgg tttcatagac aataaaaagc aggaacaagc      60
gcagagaatg gttaatcctc cagaaaatgt gataaaaggc gccaccaaga ccagtaatcc     120
ctttaccaat cacagaatac tcaacaagaa aagcgattcc agcaaaaacg aagatgaaac     180
tctcacttac aagaagaggg tcgacatttt cccgcaaaac gatgagaatg gcgagtgccc     240
agaagaagaa aatggccagt gattgctggg agaatgcgaa tctgtaagtg gggtttccgg     300
aaaaagcgag aaaaaggaaa atttcagaga aggcgacgat ggggaggagg aggatgaggg     360
aatataaatc gaaattttc catttcggtt ctgataaata ccaggttttt gatcggtaaa     420
gagatgggtt gttgaggtaa atggaggaag aacagaggag gcgacgaagg ccaatgggga     480
tgaggaaaag ggaggcggag agatgcgttg ctagtgatgc cattgaaagg cttttgaat     540 ttgttgaagc attcagattc ttctctgtct atggttccgt agattgttct ccaattcttc     600
cattgggaag acggagttcg gtggctgaac gttgaccta acaagtttga tcacgttgat     660
ccgttcaatg ttaaacagct cgatgatttt cgtctaaaaa agaagtgatt ttttttttaa     720
cctttttatt attgaacaaa aaaagatct gtttatacca tagtttacgt tcttccacat     780
gagaagtttt ataatagttt atagaatcta tccaaattgt gttttattgg gtttcgattt     840
tatagaaatg tcatatcaaa aaaaaattta aaatgataaa aaatcattat aattattta     900 tgaaatttt actgtgactt aattagatta taaaccgacc attctttaat cattatttg     960
```

```
gatgtctatc gtatgtgtat ttatagatgt caaacatgag agcatagatt taaaaaacaa      1020
atagcttaaa caaacaacaa taacttttta tctttcagaa aagnnnnnnn nnnnnnnnnn      1080
nnnnnnnnnn nnnaagaaa  agaaagaaa  agaagtcttg aaaaaagtat taaatttcac      1140
aataaatttt ttaaaataaa atacattaaa tggggatgag gaagaaacaa ctaagagtcc      1200
aagaagagaa ataaaaaatg agaggtggtg ttttttttgg tatgttaatc aaattatggt      1260
ctccacatac aagaaatgaa gccacgttaa tgacccaaca acactaacac atcaattctt      1320
aaaattcaat tccttctttt cttcccttcc aaaattatgg gtcctccaac ttacaaatta      1380
acaattgact ttagctaact atgtttttta aatataaaaa acgaatacaa gtcagtttaa      1440
taggacttga agattgtata aaccaatatt agacaatcaa aacaatcaat tttaggttca      1500
ttcccaacga tacatcaatt tggattagat taattttttca ttatggtttg atagagtgga      1560
tttagtttta gtggaatgca gggagggaaa agtaatttga aagaaaagga atgaggttgg      1620
tcaattccga agcctaggta tccaaataca agaatccata tcaaatttat gaacacctag      1680
aaaataatag taattttaat aataaaatgg agaaatgggg tccggtcgtc ctcttcctcg      1740
cggcggagat gaagccaccg cgataagaga aagagaccct tttcaataca attcaacaat      1800
cacatgaatt attccaattc acatctctgc ttttgaaact aaactaaacg ccaaaaaccc      1860
ttctgtggct cataagtttc ctctctcaaa tctccgattt ccctcaccca catcccacat      1920
ttcgcatcca aataaaaaag ggacacggac aacaagaagg agttttttaat tcagtagtgc      1980 ctctggaaga agctgtttca                                                 2000

<210> SEQ ID NO 94
<211> LENGTH: 2000
<212> TYPE: DNA
<213> ORGANISM: Cucumis melo

<400> SEQUENCE: 94
ttagtgaaag ttcaagatgt aattcactct ctttaacaag gttgtttctt tgcttcacta       60
cgcatcaatt caaatattta gatattgatg tttaagctta atctcctatc ttagctcaga      120
acaaaattgt caaatctcca ttcttatttg tctacctggt aactttgctg ctatagttat      180
ttgtgggaga ttgtagcaaa tgactgtaga tcgaaaccat ttcagcatca atttcgaccc      240
actcttctcg tcaacaactt gatcggcagc ttcgacattc ttcaagcgcc agcttctatt      300
ggatctttag ctcaaccaca tcttcgtctt tgaattgcat gtgagctgtt gggctccttt      360
cttttgtgct tatcagttgg gagattatta ctataaatac aaagcctcac gggtatttta      420
agacacaaca aaaaattaaa agtctctcct ctgaatcacc acttccatt  tctataaatt      480 ttgttctgag caacttttgt ttgtttctat ttcttattct gaagagtgca tgtttgagta      540
tggggagtaa tgttaacctt gaggaacaat tggcaacacg attggcacct cggtcaatca      600
tagttgcttt taggacagtg gttcgtcaca acacaacaat ttattttaag ttcaacattc      660
tcattctttt cttctacagt attcaaagtt atagtgttta tttctcttat tgttccttta      720
gttaacaatc tacccttaa  ctaaagtaac aacttaaaag taaatggat  tattctactt      780 tttcttaatt gttactttta aaggtttaag aactgaattg ttactccgat gaaagtctaa      840
agaccaatag tggtttctat ccttaaaaaa ctattcaatg aaatttatgc taaaaaaata      900
atcactaatt catcgtgagc ttccaaacca cttgaaatta gctcaatgag attgtaactt      960
ggtcgggatc tcatcaaagg gatggtcttg gctagattct taaagatcat tttagaaagt     1020
```

|  |  |  |  |  |  |
|---|---|---|---|---|---|
| agatcatgaa | aggttgcaaa | gatgctagaa | acaactgggt | tgtcgacgtt | ttggaagcta | 1080 |
| aagcggtgat | gattgacgta | atagatatca | ctaaacattg | gcacaatcat | acttggaaat | 1140 |
| agcttctata | gatatattcc | attttgtaag | gtcttaaaga | caagaacaaa | gctacctata | 1200 |
| agcttgtatc | ttagtttcct | cttgcgatct | tcttgtcgag | agatgacttt | ccggttttgg | 1260 |
| gttgtgtctt | tgtttgtttt | tctttataaa | aaagtcaaaa | caaaataaat | ttggattaat | 1320 |
| tatcctcgta | ctgaaatcaa | ttggtttgga | actaagtaac | aataggatac | atgcggcgca | 1380 |
| ccggatcatg | ccattctccc | tctttaaata | tcaaagcaga | tccctaaacc | ctaacaaaga | 1440 |
| tccaaatatc | aaacctcccc | tcttactaca | cgctccggca | cctccaaaac | tccatctcga | 1500 |
| ggtttgtcac | ttttatgttc | ttgttttct | ttatttagaa | tatgatgatg | attagaccga | 1560 |
| tggctatttt | cttaaatgc | ctttactcct | ctgactagaa | tggtctgtac | tctgaatcag | 1620 |
| agggttcatt | tcgaatcttc | gaacgttgta | tttcgcttca | aaagctagac | ttttcccaat | 1680 |
| ttacttgaac | ttattgtaat | tttagtgcta | gcccattgat | cttggtctcc | aatgccactc | 1740 |
| tctgttccga | ataactgccg | attattgagg | ggtttttttt | ggacttcatg | atttcgagtt | 1800 |
| gttgtaaaat | gattggggat | tcatttaaat | atgaaatata | tccatcgttt | atctcaaaag | 1860 |
| tatatatctt | aagataaacc | atgaacaaga | agtttccgat | ctaattccca | tgggttgtct | 1920 |
| aacgagttat | tctcaacaga | ttacgaactg | ataactagac | gtttgaattt | tggcacagag | 1980 |
| agaaatcgca | tcactttgaa |  |  |  |  | 2000 |

<210> SEQ ID NO 95
<211> LENGTH: 2000
<212> TYPE: DNA
<213> ORGANISM: Cucumis melo

<400> SEQUENCE: 95

|  |  |  |  |  |  |  |
|---|---|---|---|---|---|---|
| taaatgggaa | attggaaact | aacttgaaac | gaccacaaac | catggggact | taaaaaagtg | 60 |
| ataatctaac | aaaggcttta | cactcctttt | tcataataaa | gaacaaaaag | aaagctcaag | 120 |
| agcaatcaag | tttatcataa | ctaattaaag | tcaaacacta | catttctcaa | agaatgata | 180 |
| taaaatgacc | aaacatctag | ctgctttaca | gtgtaatgaa | cacccaccat | taaaggaacc | 240 |
| aaggcaactg | aataaattgg | taacttaatt | gccctccaaa | tcagagtccc | cataccaaca | 300 |
| tcctcttccc | cattctcttg | gggcatcgaa | tcaacctcca | tcgctttaca | ttccgataac | 360 |
| aaacctctaa | aacggacatt | tctgcacaac | cccaattgcg | ttctacgact | cccgcaggca | 420 |
| aatttatgag | catcagtcga | caaactcgat | gaatttaaac | gacccagatg | aaagctgtga | 480 |
| tagtagaaga | gtcaagaaga | taaatggggc | taaacgataa | ggttttgaaa | gaagatgtag | 540 |
| ttgccattgt | gaagtggtac | ttgccttgga | gtaatggtgg | tgaaggagag | gtggtcgttg | 600 |
| agtttgttct | ttagggcgcc | gagttgggtg | gtatgcaga | ctatggaggc | cattggcatc | 660 |
| acatagctga | agatgaaact | gcagagtgaa | gctgcttgtt | gaagcagagg | atggattaat | 720 |
| taaagtggga | cgatttagt | tgtgtcttat | cttcttcaac | tttatgtttc | ctcttggttt | 780 |
| gacacggttt | taccattatc | gctaccattt | taagtaacaa | tagtagtgat | gaatgggtaa | 840 |
| aatataaatc | ttattccatt | gttagaacct | tcgacaagtt | ttccattatg | tgtggctgtg | 900 |
| tttgacccac | caactcgagt | agagttgaat | ttgtttggtc | tactatattt | acaaactaat | 960 |
| attaaataac | aaaactctat | taatttcatc | ggtgttcact | gttgaaatat | atacatttag | 1020 |
| tatgaatctt | tatctatttc | tctcttaccc | ttcctctaac | atttctagtg | cctccatcat | 1080 |
| caattgtcat | caacgacgaa | atgtgacgat | aactatagtc | aacgagtatt | tccaccttac | 1140 |

```
tttgacaata ttcattgcca caatatgctc ttgacgacct ctagcactcc acgtatgata    1200
aagactacat ttgatgacca attaaggaaa tcgtatttga caccacattc caatggctat    1260
ctctagtgat caatttcgac tatcacttgt ggttatcgac tttcaaccat ttctaacgac    1320
taacttgacg accatcttaa tcaatcatat actagaaaaa caaaaaaaaa aataactcat    1380
caaatggaaa cattttttaaa tgcaattttg aaactaccac ttctctgtat ttaatagtaa    1440
tttgacatta acaaaaacac ttttaagtac ataaaaaacc aaacaaactt gtatataaaa    1500
cacttttgaa aaaacggat gtaaccaaac acacaagtat ttttctttta gattatgttt    1560
taaaagatag aaataaaaat attaaaagaa aagcaccttt ttacaaacat gtaaatccaa    1620
atcaaacatg ctattttttta atactaaaag aaatagaaaa aacatgttaa acatatccat    1680
tagcaaaata aagtgaaatt ccaagaatta gaaagatggt ttgaaaattg attttataaa    1740
gcgaagaaaa acctttttcc ccaaaagaat aatattctta ttttggaaaa aacagaaaac    1800
aaaaaatgtg acaaaaagtt acattcctgc ggatttgacc ctctggtggc tgcattcgaa    1860
tctttgattt cgaataactg aagtaaacat taaccaaagt ccgtcgaaat cttcctttttt   1920 ttcatttggg attccctcaa tcttcatcac caccatcacc atcctccact ttcactctgt    1980
ttccctccaa acatcaaaaa                                                2000

<210> SEQ ID NO 96
<211> LENGTH: 1373
<212> TYPE: DNA
<213> ORGANISM: Cucumis melo

<400> SEQUENCE: 96
tttaaatgtt actttgatat gatctatgtt tagatttgaa gtatttttct catcattaaa      60
aagaactaca cgatcgtatt catttagaag aagaattgta cgtacgcgtg tagccgatta    120
atcacgtgtt gagtgaaaca tttttttatat ttttgctaat agacctatat attgttttca    180
tttttaaaat tgatatgtaa atattttggt ttgttatata tatatatttt ttttggaaaa    240
aaaactcctt tatttatttg tcgttaagta ttaatttctt tttttagtac ttttattacc    300
attgtggcct tgttttgctc ctcaatttag atatttatta tttgtggttt atttatttct    360
tttgttttcg ggacaagtga tgtttgggat attaaagtaa aggaaaaaaa agagagatat    420
tttgattgtc aaaatgtcag aaatatctaa acccggagct tctgccacgt aggcatcact    480
ttcattacct tttataaaaa gtacgaattg aaccttcatg acactgctcc cctgctccct    540
tatataaaac ccaatcctct tccatgctca gtattatctt cactctttgc tcgaaccgcg    600
tgtttaacag ataagattca actcacaagc attcatcgct aggttcttcc aaacaaaaac    660
cctacatctt ttccatttcg cctccttaat tctctcatat ttctgtatct taatccattc    720
taaaactaca ttttaatgca ctgccttgtg ttctgtattc cactatctgt tatcgtttta    780
ttgcgttttc tttgatcaga tcgctttgtt gttgcatgaa ctgctgagtt cgtttgatga    840
ttttgtttgc gcttcagttt tcatcgtttg ccgtccagat tgtttgattg gcgagagtga    900
agtgaaaatt ctgtatgata ttggagcgtt tcgtgtaaaa tctgtcttgt ttttctatta    960
tctgtatttt agtgatttgt tttcgttga cgattttgta tgacgtaaag atattgtcca    1020
ttttaaagga tttttcttcca ctggttacta gagatcttag attgagcttt cattcggctg   1080
tattttgatg atgcttttg tgttttttttt tcctttctttt ctttagcttt tgcggactca   1140
tggagtcttt ttctgaacga catcttaaga tgtttaagat gcttatttgc ttttttctat   1200
```

| | |
|---|---:|
| ttttggtatg acggggtcga gtctgatttt gaacgacatg ttaatattta tgatatttt | 1260 |
| gaagctagtt gtgcttgatt ctgaaaattg cttttgatac acgagaaact tttttgtttt | 1320 |
| cttcaatggt aggattttga ccattattat tattattttt taaaagatca aat | 1373 |

<210> SEQ ID NO 97
<211> LENGTH: 2000
<212> TYPE: DNA
<213> ORGANISM: Cucumis melo

<400> SEQUENCE: 97

| | |
|---|---:|
| ccgaattcgc tattgggctg cataaccttta tcacttgctg ggagactgca atttgtttgt | 60 |
| ttagtgctat gtagttttca gtttactag gctagtatgt ttgtattgcc tgagagtgtg | 120 |
| catcatgagg tggataaaat tcttaggtct tattttgga ggggtaagga ggatggtaga | 180 |
| gggggtgtta aggtggcatg agcggaggtg tgtcttcctt ttgaggaggg caggcttgcc | 240 |
| atccatgatg ggccttcttg gaaatattgc tatgtctatg aagattcttt ggtcgctatt | 300 |
| ggcgaattct ggttctcttt ggtggcttag gtggaggctt acattcttaa ggggaggtcg | 360 |
| ttatggacga ttgatagtga ggttggttga tattgtgtct tcgggctatc ttgtgtaagt | 420 |
| gggatagttt gaaagcactt gttcctatgg aggtggggga tgggagaagg tgtagagttt | 480 |
| ggcttgatac gtagttgcat ggcggtccta tccttgatta ggttggggag agggtgcttt | 540 |
| atgacgcgac gagtcggagt gaggcttgac tttctaattt tcttggtcat gatgaggagt | 600 |
| ggaggtggcc acgagtttct ttggagttgg ttaacttatg ggatacggtt cagactgttt | 660 |
| gttcgtgtct tagtgttagt gataggtgag tatgaattcc tgacagtcat ggtggttttt | 720 |
| cgaccgcgaa tgtgtgggat actctctgtc ctcgaagtag tcaggttcct tggactggtt | 780 |
| tattgtgggg tagggggaa ttgttttcca aaacatttct ttttgagttt gacttgccat | 840 |
| caaagatagg ttgttctttt tgtagttctt tcttttggtg ctttttgttt ctatggatcc | 900 |
| tgtgagggt ttctgctctc gtgccttaaa ctcaggctgt gaggtcctcc ttgttatggt | 960 |
| ataataatat tacctttca aacaaaaaaa aaacaaattg attcagaatg atttttttt | 1020 |
| cttttcttttg tatttattct atgtttcctt attcaggcta ctagatttga atatgttatt | 1080 |
| tgttacttcc ttttctaaca aaattagtta taattaattt tatttggttt ctttaaaaag | 1140 |
| tgtgggttaa agcttcttg cagaatatag gatcacaaat gcctaataca cttcttctta | 1200 |
| cttctttgtt ttgcagcagg gtatgaaaaa acaaattaat atgtattttt tatacttctt | 1260 |
| tctcgtatgc attattcttc ttttgtttct gttggctttg cattgtagcc gttttcttgt | 1320 |
| tcttgtctca ttttttctct acctttttgtt tcttctctaa attccttttta tgttcatttt | 1380 |
| tcataatgcg gatttttca aaaagaaaa ttatagttgt tagttgtgtt tgatgagaaa | 1440 |
| caagaaaaga gagtgaaaag agaaaagagg tagaagagaa aagaaaagaa gaatctgagt | 1500 |
| agaggaaaaa aattgaacaa aaaagttgga attgtgttgg atgaagtgag agcaagaact | 1560 |
| aaattttgtt tgagcgtcaa gcccccaccc cacacgtttc taagaacaag atggtaattt | 1620 |
| taaatacaac taatataagc aaaatacaat ttctcgagga aataggaaac ttcattccag | 1680 |
| gcttcaaagg aaaaaagaaa aaaaaagaaa agaaagtaa aacgattaga acgtgaattg | 1740 |
| cacgtcacta gacaaaacca tcttttggta gagaaaaaca cgtgattaca aaaaacaaac | 1800 |
| gaaacccaaa taaatatata tagaaaaaaa ataaataaaa gaaatagaaa aatctaaaaa | 1860 |
| aattgggtta gcgggcaaac aagaaaccct tgtttcgatc ccccaaaacc ccccacccct | 1920 |
| ttctcccatc ttctttcttc ttcttccctt ccccattttt gaagaaccaa ccagcacctc | 1980 | tgaccaacat ttgcttaccc                                                    2000

<210> SEQ ID NO 98
<211> LENGTH: 2000
<212> TYPE: DNA
<213> ORGANISM: Cucumis melo

<400> SEQUENCE: 98

| | | | | | |
|---|---|---|---|---|---|
| tagtttggtt | cataggttat | agtttccaaa | tttgttaggc | tatcattaat | caaacacaat | 60 |
| acttctcttg | taggatggct | gccccctata | gtactttttt | aacttaggag | aaggatataa | 120 |
| taattatatt | cctttagaa | aatataataa | taattgtgta | gtgctttgat | ataccttaaa | 180 |
| ttagctactc | acgtttttag | gaggaagctt | ccgttgcttt | tcatggtgtt | atgatctttt | 240 |
| ttattttata | aaggactgaa | ctttaaaatt | tctctttcat | ctattttgga | ttggattcca | 300 |
| tctattttat | acgggaagtg | aactctaaga | tttctcttca | cctattgtga | atcggactcc | 360 |
| gtcatgtagg | tcaagactac | gacagataag | aatagacttc | cacgaaagaa | agtggtcaat | 420 |
| cgagatggct | atatttggct | ctttcagctc | aatttcttct | ttttccttg | catgttcttc | 480 |
| cgttggtaca | tttcttgcac | tttttttgtt | ctcacatgac | taatgtattc | caagtttatc | 540 |
| attggcattg | tgcctctttt | aggcttgtaa | actctcgatc | caaaattatc | taggacatat | 600 |
| gtttcctagt | gaagaaatac | tagtatattc | cttatgtcaa | tatgtcaaaa | ttttcaattt | 660 |
| cttaaccttt | gagtaaatca | atattatatt | tttatggagg | ttatttataa | ttggaaaaaa | 720 |
| gttacaccca | tctcaaccct | aattaacacc | aaatgaaatt | gtaccatgcg | gcacaatatt | 780 |
| tttttgtgag | ttttttgcaa | agagaaacaa | agtagcagac | aaagaacaaa | cattccccca | 840 |
| aaaacagcag | agaataccta | agagagaatg | ctctctcgta | aaaaataata | cccaagaatc | 900 |
| ttcccaaaaa | gagggagtaa | aagagtccaa | aacaaacgaa | ccgaagattg | acaagaaggg | 960 |
| cactctcgcc | ctccactgcg | ccgctaaatt | gtaagaagca | tattttcttg | agttaacata | 1020 |
| ggaataggtg | taactcaaga | gaaatgtaat | tcgtagaatt | gaactttgta | tattaattta | 1080 |
| tatggtgttg | tagatacaat | ctttagtatt | tactcatttg | gtgctttctc | tcaaatacaa | 1140 |
| tttaaactta | gaacttttg | atcttcgatt | ttcaggaagt | tggagttgca | aatcaattcg | 1200 |
| agtttcaatc | tctggaattt | aataaaagtt | tgatcttcca | agttttcaat | ctttcagaag | 1260 |
| acgatgatct | tgatatggat | aaaaaattgc | acatcatgag | agcttttga | agtttaaatc | 1320 |
| ttcaattctc | tagagcttaa | attcttcctt | aaaccaaaga | tcaccaaatg | aatgacaaat | 1380 |
| gtctctattt | atcgaaaaat | ttcatagact | tttagatggg | cttaggcaca | ttacttgttg | 1440 |
| ggcttggact | tgggcttatt | tgcttggcgg | gctcatgctc | gagcccatta | tttctttggc | 1500 |
| ctattttca | tgaggggctt | gaacttggtt | gtatacgaaa | aaacttgact | acctaaatct | 1560 |
| aatcaaatta | taatcatcac | aattttgacg | tgttacgatt | taattggcca | aaaattcttg | 1620 |
| ttcaacactt | gtctctaatc | attttcctat | ataatttaac | taaaatattt | aactttaagt | 1680 |
| aacttaaaag | atatagttta | attcgaatca | aaatacaaat | acaatttcgt | ctatctattc | 1740 |
| ccatcataaa | tgttgattga | gattcatatt | ataaacttct | ttcaggaaaa | gaaagaggaa | 1800 |
| aattcaccta | aaccacgttt | tcctattttg | gtaagaatcc | ccaaaccata | aatcattcca | 1860 |
| aaattatttt | ttttagaaaa | aagaaattca | catggcgtaa | aatttcagcc | ccgtgagata | 1920 |
| ttttcgaacc | cccagataca | atctacaccg | tgaaaacaaa | atcggacggt | ggagattgct | 1980 |
| ataatgtccg | tttagaggca | | | | | 2000 |

<210> SEQ ID NO 99
<211> LENGTH: 2000
<212> TYPE: DNA
<213> ORGANISM: Cucumis melo

<400> SEQUENCE: 99

| | | | | | | |
|---|---|---|---|---|---|---|
| acactttgaa | agtccatttg | agagattagg | gtaaatttga | gtgaggatgg | cgtgatgaca | 60 |
| acgataaaag | tgaaaaatgt | cagatccaag | agagactcaa | aagtgaatga | cgtgaagaca | 120 |
| atcggaatcg | aaattgaaaa | atcagatttt | aaattatctt | aaaccacata | ttaattaaat | 180 |
| ttcgattcca | gtttcaattt | ggtttgctgt | gataaaacta | aattcttaat | tgtacctaat | 240 |
| tttctattaa | ataaataggt | aaaaaaagta | tagtaaaaat | attggcgtcg | cccggactcg | 300 |
| aaccggagac | cttcagtgtg | ttagactgac | gtgataacca | actacaccac | gacaccgttt | 360 |
| tgttacatga | gtaaaatgtt | tcctatttgt | ctaatattat | tattactact | actacttctt | 420 |
| cttcttcttc | gagaaaaacc | aatttctatg | ggtttaaatt | tccaaattga | tgttgagtgt | 480 |
| atcaataata | tagcactcac | atgctactta | acaaaaatca | attctttctt | tttagttaaa | 540 |
| acctttcttt | ttatatttag | tgaaaggatt | aagctatgtt | ctacgttaaa | ttgttataaa | 600 |
| caaaatttga | ttgttactta | tcgagattaa | tttatttaag | tggatatgtt | ggaatatgtt | 660 |
| actaaaatga | taattgatag | tgatacgtcg | agtttatgct | aaacacattt | tgatatggtt | 720 |
| ttcttttttca | atataataat | ttgacattaa | ttacatttttt | ttttcatata | ctctcaagaa | 780 |
| tgtttatttt | tattatgtac | ttttaaaaat | taagattttt | tatggttttta | tccataaatt | 840 |
| tgtttcattt | tttaatcgaa | attttagtat | tagactttag | ttgttaaaga | tcctaaaata | 900 |
| tagtcattat | attttattaa | agagtctccg | tcacgtgtat | aaattaaaat | agtcttaacc | 960 |
| gttaaaagta | tagtgaacaa | aatttctaac | aagaattgga | tcggagtaga | agggtgattg | 1020 |
| attcaacatg | atccttgtgc | cattattgtt | gttactcaag | ggacgttcat | caatagataa | 1080 |
| cttgaaatca | aaatggcata | aactattgct | cagttgaaag | gttgtttgtt | gattgaagag | 1140 |
| ttaggtttgg | atatttgggt | ggaagccaat | ggccttgtcg | tggttaataa | ggtgctttca | 1200 |
| tttaattttg | cactctctcc | tcatggggtt | tattacacta | aagtggttca | tttaattgag | 1260 |
| agcatattgg | acgaaaataa | acaattaaga | ctaaggacga | aagtaatatt | taaacattat | 1320 |
| tttaagaaaa | agtcattttta | attcctaagt | tcttttttag | tataatttttc | atttgtttgc | 1380 |
| tatatttttaa | aaggttacgc | ttttatcaat | aattctttag | tttagttttc | atttgaccta | 1440 |
| taaattttaa | aatatcacct | ttttcctttt | atattttggg | tttaattttc | cttccttgca | 1500 |
| ttttcatatt | ttacactaat | acctttaaac | aactaaggct | tactcctagt | ctttgaaggt | 1560 |
| taaacgttga | gtttcaacta | attgatttaa | tcatctaaaa | ttttgagatt | ttttttaaaag | 1620 |
| caatgattag | gtgcagtctt | ctgcttccca | tttatttatc | acgtaaaaaa | attataaaaa | 1680 |
| aatcattttt | taaaattgtt | acctgacaat | tttttgagtg | caactcgaac | tgcctatcgt | 1740 |
| tgtaacccga | ctgtacctaa | atattttcaa | tattttaaaa | cctttgatta | aatgataaac | 1800 |
| aaattaaaac | taaggggaa | attacatttt | ccttaattta | aaaacaattt | tgttgataag | 1860 |
| atggggcctg | gcccatgagg | ttttgggctg | ggccttttcg | aatcgtctat | ttataatgag | 1920 |
| caaacgagtc | tgagcttcga | agaaatcccc | ttttttttcac | ttgcgaaaga | gacgaacaaa | 1980 |
| cgcaaaacag | tcgaaggaag | | | | | 2000 |

<210> SEQ ID NO 100
<211> LENGTH: 2000

```
<212> TYPE: DNA
<213> ORGANISM: Cucumis melo

<400> SEQUENCE: 100
tgttggcaat gatttctttc agaaactttt gccaccttaa tgcttgcgta gtttcaaact      60
aaatgctgat tgctgtcagt aactgattaa attttgattt aagtatagta gctgccttat     120
tgtgttaaca gtttctcca tcattttttg cattgacttg atgatttgac ttcttttggg      180
tcatatcttt gattctttcc atgtttgaaa gttctaattt agatgttggt ttgtatagcc     240
attgagaagt ttaattggca aaacatttta tagcgacctt gacatagaag aagatgatat     300
cttcgttct gatggtgcaa atgtgacat aacacgactt caggtatgat ttgttttagt       360
ttggaacatc tttcatccat gtaatatttt tattttcctc attttttttg aactttaatg     420
ttggttacta accttagtta aatatgtaag atagcctggt aatcgtatct ttcatcttgt     480
tactatttaa cttctcttcc caattttggc agcttgtttt tggatccaac gtgtcgatgg     540
cagtgcagga cccatcatac ccggtgattt tctcttctca ttaatgaaaa ctttcgatga     600
ttaattggta cactaataat attttgcctg tccacctata tatcagacat ttacttaaat     660
gatcatttga aaaatatcaa gctcttgggc aatcattttg tgtgtctcat ctttactgtt     720
gtgcttgaat gagtgaccac gatggataga ctttttgaga aagatcccttt tgttaatggg    780
tcttttttgt tgtattcttt gtcggaaagc ggaggaaacc cagatcatct tatttaggag     840
tcttagtttg tgaggtctat gtggaatttt ctttcaaaag ttttgatgtt gtacttgctt     900
gctagaggga tgttcatttg atgattagag agtttctcct ctagttgcct ttcaaagaga     960
aatgacaact attgtgggtt ggcctagtac taaaatagga gacatagtct caataactaa    1020
ctaagaagtc atgggttcta tccatggtgg ccacctacct aggaattaat tttctatgag    1080
tttctttgac atccaaatgt agtagggtta gacgggttgt cccgtgagat tagtttaggt    1140
gagtgtaagt tggtttggac actcatggat ataataaaag agaaatgttg ttttctattt    1200
tgtggtttgt gggtgtgtca tgtgtgcttt gttgtggaat ctttaaggaa agaggaacca    1260
caaaccctat tgaggtttgg ttcttggtga agagtgtgag gtttcatgtt ctgggcttcg    1320
gtttcaaaga ctatttgtaa ttattcactc tcacttagtt gcaaacactt tctttgagg     1380
gtttccgtgg gcttggtttt ctgtatgctg ttgtgttttt ttcactttt ccctcaatgg     1440
atgcaattct ttattcaaaa gaaatctttt actcttgaat ttgcatatgc accctttgat    1500
aacttttggt aggttagtca cttcagatca aaccacaaat aataatatat tttgttttcg    1560
caaaacttag aaaatatatt tttgatatca gtctgttggt ccattctccc acttattggt    1620
ttatgttttt ttggtagtta tgaagtaaca tccaaaggcc tgtattgttt aggctgtaga    1680
actttataca aacctctgct aagtcaattc ctaatcaaga atttgtggaa ctgtaggctt    1740
atgtggactc gagtgtcatc ttggggcaga ctggacagta ccagaaggat gttgagaaat    1800
atggcaatat tgaatacatg aggtgtacac cagaaaatgg attttttccc gatctatcta    1860
aggttcctcg aacagatatc atatttttct gttcaccaaa caatcctact ggctcatctg    1920
caactaggga acagttgacc caacttgtgc agtttgacta aaagaatgga tcaattatag    1980
tctatgattc agcatatgca                                                2000

<210> SEQ ID NO 101
<211> LENGTH: 1078
<212> TYPE: DNA
<213> ORGANISM: Cucumis melo
<220> FEATURE:
```

<221> NAME/KEY: unsure
<222> LOCATION: (1)..(1078)
<223> OTHER INFORMATION: unsure at all n locations

<400> SEQUENCE: 101

| | | | | | |
|---|---|---|---|---|---|
| ataatattaa | tttcatttaa | aaataacttg | aattttttcc | tcctatattt | atcatgcatt | 60 |
| tttacaaatc | cacgttcgaa | atcccatta | atcataggag | ttaaattgtc | atcacttgat | 120 |
| ttgaatattt | atttttttt | aaaattaata | aataaataat | gtcacgaaaa | tgataaaaat | 180 |
| gcaaagtatc | gaatttaaaa | attaaacaga | acaaaattta | aaaattaaat | gataaaaata | 240 |
| aatataaaat | ataggtggat | gttaaagata | ataatttaaa | tctttatcta | tcatcaaatg | 300 |
| acgatcctcc | aatggaaaaa | gaaaaaaaaa | actttattct | ttacctcaaa | ctcctcgcta | 360 |
| aaaagtaaca | atggtaagat | aaaactttat | tttaaattat | tcttccactt | gcaagcaaag | 420 |
| taaatagtta | tttgattctt | acacaaaaga | gaattttttac | ttttttacttt | tcattagtta | 480 |
| tatataactt | tataatacat | ttccctctca | tggaatttaa | aactaccatt | tgagcaaaat | 540 |
| attttaaact | aaagaaaaat | atgaaactta | aaactatgtg | acagggatga | taatgacgtt | 600 |
| tactccaaat | tttcatttta | aattaacgta | cgttatttta | taagtatatg | tcaaaatttt | 660 |
| aaggatctat | tttattagac | aattcaaatt | atatgttgtg | ctttcatatt | ttgttaaatt | 720 |
| caataaaatat | gcctttggtt | gattatacta | ttttttctaat | taactctgga | gacatttcaa | 780 |
| aagattttt | atttatttat | ttaagaaaat | atattaatat | ggtcaataga | tatgtattat | 840 |
| gcacatgata | taaaaannnn | nnnnnnngta | ataatattat | tacataatta | aattctttca | 900 |
| tcttcctaac | agagagagag | gatcgtcctc | tcagcgacgc | tgatcccaac | tgttccagta | 960 |
| ccaaatctct | gtgtcccaat | ccaacagatc | cttcttttaa | gctaaaccca | ccatttttt | 1020 |
| tttttttctga | aacccatttc | ttatctctcg | ccggaccttc | agattttacc | tcaaaacc | 1078 |

<210> SEQ ID NO 102
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 102

| | | | | | |
|---|---|---|---|---|---|
| cactatctat | catagataaa | taagtgatag | atctaaacga | tcatttacca | aagtctcaaa | 60 |
| gatcatgtac | caatatctaa | acgagtttgg | tacaagattg | tataccaaaa | tcatttgatt | 120 |
| tgatacaaga | tcgtgtacca | aaattgttta | gatttgatac | aatatcatgt | acaagatagt | 180 |
| gtatcaatat | ttaaacaatt | aatcgtctat | cctagataaa | caaagataaa | ccactaggaa | 240 |
| atcgcacgaa | gagaaataga | ggaagtgaag | aaaaaaatta | ctcatataaa | ttgatgaaaa | 300 |
| atgttatcct | tctctaatat | ggttttaatt | tttgcactag | gaaatcacac | attaatgatt | 360 |
| ataatacaaa | gtcctacaaa | gagatctgaa | ttgattcatt | tgtgaaactt | acaatttta | 420 |
| atcgatacaa | ttattaactt | aagagtgtaa | ttgatttaag | ctacaaggtt | taagcaaaaa | 480 |
| actaaaacat | aaacagaagt | caaacttttc | ttaattttg | agtttagtga | gctacttatt | 540 |
| tattgggtag | ctttagaaaa | gtcaaacttg | aattgtcatt | tttaagtatg | atcaaactta | 600 |
| atttaaccca | aacttctgtt | gtaggtgaat | tagcagctag | tttgtatata | ttgactgatt | 660 |

```
tacaaattct tatttaatt aattttaacc atccattaaa atggagagtt atagttattc    720
aaggatttta actactctca aaatcatcaa gatcacttgc atatttagta taagttcaag    780
gacttaagtc cttattgata ttttcatcat catctggaaa actaatcaaa taatcatgtt    840
gatgcaactt agatgattaa gattaaagct aagacttttg aaatgataaa gaatataaat    900
aaaaaaggaa gttttttaaa aatataacaa ataggtaaaa tatttacatt atataaaaca    960
attctagaaa cgaaaaaaac ccacggtctc acaatgaaaa atacaaaaaa taccctagtc   1020
aatagcaatt aatcagccag cttgcgcgaa gaatattctt ttaaacgact gtgtactaca   1080
atttcaacga ataatccagt attgtttagg tcatgacacg atcatgtagt tctattttaa   1140
cgatgggaaa aaaggttttg aatttaaatg atcgtattga tcatgaaaaa caactatgtt   1200
gattacgata agcgatcatg tagtccaatg taaatgaatt tcaagtctaa cgatcatgtt   1260
gaccatgcta aacgattgtg ttagctatgg taagcaattg tgtagatcat gtcaacacga   1320
tcgtttagat cattttaaac gatgtgaaaa agactnnnnn nnnnnnnnnn nnnnnnnnnn   1380
nnnnnccatg ataaacgatt gtgttgacaa tggtaaaaga ttgtgttgac gatgataaac   1440
gattgtgttg ataatggtaa agatcgtgtt gacgatggta aacgatcggc taaatcatgt   1500
caaaatgata tttagacgat gtagatattt ttgaatatga aaagatgaa gtgactttaa   1560 agatgaagta gcttttaggt caaaagcaaa taaaaacata taaaaacata cgaggaaaag   1620
ttaacatatt tttagtctat tcagactcat ccaaatttta attgtgtcat caaatctcaa   1680
tccacagctc tcaccttgat taaatacata acatatctaa gatcttataa ttaagttcat   1740
gaacgtatct aactttttaa ttcattgatc tgccttgctt agttcaagtt acatacc ctc   1800 ttgcttaaaa aaaaaagtta catacc ctct tgcttaaaaa aaaaagtta tacccctct   1860 ttgacaaata tcaaggaga aaaagacaaa aactgacatt ggcttcccat catccagaga   1920
aaagaaagaa aagccgcgcg ggttgtttat ccacttgttt cccttattat cctcatcgat   1980 tccaagttt gaactcaaca                                               2000
```

<210> SEQ ID NO 103
<211> LENGTH: 2000
<212> TYPE: DNA
<213> ORGANISM: Cucumis melo

<400> SEQUENCE: 103

```
ttcctattta aattaactgg ttttcttaga aaataacaga attcctgtgt ggaatcccgg     60
ctctaatcca aatttcatag ggatgaaaaa tgaaatgggg agtagacatg gagatgggga    120
gtggcattcc tgacctcacc ccgtccccgt ggacatcttt ggtgacagaa tcatcccatc    180
caaatcaatc tgtgggcaaa tttcaacact cacaacaagt tgaaagactt tgttttgtaa    240
tgtatttcga gttcaactca catgtggttg tatagtctac catttcaaac ccactccaaa    300
taagaaaaaa atataaaaaa acatatttta gaaccccaca acattttttt tatttgaaac    360
aaacaaatat ctccacgtgt ttctgttga tctcaaattg tacaaagg gagacaaacaa     420 gagcaactta atcgtgtggt cgaaagttca taaaaacgt tgtttttcat tactattatt    480
acatcaacca atgcgatctc aatcttgtga agatttttct tccatgtgtg agtcatttct    540
tctcgatctt aattatcttc tcacaatcca tttattatag cataatctaa gttaatttag    600
attcaaaact atacaataat aataattaag aaaattacaa atttaaatag caaaagaacc    660
atttgttctt tatagtttct acactaactt ttgaaaggt taaggttatt ggaaatcttt    720
```

```
ttctggggca ttttttctcca attctacaat agacaattt ttttaattaa ttaattaatt      780
aaatttaaag tttaccttgg agtagtcaat aattaatttt tatgcacatt tgtcttttat      840
atgattgaat gtaacaaaca ataacttatt cttcttcttt tattctattg ttttgatgca      900
aacccacaat atttaatgag ctcatagtta tgtgtttgct ttactaatta attattttct      960
tttcataaaa taaaaaaact tgtacaatat aaactctatt atcattgaat ttttagtact     1020
taatttaaac gtactaaaat aaaatacatc attctgactg acgatccatg taaataaaat     1080
ctaaaaataa aagaaaaatg tcagaaatag caaattgaca aaatatttac aagccatagc     1140
aaaatttcat attctaccga taacaaacat tgatagaca ttgatattct tctgtcagtg      1200
gtattggtag acagtgatag aagtctatca atttctatca tcgatagaat tcaaaattt     1260 gttatagatc gtaaatattt taatttattt gttacttta aaaatgtctc aatataaaaa      1320
ttattaaata aacattaatt ttttattttt caattttaat atctaagctc ataaatatta     1380 actttacccca ttatttattt ggtttcttac cgcttaaatg ttgcaaaaat attttaaatt    1440 ttattttttga aatttggtta aattcgtttt tacttaaaaa tttccgtgat aaaaatattc    1500
gaatttttta ggttttata agatttaaa gtaaactaca taaatgaaat cgttatttc      1560 taattctcaa tttaactttt ttatactttt taattaccaa atggaaacat gaatttaa       1620 atatatttat tttaaatctt actcgttaca aacaaacaa taaatttaaa attattttc      1680 cgagttttaa attacaagat ttaaaattaa ttttcaaca agaccaaaag aattgtaagt     1740
ttcgaataaa aaggttctt tttgggctat aaagtccaat ttcctataaa agaatttgat    1800
caattggagc ccaaagtcag atccattaac ttttgggccc aaatagaaca atgaaaagaa   1860
agcccaaaag ctgacccacc aattaacctt attattaggg ttttgctctc tcttttaaca   1920
tccgaaaatc aggactctct tgccgctttt ctcttcgccg tcgccttctt cgagcttcaa   1980
gtctcccatc ctcttcagcc                                                2000

<210> SEQ ID NO 104
<211> LENGTH: 1974
<212> TYPE: DNA
<213> ORGANISM: Cucumis melo

<400> SEQUENCE: 104
tttgctattt tcgtttcatg tgggaaaaat agtatagtat gtttacgtct taaattattc      60
caaattccta gctaggaatt aaaactttaa tatatccaaa acgtttctta tttattataa     120
agatctgcaa tagcacaatg ccaatttctc ttctttgaaa tccaggttca atcccggtt      180 gcggaataat gttttgctat tttcgtttca tgtggaaaaa atagtatagt atgtttacgt     240
cttaaattat tacaaattcc tagctaggaa ttaaaacttt aatatatcca aaacgttcct     300
tgtttattac aaagatctac actagcacaa cggtaggtag tttctcttct ttgaaatcca    360
aaatctttgc tattttcatt tcattttcaa attgaatgca tagctttaga ttgtagtaaa    420
cattgtatat atatgtttag gttgtgctaa ctttaaatgt acaaaattca aaatgtaata    480
gaattagatg tacatgataa agagttgcaa tatttagatt aaaatataag aatttaaatg    540
taagacttgc atatatcaaa aaaagatttc tttataaaca atatttttt atacaatttg    600 aaggcaactt attgttactc atgggcttga tccaaacttt tgttgtcttc actaaaattc    660 ctctaaaatag ttcaacataa agttgttcat gagaaaactc attaagatat attccaacat   720
tatgaattgt ttgtccttgt attttgttaa ttgtcattgc aaagtataaa tgaatggaga    780
tttgtttcct tttgaacttg aatagatatc cattatcatt tggtgggttt aatggtattc     840
```

```
atggaagaaa aatttatttt tctgcataat cacccattat tatttcagca tgtataatat    900
ttttgctaaa taattgacat actaatcttg tctcgttaca caatccatta gatgaatcca    960 aattttcaa taacaacgtt ggtaaaaaaa atcaagacag ccttttatat agtaaaaaaa    1020
atgttacaac aacttttcaa cgttcaagtc tttaaatttg tattgttgat tagaattaat    1080
aagatatttg atttgcaaca aatttctaaa atgtaaataa aaaaccatttt gcattcaaac    1140 tcttacatc caatacttta attccttcgc atcctatact ttaattccac tcacttaaat    1200
ataattaatt aaaaatatag tggataaatg aaaaccaatt tgcatttaat ttttatatat    1260
gcatacttta attccactaa acttcgttag aattaattca aaaagttgtg ggagagaatg    1320
tgcattttat catattacaa gaaaaataaa attaaaaaag aatttaccat aaagtcatta    1380
aacaaaattc aaaggttgaa tggagagaat aaaatttctg cacgctttga tatatacaag    1440
atatttaaaa ttaaaaaaat agttttaaag agaatgtttc taaattatta ttctaacttt    1500
aaatataatt actcataatt atacttattt tttttaaat ttagaaacta aaatgataca    1560
ttctcgaaaa ctataatcaa acgagttaat gttataaact ttgaaaacta ttttttgttt    1620
ttaaactctg catagcaaat agcatataga ggttttttaa aaaataataa taattaaaaa    1680
aacattaaag gcaaaatcta ttattccttg atttgtgtat agggtgtaaa tattttgtta    1740
ctgtgttatt tttaaccatt tgcgcactga tacggactaa aagtaaaaaa cataattttc    1800
tcgaattgtt attagaaaac tggggaagaa aaaggaaatc aaatcgcgcg aggtgggatt    1860
tgacccggga acctaagact agctcggtgt ggtgttgaaa tccacgcgtt gttcaccgat    1920
tttcttcata caaacgcac ccaggctacg gcagtcttcg aagctctctc aatc         1974
```

<210> SEQ ID NO 105
<211> LENGTH: 2000
<212> TYPE: DNA
<213> ORGANISM: Cucumis melo

<400> SEQUENCE: 105

```
gtcgtcgagc agagctctgg cagttaccct acaacccgga gcacgataac tgcagtgatc    60
cctatcctca gcatcagtta aatgggccga ttcaaaactt ttatgggcct cagcccactt    120
ccacttacaa ctattacaaa catggatacg atagtcacga tcaggcccat catcttaatt    180
actccacaca ttccaatatc ttcggccgcc aaactgcctc cgttttagc gacgaaaatg    240 tccataattg ctctattatg taataaggct aaacactaat catctatccc tttaaatctt    300 gaattttgt aataaaacca atctatactt tttgccatag tttatttcta gaaaagttta    360
gaatacattg aagatttgag aaacttgtct acaaggcatc aacaaaacta cgtgaaaatg    420
acaaattgga aacaaataaa aatatcttat gtttgagtat atggaatgaa gggattgatg    480
taataaaact taacgtcaag tgttaatatt acgctatagt tatttcttg ttgtagtaat    540 tttctcttag ttaattttt tattattgaa ataagtgata aattttctaa taagaacgta    600
aagatttaaa cctctaatta agttaaaaaa aaaaacttga attattgttt gagttatgag    660
gtaacgtaaa agacaactta aattttaaag tcaaaccgaa aggaaaagag ttaaataccc    720
acaaatggat caagaagtt aataacacac acgcacgttg ggaagcttaa aaattagcaa    780
caaacaagca atcattggtg tgggacagta ttgaaattcc acaaaactac aagggtatat    840
tggaaaatcc aatttatta tttattttt aataggaatt aaatttactg taaaaaaatg    900
taagaccgtc gattgacaat tggtggactg tgaaacgtgg caaaagttaa ttggcgaaaa    960
```

```
ggagaggaaa gattttctct tttcattata atgaaaaaaa ttaatgatag tacacgtggc   1020
aaaaaagtat tggagagaaa tttccgggaa ttatctctaa tacgcggcta atttggatgt   1080
caattttgca aagaccagaa tcttttttgaa cagcgaagaa gaacaaatat atagacatac  1140
aataataaat aaaaataaaa atatattaag cataagagaa aaagaagatt tgaaggttat   1200
attgaagtga tattgttggt ttctccattt ctgtgggtct gactctgcct ctctctttc    1260 gagccagaac caccaaaacg aaaaaaccca cacactgtat agcaacccct aattctttgg   1320
tctcagatcg cccatggctt ccactaaaga acgcgacaac ttcgtttaca tcgctaagct   1380
cgccgagcag gccgagcggt ttattgtatt ggttttccta ccttcctttc cactttttt    1440 ttttgggttt gcttctcatt tctattttat gcttttctta atttgtgttt tacttttcac   1500
tctctctttg ctcagatcgt atttcttctg gttgttaat tttgtgttta tgttttttga    1560
cttcggattt aagccacgat cgcttgcctt tttgtgtact attttcagaa gtgttgttat   1620
gtttatccgt ttacacgatc tgtttgaaat ttatggaaat ttagtttgct tataaatttg   1680
ctacatttct attgtttagc ttctcgagca gttttttttt tttttggccg atccattgat   1740
ttatactgtt tttctgtctg atctgttta tttaatggag aatactctttttttgcgaag     1800 cttggtagct cattttcac tcatacttac acagactact tggtcattgt ttttatctgt    1860
aagcacaaag caaattcaag tttctgcctg ttctttcttt gcttgtcaaa cgacaaaact   1920
atgtttgtag ttgcttttgg atgatagatg gtgattctga ttttaattta cgttttcctg   1980
ctgttttttt tttaaaagaa                                               2000

<210> SEQ ID NO 106
<211> LENGTH: 1643
<212> TYPE: DNA
<213> ORGANISM: Cucumis melo

<400> SEQUENCE: 106
tccattggcc ctctcaaacc tttatgtgca tatcactaat atggttgaat atgtatatct     60
tctttctcga atagatgatt cttggtggtt tcaataatca tttagcaaat ccagaaattg    120
ggacctcaag ttcggttgcc gtggaaatag ctaaattaac tctgaaatcc tcaaactgaa    180
atgtgagaat aatcacgatg aatctgaacc gtcaacggcg gaacatagca acagtaatca    240
gaattaccaa atttcaattg ggggaattcc tttgtatgat ccttccttgg gcctaacagg    300
gattcttgat ttgaacctct cttcttcgta aaaattacac aaaatatttta gctgctagag   360 ctagacaaaa caagatttag attggaaaaa caacaatgca gctcccaaat tgcaatccta    420
attccactat ttcttttttc ttttctttt tttaatctt aggattcaat tcatcattca      480 tcaatttat tgttactgct cattgatgac caatgttttg gatttgtgt gtcaaatatt      540 ttagtttata tatggtgaaa agataaaatg aatagtttca aattttgtgt tttatgaatt    600
cctcactacc tctttctttc actaatacgt atgaaatgtg tatggttgtt tataaataag    660
atggatggat gttttgattt tgatttgaat gttaatgtta cttaaattat agattttaac    720
catttgaatg aaatatggag agaacagttt ttatatgtaa aaacaaatta atgtgagaaa    780
gaaataaata gcaatgcctt tcttcactaa taaatgtatt tatatttttt attaacaaaa    840
taaaatttat attaattatt agtgtatgag gtgtgttctt gtacaaagga aagtattgca    900
aaattacaaa aatggaaagt tgaaattact gcactcattt gctaaatca aattagttaa     960 ttatagaacg aaaaataaat aaataagttg tatttgatga tcctagataa ataacttttg   1020
aagaataaag atcaactatt taaaaaaaat atgtgtatca caaaaaagaa tagagaaaaa   1080
```

```
aatcacaaaa atcacatccc aaattataat aattcatatt ataataattt atataccaaa    1140
cataaactat aataatcacg tattattata actcatagac tataataact cactccacgt    1200
cccgtagtta ttaaataaaa gaaagtaacg gtaacattaa cattataact tcgccctcat    1260
ttatggcaag gaaaaattgg ggggattggc aagtattata tttgtttatg gaaaacttttt   1320 gtgaaggtgg aaaatagaga gagccaaatt aacaaaaata ataacaaaat caaagggtgt    1380
agaattcatc cagtttgaga gcggaagatt agatgggtga agaaaggatt attctagaac    1440
cctagcccac gtgtcataat ccaaccctca ccttttcttc aaaaacccct tctttcttct    1500
ccctccccta tatctccttc ttcgaccacc aaactcttt ctctcaattt cccagcatct    1560
tcttcatttt tcattcttaa ttcaacccat ttcttctctc ttttcgtttc tattttcatc    1620
gtttctctat aatttctccc tta                                            1643

<210> SEQ ID NO 107
<211> LENGTH: 2000
<212> TYPE: DNA
<213> ORGANISM: Cucumis melo

<400> SEQUENCE: 107
ggatgggcaa tcgtgcgaca cttgttctac tcgattaaca aattagccgt gtaaaatcca      60
aaaattgtgg acaatttacg gtatgatgta gcccctcttc acgttcttaa gaaattttt     120 ataaaatgag aaagggaaag gaaatcattg aaaagatcat aaaagaaagc attgaagact    180
gttaattgca aagaaagctt agcttaaaaa gagtgcaaca aggcttagtt ggggatttaa    240
ctactatgtc tcccttattg tacattttga atattttat ccttggcaga cttgcatatg     300
aaaatgtcga aacgtcacac actaggtcga aacataaaa atgaaagcaa tagagcaata    360
gattaaacta agtagaaaac ataaagacaa ggtgatttga aggtatttgg atatgtggcc    420
ataggcaaat aacgcgctgg acaagcatgt tcatgacata tgacactttg cacgcatgct    480
caatgtggat atatcagcat ggcgcacgtg cctcactcgg acacataaac atggtatgcg    540
cggcatcatg tgcgcacgcc ttacacgacc aacgagctag gtgtagtcca agcacacacg    600
cgatgggcaa acgtgcctat ggctgcccct ggcgcagaca gtctcgaaag atgcatgtcc    660
atcctaggcc catctagaca cgtccaaaag ttccaatgac ggtccaaaag gatacaatac    720
ctttagaagt gtcatggtag gtctagaatg ttctagagtc atttgtaaat tgttaaactg    780
ccttatatct tctagatata caggtcctcg gccgaccttc aaagcaccta ggtcggttag    840
gaaagctata aatagatgta aggtggctta tttgtaatca ccctaaaatc ttggcataac    900
ctagccaagt aagacaacct tgcctcatca tttgtacaca aggtaccttt acaaatggta    960 atacccctggc aaaggactac actcatttgt atacaacttg tacacaagca atcttggaac   1020
gcaaagtact cttccaagaa gtgtcaagct aagctccatc attctcacaa aatgatctct   1080
cttgcctttc aactatctta aatcttctac tgccatattc tttctcatag tgcttagtgc   1140
actaacctct caaaggctta cttggctacg tgggcgttaa tattagtcaa gtgttgtacg   1200
tttggttagt tgaaaaatct aaccacgtga caatagacaa acatcaattt tatttatttt   1260
tagagtctca ccaagttctt aaataaaatg tttattgtaa gacaaacaaa aatgaaaata   1320
tgttattata gtgatataga attttcacta ttagtacaag atataaaagc gaaaggaaga   1380
atgaatgaac actcaacatt tagaaagtgt tttgagtaaa gaagtaaata gtgagaaata   1440
acgagtacaa atgtgtggaa agttataaac ttctaagatc tacagaacaa aagattgata   1500
```

| | |
|---|---|
| agatataaaa ttgatgttag gataggagct acaaactcct ttgaccaaat atcgagcagg | 1560 |
| attcacaagt catactctct tactctacca aattcattag aagtacataa tgggcatgca | 1620 |
| tgtgaacgaa ttaaaaaatt ggtattttta tttttatatt ttaaaaaaat tggatgaatt | 1680 |
| ggcaatggcc atgaatgaac cagttgttaa agtttagagg acaaaaccca aaagagagaa | 1740 |
| gtgtacctca taaaaaacaa atccaccaat tgagaatcac ataaattata ggaagacgtg | 1800 |
| tcactctatc ggccgatcct caaactcttc caccaaatcc acatgcacaa tctccttctc | 1860 |
| ttcccttcca ccatacactc aaaatcccac tgatcttctt cttcataaaa acccatataa | 1920 |
| tcataaatta atttcctcaa gttttctttt tccaattaaa caaacaactc tgcaaaagag | 1980 |
| gcctttcttc caccatttcc | 2000 |

<210> SEQ ID NO 108
<211> LENGTH: 2000
<212> TYPE: DNA
<213> ORGANISM: Cucumis melo

<400> SEQUENCE: 108

| | |
|---|---|
| agacgaagaa gaagacaggg tgtgatcatt taagaatatg cgttttaact ctgccctttt | 60 |
| tagggctttt ttctttattt tatttgcctt ttttctcgct cctagggttt ttccctccat | 120 |
| tgaattagaa ggatgactgg gccacagact tatgatgggc ttcacggtca ttatttgaaa | 180 |
| gtgtgatatt ctaaaaaaaa taaaaactca tttgaattaa aatagggttt ccctccatgg | 240 |
| gagtatgaaa gacttttaat tgaattgggg ttttttaaacc ctaaattgaa ctaaatatat | 300 |
| ttttatgatt tttacaaaaa ttaatactac aaaacaaatt atgattaata aaatttgttg | 360 |
| atattttca aaaacaatt atataataaa acaaactaaa tattcaattt ggtatttta | 420 |
| accatgctat aggaaaagat tcatatgggc atcaaaatga agcaagaaca tggcaaagca | 480 |
| agttgggtga agataagtat tgtcctaaat cgaaggacga ggcaataaac tcgatatctc | 540 |
| gaagagtctc caggtcaaca tcacaacgcc tgcacaaacc aaatattatt atatatatag | 600 |
| ccatcgttta ctataagact atgtatttac gaaaaattct atattgtttt cgacgattac | 660 |
| atttatatta tataggaata aaatacaaac ttttcgaaaa gtcatatatc ccaccatata | 720 |
| aagatcaaac gtggtagatt gaaaacatta tacagtatat tctctatttt tttctcataa | 780 |
| aacttattac gctttgtcaa gttataaaga ttaatggttt tggtatattg tgctaacttc | 840 |
| gtccatttgt tgtgaaatta catttttcact acttttttcc acattgcacc atttttcata | 900 |
| tgtttttattt ccattatctc gtagaatatg agcaaagaaa aagattaaag atgaaatttt | 960 |
| tcaacgtgtg agagaaacat cattaaaggt tacttaataa ggaattagaa aaaagagcat | 1020 |
| gaacctagaa caacaagata caaaatatca aagacaaaag agttcgatgg agagctagaa | 1080 |
| agataaatca agattttgta aaagaaaagt gctcggtggg gaactagaaa aatgttatag | 1140 |
| aagctagaaa gataagccga taatttgtaa actataagag gccgtttaga ggaagagttg | 1200 |
| ggttgtgaaa tgttagtgtt atgataaaac tattgttatg tttggggaaa gagtttaaaa | 1260 |
| aggtactttt atgataaaat atgtctggga taagagttga aaaacgtagt tttatgggag | 1320 |
| agttgaagat atagggttat gaagagttaa aaaaggtata agaaaaggag agagagagag | 1380 |
| ggaatagggg ttatgatcat agtcttaaaa cagaattatc ataacccaat ccaagtgata | 1440 |
| acccttggac caaacgacct aaaatatcaa agagaaaact gtttggtgag gaactataaa | 1500 |
| aatgttatag aagctaaaaa tacgaactag aaagataagc ggagccaatt ataagggttg | 1560 |
| gttaagtgta gggtttattt atttgagggg aatgataatt taagatataa attaatagaa | 1620 |

-continued

| | |
|---|---|
| tggcaagttt tgtaagaaaa attaataaca actcgataaa cttttgtttg tgttggtaga | 1680 |
| gaaaacatgg gccacaaaca tgagcccaaa tgtggagaag cccagctgat aatttaattt | 1740 |
| taaaaataat aaagattaga ttattttttgt tcgcccaaaa ttcggcgcgg ctaggaggtt | 1800 |
| gcttataaat ggaaataaat ggaaagggtg ttaggtctcg aacaagtgtg cgacggtatt | 1860 |
| ttaaaggtcg gccacgttga ggcggccctt ttcactcctt tttcctcgct cgtattcaat | 1920 |
| ctagggtttt aggtttccaa cttctcttcc tccccttccc cttcccctttc ccttccttc | 1980 |
| tctactcatc actattctca | 2000 |

<210> SEQ ID NO 109
<211> LENGTH: 2000
<212> TYPE: DNA
<213> ORGANISM: Cucumis melo

<400> SEQUENCE: 109

| | |
|---|---|
| atgggtagtt ttcaaattaa tccgaccttt gaagtacttt ggttttttaaa ataattttt | 60 |
| atcatctgaa atcactccat agacttatgt taccgtaaat cattattctt tacaaatgat | 120 |
| ttgattttac ttaaaagtat attatttcaa acacgttata ggtattatga agttttaccg | 180 |
| tcaacaatta tagttagtaa gccaactatt tataaaaatt taaaaaggaa tatttgaagc | 240 |
| atggtgcatg atgtatgttc ttctctctct taagttgact atcaaaactt aatcatgctc | 300 |
| agaataacat acctcacata gcatgtgcaa tttaatctaa gcaattcaaa attcattaac | 360 |
| aataattcat acacactaca aagtcatacc acctatgtca cccaagaact actattattg | 420 |
| taacaagtca ataagaagt ccctatccta tccatcctaa gatggagtaa ttttttctttt | 480 |
| ccttaaattt ttggaaagaa gaatattgaa attcaggaca ttaaatcaaa gctgttcgga | 540 |
| gataaatgaa ccattcttca agtaaaaattc atatttgtca tcatgcaaac aaatattgaa | 600 |
| aacatgatat caagaaaaag aacaaattat ttaaaaacat cataccgcac atcaaactta | 660 |
| aaataacctt ttgtgcatat caaacttaaa ataacttttc tcaacaaatt aaagcgacat | 720 |
| aaaattgata atttttgttt tttttttaaa tatatattca agaaaatcga caaatccaaa | 780 |
| tgacaagttg ttcacctgta tattaaaaaa aacaataatg aaaatttgaa aggagagatg | 840 |
| agaaaaaaaa aatcaatcca tcaatccaac ttgaatttttt gggtcgacag catatccta | 900 |
| attataatag gaagcaccct acttttttta caaagtatc gaaattatta gtcgaaaatc | 960 |
| ttaattagag tccaaattgg atgcagcaag gatagtttta aatccaatta atagcatgcc | 1020 |
| taatgctatt acaaatatat tttggattat acataaatag aaaaaaaaaa gtgaacttcc | 1080 |
| agactcaaat agattttact ctattgttat aaaaactata cattaaaatt agatgtagag | 1140 |
| aatgagagct caaaaccaag aaaagtaaat gataaaaggg aaacaggagg tgaaaagaaa | 1200 |
| aggtgatacc gcggatttga tgtggctctc ggttttttgcc tcccaagcaa tccccattgc | 1260 |
| ccatctcctc tacaccaacc cacttttctc cctttcttttc tttctttctt tctaaaactt | 1320 |
| ttgttttcca attttgacct ctcttcttgg gcccacttac taacaaatca aaccaatttt | 1380 |
| tcatttttttt ttcttttctc tattcccttc cacaaataag aaaaaacttt atataaatca | 1440 |
| atacaagaat gacatttatt ataatagtat atactataag gtgggaggga tggcaattgc | 1500 |
| caattgtata agtaactatt aatagacagt aaaactttga aatagaaggt atttagatgt | 1560 |
| ctgagggtaa acttataaca ttttatgaaa tctaaaaact aaaattaaaa ttattgggac | 1620 |
| aatataaact ttagacataa gaagaaaaca tattttttgtt aataatttaa caagaacac | 1680 |

| | |
|---|---|
| aacaagaatg gtagagtgtt gattaagagt gagcataata gacaaaaaaa aatatagtca | 1740 |
| atcagccaaa atagacggtg gttggtcgga gatgaagaga gtttcaatct aatcagttgg | 1800 |
| taaaaaattc aaacatcgtc acattcttta aaacttttaa aggtttaaat ctgctaagat | 1860 |
| ttatcgaaca atgacctatt tgtactactt tatgattgac atcaatttaa atatttaccg | 1920 |
| gtgaatttag taacgattag ggcgagagcg gttttaaaaa caggagtgga gtagtggaca | 1980 |
| aggaggggc ggaccaaccg | 2000 |

<210> SEQ ID NO 110
<211> LENGTH: 2000
<212> TYPE: DNA
<213> ORGANISM: Cucumis melo

<400> SEQUENCE: 110

| | |
|---|---|
| ataatactat aaaacaaata aattttaatt aagttgtttt tactttcata ttatactaac | 60 |
| aagaacagtt tgttaagttt tatatgtatt tataaaagat atatgagtta ttggttaatc | 120 |
| tataatatca atgtcgaatc tctaacaaat attttagtgt ctagacctta tgtaaaaatc | 180 |
| agaagtgacg ctcaatattt ggaaacagga atcattggga tacgtggaaa tcaatctttc | 240 |
| tgacattgtt acaaacaaaa gaataaacga aaagtatcac cttatagact caaagaatgg | 300 |
| aaggattcag attgagttgc aatggaggac ttcatcctga agtacctata tattttctt | 360 |
| cttggttagt ttttcagtct tctcttctat ggatcaagtg gggaatacag caagagacaa | 420 |
| gaaagacatt ttcctataca aattcatttt attattcttt cattgtctct ataaataaag | 480 |
| aggcatttaa atccttttcc taatttaggt ttggtatcaa tattttgttt gtaacagagt | 540 |
| aatagaacca aaatatttca ttatgttact tgaaatgttg attttttgt gcccattctc | 600 |
| ttctgagtcg acaagtgaga gtagatatga aagtagctta catttatatt ttaagagttt | 660 |
| ggaatctctt accttaaata ttttctaaaa gaatatcgtt gtgggaatat gattttcta | 720 |
| ttttataaat ttgacactat cgatcaattt aaacacgacg tataaatttta gttttattt | 780 |
| tagaaaaata agctttttag tttaagtttt tttttacgta attactattg aatccctaaa | 840 |
| gttttaaaat gctatagctt tactcttata ctttgagttt agtttgtata tatggtcgat | 900 |
| aaattttaag attatgtacc gtaattctaa gttaaaacat tgctcacctc ttgtcctcaa | 960 |
| agttaatgta aatgaaatta taatactcat acataataga actttttttt attcttaatt | 1020 |
| atgcaaaaag aatagtgaag gttaatttag ttataatcag ttctagaaaa ttaacacaaa | 1080 |
| cattctaaaa gtagtttgaa attgagataa aatgaaagtc aaattcaaaa caacgaaata | 1140 |
| aagttataaa tatgaaactt tgaaaaatat agataaaatt agaactacgc atgaaaactc | 1200 |
| taagacaaat agacaattct cgagatagaa gtttgaaatc gaaatctggg gaaggaaaaa | 1260 |
| tctttacatt tccatttat tcctatatct actaataagt tttgtattaa aaaagaacat | 1320 |
| caaatagagt aaataactgc acactaaaca acactcaccc aaccacccca tatctcaatg | 1380 |
| agaaatctta atgtgaacta caaagctagg gacagaaaaa tgattcatta gattccagaa | 1440 |
| caataataat tatgattaca ttttggattc attagattcc aaaataataa taattatgat | 1500 |
| tacatttggt gtttgaccta tttattat tatttatat aaatatttg tcgaagagat | 1560 |
| agaaaaaagg atgcatttaa attaaaaaag aaaaattata ttgataaaga agaagatggc | 1620 |
| gggctgacaa gagaagaccg ggaggctgat gtggcaatgg gaattccaat tttccaatca | 1680 |
| aaactaaaa acaaaaaga aaaaaaaaa gcaaataat tttggttcac tgaaaatttt | 1740 |
| catataaaata catgtggcgg ttgatggccc aaaggatgag ctttgaaggt cgcattatca | 1800 |

```
aaagtttggg gaagcagatt tttgctaact tcgaggtact ctcctctcct ctcctctcct    1860
cactttcctt tctctctata ctaactataa tttccattcc tcctccatca ataatttctt    1920
catcctcttc cttagctaat ctctctcttc tctaccagtc aaacgccctc ccttttggtg    1980
ctctctagcc tcctcctccc                                                2000
```

<210> SEQ ID NO 111
<211> LENGTH: 2000
<212> TYPE: DNA
<213> ORGANISM: Cucumis melo

<400> SEQUENCE: 111

```
ttctctctct cttttaatct acaacgtatc caattatatg gagaaagttg aggttgttgg      60
atttaattca ttttttcaca ttttttaggg ttaaaatcta aaaacacatt tcgatttttgc    120 gactgttcaa ggcgtatatg tttctttaaa tattatagtt gaaattacga tcaaattctt    180
acgctggtta agaaagagaa aatcgtagga gagaaattgt gagcatataa gtgaaaataa    240
cctcctagag ttttttggat ttttgagcga aacaaaagta aggttgtaac gatttatgtc    300
taaaatgaac aatgtcatat cattgtggga atatgtgtga atgataaatt atcacaactt    360
ccaacaatga gtatcacaat acatatcatt gatgggtttt gagaaaatga gggttgactt    420
ggacatgaca acttgataga cttataactg tgtggtgtac ttataagaaa tcggaagttg    480
gtttaaaagg agaatcattt gcgtcgacaa gatgattatt attgcaaaag atgcaaccaa    540
ggtatgtcga tacataggct agataaaaag aagatcaagt aatgatataa ctatgtctct    600
gttgatatgt tttaagtga aataaaaaac aaaactatta atcctatacc taaaatgaac    660
catatcgtac tatattagaa agaataatg tacctcttga tagaaactta tagtaaaagt    720
gattaataaa atatcactag agagatacgt aaatacttcg ttatcataat ttattttact    780
tataaatgaa ctataacaaa aagtatttat atccacaaaa tcaacgttaa gaatattagg    840
gcgtcgaaga agacgccaaa ctattttaat ataggttacg tttggtatct catctacata    900
acaatctttt gctttcaaat acactcaata agtaaatgg aatgattttt tgttttctaa    960
ttttgtcatt aaaacagtg ttttacattg tacttgaatt tgtgacatat aatgatatat   1020 ttcttttac aatacccaaa atcaacagta aaaaaacaaa tacttacttc ttttcattca   1080 aattttcat atgcttttga ccgttattag cctttagtag tttatcgtaa atagattgtg   1140 atattttat caagaagttt tattttttaa aataaatttc cttttttcata accacaaaaa   1200 gcacccttgc aaaatcaata tttcattttg gaccggttg acattaggtg ctttaaggat   1260
cggcccaatc tagattcaat aatctcagta aggcccactt gtaaaccaca aaaaggcatg   1320
gcccaccgag cccactatgc caatagttgg gcctttcttt cgcaaatgca cgcagctaat   1380
taaggcttca ttacttaata atcagtaatt aattttgctc caaaacgggt caaagagcga   1440
cccgacccgc gaatatgtat ctgggccgtt gattatttta gtagtaatct caaccgttca   1500
gtcggtcctt ttatatgtct gtcctccctc gtaatcaatt cttagggttt tctagggttt   1560
ttagttcttc tctacgcttg gttggaagtg cccttcctct cattcttcct gctttactac   1620
aggttttcaa tcttcaacaa tttaaatctc aacatttaat ttgttttgca cattgattca   1680
agtgtgtttt ttttctttcg tttgggcttt tgttgattga aattactcaa gaaattgcag   1740
ccacaaggat agtctaaaaa tgcatttgat ttagtgtagg tgctgctctc ttttttgtga   1800
ttgttcttag cttacttgga gctgtatgtt aatgctagag ttcattgagt atcaatgctc   1860
```

```
aattacagat agttttgttt tgtaatttcc acatatattt tcgtatttgt gaaattaagc    1920
tcgtttgttt tcattgtttg ttggcaattt atgttttatg ttatgccaac gattcatgat    1980
ttgtagcttg actcgaaagg                                                2000

<210> SEQ ID NO 112
<211> LENGTH: 1027
<212> TYPE: DNA
<213> ORGANISM: Cucumis melo

<400> SEQUENCE: 112
ggggggggtt gtcttcctca aactctgtta tcgaaattag gtttacattt agtatctggt      60
tgacgttttg attgtattcc tgggcctgaa atatgataaa taaatatgac cattgaagtt     120
ggtgtttatt ctgggtttct atcattaaga gggtgtgaac ttacgaggga accaagaaag     180
ggatggaaat aggaatattt agaatagtag gaagctcaaa tgaattattt cgttcgataa     240
ggcggagtga atataaataa tatgcaagga gatgcggaga atattaccca ccttatgaga     300
gagagccaca aatcagaaaa cagtaacaaa tataacaaat caaacaacac catttgcaag     360
cgaattcaaa cgttttttcgg gtatgttgtt ccattaccac attcaaacat gaattgaaac    420
ctgagctctt gggcactta atttattttt caacacatta cgtttaaatt gccgagtggt      480
caatatcatg tattgcttag tactaggtgg atacaaacct tacatataag gtcaaagtat     540
tgtgggcatg atataaatgc tctagcatat tggtctcata gagttttta acttttaca       600 tatccattaa tgagataagt taatgtttca acattaaatt tttagttaat atgaattcta     660
gatgcatttg ttatacaaat ggtctgatgt atttgaggtt ctgaatgtca ataggattg      720 tagtttattc acgttgaata ttgtaaagag ttaggacgtt ttttaagat tagatgatgg      780 gtgccatatg ctaccccata cgccaacaat tataatgaaa attatatttt gtcatttggt     840
atttaacaat tttttttaaa aataagcta ataacgcata gaattcctga gatttaaaca      900
actttctgta atttctttc tatgtactaa ttgttataga acctgtgatg tgcttgtcca      960
tcatgcagat tacaacgact ttgaacataa cttcaaaatt gttgataatg gtagccgagt    1020
tttttgcc                                                            1027

<210> SEQ ID NO 113
<211> LENGTH: 2000
<212> TYPE: DNA
<213> ORGANISM: Cucumis melo

<400> SEQUENCE: 113
agccaaagtt taatatgatt caatcttgca caaatgcagg ttacccaaat ggttaaggtt      60
aagacaggca acaccactct agcagttggt gatggtgcaa acgatgttgg aatgatccaa     120
gaagcggata tcgggatcgg tattagtggt gtagaaggga tgcaggtaaa tttaaaacag     180
atcccagctg gagtgataaa atatagcttt cattcatctc aatttgtttt tatacttctt     240
atctttctga atttcaggcg gtcatgtcaa gtgatattgc aatcgcacag ttccgatact     300
tggagcggct gctccttgtg catggacatt ggtgttacag aaggatctct tccatggtac     360
attatgatct ataaatatta ctttatatta gcttcttagt gagaatcatc cagattaatg     420
tgcaactata cagtctcaac atcatttca gcttgaaaat ctttgaaata tgtcgaactc      480
atcgcatttt atatatggca gatatgctat ttcttctaca agaacattgt ttttgggttc     540
actctattct tctttgagat gtatgcatca ttctccggcc aaactgtata caacgactgg     600
ttcctttctt tgtataacgt cttttttact tctctccctg tgattgcttt gggagtgttt     660
```

```
gaccaagacg tctcatcccg gtactgtctt aaggtaagtt caactttcct ttatttcatt      720
ggtgcaatct tttgccttcc ttaagtacaa tatcaaatgg ctcattgccc tcaacatttt      780
tggattttca gttctcactt ttataccaag aaggtgtcca aaatgtgtta tttagttggg      840
ttcgaatttt cggatgggtg ttcaatgggc tactcagttc tgtcatcata ttcttctttt      900
gtgttggggc aatggaccat caagctttcc gcaacagcgg agaggtcgtc gggctggaaa      960
ttcttggtgc caccatgtac acttgtgttg tttgggttgt aaactgccaa atggcattgt     1020
ccatcagtta cttcacctat attcaacatc tcttcatctg gggcagcatc attctttggt     1080
atttattcct catggcatat ggagctataa acccagccat atccaccaca gcatttcagg     1140
tattcattga ggcctgcgcc ccggcaccat cattttggat cctcacacta ttggctcttg     1200
gagcttccct tcttccatac ttcgtctttt catcgatcca aatgcgattc ttcccaatgt     1260
atcatcaaat gattcaatgg ataaaagctg acggacaatc gaacgatcca gaatactgtc     1320
aggtagtgag acagaggtca ttacgtcaca caaccgtcgg ttacacagct cggttcgaag     1380
catcaaagca ttttgaagaa ttctcagaaa tcaagagtca ctaggtttga tgattagatc     1440
gtagaaagat tcaaaacatt ttttctacgt aaagtttctt ctcagtgtat atatatatat     1500
acatttatat atttatacaa catgtgtaca taagattctt gtgtagtttt gatctccttg     1560
tagcttaagt gaccattccc aattcaaatg gtcaaaaatt ttcttccttt catgaaattt     1620
ttaggaaata agccaattgt agtattcaat cgtatatttc aaatagtcat tgagaagttc     1680
taactctact atagttctca attataagta tgatggtttt gtcttattca tcttgtagta     1740
gaaacaaaag aataaattta cgaaggatga agcattgtta ttttaattat aatttgggaa     1800
atttggagcc acgaaatgaa atccaatttt gtgccaagta gatgtgcaac aatgggcaaa     1860
gaatcacttt ttcttttttca taatttttccc ttccaacact caccactaat tcatcacctc     1920
aatcctcttc ttcttcttct tcttcttctt cttcttcttc actcgccttt gggttgaggt     1980
tggctctgtt acagtcatcc                                                 2000

<210> SEQ ID NO 114
<211> LENGTH: 2000
<212> TYPE: DNA
<213> ORGANISM: Cucumis melo

<400> SEQUENCE: 114
aaaagagtca tagtgaaaaa agctgagatc ataatagttt caccctaaac acaacttata      60
ataacacata ctatcataat atacacacca aacacagact ctatagtctt cactctaaac     120
gcagattaca atagtctgca ccccaaacgt agactattat aatcttctga ctattataat     180
actcttttca cttatcgccc caaacgtccc ctaagagaac aaagataggt tataaaagag     240
agatgagggt ttatattatg caacaagtat aaggttctag aacgatgtag tcttcaaagt     300
aacgaaagca ataggctaca cgagaaaaat atttttaaaa tatagtgctt tccctaaact     360
agatttcaat gacaaattat tataaaaaat agaatcatta atccaacatg gcttgcatgt     420
cacaccttgg ccaaaactga agacggatgt catactcgac ttcaatatat tttttttaatt     480
aattttcatg tgacaacaca taaatattta aaatttagat tgggttggat tttttttcaa     540
gtgggtccca aaatactctt caaacccaaa ccaacccaac ttgtttaccc atctaataat     600
aacccaccag gttcaagaag acgaaccgaa ccgaaccgat ccggtctaac tttgtttcat     660
acttaagtcg aacttagcgg tacttttggt tcggttctcg gttcccccaa acagagccac     720
```

```
tcaaaattag atttagggtt ccgttcgcaa ttttcagcgc attttatttt gaatcggtcg      780
tttgttgaac acgttctctc tcagctggtt tagggttcat cgttctctct tctcgcgcta      840
tatctttctc tctctcaggt tcgtttcttt ctcttaggcc attttatcag aaagatcctc      900
ttcgtttctc cgattttctt tccgtgttcg ccctcggttt ctcagcagac gtaggaagtt      960
tggtttccgt ttagtgaatc tgtttggggt attacgaatg atattttgta ctgggctttc     1020
cgcatagtct ttttctttct aggaatatat gcatctgaga atttatttgt ttggcttttc     1080
tttataaagt atgaggacat atacatctcg attgctaatc cttgattata atctttttt      1140 ttctatgttg tttgaatctg tttttttttt tttaatttct aggttttttg aatctaaaaa     1200
tgtatttctt ggatgaattg catactgttg aattagaagt ttattgatta gattgttgat     1260
atttgcccta agttccatgg ataggtttgc gtctttcacc ttttcgtttg cttttttctt     1320
tggctgacga catcttacat agcctctgct ctaaaggtg ccatgatttt tttccctggc      1380
tttatctgag tttgcgcaat ttagatttga agtgatgatt tgtctaaata taaatatcta     1440
tcggccatac tattttttgt tattttgagt ttttcaagga tgactgctag agaatgaaaa     1500
atcttgaaaa cattgtgttt tgaagttcaa ggatcttgta gttttgttct tttctagact     1560
atctcatttg atatagccct ttaaatttaa tcaaatttg ttaatattca aatcctcgga      1620
cattttaatt atttatctaa atagttgttt aggcattact caggttgccc actattttaa     1680
gcttagaagc ctactctggt tgacctaaag tttgcatgct atttgcctta tttcgcacga     1740
ctctaaactg ttatagacat ctttttttcag ccttcaggta aatgaacaca aaaaggagtg    1800
aaagtctgac ttctgtgtga tggtcttta atcaattata gggattaaga tggttttttt      1860
attcattgta taaatattaa attagaatga tgacaaccaa taatattaaa actgacaatg     1920
gaaggttcct tatattattt ggagtgtaca ttacaacagc ctgattcttg gcttggcagg     1980
ttcctgatca ccttgtaaac                                                 2000
```

<210> SEQ ID NO 115
<211> LENGTH: 2000
<212> TYPE: DNA
<213> ORGANISM: Cucumis melo

<400> SEQUENCE: 115

```
aatgtaaata gtttataaac ttaagataaa attggtaatt gtttaataca aatacaaatt       60
gttaaatgaa atgacacacc ttgagcaatt ttcttttcta atcttctctt atagattaat      120
tttatttaat catgaaggtt agaatttctt tagcattatt tatttattta tttattagaa      180
aaagatagtt tgtgtatatt ttatatcata aagtttcaga agaaaccata aaattaatgg      240
agaataataa aaggtgggga tctctaacat ttttgccata aacaaatcac taagttaaga      300
atatgacact aaacttcttc taatttaata ttatatacaa agattttaaa attataaagt      360
aagagccttg aattgtagct aatttaagaa tatgctctaa gttttttaaa atcacttttg      420
ccctacggtt attatttatt tttttgttga aatatgttta atccaaatca atttcaatcg      480
aacatagtca aggatatgac tgcggattcg tatattagtt gattttgaaa cgattaaatg      540
tttgaaatat tgtagtttag gaacaattac aattataaca atcagattca aaattttagt      600
atatacagta acatttaaaa gaataataaa tatatcaaaa tctatcgaca atagacttct      660
cttcatagat aaattatcag ggtctgactt ctctcataga taaattatca gggtctatta      720
gcaatagact aaatccttga tggtttatca ttggtagacc aaaagagttt attagtgtga      780
tagactttac tacataattt gcaatttgtt taaaatgttg ttatacattt ggttgctatc      840
```

```
cttaacatta caatccataa catttgtcgt gtctttaact tgaattgatt gttatctgtg      900
ataaaaagag atgatcactt tttgtcatga gatttgaaca attgatgtta aaagtggtaa      960
ttaatgtacc attcactaac caatgtcaat atttattttg tttaataaaa agaaaaagga     1020
gattgtgaca ttagttttat actcttttct aaacataggt ttggtttgtg ttagatttgg     1080
cctacactta gctcaaatcc actctttata aaattccctt acttattaca agttatattt     1140
tcactccaat cataatcttt taaaggataa tatttgtatt agaagatacg acacatgtag     1200
aagataattc tttttaacc aaaacaacat acaatttcga ggatatgaca aattacccttt     1260 tctattttta actatttgat cttcaagtcc catctaaaca tcaaatgaaa gttgattagg     1320
ttaaagaatt ggacaattag agaaggaatg gagaatcaaa cctctaactt ttaaggaatt     1380
aggtcattca cattttcatt gagctaagct cacattaaca agatcaatat tacttgtatg     1440
tagttaattc agatgtgaat ccttgaggtt tcaaaagtga cactttagtt cgaggtttaa     1500
aaaatattta tatatataca catgttacaa cccaaattta aggtatatat ataaatatat     1560
ataatttaat tatcttgaat tataattacc ttaaattact taaagtaaag attggtttat     1620
ttatgattaa gttatgatga atgttaagta atttgaaaat ttgaagttta gaggattgtt     1680
aattcacttc attgtgggcc tcattaattg gcccattaaa tctccatatg ggcctgtcta     1740
gggcttcatt tccccaagct tccaactgta atggcggcca cagttctctc ctccatctcc     1800
tctcttctta cctacttatt atgttaatat ctacgttttc cagattcatt ttcttttttat     1860 ttgtattatt ctaaatctcc agaactgctt agctgctctg gttttgggg attttagggg     1920 gctcgatctg gtgggtttac ggttaaattt tgcagctttt cgaggtcctt ttcggcttcc     1980
attttgtcgg aagttacaaa                                                2000
```

<210> SEQ ID NO 116
<211> LENGTH: 2000
<212> TYPE: DNA
<213> ORGANISM: Cucumis melo
<400> SEQUENCE: 116

```
acacttgtaa tgttgagcag ggtaacttat ggtaaatttg acatgagctg gcgcacaaag       60
gcctagcatg ctcggagctg tttttccatg gagtcaatgc ttgatcgcat tattggctat      120
attctaaatg aaactaaaat tattgatggg ttccatctgt ttggatacca acttatacaa      180
caggtgtttt tctatttatg agtgtaaagt ttgatttgct tcatcatcgt atattcaacg      240
tagagtttct tagttaatcc aatccatatg cctcaactat catgctcttt tccctgtaat      300
tgaatgtttt ttttggtgtc cacatggtca tggaggtttt gttctgcact agcttcacga      360
tgctactaaa catgatgatg aagcttgagt ttatttattt cttagtactt tgtgatgaaa      420
aaaaagtaga agaaaacggt agaaaattgg aatggatacg gtacaatgga tgggttgtgc      480
taagtcacgt ctcgtggata caactacaat tagttatttt gttttgtaga tttcatatta      540
gcatttcctt ctgaatagtt gaaatcacca tagaatgtgt actgatgttt tgtgattta       600 gtgcttcggt ataatttgaa cgctttacaa gtaaaaattt cctcaggtaa acgagtcttc      660
cgaagtactt gttcataaaa tgttcttgtg tgggagagtt gattggagag atcatggtc       720 aaattcttct tggtgtgttt tatataaggt tttaatgatt cttttgaaatt gtaatgtttc     780 cttagttttt ttaagtgata ctggtggggtt ttccttggaa taaatattaa gggctgaaac    840
ttaggaatta tatggatttg agggaggttt gtggattctc aaatcaaatc aaaccaaaac     900
```

```
cagataattt taaattctag aattttgaag ttactatttg tgtttagaaa taaaaagaaa      960
gaatatcgct tctttgtcct tccaatattc tttagaacca aaagagaacc aaaattatat     1020
ataaaagagt cgataaaatc aaatatatat ctataatata gtttattatt attttttcatt   1080
tgctatcaat aagaattttg aaatgtaata tttgctccaa attatattaa aaacagctgt    1140
tgaaatttca acaaaatgag aatttgtact ctggattttg ttattagttt ttttttcaat    1200
atcttaaact atttcttaaa tattctcatt gcgagtcctt ccatttacat agaactaaaa    1260
atggattgag tttggttaga gaataatccc aatcttactc atattttttag gttgattaga   1320
ttggtaattt gattagcggt taagttattg ggttgtattg tttcataaat tcgatagatt    1380
acatcgatgg caatgtagtg tggaacataa aaaataatga aataccagcg gaacacaatg    1440
gagactgaaa aggatagacg atcgaagatg atgaaatgag aagctgacaa caatgagggg    1500
cgtgagttga gaagccgaga caagagggag agagtgagtc ggaaagagat gtggggcgtt    1560
acaagttgtg ttgaacaaag tgaggtcaaa tttaaattta ctatttgcta aattaataat    1620
aaaataaaat ataaatataa acatataaat atatatatga ttgggttggg ttgatacaaa    1680
atttctaacc ctaactcgat aaagcaaaat gcaacccaaa ttttaaatta accagatcgg    1740
gttattctta tcctaacctt aggacagtga ttacttaatc tgtacgcagg ggcaattttg    1800
acctttgata aactctccca ttttgttttc ttttttcggc aattttccct ccctctctag    1860
tctcttctgt tctcagttca gctctctagg gttttgtcga acagccattt ctaagtgtac    1920
atctcctctc aatttccctc gctttattcc attttttcac gtactatcgg cggatccttt    1980
gagctccaac tctctcatcc                                                 2000

<210> SEQ ID NO 117
<211> LENGTH: 1025
<212> TYPE: DNA
<213> ORGANISM: Cucumis melo

<400> SEQUENCE: 117 ttttttcttac ttcattatcg aacaataatt tgatttccaa gcgaccctttt caaattcaaa    60
caaacccatt tctcctctca gccagagcaa gtgattgaac tgctgcgctg cgcgtgacct    120
gttatcttct ccgttttttct taccgccgcc cgcccctcac ggcggagtag tttcaccgcc    180
gacccatttc gccggccgcc ggcggtgttt cgattcctct tgttttgtcc cttttcgtct    240
tacccagtttt ctctctgtct acattgtgtg ctcgttaaca gccagctgta tagccactgc   300
ttttttttatt gactcttgaa acagagagat aggggagatt ctgtatagtc ccactgtttc    360
tgctcaactt tttcggttta atgtctgttt ctatattcga ttcttcgttt tatgttcgtg    420
attcgatatt gcttttgctt ggaatcgttt agaggcaagt gattgtctct gcttttgcta    480
tgtagttact ctgtttttttt tccctttctc tctctctctc tctccccccc tctttctcaa    540
aagggggttg gtttttttat cgtcggagga tgttgggttg atcttttgat agggtctgtt    600
gactaattta gctggtgttc ttggtctgct gaatccgaac ttctcttagt tttagagttt    660
tcgatgttgt tggtttacac tgattcttct tcgtttgttt gggattattt ttgacaggac    720
tatagtgttt aactgctagc tgccatggaa catgcagaat ctgcggtgag tttttagaat    780
aaacttgttc ggttggtgag aaaagcatgg gaaagaggag ggggaggttt tctttatgt     840
caaatatttt ctcaaactca ggttttagaa taaaaaagcc tttgtttctt aaccaaatag    900
tttatttgat aatcagctgt tttgttttag ctccctcatc tcattttcgg aaatcttagt    960
tatcagttta atcaactctg tgttctatga tgctcatttg tacttaggca aaggttataa   1020
``` agaac                                                          1025

<210> SEQ ID NO 118
<211> LENGTH: 2000
<212> TYPE: DNA
<213> ORGANISM: Cucumis melo

<400> SEQUENCE: 118

```
tgcattttat cagagatgaa attgaaaaag gaagaataaa cacgtactgt aaaatcaaaa      60
cataagaaac ccagctgact tagcttgtta attaaccaaa caaagtttga gcattgtcta     120
aattaaagtt gttcaacttg actgttgtag ggttattaat ttttcttgaa aagaaaacgc     180
agcatataat attaaaggag tattttgtct cgaggggaaa gattattggt taaaagtata     240
tatggtgtga cataattaaa tactttgtaa ctaaaaaata aaacataatg ggaagttatc     300
tctaccaatt tttttgttaa agggctgaat atataacctc caacattact tagttactga     360
tatatcagtt tctctagccg tcaacagtac tacatagttg ctgatcataa atagaagaaa     420
caagttagaa attttgtgaa gagaaaggcg agattatgtg attttttgctt tgtataattt     480 tgaaaaccct tgatataagg aagttccttg ttgctgcatg ccttcttaga gatcagcagt     540
tactgtatgt ctatatataa ttctctctct caatattttt ttctgttctt gagcttgatt     600
gtttactgct tcagaaatct tctttacaac tactactgta tttggaagtt ttagttccat     660
atatatttct attttttttaa tgatttcaaa tcttgttgtt tcaaacagta ctctcctaat     720
tacaaataca ataaaattat atctagcatt acaattttac aaagtccttt tcttgtgaaa     780
aataaattac gtgagacttt gtaaatggta ttttgaatgt attaaggtac tatatgacac     840
ttagaattgc tttgctttag ctctaaccat gggttcaaat gtaaagttaa aaataaaaca     900
atcaactatt taaggtttta cttaaaaatg taattatttg tcaaaataag cataataatt     960
gagtagtaat ttacatatat tgcctccaca tttgagatca aaactagaga tgttcatttt    1020
cttagatata ttattaagct aagaatgaga gaatgggtga ggggaaaagt gaacggaggc    1080
aggaagacca aatcacccat tcctgaaaat ggaaggatta aaattgcaat tttccttgca    1140
atttaatacc aacatgattt tgtatatata tatttgaaga ggggttttaa aaaaatataa    1200
caaactgtta aaatatttac actatataca acaatcgtta agataaaaaa actcataggt    1260
ccacaatgaa aaatataaca aatgtcatag tcaacacgcg attaatcagc cacactcacg    1320
ttcgagtaat cttcttctga atgattgtgt attacagtca aaatacacaa tcgtagagtt    1380
cttttctaat gatgttgaaa aatacttcaa atttagggtt tagggtttag ggtttaatga    1440
tcgtgttaac cgtgaaaaat aatcgtgtta atcaatggaa aacgatcgtg ttgattatga    1500
taagtgatcg tgtagtccaa tgtaaacgat cgtgtttgac tatgttaaat gatcactatg    1560
gtaagtgatc gtttaaatca tataaacacg acgatcatgt agttcttttt aaaagatgga    1620 aaagaattc aaatgcaaac gttcgtgtta acaatgacaa atcattgttt agatcatgtc     1680
aaaattaata tttaaacgat ctattgatat tcttaaatag gaggaagatg aagtagttct    1740
aaagaatact gtcgaaaaca ataaagatag aatatgatat ttaaattaaa aaataaatga    1800
tatcggaaga gaagatgaat aaatcagaga aacagatata aaaggggaag tgactgatcc    1860
tccaaatcta aagataaaaa atattttaca tgactctgta aactttggtt tcttttgcta    1920
ggcagtaaat atttgagggt tttggtattg tatttgtggc ggaatggagt aagtgggcct    1980
ggcattgggc cgtatacgta                                                2000
```

<210> SEQ ID NO 119
<211> LENGTH: 2000
<212> TYPE: DNA
<213> ORGANISM: Cucumis melo

<400> SEQUENCE: 119

| | | | | | |
|---|---|---|---|---|---|
| tcattccaga | aaaggtaatc | tttgattttg | agaagttaat | ttgaatttta | ttttaaggga | 60 |
| attcaggcag | caagattaat | catctggctt | cctggaaaaa | ggtcaagttt | tctcaatcag | 120 |
| aagggggggct | aggtttgggc | agtttaaaaa | ataaaaaaaa | taaggccctc | tttctttact | 180 |
| aaataaatgg | tgttggaggt | ttttgaaaga | agactccaca | ttgtggggta | agttatcaaa | 240 |
| agtatccatg | gcttcaaaaa | aatttaattg | gcagactcta | aacaaactag | aaaatagcct | 300 |
| tagaagttcg | tggatcatgg | gaaagttgag | ttggcaactt | tcaaaacaga | gaacgaaagg | 360 |
| agagtaactt | tctggacaga | ttcgtggatt | agtgatctcc | ctcttaaata | tccatttcca | 420 |
| aatatattca | gattagctca | acacccaat | gattcaatta | ctgcgcactg | ggattatgtc | 480 |
| actaattctt | ggtcattagt | attttgaaga | ttgctaaaag | atgaagaaat | tcaagatttc | 540 |
| caaaggcttt | taacactcaa | atcctagaaa | gtaatagact | tggatgatag | aagagtttgg | 600 |
| tcattaaaaa | cctcaggcca | tttttcagtt | aagtcccttt | cgaagcacct | ctctccttct | 660 |
| tcacctttgg | aaaagatta | ctttaaagca | ccttggaaaa | ccaggagtcc | aagaagaata | 720 |
| aatgttctgg | tttggattat | agcagtgggt | tctctaaact | gttatgagac | tatataaagg | 780 |
| aagcttccta | atatgtgttt | actaccttta | gtgtgctcca | tttgcttgaa | aaacagtgag | 840 |
| ctcctaatac | acttattcat | tttttgtccc | ttctcatcta | cttgttggtt | tagcatattt | 900 |
| tctatgctca | aacaacttgg | gtctttgatg | gttcattaaa | caccaacgtt | gttcctaatt | 960 |
| ttttaggggg | tccttattta | tatatatata | taaaaaaaa | actttctaa | tttgggttaa | 1020 |
| tttgataaaa | gcactcctag | ctgagatttg | gtttgaatgt | aaccaatgca | tcttccatga | 1080 |
| taaaagagag | agagagagat | tgggttgaca | ttgtagacaa | ttctaaaaga | aacgtggtag | 1140 |
| cttggtgttc | ttcaaatgca | gaattcaaat | gcaggatatc | tacttattgg | actaccttca | 1200 |
| tatgaagaga | ttcaatgcag | tttccccccga | ctactagttt | agaatttgtg | ttttttgtagt | 1260 |
| tttaatgggc | tgtaatatgt | atttctacct | ttaagttttt | acttttcagt | cttgcttctg | 1320 |
| tctaccatag | gtagtattgt | tattttgggt | atttactttt | gtcttttcat | gaccttagtc | 1380 |
| ttgttcttgt | attttggata | taatgagggt | gctatcgggg | tatcaaccta | gttgagatgt | 1440 |
| tcgagtgcac | ctactgatcc | ccttatttgt | aggcttctct | attattctca | atgtataact | 1500 |
| ctcttgtact | ttgagtttat | caataataaa | gaagcttgtc | tcattctaaa | aaaacaaaaa | 1560 |
| ggaaaaggaa | gataattgct | cctaatcgtt | gaaattacta | ctaattactc | ttaattactc | 1620 |
| caaatgatcg | tataacatac | atttataatt | tttaactttc | ttttccttt | taaataccaa | 1680 |
| cattaaattt | taaatacatc | cattaatttg | aaattagttt | tcaaattcca | aatcgaaaga | 1740 |
| tttaaagtcc | tttgaatcca | aagggagaat | gagcccatcc | aagcaagttt | ttgtgtcgta | 1800 |
| gttgcatatt | ttaagtcgtt | tcatattagc | ctcgagtttg | gcttaatgac | ttggtggtgt | 1860 |
| ctagtgcagg | cttgtggcga | ctggcgagcg | tggttctaaa | gataaggttt | gcattcgctc | 1920 |
| cttctcctc | cctttcacta | cttcatatcc | atttccttc | tcgatttctc | gtcttccctt | 1980 |
| ctgaattccc | cattccagcc | | | | | 2000 |

<210> SEQ ID NO 120
<211> LENGTH: 2000

<212> TYPE: DNA
<213> ORGANISM: Cucumis melo

<400> SEQUENCE: 120

```
atttatttgt ttagagataa gacgcacatg agaatatgag atggattcca ctccactcac      60
actccaattt ctacctatcc tattactgtt tactattatc attccacccc tcgaccsctc     120
attcttcttc tcaccttact tttttatgat ttactactac ttcattttgg atcacaatct     180
gatcaatgct gggtgggctg ccctcggcct gtcaccaggc ccagcccact tccaaattaa     240
acctcttggc ccaccgccca ttgtccccat ccattccat ttaatattcc caaccttccc      300
tttttcttc ccaatgcgat gcttctccaa tatccttc ctgccctcca tgtttccttt        360
ttactgcttt cttatattta aacacacct tctacagtct tttggctggg aatgctgcgt      420
atgtgaatga gattcaagat ttcgttgatg ttatttgagt ctctatattc ataagttttg     480
ttcttagttt tctctagacc aactgcaaga gttagcgttc catatgctca taagtttcag    540
atttctgctg tgtggtttga agacagtcat cgatccatgg gtgaattcgg ctttttatta     600
ttattattat tattatttat tgttgtctta cttttctatt tgaatcttcc tatctttta      660
ctcattgttg gactctaata attcttgcta aacacaatct ccattttat tggacatttt      720
aaatcccatc tcaactcata attttagtta ccttccacca tcaccatatc caaatccgaa     780
ataaactcaa ataaaatcct tcacgtgcat gtgctctcca tatatttttt ctacatggta     840
aaaataaaat gaaaacaatc taaatttaat aaaataacat atatgcaga cttttattga      900
tgtagagact gggtgttgta caagaacagt gcagccaaga aaaaaaaat acttccaatg      960
aatcgtacat tttaaggatt atgaaactaa ctagttccaa ccattttttc acgaccacgt    1020
gcttgttaaa cacgcaagta gaatcaaaat gtgggcttct tcgctttata taactgtgaa    1080
tcattctcca aaaagggaag gggatctcat tccctaattc aataaagaaa agaaaaatg    1140
ctagcgaact tcatccatct cattccttt acctatttca tgagatgccc attgtatata    1200
agtattttt ttttttttat ttcattttac ttagtttact cctcacctct aaaaaaaatt   1260
aggagagttt gctaaatcca ttctcaaact tagctttatt ttttaattt tatttaaccht   1320
cgtcgtggat gttaacctca aatgtcagtt ctttttattc tatttattga tgttataatt    1380
tactttagga ttccaatttt ataaaaataa gaatacaaat aaagataaag agtgtgaaag    1440
ccagaaagaa aaaagggaaa tcgtaatatg ggtaaaattg gtacaaattg ggtcccgtta   1500
aatattaact caaaaaatgc gagaaaatgg tagaaaagga aatagggggt aagagcaaag   1560
tagtggaagg agagcattga acatattctc tagtttttgc acttggatct aaacacgagg   1620
aattataggt ttattcattt actaattaca taaataggat tggattttaa aatttgaccg   1680
agtgattatg catatttgat agagttagaa aatagtggtg gggcaggtac aagttacaag   1740
taatgtataa gagatatgat gagcatatta ggaaactata gatttaaatt cgtccgtaaa   1800
taaataatta gaaatataat attcgagtgg aagggtatta gggttaggcg aaaccaattg   1860
cagttgcacc tataaaaccc cttttacgcc tccacccgct tcaacagcgg tctcggcgtc    1920
tacaactaca cactcacac tacacactac acactacaca gttgcagacc agaagcataa   1980
cgtaacgccg gtccacaaaa                                                2000
```

<210> SEQ ID NO 121
<211> LENGTH: 2000
<212> TYPE: DNA
<213> ORGANISM: Cucumis melo

<400> SEQUENCE: 121

```
tgaagagccg aaaagcatg gcaaggtcaa ggcatttcag caagaatacg aggatgaatt      60
ctgggtttgt aagtccggtt cttcttcgga gttgtggttc gaatttcaaa cggccatgag     120
gagccctaca gcttaggaag cttcaggtct gagactctga ctccgacaga aattgctgat    180
ttttgtgtgt gttttgaata accattgtat gagtatgatt ggttgtatag gtttgaaatg    240
agggaaagtg atccatctcc ttgttgtctt tgcaggaaag gctcatattc gaccaagaac    300
gctttgtcat tgctttcgat aatcatagaa tccacaatgg tttggcatat agcaaacaa    360
atcttcttta ggcattgcag acagaaaatt ggagagtaag ttattataat taaggattct    420
aaatgagtaa gaataataag atcaggcaaa gattggaaga actaaagcgt ttagtatttt    480
gtgtggtaca gaagaattgt aattagatac gtagtctaga gaagcagatg gtgagatttg    540
tgaaagacaa atgttagtgg agagtgaaga gtgtttctca acaaccgaca tagaaggatt    600
ctcagaaaat gagaaagatt tttattgcgc aaaatagctc ccatatcatc atatgccgtt    660
gccattccct ctggggttgc atgtaatgag taatggaaag ctgtagacag gctaacttca    720
cccttttgtct tgggtatagg gtgcattttt ggtcactcca ttttaagttt tctaataata    780
aaaggatgaa gaaaagatat tgaaaaacag ctcaggtttt aaagttgtca cacttgagaa    840
taatgcattt aacagttaga attttgcatc aacgtctttc aaatagaaaa gtaaaggaga    900
gtctagtttg agctgatag ctaaactggt ttaatcatat cttctatcaa gtggttagag    960
ttttagacct cccaacttta tatgtcgttg ccctaacaat gttgatggat gtttagtcct   1020
aagctctaac attgtccccg tatcatattt cataatagaa tgtactgagt aatggaaaac   1080
tagagaggta ggaagttgga cgaactttga atctatattg attttactat agtctttctt   1140
ccaagtctta atgagagctt tagctaaagt ttttcaaaaa ctcaaaagaa gttttttgttt  1200
tccaattctt cgatccatag attgtcaaga tggctataat atccttgaag ttaatagcct   1260
tcaaagtttc atagctttta tcctatgatc tttagaaatt caagagttat attctttaga   1320
actacagaac tttgatcttc gattcttcac ctcttccaga acctttatag tagagtttct   1380
tgaccttaca tgggcttggg attgggcctg gctacttatg ggcttagaga ttgaccttgg   1440
gtttaagcac attcgtttta cttggcccaa ttttcttaaa cttctgcaaa atcctaatta   1500
actaacacct caacaaaagt ccagtattaa atgggggcata taaacaaaag ttaaacaaaa   1560
ttgtcgtaca gaatcctaat ttgctaacct cagcaaattt tatgccattc gtccttgtgt   1620
atctaattag tgttaatttg aggaaatata ataatataga cgtaggacgg atattggtat   1680
ttggtgcaac atcctccgaa ccaattcctg gaaagtaatt ggggcaacaa gataatgtta   1740
tcgtcagttt caagtgcaaa acttgccacg tggaacagcg gcaacatgat atctcaaata   1800
tggacctctc acccggtcaa gcttccacca ccaccaccac ctccgtattc taaaataaag   1860
tcaggaacaa gaacagacac accttaacaa aaccatatt cttcatctct atctctctct    1920
catttcagca tagaagagag ctgagtaaaa ggaaaaaact tcaatcaaat ttgacagaga   1980
agagcccaag agaaaaccaa                                                2000
```

<210> SEQ ID NO 122
<211> LENGTH: 2000
<212> TYPE: DNA
<213> ORGANISM: Cucumis melo

<400> SEQUENCE: 122

```
agatgaacca gaaagatgga aaatctactt ggggttcagc agtgagtttg gaaaagagag      60
```

```
aactatttga agaaagagca gaaaccatct tgctaatact taaacaccgc ttccctggaa        120
ttccacaatc ttcactagac atcagcaaaa ttcagttcaa ccgggtaaaa gaacgctcct        180
tccttgtcta taatctcatc taaaattatc aacaatccaa acacaattta tacaaactaa        240
aatgaaagct tctcaacttt aggctacaaa acagatgct tattataatt ctgcccaaca         300
atatcttctc ctaaataaga tgatatatgt ttttgccca tataatcaaa taggaaataa         360
caatcctgtg cccatttctt tggagtgtga gatcataaaa cactgtctaa acaacatgt         420 ccaaacatat cgtaaatacc tagtttcata gtgtgatgaa ccaccacaaa caaacttact        480
ctttggtgaa ctgcaggacg tggggcacgc cgttttagag agctactcca gaatactgga       540
aagcttagcc ttcacagtga tgtcacgaat tgaagacgta ctccacgccg ataggttaac       600
tcagaaccca tcacaaatag caacaaggag gaaaccgacg agcgaacccc caatggagaa       660
atcagaagag ttgaacaaca acggcccaga aacgccagct tcaatgacgc tgttggattt       720
catggggtgg ggacaggatc aaaacgagtt ggagatgaag aaggaatggt ttgggaattc       780
agatgattta aacgcggatt cagatctgaa acaagggaat aagccaggga atatagtgac       840
gaacaagagg gtttcatacc tggagaattt gagcgctgtg agaagtccaa cggcgcgcca       900
ttgaagaaga agaatagata gagagatgat ttggaggcaa aattccatga tttcagttat       960
atacattcct tttgtgtaaa taggaagaag aagaaggaga atgagatcaa ccccattttt      1020
ttctctcttc tttttttaat ttggattttg gaatcacaac tctttgtgtt tgtgtaaaac      1080
caaaattgtt ctatgtatca tttgtatcaa ttaatgtagt cattttagat tcatacattc      1140
aaaaatatca actccatttt ccaactacta tcttcctcca tctcacctct aatcataatt      1200
caaagcggat acaaattcat gttagaatga aagattcgag tatagcctat tccattgatc      1260
aaatgcatgt atctatacta ttgacacttt tcaactcaag tcatgcttga acaattgttt      1320
tttataaatg ttaattacaa gagtgtacac aaatcgagtt gggaaaaaat atgaaccaac      1380
ccaaaccaaa aactttgagt tggaccgaat ttgaataaat aattcaattt tcattatttt      1440
tatatagttt ttcaaccaaa tttttttatct ttttttttctc aaatttcaag tttacaataa    1500
tgtccattca aaagtttaaa ttttcatatt tcgaacattg aagttggaag gtccaaacga      1560
aagaactaaa tgattatgac acatgtctag ggtttatata tattgttgag ttgagtaatc      1620 caagttttttg aaacaccact agttatttat gttaaataat taactgagta ctcgactttc    1680
ttagttcgag aatatttttt agaaaaaaga agagaggatg tgtttagaaa taatagcaag      1740
ttagggtgtt ggtgagtgag aaatattttg ggatcttctt gtaatagtta ttaagaagat      1800
ttttcaaaga atttgagagt taaagaaata ataataataa ataagtaaac atttaatagt      1860
aaacgacatg tcgtttttata cagcatcgta tttacttacc atgtgctcat tcacacacga     1920
ttcctcctcc tcctcctccc gttcatctct tcttatcttc gtcttcttca tttcggataa      1980
cacaaaaatc cctaaaaaaa                                                   2000
```

<210> SEQ ID NO 123
<211> LENGTH: 2000
<212> TYPE: DNA
<213> ORGANISM: Cucumis melo

<400> SEQUENCE: 123

```
tcattttcgt ttggttaaag aatatatcat cgtttctttt ataaaatgtt tttgtagaat          60
taatcttcga gtacttctca taaaaacatt tttttttaatt acatagagtc agtaataatt        120
```

```
agaactatct caaaccaaag tactataaca tttcaaacca taacactgta ttttttagaa      180
aagttattgt aaaggataga attacaaaaa tattatagca tatgaaacat tattgttata      240
ttttataaat attccatata caatataatt gattctagat gtctctaaaa atagggaagc      300
atatgtgtta ataactaaat ttaaaaatta aaaaattact cgattactgt ttatttattt      360
atgtgttgag gctatacata ctatatttta gtaattattt taaaattaaa aacaaaatca      420
catggctaat agaaacgata gatatctagt agtaaaattt tgttatattt ataataagtt      480
gtcttatttt acttaatgta actacaaata tctcactgtt attttccttt tttttcagc       540 ttattggttt atatgtttag aaaatttggt aaaatatttg tgtagctgcg gttatcatgt      600
atcaacttaa ctatgtaatc tatgaaaaaa tagtcattct ttaaaaaaaa aatgaaaagt      660
taaaaaagaa aaaaggata aatttataac aatattcttt aattgaattt tatcatttga       720
ttcaaagata ttcttatact tttaaaagct gcaatgttat ttatgaaatt gttttaaaat      780
tacatttata atgaaaaaat ctttaaaaat gtagaaaaat caaggcttag aattgtattg      840
tcatttccat caaggagagg atgtaatttt ttctttatca ctttatttga atcctcaaat      900
tttcgataag tatatatttt gacatttgag aatattttg tttactttaa atttaaagtt       960
attttttaaa caaatgaaac aaaatattca taacgtggat caaatcacca taatttagaa     1020
agcgttcttt tgaaacatga ccccaaaact ttagaagata aattacaatt tgaactattt     1080
tgaaaatggt agcaaggaga caggtaaaaa aagaccacat aaatcacttt aggctttaaa     1140
gaaacaatgt taattggaga agattcatt ggcatataat tttgaaatat gattgtattt      1200
tatatttcaa atcatattcc atgaatttat ctatctttgc ttgtagtcta aatcatgcaa     1260
actttgaaaa taacaatgtt attgtatcaa aatttaaaag tttaaaacat ataattgatt     1320
aaataaagaa aaatatttag aaatgttgta tgccaatagg tattatgtaa taattataa      1380 atgatataat attaaaaaca ataattcata ccatttttta aacataaaaa catgcttagt     1440
agattagtta taaacagttt caagtaatat ttaaaagaga gtcataagta gttttataat     1500
ttataaaata caatatcaaa cgtacttaaa actaattgct tttaacttca aatctaaatt     1560
aagaataaga aaagggagag tgggaaagag caaaatgaga gaaaatgtcg aaaatacgcc     1620
caacggttcg gaccggtcca tttttgtccc gcgcaatggt aaaaatagat taggttacga     1680
caatcaccat gatgatgagg atgatgatga tcatagcaat tcaagaagca tagggcccca     1740
cttttggccc tcttattttc tcttctctta cttactttaa agaatctaac tgtcctccat     1800 tacccgccg atcaatgctc tattttctc tctctttttt cttttcttta ttaaacaata      1860
ataacaaaaa ccatcaaatt ttcaaaattt tgaattatat tcccttaaca caaacactc      1920 tcctcttttc ctttctctta taaatacaag tggagctcca cacacttgtc attttgtacc     1980
cttcttcccc aacctcccaa                                                 2000
```

<210> SEQ ID NO 124
<211> LENGTH: 2000
<212> TYPE: DNA
<213> ORGANISM: Cucumis melo

<400> SEQUENCE: 124

```
gggcttccat tggcctcctt cccgtcgccg tagtgagaga aaaagaaag aagggagga        60 ggcagaagaa tttgagagat ggatcgagga gaggttttgg aatgaatggg aaatttgaag     120
gaagaggttt aaacataaaa gtgaggcacg tgcgagaatg caaatattta cggggctaaa     180
aatgggagag ccaacggatt caccccagta aaaaggtaaa ttcaaacacg tttatgcctt     240
```

```
tttaccttttt tctttctttt tttaacacct atagatgtaa gatatttcat attcttaact      300
ttctctttct cttttctttt ttgttttact atttcccttt cgttggctaa taataaaaat      360
tgatggatac agtatatttg gtatgtcatc ataaatttag agaaggtatt aagattttgt      420
gacataaaaa cccaatttct tttaatgaga ttccttagaaa ttttattgaa gagaattata    480
aactttacgt aaattaggta aagtctttcc ctccttctcg atagaagttg ataataaaca      540
tagcatacct agataaaagt ttgggaacat ttttgttgtt tggaggggttg aaaaaaatta     600 agaaatttca atttggttag gatttgatgt cttgattttt tgaaatataa actttcaatt     660
ccaaatggtc ggacttggaa cctaacaaat cgtgttttca atttttacctt gatattttag    720 atgtgtgaga ctccattaag tattctcttc gctctcttct tactatttct ctgttttgct      780
atcgaacgat atttttttta aaagatttat ttttttaattg gtggaatgtt tgtatgagag    840
tatataagtt aaggtaaaca aataataatt ggttatttag caatcttcct agtcaataag      900
caaaacagac ctaacatgca tcaaagaaac aaaatcaaaa ccttaaaata tcatggttgg     960
gcgttgattt ttttttttctt ttaatgtttg aaaatgtggg ctttgggtgc cgcagtcgta    1020
tggttgtagg gatttctttt aagaaaatta ttttatattg tattcgttttt gatctgaaga   1080 tatcaattat acaataattg gaatataagg agtaatttaa ctttgttcgt gattgttttc     1140
tactttattc gatgtgtatt ttggaattaa atatgatttc aaatgatttt gtttatttct      1200
ttttattgat tttgttttga ttttactttg tatcaatttt gaatatcaat gtagtgatgt     1260
gcttgtatta aatgtattgg ttgataaatt tactatgcaa atttttttttc aaaatttatg    1320 caattcattg tagtattatt aactatatca acacatcagt aaagtgaatc attatcaagt     1380
atatcaatta agttacaaag tgtatatatc aataatgtat caagtttatc agtagcactt     1440
taagcatata aagtgtatt aatcaattaa ctgtaccagt gaatcttact agatgtatttt    1500 gcagtacatc cgacgtatca aacatatcat gtgtatcata tgtttaaatt tgttgagtat    1560
attagtgaaa cataacaagt ttattagtag tgcatcaagt atatcaaatt tatcagttaa     1620
acatttaagt ctactaagaa aaaatgagtg caataaaaat tattttttcgg atatataaaa   1680 aaatattgag tgtatcgaag agttccatgg tgcatcaaat atataaagat aaaaaaatat    1740
caagaaatat taaatgtata tccatatatc aagaaacaaa cctaacatgt atttcgtgat    1800
ccaacaaccg gactggaaga caaatttcgg cccgggactt tcatagtcca aataaaggcc    1860
cattaaactt aacctgggcc caaattaatt tgtaaatttt aagtataaaa agaagagaaa    1920
ccctagggtt tccttcattc accaggcctt cctatcccct tcccttcccc ccctcccccat   1980 tcccattttt gccggccgcc                                                 2000
```

<210> SEQ ID NO 125
<211> LENGTH: 2000
<212> TYPE: DNA
<213> ORGANISM: Cucumis melo

<400> SEQUENCE: 125

```
ggacttatgg ggaatgggtt caagtgatgg taactagcta cttcagattt aatatcctaa     60
attgccttgg caacccaatt caaatgtatt aggattagat aggtgttttg tgaggatagt    120
taataaggtg cttgcaagtt ggtgtcgaca ttcccaaatg tgaagggaaa aaaaccccaa    180
tctttggtct caactggact ttggttcatt gcagttgaaa ataaattatt ttagttcaaa   240
ccaataaaac acatttttta aaatctttgg atatttgttt cttaaagttc ctgaaacagc   300
```

```
ccaccaagtc catagcaatt aggaaggcat aagttagagc tagtatgctt ggcatggttg      360
ggggtgggtt accttgttat gtaaattcat agaaatattc atatcttgtg ctaaaagtca      420
aatggaaaga gggtgattgc tgtgatgctg tctaatacaa agtgctagaa gccatatgga      480
gaaagggtat ttctacagtg tctaataagt taattacata ataaatttct aggttatgag      540
aatccaatcc gcatgaattt aaggactgca cacttgctcc atttgcaaca tgtgtaccac      600
tttagaatca tatttcacct gagttcatta ttcaactaga ttaatgtatc tcttttggtg      660
ttacatgttt ttaagaacat aattatttta gtttactgtc ggagagaagc aagtactggt      720
tatgcatggt tctagtgagc ctaatagagt aaggctatgg tttgggcatt tggaagtttt      780
agtggattag aattttgaag gcaaagctaa ggatcataca cgcccttctt ccctttttgac     840 cagttggaga tctatcatgt aactctattg tcttgggctt cggccttatt ttataaattt      900
catatatcaa tgaaatttat ttcctataaa aaaagaaaa aagaaaaaaa gctaaggatt       960
ttaatatcat tgttagtttc tttaatttt tctttggga agtgtgcatg tagagctcct       1020
ttgaaagaga aaaagcaaag aactcttgaa tgtaaaatct ctatgtttga gttttatagt     1080
agcgtaccac attcacttca tggtgatgta gttatagttt tcctatggaa tatggctatt     1140 aattttgcg aggctcttat tttatagttc ttttggggtg ttctttcctg tacccctcc      1200 ccttttgtg agaaggggag gtttctgtgg ctagctgggt tggtttagat ttgtggacct     1260
tttttgtgag aggaaccata gaacctttg atgaggacct cgagcactat ttgatcattt     1320
ataagtttcc ataggctttt gtaattacct ttttggtctt attttaattg gagtcccctt     1380 cctcccttt tgttggcttt tttgttgtat ggtgggcat tctttcgtta gggaagtttg     1440
ataattcaca taataaacat acaataaaca accatcaata caatcaacaa gcaggattag     1500
tgtaatactg taaatgtctt ttattttctt tactcctttt ttcttttgag gtctatgata     1560
attgatatcc aacagtgtat tggccaaaat gatttatcat ggtcagtacc ttaggggttt     1620
gacttccaat ccaggattta aggtttgaga ccagatattc tgtgcctcaa ggccctcaac     1680
aaccttctca tggcttttc ctgtatacat attattatat aaagttataa ccaataaaag      1740
ggacaggtca aatcctctta atatatgcga aaatcaacct aatgtctact gtataccttc     1800
tcaatcgcca ccttcctcct gctgtcatcc aaggtagggc cttattgtat cagctagctc     1860
cctttactta tttatttatt ttttgaagtg cgcagtttgt ttgtttacct tgttatagga     1920
aattcaatct attctcattt tattggtgca ttcgtctcag aaattcttgt acggtttcag     1980
gttatcatct acccttgtag                                                 2000

<210> SEQ ID NO 126
<211> LENGTH: 1397
<212> TYPE: DNA
<213> ORGANISM: Cucumis melo

<400> SEQUENCE: 126
tatatatatt aactttttaaa attttgaaaa cgtcatagat aaattatata caaaataaaa     60
agtttgatta tttacgaaag ttaaaaagtt tatccgaaag ttgactcaac gataaaaaca     120
ctaaatatca cttttagaga tgatgatatt atacataaac atacgaactt acgcgtcaaa     180
cttttatact aacacaagat caaaacaact tgttgagta gtgagaattt tatctgctga     240
tatggttgaa acttgggaag caagcagagg aagttccatt cattaccaaa atccattttg     300
tattcatcaa aatatgaagt ttagcgactt gataaagtca agtcaagtgg tcctatcgat     360
ttgttaatgt caatgtttgg ttttgaattt gataccatt agacaatgat atataatttt      420
```

```
aagtatggtt tacactgtga tgctttatat attttaaat gtaaaatatt agaacttgta    480
atttcaataa attttaaaaa tgattttgtg ttatttcctt ttttaaattg aaatatcaat    540
gtatcaatat tgcgtcatag agtattgcaa cacaaccta tgttaaattg tttattgctt    600
attgctctaa ttcaactcct tcatcaaatg tgcacagaat ttaaacaaga aaagagtag     660 gtgcttttt actaaaatat actaaaagct ttttatacca aatcttatga caaaatcatt    720
ccaacaaaat gactatttaa atataagatc gaatccctaa tttaaaaaaa aaaaatcaaa    780
gatgttaatt tctattatta aactcacttt agcgtagcta acaaaaaaag gaaaaatgag    840
aggctacaaa gcttgagccc tctgcctccc tttattgcat tgtttgaaat tagatcaata    900 ctttgtatt ttttcaaaat gaaaaatcgt acatagaatt aattctatgg acaaaaaatc    960
agagaaggaa ataatctaga ataaaattcg atttttaacc caaaaaaaaa aaaaaaactc   1020
gattctgatt tttgtaagca atcacccaaa ttaccataaa taaatggtat tcaattactc   1080
aattatggat atttagaaa tgataaattt ttattcataa actcttttct ttctctttca    1140
aaaagaaaaa aattagcata aacttcaatg acatttattt attcttcttc gtttggagtc   1200
aaaagtttaa attgagcatc agtccagccc aaaagcccac gaagaagccc aagaatcttc   1260 agcttttcg ttcaaacgtc ccttttggt ttataaaatt aaagaaaata aaaactaaat    1320
ttatttgtta tttaacaaaa catttttggt taagacattc tctttgatta ttttctcc    1380 attcttcgtc gtcaatc                                                  1397

<210> SEQ ID NO 127
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, c or t.
<220> FEATURE:
<221> NAME/KEY: unsure
<222> LOCATION: (1)..(2000)
<223> OTHER INFORMATION: unsure at all n locations

<400> SEQUENCE: 127
tttatattta tgaaaatgaa gtctctaaac aattttttcta ctcccaaatt tgttgattt     60 tctgcctatt ctttatcggt gctttaaaaa atgaaaccaa atttcaaaac taaaaaaacc    120
aagcttttaa aaaatgttta ggttatttt gaaattcaac taaatgttga actcttttac    180
ttattaaata ggcaaattat tgaaataaat ttagagcaag taagcttaat ttttaaaact    240
aatatactta ccaaatcgag gactaaaata ttcaaatact ctttaaaatt aagattaaca    300
ttaatcactt tgttatgttt aaaaagttgc agtgtcactt gaacctttt aaattaatat    360 aatgaaaatg aatccaactc aatatatata atatctatat tattaatctc gatgtcagat    420
gtttgatacg cacatatctc aaaaattata cctcaactaa catcggtgca cgatgtatta    480
tttcgtgagg ataaaaatcg ttttagtat aaattgatgg aaagattatt tgaattactg    540
aaaaatgcac cggtacatta tttgaaactt cccttcatt taaagaggct aatattagaa    600
aaagacacgc tgaggctatt tttacaatta atgtgggctg ttgacttggc ccagcccaaa    660
acataaaccc taaagtagca caaacaaacg cctctttctt cttgaaaccg catattaagc    720
gttttatcac ttctcaccac ctctcattcc tcctcttccg cacgttgttt cgctcctcaa    780
cgggagtgcc ttcccttgc tctccctcca ggttcttctt ccttctcatc tcatttccaa    840
```

```
gtaatttcat tccgtttctt ttctcttaat cgtatcttgt tcagactctt tcgcgttttt    900
ttttagttgc gccttaccag atctgtgttt tcactcgttt ctattcgata catgcttcca    960
agatccattt cttaatcgca tgtattcggt tgattggatg attgtctttt tgtaagtttt   1020
gattactttt ttggaatgga tcggttgaac caacggggtt taagtcgatg gaagtaggtt   1080
atgttaaaga tttgcttctt ttttttatg aagatgtgtg tgttcttttt ctttgctaga   1140
tgatgttatt atttgattgt tttaacagtc gtgttttgtt tttctgcagt ttatagtcct   1200
cggtcttttg aagacttgtc aagatggtta gtacacctct tgtcatcgtg attttgattg   1260
agtgatgtgt taagtgcttc tttaggttac agctaacgcg attttttata ttcaattgtg   1320
cctgtgcagg tgaagtttac agcagaagag ctccgtcgga ttatggacta taagcataac   1380
attcgtaata tgtctgttat tgctcacgtc gatcatggta agctacttag tttaagttta   1440
tttatgccga gcgtctattt aagaagatta acatcttagc tttcatttat tgtttatttg   1500
gtaagcatcg tttctttttc tccgaggaac tgtacatgtc agttcacatg acaataaaac   1560
gatcttcctt ggacattagt ttttgaagtt caattagacg ccaaattttg ttggttaaaa   1620
gatgcttgtg gagcatatgg acctaatgga atcagtactt tttgatggat ggacttgtct   1680
tttgttcttt tattttcaaa agaaattgca tgtgcaatta catcatcttt gatcgaaaga   1740
ttgggtaatt gggtaattgg ggtaaagaca tgttgtaaaa actaatgtta attatcaatt   1800
accattatat accttattta gtgcttattt atatcctttt tccccatttc agggaagtcc   1860
actctcacag attctcttgt ggctgctgcc ggtatcattg cacaagaagt tgcnnngatg   1920
tacgaatgac agatactcgt caagatgagg cagagcgtgg tatcaccatt aaatctactg   1980
gaatctccct ctactatgag                                               2000

<210> SEQ ID NO 128
<211> LENGTH: 1657
<212> TYPE: DNA
<213> ORGANISM: Cucumis melo

<400> SEQUENCE: 128
ggcaaaatgg agagaaaaaa gtttctccct attgccacat ttatatatag tatatagata     60
tatactatag acatgatgga gaatcataag ataaggtaag gctgaggaag attttgacga    120
tatagaatgg aaaattttga agatataaaa tggaagattt tgaaaatata gaataagatc    180
atcaaatgat agcaaaaaaa tccaaatgag tcagatgaaa cactacgcca aattttcatc    240
actccaaaat tgttgcaaag gagattgatt aatagggtat tatacacaat catattttc    300
gtagcatgat aattggttaa taattagaca taatggcaat caattagtta actaatacaa    360
cattttaggt agcaatatta aaattggaga tccggaaaaa aactaaaaac tcagaaaaat    420
cttgggcaaa atgagcacgg tttatcaaat ttttaggctt ttttggtaca attttgtcta    480
ggatgaaacg agatccataa ttttctttga gaagataaaa aaaattaaga tttggtgtaa    540
gatttgggaa gatttgaata atttttttaa aagaaaaaat aagatttgga aaatggtaga    600
ataacggtct aatgtctccc aagatgcacc gggaaagcaa aaacaaccaa aacaataaa    660
taaattggaa aattttaata ttttaggaaa atctcgatgt caatttcgtc taagattgga    720
tcgagaaaaa cagttttacg agttttttaaa aaatgtgtta tatttaaaaa taaaatcaaa    780
attgtgctac ttttgtcaat ttcccaagat aaaaatgtat gcttccacgt aaaaagtaac    840
attactaccc ttctttcatt taatctctat atttggaaat gtcgcactag ttcttggtag    900
ctaatatttg gatactaatt atcttatatg acaaaatatt taatgtactt tttttttaca    960
```

| | |
|---|---|
| acaaatattg aatgaactta aataatcttt tcactgcaat gaaaaaagat aaattagagc | 1020 |
| atcccaaaaa gatgaaaagt tcgaaagtct gctaactaca ttgaaaaaca aagcatttaa | 1080 |
| ttcttcaaac ttgatagttc aattaaattt ctaccaacta actcaagtaa atctattatt | 1140 |
| agtgttttgag tgaggctatg aactctaaga ctaagcctat aagtttggtt aaatttaatt | 1200 |
| ataccagccc ttttgtaagt aatttgattt gaaaggtaag acgtaatacc gattacccaa | 1260 |
| cccaaaatta ctgtgaatga gttaaaaaat aaaattagtt gaattttaaa taaaaagcat | 1320 |
| accaataaga cgatgacaca tgtacaaaat cttagaagga gaagcttcat ttgaggacaa | 1380 |
| aaaagagtgt gtggagtgag aagaaagaat agtcacgaat attgctgact gtgcaacaaa | 1440 |
| tgtacatttg gcaccaatca aaacctataa aaccttatcc aaaaatcaat aatctcatcc | 1500 |
| cttcttcgct gttcttcccc aatccaaacc ccaaccattc tcctccacac acacacacac | 1560 |
| tcacatacac aaatccttcc aacattattc tatacccact tcccaattct cattgcattt | 1620 |
| cacaatcatt gttctaactc acttacaacc tccatca | 1657 |

<210> SEQ ID NO 129
<211> LENGTH: 2000
<212> TYPE: DNA
<213> ORGANISM: Cucumis melo

<400> SEQUENCE: 129

| | |
|---|---|
| atgaacgaag gagaatatcg gataatgaag aggagatcca tgaatcacag agaatgaatg | 60 |
| aaggagaccc acgtgaatta aatagaacga aggagaatga agagaaagga tgaatacttc | 120 |
| ttttctttaa ttttaaccta atcgggtgaa tcaaactcaa atcgaaactg gtttagttcg | 180 |
| attatgtttg gtaccattgt cttttaaacc gatcaaacct gaaccaaacg aatcggtacg | 240 |
| gttttttgca cccctaattt atatcatgtg aaaggtttta agttaagggt cagctagtgt | 300 |
| cgtttagagg gaatgatatt ggttgacttc atgtcgtctc ttggatcaag agtaggagat | 360 |
| tcgggagggg tgtgacgaaa tcaaccccga gattgtccta cagatggcat gtaaaatgca | 420 |
| tcatatctcg ggactccttc tacaaactcg agaaaaatgt ctcttgagat tcttcttcta | 480 |
| cacagcccca aattgatgaa atgactgaga ttctttgaaa gacaccacat gcattaactg | 540 |
| aaactaatgt tgtacatcta aaaaactaca tcacgccacc aactaaaaag ttttccattt | 600 |
| gcctgatttc aaactaaaaa caaagagactt aaacgataaa ctaaaaacta aaccacaaac | 660 |
| aatgaaatcg ttaaaagtgc accttgagag atttaagaga gtaaatgagt tcacatagtt | 720 |
| ttttgaagga aaaatcacta aaacaagttg gattgtagga gcgaaattgt tcactcctta | 780 |
| accgaaatta gcaaaatgtt tggagtttag cgttttttaga gaatatgtaa cgttatgaat | 840 |
| aataagggta ttttggtaat ttgatatatc cctttatttt caattttta ataaaaaaca | 900 |
| cacatcttgg tgacacactc gactgaaaag gaccaagata tttccttgaa agatttttt | 960 |
| ttttaaattg ggaagaatc ttggggtcga tctcgatcga gattgatcga gaaaaataga | 1020 |
| attacgagtt ttctaaaact gtgcttttga aatatcacac caaaaaagcg ttatttctca | 1080 |
| aaatttccca gtttatatg tggggttat tgcgagttag cttttgatgg gtttgctttt | 1140 |
| gggtgtttgt ataggttt gaaatgtacc tttaatgtcg attttgaag aaaggtacct | 1200 |
| ttattgttta aaattgacat tgtaccttca tatttgattt cagtttaaaa ttgatattaa | 1260 |
| ttatccgcat tttaaaaacc aacatcaaac atccatgttc atttcttttc aaatttaagc | 1320 |
| ttgaggatga cttcgtgaaa cttttgagc aaacacgttt atcggttgtt caaagtaaat | 1380 |

| | | | | |
|---|---|---|---|---|
| caccttcaca | aatttaagct | tgaggacgac | tttgtgaaat | ttcggcaagc aaaaatcaga | 1440 |
| caaatctctt | caatctttt | tgagcaaaca | cactttatct | ctgctgaaat gagcacaagg | 1500 |
| tttagggttt | tgagaatatc | tagcatttag | gctttcaatg | gtattttggt catttgagaa | 1560 |
| taccatttat | tttgaaattt | taaaacaaaa | acctaccatc | ttggtgacga tcatttaggc | 1620 |
| cgagatgtat | tgaaaaatta | tgttaaaatg | agtttttcaa | atttgattag aacctcgtgt | 1680 |
| tgaggtcgac | cgaaattgac | cgagaaaaat | aaatttacga | attttttttc aaaatgtgct | 1740 |
| actttaaaa | tataaaacta | aatgggttac | ttctcaaaag | ctaaccgaaa ctattagtta | 1800 |
| tattgcggaa | atatcaattt | cgcccaattt | tagtcatcca | gagcctgact catcgaattt | 1860 |
| aggagattct | agacgttgca | ttcaggagat | ttttatccgt | tgtcgccgac tctctttact | 1920 |
| gatctacatt | gtacttcatt | gctgaactca | acgagtcaac | tcaatcgttt ctagatttgg | 1980 |
| aagaatctgc | ttcagcgacg | | | | 2000 |

<210> SEQ ID NO 130
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 130

| | | | | |
|---|---|---|---|---|
| aaaaggcgaa | aaaaaagtta | gcttcccgag | aaggagaaga | cgaggaagag tttgacttcc | 60 |
| cggggagata | aagtttgtgt | ctcgagggaa | tctctaatct | ggagttgacc gtcgacttat | 120 |
| gtgtcgagcc | tggatttagt | tgcatggtgc | gacaaagcga | taaggcggca tatgtaaagt | 180 |
| agtaattcaa | aactagcggt | taaagaaata | atcagccaaa | aaatttagta caaatacggg | 240 |
| tggaggccct | aagtgaagtg | ctgctattca | gaggttttgg | caaaagagtg caaagagttg | 300 |
| agttgtgcag | agaaagtact | aggtgaggag | aggcgtttgg | aaaagaaaag gatcaaacat | 360 |
| ttgcatgagt | gatattctta | aactaaacac | tcttgtgtga | gtgacttgcc taagctaaac | 420 |
| actcttgcat | gagtaacttt | cttaaactaa | acgttttgta | atgttttctt aatggattct | 480 |
| tttcgagtct | gagttatgct | taacacgttt | tgtttctctc | gtgttattgt tgttgttgtt | 540 |
| tgaaaagaga | aaactattgt | tttctatgtg | ctgattgtga | tgaatgtgtg cgaaccatta | 600 |
| gccttaatcc | tatcaagtga | atagtgatta | tgtggtgtgt | gcacataatg taaatgacat | 660 |
| tgtgtggatg | gccagtgcaa | caagaaatga | atcagaaagc | ttcccaaata ctgtgaatgg | 720 |
| agtgaacatc | acactagctc | aatggcaaga | tattggcgat | agtgaatcac aataggcttg | 780 |
| acaaggggaa | ggattcatgt | tcttggttga | aaggaataag | agaggctaat gtgagatttc | 840 |
| tgtgatttgc | aaaatgaggc | gttggaagac | acgtttgaga | aatgaaaacg aattagtgct | 900 |
| tgacttgtat | tcctaaaaaa | gttgtccaat | atcttcaatc | actaaatatt tgatgtgcct | 960 |
| aagttttcct | tccttagttg | ttgaggcgtt | gaggccgagt | aaggaaagat aagataatta | 1020 |
| tgacgttgaa | aagctggtca | agttatccat | ctttggatgg | tttaaagtta ttacatgtag | 1080 |
| ggagggttgc | attccaattt | tgtgtgtgag | atgagtctta | ttttcgagat gggttgctag | 1140 |
| gcgatcaagg | agaagtataa | gaaatgagtt | cttatactct | tgaacaactt gacacgaaga | 1200 |
| ataacatcct | agtggatgaa | ggaaggtgat | ggaacttaaa | gtttaggttt tatttnnnn | 1260 |

```
nnnnnnnnnn nnnnnaaatg taattgtaaa gtattagatc aagtaataaa acagagttgt    1320
gttttctatt tttgctgtgt tgggttgtgt atctttattg tgcttatggc ctagttgcta    1380
aagagttaag gttattacct aaatgtttta cggtgtgttg agttgtaaag atctcctgag    1440
ttaaagttgg aattttgtat tggagattgt tttgagaagt ttagcttact aattgtttaa    1500
ctcattaggt gtctaagcga cacgcctcct tttggtcgca tgaagtggct agcagggtgg    1560
ggcggaccgg ggtggggtgt gataataaac ctaaaaaatc acccagataa gcctaaatta    1620
tacgttgaag ttaaacttac aatttgatta gaagaagaag gaatatctga tttggacatg    1680
aattaattac aaatacggcg ccaatcatac aaagcacatg taagatcaac gcattctaca    1740
ctcaatctca gccgttgatt gctttcaatc cttcaaaaag aaaaaaagaa gggcagttcg    1800
ggcagagtca tacctacccg ttgactataa aagcaactac aaatcgaaaa cctccatttc    1860
tccgttacca ttacagagaa aatcaaagaa atttggcgtt gagagattgg gagagaggtt    1920
tctcttctcta gggttgcttc ttcttcttca tcctccattg ttgcaaattt cacttccttc    1980
tcctcttgtt ctcatctccc                                                2000

<210> SEQ ID NO 131
<211> LENGTH: 2000
<212> TYPE: DNA
<213> ORGANISM: Cucumis melo

<400> SEQUENCE: 131
atagagtaac caatatgccc ttttcagcag ccaaagtttt ctatgggcag acttaatcaa      60
ttaaggttcc tattgaggcc ccactcttag tgaaaagcct agacccttct ttccaacatg     120
tctcaattgg tcacctccat caaaagcttc tatcatttaa tctaaaagca tactcttttt     180
tccttttttaa atttcatttt gatggtctat atttgaaaat aataatcact acaacgacga     240
cacgttgttt tcaaactatt attttgtatg aattaataat ttttttaata gtatagttgt     300
tttacttatg gaatctatac gtttaatcga ttcggtcaca tctatttact ttgatgtttt     360
tgttatttta tttagacgtg gttgtaaaga gtttaaagca atggagaaga aattgatgct     420
ttccaaagca atacaaattt atatatacct tcaaatgaga ctaacattag acaatacata     480
aactataata aacattttga aagtacatag atcaaaatga accaaagtcg aaaaagtaca     540
attatcaaat tagttttttaa accttggata aacttcagca ttcaaacttt gtatttctttt     600
tttttttcga tcgatatata tagtgataga agattttttt tttctgttta ttattttttga     660
cgatacgtta agtagaagaa tcgaacatca aaccttaaa tcaataatat atattttacg     720
actcaatatc tagccatcaa tattttaaaa tagcaattat tattcactaa attatgttag     780
agattggatg tcatacaaca attgttaaag attatttgtc tagtttgttc aattaatcaa     840
gagagcatta agcattaaag tcaattattg tgataagatg cttttgcact atgtaactaa     900
aaatagttgg atacaccatt taaggcccta catgcaaacc atgataggcc cacaaaaaaa     960
aatctctttt tggaaacaat ggtcaaataa tttctttcaa ataataataa taattacaac    1020
aaataaatac ataaaccaaa ttactaaact aatgtatcaa gttctagaga aaacaaaatt    1080
atgcccttttc aagttgcaac atcccctact ataattttttc ttcaaatttt ccatttaata    1140
taatccaatt ctaaacatgg aaaagaaatg taacaatatt tacattattt caatcttttcc    1200
tatattcatc gactaatttt aataagacgt gaaatcaaca tttttctaaa ctcgttgatg    1260
tcataaaaaa taaacttaaa ttatgtacaa gatcgtctat taaattatgt ataacacgtg    1320
```

| | |
|---|---|
| tggtgtatga gtaatagaaa ctttaaactc ttgatcaagg acatgtacct ataaataaat | 1380 |
| agatttcttt aagtcttgac tattaaccaa cttgtattca gtaaggttaa agtgatctat | 1440 |
| tatcatacta aatacacaag tttatttcga gtatgaatgc aaagaatcaa agatatatgg | 1500 |
| tttaaacaaa atctattata ccaataaaaa aggttaacca tatgcaataa aaactaaaaa | 1560 |
| gtctattgct caaatctctt tcgagaccat attaaaaatg ttagtttaat tgacgtatgt | 1620 |
| atttattgga tttatctaat aacatttaa gagattgttg caaatatagc tattagattc | 1680 |
| aaaataatta agtatatagc aaagtctgtc aaattctatc gatgatagga ctatgttaaa | 1740 |
| attgttgttc gatcgttggt aaactataaa aatctacgac aataaactac tattcaaaaa | 1800 |
| tttttttacta cccaaatttt aaatccatct catggatcga gtcaagccca cttctaaatt | 1860 |
| gggccacgaa tattgattgt gaagctcaat aatcccatac gtatggctga aaacgcatta | 1920 |
| cgaacgaacg cccttcaact atccaaatcc gaacccaccc aaattccggt taggcttctt | 1980 |
| ctccgagatc gacgaccgcg | 2000 |

<210> SEQ ID NO 132
<211> LENGTH: 2000
<212> TYPE: DNA
<213> ORGANISM: Cucumis melo

<400> SEQUENCE: 132

| | |
|---|---|
| tgcagctgca caaagattc caaatgatat aacataatag tttatgaaaa tttaatgcat | 60 |
| ttaatttccc cttccacaga agacactata ttttcaact acccaacaat accaataatt | 120 |
| atcattatta ttatacctct aattagtaat tagtcacaac ataaacagct attctcatta | 180 |
| atacatataa tcaacaactt cataaattct taaatttgta tgtgtacttg atgggtgtag | 240 |
| atttaagaag tccaagagtt tgacacccctt tgttaaaatg atatacaaat tcctgcaaat | 300 |
| taaatttacc attggtatga ttgttgttgg agtggtcaca acactaattt actaattagc | 360 |
| ttcgtattta acatagttgg ccatgcgagg aggtagcttt tgaacttcca ataacctggc | 420 |
| ttggaaggac gtcgataaac agaataacaa ctatgctaaa ttttgaataa tatactttat | 480 |
| atatattata taaagacgac aaagttgagg agcatccgtc ccctacattt gttggtgctc | 540 |
| atatcatcct attgcatatg cctttaccca atgaaaccct atctccttaa ttatttctac | 600 |
| tccacactca taattatcat tcattttattt tcatgcatga cttctttta ccaaatttag | 660 |
| tttccaatta aactccatta actaccaaca atcaactcca ataacgtaac tcacattcat | 720 |
| tctaaccaat tgtttggatt gactcgagaa aaaaaaatgt ttttttctaac tcattttttac | 780 |
| ttatacattt aaaaaattctt ttggaagtga tcgtcaaaca ttttgatatt ttttttccttt | 840 |
| taaaatgact tattttttaa aaaacttaaa tattcaaaaaa gttttccaa atgaatgtaa | 900 |
| ttaattactc aacatagatc tccattaatc attattatat gtaacaatag taattcaaag | 960 |
| taaaaaaaaa attatgtgga gtgcaaagat gaaaatttg acctattta catgatttga | 1020 |
| actatatgtt tatgcgtacc tatgatttaa ctcttatata cacatatttt tgtctcaatt | 1080 |
| taattaatt ttacgatttt cttgaataat ttattctct aaccactttt gaaaaacatt | 1140 |
| ttttaaactt tagaaaagaa tatctttacc aaacttaatt caatatatga aaatagctaa | 1200 |
| ataaaattta aaaaacagat aaccacccctt tgataactgt agctgatatt attaattaat | 1260 |
| tgtcatattt atatttgcaa tatgaaaaag gagatgtcat gagttttttt tttttttaatc | 1320 |
| aatctaatgc aattttctta aatttaatta atgtgaaggt gagagagaga ggcaatttca | 1380 |
| aattttaggt aagtattatg aataaggtta cttaacatta ttttaattta atttttacatt | 1440 |

```
atgttttatt tgaattttt taaagactct catttttcca ttttggaact tttggaaaag    1500
aaaattttac ttcaatctct tatgcaagca agttaaaact acatttgtct tttcatggga    1560
tttttaagga gatgtgtggg gaaatacaat aagccttttt ttatttgcaa tttgctaaat    1620
gtgtattctt ccaattggct aattattaaa gtgaaattta gattgaaaaa agagataaaa    1680
ttgaattgaa gttgtataga tgggttagga atatgaaaat tgtttgagat atagtgagta    1740
ttggttttat ccaatgccat gtcataggg tggaatccaa atgaaccaat gagaatcact    1800
caaaagaaaa cagatataat gcactatcca aacctaaaac taaaagccac acattgctca    1860
tccattcact cccattctca aaaccacaca aaaataaata tcaaatcaat ctctttccct    1920
tttccatata taccactttc cctctcttc gcctctttga ttattaccca ccaaatattc    1980
ccatatatct tacaacaacc                                                2000
```

<210> SEQ ID NO 133
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 133

```
aagcttgttt gaccctattt ttaatgtctt aacacaggat tatgaacaaa agaagaaact    60
agtgaatcac agaggaactc acgcaaagac taggtgagaa gatcatatca aaatgagaga    120
ataagttcgc tagaagataa aagtggtagt tgaagttgat gtgacttgac caagaggcag    180
cttctggtgt tgatatattc agaagactag atttcctgcc taaatctacc tatataaaga    240
actccatctc cattaagaaa atgaggcctg aatggaccac ccaagtggtc gactgtgtga    300
agagccaaat gtttgtgaac tgcccatgag tgcctgaaag gcccgatcct agagagtggt    360
gggaaggagc agccttttcca ccatctgtaa agtcttctt catcttctcc agttagttta    420
agagtgaaag tttgaggttg agtgaagaag attccattcc tatcttttc taactggtaa    480 tgtcatttct attcttttcca ttttttgtata tttctttgta atgtatttnn ncatattgta    540
cagtggccta agacctatat tctttaatac atttcatgtt tatatctttt caatctatca    600
cgtttgttat tattcatctg tccttgtgct attggtagct taagatttat gataagttct    660
tgataagaag gttagcttat atttcttatg tgtgttagtt gtgagctatt ttcatcacct    720
ggctagtgta tattgcaaac tacctgagag ggtaagtagc aaagatatgg cttaggcgca    780
caaggaggag tttggagaca aaatccacat tggcaagata acttccatca tttgtgtctc    840
aaaaggagaa caagtgtggg tattaagcat tgagatgttg tgacccttaa acgagaagct    900
atataagtct tagtgaaggt cgtttggatc tcgagaggtg agcaagtgtg gtgtttaaag    960
acaccgagag gtgctcgtct taatcataag ctcgttaact aagttatatt gcattaggga    1020
tattttattg cttaatttct tggtaatgca cgaacttttt ttcacccatt cttttatgcc    1080
agctagttca caattccatc tcgcatccat tttaatcccc ctttacagat tctccggtgt    1140
agataagtag atatagtta aacttacatg ctttcacact atatatttta ttcttttata    1200
ctacctaaat gcctagtgaa gcctagaact aagctttgat atcgattccc tgcattcgac    1260
```

-continued

| | |
|---|---|
| tctaaatcgc ccatataaac ctattgtttc gcttacactt gggcaagcaa taggaaaact | 1320 |
| tgtactcaac gaggacttat gagttacatg atgacgagat acatagagag catctaatat | 1380 |
| gcattgacca tgatcattga ctcttcatgt agatttaaat acctttcagc ttaattagat | 1440 |
| agaagatata taataaagcc attccattag tttaaaagaa ttaagttaga ggtagttgaa | 1500 |
| atgctttata agtgggggtt aattctattt tagctgtaat gctgagctga tctcaagcca | 1560 |
| aggttgcctt gagatatccc cgagtttaaa aacagaagct aaaatggaaa ctaaaaacta | 1620 |
| agacatataa acttttagt tacttttagg gaaatatctt agctataaat taagaatat | 1680 |
| gaccaacatg gaagttcctc catcactttt ccaccaactc attttattgg gggttagtca | 1740 |
| ttttaaggcc aattagttta aattaaagtt caatctcagt gatgcactag gccgagagag | 1800 |
| accgagataa atcattcaaa tattttttta aatttgggaa gaatcttgag gtcgagattg | 1860 |
| atcctgagaa aaacaaaatt acgagttttt taaaactgtg aaatataaaa caaaaaagtg | 1920 |
| ctagttttgt caattcccat ttatcttgct cattgttgat acaagatcat taaaagttta | 1980 |
| tggataaatg ttggttgaga | 2000 |

<210> SEQ ID NO 134
<211> LENGTH: 1696
<212> TYPE: DNA
<213> ORGANISM: Cucumis melo

<400> SEQUENCE: 134

| | |
|---|---|
| tatatatata tataaaaaga ggaatacaat taagacatcc cattgttaat aaggggtgga | 60 |
| ataaattggg aaattaccat tcgagaaatc attgacgaga gcaaatatgt caaagtagaa | 120 |
| aattagtcat ctcaaaagaa tgtaatcgtt acaaaaatta aaagtacgta aatttaatca | 180 |
| tcgttacaaa aattaaaaga atataaatta caccgttaca caataatacc aacaatccat | 240 |
| ttataatatg ttgttttat ttcaactttg aataaaattt gaactctttg ataaaatttg | 300 |
| tttaaaataa atttaaaacc atttcaaaag ctattttat attatccaaa tacatatatt | 360 |
| cttttctttt tccaaaatga cttgtttcta aattcgaaca tccaaaaatt aaaacataac | 420 |
| attttagta tattaagaat tataaattaa gagataaaat attcaatact attataataa | 480 |
| aatcggtgtt ttcagtaatt gtatttgtac aagtaaataa aattaatagt aaaattttta | 540 |
| atatataaac aagttttaaa agaaacttaa agatataaaa aataaattga ataaaaattc | 600 |
| aaacccatca acaaataaag aaaataaaga tggtttttatt gaaatgaatg aactaaaatt | 660 |
| tgaaggaggc aaaagtaagt acaccaaaaa tagaatacta aaatggtaga ggacaataat | 720 |
| tgcatatgtt tggtagattt ttcattaact atcataccaa ttaacaataa tgaaataaac | 780 |
| tttctcgttg atattgatta caatcgtaat agggcaaccc actgtttaac ttgtcaaagt | 840 |
| tttcttaact ttattatttt tgactttatt tgtttgtttt attgattaga ttgatagatt | 900 |
| atatatttta atcatattat ttatagtaca caactacga ggtaagtgat tgaagcttta | 960 |
| gtctctaaga acaaaggttc gacctaattt tttagtctgt tttatttga catattttgt | 1020 |
| ccattgatag aattactatc acttaagtta aatgtattat tattgcaaac cactaattct | 1080 |
| acgtaaaatc tctaagtagc aagtgttatg tcaataaaat agcaattttt tttttaccaa | 1140 |
| ttacacacat catggtgata attattatca tgcacgggta aatttttaat tataaaattt | 1200 |
| caactttcaa aattataccaa atactaaatt tattacaaaa gttatttag gtaaattata | 1260 |
| aaacttgat aacaattaca agtacattct aaaactttca ataataaaga ttgaatcatc | 1320 |
| caattcatcc aaatgttaaa tttataatcc gatttcaaga agaaaattaa aaactcaatt | 1380 |

```
tttatgaaaa tgtaactaca accacaacca tattaaacaa aaactcacaa tttgtccata    1440 tttttttaagt taaaaatata ggtttaggat tcaaatattt ataaaataaa ataaaatgaa   1500
actatttgaa aacatagttt aaaaaagaag aagaagaagt gttaaataaa gtcccatttt   1560
ttaaaaaaat atcaagaccg atattaatat tatatatata tagaaatgta cacaaagtta   1620
aaaaaaagta tcctataaat atctaagttt ctccccgtct agccttcgcc aaccttatct   1680
caaaaactcg gaagcc                                                   1696

<210> SEQ ID NO 135
<211> LENGTH: 2000
<212> TYPE: DNA
<213> ORGANISM: Cucumis melo

<400> SEQUENCE: 135
tttacatatt tatgaacatt ttcctatttt tgtaaatatc ttgattcaag attttttgttc    60 gatatattta aaaataaact tattttaaat tcatacttct ttctccttct atatgattat   120
ataagtattg tagttactat agattaaact cataacctcc tagttagata ttgagattat   180
tactttcttt tattatcggg ccagtacaga aacgctttta tgacgattac attcgtcatt   240
cgtcacttat ttgtgcatta aagttggcat tgtaatgttt gttttacat gattctctat    300 tccatagatt tcctttatcc tttttccttgc atttgagtgg ccctttccta agatgtattc   360
ttcggacttt caaataaata aagattagaa gcattttttct cttcaatatt gacttcatcc   420
ttaatcctta agccttaagc ggaggctaaa aaggctttat ttgcctcgaa tcccaactaa   480
ttctccctct catgcccatt tcaatctctt gcctaattgt taattaatgg gtcaaatttc   540
gtattgaatt tcaattttgg atcaatccta cgattatctc aattaggggt caaaattaat   600
ggttgatgta ggagcaagtg gaagacacaa ttttggtgta gcaattggag cttcatcatc   660
aacaacatga gatttaatcc cgtggttgca gttaaatggt gtagaagaag tagtcaacac   720
aacccaaggt gaagaagagg gagacaagag aagtggttga ggttgtggct ctatttgcct   780
atggcagcct tcacctcttc tctctcgctc cctctccgtt tcaatcccctt atccccttcc   840 tctccccgcc attttcttct tctcttcttc ttccctccac caatttcacc tcccgattct   900
ctgccctaac catctcttcc tcctccttgc actccgcctc cgacaatttc gatcatgcca   960
aaagctcccc ttttcatct aaggtctgat tcatttctgt tgtttgttta actcaatttg  1020
tcttagttat attcaatcgg gattttgctt gcttgtggaa ttaattttcg tttattaagt  1080
ggaagatatg ggtatgcttg gtgacactgt atttactgtt aaatttcaaa caatcctacc  1140 aaatttggt ttaaattgag tattttttagt tccttcttgg taaattggat ttgcgaatga  1200
ttaacttaac tatgttggca cttcgttgta agaccgttaa ctatttagct tccttacggg  1260
taatgatgtt tagaaggggg gtgcttggtc cactaagtgg agttaagtct atggtaaaca  1320
tgttggcatt agtaagtttt tggtaaacat gttggcatta gtaagttttt ggtaaacacg  1380
ttggcattag taagtttttg gtaaacatgt tggcattagt aagtttttgt ttgtgatgta  1440
gagttgtaag attgagttct ttaataattt gagttgtaag attgaattct tcgataactg  1500
tgaaaagtat attaagaaag taagatagag ttacttgata aatttgaata gtggagatag  1560
gggcaagatt gagttccttg ataaaagtat aataaagtaa atgtgcaact cttgcctata  1620
tacagcttag caggaactct tacttttgtg tgtcatgtat tcttattggt tcgttcttat  1680
tgcatttagt agatagtgga tcccagtgaa ctttttttaat cgctagaatg gcgccttaaa  1740
```

| | |
|---|---|
| aagttagttg gagcttctac ttgttggttg gtatggtgcg gttgcaagta ttttcctttt | 1800 |
| ctatgattat gtttttagat ctaaatttta aagcactcga tgaatgctga tgcttgatat | 1860 |
| gttttctgtg ttaaattctt ttgttgatga atattatttc cattttcag aaatcagttc | 1920 |
| tttcatcttt gatacaagag atagagccgt tagatgtaag cttaattcaa aaagatgttc | 1980 |
| cacctactac tgtggatgct | 2000 |

<210> SEQ ID NO 136
<211> LENGTH: 2000
<212> TYPE: DNA
<213> ORGANISM: Cucumis melo

<400> SEQUENCE: 136

| | |
|---|---|
| ttcttgatta gcttggtgtg ctgttgtata tcatatttgg tgcgagcata acttaccctt | 60 |
| ggctaccttg catctaccct aagtggttta gtcagattgt atgatttgag gtatttcgtt | 120 |
| tctttgttgc tctaagtggc tttgagcttc tactgaggga acctaggacg tctcttcttt | 180 |
| ttgggatctt ttttctcgag tagttggatg cctagttggt ttttttgttc ctttactcaa | 240 |
| gtcctttgtt tgtcatttga tcgtgtcaaa gtccaaatgc tttctattgc aattcagtat | 300 |
| cttaaaaaac tgttctttgt tgatttatgt aaatgacata ctgtatgtat aaaaggacag | 360 |
| aatgctacca tttcttgaag tttctggcac ttaccctgat aatcgttacg gtaattatta | 420 |
| tgtgcagatt gacggcaata acgcagctag cacatcatgg tatgatattt gtacctcttg | 480 |
| ggtacacatt tgggagtaag atgatggaaa tgaatgaggt gaaggtggc tctccttatg | 540 |
| gtgctggaac ctttgcagcc gatggaactc gacacccgac tgagttggag cttgaacagg | 600 |
| cttttttacca aggtaagtat gttgctgagt taaccaagaa actcaaaaac taatgccatg | 660 |
| tttgaaatgt tgttgggtat ttgaaaacgt gttattacac tagcacactt ttactgtact | 720 |
| tccttccaac atctattatt cagcttctca catcatggct atataaataa aggttaatgg | 780 |
| aagttactaa aaatgatgta aatctatcac attgttaata ctcctgtaat tatattgatt | 840 |
| gatgaacaat tcgatcacca tcttttgtta tttaaaatta aacttgtaat atgtattcga | 900 |
| acgtttttag ctttattgca tgcttattat ttcactgttt taaaactatc tttagacttc | 960 |
| aaatcaaatt ctgaaaaaca aaattaagtt ttcacataca ttatgtcatg aatataaaat | 1020 |
| tttagatatt ttagttcatt ttactatatt taaaaatgtt ttattattat taattttgta | 1080 |
| aaacaaccat gatcgtttat taattgaatt gtcacaatta agccattatt tttttttta | 1140 |
| ctttccttt tcccatcaat ttctttattt tctaaaaatt attggcctcc cagactcttt | 1200 |
| gttatttgca aataatgagt ctaatcataa tagaatttca ttgataaaac caatcatagc | 1260 |
| gagtcttaaa accaatcata gcgagtcgta attataaata ttattgaatt gctcttggtc | 1320 |
| cagtttagct agaattatga atttgatcaa attttctgtt atcattaccg tataacaata | 1380 |
| aatgataaaa ttcaaaaaaa aaaagaaag aaaattgata tgttaacgac aatggtaatg | 1440 |
| ataaccataa ttgtaatggt aaccgtaact acaatacata ttttttgaat ccaatgagat | 1500 |
| gaatcactta cttagttgat ttgcgtacca aattatagaa caccaatcat ttttgtaatt | 1560 |
| aggattgatt tactagcgtt agattagaga aaagcttggc ttatttctaa ttcctcctcc | 1620 |
| ctcttccact catttttgtcc ttaactaaaa catagtgata gttcccttttt tcttttagag | 1680 |
| aaaagaaaag aaaagaaaag aaaagagtg ttaattggta atacataata acatatcaca | 1740 |
| tacataaata aatcatgccg agttcgcctt agaaacgacg ccgtttaaag taagtcaaca | 1800 |
| agtcaacact gacagctaat ttccgcaata aatacgtaaa aatgaaaaga aaattaaaaa | 1860 |

```
acgatataat ataaatagaa gcaagaggct cccatcacaa gatcccattc gcaaccacat    1920
tccggccttg aggcttcaaa aaatcgaagg aaaacactct ctgtatctct cccctctacc    1980
caccgattcc gtcgcggccg                                                 2000
```

<210> SEQ ID NO 137
<211> LENGTH: 1575
<212> TYPE: DNA
<213> ORGANISM: Cucumis melo

<400> SEQUENCE: 137

```
atatatatat ataaattta actaaataaa caaatgaaag aaaaaagtga gttcccattc      60
ggaaaatgca gatggatcca tttcttcaaa tattaaaaaa taaaaaataa aataaaataa    120
cttaaatatg caaatagaaa gaattttaat ttctggatta tccatatggg acaatttta     180 aaactcattt atttattt ttttatttat ttgattttga tatatctatg gggaaatttt      240
tcgtaataat tttcgaaaaa atattgcaat atatcatttg atcagatcgg tattattaaa   300
tctctatcac atttggtctt aaattatcca agattcctt taagataatt tagataacca    360
tctacagatc actactataa tcaacaaaag gaacaactta aattatttaa acaaattcat   420 taatattga ctttgtgctt cattagaaaa tgatcttatc acaaccacaa ccatagtggt    480
ggtttaaaat tttatttaa actcttatta gtattatttt aattcatact taatcaaact    540
aattacttta aaaacatat atatataat aagttaaatc attccccctt atctaaataa     600
cataaaaaaa aattgtttac tctacaagaa gtttgtatat atatatgctc ggtactattt   660
agcatcttta taataaaatt tctaaatcaa tttttatat ctctttatta aatgtatagt    720
catcaaaaaa tttaacgaga taatgtgtca aagatttatt ttattaacgt tcataaatat   780
caaattatac ttagcttata attgaaaaca tgttcgataa atataagtaa ataaaatttt   840
atttttttta aatattacaa aataaactaa ataagttata aatatgacaa taaacattat   900 atatttatt atatttataa atacttaata atttagtcgt ttaaaataat tttcttaatt    960
ttcaaaacat gtttcatatg ttaataataa ataaatggaa aaccttccaa aagaagaaaa  1020
aaagatatct taaaattaa aaattgagat tttgaggatc ataattaat aaaagaagga    1080 ttaataaggg tgaaattaaa tcccaaaaag aaaattgaaa atgaagaaaa gaaaagtgaa  1140
gaaataattg aacgtgggaa gtggattcga tgtctccaga gaacaagcga aaggagacga  1200
aatccacata atttgcacgt tacgtgtccc tatcaaccgt agacacgtgt caacatctca  1260
acaccctacg ccgaattgct tcgctggatc tggacggtca tcggataaca gcggcaacca  1320
attaatattt cccctatat ttcacagcct ggccatgtcc accaatcacg ttcaactatt   1380
aattcatttt tcatttcctt tttctttttt tttttaattc ccctcaatta ttaccgacaa  1440
cctgttgtag ccggttaacc ctaccctcca acgttccatt ataaggccta gaaaatggac  1500
gtgaaaatgg agtactacaa actacaatta attttaaaga atttttattt taaagttctc  1560
taattactat tagcc                                                    1575
```

<210> SEQ ID NO 138
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:

<221> NAME/KEY: unsure
<222> LOCATION: (1)..(2000)
<223> OTHER INFORMATION: unsure at all n locations

<400> SEQUENCE: 138

```
ccgtcgggaa cctctgctct gacataatta atattcatgt atttcctgat acccatgcaa     60
gtcgtcggga aatatgttac caattttcga cgccagacga gaatcgttag gaacaagtgt    120
caccatgccc aacttcttgt atggggcatc aggataagtt aaatttcttt tttagttgtg    180
aactattccc gacgccataa acctagatgt cggaaatgtc ttcttgtttt tcgacggctt    240
cgtgaatctt cgaaaaaacg taagattaaa ataatgtttt cgacgagttc cgacctgtgc    300
aaaacgacat cgggaatagg tatttattcc aacgttctag cttctgacat ctagaacccct   360
tcaatttctt gtagtgccag tgcaaagatt gacactctta aacgatggga cttgtcaaat    420
agatgttgcg cagatatcca taggttatct aaggttttgt tttgttacct aagttatcat    480
caaacttctt catgaattct cttagctatt tctaagtacc taagttctcc tctatccact    540
aggattgtct ctcttaaagt caagggtggc tgttggtagg atgtagactt tgtcggcatt    600
ggtctaccaa tttaatctct tatatcccta aagacctaga ctccatggtc tccacctatt    660
tccataaatg tacccataac atcattaaat gaaattatta ctcaagtaca aaaaaattgt    720
ttaatttat tgataaaaac catatgtgaa aaaatagatg acattttaa aagcttgtaa     780
acagtgtgtg aaataagtat cctaagtgaa ggctattaat ttaacttaaa cacaataatt    840
attattgttt taatgatgaa ataattaac ttatataacc aattttcatc aacacataca    900
tacctttttgt ataacatttt atttgaacac aaatgagaga caaatagaca ttttatttg    960
gtaattttct cagcattatt aattatcatt ttcagatatc ttaattgaaa tttctgaata  1020
attttttatt tttcggattt tcacattata atattttgaa ttagttagtt gaaaaccaaa  1080
gccagcatca gtgaaaactc attaatacat gtaaaatact aaaattgttt ttttaaactt  1140
ctcaaagaaa aaaagtctta atttttattt tcttaacttg acataaaaat cattggtgtt  1200
gttttttaata aagtaaatgt taaagtagac tcagttaaaa acgaaaaaaa aagttaaagt  1260
ggactcaaca cttggagtaa acatttttttt taaaaaaaat taatcctaaa attatgatta  1320
taatttttat ttggcttaaa tatttcaaaa tgtgttacac atggtttagt ttcaatttag  1380
ttgttacaaa atttattatt gtatttgaat ttttgataga ctaattaaaa tttgaaaatc  1440
aatttatttta tacagttgtt tttctttttaa tgatgtaaat agaggtctaa tgattttaac  1500
ttgtaagggt taatttttct tatgatctaa tgtaattcaa tgagcattaa ttttagaaga  1560
aaatgtgtac ttattttgtg taaaaataaa ttataataac aattttttca ttttggtata  1620
acgtatgatt aagttccatg aaaaaacaaa ataaaaaaga ataaaatatt tttccatta   1680
aagaaaaaca ataataaaaa tggagggatt caataggaat ttcggagggc ccacttccca  1740
attccaactc cccactcact cactcactca cnnnnnnnnn nnnnnnnnnn nnnnnnnnnn  1800
nnnnnnnnnn nnttttttt attattatat tagaaattaa taattattgt ttatttcgct  1860
gtcaaataaa aataaaattg tggggcaggt gcagctcacg tgcctcctca cattgacacc  1920
acatttaaac actttcattt tcaaaggctg ctgctttata ttcttcacaa aaacttcctc  1980
ttccctttct cacactacta                                              2000
```

<210> SEQ ID NO 139
<211> LENGTH: 1006
<212> TYPE: DNA
<213> ORGANISM: Cucumis melo

<400> SEQUENCE: 139

```
ataataataa taaatacata aaataaaaaa ataataatag taatgaaaat caatagaata    60
atttttaaaat cgggaaggaa gtcgtgtaca atccttgcac gttggagagt caaatggcct  120
aagtggtgat gtggaagtcg tgtaccgggt acacgatttt cctacaagtc aataataata  180
atatggttat ttttttttcta gtttagggtt catgacaaaa gattgttcag tcgactggat  240
gtagacaaat ctaaaaaata aattaaaatc taatatgaaa actagttta atttccaaat   300
tattaagggt tgaattcgac caataaataa taataatacg gttattttga aatttaggaa  360
attgaataaa gttgttaaaa tcttcaagca aattgttaag ccccgagata ttaagaagag  420
gtaataatag aggattctat atttataaca tgttaaaatt aattgcaaac tcataaatgc  480
atcacacaga ttaacaacat aggagggact tccgataaaa gtgcaaatat tgaaataatt  540
acagttcgcg aacatgagta ttttaatatt ttataaaata gtatgcacgt gtattttgc   600
caaaagaaaa aaagaataga ttttgccatt tttcaaagtg actctcggtt atatctttta  660
tggcgattgt attttatagc gtatgttgtt tgtagttaac ccatttctca ttggcaaatt  720
caatcgtggg ccacaacgtt tgggcatagc ttcaatttgg attaactcaa ttatgtctga  780
atgggttgga ctagttcgga ctcttcggct gggccagaat cagattcggg ccgcaatctg  840
ttcatttcac acctatatcc aaacaccccc aaaatcgata cccatcaaac cctaactctc  900
aataacccc atatataaat tccttcttta gggttttca tcctcataca ctctcaaacc   960
tccggtcatt ctcatttttcc ctgccgcttc ttcaataacc ctaatc              1006
```

<210> SEQ ID NO 140
<211> LENGTH: 2000
<212> TYPE: DNA
<213> ORGANISM: Cucumis melo

<400> SEQUENCE: 140

```
aaggagtaga ctctcaagtc cactattcta acttcttacc cgaaagagcc aaaacttttc    60
attcaaattc aactagaaag ttattattga tctatcaatt tgattttaat ctacaggcgt  120
gcgttgcaat ttgggaaggg attgagtttg taactggagt acgggcaacc tcattgaatt  180
ctcttcgatc aacgtgggga tgaagttctt tcaccagttg gagtctggaa aaacttttgc  240
tagactaacc tattgctact gcctttttggt gaaatctttg tgctctaata ttaaaaagac  300
tccaactttg aatcgttaat tataaactag tgttatttgc ttgtaaatct tacttatagt  360
ttgaaatgag tgcttggcga aagtgttgtt caaatcggta cgtgtaagtt taaagattct  420
tatttcagct ttgaatcaga tcagagtctt ttaaacttaa tcaaccgaca ccaccacacc  480
ccactcttgt tcttctccac gtgggagttc ccaaattggt tgatttgtta tctctttgaa  540
tcatctcaaa tcaagaaatt tcagaacagg tttggggaaa tttgataaac tacactctct  600
tgctcgaact ttgcaaggtt tttactgttt gttatatgat tcaatattcc catttcttct  660
aattggatga actgttgaaa attggaaatg ctcagctgcc aagttttttt ccgaaatagg  720
tataaattca aagattcaat cagtgtgggt ttacccaaaa aaccaatggg gtaagtccat  780
tttggactca tgtggagggc acatgtttag gcaaagcctt atctctttgc cagtgggctc  840
acaatcaata cggacaagac aagaaatgct tcctaacacc gtcattgtca gcgaccatgt  900
gagctttcag caaattggat ccttcaagta actcacgtga aagatattta gtgattgact  960
taattactct cccccttcctg tttatctaaa ttaggcgaat agatccaaag tgggtatttt  1020
```

| | | | |
|---|---|---|---|
| tggagatcat | ttatctgttt | cctgttcttg | tttatcgttt | ataattattg | attgtttttc | 1080 |
| tggctcaagt | aaaacgagga | ctttgacatt | tcaataccc | cttttttgtt | ttctggtagg | 1140 |
| tagcgctaag | tgggtttctg | atatcgtact | gaaaaagtta | tagttttgct | agaacactcg | 1200 |
| atagatttta | gcttttgtat | tgatttttt | gttgatattt | cctggtttca | gtgaatgaat | 1260 |
| gatattcttt | tatgacggtt | gttgtgaaga | ctcataagtt | tgtctcagat | cttcagttat | 1320 |
| actcttgaag | cttcttcgtt | catacttcaa | cagttcttgt | acattttacc | ccctctgttc | 1380 |
| ctcttccat | cggcttgtga | atctgtgatt | gtaaattgtg | ctgatgattg | ttttaagct | 1440 |
| gttgagatgg | cgttgggtt | gtgtcctaat | ttgagactgg | tcaacttgat | catttggggt | 1500 |
| agtgatggcc | ttctttcta | tatcattctg | tgaagagtac | tttctaaccg | attttgttaa | 1560 |
| aaacacatgt | cggattgctt | gcttgttttg | tggtgtttct | gatttgtgat | atgatttgat | 1620 |
| taatctctga | tcgagttgtt | atgaatttga | ttgacagcaa | ttgggggacc | atggaatcat | 1680 |
| tgtggttcct | ctcatagatt | ttgatttctg | aggtgttgag | aaggcttaa | ccttttttgtc | 1740 |
| actgaaatgg | atggtggaag | ctctgaatcc | ccagatatgg | gttgtaacaa | gaccatagta | 1800 |
| tggtttcgta | ggacctcagg | attgaggaca | accctgcttt | agctgctgct | gctaggaatg | 1860 |
| gttttgtata | tcctgtgtac | atatggtgtc | ctaaagaaga | gggacaattc | tatcctggtc | 1920 |
| gggtatcgag | gtggtggttg | aagcaatccc | ttgcccattt | gaaacagtct | cttaaatcac | 1980 |
| ttggtgctga | cctagtgctg | | | | | 2000 |

```
<210> SEQ ID NO 141
<211> LENGTH: 1556
<212> TYPE: DNA
<213> ORGANISM: Cucumis melo

<400> SEQUENCE: 141
```

| | | | | | | |
|---|---|---|---|---|---|---|
| ttttagtcat | tatacttcaa | catctcgttg | gttttaggtt | tttggaaagc | aaacctacaa | 60 |
| aacacactct | ttcattcatt | ggttttaagt | tttgttgaca | acttttagg | agtgctttga | 120 |
| ctaagatttc | aaagtcttgt | acttaaaatg | atgcatacta | tcgtaaaatt | agtataagag | 180 |
| actagatttt | taaaaaagaa | gaagatcggt | ggaagtatgt | tctaatttct | aagttttca | 240 |
| acacttacaa | atttattgaa | aaacagctgt | cggtacatgc | acacatacta | tttatggatc | 300 |
| tacaattcca | agcatagaag | agtttagtat | atatccaaat | tcttattttt | aaggggaaaa | 360 |
| aatgaacgaa | agaatgcatt | gtattctcgc | ttttgtcgtg | ataacgtatg | attttcaagc | 420 |
| tctttcgtcg | aaaacatca | acaaacaaac | aagctaagtg | taatctaaat | aatcttcaac | 480 |
| atccttggaa | atttattgaa | aaataaagat | ggctagcaat | gcatactttt | tatggatcta | 540 |
| tatcccattt | caaccgtaga | agattcaaag | tattcgaatt | cttaaaaaaa | caaaacaaac | 600 |
| tgccttgtta | agataaaatg | gaattagaat | gaaattttca | aaattgaagt | ggggccttgt | 660 |
| aaagaataa | actttgtttg | aaaattaatt | tccatcgttg | gttggtagat | gtgtccttaa | 720 |
| ttgaaaaagt | ggaagaaatg | aaggatgaat | atgaaagttc | tgaaagaat | atggacggaa | 780 |
| ttggaaaaaa | caaaaaacct | aattcataa | attaaccaga | atctaaacat | tgggggatga | 840 |
| agggagcgga | ggccattcat | gtaattggcc | gtacagattc | atggtttaac | aaaagccaca | 900 |
| acgactccca | ttcttccacc | acagaaattt | cctctcctcc | taaattcact | tatctctttc | 960 |
| tatataattg | cttcgttccc | caactttcta | tcttcgtgca | gccccattca | atcccccatt | 1020 |
| ttacccactt | cgtcttctcc | tttctccttc | gtcttccagt | tccgtttcc | ccatctgggt | 1080 |
| tctcctgatt | tctctttaaa | atcaactacc | catgttcgac | tttgaggaac | tggtgcgttg | 1140 |

| | |
|---|---:|
| gaattgagct tcgaaggag atttattgtt tttatcacaa cccatctgct cgaggtaagg | 1200 |
| ggtaaaaccc gggttcgtca ggctgtagac atcacggcta tacacgtagt ttcccggtcg | 1260 |
| ttctttcatg tccgggctgt acgacggaag ggttgtataa ctccgacaaa cccttcgccg | 1320 |
| cacggcggac gtggtgcttt gccttccgaa ggtggtagtc cttctgatct tcttttctc | 1380 |
| gccggcggtg gattctcttg cttcttctct tcttcgtatt agctttgcaa cgagtccgtt | 1440 |
| tgtgttttag ctctaccggt ttaggatttg acatcagcaa gttctgtttt tgcgtttctt | 1500 |
| tgttttgggt ggggagattt tggtgttggg tttggtttga attagaagca gacgat | 1556 |

<210> SEQ ID NO 142
<211> LENGTH: 2000
<212> TYPE: DNA
<213> ORGANISM: Cucumis melo

<400> SEQUENCE: 142

| | |
|---|---:|
| gagtacctaa tctaaactaa ttaactcgct caccctctta tttactgccc catactaatg | 60 |
| atcctaatag attgtttggt tgggttgata aattctcttt aaaattatca gttttccaa | 120 |
| tttttgccac ctaagttgtt ttcttacaaa aaataaaaaa taaaaaaagg caatgttatt | 180 |
| tctcgtatgc attaattgat tgattttctc aactaaccct tcaatttgac tttatatgta | 240 |
| ataatagtgt aaaatatata cgcacatacc tacatatgac caacaataaa aacgataaca | 300 |
| ttaaattcag acagaaataa aaattacgat tatgatttta ataaatataa atgcacataa | 360 |
| ataaaattta cagttcatag aaaaatccga tgtaatgaag tttaaatcgt tagttatttt | 420 |
| atttcgtaaa ataccaattt atgatttgca tgacaaattt ttaaaatata acttatgaaa | 480 |
| ttaaaagttg gttttgagaa acattcaag actttattac aaccaaacaa aaattttatt | 540 |
| gagttttgtt tcattaaaaa aattattaaa ttacaaatat ttggacttac gtaatttgtt | 600 |
| ttctttcttt ttagggtaga aaaatatgat agattaaaag gattcgaaat caaactttat | 660 |
| atcaatttcc ttttaaataa ttatttcttt ccaaatttag ttttttatatg atagcctaag | 720 |
| tctccatcat aagaaacaac gttaattata ataaaaaatg gatgtagatt caccaatatt | 780 |
| ttccaactat attattactt tcacgtttac attaaaatta aatccacaca ataatataat | 840 |
| agttttcttt gtttgattca agttttctct tggttaaaat taaatttcga atgataata | 900 |
| aataaactcg tgattaataa acttaatttt aaatttcaaa cttaggtgtc taataaattc | 960 |
| ctatattttg tatcacaact tttcaattat gtgcaataaa ttttctaatg atttattatt | 1020 |
| ttttttaaga atgtaaagtt gattatattc atattaaaca taagattgaa aagagagagt | 1080 |
| tgattatata ccgagtagcc gacagtcatt ggaagcatta acccattatc atctccggcg | 1140 |
| agcaaaagca aggatctaca aacaaacatg acaattaata tgaaactcat caatccacgt | 1200 |
| atccaaacat tccatatgtt agacatggaa gagcaataat tacaaagctc tctcatcgtc | 1260 |
| tccgatcact ccatttatcg tacaaatccg tctttcttca ccttaatcat tttccccgaa | 1320 |
| attcatccca ctgtttcgca acaaaatcca gtttggaaa gatgagtttg ttttagtga | 1380 |
| tcaaggaaag gacaaagaat gtagcattgg caatgacggg caaacaagag aggtgtggct | 1440 |
| aaacttatac atgcttttgt ttggtgaaag gttaaagcga agaacgccaa agacagagga | 1500 |
| aaccgtataa aatatgagta aatgtcaatg ctaatgaatg ggcagaggtg aagcggtcgt | 1560 |
| ctatggctgg agaagggcag atgtgaaaca atatgaggta gacgaaggtg gagacaaaac | 1620 |
| aatttagtaa agtcaaaaca attcatccat atcctaatcc aattatattt ctttaaaaag | 1680 |

-continued

| | |
|---|---|
| tttaagtatc aaaattggac tgcttgatca tctatcaagt tatttttgaa ctttatttta | 1740 |
| aaaagtttaa gattattaat aaaaatgtaa tgtttaaagt ggttagtgct ttggaagcca | 1800 |
| ttacgtccta tggattatgt ggtgtgttgg gctactctct atttggacat gttttgacgt | 1860 |
| accgtgcgaa gtcctgactc tatttgtaaa acgtcacccg gcaaaaaccc aacttaaaaa | 1920 |
| acagaacttt atttcattta atttgcgggg tttatccgga aagaattgtg agagctctct | 1980 |
| tgtgtttggt ttgcttatct | 2000 |

<210> SEQ ID NO 143
<211> LENGTH: 2000
<212> TYPE: DNA
<213> ORGANISM: Cucumis melo

<400> SEQUENCE: 143

| | |
|---|---|
| gtaatgcaat attagcaatt attttggagc aatacaaaca actaggtttg gatcaaatat | 60 |
| cacgaaatac aggagcaata acattaacaa caaataaatg cacgaagttt ttttttttga | 120 |
| acaaacactt aactctctcc aaaccaaaac gagctaagta agacctaaaa aaacaaagta | 180 |
| tcggaataca atatagctta aacaaaaatc atgtttagat tattggttag gttcatctaa | 240 |
| actagtggtt agccattttt caaagaaaa atatgatttg tccttgctaa ttttccaaat | 300 |
| ctatatttta aaagtatcac tctcgtcata attttccata gctcaattaa tactaatctc | 360 |
| acggtagctt ttaattgttc ttgacaagta atggattaac ttaaaacatt tatataactt | 420 |
| tgtaggtatt attttataga aaaattagtt tatacgtgaa aacttcttaa atatctaact | 480 |
| acaatcaaat acctagatta cataatgtat ttttcataat atttatacat tatatttgaa | 540 |
| aaaggactct catttcttt attggtatct acgcagaaat taagatttc gagttgcgac | 600 |
| atctcaatca acgaaccagc taagaagacc ggcaaattcc aaacgtatcc ttcgggaagc | 660 |
| actgagtgtt tccacgtcaa taacaaaata ttgacccaat aaatttcagc cacgtagaaa | 720 |
| caaagcaatg aaagccgtcg gattctccac atcggctacc gtatgccgtt aagatcatca | 780 |
| agtagacttc taattcccat gtcttccgtg ggggccagaa atggaaaatt gaaatcgctt | 840 |
| tatccacgtc aagctaacaa aaaacaacca ataataattc gccacgtttt ctcattagaa | 900 |
| aagtgcaccg ttggatcatc cacgttggca acatagatcg atccgatgga cttatataaa | 960 |
| tttgggtagc tcgtcgagaa atcagatcag tgatcgaagc tactggaagt ttttgctaag | 1020 |
| aaccatgagg aagtggacga tcgcttctgc tcttctcctt ctttgcattc tctctctcgt | 1080 |
| tcccgatgaa ggtgtgattt cgtttcttcc ttcagcagtt tgatttattt gttgaatgt | 1140 |
| aaactgaatg cattgcatta tcttaatcac gagggctgat gctttaattt ttgggggttc | 1200 |
| gaggagaaat ttggatgaga ttcgagcttc gtttgaactg cgaaggtttg atggtgatat | 1260 |
| ttctattgtg tttgaatttt caggtcctag atttcatgcc aaggccgacg gtgatgccga | 1320 |
| cgaggttgta gatccaccaa aggttgagga aaaaatcggc gccgttccac atggtctttc | 1380 |
| cactgattct gatgttgtta agaggttcgt gaatgtctaa tctcgttgat acacgcttca | 1440 |
| agtatagatt tgtccacttc gggaaaaaaa attatcgaac cttctttga atgttgattc | 1500 |
| agagagtcgg agtcaatctc gaagagatct cttcgcagta gcggggagaa atttgagttc | 1560 |
| caagctgagg tgtctcggct catggatatt atcatcaatt ccttatatag taacaaagac | 1620 |
| attttcctaa gagaattgat ctccaacgct tctgatgtaa gttcactctg cctcttctca | 1680 |
| cttcattaga tctagtaatc tcattgttag atttgtgtta gttaataatg gcgtctctgc | 1740 |
| atttcaggcg ttggataaga ttaggttcct ttccctaacc gacaaagaga tattgggtga | 1800 |

```
gggagacaac tcgaagctgg agattcaagt gagttcgacc ttcatactga catattgttt    1860
tcttattacc tcgctgaaaa aagctgctcg ttctggttga tgaaccttgc atacttttat    1920
tgttgtccat aaatcaaata tcgcagatta agttggacaa agcaaacaaa atcctttcaa    1980
ttcgcgacag aggtattggt                                                2000

<210> SEQ ID NO 144
<211> LENGTH: 1337
<212> TYPE: DNA
<213> ORGANISM: Cucumis melo

<400> SEQUENCE: 144
ttttttttaa ttttcttttt gcagattgtg gggctgatcg tccacgatat gattccactt      60
tggctacgag gggtgtcggg caccttgtcc gtaaggcac  tggtgggaga tcgtctgtta     120
ggtaacctag ccctagcttt tcgtgtttg  gattcttcta tttaattgtt ggcttgatgt     180
tgtagatgta atgctgggtt tgagtgcttt gaaatgttga gggaaattta agaaatttaa     240
tgggatgaag atgaacagtg gtacttcaag cctcaaattg aattaaaatt attttaaaca     300
tcctaaattg gtatgactaa gtattgctaa acatgatagt catataaaag cgcaaaagaa     360
aagaaaaatc acccctctac taggattggt ttattctatg gattttttgcc ttcagtgttc     420 ttgaagtcac aataataaaa gtagtaatag ttgcagtcac aactcaaacc tttatatgtt     480
ttttaagatt gtggtaaata ttgttttgat cattagacaa gacatagaga ttttaagtct     540
ctgggccttt tcacgaagcc ataagcctct tatggttcag caaaggcata ctcaaggcta     600
gaagttaaaa aagccttgcc ttgagatgta attctgaata ccttttttaaa acatttggta     660 cttcaaatt  ataagtttat tagtggaaaa tataatcttt cagtctcttt tttagctgaa     720
atacttatac cttttttccc cattgtcatt gatttcttaa ttcatatgca gaggaaagga     780
ctaattagat atactttgtt ttattgagta atctaaaaga tgtggcacta cccactatga     840
acattttgac gtcattccag cttttatggg atattgaagc aggcaatttt aatctgagct     900
ggtttctctg tcgctgtcag ataatccttg tttgtgctta tgtgttctct ttcaagcatg     960
cacattagga ttctcaggca gatcagatca ttgatattta attcaatttg tggatttagt    1020
ttgtagtgaa tacactaaat tctgtctctg gtttctctga tcttactgtt ttattacaaa    1080
attgttttgc agtgggattg ttgctactgt cttcggagct actggattcc ttggccgata    1140
tgttgtacag caactaggta ataggtgaac ataaatggta ctagcattcg actttctttt    1200
tgcttagata tgtaatttat tacgtttctc tataccttct actactagtg ggttttggca    1260
gctttggctc tattcttgat ttttatatca attttatgct aagcatgatt ttggaaatga    1320
attgtgtttc agctaaa                                                  1337

<210> SEQ ID NO 145
<211> LENGTH: 2000
<212> TYPE: DNA
<213> ORGANISM: Cucumis melo

<400> SEQUENCE: 145
atatgtgacg attaattacc taaaaattaa ttatttacat agggttagtc aagttgtccc      60
gtgagactag ttgaggtgag cataagttga tccgaaagct cacaaaaata taaaatacgt     120
caatctccat gctttcataa aaataacaat ttgattctca tgactactca ttcacttatc     180
gtaaactctt ttaaagaata ttaagagcgt attagtgtag tgggctagtt tgttacaaaa     240
```

| | | | | |
|---|---|---|---|---|
| gttggcgaca | aatagatgaa | attagagtta | tctcgagatt | cgacgagggt | taaaaagagc | 300 |
| atttgcttta | ccctgtattt | tcatcgtagt | tcatatttat | ttatattcaa | attctatcaa | 360 |
| gttaaggcca | cgtatattcc | aagaaaacat | aatccattaa | tggtaatatg | aaaaatgagt | 420 |
| tttaatttga | tcatgttgtc | ggcattatgt | aatcacaaag | atatctaaag | ctcaatgtta | 480 |
| aatctaatta | atggaggccg | ataatccaat | tatatttgaa | aattaagtgg | aacctacggt | 540 |
| gagatatttg | tactatcaca | attacaatta | ctcttacttg | ttcggaaaag | aaattttgta | 600 |
| aacatgtcaa | aattatcgtt | actattccaa | atattgtcac | tgacctgaac | attgtcaaaa | 660 |
| agaaataaat | aaataaaata | atattagata | atgtaaaata | aaccacctaa | actttaatct | 720 |
| attatggtcg | caaatgcttt | gataacacat | aaaccgattg | atccgtcaat | gaaattttac | 780 |
| cataatcttt | attatggatc | gataaatatg | acttaatttt | cttttaaaaa | agtgtttttt | 840 |
| aatttaaaaa | aaaaaaagga | aaggaaaggg | ggaggggcaa | aggttctaga | gtgttccaaa | 900 |
| taggacaatg | gaggagggtc | tccaatggag | ggaggagcca | aatccaacgg | ccaacaattg | 960 |
| ctggaagctt | caggagccta | catgattctt | gggttcgttt | ttctctcctc | ttcctatcca | 1020 |
| tcctttttgaa | atttgctata | aagaaaccta | cttctcttct | ccttacaaaa | aatccatttt | 1080 |
| acactctctg | taataccccc | agttttgcct | cactcgcagc | gctcatttct | caccctctta | 1140 |
| tccaaatcaa | tccttctccc | tctaaaccct | aaaacccctt | tgcacctccg | ccgttttctt | 1200 |
| gtaagattcc | ccctctcttt | tcattctgtt | ggactttctt | atccttttac | tttactgggt | 1260 |
| catgcttaca | tttctatttg | ggttttgttt | ttgcttgccg | attcagtctt | ctgtattgtg | 1320 |
| tttttgagctt | tctgactgtt | ttggctttct | gggtttcaat | tgttggtgta | gacttatcga | 1380 |
| ttgattcgtt | tgttttgtgt | cctttcattt | ctgggttttg | atttctttaa | cattttcttc | 1440 |
| atgggttttg | gattttgggt | cttcttcttg | tgtgcatctc | tgtagcttgc | tgattcattt | 1500 |
| gtatctcgtg | tttatctatt | tgtttgagtt | cctgacatgt | gggttttttgt | tgttgtctga | 1560 |
| gaattatgtg | tcaaatgtca | attgtcaatt | cctatgttct | tgaatttgtt | tatgtcattt | 1620 |
| cctttctggg | ttttctctgt | tcaatcttgc | tacatgggtt | ttgggttttc | ttacccttgt | 1680 |
| tgtgtgtagt | tttagctgat | ttttgtttat | gcttactgat | tcggttctgt | attctcgatg | 1740 |
| atttgcttac | ctggtttttt | atgtcgtttg | agaattgtgt | gtcaattcct | tgttgttga | 1800 |
| ttttgtttgt | catttctggt | ttgacattcc | atccaatcct | ctctgctcta | agtctacttg | 1860 |
| gttttcaatt | catgaatttc | catcagacgc | attgtcggcc | ccctgctcta | tttgtttaca | 1920 |
| attctggttg | tgaagttgtt | tcagtttgaa | ctaattgatg | gtctggtgat | tacgttctgt | 1980 |
| atcagtttgg | aagagggtaa | | | | | 2000 |

<210> SEQ ID NO 146
<211> LENGTH: 1212
<212> TYPE: DNA
<213> ORGANISM: Cucumis melo

<400> SEQUENCE: 146

| | | | | |
|---|---|---|---|---|
| atatatatat | atataatgga | ataggctatt | tgatttagat | gaaagctatt | acgtcctggg | 60 |
| gtttacatca | taatctctat | tataatgtta | atcgagaaac | tttataaagg | ttaactcatt | 120 |
| atctctcttg | tcttcagttt | attattgttg | ttttttatatc | ggtggaattc | cacctttcac | 180 |
| caactctcaa | gctgtggtgt | gaatctatgg | gattaatcta | gggcgaataa | gggagctgag | 240 |
| tatttttctat | ttgtggaatt | aaatctatag | tacacaaaac | atttgctcaa | ctactaagga | 300 |
| tatgaaaacc | cttggctctg | ccaacatggc | ttatagaaag | tatctgaaaa | cgttcaccac | 360 |

| | | | | |
|---|---|---|---|---|
| tttgcaattt | caacaataag | tgtaaattct | tttcctattg | ttgttattta gtcgatttga | 420 |
| tcgttgtaca | atatttgctg | taacatgttt | gatttttggc | cattttagtg ttcacaagaa | 480 |
| gatattgttt | gttataagaa | tctacctgat | cctttcaat | tgttattcaa tatattgcct | 540 |
| actccgttga | cagcaggtcc | atgcagagga | acaagttcta | aagttcaaac tcgatgctga | 600 |
| tattcttcag | gtactacttt | tctgttttca | caagtttgtt | gtttcaatag ttctaagaca | 660 |
| gtgacactca | tccctttatc | tccgtaaccc | aattcattaa | cgatgacttt tgatcggttt | 720 |
| gaagaaaaaa | tttataacac | tttctcatct | cgttccctt | ggattttcag ttttaaaat | 780 |
| tgcatctata | tgtattcttt | tgttatcaaa | ttttacttga | taatgacttt taaattgtac | 840 |
| taactcattt | agatgtgaat | attaataatt | ttaaacttca | tttctgacgt ctaatactaa | 900 |
| taaaataata | ataacaatta | tccttcttaa | ttaaatatgg | tttacctacc ggtctattgt | 960 |
| tctgaactgg | atatattcaa | tttgttttat | ctgaataatc | ttttgaggtt gagttatcaa | 1020 |
| gagcctgttt | aacttaccta | aagcatttct | aacctgaact | atgccccata tgaatacttc | 1080 |
| attttcttta | ttctattgta | aaacattgtt | gttattataa | tttgaaacgc ctgtaatagt | 1140 |
| ttttacgatg | tcttgcagga | gtctatcgtt | cggcatgtaa | acgaacaccc acaggctggc | 1200 |
| tggaaagcta | cc | | | | 1212 |

```
<210> SEQ ID NO 147
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations
```

<400> SEQUENCE: 147

| | | | | |
|---|---|---|---|---|
| acatagtatt | aataaattag | ggaatgactt | agttatttaa | tttaagcggt agtaaatatt | 60 |
| attaactttt | gttcgttgtg | ttattttact | ttcaaaacgt | tcatcttgat ctttatcctt | 120 |
| tctaatatt | atttattta | gttaatatca | aaaaactaaa | tttaatttat acgttaagtt | 180 |
| acaacttcat | ttatttcaat | ctaaaacttt | tagaattaca | ctttattcac taaaaaatta | 240 |
| ctcgtaaatg | caaccattcc | aaaaaggttt | caatattata | taaaatatca taatttttcg | 300 |
| aacattctta | aaataaatta | aacaaaatag | tagttttcat | atacataaaa ttcgaataaa | 360 |
| tcctcataca | aaaattttaa | atttgaatca | tcacattgtt | ttattttaga taatcaatca | 420 |
| aataatttag | gaaagagaa | gaaagaaaag | taaaggaag | ttgaaggtat tttatttagt | 480 |
| gatagaatta | taaaataggg | tattttagaa | ataaaaacac | aaatatataa aaatacagaa | 540 |
| attgatgcat | ttaatggaac | actatttgac | aatcaataag | aaagaaaaaa aagaannnnn | 600 |
| nnnaaaaaaa | gaaaaagag | aaaaggtttg | gtattgggtt | tgtgggattt tattaataaa | 660 |
| tgaaataaaa | aaaaagaaa | gaaaatttta | attgattaat | ttggtgggag aatattacaa | 720 |
| tgaaaccca | ctttgtgaac | aaatacattg | catttgggt | gtaatcaagt gtacatgcat | 780 |
| ctacccaaac | ctttcttgaa | ctcaccataa | atccttcttt | tagaccgctt cgacttccca | 840 |
| attttcttc | actttttttc | ccccttctct | ctcttcctcc | gttccccccc ccttttttt | 900 |
| tccctatctc | atagggtttc | catccacctt | cttcttcttc | cgttctctca tgcattgtca | 960 |

```
ttcacaatct cattctgaat tcctcttgat cttcttcatc ttcatttcct ccttattttt    1020
tgctctcttt cgagggtttt tcggttcatt tccgtccaga ttccaccacc tcccgtggtt    1080
ttttcaccca tactcatgtc gaagctcttc gccttttccg gtaagtttat ggattttac    1140 tgattttttt tttttgtttg ttttgccttt ctttggattt gacttagatt gggtagctgg    1200
tagggttaag cgtcgtgttt tgtatgggtg tttggattgt tatttggatc gtagggaaag    1260
atttggaatt attggttta gttttgggg gtttcttgat tcgccaggtg gcggatcatg    1320
gcttggtatg aattgtgagg gaatatggat ttgggtttct ttctattagg attgttttat    1380
tgtgttgatt gattggctat tttattgtct tgaacagtcc atgccagatg taagtttctt    1440
gaaaagagat atcgtagttt gaagatgggt ttacctttta agtgatgtgt atgtgttgtt    1500
gatctgtcgt tcccgtacag atttagattt gaggtttaga ataagagagc acatcaatag    1560
taaatattaa agggtcaaat atagttttgc agagattgct tcttgttttt ctctgttgat    1620
aaattttcga tcttttgatc tagaagttga ggggtatttt ggtctgagga tttatttgtg    1680
atgttggatg atgtatctaa cttgtagttc ttgttgttga aatttcaggt agtgaagatt    1740
tttgcactgg agggtcaata tacccaaatc ccaaggactc cagtttattc ttgtcccttc    1800
ctcaccacgt tgatgtctat tttcctcctc gaaagaggtc tcgcatcact gctccatttg    1860
tgtttggtgg agaagaagtt gaatcaaaag caaatgtttc tatcgagatt cttccggatg    1920
agtgcctgtt tgagattttc agacggttgt ctggtggcaa agaaaggagt gcctgcgcaa    1980
ccgtttctaa acgatggcta                                                2000
```

<210> SEQ ID NO 148
<211> LENGTH: 1254
<212> TYPE: DNA
<213> ORGANISM: Cucumis melo
<220> FEATURE:
<221> NAME/KEY: misc_feature
<222> LOCATION: (1)..(1254)
<223> OTHER INFORMATION: n=g, a, t or c.
<220> FEATURE:
<221> NAME/KEY: unsure
<222> LOCATION: (1)..(1254)
<223> OTHER INFORMATION: unsure at all n locations

<400> SEQUENCE: 148

```
tcataaatat atatataaaa aaacaaatat tataacctac cttttgcaaa tgataaaatt      60
gtaaagtctc gtgccgataa tgtgttataa aataaaagaa caaagaaact aaataagaac     120
aatgcaacaa nnnnnnnnnn nnnaatagag aagagaggaa gaaggggaaa caattaaaaa     180
ctcaattgta gtgtgactta cacaaatgca acacatatat ctatttatag gacatatcat     240
ggtatatgtt atattatgaa attcaatgaa atgaatgtta caataaagaa ttgaatgaga     300
gttgtatgaa aattgtaacc ttcataaatt atggatatct actcttataa tatatcatta     360
tatttataat gtatactata tgtttgtatt ttaataagaa aattatccca ttggatttgc     420
gatcttagat ctaacctact aaacaaatat tccaacgaag aggaacgaga tgagaacgcc     480
gttctaacct acgcaatatc aatcgtttct tcgctgctac tttacgcctc aagttcctac     540
ccttcaagtt tcatcttcaa cgatcaaccc aacgattaac ccactgcacc accttatctc     600
ttgttggtgt catctaatcc atcttcttcc tgcatcttct gcaaatgctc tcaggttctt     660
tcctctctct tgtgcacaaa ctgatcaccc atgttgttcg ccggaaaatg attcagattc     720
ttcgtatctt gcctgcattg tctttgacta taatatgatt gaaattccact tgttgattgg     780 ttttcaattg ttaattaccg ttggttttgc tgtttagtga tagtatatta tgaggttttt     840
```

```
gttcgttttc gggttttttgg atgtgatttc atcctataga atgaagagta tgcaacgtat       900
gctgtcacct tgcgggggaa atggtacacg tggacccgaa atggagctag gttttgatac       960
gtgcagtttg agttttggtt ttgggaggat ttggcattcg ttatatgaat tttgtaatta      1020
actatgccgt ttgattgtta tttataacgg tgcattgctt tttgaggttt agaatttgga      1080
cttaacgcct ctttctattc atggttattg gttttatttc ttccttttg ttgactgaga      1140
ttggtcgtag aactcgttgc ctgtctatgt tttaatgttg gcctgatttt gaatttctaa      1200
tccatgacta agtatttctt tattgtcttg atatagttga ttgaatcatc aatc            1254
```

<210> SEQ ID NO 149
<211> LENGTH: 2000
<212> TYPE: DNA
<213> ORGANISM: Cucumis melo

<400> SEQUENCE: 149

```
cattttaaat tgacctttca tgaaaaatcg tatgttttg gtgtgatttt gagtataata        60
aaaatgattt taaccatttg aaaatcactt taaattacac ctaatgggtg actgaggttt       120
tagctttcgt ctttgtttag ctctaaattt gcatggcaag ttttccattc caatgattga       180
tgtggcttgt aatagttgaa atatatatat atatatatga ggtatcaaaa tccccagcct       240
tgtgttaggt tgaatatgga gggagtgggg agttatttt cctgctctta ccccgttcct       300
aattcccacc ttgtttacta tgtgttattg ttattgccat atttactatg tacataatat       360
ttcgattaga aattttattg tttaaccatt agacaatttt atatgtctaa accataggtt       420
tgaacaaacc atttagatta tatatatgtt gacaattaga ttgatagggc aattattttg       480
tttatcctaa aaatggtaaa taatgttctt aaacttggtt ctttgtgaaa taccttcaac       540
tttcaaagtt tttaataata ttcttacgct tataaaaaga aaaaaggat aagttgaaaa       600
aagaatactt ctatgataag ttttagatgg aaactattta cttttcatt taaaaaatac       660
ttttcaaatt tatgaagttc caaaagtatg acttaaagaa atagttatac ccttattgat       720
aatatacgac aaaaacaacg caatatttcg ttacaaaaat aaatctagct gcattactat       780
cttactttaa agatactctt atcgtctatc taaactacct tactctagaa ttaataatta       840
agttcctttt actttataaa ataacttat tcctactatt agtatatatt tatattggta       900
tctaatagct aattttgaat tttgttccaa aaaaaaata tcgctgagtt ttgttttgaa       960
gtcttttttt tttttaaat atatattttc gattaaagct agatgttgca gttgatatgt      1020
agatttaaaa gaaatgtgtg agatcgttta aactatata gaagattaag catttattac      1080
ttcaaaatat atcgttaaaa ttattcacat aaccaatttt tactcatcaa atattatgtc      1140
agagaaaaga aaaacgaaaa agaaaaccta cttcaacgga caaagaagtc cttagttcaa      1200
atcttcaaac ctttatttgt attaaaaaat ggcatataaa tttttttcaat ttttacgcat      1260
tacctgttgc gtgaaaaaca ttgatttaat agaaaagaac tgtcctttca gttttgttt      1320
tttaaaacca atttcgaaat tcaagaatag aaacaaaact ttaagtctag aggatcacta      1380
aaatctatca taaggctaga aatacatctt gtaatctgca gtaggcattt gccgggatga      1440
caattttctg gtgcttggat taagaaaaaa gaaaaaaaga aaaagaaaa aaaaatggtg      1500
aggacttaga ggccataatg agtttggcat tgggcccaca gtaggatgag taaattataa      1560
ttgggagaaa atgagcatag ggtgtggagg ggaaaaggag aaggctaaaa cactatcaca      1620
aatcacacag tagaagatac acagaagaag taaccacagc cattcattga gtgagaggct      1680
```

-continued

| | |
|---|---|
| atccataatc tcatcctctt acccttctca tcattcattc aaagccattc aactcaacat | 1740 |
| cccactctta gttaaccaac aaaatatata tacatccttc tcaatttccc ttctctctac | 1800 |
| tgctttaatc ttttgcttct tcttcttctt cttcttcttc ttctgctttc tcaataccct | 1860 |
| caaccatggc tacggctact ctatcagtag ccaaaccatc tattcaggtt cctccattac | 1920 |
| taaacaccat cctctttccc ttccactctt ctttaatttt ttgtatctga taaacattac | 1980 |
| tgcattttct tgcatagcag | 2000 |

<210> SEQ ID NO 150
<211> LENGTH: 1680
<212> TYPE: DNA
<213> ORGANISM: Cucumis melo

<400> SEQUENCE: 150

| | |
|---|---|
| tttttatgaa gggagttgtt atttttccttt gggatttgga gggatatgat atatatcctt | 60 |
| ttttttgcaat ttgatgacag aattctgctt ttagagactt ttcaaactgt ttcgtaatga | 120 |
| atttgatggg ttgggggtgg cttagttcaa tactttgtgg gttgaaaatt ttgatttgca | 180 |
| ataaatgaaa gccaaaaatg tggggaagct ttcagttcaa gtaagttaag ggaaaactgc | 240 |
| agaatatctg gcttgaaata agagatgtct tcgaaggtta atagttttac attgactttt | 300 |
| ttaaaaaaaa gattatatta taagtacaaa tatgggtgga tgtgaactta tattattcaa | 360 |
| agagactaat ataagttttg gcgcttaat atttttatatt ttcatttagc agtcaaagat | 420 |
| gtataagaaa actttggtaa tgcatttttat actagtttat ttatgtagga tgtaggatct | 480 |
| atcgaataat acaacatatt tttaaatgat gtgtacaatt gtgaaaaaaa aaggaacata | 540 |
| cagtattgta gaaactaaaa tattttctaa gatatatcga gatgtaaaaa aaatgaatgg | 600 |
| atgtcaattc cagcataact taattgttga actaaaaaca aaaagaagaa ataaaggggg | 660 |
| caatggtttg atcctcatgc cccacatgaa agtcaaagtt atgtaaaggt tccgtgtagg | 720 |
| atatccttcc tcctaataag gggagatagg attttatgag ggtgccaaca gctcagaatt | 780 |
| ccaaattccc aaaataccct cttgcttgaa aatttcaaac tcttctgttt ttgccttgtg | 840 |
| taccattcac tattccgatg cgtacagttc attaaccaca caagttctcc ttttgcaggc | 900 |
| aggtttagct aaacttattg gacttgctgg agagaccaat gttcaggtaa gatcttattt | 960 |
| gttataatga actcacaaac taatttagat tagccaaaga attctgtttc tgaagaaaga | 1020 |
| gaggatgaaa atcatctcat accaaatttc tttcttttttt tggaattatg tcttcacatt | 1080 |
| tattcattt ccttgtcaac agggtgaaga gcaaagaaa ctggatgtgc tctcaaatga | 1140 |
| agtctttatc aaagctttgg tcagcagtgg cagaactgta agctgctatc taatcataca | 1200 |
| aatgacacga caaaaatatc tggtgactta ctctaatagt tgacaaattg gtggcagtgt | 1260 |
| attcttgttt ctgaagaaga tgaagagcca acatatgtcg agccatctcg gcgtggaagg | 1320 |
| tttgttttcc attcttgatg attttttgtct aatgcttaca attatcatca gtatcaactc | 1380 |
| ctcttacttt gttttaattt taatgttatt tcttcttatt ttccaatgac aaaggtattc | 1440 |
| tgtggtgttc gatccactgg atggttcctc caacattgat tgtggtgttt ccattggaac | 1500 |
| ggtaacatcc ctatgctacc ttctgaatga gatttcaaat attttggta taatttcttt | 1560 |
| ccaataagct gagtgtatga ttgtttgaat atctacttttt tcatgtagat ttttggaatt | 1620 |
| tatcacttga acgacagcca cgaacctaac ctagaagacg tcttgcaacc tggaaagaat | 1680 |

<210> SEQ ID NO 151
<211> LENGTH: 1524

```
<212> TYPE: DNA
<213> ORGANISM: Cucumis melo

<400> SEQUENCE: 151
tatatatata tatataggta atgagtaaag aaatgaaaaa gaatgagttg aagaatcaca      60
cccttaccat tctatttgaa actcgtgagt cttgtagact tttacatgtc ttctccttca     120
cttaatatca ttctggattt tgattatatg tatctttatt tctaaacagc ttggacagat     180
ttattattgt tagaatacct tgaatatgtt ttctggtgct tagaacgatc atacatgggt     240
ttttctaggg ttagaggagt gcgctataca taaactttct agttctagag gcattgctgt     300
aatcttaagt ttaacagttt ctctttaata acaaaaactg ctcttcccct acggtttaag     360
ttttctcctt atcttaacag ttataattat gaaaaatgat ggaaccaaaa caaagttctg     420
ttaaaatttg actaattgat tgaatgaact tttgtttcca agattcttaa tttgtaaagt     480
aataatgttc ttacaaatca ttattttgat gtctgagtta taaccttaa gcttggtggt      540 tcatattcca ttcaggtgaa gaagattgtg agtgaaagct gttcccaaga ggttttagaa     600
gtggcgttaa actccatctc atccctaatt accatcctct cctccatgtc atcgtctacc     660
aaactccatt cttcactttg atggtataag aaagtgaatt agatttggga ttgagcttca     720
aaacatgtat gatgatgtga atatttactc gtgtaaataa tataacatgt tgtattcttg     780
cttgtttctc tttgctcatc ttcgttttgt taagagcaaa gaaaagctta cgagcatgaa     840
catgtgcaaa tttatgaagg tcaatgggct tcgtaatttt ttttccccat tgatttaacg     900
atttatggaa gatggatata gtaaatttag gttaagctgt acaaaaccag agaattttca     960
ttatagtaaa tactttacaa ttttcaatta gctacaataa acaccgtttc aaaatctccc    1020
tcatttgcta ccatatttac tattcgatat ttatcatttt ttttattcct gttgtaatgt    1080
ctactatttt tcttttaaac tattcacacca caaacacata ctattataat tcaaattaaa    1140
ataatcacta gtataactca actataataa ctcagatgat ttcattccat gaaagtggta    1200
attataaata tttaatatct tatatgataa ggataactat ctatttggtg aaaccaaatc    1260
acaatgatgc agtggtaagt gctttggact ttgaatctct tttttatagt atttcattct    1320
tttttcaacg aagcagcatc atgggccttg aatggaggcc agctagaacg agcccattac    1380
atttgacaga gcatctcttc ggcccatgag cccaaacact attcatcttg ttaaaccacg    1440
aacaaatcga gactgccgag agtgtaagag aattgagtaa ttttttttcga gacacaggga    1500 gtttagagag taagtcggag aaca                                           1524

<210> SEQ ID NO 152
<211> LENGTH: 1851
<212> TYPE: DNA
<213> ORGANISM: Cucumis melo

<400> SEQUENCE: 152
ttgggtcgtt acaatatcac tgtttaaact taagtttatt tttatttatt tttttatttt      60
ttaatctttt tcccttcttc ctttcatctt ccattcattt atacaaaaat aaataatgag     120
aaaattactt ttcactttg agttaattta ttttttaagtt ctaaaatcta cattttaatc     180
tttaaattta aaaaaaaaag gatttacaag attcttgagt aatttattat tattattatt     240
ttgaacgtaa atataaccct ttacaaaatc taaatgagtg tttgggacaa tgagttgatt     300
attataagta ttgaattata ataattttttt gtggggtata gactatttta atttgaagaa     360
taataggtac gtgtttgaaa tataaattat gttagttggg aaagaaaata gtaaatatcg     420
```

```
tagaaaaaaa taaaataaat gaacaataag aatataaaat atggtaataa attgggactt      480
tgaaataatg gtaataatta attaattaat tgaaagctac aaaacaatgt tcacttcatt      540
gctatagttc taaacagact aacaatctca atcaatgacc taatgggtca ggccattata      600
ttgggctcaa atagattttg gcaaaacgaa tcgaaagccc aatggggcct atattatgta      660
gggccgaaat gaatttcaac gaaaggaacc caaagcccaa taggcccaaa ttgagactta      720
caaaggcgca tgttagcatg aagagagaat tgaaagctta acagcgcca tcacaaaaca       780
tttgcatttt cgtgttgaaa tcgcatttgg gccgtaaacc aatgaaacac aaaacaaaca      840
aatcctggaa tagcctcaac ggttctggaa gaagaagaat cttctggaac tccaatccc       900
acaataaaaa tcaaacccta aactcttaca ttcagctctt tgcttacctt atcccaacaa      960
accttcacca acgctctacc ggaactaaaa cccctccgac ctcccacttc cgacttacga     1020
cctctgttgc ctgaacatgg cgtctgccaa tgctctttct tccgcttcta ttctatgttc     1080
ttctcacaag gtacttcact tataaccccc tcatttcttc cttgtatttt tcacaattcc     1140
tctttggaaa tgatgatatc tagattgtag tagttgggat tgtatgttag gtagagattt     1200
tgtggagtta gctgagagcg gctgagaata ctaatatatc gtttccagta gcttacgttg     1260
cgtttttcta atgttgcaga gcttgagaaa ggtgaatcaa acgcagaaca acagagtaaa     1320
ttacagacag gctggtagta gatttgttgt gagagccact gcaaaggaga tagcattcga     1380
ccagagttct agaactgcac ttcagtctgg gattgataag cttgctaatg cagttggttt     1440
gactcttgga cctaggggta actttctgtt tatatttatt tatgaattgg ttagtattgg     1500
atgttgttct aatattgaaa tccctacagg atatattcat cacatttata gattcgtgtt     1560
atggttatgt tgagaaattt gggttcttca cataattctc aatcttgttg tgatattttg     1620
tatttgaagg gaggaatgtg tgttggatg agtttggtag tcccaaagtg gttaatgatg      1680
gtgtgacaat tgctcgggca attgagttac ctgatcccat ggaaaatgct ggtgcagctt     1740
taattagaga ggttggtttt ttatacttgg ttatgaagca aaattttctc atctatcgat     1800
tattgaagtc ttattagttc ttacattgcg ttgacaagta ttctatatgt c              1851
```

<210> SEQ ID NO 153
<211> LENGTH: 2000
<212> TYPE: DNA
<213> ORGANISM: Cucumis melo

<400> SEQUENCE: 153

```
actaattaat agtaatttgt atgggatata tgtatatgtg tgtataacag gaactacaga       60
gatagagatt cactttctag aaataaagtt gactgccatt ggagtttatt tggagccttc      120
agttgtggag catttgcaac aatggaaggg aaaagctgct aaggacttag tggaagatga      180
tgacttcttt caggctattg tttctggtat ctccctagtt atcctatttt taactatact      240
atctcatcac attcctaaat gtgaattact tgacgatctg ttcaaacata tatatttcat      300
tgtttgatcg taatgtttca tatttatgat gtttcatata ctacctcgtc acacgtgcaa      360
aggatttaga tccgttcaaa catatttcat tattggatcg taatgtttca tatctatgat      420
gtttcttata ctatcgcatc acacatgaga tccattcaaa catatctcat tgttagaaag      480
attatacatt atttcaattc aaatagctct aaccaatgac aaaattagat tcgtcccgtt      540
tagcttattc tatatatata gatagataga tagatagata gtatggatat gcttgtgata      600
agtgtttttt tcttcttttt tttttctttt tttgttttttt ttctttttttt gtcactttct    660
aaattatcta tctcacagtt agctagttgg cggggtgatg acttttggtg tgtcagtcta      720
```

```
gtgagaagtt tggggttat ttttattttc gaaagcttcc taattgaatg acttgtaaag    780
gttaatgttt atgttttgt acatgttttt catgaactat tggttttaca agagttacaa    840
ttctatttat ttgtgtaaga aagatcatat cacattttta ccctggtgt gttcgttta    900 tgttcttgat ttgcttttg tttttcaata atttacgggg aaagagagaa taaaattttc    960
tttctccgat ctccgcattc aattttttt ttttgaaag gtgcattcaa tttttttgtg   1020
cttattaaat attcacttac atcttttgtt ttgtttattt ttttatttc atctttctta   1080 tatgaaaata aaatatttt tagtacaaca atagaacctc ttgttaccat tgaaatgaat   1140
tacaggaaat taaaactttt actttttatt tgagagaatt aaaagagtag tttttaaata   1200
taacaaaacg actttcgcaa tagatccaga tgatcattta ttaacaattt tctaattaaa   1260
attgttacta aattttaaca attattaaaa aatattaatt gaaaaacacg tgtatatata   1320
taggaacatt ttcaattata gccaaaagtt ataattattt actctataaa attctttaga   1380
gtctatttaa ccttttgtt aaattttgtt aatagtttta ctttgccatt cataaaaatt   1440
tctcatatta tatacagtga gaattttata agtctcaaaa gtcaaagatt tgattaaaaa   1500
aaaaagaaat gaaagcatat ctaaatatat tatttatact ttgaaaatta cttccgaagc   1560
aaaatgtaaa accgttataa gtgaacttag aatccaaaaa catatattaa attaagttta   1620
aattatataa caacacctt ggattttgtc attttctaaa atacctttta tcatttcaat   1680
aattgtaaaa tgagtcctaa attttcacaa atgtttcaaa aatatttgga ggagacaatt   1740
ccttgagaat ttcaaagata tattaaagag gacgtattga cccaaatctt ttgttctatg   1800
tcactatgat caccctttta tatcacaatt tatttccatc tacaattcta aagaatttat   1860
aatttaaaag tagtttccaa atgtttctaa atttcgagg gtaatatttt aacttttgga   1920
agtacggaaa gttaatcaaa tctttgtctc aaaatctcaa ctaataactg gaattgggaa   1980
agctaaagtc tagaccttaa                                             2000
```

<210> SEQ ID NO 154
<211> LENGTH: 1288
<212> TYPE: DNA
<213> ORGANISM: Cucumis melo
<220> FEATURE:
<221> NAME/KEY: misc_feature
<222> LOCATION: (1)..(1288)
<223> OTHER INFORMATION: n=g, a, t or c
<220> FEATURE:
<221> NAME/KEY: unsure
<222> LOCATION: (1)..(1288)
<223> OTHER INFORMATION: unsure at all n locations

<400> SEQUENCE: 154

```
cgagaagtac ccggcgttgg tcaccggatt tttcttcttc atgtggtggg tttaattgtt     60
ggtcacgtgt tttgcacggc gaaggccggg tggtaattat tacgttgcgg caagtttgag    120
cttggttgtg tgaaattacc gtgttgtcct ttctgttttg taggtacttt ttgaacgtga    180
ttttcaatat cctcaataag aagatatata attacttccc ctatccatag tatgtatttc    240
caatttacat tttcatccct gtattttct tcttcttctt cttnnnnttt tttttttaat    300
attgttatta atatttgttt acgttccagt tttgtgtcgg tgatccattt agttgttggg    360
gttgtgtact gtttgataag ctgggcagtg ggtcttccta agcgagcagt aagtcaactc    420
tttctatagc ccaatatgcc aatttgtct tttctttca ttaaaattgt tattttaac     480 ttttcatac ccaatttagt tttttagtc tgtttattag tcttgttttc ttcaaattta    540
```

| | |
|---|---|
| gtagtattgg tagtctaatt ggtagggctg ttttgaaagt aattacctaa tataatgagt | 600 |
| atttagattg agacagtact atagtctaaa cgatgtcatt gcagttttga ttgaaatttt | 660 |
| ttctccttta tttatttcga aaatgacaat ataacttctg taatctttgt aaccatgttt | 720 |
| atttgaagct acgttgtaaa ggggaaaaag aaaggaaag tgtaaaatgg tcaaataaat | 780 |
| tatatttta agtgaataga ttatataatg tgcggtaaaa tatagcactc acaagtaaat | 840 |
| gcaacttagt aatctaaaga ttgaactatc aattcatgaa ttttttttata attagcatgg | 900 |
| ttttctatag ttttgggag tctgttttc aatgaaaata ttgccagtat ggtaatcttg | 960 |
| tatgacaatg tattttctaa agtatggata taattaaatt ttctttaatt tatcggctta | 1020 |
| aacttttcgt tgtactaaaa atctaggata ggacgtttaa tatttgaacc tttgtaatgc | 1080 |
| catttaatca ccgattaata tagatctaac tattgaaact tcttcaaaag ttttaatcca | 1140 |
| acggatggct aagagtgtta aaatattgat acaattaaat ttatcgtagc ttaagctttg | 1200 |
| acagtgtcaa aagctaattc agttattttc tctgcccttg gtataagggt aactctgttc | 1260 |
| tctctatttc acacaagtga ttgctaac | 1288 |

<210> SEQ ID NO 155
<211> LENGTH: 2000
<212> TYPE: DNA
<213> ORGANISM: Cucumis melo

<400> SEQUENCE: 155

| | |
|---|---|
| ttatgtttta ttaactccat agtttacta accccatttc acgggaaagt acaataaaac | 60 |
| atttgtgtta aaaggagtt gtttgtatag atcgaataaa catttgtac taattccaat | 120 |
| catattacca aatgttttaa gagcatgcgt tcttgtgtgc ttgaataggg gtgatcatca | 180 |
| attgagtggc gtcagattta aatttaaagt ggcaccaatc atcgacttgt tggtttagat | 240 |
| cgatcggtag ttgttgtttg tgggacaatc atagttatca ttttctcct tctatatgaa | 300 |
| taatagtcaa ctagatagaa ttgacatttc ttagtattaa aaaaacgacc actgacctgt | 360 |
| ctatatcact aaactgcttg acctaagtga gtttggttgg acttgattgc ttcgttgtgg | 420 |
| tctaattcac ttaaccctac ttgaaagtaa aggtagaata taacatgatt ctttccaaat | 480 |
| tggcaagttg tgacttgatt tatgcatgca cgaagattct tccactctcc acctaactag | 540 |
| tactcgatca cattggaaaa tggatctgtc ccgtgaagga tcgcaatatt acatgccttc | 600 |
| ctactttttt cttttcttcc accaaagaaa aagaaaacgg gacacacaat aactatacat | 660 |
| tatcaataat aattaaacga atcatcccac caaatgtaaa ccatgaatat tgaaatcatc | 720 |
| atgttttaag aatcattta ataattatgt tatttcattg ttttatatag aacacaccgt | 780 |
| tcatgaaatc aaacaaagag agagaaatta taattttgta acaaattacc aacattcttt | 840 |
| ttctttctat ttttcataaa tgagcatatg tttgtgtata tatacatact gttatttgat | 900 |
| ctccacattg ttgaacaaaa aagttggtgt tcttgaaaat agctatcacc gaaaatacgt | 960 |
| catatactgg gttgttatgt accaaggccc agaagaaagc ccaaaatcac cggcccatga | 1020 |
| gcagtgaaca ataattggg ctaaaagccc aatatacgtg atgatgggcc aacccagaga | 1080 |
| agttatagt tatgttatta tagaattcca gatcagggag tatcgaaaca aaagcctcca | 1140 |
| ttgtcctcgt tctcttctcc ttgtgctctc tctctctctc tcttgctctt ttctctttct | 1200 |
| ctttctctcc gacgacaggt tcctgaagct cgaccagcca agggcattga tctaggtgag | 1260 |
| tccgctttca cttttccact ttcctctgcc gttttcttg tcatttccaa ttctccattc | 1320 |
| tttgttctgg atttcacttc tttacttcgt cgttgattag aagataatag tgagatcgaa | 1380 |

```
ttctatgtct cgcataccatt cagtttcaag gaacaagaca atgattcaac cgcgccgtcc    1440
acgttatgga tagagggttt tgattctcac ctttatagct gcataacacc gttcttaggg    1500
ttcggacctt tgaatctgcg atatttctca cactgttttg gacgttttta ccgttttcct    1560
atggttcttt agccttacct tatcttgcct tcagatcttc gattgcggat ctgattcgtt    1620
catttctact tgttactttt tcttggaagt cgaggattat aaatcaacaa caaagcattc    1680
aaaatctcta gtgcaattag tgttttccat ctagttattg gagatcgttt gtagctttga    1740
ttttgtccac tttcttattt tgaacgtctg gaagacgttt tatacatgtt ctttgggtaa    1800
agttgcgttt gggcactgtt cttcacctct gggttttcgt tcttatgcta tgtttcatga    1860
tttcttttga tatctttgtt attgtttccc catcatcgag tatctgattc ttattcggaa    1920
gccgtcttct tgaagctgcg aaccggtttt cttttctcc ctcatcaagt ctttaatttt    1980
acaggaaagc gctgaataag                                                 2000

<210> SEQ ID NO 156
<211> LENGTH: 2011
<212> TYPE: DNA
<213> ORGANISM: Cucumis melo

<400> SEQUENCE: 156
ttgttagagg agttagcttt tcagggagtc ggttacaact tacaagacag acaaccatac      60
tgtacaatca atcactactg cctcaaagtc gaaaccattt aataccagtt gagcctcatt     120
gtgactgcat aattttgacc cctaccacga ggtaatttca gttcaaatca attgtatctc     180
tcttctggat atcagtcaag aatctcatgt tctcaagtta tagtacattg ataattactg     240 tgcatttta ttaatttatg agttaaaatc ctgctgatta attcaactaa aggaataaaa     300
tagttattgg catttggatg agaatagaat gtgaatccca tcattcatcg ctagattgga    360
ccgtaattat aagtgagagg gagaaacttc tgttgctatt ccctttttat ttcttaattc    420
atttataaat tgttttttagg ccttttatat atatatattt ctaccatttt tacatttaaa   480 attctttaa ctttattatg tatggactca aactaacaag ctttatttga taaaattgtt     540
caaactatta tattagtttt atatttgtaa accataaaac aaatccataa aattccacct    600
gcatcactca ctcatgttgt tgaatggtac gaaataaaca atacatgtga aagatgaaaa    660
taagaattgt tctcttatta aatctaaaat ctagattttc ttttttagtac atttaacact    720 tcaatgaaag gtctaaaaca ttattgaatg acgtcacgaa ctattacaaa agattattcc    780
gatttatctc aaaaggggtc tatttcacta attttggtgt cccacatctg taagagaat    840 tttcgtgata tgtgtagata tttaaatata attgaattcg atgaaagcaa agcaagaatc    900
gatatccgta gttattttga tatagatcgg tgataaataa aagacaatat gcataaagtt    960
tgtgggtaca gagtcggcta gttgcaatga ggggtatggc ccaagacttt tcccccaacc   1020
ccaacggtca attaatcacc ccaatggggc atcgaatctt ccccaccatt ttcctttct    1080 tcgccgactc ttctacccat ctcttttgcc gactcttct cacaggtttg attaaatccc    1140
attcatattc agatacacta tttcaaaata ctcgcaaatt aatttgtttt tttaaatatt    1200
ggtataataa taaaattaat tataaattgt gacctaaaaa gtactttgtg gaagagggga    1260
tatagtctgt ctaatatatt attgattaaa tatataatag aaccataaat gcaaaccact    1320
agaattgtta ataaaaatca acgctctttt aagtctttcc atagaaagaa aggcaaagac    1380
gcgcaacgtc tagaattttc tttataacgg aagctaactc tgttataacg gccgtccaca    1440
```

-continued

```
taatatggta gatttaaaat gacgtcagca tgtcgcttct aaatttgggt ccaaggggg   1500 gattcattta tagggaaggg aaacggcaaa tgcaagcata gtgagtaaat acgtggcggc   1560
aaagtaatgg ataattctgc ctctgccgtg acgacattgc ccttccattt cactataaat   1620
acacctcctc tatccctcga tttcttcgca attgaatttc tcttctcatc tctgtcgtag   1680
caaaccaaat cgatttcttc aaaggtattt cttcctttcc tttttttttt tttttttttt   1740
tttttaaatc atgttgttca aactttgaga gatgaaatga ttaggggctt tcaaagtggt   1800
tttcgtttga tatgtttctt agatcgatag ggtttagaat cgagcatcct tgtaggtatc   1860
ctgaggtttg gtggttggat ctgcttaatt tttatgtggt tgcatggaaa attgggattt   1920 ttttttttcta attacgtgat tctggaaata ttgatctgtg gttcagatgg aattgaatct   1980
gatctttctg ttttgttctg tataggtggg c                                  2011
```

<210> SEQ ID NO 157
<211> LENGTH: 1698
<212> TYPE: DNA
<213> ORGANISM: Cucumis melo

<400> SEQUENCE: 157

```
ttgttagagg agttagcttt tcagggagtc ggttacaact acaagacag acaaccatac     60 tgtacaatca atcactactg cctcaaagtc gaaaccattt aataccagtt gagcctcatt    120
gtgactgcat aattttgacc cctaccacga ggtaatttca gttcaaatca attgtatctc    180
tcttctggat atcagtcaag aatctcatgt tctcaagtta tagtacattg ataattactg    240
tgcattttta ttaattttatg agttaaaatc ctgctgatta attcaactaa aggaataaaa    300
tagttattgg catttggatg agaatagaat gtgaatccca tcattcatcg ctagattgga    360
ccgtaattat aagtgagagg gagaaacttc tgttgctatt cccttttat ttcttaattc     420 atttataaat tgttttttagg cctttttatat atatatattt ctaccatttt tacatttaaa   480 attctttaa ctttattatg tatggactca aactaacaag ctttatttga taaaattgtt     540
caaactatta tattagttttt atattgtaa accataaaac aaatccataa aattccacct    600
gcatcactca ctcatgttgt tgaatggtac gaaataaaca atacatgtga agatgaaaa     660 taagaattgt tctcttatta aatctaaaat ctagatttc ttttttagtac atttaacact    720 tcaatgaaag gtctaaaaca ttattgaatg acgtcacgaa ctattacaaa agattattcc    780
gatttatctc aaaagggggtc tatttcacta attttggtgt cccacatctg taaagagaat   840
tttcgtgata tgtgtagata tttaaatata attgaattcg atgaaagcaa agcaagaatc    900
gatatccgta gttatttga tatagatcgg tgataaataa aagacaatat gcataaagtt     960
tgtgggtaca gagtcggcta gttgcaatga ggggtatggc cccaagactt tccccaacc   1020 ccaacggtca attaatcacc ccaatggggc atcgaatctt ccccaccatt tcctttttct   1080
tcgccgactc ttctacccat ctcttttgcc gactctttct cacaggtttg attaaatccc   1140
attcatattc agatacacta tttcaaaata ctcgcaaatt aatttgtttt tttaaatatt   1200
ggtataataa taaaattaat tataaattgt gacctaaaaa gtactttgtg gaagaggga    1260 tatagtctgt ctaatatatt attgattaaa tatataatag aaccataaat gcaaccact    1320 agaattgtta ataaaaatca acgctctttt aagtctttcc atagaaagaa aggcaaagac    1380
gcgcaacgtc tagaattttc tttataacgg aagctaactc tgttataacg gccgtccaca    1440
taatatggta gatttaaaat gacgtcagca tgtcgcttct aaatttgggt ccaaggggg   1500 gattcattta tagggaaggg aaacggcaaa tgcaagcata gtgagtaaat acgtggcggc   1560
```

| | |
|---|---|
| aaagtaatgg ataattctgc ctctgccgtg acgacattgc ccttccattt cactataaat | 1620 |
| acacctcctc tatccctcga tttcttcgca attgaatttc tcttctcatc tctgtcgtag | 1680 |
| caaaccaaat cgatttct | 1698 |

<210> SEQ ID NO 158
<211> LENGTH: 313
<212> TYPE: DNA
<213> ORGANISM: Cucumis melo

<400> SEQUENCE: 158

| | |
|---|---|
| tcaaaggtat ttcttccttt cctttttttt ttttttttt tttttttaaa tcatgttgtt | 60 |
| caaactttga gagatgaaat gattaggggc tttcaaagtg gttttcgttt gatatgtttc | 120 |
| ttagatcgat agggtttaga atcgagcatc cttgtaggta tcctgaggtt tggtggttgg | 180 |
| atctgcttaa tttttatgtg gttgcatgga aaattgggat ttttttttc taattacgtg | 240 |
| attctggaaa tattgatctg tggttcagat ggaattgaat ctgatctttc tgttttgttc | 300 |
| tgtataggtg ggc | 313 |

<210> SEQ ID NO 159
<211> LENGTH: 2010
<212> TYPE: DNA
<213> ORGANISM: Cucumis melo

<400> SEQUENCE: 159

| | |
|---|---|
| tagaaaaaaa ttgaagatct tcttaatgct aataataaaa gcatatataa aaaggcttca | 60 |
| tattacacaa gcatcttaaa accaaaccga acttgatttg aaattatccc actaattctg | 120 |
| tagatttcac caaagtcctt aacctttata ctaacatctg catttgactc tttcatttga | 180 |
| cctccaacat attctttctc attttccttc cattcaccac aaaaaccaac aaatacaaaa | 240 |
| aaccacaaat acatagaaaa ttaataaaaa aatcaaaatt tcgagatgaa atcattataa | 300 |
| actcatccga taactttgag atttgaaacc ttacactata taaagaaact catccgataa | 360 |
| ctttgaattc gcatcgaaat tacgtaagtg aagacgaaaa tgtaaatgat tagatgcgaa | 420 |
| taacaaaaaa aacataattt ctaaacgtaa aacactatat tcaccttatt atacttgatt | 480 |
| attttggaaa agtatgaaat ttgagtgtgg gagaggagcc aaagaattgg aaacttgtta | 540 |
| ttaggagtcg ttatgaaaca ttttcaacaa gccaatattc tttcacatac tataatgata | 600 |
| tacatagaaa taatacaata atattttga aattgaggca ttttttgtcgt aatttatcta | 660 |
| aaaatgtcag ggtagattca tcatgtatac aaatctctcg ctatcaaaac tatataaaaa | 720 |
| tcttgtgaat gatttcaatc gaaatggacc gagaaaaaac atcgtaacca cctctaaaat | 780 |
| cgataaattt gtttcaattt caaatcccta aaactaaagg tgctactttg tacaatttcc | 840 |
| cctgattagg gtgctaaagt taaaccctaa ataaaggtgt gtacgtttcc ggaagtttct | 900 |
| agaatcccca gcgaagttct ccaaatcgtg gcttgcagac caaggacccc cattaaaatt | 960 |
| cgtttcttcc tctaaacctc ctcccttaat tttggcattt tggtatttg gctcctataa | 1020 |
| attcaccccc tccttatccc taatcctttg tcttccaaat tttccttcaa agcctgcttt | 1080 |
| tcccatttcg tcgtgctttt tcttcatcta aggtatatt tcagttctag ttttctttct | 1140 |
| ctgttgatct cttggatttg agggacgttt gaagttggct tgtttaatt ctttgttatt | 1200 |
| caatctcttt ttttgttaga gttgttgttt aatcgtttcc cttgttgttt ttctcccttc | 1260 |
| tagttcgatt ttagaacgct ttttgtgggt tgattttaat ttctccgttt tcttacatct | 1320 |

```
ttcacaaaga aacgattgaa atcgtgtttg ttttttttcc cacggcatac gttattagat    1380
cttgtagata atgatctcaa tctattgttt agttttttgca aataagaagt tggttttta    1440 tctccaactt ttatatattc gattcgatga gatgttctac accgttagga tggaaccaag    1500
aagtgaggta agggtgtttg attgaaaaat tgaactgaga agttaaagtt ccttcctaac    1560
tttttaatgg attgtataat tcgttcaatt ccttgtcgtt ccattttat ttctgtttcg    1620 tttttcgtgt tgctgcgtat cgcttcccctt gttgttttcc tccctattg attttgcgtt    1680 tcttggagtt tctctgtttt ctctcttcat ttttctacaa aaatcaattc tatttttatt    1740
cgttttcaat tcccgagctc cttggaatgt tatccttttc tcctgtgtaa ataagaaccc    1800
gtattcaatc ccagttcata gtttggcttt cccaaataag agcaaaaaga ttgtactgag    1860
aagttgaaga tttcaaaatt ttgtacatga tttcttctaa tttatcaatt tgattggact    1920
ttttgtatat agatttggtt cttgagctat ttatgttatg acgttttcat attgaggcca    1980
tgcgttgaat tggtttctta acaggtgggc                                    2010

<210> SEQ ID NO 160
<211> LENGTH: 1107
<212> TYPE: DNA
<213> ORGANISM: Cucumis melo

<400> SEQUENCE: 160
tagaaaaaaa ttgaagatct tcttaatgct aataataaaa gcatatataa aaaggcttca      60
tattacacaa gcatcttaaa accaaaccga acttgatttg aaattatccc actaattctg     120
tagatttcac caaagtcctt aacctttata ctaacatctg catttgactc tttcatttga     180
cctccaacat attctttctc attttccttc cattcaccac aaaaaccaac aaatacaaaa     240
aaccacaaat acatagaaaa ttaataaaaa aatcaaaatt tcgagatgaa atcattataa     300
actcatccga taactttgag atttgaaacc ttacactata taagaaact catccgataa     360 ctttgaattc gcatcgaaat tacgtaagtg aagacgaaaa tgtaaatgat tagatgcgaa     420
taacaaaaaa aacataattt ctaaacgtaa aacactatat tcaccttatt atacttgatt     480
attttggaaa agtatgaaat ttgagtgtgg gagaggagcc aaagaattgg aaacttgtta     540
ttaggagtcg ttatgaaaca ttttcaacaa gccaatattc tttcacatac tataatgata     600
tacatagaaa taatacaata atattttga aattgaggca ttttttgtcgt aatttatcta     660 aaaatgtcag ggtagattca tcatgtatac aaatctctcg ctatcaaaac tatataaaaa     720
tcttgtgaat gatttcaatc gaaatggacc gagaaaaaac atcgtaacca cctctaaaat     780
cgataaattt gtttcaattt caaatcccta aaactaaagg tgctactttg tacaatttcc     840
cctgattagg gtgctaaagt taaacccctaa ataaaggtgt gtacgttttcc ggaagtttct     900 agaatccccca gcgaagttct ccaaatcgtg gcttgcagac caaggacccc cattaaaatt     960
cgtttcttcc tctaaaacctc ctcccttaat tttggcattt tggtattttg gctcctataa    1020
attcaccccc tccttatccc taatccttg tcttccaaat tttccttcaa agcctgcttt    1080
tcccatttcg tcgtgctttt tcttcat                                       1107

<210> SEQ ID NO 161
<211> LENGTH: 903
<212> TYPE: DNA
<213> ORGANISM: Cucumis melo

<400> SEQUENCE: 161
ctaaaggtat atttcagttc tagttttctt tctctgttga tctcttggat ttgagggacg      60
```

```
tttgaagttg ctttgttta attctttgtt attcaatctc ttttttttgtt agagttgttg      120 tttaatcgtt tcccttgttg ttttttctccc ttctagttcg attttagaac gcttttttgtg    180 ggttgatttt aatttctccg ttttcttaca tctttcacaa agaaacgatt gaaatcgtgt      240
ttgttttttt tcccacggca tacgttatta gatcttgtag ataatgatct caatctattg      300
tttagttttt gcaaataaga agttggtttt ttatctccaa cttttatata ttcgattcga      360
tgagatgttc tacaccgtta ggatggaacc aagaagtgag gtaagggtgt ttgattgaaa      420
aattgaactg agaagttaaa gttccttcct aactttttaa tggattgtat aattcgttca      480
attccttgtc gttccatttt tatttctgtt tcgtttttcg tgttgctgcg tatcgcttcc      540
cttgttgttt tcctccccta ttgatttttgc gtttcttgga gtttctctgt tttctctctt    600
cattttctca caaaaatcaa ttctattttt attcgtttc aattcccgag ctccttggaa       660
tgttatcctt ttctcctgtg taaataagaa cccgtattca atcccagttc atagtttggc     720
tttcccaaat aagagcaaaa agattgtact gagaagttga agatttcaaa attttgtaca    780
tgatttcttc taatttatca atttgattgg acttttttgta tatagatttg gttcttgagc    840
tatttatgtt atgacgtttt catattgagg ccatgcgttg aattggtttc ttaacaggtg    900
ggc                                                                    903
```

<210> SEQ ID NO 162
<211> LENGTH: 1235
<212> TYPE: DNA
<213> ORGANISM: Cucumis melo

<400> SEQUENCE: 162

```
aaatttttaat aattaaaatg aacaatttttt caagagtaat agagtttgag agatgtcaga    60
gaagtttgag gaagaagata acaagtggga gaagagaata agtttgttgt gtgaaagaga    120 agggaaatt tcattcaagg gtatattgaa cttttttactc aaattttgta agtctatttt    180
ttccgatcaa tcctaaaatc acacacaccc ttaaaaaatg gattatattt ggcaattttc    240
catgataaac tcatttttaa tttagagtta ttttttcaac gagatattaa cagttttagt    300
tcatatacta attgtaagaa tagtttcttt taagttgaat agaattttttg aaactttttaa  360 tagttcaaaa ggtattttttg aaacaaaata agaatgtttt tgaactttttt ataaaaagaa  420 ttgagatttt tttgaaattt ttgataaaga gaaagaaaa gaagaaagaa aaagaaaaa    480 caagtttgta gaactccgtg ggaaaatcgt cgagggcct gtgaaggaat ttgaaaatta    540
taatgagggt attttcgtca acaagggaat ttagacatcg tatataagca tcctcaaacc    600
ctataattaa gcccttcaat ccaattgcca ttctccatct ctcgccgcaa gggtttaaga    660
gcagcttctc tcctcaggtt ggggttttccc cctatcttct tcattcttcc tcttctcgat    720
ttctttcttc tatttgctcg atagtctctt atttcttgag cttttgctgt ttttctcctg    780
tacatcctaa catgaattat aacttggttt tgattttgtc ttttacttct gtattaaaca    840
acttttctta cccttttatt cttctcttct tcttcgtgtc cctgcccttt tgttttttatg  900 ctaattttat gtttctgttt atcaatctat cgaggcgtga cctgtcgttc ttccaatagc     960
gtagatctgc acttaatcta ttctagctga ttggattggt cgttttttcgt ttttttttaatt  1020 tattttctct gttctagttc cgataaattt tttttatatat aattaacaag ttctccagcc   1080
aaaagggtta atattgcgtt ggatattttta attttttacgt tatttagatg tgtgaatcta   1140
ataaaattag ggttattcat aaatttcagt aatgatattt tggttatctg ttcttgctgt     1200
```

```
tcctgtttcg cagttctttt acctaatatt caagc                              1235
```

<210> SEQ ID NO 163
<211> LENGTH: 617
<212> TYPE: DNA
<213> ORGANISM: Cucumis melo

<400> SEQUENCE: 163

```
aaatttta at aattaaaatg aacaattttt caagagtaat agagtttgag agatgtcaga    60
gaagtttgag gaagaagata acaagtggga gaagagaata agtttgttgt gtgaaagaga   120
aggggaaatt tcattcaagg gtatattgaa cttttactc aaattttgta agtctatttt    180
ttccgatcaa tcctaaaatc acacacaccc ttaaaaaatg gattatattt ggcaattttc   240
catgataaac tcatttttaa tttagagtta ttttttcaac gagatattaa cagttttagt   300
tcatatacta attgtaagaa tagtttcttt taagttgaat agaattttg aaactttta     360
tagttcaaaa ggtatttttg aaacaaaata agaatgtttt tgaactttt ataaaagaa     420
ttgagatttt tttgaaattt tgataaaga gaaagaaaa gaagaaagaa aaagaaaaa      480
caagtttgta gaactccgtg ggaaaatcgt cgagggccct gtgaaggaat tttgaaatta   540
taatgagggt attttcgtca acaagggaat ttagacatcg tatataagca tcctcaaacc   600
ctataattaa gcccttc                                                  617
```

<210> SEQ ID NO 164
<211> LENGTH: 54
<212> TYPE: DNA
<213> ORGANISM: Cucumis melo

<400> SEQUENCE: 164

```
aatccaattg ccattctcca tctctcgccg caagggttta agagcagctt ctct           54
```

<210> SEQ ID NO 165
<211> LENGTH: 545
<212> TYPE: DNA
<213> ORGANISM: Cucumis melo

<400> SEQUENCE: 165

```
cctcaggttg gggtttcccc ctatcttctt cattcttcct cttctcgatt tctttcttct    60
atttgctcga tagtctctta tttcttgagc ttttgctgtt tttctcctgt acatcctaac   120
atgaattata acttggtttt gattttgtct tttacttctg tattaaacaa cttttcttac   180
ccttttattc ttctcttctt cttcgtgtcc ctgcccttt gttttatgc taattttatg     240
tttctgttta tcaatctatc gaggcgtgac ctgtcgttct tccaatagcg tagatctgca   300
cttaatctat tctagctgat tggattggtc gttttcgtt ttttaattt attttctctg     360
ttctagttcc gataaatttt tttatatata attaacaagt tctccagcca aagggttaa    420
tattgcgttg gatattttaa ttttacgtt atttagatgt gtgaatctaa taaaattagg    480
gttattcata aatttcagta atgatatttt ggttatctgt tcttgctgtt cctgtttcgc   540
agttc                                                               545
```

<210> SEQ ID NO 166
<211> LENGTH: 19
<212> TYPE: DNA
<213> ORGANISM: Cucumis melo

<400> SEQUENCE: 166

```
ttttacctaa tattcaagc                                                 19
```

<210> SEQ ID NO 167
<211> LENGTH: 2003
<212> TYPE: DNA
<213> ORGANISM: Cucumis melo

<400> SEQUENCE: 167

| | | | | | |
|---|---|---|---|---|---|
| cagtgtgctg | gaattcgccc | ttatccaagg | agattaatgt | cgagagatta | ttatcgaggt | 60 |
| ttgaatttat | tttgtccaat | catatgattc | caagagctga | ccatcaattc | aacagaacat | 120 |
| gaaccggaac | ctcatacctta | ttgtaatggt | tcacagcatc | ctaatacaga | acatgaaccg | 180 |
| aaacctctta | cccattgtaa | tggttcacag | catctttata | cgtattatag | gtagtaccat | 240 |
| tgaagatgca | tttaaatgct | gtccatgctc | tgttctctaa | aaagttggac | ttggacttgg | 300 |
| acgtcagctg | aaagtatgaa | atgcactgta | gccaacgaag | ctatgttttc | aggcttcaac | 360 |
| atggttttag | gaaagtggag | gctctttggt | tgaagggttg | aatgaatgct | tttctaattc | 420 |
| cagcatgatc | ttcaaatttc | gacacaaaaa | gcttaagtat | tttgttccgt | tattctttta | 480 |
| atccttgtat | tgttatatat | tcttttctct | gaactgaatg | tacgatgatt | gcagggtcg | 540 |
| agagcaagtc | cgatataatg | aaacacgtaa | ggacgtgatt | gaatgaaaaa | ctatgagcag | 600 |
| agatacaaag | tctaacttac | gggatgaacg | atgagaggtt | tgaccaagag | ctgtgacgcc | 660 |
| tgtatatttc | aacaaaagtt | gatgactaac | atcacatgtc | agagtaatca | aagaaatgca | 720 |
| gccgcacata | tatatatcta | tatatatatc | gagtttttt | tttttttttt | tttttttttt | 780 |
| ttttttatc | taatatattt | taatctattt | tcctctgccc | tcctcccct | cctcttcccc | 840 |
| cacccttctt | ctgcacatag | tagccaagga | ttgatcggtt | tcttttgatt | cggggggaaa | 900 |
| atgttgtaca | atttttgctt | ccatagaagc | ttgaaagttt | tgcagattat | gttgtaaaat | 960 |
| taccccttgtg | tactcacact | agttcttctc | gtggaaactt | atattacaat | ggttgagttt | 1020 |
| taaggggcat | attcacactg | gtaactacca | ttttctaatt | tatgaatgcc | gagtttctct | 1080 |
| ccatgaaaga | cctttcaaat | gcccttttcct | ccgcggtgcg | tttgttgttg | taaatgtgca | 1140 |
| gtgtcgttgg | atacacgatt | gtgtgaaagg | gaaaagggaa | tacgattaac | tcttaaattc | 1200 |
| aaccccctatc | tccatcagta | tcaatcacat | ttcagcaact | agctcttgaa | taacattgag | 1260 |
| attcttgttt | aatccacgta | ctactactac | tattactact | atttgacagt | tgatatctca | 1320 |
| aataacatcc | atatttatca | aattggtatt | ttaaggactt | ttaatttctt | cgtacatatt | 1380 |
| tcattataat | ttaactactc | tgaccatcat | tgaaaatttc | acaagaaga | catttttaaat | 1440 |
| tgaattgagt | tgaattaagt | tgatataatg | gttgaacgtt | ggatttaatt | tataatttag | 1500 |
| tggtgtatgg | gtccattgta | ataattctta | aaaaaaatat | catattctga | attctaaaga | 1560 |
| accatctaag | accaaaacta | aggggtcacc | aatgagtatg | gtaaagtcaa | caaagtttgt | 1620 |
| ctactttttct | tatccttatc | atcaagagtg | caatatgata | tcaaagataa | attgtacgtg | 1680 |
| ggcgtcatcc | attgggtaag | accaagaagc | aaaatatcat | agagaagttg | ttttagtagc | 1740 |
| cataggaagg | aaggaagcaa | ataataata | tagatttgaa | attgtggatg | ataaactgcc | 1800 |
| aaatgggaat | tcaaaataaa | ctaaataaat | aaaataaaaa | gagaaatctt | gggagttttcc | 1860 |
| atttttagcca | atgaggaaac | agatagagat | ctcatcaaga | taaggaccct | attctcttct | 1920 |
| tcatctataa | aacaaaaaca | aatcaaaccc | tcatttcact | cattcaaaac | aaaaagtact | 1980 |
| ccaaagtcaa | actaacaaat | acg | | | | 2003 |

<210> SEQ ID NO 168

<211> LENGTH: 2004
<212> TYPE: DNA
<213> ORGANISM: Cucumis melo

<400> SEQUENCE: 168

```
tggatcgacc atgacattca aaaccttta agatatggat cttataaaat aaatgtaaag      60
ggtaaacaat tcttccttgc ttaacccaag ctatatattt tatgcactaa tttaggtatt    120
agagtatatt cagctgaaca ccacctacca atgctagtac tttaatcagt caattctaac    180
ttcgataata tatctcaacc aaattagtga aaaagagtcg taaatgaaaa actatgtacc    240
aagatattct atttgttttt tttatgttta aatatctcaa agataatacc taaaacgttt    300
tctcctcgta caaagattcc tcatttactt tttattgtcg taaactctaa tacaataaac    360
taaaacaagt acaaatacac tagctttaga aatctacttt ttattgaaac caaaccaat     420
aattcaacat ttcattttca ccgacaaacc tttgtaaaca attgaagtaa ttttttgttgg   480
tactatgaat agtaacatca agtcttcaag tgcatcatat caaccaagac atgttcttaa    540
aagcgacact aaaagattta aaaccaaaag catttatgaa atccgaactt aatcaaatcc    600
taaatatttt tcacttaaaa aaaaaaaaat aggaagaaaa attgacataa atgggatatt    660
ttcgtttttca aactggcaag ccagcatgca ccacgttgtt gacgtgtcct tccacgtcgg    720
aaaaaaaaat attaccacag taaaagaga ataaaatgaa agtcgttgac tctcccttag     780
tcggaggaag cgcgtgaagc tgaagccgga ttagaaatcg gcaataaccc cgacacgtca    840
tcgaaatgct agtatcaaat attgtccgtt ggatcttcct tcaccaactc tatttgaacg    900
gccacgatct tccaggtcca acggttcgga agaatctttt cgaaattcca tggctagtcc    960
ctacactcct ccctattggc tccctagggc atcccgaccg gttattccgg ttgccgggaa   1020
ggtggctgga cgctataaat acccgctttg ttcatctcgt agtccttgta ccgttgagct   1080
tcgccttcta atagagctct ggttcggttg gcgtattagc tcgaattctt tctctcttcc   1140
agatctacgc tgccgatttc atcaggtttg cgagctctgt tccaccattt ttcttttcct   1200
gaagctttga gcatgcttgt gattcttcat ttcctcattt ctttgatggt ttatgaaaga   1260
atttagggga attttctctt tttgtattct agtggtactg gtagatttgt ttgaagtttg   1320
tttctcttct tctgagaagt gaattcttcc agatctgaca gttgcttttg atttttcttt   1380
tgggaattag tgaatgatac ttcgatactg ttttttgctc tctgagattc tggatctcgg   1440
gccttggggt tttctattgt cttttggtag ctatgtttcg tttgtcagct tgtatttgtc   1500
attgttgaat ggttcgatcc ggtttgtaaa taaaataaat tttgtaggcg cacttgttt    1560
ccacggtttt cgtgttacgg tttcatgatt ccctagatct ctggttagaa ctaagttttt   1620
tgtcggtaat tggatttggt aagggactgt tactgtggtt gaattgtaga tccagtcatc   1680
ttctacatga gtgtagggtt ccttagggca gatcttgtgt tttataattt taattttgtt   1740
gtttccctga ttttgaacct gttttggttgt tcagattcgt cgagtcattt ccattcatta   1800
aaagtttcta aatttttatt tgaatcttct gaatctgtgc ttgtattacc cagatttcta   1860
taaacctatc ttgatttcaa gtgtgctatg tggtaactgt tgatattttc aagcttaagc   1920
aatactgatg tgactaaaac ttaactaatg aactgaatgt tttttgtaca cgaactaata   1980
tggtgttttg ttatgtttca gagg                                          2004
```

<210> SEQ ID NO 169
<211> LENGTH: 1067
<212> TYPE: DNA
<213> ORGANISM: Cucumis melo

<400> SEQUENCE: 169

```
tggatcgacc atgacattca aaacccttta agatatggat cttataaaat aaatgtaaag      60
ggtaaacaat tcttccttgc ttaacccaag ctatatattt tatgcactaa tttaggtatt     120
agagtatatt cagctgaaca ccacctacca atgctagtac tttaatcagt caattctaac    180
ttcgataata tatctcaacc aaattagtga aaaagagtcg taaatgaaaa actatgtacc    240
aagatattct atttgttttt tttatgttta aatatctcaa agataatacc taaaacgttt    300
tctcctcgta caaagattcc tcatttactt tttattgtcg taaactctaa tacaataaac    360
taaaacaagt acaaatacac tagctttaga aatctacttt ttattgaaac caaaccaat    420
aattcaacat ttcatttttca ccgacaaacc tttgtaaaca attgaagtaa tttttgttgg    480
tactatgaat agtaacatca agtcttcaag tgcatcatat caaccaagac atgttcttaa    540
aagcgacact aaaagattta aaaccaaaag catttatgaa atccgaactt aatcaaatcc    600
taaatatttt tcacttaaaa aaaaaaaaat aggaagaaaa attgacataa atgggatatt    660
ttcgttttca aactggcaag ccagcatgca ccacgttgtt gacgtgtcct tccacgtcgg    720
aaaaaaaaat attaccacag taaaagagaa ataaaatgaa agtcgttgac tctcccttag    780
tcggaggaag cgcgtgaagc tgaagccgga ttagaaatcg gcaataaccc cgacacgtca    840
tcgaaatgct agtatcaaat attgtccgtt ggatcttcct tcaccaactc tatttgaacg    900
gccacgatct tccaggtcca acggttcgga agaatctttt cgaaattcca tggctagtcc    960
ctacactcct ccctattggc tccctagggc atcccgaccg ttattccgg ttgccgggaa   1020
ggtggctgga cgctataaat acccgctttg ttcatctcgt agtcctt                 1067
```

<210> SEQ ID NO 170
<211> LENGTH: 92
<212> TYPE: DNA
<213> ORGANISM: Cucumis melo

<400> SEQUENCE: 170

```
gtaccgttga gcttcgcctt ctaatagagc tctggttcgg ttggcgtatt agctcgaatt      60
ctttctctct tccagatcta cgctgccgat tt                                    92
```

<210> SEQ ID NO 171
<211> LENGTH: 845
<212> TYPE: DNA
<213> ORGANISM: Cucumis melo

<400> SEQUENCE: 171

```
catcaggttt gcgagctctg ttccaccatt tttcttttcc tgaagctttg agcatgcttg      60
tgattcttca tttcctcatt tctttgatgg tttatgaaag aatttagggg aattttctct    120
ttttgtattc tagtggtact ggtagatttg tttgaagttt gtttctcttc ttctgagaag    180
tgaattcttc cagatctgac agttgctttt gatttttct ttgggaatta gtgaatgata    240
cttcgatact gttttttgct ctctgagatt ctggatctcg ggccttgggg ttttctattg    300
tcttttggta gctatgtttc gtttgtcagc ttgtatttgt cattgttgaa tggttcgatc    360
cggtttgtaa ataaaataaa ttttgtaggc gcacttgttt tccacggttt tcgtgttacg    420
gtttcatgat tccctagatc tctggttaga actaagtttt ttgtcggtaa ttggatttgg    480
taagggactg ttactgtggt tgaattgtag atccagtcat cttctacatg agtgtagggt    540
tccttagggc agatcttgtg ttttataatt ttaattttgt tgtttccctg attttgaacc    600
```

| | |
|---|---|
| tgtttggttg ttcagattcg tcgagtcatt tccattcatt aaaagtttct ataattttat | 660 |
| ttgaatcttc tgaatctgtg cttgtattac ccagatttct ataaacctat cttgatttca | 720 |
| agtgtgctat gtggtaactg ttgatatttt caagcttaag caatactgat gtgactaaaa | 780 |
| cttaactaat gaactgaatg ttttttgtac acgaactaat atggtgtttt gttatgtttc | 840 |
| agagg | 845 |

<210> SEQ ID NO 172
<211> LENGTH: 2018
<212> TYPE: DNA
<213> ORGANISM: Cucumis melo

<400> SEQUENCE: 172

| | |
|---|---|
| actattggag acgacgaagg aaaactctaa tgtgagctta gaattgaaga tggtgaacaa | 60 |
| ttgggagtct tttttaaaaa tctttcgtcg gtatattgaa atttcctttt acactcaaat | 120 |
| aaccccctt ttcacgcgtt caacgtcttc aaaccttcct ttttcaatta ttttttcgtt | 180 |
| tacattaatg acatttaggt aataagataa attagtggat tcttttgtga aaaatgttag | 240 |
| cccatttaag acttttatga aatatattag aaaaaaatca tatagcaatt tatattattc | 300 |
| tagttaaaag cccataatag aaactaaccc aacctaaagt aacgtaaaca ttcaataaga | 360 |
| gagacaaatt ttaaaataat ttctaattaa aaaaaaaatt gtcaagaccg tccgggtcgg | 420 |
| atccaaaata taacccgaac cggccggttt agcatctata taaatacacc tttagggttt | 480 |
| ttattctctc aagacttcac cgcatttcca cttctctgag ccacggtca gccattggag | 540 |
| cagctcaata atcctttgac tccctactac ggtaagtcga ccttactgct ttcggcttct | 600 |
| agtttttca atcctgtcat tagtcctttg gagttcttct gtacatttat gacgttttcg | 660 |
| gctcgtgttt tgtttcgcct gtatgtagtg ggttttcga gttttgtttt tcttttttt | 720 |
| tatacttgca ggaattagtt gaaatctatg tacttcatgc cttggataat actcttgatc | 780 |
| tgttgtgtta ttcaaaaatg aattgtttta agatggtatt tgagaatggt catgtgagtt | 840 |
| ttgcctactt ggttattaaa atgaattgtt ttaggatggt attttgagaat ggtcttctgg | 900 |
| gtatttggtt ggaacctttg tgctctgcta tgaattaggg tgttctcccc gtttttttt | 960 |
| tttttttct tttggttatt aatatatctt ttatgactac ttattcatat atgatatctt | 1020 |
| ttactcgtaa atttttgactc atttgaaagt tttatcctta gtccttctc attcaggtg | 1080 |
| taaaggtatg ttgttagggt taaaatagcc tatgcaggaa agttctgtat tgttctaat | 1140 |
| tattgcatt gtgtgcattt gtatctagtt tatttcttgc tgagagtatg cttcattttt | 1200 |
| tagtacacat cacttgtgcc actttattat agttgcacat ttttgtttat ggagaggatg | 1260 |
| aatagcattt agggatgtca attttttatt gagaaaccc tctctcctac ttaagcttgg | 1320 |
| ggaattttg ttctaaatgt ggtaaacata atacttcttc ttatttaat ttgaatggaa | 1380 |
| ggggaagacg aatactaata ttttcaacga accttcacaa cttttttttc ttatttagga | 1440 |
| agccatgttt tcaaaattg tactgtgtga tccacatatt tatcgattat tagtgaatcg | 1500 |
| aataataatt agagttttat tggtataatt ttgaagttca gacttattac atttgtggaa | 1560 |
| agttggttta caatttttcaa ttttattgga atcctaagaa ctttgtgtta acatatattg | 1620 |
| agttttcttc tctttttttt tactcattaa gttctctatt aggaatgttt ggttcaatgt | 1680 |
| cacatagtcg atagctaaga ccagtgaccc acaaagctat gattgaacga aaaacaagcc | 1740 |
| tttcacatct tggtaggaat tgttatttc tcaatagatt tacagagctg ttcatgtga | 1800 |
| tcacaatttt tttctatttt tctgaagttc tctattagga atgggctatc tggttagttg | 1860 |

```
cttttgagag aacatgtgga ttggtgttgc tcggtttcct tgcctttgta attttgtcct    1920
tggaaaaagc aaaatgatta ggtatcctga tatgcataac atgtttaagc caactagttc    1980
tcactttttt agtgcaaata attgatcttc aggaatcg                            2018
```

<210> SEQ ID NO 173
<211> LENGTH: 565
<212> TYPE: DNA
<213> ORGANISM: Cucumis melo

<400> SEQUENCE: 173

```
actattggag acgacgaagg aaaactctaa tgtgagctta gaattgaaga tggtgaacaa      60
ttgggagtct ttttaaaaa tctttcgtcg gtatattgaa atttcctttt acactcaaat     120
aacccccctt ttcacgcgtt caacgtcttc aaaccttcct ttttcaatta ttttttcgtt    180
tacattaatg acatttaggt aataagataa attagtggat tcttttgtga aaaatgttag    240
cccatttaag acttttatga aatatattag aaaaaaatca tatagcaatt tatattattc    300
tagttaaaag cccataatag aaactaaccc aacctaaagt aacgtaaaca ttcaataaga    360
gagacaaatt ttaaaataat ttctaattaa aaaaaaatt gtcaagaccg tccgggtcgg    420
atccaaaata taacccgaac cggccggttt agcatctata taaatacacc tttagggttt    480
ttattctctc aagacttcac cgcatttcca cttctctgag gccacggtca gccattggag    540
cagctcaata atcctttgac tccct                                          565
```

<210> SEQ ID NO 174
<211> LENGTH: 1453
<212> TYPE: DNA
<213> ORGANISM: Cucumis melo

<400> SEQUENCE: 174

```
actacggtaa gtcgacctta ctgctttcgg cttctagttt tttcaatcct gtcattagtc     60 cttggagtt cttctgtaca tttatgacgt tttcggctcg tgttttgttt cgcctgtatg    120
tagtgggttt ttcgagtttt gttttttactt tttttttatac ttgcaggaat tagttgaaat    180
ctatgtactt catgccttgg ataatactct tgatctgttg tgttattcaa aaatgaattg    240
ttttaagatg gtatttgaga atggtcatgt gagttttgcc tacttggtta ttaaaatgaa    300 ttgtttttagg atggtatttg agaatggtct tctgggtatt tggttggaac ctttgtgctc    360
tgctatgaat tagggtgttc tccccgtttt tttttttttt tttcttttgg ttattaatat    420
atcttttatg actacttatt catatatgat atcttttact cgtaaatttt gactcatttg    480
aaagttttat ccttagtcct ttctcattca gggtgtaaag gtatgttgtt agggttaaaa    540
tagcctatgc aggaaagttc tgtatttgtt ctaattattg catttgtgtg catttgtatc    600 tagtttatt cttgctgaga gtatgcttca ttttttagta cacatcactt gtgccacttt    660
attatagttg cacattttg tttatggaga ggatgaatag catttaggga tgtcaatttt    720
ttattgagaa aaccctctct cctacttaag cttggggaat tttgttcta aatgtggtaa    780 acataatact tcttcttatt ttaatttgaa tggaagggga agacgaatac taatattttc    840
aacgaacctt cacaactttt ttttcttatt taggaagcca tgttttcaa aattgtactg    900 tgtgatccac atatttatcg attattagtg aatcgaataa taattagagt tttattggta    960
taattttgaa gttcagactt attacattg tggaaagttt ggttacaatt ttcaatttta   1020
ttggaatcct aagaactttg tgttaacata tattgagttt tcttctcttt ttttttactc   1080
```

| | |
|---|---|
| attaagttct ctattaggaa tgtttggttc aatgtcacat agtcgatagc taagaccagt | 1140 |
| gacccacaaa gctatgattg aacgaaaaac aagccttttca catcttggta ggaatttgtt | 1200 |
| atttctcaat agatttacag agctgtttca tgtgatcaca atttttttct attttttctga | 1260 |
| agttctctat taggaatggg ctatctggtt agttgctttt gagagaacat gtggattggt | 1320 |
| gttgctcggt ttccttgcct ttgtaatttt gtccttggaa aaagcaaaat gattaggtat | 1380 |
| cctgatatgc ataacatgtt taagccaact agttctcact tttttagtgc aaataattga | 1440 |
| tcttcaggaa tcg | 1453 |

<210> SEQ ID NO 175
<211> LENGTH: 1999
<212> TYPE: DNA
<213> ORGANISM: Cucumis melo

<400> SEQUENCE: 175

| | |
|---|---|
| ggtctcagac ccataggaat agatcattta ttgccttatg aattagttta tgagtacata | 60 |
| ataattgtca accgtataca aatcaacatg aaagaatata atgttgtaca tagtcattcc | 120 |
| aagtttacta atattatatt ttaggagtgt tctacaccga acctgtcaca tgtacactgg | 180 |
| gtatgctacc cctgaattca atatcataaa gcaactttaa ttgtcaagca ttctcttgac | 240 |
| catttgtgac ccatttgctc ctactttttc aatcaataac tatcacaaaa agctagatac | 300 |
| cacatgtgat aaactcactg aaatcaggta tatggttacc tgtgcttggt cagcactcaa | 360 |
| tcagattcga aggcctagtc tttgtatttc ccccctctg cacactacaa atagtcctcc | 420 |
| acgtaaagac ccataacaaa acgcaaacca agtacagaaa atctagccga aatccagacc | 480 |
| actcaaacat aacaaatctt ctggtaagtt tgaataaaat ataaaactaa cctatttaat | 540 |
| caaataatac aataaaatgg aagcaactaa cataacatat ctaaatatga tcacgtagta | 600 |
| ggaaaaaaaa aaacattcca aaactattaa caatcattct taatggtatg ggtcaatccc | 660 |
| cattatttag gactataaca agaattcctc ataccctaatg ccacatccta tgtccaaccc | 720 |
| tcgagattac ctcgtgagta atcaatctta ttcatcctta tttcaaatta tgtgaaattt | 780 |
| ctcatcaggt tgatcatatt gactttcaat acaacttatg attaatcttt cccttgatat | 840 |
| aatttcgtat gaaaaggaag ttgacattat gtgattttct cataaggtaa accaagtaaa | 900 |
| cttgacatga cgtcttaaca agtcttggtt tctaagtgta atttactgca gaaaaaatcc | 960 |
| taaattctat gacttttcct atgagattga ccaaatcaac tttacgagaa atcttgggaa | 1020 |
| gccataccta caaagtcttc ccccaagaaa ttacaatttc tagtaaagat tgttgaaatt | 1080 |
| taccctccaa tttttccgtg aaaatttgac aaacttgtaa gaatatcaaa tttgggttgg | 1140 |
| atattgacat tccaaaataa gtagttttaa aaaggattta tccaacaata atagaagaaa | 1200 |
| aaagatagga aataacatac ccacgtaaat ggaatgtaaa tatttatata ttaggtgtct | 1260 |
| tgaacgaccg tcaaacgaaa ataaattgtt catccgaagt tgaaactctt taagtgtaca | 1320 |
| tttatctttt cgtaagaata aaatgtaaaa ttaacgtgtg aaaggttggg ttaaataagt | 1380 |
| tatgtagaga taatattgaa gatgatagaa taatcacgat cgatgaatta gtatagtccc | 1440 |
| agagcggatt taaacctctc tcactttcat gctttctata tatatcaaaa taatttcaag | 1500 |
| tagttggttt agtcgtaaaa aagtcaacca atctctttta gataaacctt gagttattaa | 1560 |
| aaaattagat caaagataat cgttgaaatt gaaattttaa gagtataatt ataacaaatt | 1620 |
| ggaaagttct aaagtagttt ttgcaatatt ctccatcaaa atagagtaga aaaatatttt | 1680 |
| agtaattttc ttatcttaat tttagttttg taatagttat taggatggtc ctaagttctc | 1740 |

```
aatccgcttt tagtccataa aaagaaagaa gagagagaaa aaaagtcccc gatccgcgac      1800
acataccaat ccaaccaatt atgcacaatc catgtgatat cgaacggtca caagaataaa      1860
tgctttctac acacggatca ccatccaacg gctttccttc catctcatcc tctatataat      1920
ctaccaactc tgtcatcttc gacacacttc aattatctca gcttttattt catcggattt      1980
tccatcaaac aaggcaaca                                                   1999

<210> SEQ ID NO 176
<211> LENGTH: 2004
<212> TYPE: DNA
<213> ORGANISM: Cucumis melo

<400> SEQUENCE: 176
tatagtttgt aacaatctac tctatgttct ttcaattttg atacatttga atcttaaact        60
ttattgagtt acacaatata gtccttgtat ttttaaaatt tataatgact ctatttatat       120
taatattata gaattttttg ttaaggttta ataaaaattt ttctgtataa ataaatcgaa       180
cacgaagtct atatttagac tgcaatatag taaaacctga catctaagtt tggtgaattt       240
tgttttgctt taaaaactaa actattacaa ttttaaaaat attttaattt agttaatgca       300
cattaacttt acggagtaaa tttttacaag attgaatata catagattaa atagttataa       360
aaccaaagat tagagtaaaa aacatttaaa tagaaagaac taagattttt ttaaaacgaa       420
aatgatacta gatacatata tatgtatcta tattataatt actcattttta acatatagtt      480 ttgaaagaac aaagattagt tgcatgtgtt gattgttttt aagaaggaaa taatttttga       540
atggaaaatt ttcaaaagtt ttaaatttga caataaactc atatttaaag tgtactacaa       600
attttaactt ttggttaaac tccttgttta gttcaatcat gtaataaaatt ctcattccaa      660 gaatcgtttt agaaaatttt attgtgcatt taataaaata tagaacatat atggcatata       720
aaaattgatt actttttttct tttttggga cgaaaaacac attagatata atcttttttg       780
aaagtttatg aactttaaaa atgggttatt ttatacggtg gtcaacttta ttttattgaa       840
attattgagt ttataaagat tgttatatca ttttcttctt ctctttcact agaatacaat       900
caaacctatc aaactctcta tgacttattt agaattcttt ttgttatatt tttgaaatta       960
ataaatgaaa agcttagagt ctaaattata acaattaaaa ttgaaaattt tgcaataatt      1020
ttatttttag caaaatgacg tttggttttt ggggattggg aatggatcga tactatcccg      1080
attccggaca aagaaaccga cccgagattc gaatttttc cattcccaaa cagagcactt       1140
aaaatttaag caacgttata acggcgtcac cgaactaaac ggaaaaatat gaagaaaatt      1200
agaaaaagaa aaacggaaca gtcaaacgtt acttcacgtc aatggcaata ttcatttttt      1260 tttttgtttta ataattgaa tttaattaat tggtttata aaaatagagt cctcatatat       1320
cgcgaatgcg catttgatcg tgaaggacag cttctccctt gtgttcaaga gagagagatc      1380
tatcattctt atttggggcc gatctctcta ttctcctctc ttctattccg taagttttc       1440 tcattcattc tcctctctca tttctctccg agatctgttt acaatccttt tgattttcat      1500
ttttcctgct tcgatctgtg ctcctggtga ttcccttttc ctgttttatc ttttgttgat      1560
cttggaattg attgttcttt tgtgggtttt cattgatttg tattttctga tctgggtttc      1620
tgttttctcg ccttgatgtt ttgtatttgg atctgatctg acgacccttt tttttttttt      1680
tttttatttg aattgctttt ccaatgttta tacctggatt tttattgatg catgggttta      1740
accgattggt tggatgcgtt ttctttgtgc tggatctagg tgtccttgtt tttaatttga      1800
```

```
attgtgggta aaaatggcat tattgtaatg tgtttggagt ttgattttga atcttggcta    1860
gttgatttt  gaattacaaa gatcggatcc tcttctttt  tgggttgtct taagatttt    1920
ggctggttta agtatttgat gtcgttgtat tttaagggt  aactgatgcc ggcttgttgt   1980
gtttgtattc agtttacttg aaaa                                          2004
```

<210> SEQ ID NO 177
<211> LENGTH: 2005
<212> TYPE: DNA
<213> ORGANISM: Cucumis melo

<400> SEQUENCE: 177

```
aattagcaaa ttgtatgtaa caacgtcatg aagaggcatt tcatcgaaca atttaatagc     60
agagtcaaga tggcccagtt ttataagttt attgatttct cgattcttaa ggtaaatgag    120
atcgcgagca tggaaatgca gacccaaacg agaatatggg tgtggtaaat ggaccggtga    180
tgttgtggct acaaattcgg atttacagc  agtaatagtt ctgacgaagg aagcgaattt    240
agtgaccttt cgcatcacag tttaagctta tcagagacct gaacaagggc tctagctcta    300
caacttagaa aggtttgata tggtccgtga tcgggaggga ccgaataaca ggcgcttaaa    360
ttgttgttca taagaagag  gattgtcgtt gatgtatttt aaccaagaga tgattagtta    420
tccacatcca cagagagaac agaagacggc tttctaaatc tacaccgata aaaataaccc    480
taccactttg tttctttaga aagggtcac  attcttaaa  aacattagcg tcgaggatta    540
atagggtata ttgactaatg ctctgtttgg atttcgagaa ataccaattt acaattgatt    600
tcaaattaat tatgttttgt tgttgcacga aagataaaaa gaatttaaaa ttcaaaagga    660
tctcaaatct tattttaac  ttaaaaactt ttatgaccca aacggtttat gtatgattta    720
aaagtagaat acctctgtga attcttaatt ttttttttctt tccaattacc acataaatat    780
gaaattttaa atacatttat tttaaatttt atatccgaaa caaaataata atttaaaact    840
atttctcata tatgaagtgt gattcgatct aaattataaa ataataaaaa tttacatcta    900
gttttgatta tttttttttc gttagatact aaattgttaa gaaaataaca tttttaatcc    960
aaagttttga agaatatatg acttttaaaa tggtatttat cttttagtg  tctgattttt   1020
aaaaaatgga tttcaaaagt tcatcaaata gcattgtatt tttattttaa ataatttga    1080
catttaaaat tagagtaatg gtttataaaa gacacttgat ctctaaaact attttcttag   1140
atataaatac gtatgattat ttttaaaaat caatcaaaat aggtaaattg taaaaaaaaa   1200
aaaaaaatca taaaacatga tagtagttgt aattatgctc tcaaactttc ggttatgaaa   1260
aataaacatt ttaactttta gacgtgtcaa agttgagtca agttggacct tcaaagttat   1320
gtagttatat aaattgtaat atatgtataa gcttgtggat tcaattttat catttatggg   1380
tccaatctct acaattatcg taagtctatg ggtcaattgt aacacatgtg gagtttaaga   1440
gctcaattt  ggacgtggat gtgttttgca accaactcca cacccttaaaa aggtgttttt   1500
ttttaattta tcaaaaaaca agaatttaga atctttaagt ttatctttaa aaatcaacgg   1560
acatttgaa  aaccaattga aactactgtt ataaacctaa caactaaaag tatattttt   1620
aagaccgaaa gcataaatcc ataaaaaaaa aatccagaac tgaaaatgta acttttatag   1680
ttgaaaattt agctaaatta tacatattaa aattcaagga ccatataaaa ttaaagtacc   1740
tgattaaata ataacgaatt aatgtttggt attttaacc  tacattagaa aaaaaaaaca   1800
aaagaaaaac ggcatactat ttgtcaagcg tccgatggga agaaaatcca acggtgagtg   1860
ttagtattga aatacgcagt tctcgtgaat gagcctggct tagatttggg aacaagagcc   1920
```

```
aacccctttc gaccgagaag ccgtcgtctt caccatattc gcctcaacca ttcgatagcc    1980
acgtttgaag aagaatagga ttgcc                                         2005

<210> SEQ ID NO 178
<211> LENGTH: 1978
<212> TYPE: DNA
<213> ORGANISM: Cucumis melo

<400> SEQUENCE: 178
aattctaaca actccggaac aaataattta gcatggattg aaatataaat cttcttgact     60
tgcaaaaaaa tcattgtaat ggtcttatgt tggttatagt tagggtatcg aaacgccata    120
caggaatatg ggattaaagt taacttttgt tcatcaattt cagcttatga acttctaaaa    180
tatcaatttt acctttgaac ttatatgtta ttaccccttt cgattgtggt atgttaatta    240
atatctgaat ctcagtcctt atgaaacttt tttatactgt cacaaacata tgaagtttta    300
ttgtaagttc ttagaaatca tctaaaaaga gtagtttgtt ggactattta tttttatttt    360
tcttattaag ttgttttcac gccatttcag taaaataact atagtgaata gagaatcaaa    420
cttctaatct taagttaagg tagtagggta tatgctaatt caataagata atccgtgatg    480
cttgacatct gacttaattg ttataagttt taaattttt attgtaatat ttaaaatact    540 agttttggt ttctaataaa gaataattg aacaattaca aatatttata caaaattaaa    600
ctagaatata tgatcatttt ccttcgtgtt agaaaaggg aaatatatgt gtgtatttat    660
acatattaga tattgtttta ctatattcca ttttcctcac gggaaatgga ggattgagtg    720
ggagataaac attgtcccca agagaattgg gaatggaaat gcaaatgaca tggccctcca    780
caaaattgtt cgcctaaaaa tgggctttct cacttctcac tccgcaagaa aaatatcgtt    840
tcccttcgaa ttcgggcaag atctcaaaac cacatgtttt tctttcttta tttttcaagc    900
ctacattatt tataaaaata taacttaagc agagaattat gtaaattcaa gtccattttt    960
cgcttcactt agctaaatca ttaacaaatc tgtaattttg ttcataaatt agctcaccaa   1020
ttatgtttta gcccactaag gcccattaga cattttatt agaaaaacat gaaccgttgg   1080
atcaagatgt gtgttttctt ttcttttct tttatttt tttgggtttt ggtggatcaa   1140
ttcgtagctt tagcaaccta ttattatatg gagggaaagg gcgtattaat ctgttagcgc   1200
cgtccgggag tttagctttc ttccccgagc ctcggtctta tccctaact ccaaaaccct   1260 agcccaaagg taatccactc cttccccctc cgctcttcat cttttctat tcatcatctt   1320 taatctgttc tccctttggg ttcttagatt cttcttttgt tggattcttt taatctttac   1380
tcatggttgg ccttgtaagt ttagacgacg ttttatatca ttggttaatc ctgcttctct   1440
atctattcgc acgctagggt tttcctattg ttttctattc tgctctactt ctgcaaggtt   1500
gtgttcttct tcgttcaggt ccctttttt aaccgaaatt aaattaatgc aaattcgttt   1560
gtgcttctaa ttaggaagcc ttttggaaca tctcgacatt ttgattgctg catttcattt   1620
cgggtatatt tctatgattg aaggatgtgg gtctgttcac tgcatggtca ttacttatgc   1680
agctatgctt atcgagtcca ttatgttgt gcaatctgtt tccggattca taatttttta   1740
gtaattgatc agtagatgaa aaagatatt gtaatattcc ttgagtgttg caccagtctt   1800
ggtgggtatc tgctcctgct ctttgcttgt ggattttact tttattatat ctgtattatt   1860
cgaaatgttc tgttcttgtt ataacttata cccgaagatg tgttcctccc cgcgtctagc   1920
gttgtgggtt acttatgatg gacatggttt tgattctgtt tggtttgtgc agggtacc     1978
```

<210> SEQ ID NO 179
<211> LENGTH: 1263
<212> TYPE: DNA
<213> ORGANISM: Cucumis melo

<400> SEQUENCE: 179

| | | | | | |
|---|---|---|---|---|---|
| aattctaaca | actccggaac | aaataattta | gcatggattg | aaatataaat | cttcttgact | 60 |
| tgcaaaaaaa | tcattgtaat | ggtcttatgt | tggttatagt | tagggtatcg | aaacgccata | 120 |
| caggaatatg | ggattaaagt | taacttttgt | tcatcaattt | cagcttatga | acttctaaaa | 180 |
| tatcaatttt | acctttgaac | ttatatgtta | ttaccccttt | cgattgtggt | atgttaatta | 240 |
| atatctgaat | ctcagtcctt | atgaaacttt | tttatactgt | cacaaacata | tgaagtttta | 300 |
| ttgtaagttc | ttagaaatca | tctaaaaaga | gtagtttgtt | ggactattta | ttttattttt | 360 |
| tcttattaag | ttgttttcac | gccatttcag | taaaataact | atagtgaata | gagaatcaaa | 420 |
| cttctaatct | taagttaagg | tagtagggta | tatgctaatt | caataagata | atccgtgatg | 480 |
| cttgacatct | gacttaattg | ttataagttt | taaatttttt | attgtaatat | ttaaaatact | 540 |
| agttttggt | ttctaataaa | gaaataattg | aacaattaca | aatatttata | caaaattaaa | 600 |
| ctagaatata | tgatcatttt | ccttcgtgtt | agaaaaaggg | aaatatatgt | gtgtatttat | 660 |
| acatattaga | tattgtttta | ctatattcca | ttttcctcac | gggaaatgga | ggattgagtg | 720 |
| ggagataaac | attgtcccca | agagaattgg | gaatggaaat | gcaaatgaca | tggccctcca | 780 |
| caaaattgtt | cgcctaaaaa | tgggctttct | cacttctcac | tccgcaagaa | aaatatcgtt | 840 |
| tcccttcgaa | ttcgggcaag | atctcaaaac | cacatgtttt | tctttcttta | ttttcaagc | 900 |
| ctacattatt | tataaaaata | taacttaagc | agagaattat | gtaaattcaa | gtccatttt | 960 |
| cgcttcactt | agctaaatca | ttaacaaatc | tgtaattttg | ttcataaatt | agctcaccaa | 1020 |
| ttatgtttta | gcccactaag | gcccattaga | catttttatt | agaaaaacat | gaaccgttgg | 1080 |
| atcaagatgt | gtgttttctt | ttcttttct | ttttattttt | tttgggtttt | ggtggatcaa | 1140 |
| ttcgtagctt | tagcaaccta | ttattatatg | gagggaaagg | gcgtattaat | ctgttagcgc | 1200 |
| cgtccgggag | tttagctttc | ttccccgagc | ctcggtctta | tcccctaact | ccaaaaccct | 1260 |
| agc | | | | | | 1263 |

<210> SEQ ID NO 180
<211> LENGTH: 715
<212> TYPE: DNA
<213> ORGANISM: Cucumis melo

<400> SEQUENCE: 180

| | | | | | |
|---|---|---|---|---|---|
| ccaaaggtaa | tccactcctt | cccctccgc | tcttcatctt | tttctattca | tcatctttaa | 60 |
| tctgttctcc | cttttggttc | ttagattctt | cttttgttgg | attcttttaa | tctttactca | 120 |
| tggttggcct | tgtaagttta | gacgacgttt | ttatacattg | gttaatcctg | cttctctatc | 180 |
| tattcgcacg | ctagggtttt | cctattgttt | tctattctgc | tctacttctg | caaggttgtg | 240 |
| ttcttcttcg | ttcaggtccc | ttttttaac | cgaaattaaa | ttaatgcaaa | ttcgtttgtg | 300 |
| cttctaatta | ggaagccttt | tggaacatct | cgacattttg | attgctgcat | ttcatttcgg | 360 |
| gtatatttct | atgattgaag | gatgtgggtc | tgttcactgc | atggtcatta | cttatgcagc | 420 |
| tatgcttatc | gagtccatta | tgtttgtgca | atctgtttcc | ggattcataa | tttttagta | 480 |
| attgatcagt | agatgaaaaa | agatattgta | atattccttg | agtgttgcac | cagtcttggt | 540 |
| gggtatctgc | tcctgctctt | tgcttgtgga | ttttactttt | attatatctg | tattattcga | 600 |

```
aatgttctgt tcttgttata acttataccc gaagatgtgt tcctccccgc gtctagcgtt      660
gtgggttact tatgatggac atggttttga ttctgtttgg tttgtgcagg gtacc           715
```

<210> SEQ ID NO 181
<211> LENGTH: 2000
<212> TYPE: DNA
<213> ORGANISM: Cucumis melo

<400> SEQUENCE: 181

```
aaataatttg tggatttat catattatgt accttagact ttgtaaggtt tataacacaa        60
gatgtggaga atcccatga tgaacattgg acgttattat atcctttgaa actaaaaaca       120
aaggaaaaaa gacaaatggc tgagtataag aaaagagaa gaaacaacca aaaagctaaa       180
atgtcatgct ctcatatgta acatatttga attgggattg atttcaagat gtattttaaa     240
ataatttaac acacgataaa ataattctaa caaactcaaa attactctta aacatttact     300
tgatatcttc gacataatga cttttgtttt aatacaactc aaaacataat taaggttggt     360
tttaaatgac aacaaacgaa aaactcgatt ctaatttcaa tactagtctt tgaaagccct     420
aaggagcgtg gttttgaatt gtatagcaag gtttcgaaaa ttttaatcat caaacaatag     480
gtatatttac ctgttcctca agtacagtta attcatagct acttgtcgtg cttcctacga     540
caacattgta agacttgcca cacactaatt gaagccgttg ttgaaggtag ttttccatgt     600
atagcttgaa tcgacggatg accaaagagg ttgaagaagg tttgaaaaat aggggaaggg     660
atatacaaag tttgagagtg agagagggag agaaatagaa atagaagaga ctgaaaaatg     720 taaagaaag gatgaaaaaa tgtggggtaa acgcaaattg gatttttata gtagtatttt       780
gaaaatgcta tagaaaggct atgtatagta gtgcttccaa agttctatat gaatgagaca     840
aatcaaaata tattttttt gattaattaa ccccaaaaag actcataaaa aaatcttata      900
aatcccacta agatattgca tgttatatgt agtaaaattt atcgttcaaa taaaccttaa     960
acataattca aacgaagaaa gtaaaaattt gaatttctta tcttacatca ttcaaccaaa    1020
caatttccat ataagagatt aaacttctaa ctttaagaga gagatatcca gcatatgcaa    1080
cctaaaccaa cagtgacttt gctatatatt tgcacaaaat gtgggggaca aagttgtaat    1140
ttcggaatat caatgattaa agaaaaggta aaatttaaaa ttcggaagct tgacgtggca    1200
acacggaatg gtgatgatat ttccaactcc tcgcgacttt tagaagttgg cctcaccaac    1260
cgcatatccg cccctttgcc acgtgtcaga ctacaacaac ttccaacaat ttcctttaag    1320
aacaccaaat tatatcaata aatatttaac ttaaattaag aatatatttg ttacaatttt    1380
cctactgagt tagatagata gacagacttg tcaattaact aataagtcca aagtcaattt    1440
actcaacata gatacaattc taatttgagt gtgaaataca tattcaaatc aaaattatta    1500
ttaagaggaa aaactgattt gctttctcaa tttaaaatat aatatttga aaaagaaaca     1560 cacatgtatt atggttttca atatatttac tttcttagtc acctaatctc aaactaattt    1620
ttgaagaaat taaatatata tattatcatt tttattttct tggttatgat attggtatag    1680
aatcaacaaa actacaagtg tcctctcctc tgctatcgat ggggattaga ctctaaactt    1740
gtttagcgat tagtaattat atattagaaa agtttatgt taatgtggac ccgacaatct    1800
caccaatagg ctcttcactt caccaacccc cgacccattc cctctaataa ttcgacacgg    1860
ctcatccccg gttcgaaccg ggccgacgtc ttcctatttta acacacctcc atttcctctt   1920
ccctccgcaa cacaaacaga gacctcaccg gaaaatcaag ttaaagcaaa accaaagaga    1980
```
agcttcatca ctctccggaa                                              2000

<210> SEQ ID NO 182
<211> LENGTH: 2000
<212> TYPE: DNA
<213> ORGANISM: Cucumis melo

<400> SEQUENCE: 182

```
gcatcttatg gatgtagtca caacatattt atatggattt tctgataatg atatttatat       60
gaaagtccca aaaggattta agatacctaa aacatataaa tcaaattccc ataaactatg      120
ttcaataaag ttacagagat cattgtatgg attgaaaaaa tcatgacgaa tgtgatacaa      180
tcgcctgagt gaatatttgt taaaaaaata atatcaatat aattcaatat gtccatgcgt      240
ttttataaag aaatcaccgt caggatttgc tattataact gtatatgttg atgatttaaa      300
tataattgaa attttgaaga gttttcaaag gcaatagaat attaagaaag aatttgagat      360
gaaagatctc agaaaaataa aattttgtct tgattttcaa atcgagcatc tagtaaaagg      420
gatatttgtt catcaattaa cttatacaga gaaaatttta aaaagatttt atatagataa      480
aacacattca ttgaacattc taatgcaagt tcattcatta aatgtgaaga agatatttt      540
tcgacgtcga gatgataatg aagaactcct tagtccagaa gtaccatacc ttaatacaat      600
tggtgcactt attttgtcaa taatcaagac cagatattgc attttctata aatttattag      660
ctagattcag ttctccaaca aaacaacatt ggaatgaagt taaacatata cttcgttatt      720
ttcgaggaac aattaatata agattatttt attcaaataa atcaaatttt aacctagtta      780
gttttgcata ttcttgattt ttatctgatc cacataaatc tagatctcaa acaggttatc      840
tattcacatg tggaggaact gctatatctt aacgatcagt gaaacaaatt accataacag      900
tcaactcttc aaaccgtgct gaaattctta caattcttga ggcattcatg aggctagcgg      960
agaatgaata tggttaaggt cgatgactca acacattcga aaattatgtg gtttgtcttc     1020
tagtaaactc cttccaacaa cattatacga agacaacaca acttgtatag ctcaaataaa     1080
atgaggttat attaaaagtg atagaacaaa acacatctca ccgaagtttt tctatactca     1140
tgatcttgaa gaaaatggtg acatcacagt acaaaaaatt tgttcaaaag ataatttggt     1200
agatttatt acaaaattat tacctactgc aaccttttgaa aaattggtgc acaacattgg     1260
aacgcgacga cttagatatc tcaagtaatg ttacatctta cttgccaagt taactataca     1320
tagtgacatt tggtggagtt gtaagaaaca ctaatattgg agaaaaatcg aaagaaattg     1380
gaaaatatgg agaattgaat ttttttttaga tttttcttat tttctaattt taggtttccg     1440
tattctgatt atgcctcatt ttcacaacat taataacttt aataagatga tttcttgggt     1500
taagggaaaa aaatcatttt tttagagttg cacgtacaaa aatattatca taacatatcg     1560
attataataa accaattcac cgtcaaccta acctaggtag agtttgagtt aaatgttaaa     1620
agaatatcca cccctcaaca ttgtaatccc aactaataaa tcagcaacct aaagtttttt     1680
ttaaaaaact aaaaagaaga gcaatatatt ttttttacta ttattttttt aaagagtgga     1740
tttatttatt aaattaaaaa atgaaaagaa gaaaatttgt tagtttgggt aatccgaaaa     1800
cccgattatt tgggcccgag aaaccgacgt tttgtttatt gttcctcacg gcaataagta     1860
atggcgtgaa tcgaccgcgt gcgcttcaag ctatctagac atttttatat cctccgatta     1920
gaaaccctaa ttcagattct ccgtattacc caccctggaa catctttgaa acgcgaaaag     1980
gtgacccgaa gaaacttgaa                                                 2000
```

<210> SEQ ID NO 183
<211> LENGTH: 1989
<212> TYPE: DNA
<213> ORGANISM: Cucumis melo

<400> SEQUENCE: 183

```
attacttgaa cttaatccac atttatgtct ttatataaag ttcgaatact cataatatag      60
ccaagaaacc ttgtttattg gattttgagt tttatcataa gcaaatctct tatccaataa     120
caaattatta aacaacactt caacaataac tttattcaac aatatattag tttaacattc     180
acaaatcacg agtattagaa cataaaacgc aacaagaat ggactaaggt actatattct      240
aacttaggtt gttaggatt tccatatgtc aatgcttttg tgattttga actagatttt       300
cttgttagat taattcaatt ctattttaa atggcttaat atcttatttt cggatgcttg      360
gggattgcta gactaccgct tgttgaagc aataagttaa atttgtttgt tacaggtatt      420
gatcaatcta acatagaatt gaatttgtat gaatatttag ttagacgctt gaaaactaat     480
tattctacca atgagccgta gatcttaatg caattgttat taatttgaac tttgtatgct     540
tctcatcgat taaatttata tcaagtagtt aattaggaca aatctattgg ctttttcatt    600
taattttgtt aagtaaaagc aacttagaat tttgaaaatg atgaacccat gatccaatac     660
attgaaagag aattttgttt aactcaaact aggattcttc tcacattgat ttcgtataat     720
ttaactttt caatttatat caatcccccc agggtgaaaa aaatttgttt gaagaattca     780
tgtgctttct aaatctgatc tagacttgcc actaaaatta acttttgata tgtaatttgg     840
ttaaatattt gattcggatt tcgacgacaa acaattgatc aatgtggtat taaattctga     900
tctccatgta agaaattac acattttcat aagttcaatg ttgacacaaa gagagtaaga     960
gcattttaaa aaaaagata cttttaatct tttctaaaaa aacaccaaaa tgccattatg    1020
taaatgtaac ctaaataata aacatttaaa cttagaattc atgcaattag gctttgtatg   1080
ggacattgaa ttgattatta aaatcagtag ttatagaccg tgagttataa tggtttgtat   1140
tagaagcata aattatttta attttgatcg taatagcatg tatttgagat ataaattaat   1200
ttagtttggg tggcaaatag taaacagtaa agcaaaatat aaaaaaatga atttaaaata   1260
gtaagatttg taacaaatga ttaatactat aacaaacgtg gttttaaaat aacgttgatc   1320
gtagctaatt gaacattatt tattgtaaaa ttgagtgttt ttaatatttg gagcctcaaa   1380
cttcgggtgg atcaccacaa tataatcata ttcaaattta aaatttttatt tttattataa   1440
atattgttaa tagatgctca ttatgggcca tctgtcactc cctccgtgca tatcctacct   1500
gaaacatcat atatcttaaa caatgtccat tgccatgtgt cactattttt acatcccatc   1560
cacttgacaa atatgttgaa gatgcctact ttttaggga tcatgtaatc tatctcatgc   1620
ttgtcaaatt gttcgataat agtgttacaa aaaatttagt aattattatt attatatttc   1680
ttcgatattt atgcttcata tgccattgtg ctctccattt ttaccatact taaaaaaatt   1740
tcttattata aatttttca aaaaaaaatt tactatatag tcatcatctt tattaaaatt    1800
aaaattgaga acctgatatt tttgatatta ataatttaaa atttgaatta atccacttta   1860
aaattattaa taatttattc gaatttgggc cttaaggaag agatacggaa acaaacccta   1920
gatcccatct atatataaat cgccacaaaa ccctaccttt ctctcagttt ctcgttttag   1980
ccggcaaaa                                                            1989
```

<210> SEQ ID NO 184
<211> LENGTH: 1463
<212> TYPE: DNA

<213> ORGANISM: Cucumis melo

<400> SEQUENCE: 184

| | | | | | |
|---|---|---|---|---|---|
| ttttcttctt | gatttgaaat | tcttcctcct | tcctgttgca | acaaaccca | gatgaataat | 60 |
| cagacaaaaa | aagcagcaaa | tttgaagata | tgcatatacg | aagaagaaga | agaaaaagag | 120 |
| agggaaggat | aagtaggag | atagcttgag | attacagcgt | agaaaccgat | cgaaccggag | 180 |
| atcaacggcg | cgaattaggt | caagaagaag | tgagggtttt | tatgaagaag | aagtgagggt | 240 |
| ttttatgtgc | cgatgaaaaa | ccctacttct | gtgttggtga | tctaacgttg | tttgatcggt | 300 |
| tcggtttttt | tgagaatcga | gtaccctcat | tattattatt | attattgtta | ttattataag | 360 |
| tttgttgtaa | gaattaataa | attatttcaa | aaattacaat | ttttatttat | atatagttta | 420 |
| aaaaatttta | taatttttt | aaataaattt | cgaaatataa | ggttggatttt | cttaaaaata | 480 |
| tatgaaaaaa | gagatgaagt | ttataaatta | aaaatgaaat | aaaaatagta | agtttgtact | 540 |
| cttattctta | tttacaattt | aattttccat | taaaatttta | aattaaatag | aaatataatt | 600 |
| aaaatcttaa | attagataga | aatataatta | aaattttcag | aatgtaaatt | taaattagct | 660 |
| tagtgtatat | ttaaaatata | taagattgaa | ataattgatt | tgtttatct | aaatatttta | 720 |
| tattattatt | tattgaataa | atataattat | atatggtaaa | ttgttttgga | taataagaaa | 780 |
| gtaaagatgg | tatttatata | tataattaac | caaaatttaa | gtttgttaaa | agaaaagtt | 840 |
| ttcaaaaata | ttttttacg | agtaattagg | aaaaacccac | attttacatc | gaagtcatag | 900 |
| actgggtcta | tgtcttcatt | gccttgtcgt | gtacccgatc | cacgataacg | cattatgaac | 960 |
| cgagtagatg | acttaacttt | ttgtaatagc | ttttcttcta | ccatattttt | gacatttttt | 1020 |
| taaaagtaac | attatttata | aaaaaaaaat | cgtagtttga | tctcacatga | aactattatt | 1080 |
| acatcattaa | ctaatatatc | tatatttaat | gtagttttct | tgacatgatt | ttaatgctaa | 1140 |
| ttgaaatagt | tacaatttt | gtgtcccatt | ttgtttagat | caatatgact | tcacgtatta | 1200 |
| tgacatatgg | ggccatctta | ccagaaattg | gtgccaatga | gaaaatgaat | gtaccttaac | 1260 |
| caatggagca | acccatgtga | gccattgatg | aacccaactt | tcttggtttc | ccatcttcta | 1320 |
| ttcatatgtc | acaataccttt | ctcttttctc | attctatata | tagactctaa | acaaacaact | 1380 |
| aatctccaac | ttcaaatctt | tcacatattc | tcattcaagc | attgaagttt | accacttcca | 1440 |
| aaaagattca | atccaattta | gcc | | | | 1463 |

<210> SEQ ID NO 185
<211> LENGTH: 2006
<212> TYPE: DNA
<213> ORGANISM: Cucumis melo

<400> SEQUENCE: 185

| | | | | | |
|---|---|---|---|---|---|
| cagcgatctt | cgtagaaact | aattcaatgc | tagctcatta | tttgactttt | ctcaggcaag | 60 |
| gctccgcgag | gaagagaaaa | ggtccaattt | caggaaccaa | gggcatggac | aggttccggt | 120 |
| cagaagaagc | ttttacgta | aacccttttgc | cagattgttt | atgtcaagga | gaattaccaa | 180 |
| atggaagtac | gacttccatt | ttcagatagt | tcagtagaac | atcaaagata | aaatgctctt | 240 |
| agagagctca | atgtatatgc | aggcgaccac | tcaacgtgtc | accagctttg | tacatccaat | 300 |
| aagccagcta | cgatggaacg | acggagtgtt | tataacctga | gttttggtag | ttggcggagg | 360 |
| cggtgatggt | ggtatagaag | gaaggtcgag | ggatggcaaa | ccctttacgc | caagtagtgg | 420 |
| aagggagtag | ttggagatga | acacattttg | agaagtttcc | aagatcactc | catttggggg | 480 |
| agaggggatg | ttggttattt | agcacaattg | ttttcatgtt | ttagtaattt | tatccaataa | 540 |

```
tgagcgaggc attgaagcaa ttaaatttat ttttaatgat ttttttcaccc ttccataggc      600 ttttctcttt ttcttttcct tttagtttgc aaactttagc tccttttatc ggctgtcgaa      660 ctcattttttg aagttattga atgaaacaca gtttgggctg tgtcagatgg gtggtgaaat     720
tttatacatt ataattacta cataaaatga aatcatattg taattttcta tctatgccac      780 aattttttttt tattgcatca tgaggattaa attgtacgag tccaaatttg tacagtcatg    840 ttttttaaagc tttcgagcat tgttactaat gcatggaaag gatcgattat caagtatcct    900
cccaacttca tgaaagttat tatttgtctt ctaaatttgt tttagaaaat gtttaattaa     960
ttatttgaga agaaagttta actaaatcct attggtttcc tctaaggttg tcatacttat    1020
ccaataacaa ttacgtttaa aatcaaaatt attctaatgg tataagacta atgttttaaa    1080
agcataaaat tgatgaggaa ggattggaag taatactatt tattttgaag gtaaacattc   1140
ttgaatgtct gtcctaaaat cactaatgtt ttcttagttt gagactttga gtcgttgaac   1200
ctctccatct ttataaaata taatacgagt ccttcacaat aacttaaaat atatactaaa   1260
tcctaattaa tgaaaaataa ataaataaaa ggtacaaaat cattaaagcc taaaaatcta    1320
ttactccttt aaaactttttc aagggtccct acaaccaatg agaaactacc acgtcatttt   1380
cacaatccgt tcagtgttta gaaaagtcaa atcgcaccgt ccatttatcc actcgtacca    1440
agtacggtag gaatctatct accgtccgat taagcacaaa gaagcacagt aaatgtcaat   1500
cgtgtccatc cgccgccata ccgcacatcc ttcgtccgac cggaaggccc tatataaagt   1560
cctttggttt tccgaatttc tacttcattc gcttttgaaa gatttcccaa tctcttcgtc    1620
ggccaaaatt ctctctcgct tctcaaccct tcttcggctt tttcatccag gtttgtttct    1680
cttctctttt ttcttccttt gttgttcttg gaatatgttt aatttcattt gttttttccat   1740 tcaatttcat gctagatttt acgattaggt tgattttctg ttcgtagatt gtaattgatg    1800
gttagggtta gcttttttctc ccattccttc tggaatctgt ttcttgacct tcgaacttcg   1860
ttgataaatc tttagaaaca tttacataac caaacaataa ttgaacaact cgtgttgtta   1920
tgcctatata atagcggtta ggaaactgga aacgccctta taattgaaat cgccttagaa   1980
atttgttttg attcatacag ggtacc                                          2006

<210> SEQ ID NO 186
<211> LENGTH: 1664
<212> TYPE: DNA
<213> ORGANISM: Cucumis melo

<400> SEQUENCE: 186
cagcgatctt cgtagaaact aattcaatgc tagctcatta tttgactttt ctcaggcaag       60
gctccgcgag gaagagaaaa ggtccaattt caggaaccaa gggcatggac aggttccggt      120
cagaagaagc ttttttacgta aacccttttgc cagattgttt atgtcaagga gaattaccaa   180
atggaagtac gacttccatt ttcagatagt tcagtagaac atcaaagata aaatgctctt     240
agagagctca atgtatatgc aggcgaccac tcaacgtgtc accagctttg tacatccaat     300
aagccagcta cgatggaacg acggagtgtt tataacctga gttttggtag ttggcggagg   360
cggtgatggt ggtatagaag gaaggtcgag ggatggcaaa ccctttacgc caagtagtgg   420
aagggagtag ttggagatga acacattttg agaagtttcc aagatcactc catttggggg   480
agaggggatg ttggttattt agcacaattg ttttcatgtt ttagtaattt tatccaataa    540
tgagcgaggc attgaagcaa ttaaatttat ttttaatgat ttttttcaccc ttccataggc    600
```

```
ttttttctttt tcttttcct tttagtttgc aaactttagc tccttttatc ggctgtcgaa      660
ctcatttttg aagttattga atgaaacaca gtttgggctg tgtcagatgg gtggtgaaat      720
tttatacatt ataattacta cataaaatga aatcatattg taattttcta tctatgccac      780 aattttttt tattgcatca tgaggattaa attgtacgag tccaaatttg tacagtcatg       840
tttttaaagc tttcgagcat tgttactaat gcatggaaag gatcgattat caagtatcct      900
cccaacttca tgaaagttat tatttgtctt ctaaatttgt tttagaaaat gtttaattaa      960
ttatttgaga agaaagttta actaaatcct attggtttcc tctaaggttg tcatacttat     1020
ccaataacaa ttacgtttaa aatcaaaatt attctaatgg tataagacta atgttttaaa     1080
agcataaaat tgatgaggaa ggattggaag taatactatt tattttgaag gtaaacattc     1140
ttgaatgtct gtcctaaaat cactaatgtt ttcttagttt gagactttga gtcgttgaac     1200
ctctccatct ttataaaata taatacgagt ccttcacaat aacttaaaat atatactaaa     1260
tcctaattaa tgaaaaataa ataaataaaa ggtacaaaat cattaaagcc taaaaatcta     1320
ttactccttt aaaactttc aagggtccct acaaccaatg agaaactacc acgtcatttt      1380
cacaatccgt tcagtgttta gaaaagtcaa atcgcaccgt ccatttatcc actcgtacca     1440
agtacggtag gaatctatct accgtccgat taagcacaaa gaagcacagt aaatgtcaat     1500
cgtgtccatc cgccgccata ccgcacatcc ttcgtccgac cggaaggccc tatataaagt     1560
cctttggttt tccgaatttc tacttcattc gcttttgaaa gatttcccaa tctcttcgtc     1620
ggccaaaatt ctctctcgct tctcaaccct tcttcggctt tttc                      1664
```

<210> SEQ ID NO 187
<211> LENGTH: 342
<212> TYPE: DNA
<213> ORGANISM: Cucumis melo

<400> SEQUENCE: 187

```
atccaggttt gtttctcttc tctttttct tcctttgttg ttcttggaat atgtttaatt       60
tcatttgttt ttccattcaa tttcatgcta gattttacga ttaggttgat tttctgttcg     120
tagattgtaa ttgatggtta gggttagctt ttctcccat tccttctgga atctgtttct      180
tgaccttcga acttcgttga taaatcttta gaaacattta cataaccaaa caataattga     240
acaactcgtg ttgttatgcc tatataatag cggttaggaa actggaaacg cccttataat     300
tgaaatcgcc ttagaaattt gttttgattc atacagggta cc                        342
```

<210> SEQ ID NO 188
<211> LENGTH: 2003
<212> TYPE: DNA
<213> ORGANISM: Cucumis melo

<400> SEQUENCE: 188

```
aactagacta gcgagtgcac aaccaaatta caaaatcctt aacagagaca accatctatc      60
tcctttaaag caacaataac atcaaccgaa ttagaatcca caatcagtaa agacgatgcc     120
gacaccaatg accaaaaccg atcaaatata gcttattacg gaccattact tcaacagtta     180
catcaacaaa aaaaaaaaaa ttaaacattg ctaataaaat ctgaaaatga ggaaaaagag     240
attaaaagtt ttgaagatag aaagaataaa tctgaaatgt tctaatttga tatataagaa     300
atatgaggta atatgacgaa agcatttttga tagttttcac caactccctt tgtgaaggaa    360
tacatccaac caattttaca atttctgttc aaatttgtc cacctaccct tctcttctgc     420
cccccaaggc tgctttcttt cttttattat ttgctaaatt accaaaaact attttcgaat     480
```

```
taaaccatct atttcaatta tatacgtcat tcgaatttta acttaattaa cattagtata        540
tgtttcggat caaggatagt ggtataaatc atcctaattt caatttgtat ttagaaaagt        600
tcaattatac ttaaaacttc taaaaatttt atattttaaa tttggatata aattaaattt        660
aagatttatg gaaggtaaat aattagagca aaacaaactt caaactatat ggaaaataga        720
aaaggaatat tttagccaaa caaaaacact tattattttta ttttgttttt ttgttttttt       780
tttaatttaa caatttttt ttttattggt tgaatgtgtt tctccactgg tgagtctcca         840
actttgacct gcaaagggtc tatatagcga gtttcacgag cacctaacca atatctgtgt        900
aataattccc attttctttt catacccact tcatttgatc atctttttca caaccccgga        960
tctctaattc ttgggaattt gcctctttct cgatccattt ccaccgtaat tgaaaaatat       1020
tcaggtttga ttcttctgg gttttcattc aactgtctaa cttcattatg cccttttatgt      1080 gtttgttgaa agcccccac ccaccatcgt tcaatgcggt ttctttacct tttgttcggt       1140
ttcaacgatg atttagaagt tatagatgga tgctaattgt ttcgttgttg gtttgatcca       1200
ctgatctgcc tttgattggc ataaaaggag attctagatc ttgttttgat gttgtgattt      1260
atggatatta ttgttatagt cgtggaagtt tttcttgtcg ttctgcggta tatggttgtt      1320 ttatttttg agtggtaaat tgagcagatt gtgaactttt gggttttatg gtgaaagcat        1380
gaattagtaa atgtagagct gctgaaacaa aatggaggtt tgctagacct ctttgtgaat       1440
tcttaatggt cagcctccat cttaagaggc taagtccaaa aatttaaggc agtctttttgt     1500 tattgttaca aaggacaaga aataacagag gagttatttt aattgaatca agttggaaag      1560
aagtactact tcatgcttct ttcaaaagca ggtcaaagtg ctttaaagtc ttcttattta       1620 tttattttt cctgaatcaa tttaaactaa tgatagaaag aagtgttttt taatgggtta       1680
ttataagtaa catcaatttt taaccattcc aaaagttaca tcaaattcat catagtgtga      1740
gtttacgaat tttggaagtt gtaatttaa gttaatactt cttttaagga aatgtacact       1800
ttgcatgttg tgttcataag gggtatttct ttgacaaacg cagcaaccac cccttaatga      1860
aaactacacc acggtggttg gtttttctt gttattttt tacttggaat ttacaataag         1920
ttgttatatt cggatatatg gcaaagcaga tatctgtttt tatccgaaac ctcataaatc     1980
ttgaatgtgc agcaggtaaa aac                                               2003
```

<210> SEQ ID NO 189
<211> LENGTH: 1024
<212> TYPE: DNA
<213> ORGANISM: Cucumis melo

<400> SEQUENCE: 189

```
tcattgatga agaaggaaac tttaagccaa ttcgacaact tatccattca acaactttcc         60
accttcagac attcagattc aactataata taacataaat tgatagtcaa gtcttttttg        120
agacaaccat aaatcatctt agcttcgaga actgtcactt ccttaaattg gtgaatatat        180
cacattccat ccattcaaaa ctttgtttcg aacttactg tagttatgaa tcaataaatt         240
gggagagata ttgttaaaaa gagagagcat atttgtttct attatttact ctctcctaag        300
agagggttaa ttagtctata aatgatctat tcttctcgtc cattgaaatt ttgttatcct       360
aaatttatga atacttctac ccaaaataaa gactttttttt tttttgaaa agtgtcaaaa      420 aaacataaag aaattgacaa acattcatt tttagtggat tttttacgga cgtaaatagt        480 ttgttttgt ttcttttaat aatacaattt tttttactt taaaaaatat ttttgttata        540
```

```
aaaccaccgt atttttattc aatttaata aataaataaa tgaaagaata taaaaaagag      600
gaaggaaaaa gaagccaacg aaccaacggt tgccacgtat caaaggtcta aagtgcgcaa      660
aacgaggcct tcggaaacca aaatgcgtgg cttcaattgg agcaagtaaa catggaaacc      720
acgtccattg taacgcttcc tgatctcttc tttacaaccg ttggattcga gtactttttc      780
tcaacgatta acgactgagt ggacctccac ttgcttctgt tccacgcgcg tgggattgac      840
gtgtggtcca cgcaactctt ctcgatagga tcattcgaga acatccttta cttaaaccgc      900
ctctctctgc ctcaatttct cgtcacttcc ttctccttct ttacccttc cactgcggct       960 gattcttctt cgccttttat tctctcgtac gccgccatat tcttcacttc tttttccggc     1020
gaca                                                                    1024

<210> SEQ ID NO 190
<211> LENGTH: 2001
<212> TYPE: DNA
<213> ORGANISM: Cucumis melo

<400> SEQUENCE: 190
attcgtcttc gcattatcag taaatttatc attttaagag tttgttcttt tttaaaaaaa        60
attaatcatt tcgataaagt tggagaattc aaaaatttct ccaaataatt tataaaaact       120
ttcggttata tatcgaaaaa attaacatgg tattaaaacg atcataactc aattaacata       180
aacactccct ctcaacttta ataccaaatt tctttattaa cgcaaaattt aaatttgtt        240 tttaaaattt tcacataaca taatagaaat acttttcttt atggcaaaaa tacaataatc       300
aaaattgatt gatggtgaca ggacaccaca caatattttt aaattttgaa tatacgaact       360
atataataag atatttatga gattcccatc ctaaagattc ctagagattt ccttgtgtac       420
aatattacac aagtatcttg gaagtccaaa gtcctgagaa aaaagctatg tataaagtaa       480
tagtgtttgt cgtaggaaat ttacttcatt cgtgtcatta gcttttatt gaaaaaaaa         540 attaggtata tcttagtgaa tctcacttaa tcgttgtcga tagttattct tttaatatca       600
ttatatacta aaatataaca atattgaaaa gctaaaactg tatataaaaa aatgttacc       660 tctaaacttt tatcgtttat ttaaaagata aatatattct ttcaaaactt acaatcaaca      720
tcctacgact atcattatag gtacaaatct tttcatgttt acacaaaaat tagatttta      780 aatggtgtaa tgatgatata taacgaaatt ttgaatgatt actatttgag gttaccattg      840
taattggtcg tgttgtttga aatttaattt tattagaaaa tttgtcaaaa gtagcaaaaa      900
tgaataaact atttaaactt taggataaaa tcaagtgtta tgagttttg tctagtttat       960 atatttttat ttttattgaa aacccttttc ctatcttttc attacttcaa aatagtttta     1020
aaatgtctat taaggctaaa gttagtataa ataaaatttc ggaaattttt tttcgaaaaa     1080
aattgataaa ttatttatat tttatattaa agtcaaaatt tattacgcgt agatgtttat     1140
caaattttct ttctttttgt tgataatttt ccaaatttg gataatttt taaaatagta       1200 aaattattat aaaaatgaaa acaaactatt tataccttaa gcaagaaata ctaaaaaggc     1260
aaaaattcat ttacttcatg aagcgtaaaa attaaatatt ttaccacttt tgttatttt      1320 ttaccatctc tatcaattat ttgtaaaaag aaaactacaa aattagatgt ttttctttt      1380 ttaaggttta atcaatatta aaatttctta aattggcaga caagttggtg ttggtaatta     1440
cgaataaatc ccgaattgac taaaaataaa ttcttctcca agtaaaatag acacgtggat     1500
gaagaaataa gtgaatcaaa ggcatccaca gttcaataaa tggaaaaaac tactttctgc     1560
tgactcattc ataagttttc ataaaatttc ataagaaagg ccaaagggct tatgaaagtg     1620
```

```
aatgtcatag cagtaaatga agcacagcgc cattgaaaga caactcaaat tgcatgcaaa    1680
cccacataat tattcaacaa acccacatca aatttcccat aaagatcaat tctttagggg    1740
gttcaattac ccaaaagtga ggtagttgaa aaccattaaa caacaagaaa tcaacaattt    1800
tgtaatttgt ttgtacagaa gtaagagata aaatcatcgt taaccattcc tttatttcgt    1860
aatacaaccc atcaaccatc tctctctctc tctctctctc tctctcggcc tttatctttc    1920
tcttcctcaa ttatttaagt actacccaag tgagctaaaa gcaagttcag tggacagtgt    1980
tgtaagaacc actacagaaa a                                              2001

<210> SEQ ID NO 191
<211> LENGTH: 4175
<212> TYPE: DNA
<213> ORGANISM: Cucumis melo

<400> SEQUENCE: 191
tagtttggtt cataggttat agtttccaaa tttgttaggc tatcattaat caaacacaat      60
acttctcttg taggatggct gccccctata gtactttttt aacttaggag aaggatataa     120
taattatatt ccttttagaa aatataataa taattgtgta gtgctttgat taccttaaa      180 ttagctactc acgtttttag gaggaagctt ccgttgcttt tcatggtgtt atgatctttt     240
ttattttata aaggactgaa ctttaaaatt tctctttcat ctatttttgga ttggattcca    300 tctattttat acgggaagtg aactctaaga tttctcttca cctattgtga atcggactcc    360
gtcatgtagg tcaagactac gacagataag aatagacttc cacgaaagaa agtggtcaat    420
cgagatggct atatttggct ctttcagctc aatttcttct ttttccttg catgttcttc     480 cgttggtaca tttcttgcac ttttttttgtt ctcacatgac taatgtattc caagtttatc    540
attggcattg tgcctctttt aggcttgtaa actctcgatc caaaattatc taggacatat    600
gtttcctagt gaagaaatac tagtatattc cttatgtcaa tatgtcaaaa ttttcaattt    660
cttaaccttt gagtaaatca atattatatt tttatggagg ttatttataa ttggaaaaaa    720
gttacaccca tctcaacccct aattaacacc aaatgaaatt gtaccatgcg gcacaatatt    780
tttttgtgag tttttttgcaa agagaaacaa agtagcagac aaagaacaaa cattccccca    840
aaaacagcag agaataccta agagagaatg ctctctcgta aaaaataata cccaagaatc    900
ttcccaaaaa gagggagtaa aagagtccaa acaaacgaa ccgaagattg acaagaaggg     960
cactctcgcc ctccactgcg ccgctaaatt gtaagaagca tattttcttg agttaacata    1020
ggaataggtg taactcaaga gaatgtaat tcgtagaatt gaactttgta tattaattta    1080
tatggtgttg tagatacaat ctttagtatt tactcatttg gtgctttctc tcaaatacaa    1140
tttaaattta gaacttttg atcttcgatt tcaggaagt tggagttgca aatcaattcg     1200
agtttcaatc tctggaattt aataaaagtt tgatcttcca agttttcaat ctttcagaag    1260
acgatgatct tgatatggat aaaaaaattgc acatcatgag agcttttga agtttaaatc    1320 ttcaattctc tagagcttaa attcttcctt aaaccaaaga tcaccaaatg aatgacaaat    1380
gtctctattt atcgaaaaat ttcatagact tttagatggg cttaggcaca ttacttgttg    1440
ggcttggact tgggcttatt tgcttggcgg gctcatgctc gagcccatta tttctttggc    1500 ctattttca tgaggggctt gaacttggtt gtatacgaaa aaacttgact acctaaatct    1560
aatcaaatta taatcatcac aatttttgacg tgttacgatt taattggcca aaaattcttg    1620
ttcaacactt gtctctaatc atttttcctat ataatttaac taaaatattt aactttaagt    1680
```

-continued

```
aacttaaaag atatagttta attcgaatca aaatacaaat acaatttcgt ctatctattc      1740
ccatcataaa tgttgattga gattcatatt ataaacttct ttcaggaaaa gaaagaggaa      1800
aattcaccta aaccacgttt tcctattttg gtaagaatcc ccaaaccata aatcattcca      1860
aaattatttt ttttagatta gaaaagaaaa aagaaaaaaa gaaattcaca tggcgtaaaa      1920
tttcagcccc gtgagatatt ttcgaacccc cagatacaat ctacaccgtg aaaacaaaat      1980
cggacggtgg ttgctataat gtccgtttag aggcaatggc agggatgaaa ttgccaacgc      2040
aagataagga acgaataaga gaaggacacg taagtacaag tttaggatgg gcgggcccac      2100
agccacaagt gccgttcgtg cttatataca agtcgctcat attcctagaa gtgtctccaa      2160
ataaaggaaa gaaaagttca ctcatagaga gaaagagaaa aataaagctt cgttgccggc      2220
gatctgaagg cggcggccat ttctctcggg agagagaaag agagagattg atagagcgga      2280
gagttcgagg ctctctcaaa cttcggtcct cttcttctct ttcaggtatc gttcttctct      2340
atcccttcgt attctgtttc ctcttttctc tttcttcgcc atcatgctct ttctcttgtt      2400
ttgtactcac tcaatgtgat tgactttatg ttgttttttct gttttatttt tccattaatg      2460
ctcgttgtaa tgtgtagatc tatgataaga tttgaattat tgctcattaa tgtgttgcat      2520
gcttttgatt tcattttaaa aacagagatt actttctcta tattgattaa atcgttggat      2580
tttaggttct tacagagttt gtaaacagtg atgttaagga ttgctgagat ttatgactga      2640
tgagagttag tgtttgtctt ttagcttgtc gttttcctct ttgaaatcac atggattcga      2700
tctggatatc tgggtttggc tcgtctgaaa tggctacact atagcatatt tgagtttgtg      2760
atgttgaaga tttgttaatt tcttggaaaa tcgggagttc gttttgtttt tcctctttt      2820
acaggtttta ttgattggtt tattgatcgg cgatatctcg ttttcaactt ccgaaatgct      2880
attttttcata agaagaaatt gtggatgtct ttttctactc gattagagat ccttgaaact      2940
atgccaaaaa aaattggttc tttcaccaaa ttgttttttg tcgtttgtga tattaatgca      3000
ttttcttatt cttaattaag ttcaagtatt cttttattat tttttaatga tggttgttgt      3060
aatggttttt tccctttttac taaaagcttt ttccatgtga ttcaaaggtg tacttggggt      3120
ttcccggtct ttgttcccaa gtcaattagg atgggcgcca attcgatttt agcttctgta      3180
tcattggtgt atattctgtt ctggggagga aaaaaaaaaa gaaaaaaatc ttccgtccta      3240
cagtgtgctg agtaacaatt tgaccagcct tttctgccga aaacttttg aaattatttt       3300
ttaattgtga tttggtgaac ttaaattgtt ttaataaata aggtggattg aatcttaaca      3360
gaaacatcaa ataaaatcga gttttaaaaa aaaaacatat ttttagtgaa tgtttatttt      3420
atttaaaaga tctccatcag tcctgatgtt tcctagaaaa cttatacatc ataggtcttg      3480
attaacaaat ttggaggaag tcaataggtt attcttttt tcttttcca ttctagtttg       3540
aaacaatttt cttttctttt ttaacttaga aaataatggg tagctagaaa tatggaaatc      3600
aatgtatttt gggcttctcc ttgaaactgg agcagcggtc aatttctctt tcgtttgtat      3660
agatgtgata gaaatagaat gtttccttcg cttacggcat cagagagttg gaattggtct      3720
ttctcaacct caatatcaat taaatcaagt ttcgtcataa acaggttttt ttttcttcg       3780
tttcaaatgt ttggtagggt caaataattt gtaaaatacc tagccgtcca atatgataca      3840
aactggagga tttcacttgc tcttttaaat tacaaaaaat attttatcat tgatgttgcc      3900
tgtctgtgtt tatctttttct ctttccgcct caagtaggcg tctaattgtc ttggcaagtt    3960
ggtttttgt acttccgccc cttgtccttt ggccttttg attaagtttt tcatttaatt       4020
ttctggtcgg cgtacgttga attattaggt ttgcatttaa tgtggtacct ggtgctttga     4080
```

```
ctcttatttg ataaggtatt ttgaagtcta aaacgttaaa ccctttgttt gatgtttatt    4140
tttttatcgt tccaggacaa tatcctttgg aaaaa                              4175

<210> SEQ ID NO 192
<211> LENGTH: 1999
<212> TYPE: DNA
<213> ORGANISM: Cucumis melo

<400> SEQUENCE: 192
aaaagagtca tagtgaaaaa agctgagatc ataatagttt caccctaaac acaacttata     60
ataacacata ctatcataat atacacacca aacacagact ctatagtctt cactctaaac    120
gcagattaca atagtctgca ccccaaacgt agactattat aatcttctga ctattataat    180
actcttttca cttatcgccc caaacgtccc ctaagagaac aaagataggt tataaaagag    240
agatgagggt ttatattatg caacaagtat aaggttctag aacgatgtag tcttcaaagt    300
aacgaaagca ataggctaca cgagaaaaat attttttaaaa tatagtgctt tccctaaact    360
agatttcaat gacaaattat tataaaaaat agaatcatta atccaacatg cttgcatgt     420 cacaccttgg ccaaaactga agacggatgt catactcgac ttcaatatat ttttttaatt    480
aattttcatg tgacaacaca taaatattta aaatttagat tgggttggat ttttttttcaa    540 gtgggtccca aaatactctt caaacccaaa ccaacccaac ttgttaccc atctaataat     600 aacccaccag gttcaagaag acgaaccgaa ccgaaccgat ccggtctaac tttgtttcat    660
acttaagtcg aacttagcgg tacttttggt tcggttctcg gtttcccaa acagagccac     720 tcaaaattag atttagggtt ccgttcgcaa ttttcagcgc attttatttt gaatcggtcg    780
tttgttgaac acgttctctc tcagctggtt tagggttcat cgttctctct tctcgcgcta    840
tatctttctc tctctcaggt tcgtttcttt ctcttaggcc attttatcag aagatcctct    900
tcgttctccg atttcttttc cgtgttcgcc ctcggtttct cagcagacgt aggaagtttg    960
gtttccgttt agtgaatctg tttggggtat tacgaatgat attttgtact gggctttccg   1020
catagtcttt ttcttttctag gaatatatgc atctgagaat ttatttgttt ggcttttctt   1080
tataaagtat gaggacatat acatctcgat tgctaatcct tgattataat ctttttttt    1140 tctatgttgt ttgaatctgt ttttttttttt ttaatttcaa taggttttt gaatctaaaa   1200 atgtatttct tggatgaatt gcatactgtt gaattagaag tttattgatt agattgttga   1260
tatttgccct aagttccatg ataggtttg cgtctttcac cttttcgttt gcttttctt    1320 ttggctgacg acatcttaca tagcctctgc tctaaaaggt gccatgattt tttttcctgg   1380
ctttatctga gtttgcgcaa tttagatttg aagtgatgat ttgtctaaat ataaatatct   1440
atcggccata ctatttttg ttattttgag tttttcagga tgactgctag agaatgaaaa    1500
atcttgaaac attgtgtttt gaagttcaag gatcttgtag ttttgttctt ttctagacta   1560
tctcatttga tatagccctt taaatttaat caaaatttgt taatattcaa atcctcggac   1620
attttaatta tttatctaaa tagttgttta ggcattactc aggttgccca ctattttaag   1680
cttagaagcc tactctggtt gacctaaagt ttgcatgcta tttgccttat ttcgcacgac   1740
tctaaactgt tatagacatc ttttttcagc cttcaggtaa atgaacacaa aaaggagtga   1800
aagtctgact tctgtgtgat ggtcttttaa tcaattatag ggattaagat ggttttttta   1860
ttcattgtat aaatattaaa ttagaatgat gacaaccaat aatattaaaa ctgacaatgg   1920
aaggttcctt atattatttg gagtgtacat tacaacagcc tgattcttgg cttggcaggt   1980
```

```
tcctgatcac cttgtaaac                                              1999
```

<210> SEQ ID NO 193
<211> LENGTH: 2000
<212> TYPE: DNA
<213> ORGANISM: Cucumis melo

<400> SEQUENCE: 193

```
atttatttgt ttagagataa gacgcacatg agaatatgag atggattcca ctccactcac    60
actccaattt ctacctatcc tattactgtt tactattatc attccacccc tcgaccctc   120
attcttcttc tcaccttact tttttatgat ttactactac ttcattttgg atcacaatct   180
gatcaatgct gggtgggctg ccctcggcct gtcaccaggc ccagcccact tccaaattaa   240
acctcttggc ccaccgccca ttgtcccat cccattccat ttaatattcc caaccttccc   300
tttttctttc ccaatgcgat gcttctccaa tataccttc ctgccctcca tgtttccttt    360
ttactgcttt cttatatttta taacacacct tctacagtct tttggctggg aatgctgcgt   420
atgtgaatga gattcaagat ttcgttgatg ttatttgagt ctctatattc ataagttttg   480
ttcttagttt tctctagacc aactgcaaga gttagcgttc catatgctca taagtttcag   540
atttctgctg tgtggtttga agacagtcat cgatccatgg gtgaattcgg cttttattta    600
ttattattat tatatttat tgttgtctta cttttctatt tgaatcttcc tatctttttt    660
actcattgtt ggactctaat aattcttgct aaacacaatc tccattttta ttggacattt   720
taaatcccat ctcaactcat aattttagtt accttccacc atcaccatat ccaaatccga   780
aataaactca aataaaatcc ttcacgtgca tgtgctctcc atatatttt tctacatggt    840
aaaaataaaa tgaaaacaat ctaaatttaa taaaataaca tatatggcag acttttattg   900
atgtagagac tgggtgttgt acaagaacag tgcagccaag aaaaaaaaaa tacttccaat   960
gaatcgtaca ttttaaggat tatgaaacta actagttcca accattttt cacgaccacg   1020
tgcttgttaa acacgcaagt agaatcaaaa tgtgggcttc ttcgctttat ataactgtga   1080
atcattctcc aaaaagggaa ggggatctca ttccctaatt caataaagaa aagaaaaat    1140
gctagcgaac ttcatccatc tcattccttt tacctatttc atgagatgcc cattgtatat   1200
aagtattttt ttttttattt cattttactt agtttactcc tcacctctaa aaaaattag   1260
gagagtttgc taaatccatt ctcaaactta gctttatttt ttttaatttt atttaacctc   1320
gtcgtggatg ttaacctcaa atgtcagttc tttttattct atttattgat gttataattt   1380
actttaggat tccaatttta taaaaataag aatacaaata aagataaaga gtgtgaaagc   1440
cagaagaaa aaaaaggaaa tcgtaatatg ggtaaaattg gtacaaattg ggtcccgtta   1500
aatattaact caaaaaatgc gagaaaatgg tagaaaagga aataggggt aagagcaaag   1560
tagtggaagg agagcattga acatattctc tagttttgc acttggatct aaacacgagg   1620
aattataggt ttattcattt actaattaca taaataggat tggattttaa aatttgaccg   1680
agtgattatg catatttgat agagttagaa aatagtggtg gggcaggtac aagttacaag   1740
taatgtataa gagatatgat gagcatatta ggaaactata gatttaaatt cgtccgtaaa   1800
taaataatta gaaatataat attcgagtgg aagggtatta gggttaggcg aaaccaattg   1860
cagttgcacc tataaaaccc cttttacgcc tccacccgct tcaacagcgg tctcggcgtc   1920
tacaactaca cactacacac tacacactac acactacaca gttgcagacc agaagcataa   1980
cgtaacgccg gtccacaaaa                                             2000
```

```
<210> SEQ ID NO 194
<211> LENGTH: 2000
<212> TYPE: DNA
<213> ORGANISM: Cucumis melo

<400> SEQUENCE: 194
tgaagagccg gaaaagcatg gcaaggtcaa ggcatttcag caagaatacg aggatgaatt      60
ctgggtttgt aagtccggtt cttcttcgga gttgtggttc gaatttcaaa cggccatgag     120
gagccctaca gcttaggaag cttcaggtct gagactctga ctccgacaga aattgctgat     180
ttttgtgtgt gttttgaata accattgtat gagtatgatt ggttgtatag gtttgaaatg     240
agggaaagtg atccatctcc ttgttgtctt gcaggaaag gctcatattc gaccaagaac      300
gctttgtcat tgctttcgat aatcatagaa tccacaatgg tttggcatat agcaaacaa      360 atcttcttta ggcattgcag acagaaaatt ggagagtaag ttattataat taaggattct     420
aaatgagtaa gaataataag atcaggcaaa gattggaaga actaaagcgt ttagtatttt     480
gtgtggtaca aagaattgt aattagatac gtagtctaga gaagcagatg gtgagatttg      540
tgaaagacaa atgttagtgg agagtgaaga gtgtttctca acaaccgaca tagaaggatt     600
ctcagaaaat gagaaagatt tttattgcgc aaaatagctc ccatatcatc atatgccgtt     660
gccattccct ctggggttgc atgtaatgag taatggaaag ctgtagacag gctaacttca     720 cccttgtct tgggtatagg gtgcatttt ggtcactcca ttttaagttt tctaataata       780
aaaggatgaa gaaaagatat tgaaaaacag ctcaggtttt aaagttgtca cacttgagaa     840
taatgcattt aacagttaga attttgcatc aacgtctttc aaatagaaaa gtaaaggaga     900
gtctagtttg agctggatag ctaaactggt ttaatcatat cttctatcaa gtggttagag     960 ttttagaccct cccaacttta tatgtcgttg ccctaacaat gttgatggat gtttagtcct    1020
aagctctaac attgtccccg tatcatattt cataatagaa tgtactgagt aatggaaaac    1080
tagagaggta ggaagttgga cgaactttga atctatattg atttttactat agtctttctt    1140 ccaagtctta atgagagctt tagctaaagt ttttcaaaaa ctcaaaagaa gttttttgtt    1200
tccaattctt cgatccatag attgtcaaga tggctataat atccttgaag ttaatagcct     1260
tcaaagtttc atagctttta tcctatgatc tttagaaatt caagagttat attctttaga    1320
actacagaac tttgatcttc gattcttcac ctcttccaga acctttatag tagagttttct   1380 tgaccttaca tgggcttggg attgggcctg ctacttatg ggcttagaga ttgaccttgg      1440
gtttaagcac attcgtttta cttggcccaa ttttcttaaa cttctgcaaa atcctaatta    1500
actaacacct caacaaaagt ccagtattaa atgggggcata taaacaaaag ttaaacaaaa    1560
ttgtcgtaca gaatcctaat ttgctaacct cagcaaattt tatgccattc gtccttgtgt    1620
atctaattag tgttaatttg aggaaatata ataatataga cgtaggacgg atattggtat    1680
ttggtgcaac atcctccgaa ccaattcctg gaaagtaatt ggggcaacaa gataatgtta    1740
tcgtcagttt caagtgcaaa acttgccacg tggaacagcg gcaacatgat atctcaaata    1800
tggacctctc acccggtcaa gcttccacca ccaccaccac ctccgtattc taaaataaag    1860
tcaggaacaa gaacagacac accttaacaa aaccaatatt cttcatctct atctctctct    1920
catttcagca tagaagagag ctgagtaaaa ggaaaaaact tcaatcaaat ttgacagaga    1980
agagcccaag agaaaaccaa                                                2000

<210> SEQ ID NO 195
<211> LENGTH: 1400
<212> TYPE: DNA
```

<213> ORGANISM: Cucumis melo

<400> SEQUENCE: 195

| | | | | | |
|---|---|---|---|---|---|
| tatatatatt | aacttttaaa | attttgaaaa | cgtcatagat | aaattatata | caaaataaaa | 60 |
| agtttgatta | tttacgaaag | ttaaaaagtt | tatccgaaag | ttgactcaac | gataaaaaca | 120 |
| ctaaatatca | cttttagaga | tgatgatatt | atacataaac | atacgaactt | acgcgtcaaa | 180 |
| cttttatact | aacacaagat | caaaacaact | ttgttgagta | gtgagaattt | tatctgctga | 240 |
| tatggttgaa | acttgggaag | caagcagagg | aagttccatt | cattaccaaa | atccattttg | 300 |
| tattcatcaa | aatatgaagt | ttagcgactt | gataaagtca | agtcaagtgg | tcctatcgat | 360 |
| ttgttaatgt | caatgtttgg | ttttgaattt | gataccatt | agacaatgat | ataatttt | 420 |
| aagtatggtt | tacactgtga | tgctttatat | attttaaaat | gtaaaatatt | agaacttgta | 480 |
| atttcaataa | attttaaaaa | tgattttgtg | ttatttcctt | ttttaaattg | aaatatcaat | 540 |
| gtatcaatat | tgcgtcatag | agtattgcaa | cacaacctta | tgttaaattg | tttattgctt | 600 |
| attgctctaa | ttcaactcct | tcatcaaatg | tgcacagaat | ttaaacaaga | aaaagagtag | 660 |
| gtgcttttt | actaaaatat | actaaaagct | ttttatacca | aatcttatga | caaaatcatt | 720 |
| ccaacaaaat | gactatttaa | atataagatc | gaatccctaa | tttaaaaaaa | aaaaaaatc | 780 |
| aaagatgtta | atttctatta | ttaaactcac | tttagcgtag | ctaacaaaaa | aaggaaaatg | 840 |
| agaggctaca | aagcttgagc | cctctgcctc | cctttattgc | attgtttgaa | attagatcaa | 900 |
| tactttgtat | ttttttcaaa | atgaaaaatc | gtacatagaa | ttaattctat | ggacaaaaaa | 960 |
| tcagagaagg | aaataatcta | gaataaaatt | cgattttaa | cccaaaaaaa | aaaaaaaaaa | 1020 |
| ctcgattctg | attttgtaa | gcaatcaccc | aaattaccat | aaataaatgg | tattcaatta | 1080 |
| ctcaattatg | gatattttag | aaatgataaa | ttttattca | taaactcttt | tctttctctt | 1140 |
| tcaaaagaa | aaaaattagc | ataaacttca | atgacattta | tttattcttc | ttcgtttgga | 1200 |
| gtcaaaagtt | taaattgagc | atcagtccag | cccaaaagcc | cacgaagaag | cccaagaatc | 1260 |
| ttcagctttt | tcgttcaaac | gtcccttttt | ggtttataaa | attaaagaaa | ataaaaacta | 1320 |
| aatttatttg | ttatttaaca | aaacattttt | ggttaagaca | ttctctttga | ttattttct | 1380 |
| tccattcttc | gtcgtcaatc | | | | | 1400 |

<210> SEQ ID NO 196
<211> LENGTH: 2019
<212> TYPE: DNA
<213> ORGANISM: Cucumis melo

<400> SEQUENCE: 196

| | | | | | |
|---|---|---|---|---|---|
| tttatattta | tgaaaatgaa | gtctctaaac | aattttcta | ctcccaaatt | tgttgatttt | 60 |
| tctgcctatt | ctttatcggt | gctttaaaaa | atgaaaccaa | atttcaaaac | taaaaaaacc | 120 |
| aagcttttaa | aaaaatgtta | ggttattttt | gaaattcaac | taaatgttga | actcttttac | 180 |
| ttattaaata | ggcaaattat | tgaaataaat | ttagagcaag | taagcttaat | ttttaaaact | 240 |
| aatatactta | ccaaatcgag | gactaaaata | ttcaaatact | ctttaaaatt | aagattaaca | 300 |
| ttaatcactt | tgttatgttt | aaaaagttgc | agtgtcactt | gaacctttt | aaattaatat | 360 |
| aatgaaaatg | aatccaactc | aatatatata | atatctatat | tattaatctc | gatgtcagat | 420 |
| gtttgatacg | cacatatctc | aaaaattata | cctcaactaa | catcggtgca | cgatgtatta | 480 |
| tttcgtgagg | ataaaaatcg | ttttagtat | aaattgatgg | aaagattatt | tgaattactg | 540 |
| aaaaatgcac | cggtacatta | tttgaaactt | ccccttcatt | taaagaggct | aatattagaa | 600 |

```
aaagacacgc tgaggctatt tttacaatta atgtgggctg ttgacttggc ccagcccaaa      660
acataaaccc taaagtagca caaacaaacg cctctttctt cttgaaaccg catattaagc      720
gttttatcac ttctcaccac ctctcattcc tcctcttccg cacgttgttt cgctcctcaa      780
cgggagtgcc ttcccttgc tctccctcca ggttcttctt ccttctcatc tcatttccaa       840
gtaatttcat tccgtttctt ttctcttaat cgtatcttgt tcagactctt tcgcgttttt      900
ttttagttgc gccttaccag atctgtgttt tcactcgttt ctattcgata catgcttcca      960
agatccattt cttaatcgca tgtattcggt tgattggatg attgtctttt tgtaagttt      1020 gattacttt ttggaatgga tcggttgaac caacggggtt taagtcgatg gaagtaggtt     1080
atgttaaaga tttgcttctt ttttatgaag atgtgtgtgt tcttttttct ttgctagatg     1140
atgttattat ttgattgttt taacagtcgt gttttgtttt tctgcagttt atagtcctcg     1200
gtcttttgaa gacttgtcaa gatggttagt cacctcttg tcatcgtgat tttgattgag      1260
tgatgtgtta agtgcttctt taggttacag ctaacgcgat tttttatatt caattgtgcc     1320
tgtgcaggtg aagtttacag cagaagagct ccgtcggatt atggactata agcataacat     1380
tcgtaatatg tctgttattg ctcacgtcga tcatggtaag ctacttagtt taagttat     1440 tatgccgagc gtctatttaa gaagattaac atcttagctt tcatttattg tttatttggt     1500
aagcatcgtt tcttttctc cgaggaactg tacatgtcag ttcacatgac aataaaacga     1560
tcttccttgg acattagttt ttgaagttca attagacgcc aaattttgtt ggttaaaaga      1620
tgcttgtgga gcatatggac ctaatggaat cagtactttt tgatggatgg acttgtcttt     1680
tgttctttta ttttcaaaag aaattgcatg tgcaattaca tcatctttga tcgaaagatt     1740
gggtaattgg gtaattgggg taaagacatg ttgtaaaaac taatgttaat tatcaattac     1800
cattatatac cttatttagt gcttatttat atcctttttc cccatttcag ggaagtccac     1860
tctcacagat tctcttgtgg ctgctgccgg tatcattgca caagaagttg ctggtgatgt     1920
acgaatgaca gatactcgtc aagatgaggc agagcgtggt atcaccatta aatctactgg     1980
aatctccctc tactatgagc agaagagctc cgtcggatt                            2019
```

<210> SEQ ID NO 197
<211> LENGTH: 1999
<212> TYPE: DNA
<213> ORGANISM: Cucumis melo

<400> SEQUENCE: 197

```
aaaaggcgaa aaaaaagtta gcttcccgag aaggagaaga cgaggaagag tttgacttcc       60
cggggagata aagtttgtgt ctcgagggaa tctctaatct ggagttgacc gtcgacttat      120
gtgtcgagcc tggatttagt tgcatggtgc gacaaagcga taaggcggca tatgtaaagt      180
agtaattcaa aactagcggt taaagaaata atcagccaaa aaatttagta caaatacggg      240
tggaggccct aagtgaagtg ctgctattca gaggttttgg caaagagtg caaagagttg       300 agttgtgcag agaaagtact aggtgaggag aggcgtttgg aaaagaaaag gatcaaacat      360
ttgcatgagt gatattctta aactaaacac tcttgtgtga gtgacttgcc taagctaaac      420
actcttgcat gagtaacttt cttaaactaa acgttttgta atgttttctt aatggattct      480
tttcgagtct gagttatgct taacacgttt tgtttctctc gtgttattgt tgttgttgtt      540
tgaaaagaga aaactattgt tttctatgtg ctgattgtga tgaatgtgtg cgaaccatta      600
gccttaatcc tatcaagtga atagtgatta tgtggtgtgt gcacataatg taaatgacat      660
```

```
tgtgtggatg gccagtgcaa caagaaatga atcagaaagc ttcccaaata ctgtgaatgg     720
agtgaacatc acactagctc aatggcaaga tattggcgat agtgaatcac aataggcttg     780
acaaggggaa ggattcatgt tcttggttga aaggaataag agaggctaat gtgagatttc     840
tgtgatttgc aaaatgaggc gttggaagac acgtttgaga aatgaaaacg aattagtgct     900
tgacttgtat tcctaaaaaa gttgtccaat atcttcaatc actaaatatt tgatgtgcct     960
aagttttcct tccttagttg ttgaggcgtt gaggccgagt aaggaaagat aagataatta    1020
tgacgttgaa aagctggtca agttatccat ctttggatgg tttaaagtta ttacatgtag    1080
ggagggttgc attccaattt tgtgtgtgag atgagtctta ttttcgagat gggttgctag    1140
gcgatcaagg agaagtataa gaaatgagtt cttatactct tgaacaactt gacacgaaga    1200
ataacatcct agtggatgaa ggaaggtgat ggaacttaaa gtttaggttt tattttggc     1260 cttgtgataa aaaaaatgta attgtaaagt attagatcaa gtaataaaaa cagagttgtg    1320
ttttctattt ttgctgtgtt gggttgtgta tctttattgt gcttatggcc tagttgctaa    1380
agagttaagg ttattaccta aatgttttac ggtgtgttga gttgtaaaga tctcctgagt    1440
taaagttgga attttgtatt ggagattgtt ttgagaagtt tagcttacta attgtttaac    1500
tcattaggtg tctaagcgac acgcctcctt ttggtcgcat gaagtggcta gcagggtggg    1560
gcggaccggg gtggggtgtg ataataaacc taaaaaatca cccagataag cctaaattat    1620
acgttgaagt taaacttaca atttgattag aagaagaagg aatatctgat ttggacatga    1680
attaattaca aatacggcgc caatcataca aagcacatgt aagatcaacg cattctacac    1740
tcaatctcag ccgttgattg ctttcaatcc ttcaaaagaa aaaaagaag ggcagttcgg     1800 gcagagtcat acctacccgt tgactataaa agcaactaca aatcgaaaac ctccatttct    1860
ccgttaccat tacagagaaa atcaaagaaa tttggcgttg agagattggg agagaggttt    1920
ctctttctag ggttgcttct tcttcttcat cctccattgt tgcaaatttc acttccttct    1980
cctcttgttc tcatctccc                                                 1999
```

<210> SEQ ID NO 198
<211> LENGTH: 1578
<212> TYPE: DNA
<213> ORGANISM: Cucumis melo

<400> SEQUENCE: 198

```
atatatatat atataattta actaaataaa caaatgaaag aaaaaagtga gttcccattc      60
ggaaaatgca gatggatcca tttcttcaaa tattaaaaaa taaaaaaata aaataaaata    120
acttaaatat gcaaatagaa agaattttaa tttctggatt atccatatgg gacaattttt    180
aaaactcatt tattttatt tttttatta tttgattttg atatatctat ggggaaattt      240
ttcgtaataa ttttcgaaaa aatattgcaa tatatcattt gatcagatcg gtattattaa    300
atctctatca catttggtct taaattatcc aaagattcct ttaagataat ttagataacc    360
atctacagat cactactata atcaacaaaa ggaacaactt aaattattta aacaaattca    420
ttaatattag actttgtgct tcattagaaa atgatcttat cacaaccaca accatagtgg    480
tggtttaaaa tttatttta aactcttatt agtattattt taattcatac ttaatcaaac    540
taattacttt aaaaaacata tatatataaa taagttaaat cattcccct tatatctaaa    600 taacataaaa aaaaattgtt tactctacaa gaagtttgta tatatatatg ctcggtacta    660
tttagcatct ttataataaa atttctaaat caattttta tatctcttta ttaaatgtat    720
agtcatcaaa aaatttaacg agataatgtg tcaaagattt attttattaa cgttcataaa    780
```

```
tatcaaatta tacttagctt ataattgaaa acatgttcga taaatataag taaataaaat    840 tttattttt  ttaaatatta caaaataaac taaataagtt ataaatatga caataaacat    900
tatatatttt attatattta taaatactta ataatttagt cgtttaaaat aattttctta    960
attttcaaaa catgtttcat atgttaataa taaataaatg gaaaaccttc caaaagaaga   1020
aaaaaagata tcttaaaatt taaaaattga gattttgagg atcaataatt aataaaagaa   1080
ggattaataa gggtgaaatt aaatcccaaa agaaaattg  aaaatgaaga aaagaaaagt   1140
gaagaaataa ttgaacgtgg gaagtggatt cgatgtctcc agagaacaag cgaaaggaga   1200
cgaaatccac ataatttgca cgttacgtgt ccctatcaac cgtagacacg tgtcaacatc   1260
tcaacaccct acgccgaatt gcttcgctgg atctggacgg tcatcggata acagcggcaa   1320
ccaattaata tttcccctta tatttcacag cctggccatg tccaccaatc acgttcaact   1380
attaattcat ttttcatttc cttttctttt ttttttttaa ttcccctcaa ttattaccga   1440
caacctgttg tagccggtta accctacccct ccaacgttcc attataaggc ctagaaaatg   1500
gacgtgaaaa tggagtacta caaactacaa ttaatttta agaattttaa ttttaaagtt   1560
ctctaattac tattagcc                                                  1578

<210> SEQ ID NO 199
<211> LENGTH: 1023
<212> TYPE: DNA
<213> ORGANISM: Cucumis melo

<400> SEQUENCE: 199
ataataataa taaatacata atagtaataa taataaaaaa aataaaaaaa taataatagt     60
aatgaaaatc aatagaataa ttttaaaatc gggaaggaag tcgtgtacaa tccttgcacg    120
ttggagagtc aaatggccta agtggtgatg tggaagtcgt gtaccgggta cacgattttc    180
ctacaagtca ataataataa tatggttatt tttctagttt agggttcatg acaaaagatt    240
gttcagtcga ctggatgtag acaaatctaa aaaataaatt aaaatctaat atgaaaacta    300 gttttaatttt ccaaattatt aagggttgaa ttcgaccaat aaataataat aatacggtta    360
ttttgaaatt taggaaattg aataaagttg ttaaaatctt caagcaaatt gttaagcccc    420
gagatattaa gaagaggtaa taatagagga ttctatattt ataacatgtt aaaattaatt    480
gcaaactcat aaatgcatca cacagattaa caacatagga gggacttccg ataaaagtgc    540
aaatattgaa ataattacag ttcgcgaaca tgagtatttt aatatttat  aaaatagtat    600 gcacgtgtat ttttgccaaa agaaaaaaag aatagatttt gccattttc aaagtgactc    660 tcggttatat cttttatggc gattgtattt tatagcgtat gttgtttgta gttaacccat    720
ttctcattgg caaattcaat cgtgggccac aacgtttggg catagcttca atttggatta    780
actcaattat gtctgaatgg gttggactag ttcggactct tcggctgggc cagaatcaga    840
ttcgggccgc aatctgttca tttcacacct atatccaaac accccaaaa  tcgataccca    900 tcaaacccta actctcaata accccatat  ataaattcct tctttagggt ttttcatcc    960 tcatacactc tcaaacctcc ggtcattctc attttccctg ccgcttcttc aataacccta   1020
atc                                                                  1023

<210> SEQ ID NO 200
<211> LENGTH: 1654
<212> TYPE: DNA
<213> ORGANISM: Arabidopsis thaliana
```

<400> SEQUENCE: 200

```
tgatgattct tgttgttgta gttcttttta aaagtcccac ctgagcctct atagactctg      60
attctctttt aagttactat tttcaccgct ctctaataag gctcgtgatt ttttgggagc     120
catactgtat actcgccggc cctctcacga tgttgttcaa ttcacagact aaatttgatt     180
tatctatttc gccaaaacat aacttcatta aaaaatgttc tccaaataac taaacgaatt     240
aaataaaaga aacctttcat gtaaagttaa aggtatgaga ctttaagggc agttgctgaa     300
cattcgtaac acatgggaga acaatagaga aagttgaaaa gaaacgtagc atatagaaaa     360
attatctttg taaccaagtt gatttagaaa aatatcacta tttgtgaaaa atactagatc     420
agtttattat tactttttttt ttttgtata ttcacaaata tcatattcat atagaagaaa     480
ataaacaaag ttgtaaaaat ctggcattta aaataaaatt gaacacttca atttatttcc     540
tttcataata ataattttgg cataagatat ttgcaaattg atctggttcg gtatggtcga     600
caaaataatt ttccacgcta cccttccagc cgtccattca ctatttgccc tcaacgttac     660
caaataacgg tccagattcc tagggcaaga tctaacggtt agcaagtaaa gtcgtaccat     720
cagaaagaat aacaattctt tcacaaagta aacataacca acggttaaca agttcttagg     780
gttaaatcag taagatccaa cggatattaa attgcaaggc ccaaatagtt ttttttgcagc    840 agataataac tcgtccccac tggcgagtga cgaccgagac tctgtgaccc tatttttcga     900
gacgataaaa gggcaaacaa tcgctctttt caaagctcgc ctcttcacca cagagaaaac     960
ttcgtctctc ttctctgctt cgccctctca tttcctgtga gataaaggcg gagtctctct    1020
ccagttattt tgctcatcca tcgattctta ggtatgactc gtttctctca gatctgtgat    1080
tctttataat ctcgtcgttc ttcaaatcat tgttatattc gtttcttcga tctgtgtttt    1140
ttagatctgt aagtaaatg agacgtttcg atctgtagat ctgattgtta tattgataga    1200
ttatgttatc tgctttgctt aaagtccgat cggaatgttt tgtgctcatt gtcgaatatc    1260
tgatgtatcg gtttcataga tctgcttctt tttgtgcgtt tcgttgatct gataatcttc    1320
tagtgatcaa aatcgtttgg atctgttgac tttagtttaa aatgtatccg atctgatgtc    1380
gaggcttcat tattggaagt tgttattgtt gtaatcctga tttaagttgc tgttcttaaa    1440
tttatatgat ctttgcgtta taatatgaca tggtagatct tggttcatgg ttcactgttt    1500
tccaataaac ttggtttgtt tggttggata gcgttctgtg atacgaccat gtcttgtgtt    1560
ggataagaat tctctgaatt tccttggctg gtttgtagta tgttattcac gtctggtttc    1620
tcatcaatga ttatgtgatt ttgcagagtt cacc                                1654
```

<210> SEQ ID NO 201
<211> LENGTH: 712
<212> TYPE: DNA
<213> ORGANISM: Artificial sequence
<220> FEATURE:
<221> NAME/KEY: misc_feature
<222> LOCATION: (1)..(712)
<223> OTHER INFORMATION: Chimeric transcriptional regulatory expression element.

<400> SEQUENCE: 201

```
ggtccgatgt gagactttc aacaaagggt aatatccgga aacctcctcg gattccattg       60
cccagctatc tgtcactttta ttgtgaagat agtggaaaag gaaggtggct cctacaaatg    120
ccatcattgc gataaaggaa aggccatcgt tgaagatgcc tctgccgaca gtggtcccaa    180
agatggaccc ccaccacga ggagcatcgt ggaaaaagaa gacgttccaa ccacgtcttc     240
```

| | |
|---|---|
| aaagcaagtg gattgatgtg atggtccgat tgagactttt caacaaaggg taatatccgg | 300 |
| aaacctcctc ggattccatt gcccagctat ctgtcacttt attgtgaaga tagtggaaaa | 360 |
| ggaaggtggc tcctacaaat gccatcattg cgataaagga aaggccatcg ttgaagatgc | 420 |
| ctctgccgac agtggtccca agatggacc cccacccacg aggagcatcg tggaaaaaga | 480 |
| agacgttcca accacgtctt caaagcaagt ggattgatgt gatatctcca ctgacgtaag | 540 |
| ggatgacgca caatcccact atccttcgca agacccttcc tctatataag gaagttcatt | 600 |
| tcatttggag aggacactct agacagaaaa atttgctaca ttgtttcaca aacttcaaat | 660 |
| attattcatt tatttgtcag ctttcaaact ctttgtttct tgtttgttga tt | 712 |

<210> SEQ ID NO 202
<211> LENGTH: 938
<212> TYPE: DNA
<213> ORGANISM: Arabidopsis thaliana

<400> SEQUENCE: 202

| | |
|---|---|
| caaaagccga gccgataaat cctaagccga gcctaacttt agccgtaacc atcagtcacg | 60 |
| gctcccgggc taattcattt gaaccgaatc ataatcaacg gtttagatca aactcaaaac | 120 |
| aatctaacgg caacatagac gcgtcggtga gctaaaaaga gtgtgaaagc caggtcacca | 180 |
| tagcattgtc tctcccagat tttttatttg ggaaataata aagaaatag aaaaaaataa | 240 |
| aagagtgaga aaaatcgtag agctatatat tcgcacatgt actcgtttcg cttttccttag | 300 |
| tgttagctgc tgccgctgtt gtttctcctc catttctcta tctttctctc tcgctgcttc | 360 |
| tcgaatcttc tgtatcatct tcttcttctt caaggtgagt ctctagatcc gttcgcttga | 420 |
| ttttgctgct cgttagtcgt tattgttgat tctctatgcc gatttcgcta gatctgttta | 480 |
| gcatgcgttg tggttttatg agaaaatctt tgttttgggg gttgcttgtt atgtgattcg | 540 |
| atccgtgctt gttggatcga tctgagctaa ttcttaaggt ttatgtgtta gatctatgga | 600 |
| gtttgaggat tcttctcgct tctgtcgatc tctcgctgtt atttttgttt ttttcagtga | 660 |
| agtgaagttg tttagttcga aatgacttcg tgtatgctcg attgatctgg ttttaatctt | 720 |
| cgatctgtta ggtgttgatg tttacaagtg aattctagtg ttttctcgtt gagatctgtg | 780 |
| aagtttgaac ctagttttct caataatcaa catatgaagc gatgtttgag tttcaataaa | 840 |
| cgctgctaat cttcgaaact aagttgtgat ctgattcatg tttacttcat gagcttatcc | 900 |
| aattcatttc ggtttcattt tactttttt ttagtgaa | 938 |

<210> SEQ ID NO 203
<211> LENGTH: 633
<212> TYPE: DNA
<213> ORGANISM: Pisum sativum

<400> SEQUENCE: 203

| | |
|---|---|
| agctttcgtt cgtatcatcg gtttcgacaa cgttcgtcaa gttcaatgca tcagtttcat | 60 |
| tgcgcacaca ccagaatcct actgagtttg agtattatgg cattgggaaa actgttttc | 120 |
| ttgtaccatt tgttgtgctt gtaatttact gtgttttta ttcggttttc gctatcgaac | 180 |
| tgtgaaatgg aaatggatgg agaagagtta atgaatgata tggtccttt gttcattctc | 240 |
| aaattaatat tatttgtttt tctcttatt tgttgtgtgt tgaatttgaa attataagag | 300 |
| atatgcaaac attttgtttt gagtaaaaat gtgtcaaatc gtggcctcta atgaccgaag | 360 |
| ttaatatgag gagtaaaaca cttgtagttg taccattatg cttattccact aggcaacaaa | 420 |
| tatattttca gacctagaaa agctgcaaat gttactgaat acaagtatgt cctcttgtgt | 480 |

```
tttagacatt tatgaacttt cctttatgta attttccaga atccttgtca gattctaatc    540
attgctttat aattatagtt atactcatgg atttgtagtt gagtatgaaa atatttttta    600
atgcatttta tgacttgcca attgattgac aac                                 633
```

<210> SEQ ID NO 204
<211> LENGTH: 315
<212> TYPE: DNA
<213> ORGANISM: Gossypium barbadense

<400> SEQUENCE: 204

```
tgatcacctg tcgtacagta tttctacatt tgatgtgtga tttgtgaaga acatcaaaca     60
aaacaagcac tggctttaat atgatgataa gtattatggt aattaattaa ttggcaaaaa    120
caacaatgaa gctaaaattt tatttattga gccttgcggt taatttcttg tgatgatctt    180
tttttttatt ttctaattat atatagtttc ctttgctttg aaatgctaaa ggtttgagag    240
agttatgctc ttttttttctt cctctttctt ttttaacttt atcatacaaa ttttgaataa    300
aaatgtgagt acatt                                                     315
```

<210> SEQ ID NO 205
<211> LENGTH: 315
<212> TYPE: DNA
<213> ORGANISM: Gossypium barbadense

<400> SEQUENCE: 205

```
accatatgac actggtgcat gtgccatcat catgcagtaa tttcatggta tatcttaatt     60
atatggttaa taaaaaaaag atggtgagtg aataatgtgc gtgcattcct ccatgcacca    120
atggtgaatc tctttgcata catagagatt ctgaatgatt atagtttatg ttgtagtgaa    180
attaattttg aatgttgttt ttaaatttta atgtcacttg gcttgattta tgttttaacg    240
aagcttatgt tatgtatttt actttaatga tattgcatgt attgttaatt taacattgct    300
tgatcagtat actct                                                     315
```

<210> SEQ ID NO 206
<211> LENGTH: 2001
<212> TYPE: DNA
<213> ORGANISM: Artificial sequence
<220> FEATURE:
<221> NAME/KEY: misc_feature
<222> LOCATION: (1)..(2001)
<223> OTHER INFORMATION: Codon redesigned coding sequence.

<400> SEQUENCE: 206

```
atggtccgtc ctgtagaaac cccaacccgt gaaatcaaaa aactcgacgg cctgtgggca     60
ttcagtctgg atcgcgaaaa ctgtggaatt gatcagcgtt ggtgggaaag cgcgttacaa    120
gaaagccggg caattgctgt gccaggcagt tttaacgatc agttcgccga tgcagatatt    180
cgtaattatg cgggcaacgt ctggtatcag cgcgaagtct ttataccgaa aggttgggca    240
ggccagcgta tcgtgctgcg tttcgatgcg gtcactcatt acggcaaagt gtgggtcaat    300
aatcaggaag tgatggagca tcagggcggc tatacgccat tgaagccga tgtcacgccg    360 tatgttattg ccgggaaaag tgtacgtaag tttctgcttc tacctttgat atatatataa    420
taattatcat taattagtag taatataata tttcaaatat ttttttcaaa ataaagaat    480 gtagtatata gcaattgctt ttctgtagtt tataagtgtg tatatttaa tttataactt    540 ttctaatata tgaccaaaat tgttgatgt gcaggtatca ccgtttgtgt gaacaacgaa    600
```

```
ctgaactggc agactatccc gccgggaatg gtgattaccg acgaaaacgg caagaaaaag    660
cagtcttact tccatgattt ctttaactat gccggaatcc atcgcagcgt aatgctctac    720
accacgccga cacctgggt ggacgatatc accgtggtga cgcatgtcgc gcaagactgt    780
aaccacgcgt ctgttgactg gcaggtggtg gccaatggtg atgtcagcgt tgaactgcgt    840
gatgcggatc aacaggtggt tgcaactgga caaggcacta gcgggacttt gcaagtggtg    900
aatccgcacc tctggcaacc gggtgaaggt tatctctatg aactgtgcgt cacagccaaa    960
agccagacag agtgtgatat ctacccgctt cgcgtcggca tccggtcagt ggcagtgaag    1020
ggcgaacagt tcctgattaa ccacaaaccg ttctacttta ctggctttgg tcgtcatgaa    1080
gatgcggact tgcgtggcaa aggattcgat aacgtgctga tggtgcacga ccacgcatta    1140
atggactgga ttggggccaa ctcctaccgt acctcgcatt acccttacgc tgaagagatg    1200
ctcgactggg cagatgaaca tggcatcgtg gtgattgatg aaactgctgc tgtcggcttt    1260
aacctctctt taggcattgg tttcgaagcg ggcaacaagc cgaaagaact gtacagcgaa    1320
gaggcagtca acggggaaac tcagcaagcg cacttacagg cgattaaaga gctgatagcg    1380
cgtgacaaaa accacccaag cgtggtgatg tggagtattg ccaacgaacc ggataccgt    1440 ccgcaaggtg cacgggaata tttcgcgcca ctggcggaag caacgcgtaa actcgacccg    1500
acgcgtccga tcacctgcgt caatgtaatg ttctgcgacg ctcacaccga taccatcagc    1560
gatctctttg atgtgctgtg cctgaaccgt tattacggat ggtatgtcca aagcggcgat    1620
ttggaaacgg cagagaaggt actggaaaaa gaacttctgg cctggcagga gaaactgcat    1680
cagccgatta tcatcaccga atacggcgtg gatacgttag ccgggctgca ctcaatgtac    1740
accgacatgt ggagtgaaga gtatcagtgt gcatggctgg atatgtatca ccgcgtcttt    1800
gatcgcgtca gcgccgtcgt cggtgaacag gtatggaatt cgccgatttt tgcgacctcg    1860
caaggcatat tgcgcgttgg cggtaacaag aaagggatct tcactcgcga ccgcaaaccg    1920
aagtcggcgg cttttctgct gcaaaaacgc tggactggca tgaacttcgg tgaaaaaccg    1980
cagcagggag gcaaacaatg a                                              2001
```

<210> SEQ ID NO 207
<211> LENGTH: 1653
<212> TYPE: DNA
<213> ORGANISM: Artificial sequence
<220> FEATURE:
<221> NAME/KEY: misc_feature
<222> LOCATION: (1)..(1653)
<223> OTHER INFORMATION: Codon redesinged coding sequence.

<400> SEQUENCE: 207

```
atggaagacg ccaaaaacat aaagaaaggc ccggcgccat tctatcctct agaggatgga    60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aaggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
```

```
tctactgggt tacctaaggg tgtggccctt ccgcatagaa ctgcctgcgt cagattctcg      660
catgccagag atcctatttt tggcaatcaa atcattccgg atactgcgat tttaagtgtt      720
gttccattcc atcacggttt tggaatgttt actacactcg atatttgat atgtggattt       780 cgagtcgtct taatgtatag atttgaagaa gagctgtttt tacgatccct tcaggattac      840
aaaattcaaa gtgcgttgct agtaccaacc ctattttcat tcttcgccaa aagcactctg      900
attgacaaat acgattatc taatttacac gaaattgctt ctgggggcgc acctctttcg       960
aaagaagtcg gggaagcggt tgcaaaacgc ttccatcttc cagggatacg acaaggatat     1020
gggctcactg agactacatc agctattctg attacacccg aggggatga taaaccgggc      1080 gcggtcggta agttgttcc attttttgaa gcgaaggttg tggatctgga taccgggaaa      1140
acgctgggcg ttaatcagag aggcgaatta tgtgtcagag gacctatgat tatgtccggt     1200
tatgtaaaca atccggaagc gaccaacgcc ttgattgaca aggatggatg gctacattct     1260
ggagacatag cttactggga cgaagacgaa cacttcttca tagttgaccg cttgaagtct     1320
ttaattaaat acaaaggata tcaggtggcc cccgctgaat tggaatcgat attgttacaa     1380
caccccaaca tcttcgacgc gggcgtggca ggtcttcccg acgatgacgc cggtgaactt     1440
cccgccgccg ttgttgtttt ggagcacgga agacgatga cggaaaaaga gatcgtggat     1500
tacgtcgcca gtcaagtaac aaccgcgaaa agttgcgcg gaggagttgt gtttgtggac     1560
gaagtaccga aggtcttac cggaaaaactc gacgcaagaa aaatcagaga gatcctcata     1620
aaggccaaga agggcggaaa gtccaaattg taa                                  1653

<210> SEQ ID NO 208
<211> LENGTH: 936
<212> TYPE: DNA
<213> ORGANISM: Artificial sequence
<220> FEATURE:
<221> NAME/KEY: misc_feature
<222> LOCATION: (1)..(936)
<223> OTHER INFORMATION: Codon redesigned coding sequence.

<400> SEQUENCE: 208
atggcttcca aggtgtacga ccccgagcaa cgcaaacgca tgatcactgg gcctcagtgg       60
tgggctcgct gcaagcaaat gaacgtgctg gactccttca tcaactacta tgattccgag      120
aagcacgccg agaacgccgt gattttttctg catggtaacg ctgcctccag ctacctgtgg     180
aggcacgtcg tgcctcacat cgagcccgtg gctagatgca tcatccctga tctgatcgga     240
atgggtaagt ccggcaagag cgggaatggc tcatatcgcc tcctggatca ctacaagtac     300
ctcaccgctt ggttcgagct gctgaacctt ccaaagaaaa tcatctttgt gggccacgac     360
tggggggctt gtctggcctt tcactactcc tacgagcacc aagacaagat caaggccatc     420
gtccatgctg agagtgtcgt ggacgtgatc gagtcctggg acgagtggcc tgacatcgag     480
gaggatatcg ccctgatcaa gagcgaagag ggcgagaaaa tggtgcttga gaataacttc     540
ttcgtcgaga ccatgctccc aagcaagatc atgcggaaac tggagcctga ggagttcgct     600
gcctacctgg agccattcaa ggagaagggc gaggttagac ggcctaccct ctcctggcct     660
cgcgagatcc ctctcgttaa gggaggcaag cccgacgtcg tccagattgt ccgcaactac     720
aacgcctacc tcgggccag cgacgatctg cctaagatgt tcatcgagtc cgaccctggg     780
ttcttttcca acgctattgt cgagggagct aagaagttcc ctaacaccga gttcgtgaag     840
gtgaagggcc tccacttcag ccaggaggac gctccagatg aaatgggtaa gtacatcaag     900
```
agcttcgtgg agcgcgtgct gaagaacgag cagtaa            936

<210> SEQ ID NO 209
<211> LENGTH: 253
<212> TYPE: DNA
<213> ORGANISM: Agrobacterium tumefaciens

<400> SEQUENCE: 209
gatcgttcaa acatttggca ataaagtttc ttaagattga atcctgttgc cggtcttgcg   60
atgattatca tataatttct gttgaattac gttaagcatg taataattaa catgtaatgc  120
atgacgttat ttatgagatg ggtttttatg attagagtcc cgcaattata catttaatac  180
gcgatagaaa acaaaatata gcgcgcaaac taggataaat tatcgcgcgc ggtgtcatct  240
atgttactag atc                                                     253

<210> SEQ ID NO 210
<211> LENGTH: 622
<212> TYPE: DNA
<213> ORGANISM: Cauliflower mosaic virus

<400> SEQUENCE: 210
ggtccgattg agacttttca acaaagggta atatccggaa acctcctcgg attccattgc   60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaagaag acgttccaac cacgtcttca   240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaagaa   480 gacgttccaa ccacgtcttc aaagcaagtg gattgatgtg atatctccac tgacgtaagg  540
gatgacgcac aatcccacta tctagacgca agacccttcc tctatataag gaagttcatt  600
tcatttggag aggacacgct ga                                          622

<210> SEQ ID NO 211
<211> LENGTH: 1446
<212> TYPE: DNA
<213> ORGANISM: Cucumis melo

<400> SEQUENCE: 211
tcccttcagc cacttaacac ttaaaaatct taggaaactc catgggctcc tctttctcca   60
atgaaatttt gacatctgtg ttgttgatag ctcctatatc ctttgagaat ttgatataca  120
cctgtcattt gctgatttgt ggataactgt tagccttttg atattgatac gttcctttt   180 ttatgaattt ttgtaaatcc attcaatttt aatgctgtcg taaatgaaaa gcccttcat   240 taatgttgtt tatatacata ttttaaaatt aattcaataa caagtttagt tctgttagct  300
tctaggtttg tatctatttt atctattaaa ggtatgtttg gcttcaggt tggaatggag   360 tagaattgaa tgggttgggg agtaaatttt ccattcaaca agttcaattt caaaatggct  420
ataagttttt gaactcaatt ttattttcaa taaattcctt aatttttgt tccttgtttg   480 taaactattg acttattcga tatattttaa aattgaggta ttttaaaaaa ataacaat   540 attaaaatta tttataaaat ataacaaaat ttatgtatag tttatttgaa aattttacta  600
tagtttcatt tttatattat tcctaaccat ttccatttaa aattattca attatttctt   660

```
ttattaatat aattgaaatt tcatggattt attagacaca tgatttgaaa ttttatgggt      720
ttattaagta ttttctaaca caaaatcgct tccgcatcgt tttcaattca ttcagtaata      780
gaagtaattt tttaaaagaa ccaaatttgc caaattttga gttccataag gactctgaaa      840
actcattatg tctattactc ttcactaatt gtagagactt aaattcaaga taagagacac      900
taattgatga taattgccca aaaaataaaa ataaaaatgt ttcttcccca tcctcaacct      960
ccatgaattc acagagccca aagattaatt attgggcccc aattcctact catatatacc     1020
ttacagtccc tcaaagaaat cttaggaagt aatcaatttc tgtttattca agatgtagcc     1080
tcccaaaaga aaatacatc acatcaaatt caaacaaaaa tatctacagc tagcaaaacc     1140
tcaaaccgtt aaaatttcaa gccacataaa tgaattttc atctgaaaaa aggacaatct      1200
atctagacgt tagatttcag ccctaatatg aatctgaagc atttggtgga cgagaaagag     1260
ccatgtagga atgcatcaaa caaggaaaa atctttgaac tccaatggga ttgaagatac      1320
agataccaat ggataagaat ctgttctctt tgcccactat ttaaactcac caaacccacc     1380
agtatcttcc tcaccacaaa atacattcca ccgttgatca caagccttat tccaccacct     1440
ccaaca                                                                1446

<210> SEQ ID NO 212
<211> LENGTH: 2018
<212> TYPE: DNA
<213> ORGANISM: Cucumis melo

<400> SEQUENCE: 212
actattggag acgacgaagg aaaactctaa tgtgagctta gaattgaaga tggtgaacaa       60
ttgggagtct tttttaaaaa tctttcgtcg gtatattgaa atttcctttt acactcaaat      120 aaccccccctt ttcacgcgtt caacgtcttc aaaccttcct ttttcaatta ttttttcgtt     180
tacattaatg acatttaggt aataagataa attagtggat tcttttgtga aaaatgttag      240
cccatttaag acttttatga aatatattag aaaaaaatca tatagcaatt tatattattc      300
tagttaaaag cccataatag aaactaaccc aacctaaagt aacgtaaaca ttcaataaga      360
gagacaaatt ttaaaataat ttctaattaa aaaaaaaatt gtcaagaccg tccgggtcgg      420
atccaaaata taacccgaac cggccggttt agcatctata taaatacacc tttagggttt      480
ttattctctc aagacttcac cgcatttcca cttctctgag gccacggtca gccattggag      540
cagctcaata atcctttgac tccctactac ggtaagtcga ccttactgct ttcggcttct      600
agttttttca atcctgtcat tagtcctttg gagttcttct gtacatttat gacgttttcg      660
gctcgtgttt tgtttcgcct gtatgtagtg ggttttttcga gttttgtttt tactttttt       720 tatacttgca ggaattagtt gaaatctatg tacttcatgc cttggataat actcttgatc      780
tgttgtgtta ttcaaaatga attgttttaa gatggtattt gagaatggtc atgtgagttt      840
tgcctacttg gttattaaaa tgaattgttt taggatggta tttgagaatg gtcttctggg      900
tatttggttg gaacctttgt gctctgctat gaattagggt gttctccccg ttttttttt       960 ttttttcctt ttggttatta atatatcttt tatgactact tattcatata tgatatcttt     1020
tactcgtaaa ttttgactca tttgaaagtt ttatccttag tcctttctca ttcagggtgt     1080 aaggtatgt tgttagggtt aaaatagcct atgcaggaaa gttctgtatt tgttctaatt      1140
attgcatttg tgtgcatttg tatctagttt atttcttgct gagagtatgc ttcattttt      1200 agtacacatc acttgtgcca ctttattata gttgcacatt tttgtttatg gagaggatga     1260
```

```
atagcattta gggatgtcaa ttttttattg agaaaaccct ctctcctact taagcttggg    1320
gaatttttgt tctaaatgtg gtaaacataa tacttcttct tattttaatt tgaatggaag    1380
gggaagacga atactaatat tttcaacgaa ccttcacaac ttttttttc ttatttagga     1440 agccatgttt ttcaaaattg tactgtgtga tccacatatt tatcgattat tagtgaatcg    1500
aataataatt agagttttat tggtataatt ttgaagttca gacttattac atttgtggaa    1560
agtttggtta caatttcaa  ttttattgga atcctaagaa ctttgtgtta acatatattg    1620
agttttcttc tctttttttt tactcattaa gttctctatt aggaatgttt ggttcaatgt    1680
cacatagtcg atagctaaga ccagtgaccc acaaagctat gattgaacga aaaacaagcc    1740
tttcacatct tggtaggaat ttgttatttc tcaatagatt tacagagctg tttcatgtga    1800
tcacaatttt tttctatttt tctgaagttc tctattagga atgggctatc tggttagttg    1860
cttttgagag aacatgtgga ttggtgttgc tcggtttcct tgcctttgta attttgtcct    1920
tggaaaaagc aaaatgatta ggtatcctga tatgcataac atgtttaagc caactagttc    1980 tcacttttt  agtgcaaata attgatcttc aggaatcg                           2018
```